US006066318A

United States Patent [19]
Feng et al.

[11] Patent Number: 6,066,318
[45] Date of Patent: May 23, 2000

[54] MULTI-FUNCTIONAL HEMATOPOIETIC FUSION PROTEINS BETWEEN SEQUENCE REARRANGED C-MPL RECEPTOR AGONISTS AND OTHER HEMATOPOIETIC FACTORS

[75] Inventors: Yiqing Feng; Nicholas R. Staten, both of St. Louis, Mo.; Charles M. Baum, Evanston, Ill.; Neena L. Summers, St. Charles, Mo.; Maire Helena Caparon, Chesterfield, Mo.; S. Christopher Bauer, New Haven, Mo.; Linda L. Zurfluh, Kirkwood, Mo.; John P. McKearn, Glencoe, Mo.; Barbara K. Klein; Stephen C. Lee, both of St. Louis, Mo.; Charles A. McWherter, Wildwood, Mo.; Judith G. Giri, Chesterfield, Mo.

[73] Assignee: G.D. Searle & Co., Chicago, Ill.

[21] Appl. No.: 08/835,162

[22] Filed: Apr. 4, 1997

Related U.S. Application Data

[63] Continuation-in-part of application No. PCT/US96/15774, Oct. 4, 1996.
[60] Provisional application No. 60/004,834, Oct. 5, 1995.
[51] Int. Cl.[7] .......................... C12N 15/12; A61K 48/00
[52] U.S. Cl. ..................... 424/93.2; 435/69.7; 435/455; 435/372; 530/351; 536/23.4; 935/10; 424/85.1; 424/85.2; 424/192.1; 424/198.1; 514/2; 514/12
[58] Field of Search ................. 435/69.5, 69.7, 435/455, 366, 372, 252.3; 530/351; 536/23.4, 23.1; 935/10; 424/85.1, 85.2, 192.1, 198.1, 93.2; 514/2, 12

[56] References Cited

U.S. PATENT DOCUMENTS

| | | |
|---|---|---|
| 4,810,643 | 3/1989 | Souza . |
| 4,877,729 | 10/1989 | Clark . |
| 4,959,455 | 9/1990 | Clark . |
| 4,999,291 | 3/1991 | Souza . |
| 5,399,345 | 3/1995 | Schumacher . |
| 5,567,611 | 10/1996 | Ralph et al. ................. 435/240.2 |
| 5,635,599 | 6/1997 | Pastan et al. ................. 530/351 |
| 5,677,149 | 10/1997 | Bauer et al. ................. 435/69.52 |
| 5,738,849 | 4/1998 | Bauer ................. 435/69.52 |
| 5,756,083 | 5/1998 | Elliott ................. 424/85.1 |
| 5,817,486 | 10/1998 | Bauer et al. ................. 435/69.52 |

FOREIGN PATENT DOCUMENTS

| | | |
|---|---|---|
| 0 225 579 | 6/1987 | European Pat. Off. . |
| 0 675 201 | 10/1995 | European Pat. Off. . |
| 0 783 003 | 10/1996 | European Pat. Off. . |
| WO90/12877 | 11/1990 | WIPO . |
| WO92/04455 | 3/1992 | WIPO . |
| WO92/06116 | 4/1992 | WIPO . |
| WO95/18858 | 7/1995 | WIPO . |
| WO95/21197 | 8/1995 | WIPO . |
| WO95/21254 | 8/1995 | WIPO . |
| WO95/27732 | 10/1995 | WIPO . |

OTHER PUBLICATIONS

D.L. Eaton et al., Blood 84(10) Suppl. Abstract 948, 1994.
Reeke et al., "Three–Dimensional Structure of Favin: Saccharide Binding–Cyclic Permutation in Leguminous Lectins", Science, Nov. 28, 1986, vol. 234 pp. 1108–1111.
Luger et al, "An 8–fold Ba Barrel Protein with Redundant Folding Possibilities", Protein Engineering, vol. 3. pp. 249–258.
Cunningham et al, "Favion versus concanavalin A: Circularly permuted amino acid sequences", Proc. Natl. Acad. Sci. USA, Jul. 1979, vol. 76, No. 7, pp. 3218–3222.
Protasova et al, Circularly permuted dihydrofolate reductase of E. coli has functional activity and a destabilized tertiary structure:, Protein Engineering, 1994, vol. 7, No. 11, pp. 1373–1777.
Zhang et al, "Circular Permutation of T4 Lysozyme", Biochemistry, vol. 32, No. 46, 1993.
Luger et al, "Correct Folding of Circularly Permuted Variants of a Ba Barrel Enzyme in Vivo", Science, vol. 243.
Hahn et al, "Native–like in vivo folding of a circularly permuted jellyroll protein shown by crystal structure analysis", Proc. Natl. Acad. Sci. USA, 1994, vol. 91, pp. 10417–10421.
Lin et al, "Rearranging the domains of pepsinogen", Protein Science, 1995, vol. 4, pp. 159–166.
Yang et al, "Aspartate transcarbamoylase containing circularly permuted catalytic polypeptide chains", Proc. Natl. Acad. Sci. USA, 1993, vol. 90, pp. 11980–11984.
Vignai et al, "Circular permutation within the coenzyme binding domain of the tetrameric glyceraldehyde–3–phosphate dehydrogenase from *Bacillus stearothermophilus*", Protein Science, 1995, vol. 4, pp. 994–1000.
Goldenberg et al, "Circular and Circularly Permuted Forms of Bovine Pancreatic Trypsin Inhibitor", J. Mol. Biol. 1983, vol. 165, pp. 407–413.
Hemperly et al, "Circular permutation of amino acid sequences among legume lectins", TIBS, 1983, pp. 100–102.
Kreitman et al, "Circularly permuted interleukin 4 retains proliferative and binding activity", Cytokine, 1995, vol. 7, No. 4, pp. 311–318.
Li et al, "Degradation of Ornithine Decarboxylase", Mol. and Cel. Biol. 1993, vol. 13, No. 4, pp. 2377–2383.
Ritco et al, "Is the Continuity of the Domains Required for the Correct Folding of a Two–Domain Protein?", Biochemistry, 1995, vol. 34, pp. 16543–16551.

(List continued on next page.)

*Primary Examiner*—Lorraine Spector
*Attorney, Agent, or Firm*—S. Christopher Bauer; Dennis A. Bennett

[57] ABSTRACT

Disclosed are novel multi-functional hematopoietic receptor agonist proteins, DNAs which encode the multi-functional hematopoietic receptor agonists proteins, methods of making the multi-functional hematopoietic receptor agonists proteins and methods of using the multi-functional hematopoietic receptor agonists proteins.

58 Claims, 4 Drawing Sheets

OTHER PUBLICATIONS

Garrett et al, "Are turns required for the folding of ribonuclease T1?", Protein Science, 1996, vol. 5., pp. 204–211.

Komar et al, "Kinetics of translation" FEBS Letters, 1995 vol. 376, pp. 195–198.

MacGregor et al, "A circularly permuted a–amylase–type", FEBS Letters, 1996, vol. 378, pp. 263–266.

Koebnik et al, "Membrane Assembly of Circulary Permuted Variants", JMB, 1995, vol. 250, pp. 617–626.

Buchwalder et al, "A fully active variant of Dihydrofolate Reductase with a circularly permuted sequence", Biochemistry, 1992, vol. 31, pp. 1621–1630.

Viguera et al, "The order of secondary structure elements", J. Mol. Biol., 1995, vol. 247, pp. 670–681.

Mullins et al. "Transposition of Protein Sequences: Circular Permutation of Ribonuclease T1", J. Am. Chem. Soc., 1994, vol. 116, pp. 5529–5533.

Horlick et al, "Permuteins of interleukin 1B—a simplified approach for the construction of permutated proteins having new termini", Protein Engineering, USA, 1992, vol. 5, pp. 427–431.

Kreitman et al, "A circularly permuted recombinant interleukin 4 toxin with increase activity", Proc. Natl. Acad. Sci. USA, 1993, vol. 91, pp. 6889–3893.

Watanabe et al, "Mutant Protein of Recombinant Human Granulocyte Colony–Stimulating Factor . . . ", Analytical Biochemistry, 1991, vol. 195 pp. 38–44.

FIG.4
I. Construct tandemly-duplicated template
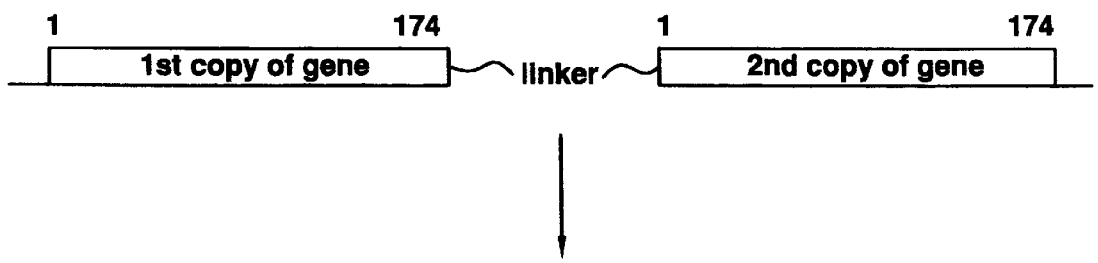
II. PCR-amplify tandemly-duplicated template
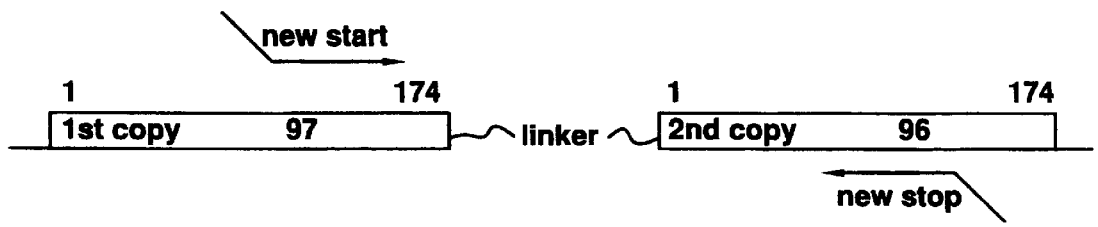

SEQUENCE LISTING (1) GENERAL INFORMATION:

(iii) NUMBER OF SEQUENCES: 313

(2) INFORMATION FOR SEQ ID NO:1:

(i) SEQUENCE CHARACTERISTICS:
      (A) LENGTH: 174 amino acids
      (B) TYPE: amino acid
      (C) STRANDEDNESS: unknown
      (D) TOPOLOGY: unknown (ii) MOLECULE TYPE: protein (ix) FEATURE:
      (A) NAME/KEY: Modified-site
      (B) LOCATION: 1
      (D) OTHER INFORMATION: /note= "Xaa at position 1 is Thr,
          Ser, Arg, Tyr or Gly;"

(ix) FEATURE:
      (A) NAME/KEY: Modified-site
      (B) LOCATION: 2
      (D) OTHER INFORMATION: /note= "Xaa at position 2 is Pro or
          Leu;"

(ix) FEATURE:
      (A) NAME/KEY: Modified-site
      (B) LOCATION: 3
      (D) OTHER INFORMATION: /note= "Xaa at position 3 is Leu,
          Arg, Tyr or Ser;"

(ix) FEATURE:
      (A) NAME/KEY: Modified-site
      (B) LOCATION: 13
      (D) OTHER INFORMATION: /note= "Xaa at position 13 is Phe,
          Ser, His, Thr or Pro;"

(ix) FEATURE:
      (A) NAME/KEY: Modified-site
      (B) LOCATION: 16
      (D) OTHER INFORMATION: /note= "Xaa at position 16 is Lys,
          Pro, Ser, thr or His;"

(ix) FEATURE:
      (A) NAME/KEY: Modified-site
      (B) LOCATION: 17
      (D) OTHER INFORMATION: /note= "Xaa at position 17 is Cys,
          Ser, Gly, Ala, Ile, Tyr or Arg;"

(ix) FEATURE:
      (A) NAME/KEY: Modified-site
      (B) LOCATION: 18
      (D) OTHER INFORMATION: /note= "Xaa at position 18 is Leu,
          Thr, Pro, His, Ile or Cys;"

(ix) FEATURE:
      (A) NAME/KEY: Modified-site
      (B) LOCATION: 22
      (D) OTHER INFORMATION: /note= "Xaa at position 22 is Arg,
          Tyr, Ser, Thr or Ala;"

(ix) FEATURE:
      (A) NAME/KEY: Modified-site

```
      (B) LOCATION: 24
      (D) OTHER INFORMATION: /note= "Xaa at position 24 is Ile,
          Pro, Tyr or Leu;"

(ix) FEATURE:
      (A) NAME/KEY: Modified-site
      (B) LOCATION: 27
      (D) OTHER INFORMATION: /note= "Xaa at position 27 is Asp,
          or Gly;"

(ix) FEATURE:
      (A) NAME/KEY: Modified-site
      (B) LOCATION: 30
      (D) OTHER INFORMATION: /note= "Xaa at position 30 is Ala,
          Ile, Leu or Gly;"

(ix) FEATURE:
      (A) NAME/KEY: Modified-site
      (B) LOCATION: 34
      (D) OTHER INFORMATION: /note= "Xaa at position 34 is Lys
          or Ser;"

(ix) FEATURE:
      (A) NAME/KEY: Modified-site
      (B) LOCATION: 36
      (D) OTHER INFORMATION: /note= "Xaa at position 36 is Cys
          or Ser;"

(ix) FEATURE:
      (A) NAME/KEY: Modified-site
      (B) LOCATION: 42
      (D) OTHER INFORMATION: /note= "Xaa at position 42 is Cys
          or Ser;"

(ix) FEATURE:
      (A) NAME/KEY: Modified-site
      (B) LOCATION: 43
      (D) OTHER INFORMATION: /note= "Xaa at position 43 is His,
          Thr, Gly, Val, Lys, Trp, Ala, Arg, Cys, or Leu;"

(ix) FEATURE:
      (A) NAME/KEY: Modified-site
      (B) LOCATION: 44
      (D) OTHER INFORMATION: /note= "Xaa at position 44 is Pro,
          Gly, Arg, Asp, Val, Ala, His, Trp, Gln, or Thr;"

(ix) FEATURE:
      (A) NAME/KEY: Modified-site
      (B) LOCATION: 46
      (D) OTHER INFORMATION: /note= "Xaa at position 46 is Glu,
          Arg, Phe, Arg, Ile or Ala;"

(ix) FEATURE:
      (A) NAME/KEY: Modified-site
      (B) LOCATION: 47
      (D) OTHER INFORMATION: /note= "Xaa at position 47 is Leu
          or Thr;"

(ix) FEATURE:
      (A) NAME/KEY: Modified-site
      (B) LOCATION: 49
      (D) OTHER INFORMATION: /note= "Xaa at position 49 is Leu,
          Phe, Arg or Ser;"

(ix) FEATURE:
      (A) NAME/KEY: Modified-site
      (B) LOCATION: 50
      (D) OTHER INFORMATION: /note= "Xaa at position 50 is Leu,
          Ile, His, Pro or Tyr;"

(ix) FEATURE:
      (A) NAME/KEY: Modified-site
      (B) LOCATION: 54
      (D) OTHER INFORMATION: /note= "Xaa at position 54 is Leu
          or His;"

(ix) FEATURE:
      (A) NAME/KEY: Modified-site
      (B) LOCATION: 64
```

(D) OTHER INFORMATION: /note= "Xaa at position 64 is Cys
                or Ser;"

(ix) FEATURE:
            (A) NAME/KEY: Modified-site
            (B) LOCATION: 67
            (D) OTHER INFORMATION: /note= "Xaa at position 67 is Gln,
                Lys, Leu or Cys;"

(ix) FEATURE:
            (A) NAME/KEY: Modified-site
            (B) LOCATION: 70
            (D) OTHER INFORMATION: /note= "Xaa at position 70 is Gln,
                Pro, Leu, Arg or Ser;"

(ix) FEATURE:
            (A) NAME/KEY: Modified-site
            (B) LOCATION: 74
            (D) OTHER INFORMATION: /note= "Xaa at position 74 is Cys
                or Ser;"

(ix) FEATURE:
            (A) NAME/KEY: Modified-site
            (B) LOCATION: 104
            (D) OTHER INFORMATION: /note= "Xaa at position 104 is Asp,
                Gly or Val;"

(ix) FEATURE:
            (A) NAME/KEY: Modified-site
            (B) LOCATION: 108
            (D) OTHER INFORMATION: /note= "Xaa at position 108 is Leu,
                Ala, Val, Arg, Trp, Gln or Gly;"

(ix) FEATURE:
            (A) NAME/KEY: Modified-site
            (B) LOCATION: 115
            (D) OTHER INFORMATION: /note= "Xaa at position 115 is Thr,
                His, Leu or Ala;"

(ix) FEATURE:
            (A) NAME/KEY: Modified-site
            (B) LOCATION: 120
            (D) OTHER INFORMATION: /note= "Xaa at position 120 is Gln,
                Gly, Arg, Lys or His"

(ix) FEATURE:
            (A) NAME/KEY: Modified-site
            (B) LOCATION: 123
            (D) OTHER INFORMATION: /note= "Xaa at position 123 is Glu,
                Arg, Phe or Thr"

(ix) FEATURE:
            (A) NAME/KEY: Modified-site
            (B) LOCATION: 144
            (D) OTHER INFORMATION: /note= "Xaa at position 144 is Phe,
                His, Arg, Pro, Leu, Gln or Glu;"

(ix) FEATURE:
            (A) NAME/KEY: Modified-site
            (B) LOCATION: 146
            (D) OTHER INFORMATION: /note= "Xaa at position146 is Arg
                or Gln;"

(ix) FEATURE:
            (A) NAME/KEY: Modified-site
            (B) LOCATION: 147
            (D) OTHER INFORMATION: /note= "Xaa ap position 147 is Arg
                or Gln;"

(ix) FEATURE:
            (A) NAME/KEY: Modified-site
            (B) LOCATION: 156
            (D) OTHER INFORMATION: /note= "Xaa at position 156 is His,
                Gly or Ser;"

(ix) FEATURE:
            (A) NAME/KEY: Modified-site
            (B) LOCATION: 159
            (D) OTHER INFORMATION: /note= "Xaa at position 159 is Ser, Arg, Thr, Tyr, Val or Gly;"

(ix) FEATURE:
        (A) NAME/KEY: Modified-site
        (B) LOCATION: 162
        (D) OTHER INFORMATION: /note= "Xaa at position 162 is Glu,
            Leu, Gly or Trp;"

(ix) FEATURE:
        (A) NAME/KEY: Modified-site
        (B) LOCATION: 163
        (D) OTHER INFORMATION: /note= "Xaa at position 163 is Val,
            Gly, Arg or Ala;"

(ix) FEATURE:
        (A) NAME/KEY: Modified-site
        (B) LOCATION: 169
        (D) OTHER INFORMATION: /note= "Xaa at position 169 is Arg,
            Ser, Leu, Arg or Cys;"

(ix) FEATURE:
        (A) NAME/KEY: Modified-site
        (B) LOCATION: 170
        (D) OTHER INFORMATION: /note= "Xaa at position 170 is His,
            Arg or Ser;"

(xi) SEQUENCE DESCRIPTION: SEQ ID NO:1:

Xaa Xaa Xaa Gly Pro Ala Ser Ser Leu Pro Gln Ser Xaa Leu Leu Xaa
1               5                   10                  15

Xaa Xaa Glu Gln Val Xaa Lys Xaa Gln Gly Xaa Gly Ala Xaa Leu Gln
            20                  25                  30

Glu Xaa Leu Xaa Ala Thr Tyr Lys Leu Xaa Xaa Xaa Glu Xaa Xaa Val
        35                  40                  45

Xaa Xaa Gly His Ser Xaa Gly Ile Pro Trp Ala Pro Leu Ser Ser Xaa
50                  55                  60

Pro Ser Xaa Ala Leu Xaa Leu Ala Gly Xaa Leu Ser Gln Leu His Ser
65                  70                  75                  80

Gly Leu Phe Leu Tyr Gln Gly Leu Leu Gln Ala Leu Glu Gly Ile Ser
            85                  90                  95

Pro Glu Leu Gly Pro Thr Leu Xaa Thr Leu Gln Xaa Asp Val Ala Asp
            100                 105                 110

Phe Ala Xaa Thr Ile Trp Gln Gln Met Glu Xaa Xaa Gly Met Ala Pro
            115                 120                 125

Ala Leu Gln Pro Thr Gln Gly Ala Met Pro Ala Phe Ala Ser Ala Xaa
            130                 135                 140

Gln Xaa Xaa Ala Gly Gly Val Leu Val Ala Ser Xaa Leu Gln Xaa Phe
145                 150                 155                 160

Leu Xaa Xaa Ser Tyr Arg Val Leu Xaa Xaa Leu Ala Gln Pro
                165                 170

(2) INFORMATION FOR SEQ ID NO:2:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 17
        (D) OTHER INFORMATION: /note= "Xaa at position 17 is Ser,
            Lys, Gly, Asp, Met, Gln, or Arg;"

(ix) FEATURE:

```
            (A) NAME/KEY: Modified-site
            (B) LOCATION: 18
            (D) OTHER INFORMATION: /note= "Xaa at position 18 is Asn,
                His, Leu, Ile, Phe, Arg, or Gln;"

(ix) FEATURE:
            (A) NAME/KEY: Modified-site
            (B) LOCATION: 19
            (D) OTHER INFORMATION: /note= "Xaa at position 19 is Met,
                Phe, Ile, Arg, Gly, Ala, or Cys;"

(ix) FEATURE:
            (A) NAME/KEY: Modified-site
            (B) LOCATION: 20
            (D) OTHER INFORMATION: /note= "Xaa at position 20 is Ile,
                Cys, Gln, Glu, Arg, Pro, or Ala;"

(ix) FEATURE:
            (A) NAME/KEY: Modified-site
            (B) LOCATION: 21
            (D) OTHER INFORMATION: /note= "Xaa at position 21 is Asp,
                Phe, Lys, Arg, Ala, Gly, Glu, Gln, Asn, Thr, Ser or Val;"

(ix) FEATURE:
            (A) NAME/KEY: Modified-site
            (B) LOCATION: 22
            (D) OTHER INFORMATION: /note= "Xaa at position 22 is Glu,
                Trp, Pro, Ser, Ala, His, Asp, Asn, Gln, Leu, Val or Gly;"

(ix) FEATURE:
            (A) NAME/KEY: Modified-site
            (B) LOCATION: 23
            (D) OTHER INFORMATION: /note= "Xaa at position 23 is Ile,
                Val, Ala, Gly, Trp, Lys, Phe, Leu, Ser, or Arg;"

(ix) FEATURE:
            (A) NAME/KEY: Modified-site
            (B) LOCATION: 24
            (D) OTHER INFORMATION: /note= "Xaa at position 24 is Ile,
                Gly, Val, Arg, Ser, Phe, Leu;"

(ix) FEATURE:
            (A) NAME/KEY: Modified-site
            (B) LOCATION: 25
            (D) OTHER INFORMATION: /note= "Xaa at position 25 is Thr,
                His, Gly, Gln, Arg, Pro, or Ala;"

(ix) FEATURE:
            (A) NAME/KEY: Modified-site
            (B) LOCATION: 26
            (D) OTHER INFORMATION: /note= "Xaa at position 26 is His,
                Thr, Phe, Gly, Arg, Ala, Trp;"

(ix) FEATURE:
            (A) NAME/KEY: Modified-site
            (B) LOCATION: 27
            (D) OTHER INFORMATION: /note= "Xaa at position 27 is Leu,
                Gly, Arg, Thr, Ser, or Ala;"

(ix) FEATURE:
            (A) NAME/KEY: Modified-site
            (B) LOCATION: 28
            (D) OTHER INFORMATION: /note= "Xaa at position 28 is Lys,
                Arg, Leu, Gln, Gly, Pro, Val or Trp;"

(ix) FEATURE:
            (A) NAME/KEY: Modified-site
            (B) LOCATION: 29
            (D) OTHER INFORMATION: /note= "Xaa at position 29 is Gln,
                Asn, Leu, Pro, Arg, or Val;"

(ix) FEATURE:
            (A) NAME/KEY: Modified-site
            (B) LOCATION: 30
            (D) OTHER INFORMATION: /note= "Xaa at position 30 is Pro,
                His, Thr, Gly, Asp, Gln, Ser, Leu, or L..."

(ix) FEATURE:
            (A) NAME/KEY: Modified-site
```

```
          (B) LOCATION: 31
          (D) OTHER INFORMATION: /note= "Xaa at position 31 is Pro,
              Asp, Gly, Ala, Arg, Leu, or Gln;"

(ix) FEATURE:
          (A) NAME/KEY: Modified-site
          (B) LOCATION: 32
          (D) OTHER INFORMATION: /note= "Xaa at position 32 is Leu,
              Val, Arg, Gln, Asn, Gly, Ala, or Glu;"

(ix) FEATURE:
          (A) NAME/KEY: Modified-site
          (B) LOCATION: 33
          (D) OTHER INFORMATION: /note= "Xaa at position 33 is Pro,
              Leu, Gln, Ala, Thr, or Glu;"

(ix) FEATURE:
          (A) NAME/KEY: Modified-site
          (B) LOCATION: 34
          (D) OTHER INFORMATION: /note= "Xaa at position 34 is Leu,
              Val, Gly, Ser, Lys, Glu, Gln, Thr, Arg, Ala, Phe, Ile or Met;"

(ix) FEATURE:
          (A) NAME/KEY: Modified-site
          (B) LOCATION: 35
          (D) OTHER INFORMATION: /note= "Xaa at position 35 is Leu,
              Ala, Gly, Asn, Pro, Gln, or Val;"

(ix) FEATURE:
          (A) NAME/KEY: Modified-site
          (B) LOCATION: 36
          (D) OTHER INFORMATION: /note= "Xaa at position 36 is Asp,
              Leu, or Val;"

(ix) FEATURE:
          (A) NAME/KEY: Modified-site
          (B) LOCATION: 37
          (D) OTHER INFORMATION: /note= "Xaa at position 37 is Phe,
              Ser, Pro, Trp, or Ile;"

(ix) FEATURE:
          (A) NAME/KEY: Modified-site
          (B) LOCATION: 38
          (D) OTHER INFORMATION: /note= "Xaa at position 38 is Asn,
              or Ala;"

(ix) FEATURE:
          (A) NAME/KEY: Modified-site
          (B) LOCATION: 40
          (D) OTHER INFORMATION: /note= "Xaa at position 40 is Leu,
              Trp, or Arg;"

(ix) FEATURE:
          (A) NAME/KEY: Modified-site
          (B) LOCATION: 41
          (D) OTHER INFORMATION: /note= "Xaa at position 41 is Asn,
              Cys, Arg, Leu, His, Met, or pro;"

(ix) FEATURE:
          (A) NAME/KEY: Modified-site
          (B) LOCATION: 42
          (D) OTHER INFORMATION: /note= "Xaa at position 42 is Gly,
              Asp, Ser, Cys, Asn, Lys, Thr, Leu, Val, Glu, Phe, Tyr, Ile, Met
              or Ala;"

(ix) FEATURE:
          (A) NAME/KEY: Modified-site
          (B) LOCATION: 43
          (D) OTHER INFORMATION: /note= "Xaa at position 43 is Glu,
              Asn, Tyr, Leu, Phe, Asp, Ala, Cys, Gln, Arg, Thr, Gly, or Ser;"

(ix) FEATURE:
          (A) NAME/KEY: Modified-site
          (B) LOCATION: 44
          (D) OTHER INFORMATION: /note= "Xaa at position 44 is Asp,
              Ser, Leu, Arg, Lys, Thr, Met, Trp, Glu, Asn, Gln, Ala or Pro;"

(ix) FEATURE:
          (A) NAME/KEY: Modified-site
```

-continued

```
          (B) LOCATION: 45
          (D) OTHER INFORMATION: /note= "Xaa at position 45 is Gln,
              Pro, Phe, Val, Met, Leu, Thr, Lys, Trp, Asp, Asn, Arg, Ser, Ala,
              Ile, Glu or His;"

(ix) FEATURE:
          (A) NAME/KEY: Modified-site
          (B) LOCATION: 46
          (D) OTHER INFORMATION: /note= "Xaa at position 46 is Asp,
              Phe, Ser, Thr, Cys, Glu, Asn, Gln, Lys, His, Ala, Tyr, Ile, Val
              or Gly;"

(ix) FEATURE:
          (A) NAME/KEY: Modified-site
          (B) LOCATION: 47
          (D) OTHER INFORMATION: /note= "Xaa at position 47 is Ile,
              Gly, Val, Ser, Arg, Pro, or His;"

(ix) FEATURE:
          (A) NAME/KEY: Modified-site
          (B) LOCATION: 48
          (D) OTHER INFORMATION: /note= "Xaa at position 48 is Leu,
              Ser, Cys, Arg, Ile, His, Phe, Glu, Lys, Thr, Ala, Met, Val or
              Asn;"

(ix) FEATURE:
          (A) NAME/KEY: Modified-site
          (B) LOCATION: 49
          (D) OTHER INFORMATION: /note= "Xaa at position 49 is Met,
              Arg, Ala, Gly, Pro, Asn, His, or Asp;"

(ix) FEATURE:
          (A) NAME/KEY: Modified-site
          (B) LOCATION: 50
          (D) OTHER INFORMATION: /note= "Xaa at position 50 is Glu,
              Leu, Thr, Asp, Tyr, Lys, Asn, Ser, Ala, Ile, Val, His, Phe, Met
              or Gln;"

(ix) FEATURE:
          (A) NAME/KEY: Modified-site
          (B) LOCATION: 51
          (D) OTHER INFORMATION: /note= "Xaa at position 51 is Asn,
              Arg, Met, Pro, Ser, Thr, or his;"

(ix) FEATURE:
          (A) NAME/KEY: Modified-site
          (B) LOCATION: 52
          (D) OTHER INFORMATION: /note= "Xaa at position 52 is Asn,
              His, Arg, Leu, Gly, Ser, or Thr;"

(ix) FEATURE:
          (A) NAME/KEY: Modified-site
          (B) LOCATION: 53
          (D) OTHER INFORMATION: /note= "Xaa at position 53 is Leu,
              Thr, Ala, Gly, Glu, Pro, Lys, Ser, or M..."

(ix) FEATURE:
          (A) NAME/KEY: Modified-site
          (B) LOCATION: 54
          (D) OTHER INFORMATION: /note= "Xaa at position 54 is Arg,
              Asp, Ile, Ser, Val, Thr, Gln, Asn, Lys, His, Ala or Leu;"

(ix) FEATURE:
          (A) NAME/KEY: Modified-site
          (B) LOCATION: 55
          (D) OTHER INFORMATION: /note= "Xaa at position 55 is Arg,
              Thr, Val, Ser, Leu, or Gly;"

(ix) FEATURE:
          (A) NAME/KEY: Modified-site
          (B) LOCATION: 56
          (D) OTHER INFORMATION: /note= "Xaa at position 56 is Pro,
              Gly, Cys, Ser, Gln, Glu, Arg, His, Thr, Ala, Tyr, Phe, Leu, Val
              or Lys;"

(ix) FEATURE:
          (A) NAME/KEY: Modified-site
          (B) LOCATION: 57
          (D) OTHER INFORMATION: /note= "Xaa at position 57 is Asn
``` or Gly;"

(ix) FEATURE:
    (A) NAME/KEY: Modified-site
    (B) LOCATION: 58
    (D) OTHER INFORMATION: /note= "Xaa at position 58 is Leu,
        Ser, Asp, Arg, Gln, Val, or Cys;"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, Pro, or Arg;"

(ix) FEATURE:
    (A) NAME/KEY: Modified-site
    (B) LOCATION: 60
    (D) OTHER INFORMATION: /note= "Xaa at position 60 is Ala,
        Ser, Pro, Tyr, Asn, or Thr;"

(ix) FEATURE:
    (A) NAME/KEY: Modified-site
    (B) LOCATION: 61
    (D) OTHER INFORMATION: /note= "Xaa at position 61 is Phe,
        Asn, Glu, Pro, Lys, Arg, or Ser;"

(ix) FEATURE:
    (A) NAME/KEY: Modified-site
    (B) LOCATION: 62
    (D) OTHER INFORMATION: /note= "Xaa at position 62 is Asn,
        His, Val, Arg, Pro, Thr, Asp, or Ile;"

(ix) FEATURE:
    (A) NAME/KEY: Modified-site
    (B) LOCATION: 63
    (D) OTHER INFORMATION: /note= "Xaa at position 63 is Arg,
        Tyr, Trp, Lys, Ser, His, Pro, or Val;"

(ix) FEATURE:
    (A) NAME/KEY: Modified-site
    (B) LOCATION: 64
    (D) OTHER INFORMATION: /note= "Xaa at position 64 is Ala,
        Asn, Pro, Ser, or Lys;"

(ix) FEATURE:
    (A) NAME/KEY: Modified-site
    (B) LOCATION: 65
    (D) OTHER INFORMATION: /note= "Xaa at position 65 is Val,
        Thr, Pro, His, Leu, Phe, or Ser;"

(ix) FEATURE:
    (A) NAME/KEY: Modified-site
    (B) LOCATION: 66
    (D) OTHER INFORMATION: /note= "Xaa at position 66 is Lys,
        Ile, Arg, Val, Asn, Glu, or Ser;"

(ix) FEATURE:
    (A) NAME/KEY: Modified-site
    (B) LOCATION: 67
    (D) OTHER INFORMATION: /note= "Xaa at postion 67 is Ser,
        Ala, Phe, Val, Gly, Asn, Ile, Pro, or His;"

(ix) FEATURE:
    (A) NAME/KEY: Modified-site
    (B) LOCATION: 68
    (D) OTHER INFORMATION: /note= "Xaa at position 68 is Leu,
        Val, Trp, Ser, Ile, Phe, Thr, or His;"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, Trp, Gly, or L..."

(ix) FEATURE:
    (A) NAME/KEY: Modified-site
    (B) LOCATION: 70
    (D) OTHER INFORMATION: /note= "Xaa at position 70 is Asn,
        Leu, Val, Trp, pro, or Ala;"

```
(ix) FEATURE:
    (A) NAME/KEY: Modified-site
    (B) LOCATION: 71
    (D) OTHER INFORMATION: /note= "Xaa at position 71 is Ala,
        Met, Leu, Pro, Arg, Glu, Thr, Gln, Trp, or Asn;"

(ix) FEATURE:
    (A) NAME/KEY: Modified-site
    (B) LOCATION: 72
    (D) OTHER INFORMATION: /note= "Xaa at position 72 is Ser,
        Glu, Met, Ala, His, Asn, Arg, or Asp;"

(ix) FEATURE:
    (A) NAME/KEY: Modified-site
    (B) LOCATION: 73
    (D) OTHER INFORMATION: /note= "Xaa at position 73 is Ala,
        Glu, Asp, Leu, Ser, Gly, Thr, or Arg;"

(ix) FEATURE:
    (A) NAME/KEY: Modified-site
    (B) LOCATION: 74
    (D) OTHER INFORMATION: /note= "Xaa at position 74 is Ile,
        Met, Thr, Pro, Arg, Gly, Ala;"

(ix) FEATURE:
    (A) NAME/KEY: Modified-site
    (B) LOCATION: 75
    (D) OTHER INFORMATION: /note= "Xaa at position 75 is Glu,
        Lys, Gly, Asp, Pro, Trp, Arg, Ser, Gln, or Leu;"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Trp, Glu, Pro, Gly, or A..."

(ix) FEATURE:
    (A) NAME/KEY: Modified-site
    (B) LOCATION: 77
    (D) OTHER INFORMATION: /note= "Xaa at position 77 is Ile,
        Ser, Arg, Thr, or Leu;"

(ix) FEATURE:
    (A) NAME/KEY: Modified-site
    (B) LOCATION: 78
    (D) OTHER INFORMATION: /note= "Xaa at position 78 is Leu,
        Ala, Ser, Glu, Phe, Gly, or Arg;"

(ix) FEATURE:
    (A) NAME/KEY: Modified-site
    (B) LOCATION: 79
    (D) OTHER INFORMATION: /note= "Xaa at position 79 is Lys,
        Thr, Asn, Met, Arg, Ile, Gly, or Asp;"

(ix) FEATURE:
    (A) NAME/KEY: Modified-site
    (B) LOCATION: 80
    (D) OTHER INFORMATION: /note= "Xaa position at 80 is Asn,
        Trp, Val, Gly, Thr, Leu, Glu, or Arg;"

(ix) FEATURE:
    (A) NAME/KEY: Modified-site
    (B) LOCATION: 81
    (D) OTHER INFORMATION: /note= "Xaa at position 81 is Leu,
        Gln, Gly, Ala, Trp, Arg, Val, or Lys;"

(ix) FEATURE:
    (A) NAME/KEY: Modified-site
    (B) LOCATION: 82
    (D) OTHER INFORMATION: /note= "Xaa at position 82 is Leu,
        Gln, Lys, Trp, Arg, Asp, Glu, Asn, His, Thr, Ser, Ala, Tyr, Phe,
        Ile, Met or Val;"

(ix) FEATURE:
    (A) NAME/KEY: Modified-site
    (B) LOCATION: 83
    (D) OTHER INFORMATION: /note= "Xaa at position 83 is Pro,
        Ala, Thr, Trp, Arg, or Met;"
```

-continued

```
(ix) FEATURE:
    (A) NAME/KEY: Modified-site
    (B) LOCATION: 84
    (D) OTHER INFORMATION: /note= "Xaa at position 84 is Cys,
        Glu, Gly, Arg, Met, or Val;"

(ix) FEATURE:
    (A) NAME/KEY: Modified-site
    (B) LOCATION: 85
    (D) OTHER INFORMATION: /note= "Xaa at position 85 is Leu,
        Asn, Val, or Gln;"

(ix) FEATURE:
    (A) NAME/KEY: Modified-site
    (B) LOCATION: 86
    (D) OTHER INFORMATION: /note= "Xaa at position 86 is Pro,
        Cys, Arg, Ala, or Lys;"

(ix) FEATURE:
    (A) NAME/KEY: Modified-site
    (B) LOCATION: 87
    (D) OTHER INFORMATION: /note= "Xaa at position 87 is Leu,
        Ser, Trp, or Gly;"

(ix) FEATURE:
    (A) NAME/KEY: Modified-site
    (B) LOCATION: 88
    (D) OTHER INFORMATION: /note= "Xaa at position 88 is Ala,
        Lys, Arg, Val, or Trp;"

(ix) FEATURE:
    (A) NAME/KEY: Modified-site
    (B) LOCATION: 89
    (D) OTHER INFORMATION: /note= "Xaa at position 89 is Thr,
        Asp, Cys, Leu, Val, Glu, His, Asn, or S..."

(ix) FEATURE:
    (A) NAME/KEY: Modified-site
    (B) LOCATION: 90
    (D) OTHER INFORMATION: /note= "Xaa at position 90 is Ala,
        Pro, Ser, Thr, Gly, Asp, Ile, or ,Met;"

(ix) FEATURE:
    (A) NAME/KEY: Modified-site
    (B) LOCATION: 91
    (D) OTHER INFORMATION: /note= "Xaa at position 91 is Ala,
        Pro, Ser, Thr, Phe, Leu, Asp, or His;"

(ix) FEATURE:
    (A) NAME/KEY: Modified-site
    (B) LOCATION: 92
    (D) OTHER INFORMATION: /note= "Xaa at position 92 is Pro,
        Phe, Arg, Ser, Lys, His, Ala, Gly, Ile or Leu;"

(ix) FEATURE:
    (A) NAME/KEY: Modified-site
    (B) LOCATION: 93
    (D) OTHER INFORMATION: /note= "Xaa at position 93 is Thr,
        Asp, Ser, Asn, Pro, Ala, Leu, or Arg;"

(ix) FEATURE:
    (A) NAME/KEY: Modified-site
    (B) LOCATION: 94
    (D) OTHER INFORMATION: /note= "Xaa at position 94 is Arg,
        Ile, Ser, Glu, Leu, Val, Gln, Lys, His, Ala, or Pro;"

(ix) FEATURE:
    (A) NAME/KEY: Modified-site
    (B) LOCATION: 95
    (D) OTHER INFORMATION: /note= "Xaa at position 95 is His,
        Gln, Pro, Arg, Val, Leu, Gly, Thr, Asn, Lys, Ser, Ala, Trp, Phe,
        Ile, or Tyr;"

(ix) FEATURE:
    (A) NAME/KEY: Modified-site
    (B) LOCATION: 96
    (D) OTHER INFORMATION: /note= "Xaa at position 96 is Pro,
        Lys, Tyr, Gly, Ile, or Thr;"
```

```
       (ix) FEATURE:
             (A) NAME/KEY: Modified-site
             (B) LOCATION: 97
             (D) OTHER INFORMATION: /note= "Xaa at position 97 is Ile,
                 Val, Lys, Ala, or Asn;"

(ix) FEATURE:
             (A) NAME/KEY: Modified-site
             (B) LOCATION: 98
             (D) OTHER INFORMATION: /note= "Xaa at position 98 is His,
                 Ile, Asn, Leu, Asp, Ala, Thr, Glu, Gln, Ser, Phe, Met, Val, Lys,
                 Arg, Tyr, or Pro;"

(ix) FEATURE:
             (A) NAME/KEY: Modified-site
             (B) LOCATION: 99
             (D) OTHER INFORMATION: /note= "Xaa at position 99 is Ile,
                 Leu, Arg, Asp, Val, Pro, Gln, Gly, Ser, Phe, or His;"

(ix) FEATURE:
             (A) NAME/KEY: Modified-site
             (B) LOCATION: 100
             (D) OTHER INFORMATION: /note= "Xaa at position 100 is Lys,
                 Tyr, Leu, His, Arg, Ile, Ser, Gln, or ..."

(ix) FEATURE:
             (A) NAME/KEY: Modified-site
             (B) LOCATION: 101
             (D) OTHER INFORMATION: /note= "Xaa at position is Asp,
                 Pro, Met, Lys, His, Thr, Val, Tyr, Glu, Asn, Ser, Ala, Gly, Ile,
                 Leu, or Gln;"

(ix) FEATURE:
             (A) NAME/KEY: Modified-site
             (B) LOCATION: 102
             (D) OTHER INFORMATION: /note= "Xaa at position 102 is Gly,
                 Leu, Glu, Lys, Ser, Tyr, or Pro;"

(ix) FEATURE:
             (A) NAME/KEY: Modified-site
             (B) LOCATION: 103
             (D) OTHER INFORMATION: /note= "Xaa at position 103 is Asp,
                 or Ser;"

(ix) FEATURE:
             (A) NAME/KEY: Modified-site
             (B) LOCATION: 104
             (D) OTHER INFORMATION: /note= "Xaa at position 104 is Trp,
                 Val, Cys, Tyr, Thr, Met, Pro, Leu, Gln, Lys, Ala, Phe, or Gly;"

(ix) FEATURE:
             (A) NAME/KEY: Modified-site
             (B) LOCATION: 105
             (D) OTHER INFORMATION: /note= "Xaa at position 105 is Asn,
                 Pro, Ala, Phe, Ser, Trp, Gln, Tyr, Leu, Lys, Ile, Asp, or His;"

(ix) FEATURE:
             (A) NAME/KEY: Modified-site
             (B) LOCATION: 106
             (D) OTHER INFORMATION: /note= "Xaa at position 106 is Glu,
                 Ser, Ala, Lys, Thr, Ile, Gly, or Pro;"

(ix) FEATURE:
             (A) NAME/KEY: Modified-site
             (B) LOCATION: 108
             (D) OTHER INFORMATION: /note= "Xaa at position 108 is Arg,
                 Lys, Asp, Leu, Thr, Ile, Gln, His, Ser, Ala or Pro;"

(ix) FEATURE:
             (A) NAME/KEY: Modified-site
             (B) LOCATION: 109
             (D) OTHER INFORMATION: /note= "Xaa at position 109 is Arg,
                 Thr, Pro, Glu, Tyr, Leu, Ser, or Gly;"

(ix) FEATURE:
             (A) NAME/KEY: Modified-site
             (B) LOCATION: 110
             (D) OTHER INFORMATION: /note= "Xaa at position 110 is Lys,
```

Ala, Asn, Thr, Leu, Arg, Gln, His, Glu, Ser, or Trp;"

(ix) FEATURE:
    (A) NAME/KEY: Modified-site
    (B) LOCATION: 111
    (D) OTHER INFORMATION: /note= "Xaa at position 111 is Leu,
        Ile, Arg, Asp, or Met;"

(ix) FEATURE:
    (A) NAME/KEY: Modified-site
    (B) LOCATION: 112
    (D) OTHER INFORMATION: /note= "Xaa at position 112 is Thr,
        Val, Gln, Tyr, Glu, His, Ser, or Phe;"

(ix) FEATURE:
    (A) NAME/KEY: Modified-site
    (B) LOCATION: 113
    (D) OTHER INFORMATION: /note= "Xaa at position 113 is Phe,
        Ser, Cys, His, Gly, Trp, Tyr, Asp, Lys, Leu, Ile, Val or Asn;"

(ix) FEATURE:
    (A) NAME/KEY: Modified-site
    (B) LOCATION: 114
    (D) OTHER INFORMATION: /note= "Xaa at position 114 is Tyr,
        Cys, His, Ser, Trp, Arg, or Leu;"

(ix) FEATURE:
    (A) NAME/KEY: Modified-site
    (B) LOCATION: 115
    (D) OTHER INFORMATION: /note= "Xaa at position 115 is Leu,
        Asn, Val, Pro, Arg, Ala, His, Thr, Trp, or Met;"

(ix) FEATURE:
    (A) NAME/KEY: Modified-site
    (B) LOCATION: 116
    (D) OTHER INFORMATION: /note= "Xaa at position 116 is Lys,
        Leu, Pro, Thr, Met, Asp, Val, Glu, Arg, Trp, Ser, Asn, His, Ala,
        Tyr, Phe, Gln, or Ile;"

(ix) FEATURE:
    (A) NAME/KEY: Modified-site
    (B) LOCATION: 117
    (D) OTHER INFORMATION: /note= "Xaa at position 117 is Thr,
        Ser, Asn, Ile, Trp, Lys, or Pro;"

(ix) FEATURE:
    (A) NAME/KEY: Modified-site
    (B) LOCATION: 118
    (D) OTHER INFORMATION: /note= "Xaa at position 118 is Leu,
        Ser, Pro, Ala, Glu, Cys, Asp, or Tyr;"

(ix) FEATURE:
    (A) NAME/KEY: Modified-site
    (B) LOCATION: 119
    (D) OTHER INFORMATION: /note= "Xaa at position 119 is Glu,
        Ser, Lys, Pro, leu, Thr, Tyr, or Arg;"

(ix) FEATURE:
    (A) NAME/KEY: Modified-site
    (B) LOCATION: 120
    (D) OTHER INFORMATION: /note= "Xaa at position 120 is Asn,
        Ala, Pro, Leu, His, Val, or Gln;"

(ix) FEATURE:
    (A) NAME/KEY: Modified-site
    (B) LOCATION: 121
    (D) OTHER INFORMATION: /note= "Xaa at position 121 is Ala,
        Ser, Ile, Asn, Pro, Lys, Asp, or Gly;"

(ix) FEATURE:
    (A) NAME/KEY: Modified-site
    (B) LOCATION: 122
    (D) OTHER INFORMATION: /note= "Xaa at position 122 is Gln,
        Ser, Met, Trp, Arg, Phe, Pro, His, Ile, Tyr, or Cys;"

(ix) FEATURE:
    (A) NAME/KEY: Modified-site
    (B) LOCATION: 123
    (D) OTHER INFORMATION: /note= "Xaa at position 123 is Ala, Met, Glu, His, Ser, Pro, Tyr, or Leu;"

(xi) SEQUENCE DESCRIPTION: SEQ ID NO:2:

```
Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Asn Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Phe Xaa Xaa Xaa Xaa Xaa Xaa Xaa
            100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
        130
```

(2) INFORMATION FOR SEQ ID NO:3:

(i) SEQUENCE CHARACTERISTICS:
        (A) LENGTH: 332 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Modified-site
        (B) LOCATION: 112
        (D) OTHER INFORMATION: /note= "position 112 is deleted or
            Leu, Ala, Val, Ile, Pro, Phe, Trp, or M..."

(ix) FEATURE:
        (A) NAME/KEY: Modified-site
        (B) LOCATION: 113
        (D) OTHER INFORMATION: /note= "position 113 is deleted or
            Pro, Phe, Ala, Leu, Ile, Trp, or Met"

(ix) FEATURE:
        (A) NAME/KEY: Modified-site
        (B) LOCATION: 114
        (D) OTHER INFORMATION: /note= "position 114 is deleted or
            Pro, Phe, Ala, Val, Leu, Ile, Trp or Met"

(ix) FEATURE:
        (A) NAME/KEY: Modified-site
        (B) LOCATION: 115
        (D) OTHER INFORMATION: /note= "position 115 is deleted or
            Gln, Gly, Ser, Thr, Tyr or Asn"

(xi) SEQUENCE DESCRIPTION: SEQ ID NO:3:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60
```

```
Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Xaa
                100                 105                 110

Xaa Xaa Xaa Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Trp Gln Gln Gly Phe Arg Ala Lys Ile
                195                 200                 205

Pro Gly Leu Leu Asn Gln Thr Ser Arg Ser Leu Asp Gln Ile Pro Gly
                210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
                260                 265                 270

Pro Ser Pro Thr His Pro Pro Thr Gly Gln Tyr Thr Leu Phe Pro Leu
                275                 280                 285

Pro Pro Thr Leu Pro Thr Pro Val Val Gln Leu His Pro Leu Leu Pro
                290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO:4:

(i) SEQUENCE CHARACTERISTICS:
        (A) LENGTH: 5 base pairs
        (B) TYPE: nucleic acid
        (C) STRANDEDNESS: unknown
        (D) TOPOLOGY: unknown (ii) MOLECULE TYPE: peptide (xi) SEQUENCE DESCRIPTION: SEQ ID NO:4:

GYSRN        5

(2) INFORMATION FOR SEQ ID NO:5:

(i) SEQUENCE CHARACTERISTICS:
        (A) LENGTH: 3 amino acids
        (B) TYPE: amino acid
        (C) STRANDEDNESS: unknown
        (D) TOPOLOGY: unknown (ii) MOLECULE TYPE: peptide (ix) FEATURE:

```
            (A) NAME/KEY: Peptide
            (B) LOCATION: 1
            (D) OTHER INFORMATION: /note= "where x=(glyglyglyglyser)n
                and where n is an interger"

(xi) SEQUENCE DESCRIPTION: SEQ ID NO:5:

Xaa Ala Ala
1

(2) INFORMATION FOR SEQ ID NO:6:

(i) SEQUENCE CHARACTERISTICS:
        (A) LENGTH: 3 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 1

(ix) FEATURE:
        (A) NAME/KEY: Peptide
        (B) LOCATION: 1
        (D) OTHER INFORMATION: /note= "where Xaa
            =(glyglyglyglyglyser)n and where n is an integer"

(xi) SEQUENCE DESCRIPTION: SEQ ID NO:6:

Xaa Ala Ala
1

(2) INFORMATION FOR SEQ ID NO:7:

(i) SEQUENCE CHARACTERISTICS:
        (A) LENGTH: 3 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 1
        (D) OTHER INFORMATION: /note= "where xaa = (gly(n)ser)m
            and where n is an integer and m is an int..."

(xi) SEQUENCE DESCRIPTION: SEQ ID NO:7:

Xaa Ala Ala
1

(2) INFORMATION FOR SEQ ID NO:8:

(i) SEQUENCE CHARACTERISTICS:
        (A) LENGTH: 3 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 1
        (D) OTHER INFORMATION: /note= "where Xaa=(alaglyser)n and
            where n is an integer"

(xi) SEQUENCE DESCRIPTION: SEQ ID NO:8:

Xaa Ala Ala
1
```

(2) INFORMATION FOR SEQ ID NO:9:

(i) SEQUENCE CHARACTERISTICS:
        (A) LENGTH: 36 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:9:

Gly Gly Gly Ser Gly Gly Gly Ser Gly Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:10:

Ile Ser Glu Pro Ser Gly Pro Ile Ser Thr Ile Asn Pro Ser Pro Pro
1               5                   10                  15

Ser Lys Glu Ser His Lys Ser Pro
            20

(2) INFORMATION FOR SEQ ID NO:11:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:11:

Ile Glu Gly Arg Ile Ser Glu Pro Ser Gly Pro Ile Ser Thr Ile Asn
1               5                   10                  15

Pro Ser Pro Pro Ser Lys Glu Ser His Lys Ser Pro
            20                  25

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:12:

Gly Gly Gly Ser
1

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:13:

ACGTCCATGG CNTCNCCNGC NCCNCCTGCT TGTGCACTCC GAGTC                45

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:14:

ATGCACGAAT TCCCTGACGC AGAGGGTGGA                                 30

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:15:

TGACAAGCTT ACCTGACGCA GAGGGTGGAC CCT                             33

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:16:

AATTCGGCAA                                                       10

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:17:

CATGTTGCCG                                                       10

(2) INFORMATION FOR SEQ ID NO:18:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:18:

AATTCGGCGG CAA                                              13

(2) INFORMATION FOR SEQ ID NO:19:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:19:

CATGTTGCCG CCG                                              13

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:20:

AATTCGGCGG CAACGGCGGC AA                                  22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:21:

CATGTTGCCG CCGTTGCCGC CG                                  22

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:22:

CGATCCATGG AGGTTCACCC TTTGCCT                            27

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:23:

GATCAAGCTT ATGGGCACTG GCTCAGTCT					29

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:24:

CGATACATGT TGCCTACACC TGTCCTG					27

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:25:

GATCAAGCTT AAGGGTGAAC CTCTGGGCA					29

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:26:

CGATCCATGG TCCTGCTGCC TGCTGTG					27

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:27:

GATCAAGCTT AAGTGTAGG CAAAGGGTG					29

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:28:

CGATCCATGG CTGTGGACTT TAGCTTGGGA                                        30

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:29:

GATCAAGCTT AAGGCAGCAG GACAGGTGT                                         29

(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:30:

CGATCCATGG ACTTTAGCTT GGGAGAA                                           27

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:31:

GATCAAGCTT ACACAGCAGG CAGCAGGAC                                         29

(2) INFORMATION FOR SEQ ID NO:32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:32:

```
CGATCCATGG GAGAATGGAA AACCCAG                                                27
```

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:33:

```
GATCAAGCTT ACAAGCTAAA GTCCACAGC                                              29
```

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:34:

```
CGATCCATGG GACCCACTTG CCTCTCA                                                27
```

(2) INFORMATION FOR SEQ ID NO:35:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:35:

```
GATCAAGCTT ACAGTTGTCC CCGTGCTGC                                              29
```

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:36:

```
CAGTCCATGG GAACCCAGCT TCCTCCA                                                27
```

(2) INFORMATION FOR SEQ ID NO:37:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:37:

GATCAAGCTT AAAGGAGGCT CTGCAGGGC                               29

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:38:

CGATCCATGG GCAGGACCAC AGCTCAC                                 27

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:39:

GATCAAGCTT ACTGTGGAGG AAGCTGGGTT                              30

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:40:

CGATCCATGG CTCACAAGGA TCCCAATGCC                              30

(2) INFORMATION FOR SEQ ID NO:41:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:41:

GATCAAGCTT ATGTGGTCCT GCGCTGTGG                               29

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:42:

CGATCCATGG ATCCCAATGC CATCTTCCTG                                         30

(2) INFORMATION FOR SEQ ID NO:43:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:43:

GATCAAGCTT ACTTGTGAGC TGTGGTCCT                                          29

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:44:

CGATCCATGG CCATCTTCCT GAGCTTCCAA                                         30

(2) INFORMATION FOR SEQ ID NO:45:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:45:

GATCAAGCTT AATTGGGATC CTTGTGAGCT GT                                      32

(2) INFORMATION FOR SEQ ID NO:46:

(i) SEQUENCE CHARACTERISTICS:
        (A) LENGTH: 83 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:46:

AATTCCGTCG TAAACTGACC TTCTATCTGA AAACCTTGGA GAACGCGCAG GCTCAACAGT         60

ACGTAGAGGG CGGTGGAGGC TCC                                                83

(2) INFORMATION FOR SEQ ID NO:47:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid
                  (A) DESCRIPTION: /desc = "DNA (synthetic)"

(xi) SEQUENCE DESCRIPTION: SEQ ID NO:47:

CCGGGGAGCC TCCACCGCCC TCTACGTACT GTTGAGCCTG CGCGTTCTCC AAGGTTTTCA      60

GATAGAAGGT CAGTTTACGA CGG      83

(2) INFORMATION FOR SEQ ID NO:48:

(i) SEQUENCE CHARACTERISTICS:
                  (A) LENGTH: 59 base pairs
                  (B) TYPE: nucleic acid
                  (C) STRANDEDNESS: single
                  (D) TOPOLOGY: linear (ii) MOLECULE TYPE: other nucleic acid
                  (A) DESCRIPTION: /desc = "DNA (synthetic)"

(xi) SEQUENCE DESCRIPTION: SEQ ID NO:48:

GTTACCCTTG AGCAAGCGCA GGAACAACAG GGTGGTGGCT CTAACTGCTC TATAATGAT      59

(2) INFORMATION FOR SEQ ID NO:49:

(i) SEQUENCE CHARACTERISTICS:
                  (A) LENGTH: 56 base pairs
                  (B) TYPE: nucleic acid
                  (C) STRANDEDNESS: single
                  (D) TOPOLOGY: linear (ii) MOLECULE TYPE: other nucleic acid
                  (A) DESCRIPTION: /desc = "DNA (synthetic)"

(xi) SEQUENCE DESCRIPTION: SEQ ID NO:49:

CGATCATTAT AGAGCAGTTA GAGCCACCAC CCTGTTGTTC CTGCGCTTGC TCAAGG      56

(2) INFORMATION FOR SEQ ID NO:50:

(i) SEQUENCE CHARACTERISTICS:
                  (A) LENGTH: 80 base pairs
                  (B) TYPE: nucleic acid
                  (C) STRANDEDNESS: single
                  (D) TOPOLOGY: linear (ii) MOLECULE TYPE: other nucleic acid
                  (A) DESCRIPTION: /desc = "DNA (synthetic)"

(xi) SEQUENCE DESCRIPTION: SEQ ID NO:50:

GTTACCCTTG AGCAAGCGCA GGAACAACAG GGTGGTGGCT CTGGCGGTGG CAGCGGCGGC      60

GGTTCTAACT GCTCTATAAT      80

(2) INFORMATION FOR SEQ ID NO:51:

(i) SEQUENCE CHARACTERISTICS:
                  (A) LENGTH: 80 base pairs
                  (B) TYPE: nucleic acid
                  (C) STRANDEDNESS: single
                  (D) TOPOLOGY: linear (ii) MOLECULE TYPE: other nucleic acid
                  (A) DESCRIPTION: /desc = "DNA (synthetic)"

(xi) SEQUENCE DESCRIPTION: SEQ ID NO:51:

CGATCATTAT AGAGCAGTTA GAACCGCCGC CGCTGCCACC GCCAGAGCCA CCACCCTGTT      60

GTTCCTGCGC TTGCTCAAGG      80

(2) INFORMATION FOR SEQ ID NO:52:

```
    (i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:52:

GATCGACCAT GGCTCTGGAC CCGAACAACC                                           30

(2) INFORMATION FOR SEQ ID NO:53:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:53:

CTCGATTACG TACAAAGGTG CAGGTGGT                                             28

(2) INFORMATION FOR SEQ ID NO:54:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:54:

GATCGACCAT GGCTAATGCA TCAGGTATTG AG                                        32

(2) INFORMATION FOR SEQ ID NO:55:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:55:

CTCGATTACG TATTCTAAGT TCTTGACA                                             28

(2) INFORMATION FOR SEQ ID NO:56:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:56:

GATCGACCAT GGCTGCACCC TCTCGACATC CA                                        32
```

```
(2) INFORMATION FOR SEQ ID NO:57:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:57:

CTCGATTACG TAGGCCGTGG CAGAGGGC                                              28

(2) INFORMATION FOR SEQ ID NO:58:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:58:

GATCGACCAT GGCTGCAGGT GACTGGCAAG AA                                         32

(2) INFORMATION FOR SEQ ID NO:59:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:59:

CTCGATTACG TACTTGATGA TGATTGGA                                              28

(2) INFORMATION FOR SEQ ID NO:60:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:60:

GCTCTGAGAG CCGCCAGAGC CGCCAGAGGG CTGCGCAAGG TGGCGTAGAA CGCG                 54

(2) INFORMATION FOR SEQ ID NO:61:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:61:

CAGCCCTCTG GCGGCTCTGG CGGCTCTCAG AGCTTCCTGC TCAAGTCTTT AGAG                 54
```

(2) INFORMATION FOR SEQ ID NO:62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:62:

GGGCTGCGCA AGGTGGCG                                              18

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:63:

ACACCATTGG GCCCTGCCAG C                                      21

(2) INFORMATION FOR SEQ ID NO:64:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:64:

GATCGACCAT GGCTTACAAG CTGTGCCACC CC                    32

(2) INFORMATION FOR SEQ ID NO:65:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:65:

CGATCGAAGC TTATTAGGTG GCACACAGCT TCTCCT              36

(2) INFORMATION FOR SEQ ID NO:66:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:66:

GATCGACCAT GGCTCCCGAG TTGGGTCCCA CC                    32

(2) INFORMATION FOR SEQ ID NO:67:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:67:

```
CGATCGAAGC TTATTAGGAT ATCCCTTCCA GGGCCT                          36
```

(2) INFORMATION FOR SEQ ID NO:68:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:68:

```
GATCGACCAT GGCTATGGCC CCTGCCCTGC AG                              32
```

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:69:

```
CGATCGAAGC TTATTATCCC AGTTCTTCCA TCTGCT                          36
```

(2) INFORMATION FOR SEQ ID NO:70:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:70:

```
GATCGACCAT GGCTACCCAG GGTGCCATGC CG                              32
```

(2) INFORMATION FOR SEQ ID NO:71:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:71:

```
CGATCGAAGC TTATTAGGGC TGCAGGGCAG GGGCCA                                  36

(2) INFORMATION FOR SEQ ID NO:72:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:72:

CGATCGAAGC TTATTAGGGC TGCAGGGCAG GGGCCA                                  36

(2) INFORMATION FOR SEQ ID NO:73:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:73:

CGATCGAAGC TTATTAGGCG AAGGCCGGCA TGGCAC                                  36

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:74:

GTAGAGGGCG GTGGAGGCTC C                                                  21

(2) INFORMATION FOR SEQ ID NO:75:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:75:

CCGGGGAGCC TCCACCGCCC TCTAC                                              25

(2) INFORMATION FOR SEQ ID NO:76:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:76:
```

```
TTCTACGCCA CCTTGCGCAG CCCGGCGGCG GCTCTGACAT GTCTACACCA TTG        53

(2) INFORMATION FOR SEQ ID NO:77:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:77:

CAATGGTGTA GACATGTCAG AGCCGCCGCC GGGCTGCGCA AGGTGGCGTA GAA        53

(2) INFORMATION FOR SEQ ID NO:78:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:78:

GCTAACTGCT CTATAATGAT CGATGAAATT ATACATCACT TAAAGAGACC ACCTGCACCT   60

TTGCTGGACC CGAACAACCT CAATGACGAA GACGTCTCTA TCCTGATGGA CCGAAACCTT  120

CGACTTCCAA ACCTGGAGAG CTTCGTAAGG GCTGTCAAGA ACTTAGAAAA TGCATCAGGT  180

ATTGAGGCAA TTCTTCGTAA TCTCCAACCA TGTCTGCCCT CTGCCACGGC CGCACCCTCT  240

CGACATCCAA TCATCATCAA GGCAGGTGAC TGGCAAGAAT TCCGGGAAAA ACTGACGTTC  300

TATCTGGTTA CCCTTGAGCA AGCGCAGGAA CAACAGTACG TAGAGGGCGG TGGAGGCTCC  360

CCGGGTGAAC CGTCTGGTCC AATCTCTACT ATCAACCCGT CTCCTCCGTC TAAAGAATCT  420

CATAAATCTC CAAACATGT                                              439

(2) INFORMATION FOR SEQ ID NO:79:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:79:

TCCCCAGCTC CACCTGCTTG TGACCTCCGA GTCCTCAGTA AACTGCTTCG TGACTCCCAT   60

GTCCTTCACA GCAGACTGAG CCAGTGCCCA GAGGTTCACC CTTTGCCTAC ACCTGTCCTG  120

CTGCCTGCTG TGGACTTTAG CTTGGGAGAA TGGAAAACCC AGATGGAGGA GACCAAGGCA  180

CAGGACATTC TGGGAGCAGT GACCCTTCTG CTGGAGGGAG TGATGGCAGC ACGGGGACAA  240

CTGGGACCCA CTTGCCTCTC ATCCCTCCTG GGGCAGCTTT CTGGACAGGT CCGTCTCCTC  300

CTTGGGGCCC TGCAGAGCCT CCTTGGAACC CAGCTTCCTC CACAGGGCAG GACCACAGCT  360

CACAAGGATC CCAATGCCAT CTTCCTGAGC TTCAACACC TGCTCCGAGG AAAGGTGCGT   420

TTCCTGATGC TTGTAGGAGG GTCCACCCTC TGCGTCAGGG AATTC                 465
```

(2) INFORMATION FOR SEQ ID NO:80:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:80:

```
TCCCCAGCTC CACCTGCTTG TGACCTCCGA GTCCTCAGTA AACTGCTTCG TGACTCCCAT      60
GTCCTTCACA GCAGACTGAG CCAGTGCCCA GAGGTTCACC CTTTGCCTAC ACCTGTCCTG     120
CTGCCTGCTG TGGACTTTAG CTTGGGAGAA TGGAAAACCC AGATGGAGGA GACCAAGGCA     180
CAGGACATTC TGGGAGCAGT GACCCTTCTG CTGGAGGGAG TGATGGCAGC ACGGGGACAA     240
CTGGGACCCA CTTGCCTCTC ATCCCTCCTG GGGCAGCTTT CTGGACAGGT CCGTCTCCTC     300
CTTGGGGCCC TGCAGAGCCT CCTTGGAACC CAGCTTCCTC CACAGGGCAG GACCACAGCT     360
CACAAGGATC CCAATGCCAT CTTCCTGAGC TTCCAACACC TGCTCCGAGG AAAGGTGCGT     420
TTCCTGATGC TTGTAGGAGG GTCCACCCTC TGCGTCAGGG AATTCGGCGG CAACATGGCG     480
TCTCCCGCTC CGCCTGCTTG TGACCTCCGA GTCCTCAGTA AACTGCTTCG TGACTCCCAT     540
GTCCTTCACA GCAGACTGAG CCAGTGCCCA GAGGTTCACC CTTTGCCTAC ACCTGTCCTG     600
CTGCCTGCTG TGGACTTTAG CTTGGGAGAA TGGAAAACCC AGATGGAGGA GACCAAGGCA     660
CAGGACATTC TGGGAGCAGT GACCCTTCTG CTGGAGGGAG TGATGGCAGC ACGGGGACAA     720
CTGGGACCCA CTTGCCTCTC ATCCCTCCTG GGGCAGCTTT CTGGACAGGT CCGTCTCCTC     780
CTTGGGGCCC TGCAGAGCCT CCTTGGAACC CAGGGCAGGA CCACAGCTCA CAAGGATCCC     840
AATGCCATCT TCCTGAGCTT CCAACACCTG CTCCGAGGAA AGGTGCGTTT CCTGATGCTT     900
GTAGGAGGGT CCACCCTCTG CGTCAGG                                        927
```

(2) INFORMATION FOR SEQ ID NO:81:

(i) SEQUENCE CHARACTERISTICS:
        (A) LENGTH: 936 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:81:

```
TCCCCAGCTC CACCTGCTTG TGACCTCCGA GTCCTCAGTA AACTGCTTCG TGACTCCCAT      60
GTCCTTCACA GCAGACTGAG CCAGTGCCCA GAGGTTCACC CTTTGCCTAC ACCTGTCCTG     120
CTGCCTGCTG TGGACTTTAG CTTGGGAGAA TGGAAAACCC AGATGGAGGA GACCAAGGCA     180
CAGGACATTC TGGGAGCAGT GACCCTTCTG CTGGAGGGAG TGATGGCAGC ACGGGGACAA     240
CTGGGACCCA CTTGCCTCTC ATCCCTCCTG GGGCAGCTTT CTGGACAGGT CCGTCTCCTC     300
CTTGGGGCCC TGCAGAGCCT CCTTGGAACC CAGCTTCCTC CACAGGGCAG GACCACAGCT     360
CACAAGGATC CCAATGCCAT CTTCCTGAGC TTCCAACACC TGCTCCGAGG AAAGGTGCGT     420
TTCCTGATGC TTGTAGGAGG GTCCACCCTC TGCGTCAGGG AATTCGGCAA CATGGCGTCT     480
CCCGCTCCGC CTGCTTGTGA CCTCCGAGTC CTCAGTAAAC TGCTTCGTGA CTCCCATGTC     540
CTTCACAGCA GACTGAGCCA GTGCCCAGAG GTTCACCCTT TGCCTACACC TGTCCTGCTG     600
```

```
CCTGCTGTGG ACTTTAGCTT GGGAGAATGG AAAACCCAGA TGGAGGAGAC CAAGGCACAG      660

GACATTCTGG GAGCAGTGAC CCTTCTGCTG GAGGGAGTGA TGGCAGCACG GGACAACTG       720

GGACCCACTT GCCTCTCATC CCTCCTGGGG CAGCTTTCTG GACAGGTCCG TCTCCTCCTT      780

GGGGCCCTGC AGAGCCTCCT TGGAACCCAG CTTCCTCCAC AGGGCAGGAC CACAGCTCAC      840

AAGGATCCCA ATGCCATCTT CCTGAGCTTC AACACCTGC  TCCGAGGAAA GGTGCGTTTC      900

CTGATGCTTG TAGGAGGGTC CACCCTCTGC GTCAGG                                936

(2) INFORMATION FOR SEQ ID NO:82:

(i) SEQUENCE CHARACTERISTICS:
        (A) LENGTH: 939 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:82:

TCCCCAGCTC CACCTGCTTG TGACCTCCGA GTCCTCAGTA AACTGCTTCG TGACTCCCAT       60

GTCCTTCACA GCAGACTGAG CCAGTGCCCA GAGGTTCACC CTTTGCCTAC ACCTGTCCTG      120

CTGCCTGCTG TGGACTTTAG CTTGGGAGAA TGGAAAACCC AGATGGAGGA GACCAAGGCA      180

CAGGACATTC TGGGAGCAGT GACCCTTCTG CTGGAGGGAG TGATGGCAGC ACGGGGACAA      240

CTGGGACCCA CTTGCCTCTC ATCCCTCCTG GGGCAGCTTT CTGGACAGGT CCGTCTCCTC      300

CTTGGGGCCC TGCAGAGCCT CCTTGGAACC CAGCTTCCTC CACAGGGCAG GACCACAGCT      360

CACAAGGATC CCAATGCCAT CTTCCTGAGC TTCCAACACC TGCTCCGAGG AAAGGTGCGT      420

TTCCTGATGC TTGTAGGAGG GTCCACCCTC TGCGTCAGGG AATTCGGCGG CAACATGGCG      480

TCTCCCGCTC CGCCTGCTTG TGACCTCCGA GTCCTCAGTA AACTGCTTCG TGACTCCCAT      540

GTCCTTCACA GCAGACTGAG CCAGTGCCCA GAGGTTCACC CTTTGCCTAC ACCTGTCCTG      600

CTGCCTGCTG TGGACTTTAG CTTGGGAGAA TGGAAAACCC AGATGGAGGA GACCAAGGCA      660

CAGGACATTC TGGGAGCAGT GACCCTTCTG CTGGAGGGAG TGATGGCAGC ACGGGGACAA      720

CTGGGACCCA CTTGCCTCTC ATCCCTCCTG GGGCAGCTTT CTGGACAGGT CCGTCTCCTC      780

CTTGGGGCCC TGCAGAGCCT CCTTGGAACC CAGCTTCCTC CACAGGGCAG GACCACAGCT      840

CACAAGGATC CCAATGCCAT CTTCCTGAGC TTCCAACACC TGCTCCGAGG AAAGGTGCGT      900

TTCCTGATGC TTGTAGGAGG GTCCACCCTC TGCGTCAGG                             939

(2) INFORMATION FOR SEQ ID NO:83:

(i) SEQUENCE CHARACTERISTICS:
        (A) LENGTH: 948 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:83:

TCCCCAGCGC CGCCTGCTTG TGACCTCCGA GTCCTCAGTA AACTGCTTCG TGACTCCCAT       60

GTCCTTCACA GCAGACTGAG CCAGTGCCCA GAGGTTCACC CTTTGCCTAC ACCTGTCCTG      120

CTGCCTGCTG TGGACTTTAG CTTGGGAGAA TGGAAAACCC AGATGGAGGA GACCAAGGCA      180
```

```
CAGGACATTC TGGGAGCAGT GACCCTTCTG CTGGAGGGAG TGATGGCAGC ACGGGGACAA        240

CTGGGACCCA CTTGCCTCTC ATCCCTCCTG GGGCAGCTTT CTGGACAGGT CCGTCTCCTC        300

CTTGGGGCCC TGCAGAGCCT CCTTGGAACC CAGCTTCCTC CACAGGGCAG GACCACAGCT        360

CACAAGGATC CCAATGCCAT CTTCCTGAGC TTCCAACACC TGCTCCGAGG AAAGGTGCGT        420

TTCCTGATGC TTGTAGGAGG GTCCACCCTC TGCGTCAGGG AATTCGGCGG CAACGGCGGC        480

AACATGGCGT CCCCAGCGCC GCCTGCTTGT GACCTCCGAG TCCTCAGTAA ACTGCTTCGT        540

GACTCCCATG TCCTTCACAG CAGACTGAGC CAGTGCCCAG AGGTTCACCC TTTGCCTACA        600

CCTGTCCTGC TGCCTGCTGT GGACTTTAGC TTGGGAGAAT GGAAAACCCA GATGGAGGAG        660

ACCAAGGCAC AGGACATTCT GGGAGCAGTG ACCCTTCTGC TGGAGGGAGT GATGGCAGCA        720

CGGGGACAAC TGGGACCCAC TTGCCTCTCA TCCCTCCTGG GGCAGCTTTC TGGACAGGTC        780

CGTCTCCTCC TTGGGGCCCT GCAGAGCCTC CTTGGAACCC AGCTTCCTCC ACAGGGCAGG        840

ACCACAGCTC ACAAGGATCC CAATGCCATC TTCCTGAGCT TCCAACACCT GCTCCGAGGA        900

AAGGTGCGTT TCCTGATGCT TGTAGGAGGG TCCACCCTCT GCGTCAGG                    948

(2) INFORMATION FOR SEQ ID NO:84:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:84:

CATGGCTAAC TGCTCTATAA TGATCGATGA AATTATACAT CACTTAAAGA GACCACCTGC         60

ACCTTTGCTG GACCCGAACA ACCTCAATGA CGAAGACGTC TCTATCCTGA TGGACCGAAA        120

CCTTCGACTT CCAAACCTGG AGAGCTTCGT AAGGGCTGTC AAGAACTTAG AAAATGCATC        180

AGGTATTGAG GCAATTCTTC GTAATCTCCA ACCATGTCTG CCCTCTGCCA CGGCCGCACC        240

CTCTCGACAT CCAATCATCA TCAAGGCAGG TGACTGGCAA GAATTCCGGG AAAAACTGAC        300

GTTCTATCTG GTTACCCTTG AGCAAGCGCA GGAACAACAG GGTGGTGGCT CTAACTGCTC        360

TATAATGATC GATGAAATTA TACATCACTT AAAGAGACCA CCTGCACCTT TGCTGGACCC        420

GAACAACCTC AATGACGAAG ACGTCTCTAT CCTGATGGAC CGAAACCTTC GACTTCCAAA        480

CCTGGAGAGC TTCGTAAGGG CTGTCAAGAA CTTAGAAAAT GCATCAGGTA TTGAGGCAAT        540

TCTTCGTAAT CTCCAACCAT GTCTGCCCTC TGCCACGGCC GCACCCTCTC GACATCCAAT        600

CATCATCAAG GCAGGTGACT GGCAAGAATT CCGGGAAAAA CTGACGTTCT ATCTGGTTAC        660

CCTTGAGCAA GCGCAGGAAC AACAGTAC                                          688

(2) INFORMATION FOR SEQ ID NO:85:

(i) SEQUENCE CHARACTERISTICS:
        (A) LENGTH: 712 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:85:

CATGGCTAAC TGCTCTATAA TGATCGATGA AATTATACAT CACTTAAAGA GACCACCTGC         60
```

```
ACCTTTGCTG GACCCGAACA ACCTCAATGA CGAAGACGTC TCTATCCTGA TGGACCGAAA      120

CCTTCGACTT CCAAACCTGG AGAGCTTCGT AAGGGCTGTC AAGAACTTAG AAAATGCATC      180

AGGTATTGAG GCAATTCTTC GTAATCTCCA ACCATGTCTG CCCTCTGCCA CGGCCGCACC      240

CTCTCGACAT CCAATCATCA TCAAGGCAGG TGACTGGCAA GAATTCCGGG AAAAACTGAC      300

GTTCTATCTG GTTACCCTTG AGCAAGCGCA GGAACAACAG GGTGGTGGCT CTGGCGGTGG      360

CAGCGGCGGC GGTTCTAACT GCTCTATAAT GATCGATGAA ATTATACATC ACTTAAAGAG      420

ACCACCTGCA CCTTTGCTGG ACCCGAACAA CCTCAATGAC GAAGACGTCT CTATCCTGAT      480

GGACCGAAAC CTTCGACTTC CAAACCTGGA GAGCTTCGTA AGGGCTGTCA AGAACTTAGA      540

AAATGCATCA GGTATTGAGG CAATTCTTCG TAATCTCCAA CCATGTCTGC CCTCTGCCAC      600

GGCCGCACCC TCTCGACATC CAATCATCAT CAAGGCAGGT GACTGGCAAG AATTCCGGGA      660

AAAACTGACG TTCTATCTGG TTACCCTTGA GCAAGCGCAG GAACAACAGT AC             712
```

(2) INFORMATION FOR SEQ ID NO:86:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:86:

```
ATGGCTCTGG ACCCGAACAA CCTCAATGAC GAAGACGTCT CTATCCTGAT GGACCGAAAC       60

CTTCGACTTC CAAACCTGGA GAGCTTCGTA AGGGCTGTCA AGAACTTAGA AAATGCATCA      120

GGTATTGAGG CAATTCTTCG TAATCTCCAA CCATGTCTGC CCTCTGCCAC GGCCGCACCC      180

TCTCGACATC CAATCATCAT CAAGGCAGGT GACTGGCAAG AATTCCGGGA AAAACTGACG      240

TTCTATCTGG TTACCCTTGA GCAAGCGCAG GAACAACAGG GTGGTGGCTC TAACTGCTCT      300

ATAATGATCG ATGAAATTAT ACATCACTTA AAGAGACCAC CTGCACCTTT GTACGTAGAG      360

GGCGGTGGAG GCTCCCCGGG TGAACCGTCT GGTCCAATCT CTACTATCAA CCCGTCTCCT      420

CCGTCTAAAG AATCTCATAA ATCTCCAAAC ATGGCTACCC AGGGTGCCAT GCCGGCCTTC      480

GCCTCTGCTT TCCAGCGCCG GGCAGGAGGG GTCCTGGTTG CTAGCCATCT GCAGAGCTTC      540

CTGGAGGTGT CGTACCGCGT TCTACGCCAC CTTGCGCAGC CCTCTGGCGG CTCTGGCGGC      600

TCTCAGAGCT TCCTGCTCAA GTCTTTAGAG CAAGTGAGAA AGATCCAGGG CGATGGCGCA      660

GCGCTCCAGG AGAAGCTGTG TGCCACCTAC AAGCTGTGCC ACCCCGAGGA GCTGGTGCTG      720

CTCGGACACT CTCTGGGCAT CCCCTGGGCT CCCCTGAGCT CCTGCCCCAG CCAGGCCCTG      780

CAGCTGGCAG GCTGCTTGAG CCAACTCCAT AGCGGCCTTT TCCTCTACCA GGGGCTCCTG      840

CAGGCCCTGG AAGGGATATC CCCCGAGTTG GGTCCCACCT TGGACACACT GCAGCTGGAC      900

GTCGCCGACT TTGCCACCAC CATCTGGCAG CAGATGGAAG AACTGGGAAT GGCCCCTGCC      960

CTGCAGCCCT AATAA                                                      975
```

(2) INFORMATION FOR SEQ ID NO:87:

(i) SEQUENCE CHARACTERISTICS:
        (A) LENGTH: 975 base pairs
        (B) TYPE: nucleic acid
        (C) STRANDEDNESS: single
        (D) TOPOLOGY: linear

```
       (ii) MOLECULE TYPE: other nucleic acid
            (A) DESCRIPTION: /desc = "DNA (synthetic)"

(xi) SEQUENCE DESCRIPTION: SEQ ID NO:87:

ATGGCTCTGG ACCCGAACAA CCTCAATGAC GAAGACGTCT CTATCCTGAT GGACCGAAAC       60

CTTCGACTTC CAAACCTGGA GAGCTTCGTA AGGGCTGTCA AGAACTTAGA AAATGCATCA      120

GGTATTGAGG CAATTCTTCG TAATCTCCAA CCATGTCTGC CCTCTGCCAC GGCCGCACCC      180

TCTCGACATC CAATCATCAT CAAGGCAGGT GACTGGCAAG AATTCCGGGA AAAACTGACG      240

TTCTATCTGG TTACCCTTGA GCAAGCGCAG GAACAACAGG GTGGTGGCTC TAACTGCTCT      300

ATAATGATCG ATGAAATTAT ACATCACTTA AAGAGACCAC CTGCACCTTT GTACGTAGAG      360

GGCGGTGGAG GCTCCCCGGG TGAACCGTCT GGTCCAATCT CTACTATCAA CCCGTCTCCT      420

CCGTCTAAAG AATCTCATAA ATCTCCAAAC ATGGCTACCC AGGGTGCCAT GCCGGCCTTC      480

GCCTCTGCTT TCCAGCGCCG GGCAGGAGGG GTCCTGGTTG CTAGCCATCT GCAGAGCTTC      540

CTGGAGGTGT CGTACCGCGT TCTACGCCAC CTTGCGCAGC CCTCTGGCGG CTCTGGCGGC      600

TCTCAGAGCT TCCTGCTCAA GTCTTTAGAG CAAGTGAGAA AGATCCAGGG CGATGGCGCA      660

GCGCTCCAGG AGAAGCTGTG TGCCACCTAC AAGCTGTGCC ACCCCGAGGA GCTGGTGCTG      720

CTCGGACACT CTCTGGGCAT CCCCTGGGCT CCCCTGAGCT CCTGCCCCAG CCAGGCCCTG      780

CAGCTGGCAG GCTGCTTGAG CCAACTCCAT AGCGGCCTTT TCCTCTACCA GGGGCTCCTG      840

CAGGCCCTGG AAGGGATATC CCCCGAGTTG GGTCCCACCT TGGACACACT GCAGCTGGAC      900

GTCGCCGACT TTGCCACCAC CATCTGGCAG CAGATGGAAG AACTGGGAAT GGCCCCTGCC      960

CTGCAGCCCT AATAA                                                      975

(2) INFORMATION FOR SEQ ID NO:88:

(i) SEQUENCE CHARACTERISTICS:
            (A) LENGTH: 975 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA (synthetic)"

(xi) SEQUENCE DESCRIPTION: SEQ ID NO:88:

ATGGCTGCAC CCTCTCGACA TCCAATCATC ATCAAGGCAG GTGACTGGCA AGAATTCCGG       60

GAAAAACTGA CGTTCTATCT GGTTACCCTT GAGCAAGCGC AGGAACAACA GGGTGGTGGC      120

TCTAACTGCT CTATAATGAT CGATGAAATT ATACATCACT TAAAGAGACC ACCTGCACCT      180

TTGCTGGACC CGAACAACCT CAATGACGAA GACGTCTCTA TCCTGATGGA CCGAAACCTT      240

CGACTTCCAA ACCTGGAGAG CTTCGTAAGG CTGTCAAGA ACTTAGAAAA TGCATCAGGT      300

ATTGAGGCAA TTCTTCGTAA TCTCCAACCA TGTCTGCCCT CTGCCACGGC CTACGTAGAG      360

GGCGGTGGAG GCTCCCCGGG TGAACCGTCT GGTCCAATCT CTACTATCAA CCCGTCTCCT      420

CCGTCTAAAG AATCTCATAA ATCTCCAAAC ATGGCTACCC AGGGTGCCAT GCCGGCCTTC      480

GCCTCTGCTT TCCAGCGCCG GGCAGGAGGG GTCCTGGTTG CTAGCCATCT GCAGAGCTTC      540

CTGGAGGTGT CGTACCGCGT TCTACGCCAC CTTGCGCAGC CCTCTGGCGG CTCTGGCGGC      600

TCTCAGAGCT TCCTGCTCAA GTCTTTAGAG CAAGTGAGAA AGATCCAGGG CGATGGCGCA      660

GCGCTCCAGG AGAAGCTGTG TGCCACCTAC AAGCTGTGCC ACCCCGAGGA GCTGGTGCTG      720

CTCGGACACT CTCTGGGCAT CCCCTGGGCT CCCCTGAGCT CCTGCCCCAG CCAGGCCCTG      780
```

```
CAGCTGGCAG GCTGCTTGAG CCAACTCCAT AGCGGCCTTT TCCTCTACCA GGGGCTCCTG      840

CAGGCCCTGG AAGGGATATC CCCCGAGTTG GGTCCCACCT TGGACACACT GCAGCTGGAC      900

GTCGCCGACT TTGCCACCAC CATCTGGCAG CAGATGGAAG AACTGGGAAT GGCCCCTGCC      960

CTGCAGCCCT AATAA                                                      975
```

(2) INFORMATION FOR SEQ ID NO:89:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:89:

```
ATGGCTGCAG GTGACTGGCA AGAATTCCGG GAAAAACTGA CGTTCTATCT GGTTACCCTT       60

GAGCAAGCGC AGGAACAACA GGGTGGTGGC TCTAACTGCT CTATAATGAT CGATGAAATT      120

ATACATCACT TAAAGAGACC ACCTGCACCT TTGCTGGACC CGAACAACCT CAATGACGAA      180

GACGTCTCTA TCCTGATGGA CCGAAACCTT CGACTTCCAA ACCTGGAGAG CTTCGTAAGG      240

GCTGTCAAGA ACTTAGAAAA TGCATCAGGT ATTGAGGCAA TTCTTCGTAA TCTCCAACCA      300

TGTCTGCCCT CTGCCACGGC CGCACCCTCT CGACATCCAA TCATCATCAA GTACGTAGAG      360

GGCGGTGGAG GCTCCCCGGG TGAACCGTCT GGTCCAATCT CTACTATCAA CCCGTCTCCT      420

CCGTCTAAAG AATCTCATAA ATCTCCAAAC ATGGCTACCC AGGGTGCCAT GCCGGCCTTC      480

GCCTCTGCTT TCCAGCGCCG GGCAGGAGGG GTCCTGGTTG CTAGCCATCT GCAGAGCTTC      540

CTGGAGGTGT CGTACCGCGT TCTACGCCAC CTTGCGCAGC CCTCTGGCGG CTCTGGCGGC      600

TCTCAGAGCT TCCTGCTCAA GTCTTTAGAG CAAGTGAGAA AGATCCAGGG CGATGGCGCA      660

GCGCTCCAGG AGAAGCTGTG TGCCACCTAC AAGCTGTGCC ACCCCGAGGA GCTGGTGCTG      720

CTCGGACACT CTCTGGGCAT CCCCTGGGCT CCCCTGAGCT CCTGCCCCAG CCAGGCCCTG      780

CAGCTGGCAG GCTGCTTGAG CCAACTCCAT AGCGGCCTTT TCCTCTACCA GGGGCTCCTG      840

CAGGCCCTGG AAGGGATATC CCCCGAGTTG GGTCCCACCT TGGACACACT GCAGCTGGAC      900

GTCGCCGACT TTGCCACCAC CATCTGGCAG CAGATGGAAG AACTGGGAAT GGCCCCTGCC      960

CTGCAGCCCT AATAA                                                      975
```

(2) INFORMATION FOR SEQ ID NO:90:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:90:

```
ATGGCTCTGG ACCCGAACAA CCTCAATGAC GAAGACGTCT CTATCCTGAT GGACCGAAAC       60

CTTCGACTTC CAAACCTGGA GAGCTTCGTA AGGGCTGTCA AGAACTTAGA AAATGCATCA      120

GGTATTGAGG CAATTCTTCG TAATCTCCAA CCATGTCTGC CCTCTGCCAC GGCCGCACCC      180

TCTCGACATC CAATCATCAT CAAGGCAGGT GACTGGCAAG AATTCCGGGA AAAACTGACG      240
```

```
TTCTATCTGG TTACCCTTGA GCAAGCGCAG GAACAACAGG GTGGTGGCTC TGGCGGTGGC    300

AGCGGCGGCG GTTCTAACTG CTCTATAATG ATCGATGAAA TTATACATCA CTTAAAGAGA    360

CCACCTGCAC CTTTGTACGT AGAGGGCGGT GGAGGCTCCC CGGGTGAACC GTCTGGTCCA    420

ATCTCTACTA TCAACCCGTC TCCTCCGTCT AAAGAATCTC ATAAATCTCC AAACATGGCT    480

ACCCAGGGTG CCATGCCGGC CTTCGCCTCT GCTTTCCAGC GCCGGGCAGG AGGGGTCCTG    540

GTTGCTAGCC ATCTGCAGAG CTTCCTGGAG GTGTCGTACC GCGTTCTACG CCACCTTGCG    600

CAGCCCTCTG GCGGCTCTGG CGGCTCTCAG AGCTTCCTGC TCAAGTCTTT AGAGCAAGTG    660

AGAAAGATCC AGGGCGATGG CGCAGCGCTC CAGGAGAAGC TGTGTGCCAC CTACAAGCTG    720

TGCCACCCCG AGGAGCTGGT GCTGCTCGGA CACTCTCTGG GCATCCCCTG GCTCCCCTG     780

AGCTCCTGCC CCAGCCAGGC CCTGCAGCTG GCAGGCTGCT TGAGCCAACT CCATAGCGGC    840

CTTTTCCTCT ACCAGGGGCT CCTGCAGGCC CTGGAAGGGA TATCCCCCGA GTTGGGTCCC    900

ACCTTGGACA CACTGCAGCT GGACGTCGCC GACTTTGCCA CCACCATCTG GCAGCAGATG    960

GAAGAACTGG GAATGGCCCC TGCCCTGCAG CCCTAATAA                           999

(2) INFORMATION FOR SEQ ID NO:91:

(i) SEQUENCE CHARACTERISTICS:
         (A) LENGTH: 999 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:91:

ATGGCTAATG CATCAGGTAT TGAGGCAATT CTTCGTAATC TCCAACCATG TCTGCCCTCT     60

GCCACGGCCG CACCCTCTCG ACATCCAATC ATCATCAAGG CAGGTGACTG GCAAGAATTC    120

CGGGAAAAAC TGACGTTCTA TCTGGTTACC CTTGAGCAAG CGCAGGAACA ACAGGGTGGT    180

GGCTCTGGCG GTGGCAGCGG CGGCGGTTCT AACTGCTCTA TAATGATCGA TGAAATTATA    240

CATCACTTAA AGAGACCACC TGCACCTTTG CTGGACCCGA ACAACCTCAA TGACGAAGAC    300

GTCTCTATCC TGATGGACCG AAACCTTCGA CTTCCAAACC TGGAGAGCTT CGTAAGGGCT    360

GTCAAGAACT TAGAATACGT AGAGGGCGGT GGAGGCTCCC CGGGTGAACC GTCTGGTCCA    420

ATCTCTACTA TCAACCCGTC TCCTCCGTCT AAAGAATCTC ATAAATCTCC AAACATGGCT    480

ACCCAGGGTG CCATGCCGGC CTTCGCCTCT GCTTTCCAGC GCCGGGCAGG AGGGGTCCTG    540

GTTGCTAGCC ATCTGCAGAG CTTCCTGGAG GTGTCGTACC GCGTTCTACG CCACCTTGCG    600

CAGCCCTCTG GCGGCTCTGG CGGCTCTCAG AGCTTCCTGC TCAAGTCTTT AGAGCAAGTG    660

AGAAAGATCC AGGGCGATGG CGCAGCGCTC CAGGAGAAGC TGTGTGCCAC CTACAAGCTG    720

TGCCACCCCG AGGAGCTGGT GCTGCTCGGA CACTCTCTGG GCATCCCCTG GCTCCCCTG     780

AGCTCCTGCC CCAGCCAGGC CCTGCAGCTG GCAGGCTGCT TGAGCCAACT CCATAGCGGC    840

CTTTTCCTCT ACCAGGGGCT CCTGCAGGCC CTGGAAGGGA TATCCCCCGA GTTGGGTCCC    900

ACCTTGGACA CACTGCAGCT GGACGTCGCC GACTTTGCCA CCACCATCTG GCAGCAGATG    960

GAAGAACTGG GAATGGCCCC TGCCCTGCAG CCCTAATAA                           999

(2) INFORMATION FOR SEQ ID NO:92:

(i) SEQUENCE CHARACTERISTICS:
         (A) LENGTH: 999 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:92:

| | | | | | |
|---|---|---|---|---|---|
| ATGGCTGCAC | CCTCTCGACA | TCCAATCATC | ATCAAGGCAG | GTGACTGGCA | AGAATTCCGG | 60 |
| GAAAAACTGA | CGTTCTATCT | GGTTACCCTT | GAGCAAGCGC | AGGAACAACA | GGGTGGTGGC | 120 |
| TCTGGCGGTG | GCAGCGGCGG | CGGTTCTAAC | TGCTCTATAA | TGATCGATGA | AATTATACAT | 180 |
| CACTTAAAGA | GACCACCTGC | ACCTTTGCTG | GACCCGAACA | ACCTCAATGA | CGAAGACGTC | 240 |
| TCTATCCTGA | TGGACCGAAA | CCTTCGACTT | CCAAACCTGG | AGAGCTTCGT | AAGGGCTGTC | 300 |
| AAGAACTTAG | AAAATGCATC | AGGTATTGAG | GCAATTCTTC | GTAATCTCCA | ACCATGTCTG | 360 |
| CCCTCTGCCA | CGGCCTACGT | AGAGGGCGGT | GGAGGCTCCC | CGGGTGAACC | GTCTGGTCCA | 420 |
| ATCTCTACTA | TCAACCCGTC | TCCTCCGTCT | AAAGAATCTC | ATAAATCTCC | AAACATGGCT | 480 |
| ACCCAGGGTG | CCATGCCGGC | CTTCGCCTCT | GCTTTCCAGC | GCCGGGCAGG | AGGGGTCCTG | 540 |
| GTTGCTAGCC | ATCTGCAGAG | CTTCCTGGAG | GTGTCGTACC | GCGTTCTACG | CCACCTTGCG | 600 |
| CAGCCCTCTG | GCGGCTCTGG | CGGCTCTCAG | AGCTTCCTGC | TCAAGTCTTT | AGAGCAAGTG | 660 |
| AGAAAGATCC | AGGGCGATGG | CGCAGCGCTC | CAGGAGAAGC | TGTGTGCCAC | CTACAAGCTG | 720 |
| TGCCACCCCG | AGGAGCTGGT | GCTGCTCGGA | CACTCTCTGG | GCATCCCCTG | GGCTCCCCTG | 780 |
| AGCTCCTGCC | CCAGCCAGGC | CCTGCAGCTG | GCAGGCTGCT | TGAGCCAACT | CCATAGCGGC | 840 |
| CTTTTCCTCT | ACCAGGGGCT | CCTGCAGGCC | CTGGAAGGGA | TATCCCCCGA | GTTGGGTCCC | 900 |
| ACCTTGGACA | CACTGCAGCT | GGACGTCGCC | GACTTTGCCA | CCACCATCTG | GCAGCAGATG | 960 |
| GAAGAACTGG | GAATGGCCCC | TGCCCTGCAG | CCCTAATAA | | | 999 |

(2) INFORMATION FOR SEQ ID NO:93:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:93:

| | | | | | |
|---|---|---|---|---|---|
| ATGGCTGCAG | GTGACTGGCA | AGAATTCCGG | GAAAAACTGA | CGTTCTATCT | GGTTACCCTT | 60 |
| GAGCAAGCGC | AGGAACAACA | GGGTGGTGGC | TCTGGCGGTG | GCAGCGGCGG | CGGTTCTAAC | 120 |
| TGCTCTATAA | TGATCGATGA | AATTATACAT | CACTTAAAGA | GACCACCTGC | ACCTTTGCTG | 180 |
| GACCCGAACA | ACCTCAATGA | CGAAGACGTC | TCTATCCTGA | TGGACCGAAA | CCTTCGACTT | 240 |
| CCAAACCTGG | AGAGCTTCGT | AAGGGCTGTC | AAGAACTTAG | AAAATGCATC | AGGTATTGAG | 300 |
| GCAATTCTTC | GTAATCTCCA | ACCATGTCTG | CCCTCTGCCA | CGGCCGCACC | CTCTCGACAT | 360 |
| CCAATCATCA | TCAAGTACGT | AGAGGGCGGT | GGAGGCTCCC | CGGGTGAACC | GTCTGGTCCA | 420 |
| ATCTCTACTA | TCAACCCGTC | TCCTCCGTCT | AAAGAATCTC | ATAAATCTCC | AAACATGGCT | 480 |
| ACCCAGGGTG | CCATGCCGGC | CTTCGCCTCT | GCTTTCCAGC | GCCGGGCAGG | AGGGGTCCTG | 540 |
| GTTGCTAGCC | ATCTGCAGAG | CTTCCTGGAG | GTGTCGTACC | GCGTTCTACG | CCACCTTGCG | 600 |
| CAGCCCTCTG | GCGGCTCTGG | CGGCTCTCAG | AGCTTCCTGC | TCAAGTCTTT | AGAGCAAGTG | 660 |

```
AGAAAGATCC AGGGCGATGG CGCAGCGCTC CAGGAGAAGC TGTGTGCCAC CTACAAGCTG      720

TGCCACCCCG AGGAGCTGGT GCTGCTCGGA CACTCTCTGG GCATCCCCTG GGCTCCCCTG      780

AGCTCCTGCC CCAGCCAGGC CCTGCAGCTG GCAGGCTGCT TGAGCCAACT CCATAGCGGC      840

CTTTTCCTCT ACCAGGGGCT CCTGCAGGCC CTGGAAGGGA TATCCCCCGA GTTGGGTCCC      900

ACCTTGGACA CACTGCAGCT GGACGTCGCC GACTTTGCCA CCACCATCTG GCAGCAGATG      960

GAAGAACTGG AATGGCCCC TGCCCTGCAG CCCTAATAA                              999

(2) INFORMATION FOR SEQ ID NO:94:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:94:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCTT ACAAGCTGTG CCACCCCGAG      420

GAGCTGGTGC TGCTCGGACA CTCTCTGGGC ATCCCCTGGG CTCCCCTGAG CTCCTGCCCC      480

AGCCAGGCCC TGCAGCTGGC AGGCTGCTTG AGCCAACTCC ATAGCGGCCT TTTCCTCTAC      540

CAGGGGCTCC TGCAGGCCCT GGAAGGGATA TCCCCCGAGT TGGGTCCCAC CTTGGACACA      600

CTGCAGCTGG ACGTCGCCGA CTTTGCCACC ACCATCTGGC AGCAGATGGA AGAACTGGGA      660

ATGGCCCCTG CCCTGCAGCC CACCCAGGGT GCCATGCCGG CCTTCGCCTC TGCTTTCCAG      720

CGCCGGGCAG GAGGGGTCCT GGTTGCTAGC CATCTGCAGA GCTTCCTGGA GGTGTCGTAC      780

CGCGTTCTAC GCCACCTTGC GCAGCCCTCT GGCGGCTCTG GCGGCTCTCA GAGCTTCCTG      840

CTCAAGTCTT TAGAGCAAGT GAGAAAGATC CAGGGCGATG GCGCAGCGCT CCAGGAGAAG      900

CTGTGTGCCA CCTAATAA                                                   918

(2) INFORMATION FOR SEQ ID NO:95:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:95:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240
```

-continued

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAGAGGG CGGTGGAGGC        360

TCCCCGGGTG AACCGTCTGG TCCAATCTCT ACTATCAACC CGTCTCCTCC GTCTAAAGAA        420

TCTCATAAAT CTCCAAACAT GGCTTACAAG CTGTGCCACC CCGAGGAGCT GGTGCTGCTC        480

GGACACTCTC TGGGCATCCC CTGGGCTCCC CTGAGCTCCT GCCCCAGCCA GGCCCTGCAG        540

CTGGCAGGCT GCTTGAGCCA ACTCCATAGC GGCCTTTTCC TCTACCAGGG GCTCCTGCAG        600

GCCCTGGAAG GGATATCCCC CGAGTTGGGT CCCACCTTGG ACACACTGCA GCTGGACGTC        660

GCCGACTTTG CCACCACCAT CTGGCAGCAG ATGGAAGAAC TGGGAATGGC CCCTGCCCTG        720

CAGCCCACCC AGGGTGCCAT GCCGGCCTTC GCCTCTGCTT TCCAGCGCCG GGCAGGAGGG        780

GTCCTGGTTG CTAGCCATCT GCAGAGCTTC CTGGAGGTGT CGTACCGCGT TCTACGCCAC        840

CTTGCGCAGC CCTCTGGCGG CTCTGGCGGC TCTCAGAGCT TCCTGCTCAA GTCTTTAGAG        900

CAAGTGAGAA AGATCCAGGG CGATGGCGCA GCGCTCCAGG AGAAGCTGTG TGCCACCTAA        960

TAA                                                                     963
```

(2) INFORMATION FOR SEQ ID NO:96:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:96:

```
ATGGCTAACT GCTCTATAAT GATCGATGAA ATTATACATC ACTTAAAGAG ACCACCTGCA         60

CCTTTGCTGG ACCCGAACAA CCTCAATGAC GAAGACGTCT CTATCCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAGAGGG CGGTGGAGGC        360

TCCCCGGGTG GTGGTTCTGG CGGCGGCTCC AACATGGCTC CCGAGTTGGG TCCCACCTTG        420

GACACACTGC AGCTGGACGT CGCCGACTTT GCCACCACCA TCTGGCAGCA GATGGAAGAA        480

CTGGGAATGG CCCCTGCCCT GCAGCCCACC CAGGGTGCCA TGCCGGCCTT CGCCTCTGCT        540

TTCCAGCGCC GGGCAGGAGG GGTCCTGGTT GCTAGCCATC TGCAGAGCTT CCTGGAGGTG        600

TCGTACCGCG TTCTACGCCA CCTTGCGCAG CCCTCTGGCG GCTCTGGCGG CTCTCAGAGC        660

TTCCTGCTCA AGTCTTTAGA GCAAGTGAGA AAGATCCAGG GCGATGGCGC AGCGCTCCAG        720

GAGAAGCTGT GTGCCACCTA CAAGCTGTGC CACCCCGAGG AGCTGGTGCT GCTCGGACAC        780

TCTCTGGGCA TCCCCTGGGC TCCCCTGAGC TCCTGCCCCA GCCAGGCCCT GCAGCTGGCA        840

GGCTGCTTGA GCCAACTCCA TAGCGGCCTT TTCCTCTACC AGGGGCTCCT GCAGGCCCTG        900

GAAGGGATAT CCTAATAA                                                     918
```

(2) INFORMATION FOR SEQ ID NO:97:

(i) SEQUENCE CHARACTERISTICS:
        (A) LENGTH: 963 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:97:

ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGACCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GGCTCCCGAG TTGGGTCCCA CCTTGGACAC ACTGCAGCTG     480

GACGTCGCCG ACTTTGCCAC CACCATCTGG CAGCAGATGG AAGAACTGGG AATGGCCCCT     540

GCCCTGCAGC CCACCCAGGG TGCCATGCCG GCCTTCGCCT CTGCTTTCCA GCGCCGGGCA     600

GGAGGGGTCC TGGTTGCTAG CCATCTGCAG AGCTTCCTGG AGGTGTCGTA CCGCGTTCTA     660

CGCCACCTTG CGCAGCCCTC TGGCGGCTCT GGCGGCTCTC AGAGCTTCCT GCTCAAGTCT     720

TTAGAGCAAG TGAGAAAGAT CCAGGGCGAT GGCGCAGCGC TCCAGGAGAA GCTGTGTGCC     780

ACCTACAAGC TGTGCCACCC CGAGGAGCTG GTGCTGCTCG GACACTCTCT GGGCATCCCC     840

TGGGCTCCCC TGAGCTCCTG CCCCAGCCAG GCCCTGCAGC TGGCAGGCTG CTTGAGCCAA     900

CTCCATAGCG GCCTTTTCCT CTACCAGGGG CTCCTGCAGG CCCTGGAAGG GATATCCTAA     960

TAA                                                                  963

(2) INFORMATION FOR SEQ ID NO:98:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:98:

ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGACCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG GTGGTTCTGG CGGCGGCTCC AACATGGCTA TGGCCCCTGC CCTGCAGCCC     420

ACCCAGGGTG CCATGCCGGC CTTCGCCTCT GCTTTCCAGC GCCGGGCAGG AGGGGTCCTG     480

GTTGCTAGCC ATCTGCAGAG CTTCCTGGAG GTGTCGTACC GCGTTCTACG CCACCTTGCG     540

CAGCCCTCTG GCGGCTCTGG CGGCTCTCAG AGCTTCCTGC TCAAGTCTTT AGAGCAAGTG     600

AGAAAGATCC AGGGCGATGG CGCAGCGCTC CAGGAGAAGC TGTGTGCCAC CTACAAGCTG     660

TGCCACCCCG AGGAGCTGGT GCTGCTCGGA CACTCTCTGG GCATCCCCTG GGCTCCCCTG     720
```

```
AGCTCCTGCC CCAGCCAGGC CCTGCAGCTG GCAGGCTGCT TGAGCCAACT CCATAGCGGC       780

CTTTTCCTCT ACCAGGGGCT CCTGCAGGCC CTGGAAGGGA TATCCCCCGA GTTGGGTCCC       840

ACCTTGGACA CACTGCAGCT GGACGTCGCC GACTTTGCCA CCACCATCTG GCAGCAGATG       900

GAAGAACTGG GATAATAA                                                    918

(2) INFORMATION FOR SEQ ID NO:99:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:99:

ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCT CTATCCTGAT GGACCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAGT ACGTAGAGGG CGGTGGAGGC       360

TCCCCGGGTG AACCGTCTGG TCCAATCTCT ACTATCAACC CGTCTCCTCC GTCTAAAGAA       420

TCTCATAAAT CTCCAAACAT GGCTATGGCC CCTGCCCTGC AGCCCACCCA GGGTGCCATG       480

CCGGCCTTCG CCTCTGCTTT CCAGCGCCGG GCAGGAGGGG TCCTGGTTGC TAGCCATCTG       540

CAGAGCTTCC TGGAGGTGTC GTACCGCGTT CTACGCCACC TTGCGCAGCC CTCTGGCGGC       600

TCTGGCGGCT CTCAGAGCTT CCTGCTCAAG TCTTTAGAGC AAGTGAGAAA GATCCAGGGC       660

GATGGCGCAG CGCTCCAGGA GAAGCTGTGT GCCACCTACA AGCTGTGCCA CCCCGAGGAG       720

CTGGTGCTGC TCGGACACTC TCTGGGCATC CCCTGGGCTC CCCTGAGCTC CTGCCCCAGC       780

CAGGCCCTGC AGCTGGCAGG CTGCTTGAGC CAACTCCATA GCGGCCTTTT CCTCTACCAG       840

GGGCTCCTGC AGGCCCTGGA AGGGATATCC CCCGAGTTGG GTCCCACCTT GGACACACTG       900

CAGCTGGACG TCGCCGACTT TGCCACCACC ATCTGGCAGC AGATGGAAGA ACTGGGATAA       960

TAA                                                                    963

(2) INFORMATION FOR SEQ ID NO:100:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:100:

ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCT CTATCCTGAT GGACCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240
```

```
TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCTA CCCAGGGTGC CATGCCGGCC      420

TTCGCCTCTG CTTTCCAGCG CCGGGCAGGA GGGGTCCTGG TTGCTAGCCA TCTGCAGAGC      480

TTCCTGGAGG TGTCGTACCG CGTTCTACGC CACCTTGCGC AGCCCTCTGG CGGCTCTGGC      540

GGCTCTCAGA GCTTCCTGCT CAAGTCTTTA GAGCAAGTGA GAAAGATCCA GGGCGATGGC      600

GCAGCGCTCC AGGAGAAGCT GTGTGCCACC TACAAGCTGT GCCACCCCGA GGAGCTGGTG      660

CTGCTCGGAC ACTCTCTGGG CATCCCCTGG GCTCCCCTGA GCTCCTGCCC CAGCCAGGCC      720

CTGCAGCTGG CAGGCTGCTT GAGCCAACTC CATAGCGGCC TTTTCCTCTA CCAGGGGCTC      780

CTGCAGGCCC TGGAAGGGAT ATCCCCCGAG TTGGGTCCCA CCTTGGACAC ACTGCAGCTG      840

GACGTCGCCG ACTTTGCCAC CACCATCTGG CAGCAGATGG AAGAACTGGG AATGGCCCCT      900

GCCCTGCAGC CCTAATAA                                                    918

(2) INFORMATION FOR SEQ ID NO:101:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:101:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTACCCAG GGTGCCATGC CGGCCTTCGC CTCTGCTTTC      480

CAGCGCCGGG CAGGAGGGGT CCTGGTTGCT AGCCATCTGC AGAGCTTCCT GGAGGTGTCG      540

TACCGCGTTC TACGCCACCT TGCGCAGCCC TCTGGCGGCT CTGGCGGCTC TCAGAGCTTC      600

CTGCTCAAGT CTTTAGAGCA AGTGAGAAAG ATCCAGGGCG ATGGCGCAGC GCTCCAGGAG      660

AAGCTGTGTG CCACCTACAA GCTGTGCCAC CCCGAGGAGC TGGTGCTGCT CGGACACTCT      720

CTGGGCATCC CCTGGGCTCC CCTGAGCTCC TGCCCCAGCC AGGCCCTGCA GCTGGCAGGC      780

TGCTTGAGCC AACTCCATAG CGGCCTTTTC CTCTACCAGG GGCTCCTGCA GGCCCTGGAA      840

GGGATATCCC CCGAGTTGGG TCCCACCTTG GACACACTGC AGCTGGACGT CGCCGACTTT      900

GCCACCACCA TCTGGCAGCA GATGGAAGAA CTGGGAATGG CCCCTGCCCT GCAGCCCTAA      960

TAA                                                                    963

(2) INFORMATION FOR SEQ ID NO:102:

(i) SEQUENCE CHARACTERISTICS:
        (A) LENGTH: 918 base pairs
        (B) TYPE: nucleic acid
        (C) STRANDEDNESS: single
```

(D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:102:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGACCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG GTGGTTCTGG CGGCGGCTCC AACATGGCTT CTGCTTTCCA GCGCCGGGCA     420

GGAGGGGTCC TGGTTGCTAG CCATCTGCAG AGCTTCCTGG AGGTGTCGTA CCGCGTTCTA     480

CGCCACCTTG CGCAGCCCTC TGGCGGCTCT GGCGGCTCTC AGAGCTTCCT GCTCAAGTCT     540

TTAGAGCAAG TGAGAAAGAT CCAGGGCGAT GGCGCAGCGC TCCAGGAGAA GCTGTGTGCC     600

ACCTACAAGC TGTGCCACCC CGAGGAGCTG GTGCTGCTCG ACACTCTCT GGGCATCCCC      660

TGGGCTCCCC TGAGCTCCTG CCCCAGCCAG GCCCTGCAGC TGGCAGGCTG CTTGAGCCAA     720

CTCCATAGCG GCCTTTTCCT CTACCAGGGG CTCCTGCAGG CCCTGGAAGG GATATCCCCC     780

GAGTTGGGTC CCACCTTGGA CACACTGCAG CTGGACGTCG CCGACTTTGC CACCACCATC     840

TGGCAGCAGA TGGAAGAACT GGGAATGGCC CCTGCCCTGC AGCCCACCCA GGGTGCCATG     900

CCGGCCTTCG CCTAATAA                                                    918
```

(2) INFORMATION FOR SEQ ID NO:103:

(i) SEQUENCE CHARACTERISTICS:
        (A) LENGTH: 963 base pairs
        (B) TYPE: nucleic acid
        (C) STRANDEDNESS: unknown
        (D) TOPOLOGY: unknown (ii) MOLECULE TYPE: other nucleic acid
         (A) DESCRIPTION: /desc = "SYNTHETIC"

(xi) SEQUENCE DESCRIPTION: SEQ ID NO:103:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGACCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GGCTTCTGCT TTCCAGCGCC GGGCAGGAGG GGTCCTGGTT     480

GCTAGCCATC TGCAGAGCTT CCTGGAGGTG TCGTACCGCG TTCTACGCCA CCTTGCGCAG     540

CCCTCTGGCG GCTCTGGCGG CTCTCAGAGC TTCCTGCTCA AGTCTTTAGA GCAAGTGAGA     600

AAGATCCAGG GCGATGGCGC AGCGCTCCAG GAGAAGCTGT GTGCCACCTA CAAGCTGTGC     660

CACCCCGAGG AGCTGGTGCT GCTCGACACA CTCTCTGGGCA TCCCCTGGGC TCCCCTGAGC    720

TCCTGCCCCA GCCAGGCCCT GCAGCTGGCA GGCTGCTTGA GCCAACTCCA TAGCGGCCTT    780
```

```
TTCCTCTACC AGGGGCTCCT GCAGGCCCTG GAAGGGATAT CCCCCGAGTT GGGTCCCACC      840

TTGGACACAC TGCAGCTGGA CGTCGCCGAC TTTGCCACCA CCATCTGGCA GCAGATGGAA      900

GAACTGGGAA TGGCCCCTGC CCTGCAGCCC ACCCAGGGTG CCATGCCGGC CTTCGCCTAA      960

TAA                                                                    963
```

(2) INFORMATION FOR SEQ ID NO:104:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:104:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCTT ACAAGCTGTG CCACCCCGAG      420

GAGCTGGTGC TGCTCGGACA CTCTCTGGGC ATCCCCTGGG CTCCCCTGAG CTCCTGCCCC      480

AGCCAGGCCC TGCAGCTGGC AGGCTGCTTG AGCCAACTCC ATAGCGGCCT TTTCCTCTAC      540

CAGGGGCTCC TGCAGGCCCT GGAAGGGATA TCCCCCGAGT TGGGTCCCAC CTTGGACACA      600

CTGCAGCTGG ACGTCGCCGA CTTTGCCACC ACCATCTGGC AGCAGATGGA AGAACTGGGA      660

ATGGCCCCTG CCCTGCAGCC CACCCAGGGT GCCATGCCGG CCTTCGCCTC TGCTTTCCAG      720

CGCCGGGCAG GAGGGGTCCT GGTTGCTAGC CATCTGCAGA GCTTCCTGGA GGTGTCGTAC      780

CGCGTTCTAC GCCACCTTGC GCAGCCCACA CCATTGGGCC CTGCCAGCTC CCTGCCCCAG      840

AGCTTCCTGC TCAAGTCTTT AGAGCAAGTG AGAAAGATCC AGGGCGATGG CGCAGCGCTC      900

CAGGAGAAGC TGTGTGCCAC CTAATAA                                         927
```

(2) INFORMATION FOR SEQ ID NO:105:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:105:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360
```

```
TCCCCGGGTG AACCGTCTGG TCCAATCTCT ACTATCAACC CGTCTCCTCC GTCTAAAGAA    420

TCTCATAAAT CTCCAAACAT GGCTTACAAG CTGTGCCACC CCGAGGAGCT GGTGCTGCTC    480

GGACACTCTC TGGGCATCCC CTGGGCTCCC CTGAGCTCCT GCCCCAGCCA GGCCCTGCAG    540

CTGGCAGGCT GCTTGAGCCA ACTCCATAGC GGCCTTTTCC TCTACCAGGG GCTCCTGCAG    600

GCCCTGGAAG GGATATCCCC CGAGTTGGGT CCCACCTTGG ACACACTGCA GCTGGACGTC    660

GCCGACTTTG CCACCACCAT CTGGCAGCAG ATGGAAGAAC TGGGAATGGC CCCTGCCCTG    720

CAGCCCACCC AGGGTGCCAT GCCGGCCTTC GCCTCTGCTT TCCAGCGCCG GGCAGGAGGG    780

GTCCTGGTTG CTAGCCATCT GCAGAGCTTC CTGGAGGTGT CGTACCGCGT TCTACGCCAC    840

CTTGCGCAGC CCACACCATT GGGCCCTGCC AGCTCCCTGC CCCAGAGCTT CCTGCTCAAG    900

TCTTTAGAGC AAGTGAGAAA GATCCAGGGC GATGGCGCAG CGCTCCAGGA GAAGCTGTGT    960

GCCACCTAAT AA                                                       972
```

(2) INFORMATION FOR SEQ ID NO:106:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:106:

```
ATGGCTAACT GCTCTATAAT GATCGATGAA ATTATACATC ACTTAAAGAG ACCACCTGCA     60

CCTTTGCTGG ACCCGAACAA CCTCAATGAC GAAGACGTCT CTATCCTGAT GGACCGAAAC    120

CTTCGACTTC CAAACCTGGA GAGCTTCGTA AGGGCTGTCA AGAACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAGAGGG CGGTGGAGGC    360

TCCCCGGGTG GTGGTTCTGG CGGCGGCTCC AACATGGCTC CGAGTTGGG TCCCACCTTG    420

GACACACTGC AGCTGGACGT CGCCGACTTT GCCACCACCA TCTGGCAGCA GATGGAAGAA    480

CTGGGAATGG CCCCTGCCCT GCAGCCCACC CAGGGTGCCA TGCCGGCCTT CGCCTCTGCT    540

TTCCAGCGCC GGGCAGGAGG GGTCCTGGTT GCTAGCCATC TGCAGAGCTT CCTGGAGGTG    600

TCGTACCGCG TTCTACGCCA CCTTGCGCAG CCCACACCAT TGGGCCCTGC CAGCTCCCTG    660

CCCCAGAGCT TCCTGCTCAA GTCTTTAGAG CAAGTGAGAA AGATCCAGGG CGATGGCGCA    720

GCGCTCCAGG AGAAGCTGTG TGCCACCTAC AAGCTGTGCC ACCCCGAGGA GCTGGTGCTG    780

CTCGGACACT CTCTGGGCAT CCCCTGGGCT CCCCTGAGCT CCTGCCCCAG CCAGGCCCTG    840

CAGCTGGCAG GCTGCTTGAG CCAACTCCAT AGCGGCCTTT TCCTCTACCA GGGGCTCCTG    900

CAGGCCCTGG AAGGGATATC CTAATAA                                       927
```

(2) INFORMATION FOR SEQ ID NO:107:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "DNA (synthetic)"

(xi) SEQUENCE DESCRIPTION: SEQ ID NO:107:

| | | | | | |
|---|---|---|---|---|---|
| ATGGCTAACT | GCTCTATAAT | GATCGATGAA | ATTATACATC | ACTTAAAGAG | ACCACCTGCA | 60 |
| CCTTTGCTGG | ACCCGAACAA | CCTCAATGAC | GAAGACGTCT | CTATCCTGAT | GGACCGAAAC | 120 |
| CTTCGACTTC | CAAACCTGGA | GAGCTTCGTA | AGGGCTGTCA | AGAACTTAGA | AAATGCATCA | 180 |
| GGTATTGAGG | CAATTCTTCG | TAATCTCCAA | CCATGTCTGC | CCTCTGCCAC | GGCCGCACCC | 240 |
| TCTCGACATC | CAATCATCAT | CAAGGCAGGT | GACTGGCAAG | AATTCCGGGA | AAAACTGACG | 300 |
| TTCTATCTGG | TTACCCTTGA | GCAAGCGCAG | GAACAACAGT | ACGTAGAGGG | CGGTGGAGGC | 360 |
| TCCCCGGGTG | AACCGTCTGG | TCCAATCTCT | ACTATCAACC | CGTCTCCTCC | GTCTAAAGAA | 420 |
| TCTCATAAAT | CTCCAAACAT | GGCTCCCGAG | TTGGGTCCCA | CCTTGGACAC | ACTGCAGCTG | 480 |
| GACGTCGCCG | ACTTTGCCAC | CACCATCTGG | CAGCAGATGG | AAGAACTGGG | AATGGCCCCT | 540 |
| GCCCTGCAGC | CCACCCAGGG | TGCCATGCCG | GCCTTCGCCT | CTGCTTTCCA | GCGCCGGGCA | 600 |
| GGAGGGGTCC | TGGTTGCTAG | CCATCTGCAG | AGCTTCCTGG | AGGTGTCGTA | CCGCGTTCTA | 660 |
| CGCCACCTTG | CGCAGCCCAC | ACCATTGGGC | CCTGCCAGCT | CCCTGCCCCA | GAGCTTCCTG | 720 |
| CTCAAGTCTT | TAGAGCAAGT | GAGAAAGATC | CAGGGCGATG | GCGCAGCGCT | CCAGGAGAAG | 780 |
| CTGTGTGCCA | CCTACAAGCT | GTGCCACCCC | GAGGAGCTGG | TGCTGCTCGG | ACACTCTCTG | 840 |
| GGCATCCCCT | GGGCTCCCCT | GAGCTCCTGC | CCCAGCCAGG | CCCTGCAGCT | GGCAGGCTGC | 900 |
| TTGAGCCAAC | TCCATAGCGG | CCTTTTCCTC | TACCAGGGGC | TCCTGCAGGC | CCTGGAAGGG | 960 |
| ATATCCTAAT | AA | | | | | 972 |

(2) INFORMATION FOR SEQ ID NO:108:

(i) SEQUENCE CHARACTERISTICS:
(A) LENGTH: 927 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(xi) SEQUENCE DESCRIPTION: SEQ ID NO:108:

| | | | | | |
|---|---|---|---|---|---|
| ATGGCTAACT | GCTCTATAAT | GATCGATGAA | ATTATACATC | ACTTAAAGAG | ACCACCTGCA | 60 |
| CCTTTGCTGG | ACCCGAACAA | CCTCAATGAC | GAAGACGTCT | CTATCCTGAT | GGACCGAAAC | 120 |
| CTTCGACTTC | CAAACCTGGA | GAGCTTCGTA | AGGGCTGTCA | AGAACTTAGA | AAATGCATCA | 180 |
| GGTATTGAGG | CAATTCTTCG | TAATCTCCAA | CCATGTCTGC | CCTCTGCCAC | GGCCGCACCC | 240 |
| TCTCGACATC | CAATCATCAT | CAAGGCAGGT | GACTGGCAAG | AATTCCGGGA | AAAACTGACG | 300 |
| TTCTATCTGG | TTACCCTTGA | GCAAGCGCAG | GAACAACAGT | ACGTAGAGGG | CGGTGGAGGC | 360 |
| TCCCCGGGTG | GTGGTTCTGG | CGGCGGCTCC | AACATGGCTA | TGGCCCCTGC | CCTGCAGCCC | 420 |
| ACCCAGGGTG | CCATGCCGGC | CTTCGCCTCT | GCTTTCCAGC | GCCGGGCAGG | AGGGGTCCTG | 480 |
| GTTGCTAGCC | ATCTGCAGAG | CTTCCTGGAG | GTGTCGTACC | GCGTTCTACG | CCACCTTGCG | 540 |
| CAGCCCACAC | CATTGGGCCC | TGCCAGCTCC | CTGCCCAGA | GCTTCCTGCT | CAAGTCTTTA | 600 |
| GAGCAAGTGA | GAAAGATCCA | GGGCGATGGC | GCAGCGCTCC | AGGAGAAGCT | GTGTGCCACC | 660 |
| TACAAGCTGT | GCCACCCCGA | GGAGCTGGTG | CTGCTCGGAC | ACTCTCTGGG | CATCCCCTGG | 720 |
| GCTCCCCTGA | GCTCCTGCCC | CAGCCAGGCC | CTGCAGCTGG | CAGGCTGCTT | GAGCCAACTC | 780 |
| CATAGCGGCC | TTTTCCTCTA | CCAGGGGCTC | CTGCAGGCCC | TGGAAGGGAT | ATCCCCCGAG | 840 |

```
TTGGGTCCCA CCTTGGACAC ACTGCAGCTG GACGTCGCCG ACTTTGCCAC CACCATCTGG      900

CAGCAGATGG AAGAACTGGG ATAATAA                                          927
```

(2) INFORMATION FOR SEQ ID NO:109:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:109:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTATGGCC CCTGCCCTGC AGCCCACCCA GGGTGCCATG      480

CCGGCCTTCG CCTCTGCTTT CCAGCGCCGG GCAGGAGGGG TCCTGGTTGC TAGCCATCTG      540

CAGAGCTTCC TGGAGGTGTC GTACCGCGTT CTACGCCACC TTGCGCAGCC CACACCATTG      600

GGCCCTGCCA GCTCCCTGCC CCAGAGCTTC CTGCTCAAGT CTTTAGAGCA AGTGAGAAAG      660

ATCCAGGGCG ATGGCGCAGC GCTCCAGGAG AAGCTGTGTG CCACCTACAA GCTGTGCCAC      720

CCCGAGGAGC TGGTGCTGCT CGGACACTCT CTGGGCATCC CCTGGGCTCC CCTGAGCTCC      780

TGCCCCAGCC AGGCCCTGCA GCTGGCAGGC TGCTTGAGCC AACTCCATAG CGGCCTTTTC      840

CTCTACCAGG GGCTCCTGCA GGCCCTGGAA GGGATATCCC CCGAGTTGGG TCCCACCTTG      900

GACACACTGC AGCTGGACGT CGCCGACTTT GCCACCACCA TCTGGCAGCA GATGGAAGAA      960

CTGGGATAAT AA                                                         972
```

(2) INFORMATION FOR SEQ ID NO:110:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:110:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360
```

-continued

```
TCCCCGGGTG GTGGTTCTGG CGGCGGCTCC AACATGGCTA CCCAGGGTGC CATGCCGGCC      420

TTCGCCTCTG CTTTCCAGCG CCGGGCAGGA GGGGTCCTGG TTGCTAGCCA TCTGCAGAGC      480

TTCCTGGAGG TGTCGTACCG CGTTCTACGC CACCTTGCGC AGCCCACACC ATTGGGCCCT      540

GCCAGCTCCC TGCCCCAGAG CTTCCTGCTC AAGTCTTTAG AGCAAGTGAG AAAGATCCAG      600

GGCGATGGCG CAGCGCTCCA GGAGAAGCTG TGTGCCACCT ACAAGCTGTG CCACCCCGAG      660

GAGCTGGTGC TGCTCGGACA CTCTCTGGGC ATCCCCTGGG CTCCCCTGAG CTCCTGCCCC      720

AGCCAGGCCC TGCAGCTGGC AGGCTGCTTG AGCAACTCC ATAGCGGCCT TTTCCTCTAC       780

CAGGGGCTCC TGCAGGCCCT GGAAGGGATA TCCCCCGAGT TGGGTCCCAC CTTGGACACA      840

CTGCAGCTGG ACGTCGCCGA CTTTGCCACC ACCATCTGGC AGCAGATGGA AGAACTGGGA      900

ATGGCCCCTG CCCTGCAGCC CTAATAA                                         927
```

(2) INFORMATION FOR SEQ ID NO:111:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:111:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGACCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTACCCAG GGTGCCATGC CGGCCTTCGC CTCTGCTTTC      480

CAGCGCCGGG CAGGAGGGGT CCTGGTTGCT AGCCATCTGC AGAGCTTCCT GGAGGTGTCG      540

TACCGCGTTC TACGCCACCT TGCGCAGCCC ACACCATTGG GCCCTGCCAG CTCCCTGCCC      600

CAGAGCTTCC TGCTCAAGTC TTTAGAGCAA GTGAGAAAGA TCCAGGGCGA TGGCGCAGCG      660

CTCCAGGAGA AGCTGTGTGC CACCTACAAG CTGTGCCACC CCGAGGAGCT GGTGCTGCTC      720

GGACACTCTC TGGGCATCCC CTGGGCTCCC TGAGCTCCT GCCCCAGCCA GGCCCTGCAG       780

CTGGCAGGCT GCTTGAGCCA ACTCCATAGC GGCCTTTTCC TCTACCAGGG GCTCCTGCAG      840

GCCCTGGAAG GGATATCCCC CGAGTTGGGT CCCACCTTGG ACACACTGCA GCTGGACGTC      900

GCCGACTTTG CCACCACCAT CTGGCAGCAG ATGGAAGAAC TGGGAATGGC CCCTGCCCTG      960

CAGCCCTAAT AA                                                         972
```

(2) INFORMATION FOR SEQ ID NO:112:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:112:

```
ATGGCTAACT GCTCTATAAT GATCGATGAA ATTATACATC ACTTAAAGAG ACCACCTGCA        60
CCTTTGCTGG ACCCGAACAA CCTCAATGAC GAAGACGTCT CTATCCTGAT GGACCGAAAC       120
CTTCGACTTC CAAACCTGGA GAGCTTCGTA AGGGCTGTCA AGAACTTAGA AAATGCATCA       180
GGTATTGAGG CAATTCTTCG TAATCTCCAA CCATGTCTGC CCTCTGCCAC GGCCGCACCC       240
TCTCGACATC CAATCATCAT CAAGGCAGGT GACTGGCAAG AATTCCGGGA AAAACTGACG       300
TTCTATCTGG TTACCCTTGA GCAAGCGCAG GAACAACAGT ACGTAGAGGG CGGTGGAGGC       360
TCCCCGGGTG GTGGTTCTGG CGGCGGCTCC AACATGGCTT CTGCTTTCCA GCGCCGGGCA       420
GGAGGGGTCC TGGTTGCTAG CCATCTGCAG AGCTTCCTGG AGGTGTCGTA CCGCGTTCTA       480
CGCCACCTTG CGCAGCCCAC ACCATTGGGC CCTGCCAGCT CCCTGCCCCA GAGCTTCCTG       540
CTCAAGTCTT TAGAGCAAGT GAGAAAGATC CAGGGCGATG GCGCAGCGCT CCAGGAGAAG       600
CTGTGTGCCA CCTACAAGCT GTGCCACCCC GAGGAGCTGG TGCTGCTCGG ACACTCTCTG       660
GGCATCCCCT GGGCTCCCCT GAGCTCCTGC CCCAGCCAGG CCCTGCAGCT GGCAGGCTGC       720
TTGAGCCAAC TCCATAGCGG CCTTTTCCTC TACCAGGGGC TCCTGCAGGC CCTGGAAGGG       780
ATATCCCCCG AGTTGGGTCC CACCTTGGAC ACACTGCAGC TGGACGTCGC CGACTTTGCC       840
ACCACCATCT GGCAGCAGAT GGAAGAACTG GGAATGGCCC CTGCCCTGCA GCCCACCCAG       900
GGTGCCATGC CGGCCTTCGC CTAATAA                                           927
```

(2) INFORMATION FOR SEQ ID NO:113:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:113:

```
ATGGCTAACT GCTCTATAAT GATCGATGAA ATTATACATC ACTTAAAGAG ACCACCTGCA        60
CCTTTGCTGG ACCCGAACAA CCTCAATGAC GAAGACGTCT CTATCCTGAT GGACCGAAAC       120
CTTCGACTTC CAAACCTGGA GAGCTTCGTA AGGGCTGTCA AGAACTTAGA AAATGCATCA       180
GGTATTGAGG CAATTCTTCG TAATCTCCAA CCATGTCTGC CCTCTGCCAC GGCCGCACCC       240
TCTCGACATC CAATCATCAT CAAGGCAGGT GACTGGCAAG AATTCCGGGA AAAACTGACG       300
TTCTATCTGG TTACCCTTGA GCAAGCGCAG GAACAACAGT ACGTAGAGGG CGGTGGAGGC       360
TCCCCGGGTG AACCGTCTGG TCCAATCTCT ACTATCAACC CGTCTCCTCC GTCTAAAGAA       420
TCTCATAAAT CTCCAAACAT GGCTTCTGCT TTCCAGCGCC GGGCAGGAGG GGTCCTGGTT       480
GCTAGCCATC TGCAGAGCTT CCTGGAGGTG TCGTACCGCG TTCTACGCCA CCTTGCGCAG       540
CCCACACCAT TGGGCCCTGC CAGCTCCCTG CCCCAGAGCT TCCTGCTCAA GTCTTTAGAG       600
CAAGTGAGAA AGATCCAGGG CGATGGCGCA GCGCTCCAGG AGAAGCTGTG TGCCACCTAC       660
AAGCTGTGCC ACCCCGAGGA GCTGGTGCTG CTCGGACACT CTCTGGGCAT CCCCTGGGCT       720
CCCCTGAGCT CCTGCCCCAG CCAGGCCCTG CAGCTGGCAG GCTGCTTGAG CCAACTCCAT       780
AGCGGCCTTT TCCTCTACCA GGGGCTCCTG CAGGCCCTGG AAGGGATATC CCCCGAGTTG       840
GGTCCCACCT TGGACACACT GCAGCTGGAC GTCGCCGACT TTGCCACCAC CATCTGGCAG       900
```

| CAGATGGAAG AACTGGGAAT GGCCCCTGCC CTGCAGCCCA CCCAGGGTGC CATGCCGGCC | 960 |
| TTCGCCTAAT AA | 972 |

(2) INFORMATION FOR SEQ ID NO:114:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:114:

| ATGGCTAACT GCTCTAACAT GATCGATGAA ATCATCACCC ACCTGAAGCA GCCACCGCTG | 60 |
| CCGCTGCTGG ACTTCAACAA CCTCAATGGT GAAGACCAAG ATATCCTAAT GGACAATAAC | 120 |
| CTTCGTCGTC CAAACCTCGA GGCATTCAAC CGTGCTGTCA AGTCTCTGCA GAATGCATCA | 180 |
| GCAATTGAGA GCATTCTTAA AAATCTCCTG CCATGTCTGC CGCTAGCCAC GGCCGCACCC | 240 |
| ACGCGACATC CAATCCATAT CAAGGACGGT GACTGGAATG AATTCCGTCG TAAACTGACC | 300 |
| TTCTATCTGA AAACCTTGGA GAACGCGCAG GCTCAACAGT ACGTAGAGGG CGGTGGAGGC | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTACCCAG GGTGCCATGC CGGCCTTCGC CTCTGCTTTC | 480 |
| CAGCGCCGGG CAGGAGGGGT CCTGGTTGCT AGCCATCTGC AGAGCTTCCT GGAGGTGTCG | 540 |
| TACCGCGTTC TACGCCACCT TGCGCAGCCC TCTGGCGGCT CTGGCGGCTC TCAGAGCTTC | 600 |
| CTGCTCAAGT CTTTAGAGCA AGTGAGAAAG ATCCAGGGCG ATGGCGCAGC GCTCCAGGAG | 660 |
| AAGCTGTGTG CCACCTACAA GCTGTGCCAC CCCGAGGAGC TGGTGCTGCT CGGACACTCT | 720 |
| CTGGGCATCC CCTGGGCTCC CCTGAGCTCC TGCCCCAGCC AGGCCCTGCA GCTGGCAGGC | 780 |
| TGCTTGAGCC AACTCCATAG CGGCCTTTTC CTCTACCAGG GGCTCCTGCA GGCCCTGGAA | 840 |
| GGGATATCCC CCGAGTTGGG TCCCACCTTG GACACACTGC AGCTGGACGT CGCCGACTTT | 900 |
| GCCACCACCA TCTGGCAGCA GATGGAAGAA CTGGGAATGG CCCCTGCCCT GCAGCCCTAA | 960 |
| TAA | 963 |

(2) INFORMATION FOR SEQ ID NO:115:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:115:

| ATGGCTAACT GCTCTAACAT GATCGATGAA ATCATCACCC ACCTGAAGCA GCCACCGCTG | 60 |
| CCGCTGCTGG ACTTCAACAA CCTCAATGGT GAAGACCAAG ATATCCTGAT GGAAAATAAC | 120 |
| CTTCGTCGTC CAAACCTCGA GGCATTCAAC CGTGCTGTCA AGTCTCTGCA GAATGCATCA | 180 |
| GCAATTGAGA GCATTCTTAA AAATCTCCTG CCATGTCTGC CCCTGGCCAC GGCCGCACCC | 240 |
| ACGCGACATC CAATCATCAT CCGTGACGGT GACTGGAATG AATTCCGTCG TAAACTGACC | 300 |
| TTCTATCTGA AAACCTTGGA GAACGCGCAG GCTCAACAGT ACGTAGAGGG CGGTGGAGGC | 360 |
| TCCCCGGGTG AACCGTCTGG TCCAATCTCT ACTATCAACC CGTCTCCTCC GTCTAAAGAA | 420 |

| | |
|---|---|
| TCTCATAAAT CTCCAAACAT GGCTACCCAG GGTGCCATGC CGGCCTTCGC CTCTGCTTTC | 480 |
| CAGCGCCGGG CAGGAGGGGT CCTGGTTGCT AGCCATCTGC AGAGCTTCCT GGAGGTGTCG | 540 |
| TACCGCGTTC TACGCCACCT TGCGCAGCCC ACACCATTGG GCCCTGCCAG CTCCCTGCCC | 600 |
| CAGAGCTTCC TGCTCAAGTC TTTAGAGCAA GTGAGAAAGA TCCAGGGCGA TGGCGCAGCG | 660 |
| CTCCAGGAGA AGCTGTGTGC CACCTACAAG CTGTGCCACC CCGAGGAGCT GGTGCTGCTC | 720 |
| GGACACTCTC TGGGCATCCC CTGGGCTCCC CTGAGCTCCT GCCCCAGCCA GGCCCTGCAG | 780 |
| CTGGCAGGCT GCTTGAGCCA ACTCCATAGC GGCCTTTTCC TCTACCAGGG GCTCCTGCAG | 840 |
| GCCCTGGAAG GGATATCCCC CGAGTTGGGT CCCACCTTGG ACACACTGCA GCTGGACGTC | 900 |
| GCCGACTTTG CCACCACCAT CTGGCAGCAG ATGGAAGAAC TGGGAATGGC CCCTGCCCTG | 960 |
| CAGCCCTAAT AA | 972 |

(2) INFORMATION FOR SEQ ID NO:116:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:116:

| | |
|---|---|
| ATGGCTAACT GCTCTAACAT GATCGATGAA ATCATCACCC ACCTGAAGCA GCCACCGCTG | 60 |
| CCGCTGCTGG ACTTCAACAA CCTCAATGGT GAAGACCAAG ATATCCTGAT GGAAAATAAC | 120 |
| CTTCGTCGTC CAAACCTCGA GGCATTCAAC CGTGCTGTCA AGTCTCTGCA GAATGCATCA | 180 |
| GCAATTGAGA GCATTCTTAA AAATCTCCTG CCATGTCTGC CCCTGGCCAC GGCCGCACCC | 240 |
| ACGCGACATC CAATCATCAT CCGTGACGGT GACTGGAATG AATTCCGTCG TAAACTGACC | 300 |
| TTCTATCTGA AAACCTTGGA GAACGCGCAG GCTCAACAGT ACGTAGAGGG CGGTGGAGGC | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTACCCAG GGTGCCATGC CGGCCTTCGC CTCTGCTTTC | 480 |
| CAGCGCCGGG CAGGAGGGGT CCTGGTTGCT AGCCATCTGC AGAGCTTCCT GGAGGTGTCG | 540 |
| TACCGCGTTC TACGCCACCT TGCGCAGCCC TCTGGCGGCT CTGGCGGCTC TCAGAGCTTC | 600 |
| CTGCTCAAGT CTTTAGAGCA AGTGAGAAAG ATCAGGGCG ATGGCGCAGC GCTCCAGGAG | 660 |
| AAGCTGTGTG CCACCTACAA GCTGTGCCAC CCCGAGGAGC TGGTGCTGCT CGGACACTCT | 720 |
| CTGGGCATCC CCTGGGCTCC CCTGAGCTCC TGCCCCAGCC AGGCCCTGCA GCTGGCAGGC | 780 |
| TGCTTGAGCC AACTCCATAG CGGCCTTTTC CTCTACCAGG GGCTCCTGCA GGCCCTGGAA | 840 |
| GGGATATCCC CCGAGTTGGG TCCCACCTTG GACACACTGC AGCTGGACGT CGCCGACTTT | 900 |
| GCCACCACCA TCTGGCAGCA GATGGAAGAA CTGGGAATGG CCCCTGCCCT GCAGCCCTAA | 960 |
| TAA | 963 |

(2) INFORMATION FOR SEQ ID NO:117:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "synthetic"

(xi) SEQUENCE DESCRIPTION: SEQ ID NO:117:

ATGGCTAACT GCTCTAACAT GATCGATGAA ATCATCACCC ACCTGAAGCA GCCACCGCTG      60

CCGCTGCTGG ACTTCAACAA CCTCAATGGT GAAGACCAAG ATATCCTAAT GGACAATAAC     120

CTTCGTCGTC CAAACCTCGA GGCATTCAAC CGTGCTGTCA AGTCTCTGCA GAATGCATCA     180

GCAATTGAGA GCATTCTTAA AAATCTCCTG CCATGTCTGC CGCTAGCCAC GGCCGCACCC     240

ACGCGACATC CAATCCATAT CAAGGACGGT GACTGGAATG AATTCCGTCG TAAACTGACC     300

TTCTATCTGA AAACCTTGGA GAACGCGCAG GCTCAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GGCTACCCAG GGTGCCATGC CGGCCTTCGC CTCTGCTTTC     480

CAGCGCCGGG CAGGAGGGGT CCTGGTTGCT AGCCATCTGC AGAGCTTCCT GGAGGTGTCG     540

TACCGCGTTC TACGCCACCT TGCGCAGCCC ACACCATTGG GCCCTGCCAG CTCCCTGCCC     600

CAGAGCTTCC TGCTCAAGTC TTTAGAGCAA GTGAGAAAGA TCCAGGGCGA TGGCGCAGCG     660

CTCCAGGAGA AGCTGTGTGC CACCTACAAG CTGTGCCACC CGAGGAGCT GGTGCTGCTC      720

GGACACTCTC TGGGCATCCC CTGGGCTCCC CTGAGCTCCT GCCCCAGCCA GGCCCTGCAG     780

CTGGCAGGCT GCTTGAGCCA ACTCCATAGC GGCCTTTTCC TCTACCAGGG GCTCCTGCAG     840

GCCCTGGAAG GGATATCCCC CGAGTTGGGT CCCACCTTGG ACACACTGCA GCTGGACGTC     900

GCCGACTTTG CCACCACCAT CTGGCAGCAG ATGGAAGAAC TGGGAATGGC CCCTGCCCTG     960

CAGCCCTAAT AA                                                        972

(2) INFORMATION FOR SEQ ID NO:118:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:118:

GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGA GGTTCACCCT TTGCCTACAC CTGTCCTGCT GCCTGCTGTG     480

GACTTTAGCT TGGGAGAATG GAAAACCCAG ATGGAGGAGA CCAAGGCACA GGACATTCTG     540

GGAGCAGTGA CCCTTCTGCT GGAGGGAGTG ATGGCAGCAC GGGGACAACT GGGACCCACT     600

TGCCTCTCAT CCCTCCTGGG GCAGCTTTCT GGACAGGTCC GTCTCCTCCT TGGGGCCCTG     660

CAGAGCCTCC TTGGAACCCA GCTTCCTCCA CAGGGCAGGA CCACAGCTCA AAGGATCCC      720

AATGCCATCT TCCTGAGCTT CCAACACCTG CTCCGAGGAA AGGTGCGTTT CCTGATGCTT     780

GTAGGAGGGT CCACCCTCTG CGTCAGGGAA TTCGGCGGCA ACATGGCGTC TCCCGCTCCG     840

```
CCTGCTTGTG ACCTCCGAGT CCTCAGTAAA CTGCTTCGTG ACTCCCATGT CCTTCACAGC        900

AGACTGAGCC AGTGCCCA                                                      918

(2) INFORMATION FOR SEQ ID NO:119:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:119:

GCTAACTGCT CTATAATGAT CGATGAAATT ATACATCACT TAAAGAGACC ACCTGCACCT         60

TTGCTGGACC CGAACAACCT CAATGACGAA GACGTCTCTA TCCTGATGGA CCGAAACCTT        120

CGACTTCCAA ACCTGGAGAG CTTCGTAAGG GCTGTCAAGA ACTTAGAAAA TGCATCAGGT        180

ATTGAGGCAA TTCTTCGTAA TCTCCAACCA TGTCTGCCCT CTGCCACGGC CGCACCCTCT        240

CGACATCCAA TCATCATCAA GGCAGGTGAC TGGCAAGAAT TCCGGGAAAA ACTGACGTTC        300

TATCTGGTTA CCCTTGAGCA AGCGCAGGAA CAACAGTACG TAGAGGGCGG TGGAGGCTCC        360

CCGGGTGAAC CGTCTGGTCC AATCTCTACT ATCAACCCGT CTCCTCCGTC TAAAGAATCT        420

CATAAATCTC CAAACATGTT GCCTACACCT GTCCTGCTGC CTGCTGTGGA CTTTAGCTTG        480

GGAGAATGGA AAACCCAGAT GGAGGAGACC AAGGCACAGG ACATTCTGGG AGCAGTGACC        540

CTTCTGCTGG AGGGAGTGAT GGCAGCACGG GGACAACTGG GACCCACTTG CCTCTCATCC        600

CTCCTGGGGC AGCTTTCTGG ACAGGTCCGT CTCCTCCTTG GGGCCCTGCA GAGCCTCCTT        660

GGAACCCAGC TTCCTCCACA GGGCAGGACC ACAGCTCACA AGGATCCCAA TGCCATCTTC        720

CTGAGCTTCC AACACCTGCT CCGAGGAAAG GTGCGTTTCC TGATGCTTGT AGGAGGGTCC        780

ACCCTCTGCG TCAGGGAATT CGGCGGCAAC ATGGCGTCTC CCGCTCCGCC TGCTTGTGAC        840

CTCCGAGTCC TCAGTAAACT GCTTCGTGAC TCCCATGTCC TTCACAGCAG ACTGAGCCAG        900

TGCCCAGAGG TTCACCCT                                                     918

(2) INFORMATION FOR SEQ ID NO:120:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:120:

GCTAACTGCT CTATAATGAT CGATGAAATT ATACATCACT TAAAGAGACC ACCTGCACCT         60

TTGCTGGACC CGAACAACCT CAATGACGAA GACGTCTCTA TCCTGATGGA CCGAAACCTT        120

CGACTTCCAA ACCTGGAGAG CTTCGTAAGG GCTGTCAAGA ACTTAGAAAA TGCATCAGGT        180

ATTGAGGCAA TTCTTCGTAA TCTCCAACCA TGTCTGCCCT CTGCCACGGC CGCACCCTCT        240

CGACATCCAA TCATCATCAA GGCAGGTGAC TGGCAAGAAT TCCGGGAAAA ACTGACGTTC        300

TATCTGGTTA CCCTTGAGCA AGCGCAGGAA CAACAGTACG TAGAGGGCGG TGGAGGCTCC        360

CCGGGTGAAC CGTCTGGTCC AATCTCTACT ATCAACCCGT CTCCTCCGTC TAAAGAATCT        420
```

| | |
|---|---:|
| CATAAATCTC CAAACATGGT CCTGCTGCCT GCTGTGGACT TTAGCTTGGG AGAATGGAAA | 480 |
| ACCCAGATGG AGGAGACCAA GGCACAGGAC ATTCTGGGAG CAGTGACCCT TCTGCTGGAG | 540 |
| GGAGTGATGG CAGCACGGGG ACAACTGGGA CCCACTTGCC TCTCATCCCT CCTGGGGCAG | 600 |
| CTTTCTGGAC AGGTCCGTCT CCTCCTTGGG GCCCTGCAGA GCCTCCTTGG AACCCAGCTT | 660 |
| CCTCCACAGG GCAGGACCAC AGCTCACAAG GATCCCAATG CCATCTTCCT GAGCTTCCAA | 720 |
| CACCTGCTCC GAGGAAAGGT GCGTTTCCTG ATGCTTGTAG GAGGGTCCAC CCTCTGCGTC | 780 |
| AGGGAATTCG GCGGCAACAT GGCGTCTCCC GCTCCGCCTG CTTGTGACCT CCGAGTCCTC | 840 |
| AGTAAACTGC TTCGTGACTC CCATGTCCTT CACAGCAGAC TGAGCCAGTG CCCAGAGGTT | 900 |
| CACCCTTTGC CTACACCT | 918 |

(2) INFORMATION FOR SEQ ID NO:121:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:121:

| | |
|---|---:|
| GCTAACTGCT CTATAATGAT CGATGAAATT ATACATCACT TAAAGAGACC ACCTGCACCT | 60 |
| TTGCTGGACC CGAACAACCT CAATGACGAA GACGTCTCTA TCCTGATGGA CCGAAACCTT | 120 |
| CGACTTCCAA ACCTGGAGAG CTTCGTAAGG GCTGTCAAGA ACTTAGAAAA TGCATCAGGT | 180 |
| ATTGAGGCAA TTCTTCGTAA TCTCCAACCA TGTCTGCCCT CTGCCACGGC CGCACCCTCT | 240 |
| CGACATCCAA TCATCATCAA GGCAGGTGAC TGGCAAGAAT TCCGGGAAAA ACTGACGTTC | 300 |
| TATCTGGTTA CCCTTGAGCA AGCGCAGGAA CAACAGTACG TAGAGGGCGG TGGAGGCTCC | 360 |
| CCGGGTGAAC CGTCTGGTCC AATCTCTACT ATCAACCCGT CTCCTCCGTC TAAAGAATCT | 420 |
| CATAAATCTC CAAACATGGC TGTGGACTTT AGCTTGGGAG AATGGAAAAC CCAGATGGAG | 480 |
| GAGACCAAGG CACAGGACAT TCTGGGAGCA GTGACCCTTC TGCTGGAGGG AGTGATGGCA | 540 |
| GCACGGGGAC AACTGGGACC CACTTGCCTC TCATCCCTCC TGGGGCAGCT TTCTGGACAG | 600 |
| GTCCGTCTCC TCCTTGGGGC CCTGCAGAGC CTCCTTGGAA CCCAGCTTCC TCCACAGGGC | 660 |
| AGGACCACAG CTCACAAGGA TCCCAATGCC ATCTTCCTGA GCTTCCAACA CCTGCTCCGA | 720 |
| GGAAAGGTGC GTTTCCTGAT GCTTGTAGGA GGGTCCACCC TCTGCGTCAG GGAATTCGGC | 780 |
| GGCAACATGG CGTCTCCCGC TCCGCCTGCT TGTGACCTCC GAGTCCTCAG TAAACTGCTT | 840 |
| CGTGACTCCC ATGTCCTTCA GCAGACTG AGCCAGTGCC AGAGGTTCA CCCTTTGCCT | 900 |
| ACACCTGTCC TGCTGCCT | 918 |

(2) INFORMATION FOR SEQ ID NO:122:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:122:

| | |
|---|---:|
| GCTAACTGCT CTATAATGAT CGATGAAATT ATACATCACT TAAAGAGACC ACCTGCACCT | 60 |

```
TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGA CTTTAGCTTG GGAGAATGGA AAACCCAGAT GGAGGAGACC      480

AAGGCACAGG ACATTCTGGG AGCAGTGACC CTTCTGCTGG AGGGAGTGAT GGCAGCACGG      540

GGACAACTGG GACCCACTTG CCTCTCATCC CTCCTGGGGC AGCTTTCTGG ACAGGTCCGT      600

CTCCTCCTTG GGGCCCTGCA GAGCCTCCTT GGAACCCAGC TTCCTCCACA GGGCAGGACC      660

ACAGCTCACA AGGATCCCAA TGCCATCTTC CTGAGCTTCC AACACCTGCT CCGAGGAAAG      720

GTGCGTTTCC TGATGCTTGT AGGAGGGTCC ACCCTCTGCG TCAGGGAATT CGGCGGCAAC      780

ATGGCGTCTC CCGCTCCGCC TGCTTGTGAC CTCCGAGTCC TCAGTAAACT GCTTCGTGAC      840

TCCCATGTCC TTCACAGCAG ACTGAGCCAG TGCCCAGAGG TTCACCCTTT GCCTACACCT      900

GTCCTGCTGC CTGCTGTG                                                   918
```

(2) INFORMATION FOR SEQ ID NO:123:

(i) SEQUENCE CHARACTERISTICS:
        (A) LENGTH: 907 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:123:

```
GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCGGTTAC CCTTGAGCAA GCGCAGGAAC AACAGTACGT AGAGGGCGGT GGAGGCTCCC      360

CGGGGAACCG TCTGGTCCAA TCTCTACTAT CAACCCGTCT CCTCCGTCTA AAGAATCTCA      420

TAAACTCCAA ACATGGGAGA ATGGAAAACC CAGATGGAGG AGACCAAGGC ACAGGACATT      480

CTGGAGCAGT GACCCTTCTG CTGGAGGGAG TGATGGCAGC ACGGGGACAA CTGGGACCCA      540

CTTGCTCTCA TCCCTCCTGG GGCAGCTTTC TGGACAGGTC CGTCTCCTCC TTGGGGCCCT      600

GCAGGCCTCC TTGGAACCCA GCTTCCTCCA CAGGGCAGGA CCACAGCTCA CAAGGATCCC      660

AATGCATCTT CCTGAGCTTC CAACACCTGC TCCGAGGAAA GGTGCGTTTC CTGATGCTTG      720

TAGGGGGTCC ACCCTCTGCG TCAGGGAATT CGGCGGCAAC ATGGCGTCTC CCGCTCCGCC      780

TGCTGTGACC TCCGAGTCCT CAGTAAACTG CTTCGTGACT CCCATGTCCT TCACAGCAGA      840

CTGACCAGTG CCCAGAGGTT CACCCTTTGC CTACACCTGT CCTGCTGCCT GCTGTGGACT      900

TTAGTTG                                                               907
```

(2) INFORMATION FOR SEQ ID NO:124:

(i) SEQUENCE CHARACTERISTICS:
    (A) LENGTH: 918 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic"

(xi) SEQUENCE DESCRIPTION: SEQ ID NO:124:

```
GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGG ACCCACTTGC CTCTCATCCC TCCTGGGGCA GCTTTCTGGA     480

CAGGTCCGTC TCCTCCTTGG GGCCCTGCAG AGCCTCCTTG GAACCCAGCT TCCTCCACAG     540

GGCAGGACCA CAGCTCACAA GGATCCCAAT GCCATCTTCC TGAGCTTCCA ACACCTGCTC     600

CGAGGAAAGG TGCGTTTCCT GATGCTTGTA GGAGGGTCCA CCCTCTGCGT CAGGGAATTC     660

GGCGGCAACA TGGCGTCTCC CGCTCCGCCT GCTTGTGACC TCCGAGTCCT CAGTAAACTG     720

CTTCGTGACT CCCATGTCCT TCACAGCAGA CTGAGCCAGT GCCCAGAGGT TCACCCTTTG     780

CCTACACCTG TCCTGCTGCC TGCTGTGGAC TTTAGCTTGG GAGAATGGAA AACCCAGATG     840

GAGGAGACCA AGGCACAGGA CATTCTGGGA GCAGTGACCC TTCTGCTGGA GGGAGTGATG     900

GCAGCACGGG GACAACTG                                                  918
```

(2) INFORMATION FOR SEQ ID NO:125:

(i) SEQUENCE CHARACTERISTICS:
    (A) LENGTH: 848 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic"

(xi) SEQUENCE DESCRIPTION: SEQ ID NO:125:

```
GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGG AACCCAGCTT CCTCCACAGG GCAGGACCAC AGCTCACAAG     480

GATCCCAATG CCATCTTCCT GAGCTTCCAA CACCTGCTCC GAGGAAAGGT GCGTTTCCTG     540

ATGCTTGTAG GAGGGTCCAC CCTCTGCGTC AGGGAATTCG GCGGCAACAT GGCGTCTCCC     600

GCTCCGCCTG CTTGTGACCT CCGAGTCCTC AGTAAACTGC TTCGTGACTC CCATGTCCTT     660
```

```
CACAGCAGAC TGAGCCAGTG CCCAGAGGTT CACCCTTTGC CTACACCTGT CCTGCTGCCT    720

GCTGTGGACT TTAGCTTGGG AGAATGGAAA ACCCAGATGG AGGAGACCAA GGCACAGGAC    780

ATTCTGGGAG CAGTGACCCT TCTGCTGGAG GGAGTGATGG CAGCACGGGG ACAACTGGGA    840

CCCACTTG                                                            848

(2) INFORMATION FOR SEQ ID NO:126:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:126:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGGG CAGGACCACA GCTCACAAGG ATCCCAATGC CATCTTCCTG    480

AGCTTCCAAC ACCTGCTCCG AGGAAAGGTG CGTTTCCTGA TGCTTGTAGG AGGGTCCACC    540

CTCTGCGTCA GGGAATTCGG CGGCAACATG GCGTCTCCCG CTCCGCCTGC TTGTGACCTC    600

CGAGTCCTCA GTAAACTGCT TCGTGACTCC CATGTCCTTC ACAGCAGACT GAGCCAGTGC    660

CCAGAGGTTC ACCCTTTGCC TACACCTGTC CTGCTGCCTG CTGTGGACTT TAGCTTGGGA    720

GAATGGAAAA CCCAGATGGA GGAGACCAAG GCACAGGACA TTCTGGGAGC AGTGACCCTT    780

CTGCTGGAGG GAGTGATGGC AGCACGGGGA CAACTGGGAC CCACTTGCCT CTCATCCCTC    840

CTGGGCAGC TTTCTGGACA GGTCCGTCTC CTCCTTGGGG CCCTGCAGAG CCTCCTTGGA    900

ACCCAGCTTC CTCCACAG                                                 918

(2) INFORMATION FOR SEQ ID NO:127:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:127:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300
```

```
TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGGC TCACAAGGAT CCCAATGCCA TCTTCCTGAG CTTCCAACAC    480

CTGCTCCGAG GAAAGGTGCG TTTCCTGATG CTTGTAGGAG GGTCCACCCT CTGCGTCAGG    540

GAATTCGGCG GCAACATGGC GTCTCCCGCT CCGCCTGCTT GTGACCTCCG AGTCCTCAGT    600

AAACTGCTTC GTGACTCCCA TGTCCTTCAC AGCAGACTGA GCCAGTGCCC AGAGGTTCAC    660

CCTTTGCCTA CACCTGTCCT GCTGCCTGCT GTGGACTTTA GCTTGGGAGA ATGGAAAACC    720

CAGATGGAGG AGACCAAGGC ACAGGACATT CTGGGAGCAG TGACCCTTCT GCTGGAGGGA    780

GTGATGGCAG CACGGGGACA ACTGGGACCC ACTTGCCTCT CATCCCTCCT GGGGCAGCTT    840

TCTGGACAGG TCCGTCTCCT CCTTGGGGCC CTGCAGAGCC TCCTTGGAAC CCAGCTTCCT    900

CCACAGGGCA GGACCACA                                                  918

(2) INFORMATION FOR SEQ ID NO:128:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:128:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGGA TCCCAATGCC ATCTTCCTGA GCTTCCAACA CCTGCTCCGA    480

GGAAAGGTGC GTTTCCTGAT GCTTGTAGGA GGGTCCACCC TCTGCGTCAG GGAATTCGGC    540

GGCAACATGG CGTCTCCCGC TCCGCCTGCT TGTGACCTCC GAGTCCTCAG TAAACTGCTT    600

CGTGACTCCC ATGTCCTTCA CAGCAGACTG AGCCAGTGCC CAGAGGTTCA CCCTTTGCCT    660

ACACCTGTCC TGCTGCCTGC TGTGGACTTT AGCTTGGGAG AATGGAAAAC CCAGATGGAG    720

GAGACCAAGG CACAGGACAT TCTGGGAGCA GTGACCCTTC TGCTGGAGGG AGTGATGGCA    780

GCACGGGGAC AACTGGGACC CACTTGCCTC TCATCCCTCC TGGGGCAGCT TTCTGGACAG    840

GTCCGTCTCC TCCTTGGGGC CCTGCAGAGC CTCCTTGGAA CCCAGCTTCC TCCACAGGGC    900

AGGACCACAG CTCACAAG                                                  918

(2) INFORMATION FOR SEQ ID NO:129:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"
```

(xi) SEQUENCE DESCRIPTION: SEQ ID NO:129:

```
GCTAACTGCT CTATAATGAT CGATGAAATT ATACATCACT TAAAGAGACC ACCTGCACCT      60
TTGCTGGACC CGAACAACCT CAATGACGAA GACGTCTCTA TCCTGATGGA CCGAAACCTT     120
CGACTTCCAA ACCTGGAGAG CTTCGTAAGG GCTGTCAAGA ACTTAGAAAA TGCATCAGGT     180
ATTGAGGCAA TTCTTCGTAA TCTCCAACCA TGTCTGCCCT CTGCCACGGC CGCACCCTCT     240
CGACATCCAA TCATCATCAA GGCAGGTGAC TGGCAAGAAT TCCGGGAAAA ACTGACGTTC     300
TATCTGGTTA CCCTTGAGCA AGCGCAGGAA CAACAGTACG TAGAGGGCGG TGGAGGCTCC     360
CCGGGTGAAC CGTCTGGTCC AATCTCTACT ATCAACCCGT CTCCTCCGTC TAAAGAATCT     420
CATAAATCTC CAAACATGGC CATCTTCCTG AGCTTCCAAC ACCTGCTCCG AGGAAAGGTG     480
CGTTTCCTGA TGCTTGTAGG AGGGTCCACC CTCTGCGTCA GGGAATTCGG CGGCAACATG     540
GCGTCTCCCG CTCCGCCTGC TTGTGACCTC CGAGTCCTCA GTAAACTGCT TCGTGACTCC     600
CATGTCCTTC ACAGCAGACT GAGCCAGTGC CCAGAGGTTC ACCCTTTGCC TACACCTGTC     660
CTGCTGCCTG CTGTGGACTT TAGCTTGGGA GAATGGAAAA CCCAGATGGA GGAGACCAAG     720
GCACAGGACA TTCTGGGAGC AGTGACCCTT CTGCTGGAGG GAGTGATGGC AGCACGGGGA     780
CAACTGGGAC CCACTTGCCT CTCATCCCTC CTGGGGCAGC TTTCTGGACA GGTCCGTCTC     840
CTCCTTGGGG CCCTGCAGAG CCTCCTTGGA ACCCAGCTTC CTCCACAGGG CAGGACCACA     900
GCTCACAAGG ATCCCAAT                                                    918
```

(2) INFORMATION FOR SEQ ID NO:130:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:130:

```
GCTAACTGCT CTATAATGAT CGATGAAATT ATACATCACT TAAAGAGACC ACCTGCACCT      60
TTGCTGGACC CGAACAACCT CAATGACGAA GACGTCTCTA TCCTGATGGA CCGAAACCTT     120
CGACTTCCAA ACCTGGAGAG CTTCGTAAGG GCTGTCAAGA ACTTAGAAAA TGCATCAGGT     180
ATTGAGGCAA TTCTTCGTAA TCTCCAACCA TGTCTGCCCT CTGCCACGGC CGCACCCTCT     240
CGACATCCAA TCATCATCAA GGCAGGTGAC TGGCAAGAAT TCCGGGAAAA ACTGACGTTC     300
TATCTGGTTA CCCTTGAGCA AGCGCAGGAA CAACAGTACG TAGAGGGCGG TGGAGGCTCC     360
CCGGGTGAAC CGTCTGGTCC AATCTCTACT ATCAACCCGT CTCCTCCGTC TAAAGAATCT     420
CATAAATCTC CAAACATGGA GGTTCACCCT TTGCCTACAC CTGTCCTGCT GCCTGCTGTG     480
GACTTTAGCT TGGGAGAATG GAAAACCCAG ATGGAGGAGA CCAAGGCACA GGACATTCTG     540
GGAGCAGTGA CCCTTCTGCT GGAGGGAGTG ATGGCAGCAC GGGGACAACT GGGACCCACT     600
TGCCTCTCAT CCCTCCTGGG GCAGCTTTCT GGACAGGTCC GTCTCCTCCT TGGGGCCCTG     660
CAGAGCCTCC TTGGAACCCA GCTTCCTCCA CAGGGCAGGA CCACAGCTCA CAAGGATCCC     720
AATGCCATCT TCCTGAGCTT CCAACACCTG CTCCGAGGAA AGGTGCGTTT CCTGATGCTT     780
GTAGGAGGGT CCACCCTCTG CGTCAGGGAA TTCGGCAACA TGGCGTCTCC CGCTCCGCCT     840
GCTTGTGACC TCCGAGTCCT CAGTAAACTG CTTCGTGACT CCCATGTCCT TCACAGCAGA     900
```

CTGAGCCAGT GCCCA                                                                915

(2) INFORMATION FOR SEQ ID NO:131:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:131:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGTT GCCTACACCT GTCCTGCTGC CTGCTGTGGA CTTTAGCTTG    480

GGAGAATGGA AAACCCAGAT GGAGGAGACC AAGGCACAGG ACATTCTGGG AGCAGTGACC    540

CTTCTGCTGG AGGGAGTGAT GGCAGCACGG GGACAACTGG GACCCACTTG CCTCTCATCC    600

CTCCTGGGGC AGCTTTCTGG ACAGGTCCGT CTCCTCCTTG GGGCCCTGCA GAGCCTCCTT    660

GGAACCCAGC TTCCTCCACA GGGCAGGACC ACAGCTCACA AGGATCCCAA TGCCATCTTC    720

CTGAGCTTCC AACACCTGCT CCGAGGAAAG GTGCGTTTCC TGATGCTTGT AGGAGGGTCC    780

ACCCTCTGCG TCAGGGAATT CGGCAACATG GCGTCTCCCG CTCCGCCTGC TTGTGACCTC    840

CGAGTCCTCA GTAAACTGCT TCGTGACTCC CATGTCCTTC ACAGCAGACT GAGCCAGTGC    900

CCAGAGGTTC ACCCT                                                    915

(2) INFORMATION FOR SEQ ID NO:132:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:132:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGGT CCTGCTGCCT GCTGTGGACT TTAGCTTGGG AGAATGGAAA    480

ACCCAGATGG AGGAGACCAA GGCACAGGAC ATTCTGGGAG CAGTGACCCT TCTGCTGGAG    540

```
GGAGTGATGG CAGCACGGGG ACAACTGGGA CCCACTTGCC TCTCATCCCT CCTGGGGCAG    600

CTTTCTGGAC AGGTCCGTCT CCTCCTTGGG GCCCTGCAGA GCCTCCTTGG AACCCAGCTT    660

CCTCCACAGG GCAGGACCAC AGCTCACAAG GATCCCAATG CCATCTTCCT GAGCTTCCAA    720

CACCTGCTCC GAGGAAAGGT GCGTTTCCTG ATGCTTGTAG GAGGGTCCAC CCTCTGCGTC    780

AGGGAATTCG GCAACATGGC GTCTCCCGCT CCGCCTGCTT GTGACCTCCG AGTCCTCAGT    840

AAACTGCTTC GTGACTCCCA TGTCCTTCAC AGCAGACTGA GCCAGTGCCC AGAGGTTCAC    900

CCTTTGCCTA CACCT                                                    915

(2) INFORMATION FOR SEQ ID NO:133:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:133:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGGC TGTGGACTTT AGCTTGGGAG AATGGAAAAC CCAGATGGAG    480

GAGACCAAGG CACAGGACAT TCTGGGAGCA GTGACCCTTC TGCTGGAGGG AGTGATGGCA    540

GCACGGGGAC AACTGGGACC CACTTGCCTC TCATCCCTCC TGGGGCAGCT TTCTGGACAG    600

GTCCGTCTCC TCCTTGGGGC CCTGCAGAGC CTCCTTGGAA CCCAGCTTCC TCCACAGGGC    660

AGGACCACAG CTCACAAGGA TCCCAATGCC ATCTTCCTGA GCTTCCAACA CCTGCTCCGA    720

GGAAAGGTGC GTTTCCTGAT GCTTGTAGGA GGGTCCACCC TCTGCGTCAG GGAATTCGGC    780

AACATGGCGT CTCCCGCTCC GCCTGCTTGT GACCTCCGAG TCCTCAGTAA ACTGCTTCGT    840

GACTCCCATG TCCTTCACAG CAGACTGAGC CAGTGCCCAG AGGTTCACCC TTTGCCTACA    900

CCTGTCCTGC TGCCT                                                    915

(2) INFORMATION FOR SEQ ID NO:134:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:134:

GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120
```

```
CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGA CTTTAGCTTG GGAGAATGGA AAACCCAGAT GGAGGAGACC      480

AAGGCACAGG ACATTCTGGG AGCAGTGACC CTTCTGCTGG AGGGAGTGAT GGCAGCACGG      540

GGACAACTGG GACCCACTTG CCTCTCATCC CTCCTGGGGC AGCTTTCTGG ACAGGTCCGT      600

CTCCTCCTTG GGGCCCTGCA GAGCCTCCTT GGAACCCAGC TTCCTCCACA GGGCAGGACC      660

ACAGCTCACA AGGATCCCAA TGCCATCTTC CTGAGCTTCC AACACCTGCT CCGAGGAAAG      720

GTGCGTTTCC TGATGCTTGT AGGAGGGTCC ACCCTCTGCG TCAGGGAATT CGGCAACATG      780

GCGTCTCCCG CTCCGCCTGC TTGTGACCTC CGAGTCCTCA GTAAACTGCT TCGTGACTCC      840

CATGTCCTTC ACAGCAGACT GAGCCAGTGC CCAGAGGTTC ACCCTTTGCC TACACCTGTC      900

CTGCTGCCTG CTGTG                                                      915

(2) INFORMATION FOR SEQ ID NO:135:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:135:

GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGG AGAATGGAAA ACCCAGATGG AGGAGACCAA GGCACAGGAC      480

ATTCTGGGAG CAGTGACCCT TCTGCTGGAG GGAGTGATGG CAGCACGGGG ACAACTGGGA      540

CCCACTTGCC TCTCATCCCT CCTGGGGCAG CTTTCTGGAC AGGTCCGTCT CCTCCTTGGG      600

GCCCTGCAGA GCCTCCTTGG AACCCAGCTT CCTCCACAGG GCAGGACCAC AGCTCACAAG      660

GATCCCAATG CCATCTTCCT GAGCTTCCAA CACCTGCTCC GAGGAAAGGT GCGTTTCCTG      720

ATGCTTGTAG GAGGGTCCAC CCTCTGCGTC AGGGAATTCG GCAACATGGC GTCTCCCGCT      780

CCGCCTGCTT GTGACCTCCG AGTCCTCAGT AAACTGCTTC GTGACTCCCA TGTCCTTCAC      840

AGCAGACTGA GCCAGTGCCC AGAGGTTCAC CCTTTGCCTA CACCTGTCCT GCTGCCTGCT      900

GTGGACTTTA GCTTG                                                      915

(2) INFORMATION FOR SEQ ID NO:136:

(i) SEQUENCE CHARACTERISTICS:
        (A) LENGTH: 915 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:136:

```
GCTAACTGCT CTATAATGAT CGATGAAATT ATACATCACT TAAAGAGACC ACCTGCACCT    60

TTGCTGGACC CGAACAACCT CAATGACGAA GACGTCTCTA TCCTGATGGA CCGAAACCTT   120

CGACTTCCAA ACCTGGAGAG CTTCGTAAGG GCTGTCAAGA ACTTAGAAAA TGCATCAGGT   180

ATTGAGGCAA TTCTTCGTAA CTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC   300

TATCTGGTTA CCCTTGAGCA AGCGCAGGAA CAACAGTACG TAGAGGGCGG TGGAGGCTCC   360

CCGGGTGAAC CGTCTGGTCC AATCTCTACT ATCAACCCGT CTCCTCCGTC TAAAGAATCT   420

CATAAATCTC CAAACATGGG ACCCACTTGC CTCTCATCCC TCCTGGGGCA GCTTTCTGGA   480

CAGGTCCGTC TCCTCCTTGG GGCCCTGCAG AGCCTCCTTG GAACCCAGCT TCCTCCACAG   540

GGCAGGACCA CAGCTCACAA GGATCCCAAT GCCATCTTCC TGAGCTTCCA ACACCTGCTC   600

CGAGGAAAGG TGCGTTTCCT GATGCTTGTA GGAGGGTCCA CCCTCTGCGT CAGGGAATTC   660

GGCAACATGG CGTCTCCCGC TCCGCCTGCT TGTGACCTCC GAGTCCTCAG TAAACTGCTT   720

CGTGACTCCC ATGTCCTTCA CAGCAGACTG AGCCAGTGCC CAGAGGTTCA CCCTTTGCCT   780

ACACCTGTCC TGCTGCCTGC TGTGGACTTT AGCTTGGGAG AATGGAAAAC CCAGATGGAG   840

GAGACCAAGG CACAGGACAT TCTGGGAGCA GTGACCCTTC TGCTGGAGGG AGTGATGGCA   900

GCACGGGGAC AACTG                                                   915
```

(2) INFORMATION FOR SEQ ID NO:137:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:137:

```
GCTAACTGCT CTATAATGAT CGATGAAATT ATACATCACT TAAAGAGACC ACCTGCACCT    60

TTGCTGGACC CGAACAACCT CAATGACGAA GACGTCTCTA TCCTGATGGA CCGAAACCTT   120

CGACTTCCAA ACCTGGAGAG CTTCGTAAGG GCTGTCAAGA ACTTAGAAAA TGCATCAGGT   180

ATTGAGGCAA TTCTTCGTAA CTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC   300

TATCTGGTTA CCCTTGAGCA AGCGCAGGAA CAACAGTACG TAGAGGGCGG TGGAGGCTCC   360

CCGGGTGAAC CGTCTGGTCC AATCTCTACT ATCAACCCGT CTCCTCCGTC TAAAGAATCT   420

CATAAATCTC CAAACATGGG AACCCAGCTT CCTCCACAGG GCAGGACCAC AGCTCACAAG   480

GATCCCAATG CCATCTTCCT GAGCTTCCAA CACCTGCTCC GAGGAAAGGT GCGTTTCCTG   540

ATGCTTGTAG AGGGTCCAC CCTCTGCGTC AGGGAATTCG GCAACATGGC GTCTCCCGCT    600

CCGCCTGCTT GTGACCTCCG AGTCCTCAGT AAACTGCTTC GTGACTCCCA TGTCCTTCAC   660

AGCAGACTGA GCCAGTGCCC AGAGGTTCAC CCTTTGCCTA CACCTGTCCT GCTGCCTGCT   720
```

```
GTGGACTTTA GCTTGGGAGA ATGGAAAACC CAGATGGAGG AGACCAAGGC ACAGGACATT      780

CTGGGAGCAG TGACCCTTCT GCTGGAGGGA GTGATGGCAG CACGGGGACA ACTGGGACCC      840

ACTTGCCTCT CATCCCTCCT GGGGCAGCTT TCTGGACAGG TCCGTCTCCT CCTTGGGGCC      900

CTGCAGAGCC TCCTT                                                      915

(2) INFORMATION FOR SEQ ID NO:138:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:138:

GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGG CAGGACCACA GCTCACAAGG ATCCCAATGC CATCTTCCTG      480

AGCTTCCAAC ACCTGCTCCG AGGAAAGGTG CGTTTCCTGA TGCTTGTAGG AGGGTCCACC      540

CTCTGCGTCA GGGAATTCGG CAACATGGCG TCTCCCGCTC CGCCTGCTTG TGACCTCCGA      600

GTCCTCAGTA AACTGCTTCG TGACTCCCAT GTCCTTCACA GCAGACTGAG CCAGTGCCCA      660

GAGGTTCACC CTTTGCCTAC ACCTGTCCTG CTGCCTGCTG TGGACTTTAG CTTGGGAGAA      720

TGGAAAACCC AGATGGAGGA GACCAAGGCA CAGGACATTC TGGGAGCAGT GACCCTTCTG      780

CTGGAGGGAG TGATGGCAGC ACGGGGACAA CTGGGACCCA CTTGCCTCTC ATCCCTCCTG      840

GGGCAGCTTT CTGGACAGGT CCGTCTCCTC CTTGGGGCCC TGCAGAGCCT CCTTGGAACC      900

CAGCTTCCTC CACAG                                                      915

(2) INFORMATION FOR SEQ ID NO:139:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:139:

GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360
```

```
CCGGGTGAAC CGTCTGGTCC AATCTCTACT ATCAACCCGT CTCCTCCGTC TAAAGAATCT      420

CATAAATCTC CAAACATGGC TCACAAGGAT CCCAATGCCA TCTTCCTGAG CTTCCAACAC      480

CTGCTCCGAG GAAAGGTGCG TTTCCTGATG CTTGTAGGAG GGTCCACCCT CTGCGTCAGG      540

GAATTCGGCA ACATGGCGTC TCCCGCTCCG CCTGCTTGTG ACCTCCGAGT CCTCAGTAAA      600

CTGCTTCGTG ACTCCCATGT CCTTCACAGC AGACTGAGCC AGTGCCCAGA GGTTCACCCT      660

TTGCCTACAC CTGTCCTGCT GCCTGCTGTG GACTTTAGCT TGGGAGAATG GAAAACCCAG      720

ATGGAGGAGA CCAAGGCACA GGACATTCTG GGAGCAGTGA CCCTTCTGCT GGAGGGAGTG      780

ATGGCAGCAC GGGGACAACT GGGACCCACT TGCCTCTCAT CCCTCCTGGG GCAGCTTTCT      840

GGACAGGTCC GTCTCCTCCT TGGGGCCCTG CAGAGCCTCC TTGGAACCCA GCTTCCTCCA      900

CAGGGCAGGA CCACA                                                      915
```

(2) INFORMATION FOR SEQ ID NO:140:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:140:

```
GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGA TCCCAATGCC ATCTTCCTGA GCTTCCAACA CCTGCTCCGA      480

GGAAAGGTGC GTTTCCTGAT GCTTGTAGGA GGGTCCACCC TCTGCGTCAG GGAATTCGGC      540

AACATGGCGT CTCCCGCTCC GCCTGCTTGT GACCTCCGAG TCCTCAGTAA ACTGCTTCGT      600

GACTCCCATG TCCTTCACAG CAGACTGAGC CAGTGCCCAG AGGTTCACCC TTTGCCTACA      660

CCTGTCCTGC TGCCTGCTGT GGACTTTAGC TTGGGAGAAT GGAAAACCCA GATGGAGGAG      720

ACCAAGGCAC AGGACATTCT GGGAGCAGTG ACCCTTCTGC TGGAGGGAGT GATGGCAGCA      780

CGGGGACAAC TGGGACCCAC TTGCCTCTCA TCCCTCCTGG GGCAGCTTTC TGGACAGGTC      840

CGTCTCCTCC TTGGGGCCCT GCAGAGCCTC CTTGGAACCC AGCTTCCTCC ACAGGGCAGG      900

ACCACAGCTC ACAAG                                                      915
```

(2) INFORMATION FOR SEQ ID NO:141:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:141:

```
GCTAACTGCT CTATAATGAT CGATGAAATT ATACATCACT TAAAGAGACC ACCTGCACCT       60
TTGCTGGACC CGAACAACCT CAATGACGAA GACGTCTCTA TCCTGATGGA CCGAAACCTT      120
CGACTTCCAA ACCTGGAGAG CTTCGTAAGG GCTGTCAAGA ACTTAGAAAA TGCATCAGGT      180
ATTGAGGCAA TTCTTCGTAA TCTCCAACCA TGTCTGCCCT CTGCCACGGC CGCACCCTCT      240
CGACATCCAA TCATCATCAA GGCAGGTGAC TGGCAAGAAT TCCGGGAAAA ACTGACGTTC      300
TATCTGGTTA CCCTTGAGCA AGCGCAGGAA CAACAGTACG TAGAGGGCGG TGGAGGCTCC      360
CCGGGTGAAC CGTCTGGTCC AATCTCTACT ATCAACCCGT CTCCTCCGTC TAAAGAATCT      420
CATAAATCTC CAAACATGGC CATCTTCCTG AGCTTCCAAC ACCTGCTCCG AGGAAAGGTG      480
CGTTTCCTGA TGCTTGTAGG AGGGTCCACC CTCTGCGTCA GGGAATTCGG CAACATGGCG      540
TCTCCCGCTC CGCCTGCTTG TGACCTCCGA GTCCTCAGTA AACTGCTTCG TGACTCCCAT      600
GTCCTTCACA GCAGACTGAG CCAGTGCCCA GAGGTTCACC CTTTGCCTAC ACCTGTCCTG      660
CTGCCTGCTG TGGACTTTAG CTTGGGAGAA TGGAAAACCC AGATGGAGGA GACCAAGGCA      720
CAGGACATTC TGGGAGCAGT GACCCTTCTG CTGGAGGGAG TGATGGCAGC ACGGGGACAA      780
CTGGGACCCA CTTGCCTCTC ATCCCTCCTG GGGCAGCTTT CTGGACAGGT CCGTCTCCTC      840
CTTGGGGCCC TGCAGAGCCT CCTTGGAACC CAGCTTCCTC CACAGGGCAG GACCACAGCT      900
CACAAGGATC CCAAT                                                      915
```

(2) INFORMATION FOR SEQ ID NO:142:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:142:

```
GCTAACTGCT CTATAATGAT CGATGAAATT ATACATCACT TAAAGAGACC ACCTGCACCT       60
TTGCTGGACC CGAACAACCT CAATGACGAA GACGTCTCTA TCCTGATGGA CCGAAACCTT      120
GACTTCCAAA CCTGGAGAGC TTCGTAAGGG CTGTCAAGAA CTTAGAAAAT GCATCAGGTA      180
TGAGGCAATT CTTCGTAATC TCCAACCATG TCTGCCCTCT GCCACGGCCG CACCCTCTCG      240
CATCCAATCA TCATCAAGGC AGGTGACTGG CAAGAATTCC GGGAAAAACT GACGTTCTAT      300
TGGTTACCCT TGAGCAAGCG CAGGAACAAC AGTACGTAGA GGGCGGTGGA GGCTCCCCGG      360
TAACCGTCTG GTCCAATCTC TACTATCAAC CCGTCTCCTC CGTCTAAAGA ATCTCATAAA      420
TCTCCAAACA TGGAGGTTCA CCCTTTGCCT ACACCTGTCC TGCTGCCTGC TGTGGACTTT      480
AGCTTGGGAG AATGGAAAAC CCAGATGGAG GAGACCAAGG CACAGGACAT TCTGGGAGCA      540
GTGACCCTTC TGCTGGAGGG AGTGATGGCA GCACGGGGAC AACTGGGACC CACTTGCCTC      600
TCATCCCTCC TGGGGCAGCT TTCTGGACAG GTCCGTCTCC TCCTTGGGGC CCTGCAGAGC      660
CTCCTTGGAA CCCAGCTTCC TCCACAGGGC AGGACCACAG CTCACAAGGA TCCCAATGCC      720
ATCTTCCTGA GCTTCCAACA CCTGCTCCGA GGAAAGGTGC GTTTCCTGAT GCTTGTAGGA      780
GGGTCCACCC TCTGCGTCAG GGAATTCGGC GGCAACGGCG GCAACATGGC GTCCCCAGCG      840
CCGCCTGCTT GTGACCTCCG AGTCCTCAGT AAACTGCTTC GTGACTCCCA TGTCCTTCAC      900
AGCAGACTGA GCCAGTGCCC A                                               921
```

(2) INFORMATION FOR SEQ ID NO:143:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:143:

```
GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGTT GCCTACACCT GTCCTGCTGC CTGCTGTGGA CTTTAGCTTG     480

GGAGAATGGA AAACCCAGAT GGAGGAGACC AAGGCACAGG ACATTCTGGG AGCAGTGACC     540

CTTCTGCTGG AGGGAGTGAT GGCAGCACGG GGACAACTGG GACCCACTTG CCTCTCATCC     600

CTCCTGGGGC AGCTTTCTGG ACAGGTCCGT CTCCTCCTTG GGGCCCTGCA GAGCCTCCTT     660

GGAACCCAGC TTCCTCCACA GGGCAGGACC ACAGCTCACA AGGATCCCAA TGCCATCTTC     720

CTGAGCTTCC AACACCTGCT CCGAGGAAAG GTGCGTTTCC TGATGCTTGT AGGAGGGTCC     780

ACCCTCTGCG TCAGGGAATT CGGCGGCAAC GGCGGCAACA TGGCGTCCCC AGCGCCGCCT     840

GCTTGTGACC TCCGAGTCCT CAGTAAACTG CTTCGTGACT CCCATGTCCT TCACAGCAGA     900

CTGAGCCAGT GCCCAGAGGT TCACCCT                                        927
```

(2) INFORMATION FOR SEQ ID NO:144:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:144:

```
GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGT CCTGCTGCCT GCTGTGGACT TTAGCTTGGG AGAATGGAAA     480

ACCCAGATGG AGGAGACCAA GGCACAGGAC ATTCTGGGAG CAGTGACCCT TCTGCTGGAG     540
```

```
GGAGTGATGG CAGCACGGGG ACAACTGGGA CCCACTTGCC TCTCATCCCT CCTGGGGCAG      600

CTTTCTGGAC AGGTCCGTCT CCTCCTTGGG GCCCTGCAGA GCCTCCTTGG AACCCAGCTT      660

CCTCCACAGG GCAGGACCAC AGCTCACAAG GATCCCAATG CCATCTTCCT GAGCTTCCAA      720

CACCTGCTCC GAGGAAAGGT GCGTTTCCTG ATGCTTGTAG GAGGGTCCAC CCTCTGCGTC      780

AGGGAATTCG GCGGCAACGG CGGCAACATG GCGTCCCCAG CGCCGCCTGC TTGTGACCTC      840

CGAGTCCTCA GTAAACTGCT TCGTGACTCC CATGTCCTTC ACAGCAGACT GAGCCAGTGC      900

CCAGAGGTTC ACCCTTTGCC TACACCT                                         927

(2) INFORMATION FOR SEQ ID NO:145:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:145:

GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA TCTCCAACCA TGTCTGCCCT CTGCCACGGC CGCACCCTCT      240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGC TGTGGACTTT AGCTTGGGAG AATGGAAAAC CCAGATGGAG      480

GAGACCAAGG CACAGGACAT TCTGGGAGCA GTGACCCTTC TGCTGGAGGG AGTGATGGCA      540

GCACGGGGAC AACTGGGACC CACTTGCCTC TCATCCCTCC TGGGGCAGCT TTCTGGACAG      600

GTCCGTCTCC TCCTTGGGGC CCTGCAGAGC CTCCTTGGAA CCCAGCTTCC TCCACAGGGC      660

AGGACCACAG CTCACAAGGA TCCCAATGCC ATCTTCCTGA GCTTCAACA CCTGCTCCGA      720

GGAAAGGTGC GTTTCCTGAT GCTTGTAGGA GGGTCCACCC TCTGCGTCAG GGAATTCGGC      780

GGCAACGGCG GCAACATGGC GTCCCCAGCG CCGCCTGCTT GTGACCTCCG AGTCCTCAGT      840

AAACTGCTTC GTGACTCCCA TGTCCTTCAC AGCAGACTGA GCCAGTGCCC AGAGGTTCAC      900

CCTTTGCCTA CACCTGTCCT GCTGCCT                                         927

(2) INFORMATION FOR SEQ ID NO:146:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:146:

GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180
```

```
ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGAAAA ACTGACGTTC    300

TATCTGGTTA CCCTTGAGCA AGCGCAGGAA CAACAGTACG TAGAGGGCGG TGGAGGCTCC   360

CCGGGTGAAC CGTCTGGTCC AATCTCTACT ATCAACCCGT CTCCTCCGTC TAAAGAATCT   420

CATAAATCTC CAAACATGGA CTTTAGCTTG GGAGAATGGA AAACCCAGAT GGAGGAGACC   480

AAGGCACAGG ACATTCTGGG AGCAGTGACC CTTCTGCTGG AGGGAGTGAT GGCAGCACGG   540

GGACAACTGG GACCCACTTG CCTCTCATCC CTCCTGGGGC AGCTTTCTGG ACAGGTCCGT   600

CTCCTCCTTG GGGCCCTGCA GAGCCTCCTT GGAACCCAGC TTCCTCCACA GGGCAGGACC   660

ACAGCTCACA AGGATCCCAA TGCCATCTTC CTGAGCTTCC AACACCTGCT CCGAGGAAAG   720

GTGCGTTTCC TGATGCTTGT AGGAGGGTCC ACCCTCTGCG TCAGGGAATT CGGCGGCAAC   780

GGCGGCAACA TGGCGTCCCC AGCGCCGCCT GCTTGTGACC TCCGAGTCCT CAGTAAACTG   840

CTTCGTGACT CCCATGTCCT TCACAGCAGA CTGAGCCAGT GCCCAGAGGT TCACCCTTTG   900

CCTACACCTG TCCTGCTGCC TGCTGTG                                      927

(2) INFORMATION FOR SEQ ID NO:147:

(i) SEQUENCE CHARACTERISTICS:
         (A) LENGTH: 927 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic"

(xi) SEQUENCE DESCRIPTION: SEQ ID NO:147:

GCTAACTGCT CTATAATGAT CGATGAAATT ATACATCACT TAAAGAGACC ACCTGCACCT    60

TTGCTGGACC CGAACAACCT CAATGACGAA GACGTCTCTA TCCTGATGGA CCGAAACCTT   120

CGACTTCCAA ACCTGGAGAG CTTCGTAAGG GCTGTCAAGA ACTTAGAAAA TGCATCAGGT   180

ATTGAGGCAA TTCTTCGTAA TCTCCAACCA TGTCTGCCCT CTGCCACGGC CGCACCCTCT   240

CGACATCCAA TCATCATCAA GGCAGGTGAC TGGCAAGAAT TCCGGAAAA ACTGACGTTC    300

TATCTGGTTA CCCTTGAGCA AGCGCAGGAA CAACAGTACG TAGAGGGCGG TGGAGGCTCC   360

CCGGGTGAAC CGTCTGGTCC AATCTCTACT ATCAACCCGT CTCCTCCGTC TAAAGAATCT   420

CATAAATCTC CAAACATGGG AGAATGGAAA ACCCAGATGG AGGAGACCAA GGCACAGGAC   480

ATTCTGGGAG CAGTGACCCT TCTGCTGGAG GGAGTGATGG CAGCACGGGG ACAACTGGGA   540

CCCACTTGCC TCTCATCCCT CCTGGGGCAG CTTTCTGGAC AGGTCCGTCT CCTCCTTGGG   600

GCCCTGCAGA GCCTCCTTGG AACCCAGCTT CCTCCACAGG GCAGGACCAC AGCTCACAAG   660

GATCCCAATG CCATCTTCCT GAGCTTCCAA CACCTGCTCC GAGGAAAGGT GCGTTTCCTG   720

ATGCTTGTAG GAGGGTCCAC CCTCTGCGTC AGGGAATTCG GCGGCAACGG CGGCAACATG   780

GCGTCCCCAG CGCCGCCTGC TTGTGACCTC CGAGTCCTCA GTAAACTGCT TCGTGACTCC   840

CATGTCCTTC ACAGCAGACT GAGCCAGTGC CCAGAGGTTC ACCCTTTGCC TACACCTGTC   900

CTGCTGCCTG CTGTGGACTT TAGCTTG                                      927

(2) INFORMATION FOR SEQ ID NO:148:

(i) SEQUENCE CHARACTERISTICS:
         (A) LENGTH: 927 base pairs
         (B) TYPE: nucleic acid
```

```
            (C) STRANDEDNESS: single
            (D) TOPOLOGY: linear (ii) MOLECULE TYPE: other nucleic acid
            (A) DESCRIPTION: /desc = "synthetic"

(xi) SEQUENCE DESCRIPTION: SEQ ID NO:148:

GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGG ACCCACTTGC CTCTCATCCC TCCTGGGGCA GCTTTCTGGA     480

CAGGTCCGTC TCCTCCTTGG GGCCCTGCAG AGCCTCCTTG GAACCCAGCT TCCTCCACAG     540

GGCAGGACCA CAGCTCACAA GGATCCCAAT GCCATCTTCC TGAGCTTCCA ACACCTGCTC     600

CGAGGAAAGG TGCGTTTCCT GATGCTTGTA GGAGGGTCCA CCCTCTGCGT CAGGGAATTC     660

GGCGGCAACG GCGGCAACAT GGCGTCCCCA GCGCCGCCTG CTTGTGACCT CCGAGTCCTC     720

AGTAAACTGC TTCGTGACTC CCATGTCCTT CACAGCAGAC TGAGCCAGTG CCCAGAGGTT     780

CACCCTTTGC CTACACCTGT CCTGCTGCCT GCTGTGGACT TTAGCTTGGG AGAATGGAAA     840

ACCCAGATGG AGGAGACCAA GGCACAGGAC ATTCTGGGAG CAGTGACCCT TCTGCTGGAG     900

GGAGTGATGG CAGCACGGGG ACAACTG                                        927

(2) INFORMATION FOR SEQ ID NO:149:

(i) SEQUENCE CHARACTERISTICS:
            (A) LENGTH: 927 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic"

(xi) SEQUENCE DESCRIPTION: SEQ ID NO:149:

GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGG AACCCAGCTT CCTCCACAGG GCAGGACCAC AGCTCACAAG     480

GATCCCAATG CCATCTTCCT GAGCTTCCAA CACCTGCTCC GAGGAAAGGT GCGTTTCCTG     540

ATGCTTGTAG GAGGGTCCAC CCTCTGCGTC AGGGAATTCG GCGGCAACGG CGGCAACATG     600

GCGTCCCCAG CGCCGCCTGC TTGTGACCTC CGAGTCCTCA GTAAACTGCT TCGTGACTCC     660

CATGTCCTTC ACAGCAGACT GAGCCAGTGC CCAGAGGTTC ACCCTTTGCC TACACCTGTC     720

CTGCTGCCTG CTGTGGACTT TAGCTTGGGA GAATGGAAAA CCCAGATGGA GGAGACCAAG     780
```

```
GCACAGGACA TTCTGGGAGC AGTGACCCTT CTGCTGGAGG GAGTGATGGC AGCACGGGGA    840

CAACTGGGAC CCACTTGCCT CTCATCCCTC CTGGGGCAGC TTTCTGGACA GGTCCGTCTC    900

CTCCTTGGGG CCCTGCAGAG CCTCCTT                                       927
```

(2) INFORMATION FOR SEQ ID NO:150:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:150:

```
GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360

CCGGGTGAAC CGTCTGGTCC AATCTCTACT ATCAACCCGT CTCCTCCGTC TAAAGAATCT    420

CATAAATCTC CAAACATGGG CAGGACCACA GCTCACAAGG ATCCCAATGC CATCTTCCTG    480

AGCTTCCAAC ACCTGCTCCG AGGAAAGGTG CGTTTCCTGA TGCTTGTAGG AGGGTCCACC    540

CTCTGCGTCA GGGAATTCGG CGGCAACGGC GGCAACATGG CGTCCCCAGC GCCGCCTGCT    600

TGTGACCTCC GAGTCCTCAG TAAACTGCTT CGTGACTCCC ATGTCCTTCA CAGCAGACTG    660

AGCCAGTGCC CAGAGGTTCA CCCTTTGCCT ACACCTGTCC TGCTGCCTGC TGTGGACTTT    720

AGCTTGGGAG AATGGAAAAC CCAGATGGAG GAGACCAAGG CACAGGACAT TCTGGGAGCA    780

GTGACCCTTC TGCTGGAGGG AGTGATGGCA GCACGGGGAC AACTGGGACC CACTTGCCTC    840

TCATCCCTCC TGGGGCAGCT TTCTGGACAG GTCCGTCTCC TCCTTGGGGC CCTGCAGAGC    900

CTCCTTGGAA CCCAGCTTCC TCCACAG                                       927
```

(2) INFORMATION FOR SEQ ID NO:151:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:151:

```
GCTAACTGCT CTATAATGAT CGATGAAATT ATACATCACT TAAAGAGACC ACCTGCACCT     60

TTGCTGGACC CGAACAACCT CAATGACGAA GACGTCTCTA TCCTGATGGA CCGAAACCTT    120

CGACTTCCAA ACCTGGAGAG CTTCGTAAGG GCTGTCAAGA ACTTAGAAAA TGCATCAGGT    180

ATTGAGGCAA TTCTTCGTAA TCTCCAACCA TGTCTGCCCT CTGCCACGGC CGCACCCTCT    240

CGACATCCAA TCATCATCAA GGCAGGTGAC TGGCAAGAAT TCCGGGAAAA ACTGACGTTC    300

TATCTGGTTA CCCTTGAGCA AGCGCAGGAA CAACAGTACG TAGAGGGCGG TGGAGGCTCC    360
```

```
CCGGGTGAAC CGTCTGGTCC AATCTCTACT ATCAACCCGT CTCCTCCGTC TAAAGAATCT      420

CATAAATCTC CAAACATGGC TCACAAGGAT CCCAATGCCA TCTTCCTGAG CTTCCAACAC      480

CTGCTCCGAG GAAAGGTGCG TTTCCTGATG CTTGTAGGAG GGTCCACCCT CTGCGTCAGG      540

GAATTCGGCG GCAACGGCGG CAACATGGCG TCCCCAGCGC CGCCTGCTTG TGACCTCCGA      600

GTCCTCAGTA AACTGCTTCG TGACTCCCAT GTCCTTCACA GCAGACTGAG CCAGTGCCCA      660

GAGGTTCACC CTTTGCCTAC ACCTGTCCTG CTGCCTGCTG TGGACTTTAG CTTGGGAGAA      720

TGGAAAACCC AGATGGAGGA GACCAAGGCA CAGGACATTC TGGAGCAGT GACCCTTCTG       780

CTGGAGGGAG TGATGGCAGC ACGGGACAA CTGGGACCCA CTTGCCTCTC ATCCCTCCTG       840

GGGCAGCTTT CTGGACAGGT CCGTCTCCTC CTTGGGGCCC TGCAGAGCCT CCTTGGAACC     900

CAGCTTCCTC CACAGGGCAG GACCACA                                          927

(2) INFORMATION FOR SEQ ID NO:152:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:152:

GCTAACTGCT CTATAATGAT CGATGAAATT ATACATCACT TAAAGAGACC ACCTGCACCT       60

TTGCTGGACC CGAACAACCT CAATGACGAA GACGTCTCTA TCCTGATGGA CCGAAACCTT      120

CGACTTCCAA ACCTGGAGAG CTTCGTAAGG GCTGTCAAGA ACTTAGAAAA TGCATCAGGT      180

ATTGAGGCAA TTCTTCGTAA CTCCAACCA TGTCTGCCCT CTGCCACGGC CGCACCCTCT       240

CGACATCCAA TCATCATCAA GGCAGGTGAC TGGCAAGAAT TCCGGGAAAA ACTGACGTTC      300

TATCTGGTTA CCCTTGAGCA AGCGCAGGAA CAACAGTACG TAGAGGGCGG TGGAGGCTCC      360

CCGGGTGAAC CGTCTGGTCC AATCTCTACT ATCAACCCGT CTCCTCCGTC TAAAGAATCT      420

CATAAATCTC CAAACATGGA TCCCAATGCC ATCTTCCTGA GCTTCCAACA CCTGCTCCGA      480

GGAAAGGTGC GTTTCCTGAT GCTTGTAGGA GGGTCCACCC TCTGCGTCAG GGAATTCGGC      540

GGCAACGGCG GCAACATGGC GTCCCCAGCG CCGCCTGCTT GTGACCTCCG AGTCCTCAGT      600

AAACTGCTTC GTGACTCCCA TGTCCTTCAC AGCAGACTGA GCCAGTGCCC AGAGGTTCAC      660

CCTTTGCCTA CACCTGTCCT GCTGCCTGCT GTGGACTTTA GCTTGGGAGA ATGGAAAACC      720

CAGATGGAGG AGACCAAGGC ACAGGACATT CTGGAGCAG TGACCCTTCT GCTGGAGGGA       780

GTGATGGCAG CACGGGACA ACTGGGACCC ACTTGCCTCT CATCCCTCCT GGGGCAGCTT       840

TCTGGACAGG TCCGTCTCCT CCTTGGGGCC CTGCAGAGCC TCCTTGGAAC CCAGCTTCCT      900

CCACAGGGCA GGACCACAGC TCACAAG                                          927

(2) INFORMATION FOR SEQ ID NO:153:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:153:
```

```
GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGC CATCTTCCTG AGCTTCCAAC ACCTGCTCCG AGGAAAGGTG     480

CGTTTCCTGA TGCTTGTAGG AGGGTCCACC CTCTGCGTCA GGGAATTCGG CGGCAACGGC     540

GGCAACATGG CGTCCCCAGC GCCGCCTGCT TGTGACCTCC GAGTCCTCAG TAAACTGCTT     600

CGTGACTCCC ATGTCCTTCA CAGCAGACTG AGCCAGTGCC CAGAGGTTCA CCCTTTGCCT     660

ACACCTGTCC TGCTGCCTGC TGTGGACTTT AGCTTGGGAG AATGGAAAAC CCAGATGGAG     720

GAGACCAAGG CACAGGACAT TCTGGGAGCA GTGACCCTTC TGCTGGAGGG AGTGATGGCA     780

GCACGGGGAC AACTGGGACC CACTTGCCTC TCATCCCTCC TGGGGCAGCT TTCTGGACAG     840

GTCCGTCTCC TCCTTGGGGC CCTGCAGAGC CTCCTTGGAA CCCAGCTTCC TCCACAGGGC     900

AGGACCACAG CTCACAAGGA TCCCAAT                                        927

(2) INFORMATION FOR SEQ ID NO:154:

(i) SEQUENCE CHARACTERISTICS:
        (A) LENGTH: 906 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:154:

GCTAACTGCT CTATAATGAT CGATGAAATT ATACATCACT TAAAGAGACC ACCTGCACCT      60

TTGCTGGACC CGAACAACCT CAATGACGAA GACGTCTCTA TCCTGATGGA CCGAAACCTT     120

CGACTTCCAA ACCTGGAGAG CTTCGTAAGG GCTGTCAAGA ACTTAGAAAA TGCATCAGGT     180

ATTGAGGCAA TTCTTCGTAA TCTCCAACCA TGTCTGCCCT CTGCCACGGC CGCACCCTCT     240

CGACATCCAA TCATCATCAA GGCAGGTGAC TGGCAAGAAT TCCGGGAAAA ACTGACGTTC     300

TATCTGGTTA CCCTTGAGCA AGCGCAGGAA CAACAGTACG TAGAGGGCGG TGGAGGCTCC     360

CCGGGTGAAC CGTCTGGTCC AATCTCTACT ATCAACCCGT CTCCTCCGTC TAAAGAATCT     420

CATAAATCTC CAAACATGGA TCCCAATGCC ATCTTCCTGA GCTTCCAACA CCTGCTCCGA     480

GGAAAGGTGC GTTTCCTGAT GCTTGTAGGA GGGTCCACCC TCTGCGTCAG GGAATTCGGC     540

GGCAACATGG CGTCTCCCGC TCCGCCTGCT TGTGACCTCC GAGTCCTCAG TAAACTGCTT     600

CGTGACTCCC ATGTCCTTCA CAGCAGACTG AGCCAGTGCC CAGAGGTTCA CCCTTTGCCT     660

ACACCTGTCC TGCTGCCTGC TGTGGACTTT AGCTTGGGAG AATGGAAAAC CCAGATGGAG     720

GAGACCAAGG CACAGGACAT TCTGGGAGCA GTGACCCTTC TGCTGGAGGG AGTGATGGCA     780

GCACGGGGAC AACTGGGACC CACTTGCCTC TCATCCCTCC TGGGGCAGCT TTCTGGACAG     840

GTCCGTCTCC TCCTTGGGGC CCTGCAGAGC CTCCTTGGAA CCCAGGGCAG GACCACAGCT     900

CACAAG                                                               906
```

(2) INFORMATION FOR SEQ ID NO:155:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:155:

```
ATGGCTAACT GCTCTATAAT GATCGATGAA ATTATACATC ACTTAAAGAG ACCACCTGCA      60
CCTTTGCTGG ACCCGAACAA CCTCAATGAC GAAGACGTCT CTATCCTGAT GGATCGAAAC     120
CTTCGACTTC CAAACCTGGA GAGCTTCGTA AGGGCTGTCA AGAACTTAGA AAATGCATCA     180
GGTATTGAGG CAATTCTTCG TAATCTCCAA CCATGTCTGC CCTCTGCCAC GGCCGCACCC     240
TCTCGACATC CAATCATCAT CAAGGCAGGT GACTGGCAAG AATTCCGGGA AAAACTGACG     300
TTCTATCTGG TTACCCTTGA GCAAGCGCAG GAACAACAGT ACGTAGAGGG CGGTGGAGGC     360
TCCCCGGGTG AACCGTCTGG TCCAATCTCT ACTATCAACC CGTCTCCTCC GTCTAAAGAA     420
TCTCATAAAT CTCCAAACAT GTCTTACAAG CTGTGCCACC CCGAGGAGCT GGTGCTGCTC     480
GGACACTCTC TGGGCATCCC CTGGGCTCCC CTGAGCTCCT GCCCCAGCCA GGCCCTGCAG     540
CTGGCAGGCT GCTTGAGCCA ACTCCATAGC GGCCTTTTCC TCTACCAGGG GCTCCTGCAG     600
GCCCTGGAAG GGATATCCCC CGAGTTGGGT CCCACCTTGG ACACACTGCA GCTGGACGTC     660
GCCGACTTTG CCACCACCAT CTGGCAGCAG ATGGAAGAAC TGGGAATGGC CCCTGCCCTG     720
CAGCCCACCC AGGGTGCCAT GCCGGCCTTC GCCTCTGCTT TCCAGCGCCG GGCAGGAGGG     780
GTCCTGGTTG CTAGCCATCT GCAGAGCTTC CTGGAGGTGT CGTACCGCGT TCTACGCCAC     840
CTTGCGCAGC CCGGCGGCGG CTCTGACATG GCTACACCAT TAGGCCCTGC CAGCTCCCTG     900
CCCCAGAGCT TCCTGCTCAA GTCTTTAGAG CAAGTGAGGA AGATCCAGGG CGATGGCGCA     960
GCGCTCCAGG AGAAGCTGTG TGCCACCTAA TAA                                  993
```

(2) INFORMATION FOR SEQ ID NO:156:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:156:

```
ATGGCTAACT GCTCTATAAT GATCGATGAA ATTATACATC ACTTAAAGAG ACCACCTGCA      60
CCTTTGCTGG ACCCGAACAA CCTCAATGAC GAAGACGTCT CTATCCTGAT GGATCGAAAC     120
CTTCGACTTC CAAACCTGGA GAGCTTCGTA AGGGCTGTCA AGAACTTAGA AAATGCATCA     180
GGTATTGAGG CAATTCTTCG TAATCTCCAA CCATGTCTGC CCTCTGCCAC GGCCGCACCC     240
TCTCGACATC CAATCATCAT CAAGGCAGGT GACTGGCAAG AATTCCGGGA AAAACTGACG     300
TTCTATCTGG TTACCCTTGA GCAAGCGCAG GAACAACAGT ACGTAGAGGG CGGTGGAGGC     360
TCCCCGGGTG AACCGTCTGG TCCAATCTCT ACTATCAACC CGTCTCCTCC GTCTAAAGAA     420
TCTCATAAAT CTCCAAACAT GTCTCCCGAG TTGGGTCCCA CCTTGGACAC ACTGCAGCTG     480
GACGTCGCCG ACTTTGCCAC CACCATCTGG CAGCAGATGG AAGAACTGGG AATGGCCCCT     540
```

```
GCCCTGCAGC CCACCCAGGG TGCCATGCCG GCCTTCGCCT CTGCTTTCCA GCGCCGGGCA      600

GGAGGGGTCC TGGTTGCTAG CCATCTGCAG AGCTTCCTGG AGGTGTCGTA CCGCGTTCTA      660

CGCCACCTTG CGCAGCCCGG CGGCGGCTCT GACATGGCTA CACCATTAGG CCCTGCCAGC      720

TCCCTGCCCC AGAGCTTCCT GCTCAAGTCT TTAGAGCAAG TGAGGAAGAT CCAGGGCGAT      780

GGCGCAGCGC TCCAGGAGAA GCTGTGTGCC ACCTACAAGC TGTGCCACCC CGAGGAGCTG      840

GTGCTGCTCG GACACTCTCT GGGCATCCCC TGGGCTCCCC TGAGCTCCTG CCCCAGCCAG      900

GCCCTGCAGC TGGCAGGCTG CTTGAGCCAA CTCCATAGCG GCCTTTTCCT CTACCAGGGG      960

CTCCTGCAGG CCCTGGAAGG GATATCCTAA TAA                                   993
```

(2) INFORMATION FOR SEQ ID NO:157:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:157:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGATCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GTCTTCTGCT TTCCAGCGCC GGGCAGGAGG GGTCCTGGTT      480

GCTAGCCATC TGCAGAGCTT CCTGGAGGTG TCGTACCGCG TTCTACGCCA CCTTGCGCAG      540

CCCGGCGGCG GCTCTGACAT GGCTACACCA TTAGGCCCTG CCAGCTCCCT GCCCCAGAGC      600

TTCCTGCTCA AGTCTTTAGA GCAAGTGAGG AAGATCCAGG GCGATGGCGC AGCGCTCCAG      660

GAGAAGCTGT GTGCCACCTA CAAGCTGTGC CACCCCGAGG AGCTGGTGCT GCTCGGACAC      720

TCTCTGGGCA TCCCCTGGGC TCCCCTGAGC TCCTGCCCCA GCCAGGCCCT GCAGCTGGCA      780

GGCTGCTTGA GCCAACTCCA TAGCGGCCTT TTCCTCTACC AGGGGCTCCT GCAGGCCCTG      840

GAAGGGATAT CCCCCGAGTT GGGTCCCACC TTGGACACAC TGCAGCTGGA CGTCGCCGAC      900

TTTGCCACCA CCATCTGGCA GCAGATGGAA GAACTGGGAA TGGCCCCTGC CCTGCAGCCC      960

ACCCAGGGTG CCATGCCGGC CTTCGCCTAA TAA                                   993
```

(2) INFORMATION FOR SEQ ID NO:158:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:158:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGATCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GTCTATGGCC CCTGCCCTGC AGCCCACCCA GGGTGCCATG     480

CCGGCCTTCG CCTCTGCTTT CCAGCGCCGG GCAGGAGGGG TCCTGGTTGC TAGCCATCTG     540

CAGAGCTTCC TGGAGGTGTC GTACCGCGTT CTACGCCACC TTGCGCAGCC CGGCGGCGGC     600

TCTGACATGG CTACACCATT AGGCCCTGCC AGCTCCCTGC CCCAGAGCTT CCTGCTCAAG     660

TCTTTAGAGC AAGTGAGGAA GATCCAGGGC GATGGCGCAG CGCTCCAGGA GAAGCTGTGT     720

GCCACCTACA AGCTGTGCCA CCCCGAGGAG CTGGTGCTGC TCGGACACTC TCTGGGCATC     780

CCCTGGGCTC CCCTGAGCTC CTGCCCCAGC CAGGCCCTGC AGCTGGCAGG CTGCTTGAGC     840

CAACTCCATA GCGGCCTTTT CCTCTACCAG GGGCTCCTGC AGGCCCTGGA AGGGATATCC     900

CCCGAGTTGG GTCCCACCTT GGACACACTG CAGCTGGACG TCGCCGACTT TGCCACCACC     960

ATCTGGCAGC AGATGGAAGA ACTGGGATAA TAA                                  993

(2) INFORMATION FOR SEQ ID NO:159:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:159:

ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGATCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GTCTACCCAG GGTGCCATGC CGGCCTTCGC CTCTGCTTTC     480

CAGCGCCGGG CAGGAGGGGT CCTGGTTGCT AGCCATCTGC AGAGCTTCCT GGAGGTGTCG     540

TACCGCGTTC TACGCCACCT TGCGCAGCCC GGCGGCGGCT CTGACATGGC TACACCATTA     600

GGCCCTGCCA GCTCCCTGCC CCAGAGCTTC CTGCTCAAGT CTTTAGAGCA AGTGAGGAAG     660

ATCCAGGGCG ATGGCGCAGC GCTCCAGGAG AAGCTGTGTG CCACCTACAA GCTGTGCCAC     720

CCCGAGGAGC TGGTGCTGCT CGGACACTCT CTGGGCATCC CCTGGGCTCC CCTGAGCTCC     780

TGCCCCAGCC AGGCCCTGCA GCTGGCAGGC TGCTTGAGCC AACTCCATAG CGGCCTTTTC     840

CTCTACCAGG GGCTCCTGCA GGCCCTGGAA GGGATATCCC CCGAGTTGGG TCCCACCTTG     900

GACACACTGC AGCTGGACGT CGCCGACTTT GCCACCACCA TCTGGCAGCA GATGGAAGAA     960
```

CTGGGAATGG CCCCTGCCCT GCAGCCCTAA TAA                                  993

(2) INFORMATION FOR SEQ ID NO:160:

(i) SEQUENCE CHARACTERISTICS:
        (A) LENGTH: 1027 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:160:

ATGGCTACAC CATTGGGCCC TGCCAGCTCC CTGCCCCAGA GCTTCCTGCT CAAGTCTTTA     60

GAGCAAGTGA GGAAGATCCA GGGCGATGGC GCAGCGCTCC AGGAGAAGCT GTGTGCCACC    120

TACAAGCTGT GCCACCCCGA GGAGCTGGTG CTGCTCGGAC ACTCTCTGGG CATCCCCTGG    180

GCTCCCCTGA GCTCCTGCCC CAGCCAGGCC CTGCAGCTGG CAGGCTGCTT GAGCCAACTC    240

CATAGCGGCC TTTTCCTCTA CCAGGGGCTC CTGCAGGCCC TGGAAGGGAT ATCCCCCGAG    300

TTGGGTCCCA CCTTGGACAC ACTGCAGCTG GACGTCGCCG ACTTTGCCAC CACCATCTGG    360

CAGCAGATGG AAGAACTGGG AATGGCCCCT GCCCTGCAGC CCACCCAGGG TGCCATGCCG    420

GCCTTCGCCT CTGCTTTCCA GCGCCGGGCA GGAGGGGTCC TGGTTGCTAG CCATCTGCAG    480

AGCTTCCTGG AGGTGTCGTA CCGCGTTCTA CGCCACCTTG CGCAGCCCGG CGGCGGCTCT    540

GACATGGCTA CACCATTGGG CCCTGCCAGC TCCCTGCCCC AGAGCTTCCT GCTCAAGTCT    600

TTAGAGCAAG TGAGGAAGAT CCAGGGCGAT GGCGCAGCGC TCCAGGAGAA GCTGTGTGCC    660

ACCTACAAGC TGTGCCACCC CGAGGAGCTG GTGCTGCTCG GACACTCTCT GGGCATCCCC    720

TGGGCTCCCC TGAGCTCCTG CCCCAGCCAG GCCCTGCAGC TGGCAGGCTG CTTGAGCCAA    780

CTCCATAGCG GCCTTTTCCT CTACCAGGGG CTCCTGCAGG CCCTGGAAGG GATATCCCCC    840

GAGTTGGGTC CCACCTTGGA CACACTGCAG CTGGACGTCG CCGACTTTGC CACCACCATC    900

TGGCAGCAGA TGGAAGAACT GGGAATGGCC CCTGCCCTGC AGCCCACCCA TCCTGGTTGC    960

TAGCCATCTG CAGAGCTTCC TGGAGGTGTC GTACCGCGTT CTACGCCACC TTGCGCAGCC   1020

CTGATAA                                                              1027

(2) INFORMATION FOR SEQ ID NO:161:

(i) SEQUENCE CHARACTERISTICS:
        (A) LENGTH: 155 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:161:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln

-continued

```
65                  70                  75                  80
Leu Gly Pro Thr Cys Leu Ser Ser Leu Leu Gly Gln Leu Ser Gly Gln
                85                  90                  95
Val Arg Leu Leu Leu Gly Ala Leu Gln Ser Leu Leu Gly Thr Gln Leu
                100                 105                 110
Pro Pro Gln Gly Arg Thr Thr Ala His Lys Asp Pro Asn Ala Ile Phe
                115                 120                 125
Leu Ser Phe Gln His Leu Leu Arg Gly Lys Val Arg Phe Leu Met Leu
    130                 135                 140
Val Gly Gly Ser Thr Leu Cys Val Arg Glu Phe
145                 150                 155

(2) INFORMATION FOR SEQ ID NO:162:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:162:

Ser Pro Ala Pro Ala Cys Asp Leu Arg Val Leu Ser Lys Leu Leu
1               5                   10                  15
Arg Asp Ser His Val Leu His Ser Arg Leu Ser Gln Cys Pro Glu Val
                20                  25                  30
His Pro Leu Pro Thr Pro Val Leu Leu Pro Ala Val Asp Phe Ser Leu
                35                  40                  45
Gly Glu Trp Lys Thr Gln Met Glu Glu Thr Lys Ala Gln Asp Ile Leu
    50                  55                  60
Gly Ala Val Thr Leu Leu Leu Glu Gly Val Met Ala Ala Arg Gly Gln
65                  70                  75                  80
Leu Gly Pro Thr Cys Leu Ser Ser Leu Leu Gly Gln Leu Ser Gly Gln
                85                  90                  95
Val Arg Leu Leu Leu Gly Ala Leu Gln Ser Leu Leu Gly Thr Gln Leu
                100                 105                 110
Pro Pro Gln Gly Arg Thr Thr Ala His Lys Asp Pro Asn Ala Ile Phe
                115                 120                 125
Leu Ser Phe Gln His Leu Leu Arg Gly Lys Val Arg Phe Leu Met Leu
    130                 135                 140
Val Gly Gly Ser Thr Leu Cys Val Arg Glu Phe Gly Gly Asn Met Ala
145                 150                 155                 160
Ser Pro Ala Pro Ala Cys Asp Leu Arg Val Leu Ser Lys Leu Leu
                165                 170                 175
Arg Asp Ser His Val Leu His Ser Arg Leu Ser Gln Cys Pro Glu Val
                180                 185                 190
His Pro Leu Pro Thr Pro Val Leu Leu Pro Ala Val Asp Phe Ser Leu
                195                 200                 205
Gly Glu Trp Lys Thr Gln Met Glu Glu Thr Lys Ala Gln Asp Ile Leu
    210                 215                 220
Gly Ala Val Thr Leu Leu Leu Glu Gly Val Met Ala Ala Arg Gly Gln
225                 230                 235                 240
Leu Gly Pro Thr Cys Leu Ser Ser Leu Leu Gly Gln Leu Ser Gly Gln
                245                 250                 255
Val Arg Leu Leu Leu Gly Ala Leu Gln Ser Leu Leu Gly Thr Gln Gly
```

```
                    260                 265                 270
Arg Thr Thr Ala His Lys Asp Pro Asn Ala Ile Phe Leu Ser Phe Gln
        275                 280                 285

His Leu Leu Arg Gly Lys Val Arg Phe Leu Met Leu Val Gly Gly Ser
    290                 295                 300

Thr Leu Cys Val Arg
305

(2) INFORMATION FOR SEQ ID NO:163:

(i) SEQUENCE CHARACTERISTICS:
        (A) LENGTH: 312 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:163:

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Glu Phe Gly Asn Met Ala Ser
145                 150                 155                 160

Pro Ala Pro Pro Ala Cys Asp Leu Arg Val Leu Ser Lys Leu Leu Arg
                165                 170                 175

Asp Ser His Val Leu His Ser Arg Leu Ser Gln Cys Pro Glu Val His
                180                 185                 190

Pro Leu Pro Thr Pro Val Leu Leu Pro Ala Val Asp Phe Ser Leu Gly
            195                 200                 205

Glu Trp Lys Thr Gln Met Glu Glu Thr Lys Ala Gln Asp Ile Leu Gly
            210                 215                 220

Ala Val Thr Leu Leu Leu Glu Gly Val Met Ala Ala Arg Gly Gln Leu
225                 230                 235                 240

Gly Pro Thr Cys Leu Ser Ser Leu Leu Gly Gln Leu Ser Gly Gln Val
                245                 250                 255

Arg Leu Leu Leu Gly Ala Leu Gln Ser Leu Leu Gly Thr Gln Leu Pro
                260                 265                 270

Pro Gln Gly Arg Thr Thr Ala His Lys Asp Pro Asn Ala Ile Phe Leu
            275                 280                 285

Ser Phe Gln His Leu Leu Arg Gly Lys Val Arg Phe Leu Met Leu Val
```

-continued

```
                290                 295                 300
Gly Gly Ser Thr Leu Cys Val Arg
305                 310

(2) INFORMATION FOR SEQ ID NO:164:

(i) SEQUENCE CHARACTERISTICS:
        (A) LENGTH: 313 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:164:

Ser Pro Ala Pro Pro Ala Cys Asp Leu Arg Val Leu Ser Lys Leu Leu
1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140

Val Gly Gly Ser Thr Leu Cys Val Arg Glu Phe Gly Gly Asn Met Ala
145                 150                 155                 160

Ser Pro Ala Pro Pro Ala Cys Asp Leu Arg Val Leu Ser Lys Leu Leu
                165                 170                 175

Arg Asp Ser His Val Leu His Ser Arg Leu Ser Gln Cys Pro Glu Val
                180                 185                 190

His Pro Leu Pro Thr Pro Val Leu Leu Pro Ala Val Asp Phe Ser Leu
            195                 200                 205

Gly Glu Trp Lys Thr Gln Met Glu Glu Thr Lys Ala Gln Asp Ile Leu
        210                 215                 220

Gly Ala Val Thr Leu Leu Leu Glu Gly Val Met Ala Ala Arg Gly Gln
225                 230                 235                 240

Leu Gly Pro Thr Cys Leu Ser Ser Leu Leu Gly Gln Leu Ser Gly Gln
                245                 250                 255

Val Arg Leu Leu Leu Gly Ala Leu Gln Ser Leu Leu Gly Thr Gln Leu
                260                 265                 270

Pro Pro Gln Gly Arg Thr Thr Ala His Lys Asp Pro Asn Ala Ile Phe
            275                 280                 285

Leu Ser Phe Gln His Leu Leu Arg Gly Lys Val Arg Phe Leu Met Leu
        290                 295                 300

Val Gly Gly Ser Thr Leu Cys Val Arg
305                 310
```

(2) INFORMATION FOR SEQ ID NO:165:

(i) SEQUENCE CHARACTERISTICS:
        (A) LENGTH: 316 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:165:

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Thr Lys Ala Gln Asp Ile Leu
 50                  55                  60

Gly Ala Val Thr Leu Leu Glu Gly Val Met Ala Ala Arg Gly Gln
 65                  70                  75              80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Glu Phe Gly Gly Asn Gly Gly
145                 150                 155                 160

Asn Met Ala Ser Pro Ala Pro Ala Cys Asp Leu Arg Val Leu Ser
            165                 170                 175

Lys Leu Leu Arg Asp Ser His Val Leu His Ser Arg Leu Ser Gln Cys
                180                 185                 190

Pro Glu Val His Pro Leu Pro Thr Pro Val Leu Leu Pro Ala Val Asp
            195                 200                 205

Phe Ser Leu Gly Glu Trp Lys Thr Gln Met Glu Glu Thr Lys Ala Gln
    210                 215                 220

Asp Ile Leu Gly Ala Val Thr Leu Leu Glu Gly Val Met Ala Ala
225                 230                 235                 240

Arg Gly Gln Leu Gly Pro Thr Cys Leu Ser Ser Leu Leu Gly Gln Leu
                245                 250                 255

Ser Gly Gln Val Arg Leu Leu Leu Gly Ala Leu Gln Ser Leu Leu Gly
                260                 265                 270

Thr Gln Leu Pro Pro Gln Gly Arg Thr Thr Ala His Lys Asp Pro Asn
            275                 280                 285

Ala Ile Phe Leu Ser Phe Gln His Leu Leu Arg Gly Lys Val Arg Phe
    290                 295                 300

Leu Met Leu Val Gly Gly Ser Thr Leu Cys Val Arg
305                 310                 315
```

(2) INFORMATION FOR SEQ ID NO:166:

(i) SEQUENCE CHARACTERISTICS:
        (A) LENGTH: 302 amino acids
        (B) TYPE: amino acid
        (C) STRANDEDNESS: unknown (D) TOPOLOGY: unknown (ii) MOLECULE TYPE: peptide (xi) SEQUENCE DESCRIPTION: SEQ ID NO:166:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
        35                  40                  45

Arg Ala Val Lys Asn Leu Glu Asn Ala Ser Gly Ile Glu Ala Ile Leu
    50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
            100                 105                 110

Val Glu Gly Gly Gly Ser Pro Gly Gly Ser Gly Gly Gly Ser
            115                 120                 125

Asn Met Ala Tyr Lys Leu Cys His Pro Glu Glu Leu Val Leu Leu Gly
    130                 135                 140

His Ser Leu Gly Ile Pro Trp Ala Pro Leu Ser Ser Cys Pro Ser Gln
145                 150                 155                 160

Ala Leu Gln Leu Ala Gly Cys Leu Ser Gln Leu His Ser Gly Leu Phe
                165                 170                 175

Leu Tyr Gln Gly Leu Leu Gln Ala Leu Glu Gly Ile Ser Pro Glu Leu
            180                 185                 190

Gly Pro Thr Leu Asp Thr Leu Gln Leu Asp Val Ala Asp Phe Ala Thr
        195                 200                 205

Thr Ile Trp Gln Gln Met Glu Glu Leu Gly Met Ala Pro Ala Leu Gln
    210                 215                 220

Pro Thr Gln Gly Ala Met Pro Ala Phe Ala Ser Ala Phe Gln Arg Arg
225                 230                 235                 240

Ala Gly Gly Val Leu Val Ala Ser His Leu Gln Ser Phe Leu Glu Val
                245                 250                 255

Ser Tyr Arg Val Leu Arg His Leu Ala Gln Pro Ser Gly Gly Ser Gly
            260                 265                 270

Gly Ser Gln Ser Phe Leu Leu Lys Ser Leu Glu Gln Val Arg Lys Ile
        275                 280                 285

Gln Gly Asp Gly Ala Ala Leu Gln Glu Lys Leu Cys Ala Thr
    290                 295                 300

(2) INFORMATION FOR SEQ ID NO:167:

(i) SEQUENCE CHARACTERISTICS:
        (A) LENGTH: 317 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:167:

Asn Cys Ser Ile Met Ile Asp Glu Ile Ile His His Leu Lys Arg Pro
1               5                   10                  15

-continued

```
Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
            35                  40                  45

Arg Ala Val Lys Asn Leu Glu Asn Ala Ser Gly Ile Glu Ala Ile Leu
 50                  55                  60

Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Glu Lys
                 85                  90                  95

Leu Thr Phe Tyr Leu Val Thr Leu Glu Gln Ala Gln Glu Gln Gln Tyr
                100                 105                 110

Val Glu Gly Gly Gly Ser Pro Gly Glu Pro Ser Gly Pro Ile Ser
            115                 120                 125

Thr Ile Asn Pro Ser Pro Pro Ser Lys Glu Ser His Lys Ser Pro Asn
            130                 135                 140

Met Ala Tyr Lys Leu Cys His Pro Glu Glu Leu Val Leu Leu Gly His
145                 150                 155                 160

Ser Leu Gly Ile Pro Trp Ala Pro Leu Ser Ser Cys Pro Ser Gln Ala
                165                 170                 175

Leu Gln Leu Ala Gly Cys Leu Ser Gln Leu His Ser Gly Leu Phe Leu
            180                 185                 190

Tyr Gln Gly Leu Leu Gln Ala Leu Glu Gly Ile Ser Pro Glu Leu Gly
            195                 200                 205

Pro Thr Leu Asp Thr Leu Gln Leu Asp Val Ala Asp Phe Ala Thr Thr
            210                 215                 220

Ile Trp Gln Gln Met Glu Glu Leu Gly Met Ala Pro Ala Leu Gln Pro
225                 230                 235                 240

Thr Gln Gly Ala Met Pro Ala Phe Ala Ser Ala Phe Gln Arg Arg Ala
                245                 250                 255

Gly Gly Val Leu Val Ala Ser His Leu Gln Ser Phe Leu Glu Val Ser
            260                 265                 270

Tyr Arg Val Leu Arg His Leu Ala Gln Pro Ser Gly Gly Ser Gly Gly
            275                 280                 285

Ser Gln Ser Phe Leu Leu Lys Ser Leu Glu Gln Val Arg Lys Ile Gln
290                 295                 300

Gly Asp Gly Ala Ala Leu Gln Glu Lys Leu Cys Ala Thr
305                 310                 315
```

(2) INFORMATION FOR SEQ ID NO:168:

(i) SEQUENCE CHARACTERISTICS:
        (A) LENGTH: 302 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:168:

```
Asn Cys Ser Ile Met Ile Asp Glu Ile Ile His His Leu Lys Arg Pro
 1               5                  10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
            35                  40                  45
```

-continued

```
Arg Ala Val Lys Asn Leu Glu Asn Ala Ser Gly Ile Glu Ala Ile Leu
 50                  55                  60

Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Glu Lys
                 85                  90                  95

Leu Thr Phe Tyr Leu Val Thr Leu Glu Gln Ala Gln Glu Gln Gln Tyr
                100                 105                 110

Val Glu Gly Gly Gly Ser Pro Gly Gly Ser Gly Gly Ser
                115                 120                 125

Asn Met Ala Pro Glu Leu Gly Pro Thr Leu Asp Thr Leu Gln Leu Asp
130                 135                 140

Val Ala Asp Phe Ala Thr Thr Ile Trp Gln Gln Met Glu Glu Leu Gly
145                 150                 155                 160

Met Ala Pro Ala Leu Gln Pro Thr Gln Gly Ala Met Pro Ala Phe Ala
                165                 170                 175

Ser Ala Phe Gln Arg Arg Ala Gly Gly Val Leu Val Ala Ser His Leu
                180                 185                 190

Gln Ser Phe Leu Glu Val Ser Tyr Arg Val Leu Arg His Leu Ala Gln
                195                 200                 205

Pro Ser Gly Gly Ser Gly Gly Ser Gln Ser Phe Leu Leu Lys Ser Leu
                210                 215                 220

Glu Gln Val Arg Lys Ile Gln Gly Asp Gly Ala Ala Leu Gln Glu Lys
225                 230                 235                 240

Leu Cys Ala Thr Tyr Lys Leu Cys His Pro Glu Glu Leu Val Leu Leu
                245                 250                 255

Gly His Ser Leu Gly Ile Pro Trp Ala Pro Leu Ser Ser Cys Pro Ser
                260                 265                 270

Gln Ala Leu Gln Leu Ala Gly Cys Leu Ser Gln Leu His Ser Gly Leu
                275                 280                 285

Phe Leu Tyr Gln Gly Leu Leu Gln Ala Leu Glu Gly Ile Ser
                290                 295                 300
```

(2) INFORMATION FOR SEQ ID NO:169:

(i) SEQUENCE CHARACTERISTICS:
        (A) LENGTH: 317 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:169:

```
Asn Cys Ser Ile Met Ile Asp Glu Ile His His Leu Lys Arg Pro
 1               5                  10                  15

Pro Ala Pro Leu Leu Asp Pro Asn Asn Leu Asn Asp Glu Asp Val Ser
                 20                  25                  30

Ile Leu Met Asp Arg Asn Leu Arg Leu Pro Asn Leu Glu Ser Phe Val
                 35                  40                  45

Arg Ala Val Lys Asn Leu Glu Asn Ala Ser Gly Ile Glu Ala Ile Leu
 50                  55                  60

Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Glu Lys
                 85                  90                  95
```

```
Leu Thr Phe Tyr Leu Val Thr Leu Glu Gln Ala Gln Glu Gln Gln Tyr
                100                 105                 110

Val Glu Gly Gly Gly Gly Ser Pro Gly Glu Pro Ser Gly Pro Ile Ser
            115                 120                 125

Thr Ile Asn Pro Ser Pro Ser Lys Glu Ser His Lys Ser Pro Asn
        130                 135                 140

Met Ala Pro Glu Leu Gly Pro Thr Leu Asp Thr Leu Gln Leu Asp Val
145                 150                 155                 160

Ala Asp Phe Ala Thr Thr Ile Trp Gln Gln Met Glu Glu Leu Gly Met
                165                 170                 175

Ala Pro Ala Leu Gln Pro Thr Gln Gly Ala Met Pro Ala Phe Ala Ser
                180                 185                 190

Ala Phe Gln Arg Arg Ala Gly Gly Val Leu Val Ala Ser His Leu Gln
                195                 200                 205

Ser Phe Leu Glu Val Ser Tyr Arg Val Leu Arg His Leu Ala Gln Pro
            210                 215                 220

Ser Gly Gly Ser Gly Gly Ser Gln Ser Phe Leu Leu Lys Ser Leu Glu
225                 230                 235                 240

Gln Val Arg Lys Ile Gln Gly Asp Gly Ala Ala Leu Gln Glu Lys Leu
                245                 250                 255

Cys Ala Thr Tyr Lys Leu Cys His Pro Glu Glu Leu Val Leu Leu Gly
                260                 265                 270

His Ser Leu Gly Ile Pro Trp Ala Pro Leu Ser Ser Cys Pro Ser Gln
                275                 280                 285

Ala Leu Gln Leu Ala Gly Cys Leu Ser Gln Leu His Ser Gly Leu Phe
                290                 295                 300

Leu Tyr Gln Gly Leu Leu Gln Ala Leu Glu Gly Ile Ser
305                 310                 315

(2) INFORMATION FOR SEQ ID NO:170:

(i) SEQUENCE CHARACTERISTICS:
        (A) LENGTH: 302 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:170:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
            35                  40                  45

Arg Ala Val Lys Asn Leu Glu Asn Ala Ser Gly Ile Glu Ala Ile Leu
        50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
                100                 105                 110

Val Glu Gly Gly Gly Gly Ser Pro Gly Gly Ser Gly Gly Ser
            115                 120                 125
```

```
Asn Met Ala Met Ala Pro Ala Leu Gln Pro Thr Gln Gly Ala Met Pro
    130                 135                 140
Ala Phe Ala Ser Ala Phe Gln Arg Arg Ala Gly Gly Val Leu Val Ala
145                 150                 155                 160
Ser His Leu Gln Ser Phe Leu Glu Val Ser Tyr Arg Val Leu Arg His
                165                 170                 175
Leu Ala Gln Pro Ser Gly Gly Ser Gly Gly Ser Gln Ser Phe Leu Leu
                180                 185                 190
Lys Ser Leu Glu Gln Val Arg Lys Ile Gln Gly Asp Gly Ala Ala Leu
            195                 200                 205
Gln Glu Lys Leu Cys Ala Thr Tyr Lys Leu Cys His Pro Glu Glu Leu
210                 215                 220
Val Leu Leu Gly His Ser Leu Gly Ile Pro Trp Ala Pro Leu Ser Ser
225                 230                 235                 240
Cys Pro Ser Gln Ala Leu Gln Leu Ala Gly Cys Leu Ser Gln Leu His
                245                 250                 255
Ser Gly Leu Phe Leu Tyr Gln Gly Leu Leu Gln Ala Leu Glu Gly Ile
                260                 265                 270
Ser Pro Glu Leu Gly Pro Thr Leu Asp Thr Leu Gln Leu Asp Val Ala
            275                 280                 285
Asp Phe Ala Thr Thr Ile Trp Gln Gln Met Glu Glu Leu Gly
            290                 295                 300

(2) INFORMATION FOR SEQ ID NO:171:

(i) SEQUENCE CHARACTERISTICS:
        (A) LENGTH: 317 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:171:

Asn Cys Ser Ile Met Ile Asp Glu Ile Ile His His Leu Lys Arg Pro
1               5                   10                  15
Pro Ala Pro Leu Leu Asp Pro Asn Asn Leu Asn Asp Glu Asp Val Ser
                20                  25                  30
Ile Leu Met Asp Arg Asn Leu Arg Leu Pro Asn Leu Glu Ser Phe Val
            35                  40                  45
Arg Ala Val Lys Asn Leu Glu Asn Ala Ser Gly Ile Glu Ala Ile Leu
        50                  55                  60
Arg Asn Leu Gln Pro Cys Leu Pro Ser Ala Thr Ala Ala Pro Ser Arg
65                  70                  75                  80
His Pro Ile Ile Ile Lys Ala Gly Asp Trp Gln Glu Phe Arg Glu Lys
                85                  90                  95
Leu Thr Phe Tyr Leu Val Thr Leu Glu Gln Ala Gln Glu Gln Gln Tyr
                100                 105                 110
Val Glu Gly Gly Gly Ser Pro Gly Glu Pro Ser Gly Pro Ile Ser
            115                 120                 125
Thr Ile Asn Pro Ser Pro Pro Ser Lys Glu Ser His Lys Ser Pro Asn
        130                 135                 140
Met Ala Met Ala Pro Ala Leu Gln Pro Thr Gln Gly Ala Met Pro Ala
145                 150                 155                 160
Phe Ala Ser Ala Phe Gln Arg Arg Ala Gly Gly Val Leu Val Ala Ser
                165                 170                 175
```

```
His Leu Gln Ser Phe Leu Glu Val Ser Tyr Arg Val Leu Arg His Leu
            180                 185                 190

Ala Gln Pro Ser Gly Gly Ser Gly Gly Ser Gln Ser Phe Leu Leu Lys
            195                 200                 205

Ser Leu Glu Gln Val Arg Lys Ile Gln Gly Asp Gly Ala Ala Leu Gln
            210                 215                 220

Glu Lys Leu Cys Ala Thr Tyr Lys Leu Cys His Pro Glu Glu Leu Val
225                 230                 235                 240

Leu Leu Gly His Ser Leu Gly Ile Pro Trp Ala Pro Leu Ser Ser Cys
                245                 250                 255

Pro Ser Gln Ala Leu Gln Leu Ala Gly Cys Leu Ser Gln Leu His Ser
            260                 265                 270

Gly Leu Phe Leu Tyr Gln Gly Leu Leu Gln Ala Leu Glu Gly Ile Ser
            275                 280                 285

Pro Glu Leu Gly Pro Thr Leu Asp Thr Leu Gln Leu Asp Val Ala Asp
            290                 295                 300

Phe Ala Thr Thr Ile Trp Gln Gln Met Glu Glu Leu Gly
305                 310                 315
```

(2) INFORMATION FOR SEQ ID NO:172:

(i) SEQUENCE CHARACTERISTICS:
        (A) LENGTH: 302 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:172:

```
Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
            35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
            100                 105                 110

Val Glu Gly Gly Gly Gly Ser Pro Gly Gly Ser Gly Gly Gly Ser
            115                 120                 125

Asn Met Ala Thr Gln Gly Ala Met Pro Ala Phe Ala Ser Ala Phe Gln
            130                 135                 140

Arg Arg Ala Gly Gly Val Leu Val Ala Ser His Leu Gln Ser Phe Leu
145                 150                 155                 160

Glu Val Ser Tyr Arg Val Leu Arg His Leu Ala Gln Pro Ser Gly Gly
                165                 170                 175

Ser Gly Gly Ser Gln Ser Phe Leu Leu Lys Ser Leu Glu Gln Val Arg
            180                 185                 190

Lys Ile Gln Gly Asp Gly Ala Ala Leu Gln Glu Lys Leu Cys Ala Thr
            195                 200                 205
```

```
Tyr Lys Leu Cys His Pro Glu Glu Leu Val Leu Leu Gly His Ser Leu
    210                 215                 220
Gly Ile Pro Trp Ala Pro Leu Ser Ser Cys Pro Ser Gln Ala Leu Gln
225                 230                 235                 240
Leu Ala Gly Cys Leu Ser Gln Leu His Ser Gly Leu Phe Leu Tyr Gln
                245                 250                 255
Gly Leu Leu Gln Ala Leu Glu Gly Ile Ser Pro Glu Leu Gly Pro Thr
            260                 265                 270
Leu Asp Thr Leu Gln Leu Asp Val Ala Asp Phe Ala Thr Thr Ile Trp
        275                 280                 285
Gln Gln Met Glu Glu Leu Gly Met Ala Pro Ala Leu Gln Pro
    290                 295                 300
```

(2) INFORMATION FOR SEQ ID NO:173:

(i) SEQUENCE CHARACTERISTICS:
        (A) LENGTH: 317 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:173:

```
Asn Cys Ser Ile Met Ile Asp Glu Ile Ile His His Leu Lys Arg Pro
1               5                   10                  15
Pro Ala Pro Leu Leu Asp Pro Asn Asn Leu Asn Asp Glu Asp Val Ser
                20                  25                  30
Ile Leu Met Asp Arg Asn Leu Arg Leu Pro Asn Leu Glu Ser Phe Val
            35                  40                  45
Arg Ala Val Lys Asn Leu Glu Asn Ala Ser Gly Ile Glu Ala Ile Leu
50                  55                  60
Arg Asn Leu Gln Pro Cys Leu Pro Ser Ala Thr Ala Ala Pro Ser Arg
65                  70                  75                  80
His Pro Ile Ile Ile Lys Ala Gly Asp Trp Gln Glu Phe Arg Glu Lys
                85                  90                  95
Leu Thr Phe Tyr Leu Val Thr Leu Glu Gln Ala Gln Glu Gln Gln Tyr
                100                 105                 110
Val Glu Gly Gly Gly Ser Pro Gly Glu Pro Ser Gly Pro Ile Ser
            115                 120                 125
Thr Ile Asn Pro Ser Pro Pro Ser Lys Glu Ser His Lys Ser Pro Asn
            130                 135                 140
Met Ala Thr Gln Gly Ala Met Pro Ala Phe Ala Ser Ala Phe Gln Arg
145                 150                 155                 160
Arg Ala Gly Gly Val Leu Val Ala Ser His Leu Gln Ser Phe Leu Glu
                165                 170                 175
Val Ser Tyr Arg Val Leu Arg His Leu Ala Gln Pro Ser Gly Gly Ser
                180                 185                 190
Gly Gly Ser Gln Ser Phe Leu Leu Lys Ser Leu Glu Gln Val Arg Lys
            195                 200                 205
Ile Gln Gly Asp Gly Ala Ala Leu Gln Glu Lys Leu Cys Ala Thr Tyr
    210                 215                 220
Lys Leu Cys His Pro Glu Glu Leu Val Leu Leu Gly His Ser Leu Gly
225                 230                 235                 240
Ile Pro Trp Ala Pro Leu Ser Ser Cys Pro Ser Gln Ala Leu Gln Leu
                245                 250                 255
```

-continued

```
Ala Gly Cys Leu Ser Gln Leu His Ser Gly Leu Phe Leu Tyr Gln Gly
            260                 265                 270

Leu Leu Gln Ala Leu Glu Gly Ile Ser Pro Glu Leu Gly Pro Thr Leu
            275                 280                 285

Asp Thr Leu Gln Leu Asp Val Ala Asp Phe Ala Thr Thr Ile Trp Gln
            290                 295                 300

Gln Met Glu Glu Leu Gly Met Ala Pro Ala Leu Gln Pro
305                 310                 315
```

(2) INFORMATION FOR SEQ ID NO:174:

(i) SEQUENCE CHARACTERISTICS:
       (A) LENGTH: 302 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:174:

```
Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
            35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
            85                  90                  95

Leu Thr Phe Tyr Leu Val Thr Leu Glu Gln Ala Gln Glu Gln Gln Tyr
            100                 105                 110

Val Glu Gly Gly Gly Ser Pro Gly Gly Ser Gly Gly Ser
            115                 120                 125

Asn Met Ala Ser Ala Phe Gln Arg Arg Ala Gly Gly Val Leu Val Ala
130                 135                 140

Ser His Leu Gln Ser Phe Leu Glu Val Ser Tyr Arg Val Leu Arg His
145                 150                 155                 160

Leu Ala Gln Pro Ser Gly Ser Gly Gly Ser Gln Ser Phe Leu Leu
            165                 170                 175

Lys Ser Leu Glu Gln Val Arg Lys Ile Gln Gly Asp Gly Ala Ala Leu
            180                 185                 190

Gln Glu Lys Leu Cys Ala Thr Tyr Lys Leu Cys His Pro Glu Glu Leu
            195                 200                 205

Val Leu Leu Gly His Ser Leu Gly Ile Pro Trp Ala Pro Leu Ser Ser
            210                 215                 220

Cys Pro Ser Gln Ala Leu Gln Leu Ala Gly Cys Leu Ser Gln Leu His
225                 230                 235                 240

Ser Gly Leu Phe Leu Tyr Gln Gly Leu Leu Gln Ala Leu Glu Gly Ile
            245                 250                 255

Ser Pro Glu Leu Gly Pro Thr Leu Asp Thr Leu Gln Leu Asp Val Ala
            260                 265                 270

Asp Phe Ala Thr Thr Ile Trp Gln Gln Met Glu Glu Leu Gly Met Ala
            275                 280                 285
```

Pro Ala Leu Gln Pro Thr Gln Gly Ala Met Pro Ala Phe Ala
    290                 295                 300

(2) INFORMATION FOR SEQ ID NO:175:

(i) SEQUENCE CHARACTERISTICS:
        (A) LENGTH: 317 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:175:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
                20                  25                  30

Ile Leu Met Asp Arg Asn Leu Arg Leu Pro Asn Leu Glu Ser Phe Val
                35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
                100                 105                 110

Val Glu Gly Gly Gly Ser Pro Gly Glu Pro Ser Gly Pro Ile Ser
                115                 120                 125

Thr Ile Asn Pro Ser Pro Ser Lys Glu Ser His Lys Ser Pro Asn
130                 135                 140

Met Ala Ser Ala Phe Gln Arg Arg Ala Gly Val Leu Val Ala Ser
145                 150                 155                 160

His Leu Gln Ser Phe Leu Glu Val Ser Tyr Arg Val Leu Arg His Leu
                165                 170                 175

Ala Gln Pro Ser Gly Gly Ser Gly Ser Gln Ser Phe Leu Leu Lys
                180                 185                 190

Ser Leu Glu Gln Val Arg Lys Ile Gln Gly Asp Gly Ala Ala Leu Gln
                195                 200                 205

Glu Lys Leu Cys Ala Thr Tyr Lys Leu Cys His Pro Glu Glu Leu Val
210                 215                 220

Leu Leu Gly His Ser Leu Gly Ile Pro Trp Ala Pro Leu Ser Ser Cys
225                 230                 235                 240

Pro Ser Gln Ala Leu Gln Leu Ala Gly Cys Leu Ser Gln Leu His Ser
                245                 250                 255

Gly Leu Phe Leu Tyr Gln Gly Leu Leu Gln Ala Leu Glu Gly Ile Ser
                260                 265                 270

Pro Glu Leu Gly Pro Thr Leu Asp Thr Leu Gln Leu Asp Val Ala Asp
                275                 280                 285

Phe Ala Thr Thr Ile Trp Gln Gln Met Glu Glu Leu Gly Met Ala Pro
                290                 295                 300

Ala Leu Gln Pro Thr Gln Gly Ala Met Pro Ala Phe Ala
305                 310                 315

(2) INFORMATION FOR SEQ ID NO:176:

(i) SEQUENCE CHARACTERISTICS:
    (A) LENGTH: 305 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:176:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
        35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
            100                 105                 110

Val Glu Gly Gly Gly Ser Pro Gly Gly Ser Gly Gly Ser
        115                 120                 125

Asn Met Ala Tyr Lys Leu Cys His Pro Glu Glu Leu Val Leu Leu Gly
130                 135                 140

His Ser Leu Gly Ile Pro Trp Ala Pro Leu Ser Ser Cys Pro Ser Gln
145                 150                 155                 160

Ala Leu Gln Leu Ala Gly Cys Leu Ser Gln Leu His Ser Gly Leu Phe
            165                 170                 175

Leu Tyr Gln Gly Leu Leu Gln Ala Leu Glu Gly Ile Ser Pro Glu Leu
            180                 185                 190

Gly Pro Thr Leu Asp Thr Leu Gln Leu Asp Val Ala Asp Phe Ala Thr
            195                 200                 205

Thr Ile Trp Gln Gln Met Glu Glu Leu Gly Met Ala Pro Ala Leu Gln
210                 215                 220

Pro Thr Gln Gly Ala Met Pro Ala Phe Ala Ser Ala Phe Gln Arg Arg
225                 230                 235                 240

Ala Gly Gly Val Leu Val Ala Ser His Leu Gln Ser Phe Leu Glu Val
            245                 250                 255

Ser Tyr Arg Val Leu Arg His Leu Ala Gln Pro Thr Pro Leu Gly Pro
            260                 265                 270

Ala Ser Ser Leu Pro Gln Ser Phe Leu Leu Lys Ser Leu Glu Gln Val
            275                 280                 285

Arg Lys Ile Gln Gly Asp Gly Ala Ala Leu Gln Glu Lys Leu Cys Ala
290                 295                 300

Thr
305

(2) INFORMATION FOR SEQ ID NO:177:

(i) SEQUENCE CHARACTERISTICS:
        (A) LENGTH: 320 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:177:

```
Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
                20                  25                  30

Ile Leu Met Asp Arg Asn Leu Arg Leu Pro Asn Leu Glu Ser Phe Val
            35                  40                  45

Arg Ala Val Lys Asn Leu Glu Asn Ala Ser Gly Ile Glu Ala Ile Leu
        50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
                100                 105                 110

Val Glu Gly Gly Gly Ser Pro Gly Glu Pro Ser Gly Pro Ile Ser
                115                 120                 125

Thr Ile Asn Pro Ser Pro Ser Lys Glu Ser His Lys Ser Pro Asn
130                 135                 140

Met Ala Tyr Lys Leu Cys His Pro Glu Glu Leu Val Leu Leu Gly His
145                 150                 155                 160

Ser Leu Gly Ile Pro Trp Ala Pro Leu Ser Ser Cys Pro Ser Gln Ala
                165                 170                 175

Leu Gln Leu Ala Gly Cys Leu Ser Gln Leu His Ser Gly Leu Phe Leu
                180                 185                 190

Tyr Gln Gly Leu Leu Gln Ala Leu Glu Gly Ile Ser Pro Glu Leu Gly
                195                 200                 205

Pro Thr Leu Asp Thr Leu Gln Leu Asp Val Ala Asp Phe Ala Thr Thr
                210                 215                 220

Ile Trp Gln Gln Met Glu Glu Leu Gly Met Ala Pro Ala Leu Gln Pro
225                 230                 235                 240

Thr Gln Gly Ala Met Pro Ala Phe Ala Ser Ala Phe Gln Arg Arg Ala
                245                 250                 255

Gly Gly Val Leu Val Ala Ser His Leu Gln Ser Phe Leu Glu Val Ser
                260                 265                 270

Tyr Arg Val Leu Arg His Leu Ala Gln Pro Thr Pro Leu Gly Pro Ala
                275                 280                 285

Ser Ser Leu Pro Gln Ser Phe Leu Leu Lys Ser Leu Glu Gln Val Arg
                290                 295                 300

Lys Ile Gln Gly Asp Gly Ala Ala Leu Gln Glu Lys Leu Cys Ala Thr
305                 310                 315                 320
```

(2) INFORMATION FOR SEQ ID NO:178:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:178:

```
Asn Cys Ser Ile Met Ile Asp Glu Ile Ile His His Leu Lys Arg Pro
1               5                   10                  15
```

```
Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
        35                  40                  45

Arg Ala Val Lys Asn Leu Glu Asn Ala Ser Gly Ile Glu Ala Ile Leu
    50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
                100                 105                 110

Val Glu Gly Gly Gly Ser Pro Gly Gly Ser Gly Gly Gly Ser
            115                 120                 125

Asn Met Ala Pro Glu Leu Gly Pro Thr Leu Asp Thr Leu Gln Leu Asp
    130                 135                 140

Val Ala Asp Phe Ala Thr Thr Ile Trp Gln Gln Met Glu Glu Leu Gly
145                 150                 155                 160

Met Ala Pro Ala Leu Gln Pro Thr Gln Gly Ala Met Pro Ala Phe Ala
                165                 170                 175

Ser Ala Phe Gln Arg Arg Ala Gly Gly Val Leu Val Ala Ser His Leu
                180                 185                 190

Gln Ser Phe Leu Glu Val Ser Tyr Arg Val Leu Arg His Leu Ala Gln
                195                 200                 205

Pro Thr Pro Leu Gly Pro Ala Ser Ser Leu Pro Gln Ser Phe Leu Leu
    210                 215                 220

Lys Ser Leu Glu Gln Val Arg Lys Ile Gln Gly Asp Gly Ala Ala Leu
225                 230                 235                 240

Gln Glu Lys Leu Cys Ala Thr Tyr Lys Leu Cys His Pro Glu Glu Leu
                245                 250                 255

Val Leu Leu Gly His Ser Leu Gly Ile Pro Trp Ala Pro Leu Ser Ser
                260                 265                 270

Cys Pro Ser Gln Ala Leu Gln Leu Ala Gly Cys Leu Ser Gln Leu His
                275                 280                 285

Ser Gly Leu Phe Leu Tyr Gln Gly Leu Leu Gln Ala Leu Glu Gly Ile
                290                 295                 300

Ser
305

(2) INFORMATION FOR SEQ ID NO:179:

(i) SEQUENCE CHARACTERISTICS:
        (A) LENGTH: 320 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:179:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
        35                  40                  45
```

-continued

```
Arg Ala Val Lys Asn Leu Glu Asn Ala Ser Gly Ile Glu Ala Ile Leu
     50                  55                  60
Arg Asn Leu Gln Pro Cys Leu Pro Ser Ala Thr Ala Ala Pro Ser Arg
 65                  70                  75                  80
His Pro Ile Ile Ile Lys Ala Gly Asp Trp Gln Glu Phe Arg Glu Lys
                 85                  90                  95
Leu Thr Phe Tyr Leu Val Thr Leu Glu Gln Ala Gln Glu Gln Gln Tyr
                100                 105                 110
Val Glu Gly Gly Gly Ser Pro Gly Glu Pro Ser Gly Pro Ile Ser
                115                 120                 125
Thr Ile Asn Pro Ser Pro Pro Ser Lys Glu Ser His Lys Ser Pro Asn
    130                 135                 140
Met Ala Pro Glu Leu Gly Pro Thr Leu Asp Thr Leu Gln Leu Asp Val
145                 150                 155                 160
Ala Asp Phe Ala Thr Thr Ile Trp Gln Gln Met Glu Glu Leu Gly Met
                165                 170                 175
Ala Pro Ala Leu Gln Pro Thr Gln Gly Ala Met Pro Ala Phe Ala Ser
                180                 185                 190
Ala Phe Gln Arg Arg Ala Gly Gly Val Leu Val Ala Ser His Leu Gln
                195                 200                 205
Ser Phe Leu Glu Val Ser Tyr Arg Val Leu Arg His Leu Ala Gln Pro
    210                 215                 220
Thr Pro Leu Gly Pro Ala Ser Ser Leu Pro Gln Ser Phe Leu Leu Lys
225                 230                 235                 240
Ser Leu Glu Gln Val Arg Lys Ile Gln Gly Asp Gly Ala Ala Leu Gln
                245                 250                 255
Glu Lys Leu Cys Ala Thr Tyr Lys Leu Cys His Pro Glu Glu Leu Val
                260                 265                 270
Leu Leu Gly His Ser Leu Gly Ile Pro Trp Ala Pro Leu Ser Ser Cys
                275                 280                 285
Pro Ser Gln Ala Leu Gln Leu Ala Gly Cys Leu Ser Gln Leu His Ser
    290                 295                 300
Gly Leu Phe Leu Tyr Gln Gly Leu Leu Gln Ala Leu Glu Gly Ile Ser
305                 310                 315                 320

(2) INFORMATION FOR SEQ ID NO:180:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:180:

Asn Cys Ser Ile Met Ile Asp Glu Ile Ile His His Leu Lys Arg Pro
 1               5                  10                  15
Pro Ala Pro Leu Leu Asp Pro Asn Leu Asn Asp Glu Asp Val Ser
                 20                  25                  30
Ile Leu Met Asp Arg Asn Leu Arg Leu Pro Asn Leu Glu Ser Phe Val
                 35                  40                  45
Arg Ala Val Lys Asn Leu Glu Asn Ala Ser Gly Ile Glu Ala Ile Leu
     50                  55                  60
Arg Asn Leu Gln Pro Cys Leu Pro Ser Ala Thr Ala Ala Pro Ser Arg
 65                  70                  75                  80
```

```
His Pro Ile Ile Ile Lys Ala Gly Asp Trp Gln Glu Phe Arg Glu Lys
                85                  90                  95
Leu Thr Phe Tyr Leu Val Thr Leu Glu Gln Ala Gln Glu Gln Gln Tyr
            100                 105                 110
Val Glu Gly Gly Gly Ser Pro Gly Gly Ser Gly Gly Ser
        115                 120                 125
Asn Met Ala Met Ala Pro Ala Leu Gln Pro Thr Gln Gly Ala Met Pro
        130                 135                 140
Ala Phe Ala Ser Ala Phe Gln Arg Arg Ala Gly Gly Val Leu Val Ala
145                 150                 155                 160
Ser His Leu Gln Ser Phe Leu Glu Val Ser Tyr Arg Val Leu Arg His
                165                 170                 175
Leu Ala Gln Pro Thr Pro Leu Gly Pro Ala Ser Ser Leu Pro Gln Ser
                180                 185                 190
Phe Leu Leu Lys Ser Leu Glu Gln Val Arg Lys Ile Gln Gly Asp Gly
                195                 200                 205
Ala Ala Leu Gln Glu Lys Leu Cys Ala Thr Tyr Lys Leu Cys His Pro
                210                 215                 220
Glu Glu Leu Val Leu Leu Gly His Ser Leu Gly Ile Pro Trp Ala Pro
225                 230                 235                 240
Leu Ser Ser Cys Pro Ser Gln Ala Leu Gln Leu Ala Gly Cys Leu Ser
                245                 250                 255
Gln Leu His Ser Gly Leu Phe Leu Tyr Gln Gly Leu Leu Gln Ala Leu
                260                 265                 270
Glu Gly Ile Ser Pro Glu Leu Gly Pro Thr Leu Asp Thr Leu Gln Leu
                275                 280                 285
Asp Val Ala Asp Phe Ala Thr Thr Ile Trp Gln Gln Met Glu Glu Leu
        290                 295                 300
Gly
305

(2) INFORMATION FOR SEQ ID NO:181:

(i) SEQUENCE CHARACTERISTICS:
        (A) LENGTH: 320 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:181:

Asn Cys Ser Ile Met Ile Asp Glu Ile Ile His His Leu Lys Arg Pro
1               5                   10                  15
Pro Ala Pro Leu Leu Asp Pro Asn Asn Leu Asn Asp Glu Asp Val Ser
            20                  25                  30
Ile Leu Met Asp Arg Asn Leu Arg Leu Pro Asn Leu Glu Ser Phe Val
            35                  40                  45
Arg Ala Val Lys Asn Leu Glu Asn Ala Ser Gly Ile Glu Ala Ile Leu
        50                  55                  60
Arg Asn Leu Gln Pro Cys Leu Pro Ser Ala Thr Ala Ala Pro Ser Arg
65                  70                  75                  80
His Pro Ile Ile Ile Lys Ala Gly Asp Trp Gln Glu Phe Arg Glu Lys
                85                  90                  95
Leu Thr Phe Tyr Leu Val Thr Leu Glu Gln Ala Gln Glu Gln Gln Tyr
            100                 105                 110
```

```
Val Glu Gly Gly Gly Ser Pro Gly Pro Ser Gly Pro Ile Ser
        115                 120                 125

Thr Ile Asn Pro Ser Pro Pro Ser Lys Glu Ser His Lys Ser Pro Asn
        130                 135                 140

Met Ala Met Ala Pro Ala Leu Gln Pro Thr Gln Gly Ala Met Pro Ala
145                 150                 155                 160

Phe Ala Ser Ala Phe Gln Arg Arg Ala Gly Val Leu Val Ala Ser
                165                 170                 175

His Leu Gln Ser Phe Leu Glu Val Ser Tyr Arg Val Leu Arg His Leu
                180                 185                 190

Ala Gln Pro Thr Pro Leu Gly Pro Ala Ser Ser Leu Pro Gln Ser Phe
        195                 200                 205

Leu Leu Lys Ser Leu Glu Gln Val Arg Lys Ile Gln Gly Asp Gly Ala
210                 215                 220

Ala Leu Gln Glu Lys Leu Cys Ala Thr Tyr Lys Leu Cys His Pro Glu
225                 230                 235                 240

Glu Leu Val Leu Leu Gly His Ser Leu Gly Ile Pro Trp Ala Pro Leu
                245                 250                 255

Ser Ser Cys Pro Ser Gln Ala Leu Gln Leu Ala Gly Cys Leu Ser Gln
        260                 265                 270

Leu His Ser Gly Leu Phe Leu Tyr Gln Gly Leu Leu Gln Ala Leu Glu
        275                 280                 285

Gly Ile Ser Pro Glu Leu Gly Pro Thr Leu Asp Thr Leu Gln Leu Asp
        290                 295                 300

Val Ala Asp Phe Ala Thr Thr Ile Trp Gln Gln Met Glu Glu Leu Gly
305                 310                 315                 320

(2) INFORMATION FOR SEQ ID NO:182:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:182:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
                20                  25                  30

Ile Leu Met Asp Arg Asn Leu Arg Leu Pro Asn Leu Glu Ser Phe Val
        35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
                100                 105                 110

Val Glu Gly Gly Gly Ser Pro Gly Gly Gly Ser Gly Gly Gly Ser
        115                 120                 125

Asn Met Ala Thr Gln Gly Ala Met Pro Ala Phe Ala Ser Ala Phe Gln
        130                 135                 140
```

```
Arg Arg Ala Gly Gly Val Leu Val Ala Ser His Leu Gln Ser Phe Leu
145                 150                 155                 160

Glu Val Ser Tyr Arg Val Leu Arg His Leu Ala Gln Pro Thr Pro Leu
            165                 170                 175

Gly Pro Ala Ser Ser Leu Pro Gln Ser Phe Leu Leu Lys Ser Leu Glu
            180                 185                 190

Gln Val Arg Lys Ile Gln Gly Asp Gly Ala Ala Leu Gln Glu Lys Leu
            195                 200                 205

Cys Ala Thr Tyr Lys Leu Cys His Pro Glu Glu Leu Val Leu Leu Gly
210                 215                 220

His Ser Leu Gly Ile Pro Trp Ala Pro Leu Ser Ser Cys Pro Ser Gln
225                 230                 235                 240

Ala Leu Gln Leu Ala Gly Cys Leu Ser Gln Leu His Ser Gly Leu Phe
            245                 250                 255

Leu Tyr Gln Gly Leu Leu Gln Ala Leu Glu Gly Ile Ser Pro Glu Leu
            260                 265                 270

Gly Pro Thr Leu Asp Thr Leu Gln Leu Asp Val Ala Asp Phe Ala Thr
            275                 280                 285

Thr Ile Trp Gln Gln Met Glu Glu Leu Gly Met Ala Pro Ala Leu Gln
            290                 295                 300

Pro
305

(2) INFORMATION FOR SEQ ID NO:183:

(i) SEQUENCE CHARACTERISTICS:
        (A) LENGTH: 320 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:183:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
            35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
            85                  90                  95

Leu Thr Phe Tyr Leu Val Thr Leu Glu Gln Ala Gln Glu Gln Gln Tyr
            100                 105                 110

Val Glu Gly Gly Gly Ser Pro Gly Glu Pro Ser Gly Pro Ile Ser
            115                 120                 125

Thr Ile Asn Pro Ser Pro Pro Ser Lys Glu Ser His Lys Ser Pro Asn
            130                 135                 140

Met Ala Thr Gln Gly Ala Met Pro Ala Phe Ala Ser Ala Phe Gln Arg
145                 150                 155                 160

Arg Ala Gly Gly Val Leu Val Ala Ser His Leu Gln Ser Phe Leu Glu
                165                 170                 175
```

```
Val Ser Tyr Arg Val Leu Arg His Leu Ala Gln Pro Thr Pro Leu Gly
            180                 185                 190

Pro Ala Ser Ser Leu Pro Gln Ser Phe Leu Leu Lys Ser Leu Glu Gln
        195                 200                 205

Val Arg Lys Ile Gln Gly Asp Gly Ala Ala Leu Gln Glu Lys Leu Cys
        210                 215                 220

Ala Thr Tyr Lys Leu Cys His Pro Glu Glu Leu Val Leu Leu Gly His
225                 230                 235                 240

Ser Leu Gly Ile Pro Trp Ala Pro Leu Ser Ser Cys Pro Ser Gln Ala
                245                 250                 255

Leu Gln Leu Ala Gly Cys Leu Ser Gln Leu His Ser Gly Leu Phe Leu
            260                 265                 270

Tyr Gln Gly Leu Leu Gln Ala Leu Glu Gly Ile Ser Pro Glu Leu Gly
        275                 280                 285

Pro Thr Leu Asp Thr Leu Gln Leu Asp Val Ala Asp Phe Ala Thr Thr
        290                 295                 300

Ile Trp Gln Gln Met Glu Glu Leu Gly Met Ala Pro Ala Leu Gln Pro
305                 310                 315                 320

(2) INFORMATION FOR SEQ ID NO:184:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:184:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Asp Glu Asp Val Ser
            20                  25                  30

Ile Leu Met Asp Arg Asn Leu Arg Leu Pro Asn Leu Glu Ser Phe Val
        35                  40                  45

Arg Ala Val Lys Asn Leu Glu Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln Tyr
            100                 105                 110

Val Glu Gly Gly Gly Ser Pro Gly Gly Ser Gly Gly Ser
        115                 120                 125

Asn Met Ala Ser Ala Phe Gln Arg Arg Ala Gly Gly Val Leu Val Ala
        130                 135                 140

Ser His Leu Gln Ser Phe Leu Glu Val Ser Tyr Arg Val Leu Arg His
145                 150                 155                 160

Leu Ala Gln Pro Thr Pro Leu Gly Pro Ala Ser Ser Leu Pro Gln Ser
                165                 170                 175

Phe Leu Leu Lys Ser Leu Glu Gln Val Arg Lys Ile Gln Gly Asp Gly
            180                 185                 190

Ala Ala Leu Gln Glu Lys Leu Cys Ala Thr Tyr Lys Leu Cys His Pro
        195                 200                 205
```

-continued

```
Glu Glu Leu Val Leu Leu Gly His Ser Leu Gly Ile Pro Trp Ala Pro
    210                 215                 220
Leu Ser Ser Cys Pro Ser Gln Ala Leu Gln Leu Ala Gly Cys Leu Ser
225                 230                 235                 240
Gln Leu His Ser Gly Leu Phe Leu Tyr Gln Gly Leu Leu Gln Ala Leu
                245                 250                 255
Glu Gly Ile Ser Pro Glu Leu Gly Pro Thr Leu Asp Thr Leu Gln Leu
                260                 265                 270
Asp Val Ala Asp Phe Ala Thr Thr Ile Trp Gln Gln Met Glu Glu Leu
            275                 280                 285
Gly Met Ala Pro Ala Leu Gln Pro Thr Gln Gly Ala Met Pro Ala Phe
    290                 295                 300
Ala
305
```

(2) INFORMATION FOR SEQ ID NO:185:

(i) SEQUENCE CHARACTERISTICS:
        (A) LENGTH: 320 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:185:

```
Asn Cys Ser Ile Met Ile Asp Glu Ile Ile His His Leu Lys Arg Pro
1               5                   10                  15
Pro Ala Pro Leu Leu Asp Pro Asn Asn Leu Asn Asp Glu Asp Val Ser
                20                  25                  30
Ile Leu Met Asp Arg Asn Leu Arg Leu Pro Asn Leu Glu Ser Phe Val
            35                  40                  45
Arg Ala Val Lys Asn Leu Glu Asn Ala Ser Gly Ile Glu Ala Ile Leu
    50                  55                  60
Arg Asn Leu Gln Pro Cys Leu Pro Ser Ala Thr Ala Ala Pro Ser Arg
65                  70                  75                  80
His Pro Ile Ile Ile Lys Ala Gly Asp Trp Gln Glu Phe Arg Glu Lys
                85                  90                  95
Leu Thr Phe Tyr Leu Val Thr Leu Glu Gln Ala Gln Glu Gln Gln Tyr
                100                 105                 110
Val Glu Gly Gly Gly Ser Pro Gly Glu Pro Ser Gly Pro Ile Ser
            115                 120                 125
Thr Ile Asn Pro Ser Pro Pro Ser Lys Glu Ser His Lys Ser Pro Asn
    130                 135                 140
Met Ala Ser Ala Phe Gln Arg Arg Ala Gly Gly Val Leu Val Ala Ser
145                 150                 155                 160
His Leu Gln Ser Phe Leu Glu Val Ser Tyr Arg Val Leu Arg His Leu
                165                 170                 175
Ala Gln Pro Thr Pro Leu Gly Pro Ala Ser Ser Leu Pro Gln Ser Phe
                180                 185                 190
Leu Leu Lys Ser Leu Glu Gln Val Arg Lys Ile Gln Gly Asp Gly Ala
            195                 200                 205
Ala Leu Gln Glu Lys Leu Cys Ala Thr Tyr Lys Leu Cys His Pro Glu
    210                 215                 220
Glu Leu Val Leu Leu Gly His Ser Leu Gly Ile Pro Trp Ala Pro Leu
225                 230                 235                 240
```

```
Ser Ser Cys Pro Ser Gln Ala Leu Gln Leu Ala Gly Cys Leu Ser Gln
                245                 250                 255

Leu His Ser Gly Leu Phe Leu Tyr Gln Gly Leu Leu Gln Ala Leu Glu
            260                 265                 270

Gly Ile Ser Pro Glu Leu Gly Pro Thr Leu Asp Thr Leu Gln Leu Asp
        275                 280                 285

Val Ala Asp Phe Ala Thr Thr Ile Trp Gln Gln Met Glu Glu Leu Gly
    290                 295                 300

Met Ala Pro Ala Leu Gln Pro Thr Gln Gly Ala Met Pro Ala Phe Ala
305                 310                 315                 320
```

(2) INFORMATION FOR SEQ ID NO:186:

(i) SEQUENCE CHARACTERISTICS:
        (A) LENGTH: 321 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:186:

```
Leu Asp Pro Asn Asn Leu Asn Asp Glu Asp Val Ser Ile Leu Met Asp
1               5                   10                  15

Arg Asn Leu Arg Leu Pro Asn Leu Glu Ser Phe Val Arg Ala Val Lys
            20                  25                  30

Asn Leu Glu Asn Ala Ser Gly Ile Glu Ala Ile Leu Arg Asn Leu Gln
        35                  40                  45

Pro Cys Leu Pro Ser Ala Thr Ala Ala Pro Ser Arg His Pro Ile Ile
    50                  55                  60

Ile Lys Ala Gly Asp Trp Gln Glu Phe Arg Glu Lys Leu Thr Phe Tyr
65                  70                  75                  80

Leu Val Thr Leu Glu Gln Ala Gln Glu Gln Gln Gly Gly Ser Asn
                85                  90                  95

Cys Ser Ile Met Ile Asp Glu Ile Ile His His Leu Lys Arg Pro Pro
            100                 105                 110

Ala Pro Leu Tyr Val Glu Gly Gly Gly Ser Pro Gly Glu Pro Ser
        115                 120                 125

Gly Pro Ile Ser Thr Ile Asn Pro Ser Pro Ser Lys Glu Ser His
    130                 135                 140

Lys Ser Pro Asn Met Ala Thr Gln Gly Ala Met Pro Ala Phe Ala Ser
145                 150                 155                 160

Ala Phe Gln Arg Arg Ala Gly Gly Val Leu Val Ala Ser His Leu Gln
                165                 170                 175

Ser Phe Leu Glu Val Ser Tyr Arg Val Leu Arg His Leu Ala Gln Pro
            180                 185                 190

Ser Gly Gly Ser Gly Gly Ser Gln Ser Phe Leu Leu Lys Ser Leu Glu
        195                 200                 205

Gln Val Arg Lys Ile Gln Gly Asp Gly Ala Ala Leu Gln Glu Lys Leu
    210                 215                 220

Cys Ala Thr Tyr Lys Leu Cys His Pro Glu Glu Leu Val Leu Leu Gly
225                 230                 235                 240

His Ser Leu Gly Ile Pro Trp Ala Pro Leu Ser Ser Cys Pro Ser Gln
                245                 250                 255

Ala Leu Gln Leu Ala Gly Cys Leu Ser Gln Leu His Ser Gly Leu Phe
            260                 265                 270
```

Leu Tyr Gln Gly Leu Leu Gln Ala Leu Glu Gly Ile Ser Pro Glu Leu
        275                 280                 285

Gly Pro Thr Leu Asp Thr Leu Gln Leu Asp Val Ala Asp Phe Ala Thr
    290                 295                 300

Thr Ile Trp Gln Gln Met Glu Glu Leu Gly Met Ala Pro Ala Leu Gln
305                 310                 315                 320

Pro (2) INFORMATION FOR SEQ ID NO:187:

(i) SEQUENCE CHARACTERISTICS:
        (A) LENGTH: 321 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:187:

Asn Ala Ser Gly Ile Glu Ala Ile Leu Arg Asn Leu Gln Pro Cys Leu
1               5                   10                  15

Pro Ser Ala Thr Ala Ala Pro Ser Arg His Pro Ile Ile Lys Ala
            20                  25                  30

Gly Asp Trp Gln Glu Phe Arg Glu Lys Leu Thr Phe Tyr Leu Val Thr
        35                  40                  45

Leu Glu Gln Ala Gln Glu Gln Gly Gly Ser Asn Cys Ser Ile
    50                  55                  60

Met Ile Asp Glu Ile Ile His His Leu Lys Arg Pro Ala Pro Leu
65                  70                  75                  80

Leu Asp Pro Asn Asn Leu Asn Asp Glu Asp Val Ser Ile Leu Met Asp
                85                  90                  95

Arg Asn Leu Arg Leu Pro Asn Leu Glu Ser Phe Val Arg Ala Val Lys
                100                 105                 110

Asn Leu Glu Tyr Val Glu Gly Gly Gly Ser Pro Gly Glu Pro Ser
        115                 120                 125

Gly Pro Ile Ser Thr Ile Asn Pro Ser Pro Ser Lys Glu Ser His
    130                 135                 140

Lys Ser Pro Asn Met Ala Thr Gln Gly Ala Met Pro Ala Phe Ala Ser
145                 150                 155                 160

Ala Phe Gln Arg Arg Ala Gly Gly Val Leu Val Ala Ser His Leu Gln
                165                 170                 175

Ser Phe Leu Glu Val Ser Tyr Arg Val Leu Arg His Leu Ala Gln Pro
            180                 185                 190

Ser Gly Gly Ser Gly Ser Gln Ser Phe Leu Leu Lys Ser Leu Glu
        195                 200                 205

Gln Val Arg Lys Ile Gln Gly Asp Gly Ala Ala Leu Gln Glu Lys Leu
    210                 215                 220

Cys Ala Thr Tyr Lys Leu Cys His Pro Glu Glu Leu Val Leu Leu Gly
225                 230                 235                 240

His Ser Leu Gly Ile Pro Trp Ala Pro Leu Ser Ser Cys Pro Ser Gln
                245                 250                 255

Ala Leu Gln Leu Ala Gly Cys Leu Ser Gln Leu His Ser Gly Leu Phe
            260                 265                 270

Leu Tyr Gln Gly Leu Leu Gln Ala Leu Glu Gly Ile Ser Pro Glu Leu
        275                 280                 285

```
Gly Pro Thr Leu Asp Thr Leu Gln Leu Asp Val Ala Asp Phe Ala Thr
    290                 295                 300

Thr Ile Trp Gln Gln Met Glu Glu Leu Gly Met Ala Pro Ala Leu Gln
305                 310                 315                 320

Pro
```

(2) INFORMATION FOR SEQ ID NO:188:

(i) SEQUENCE CHARACTERISTICS:
        (A) LENGTH: 321 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:188:

```
Ala Pro Ser Arg His Pro Ile Ile Ile Lys Ala Gly Asp Trp Gln Glu
1               5                   10                  15

Phe Arg Glu Lys Leu Thr Phe Tyr Leu Val Thr Leu Glu Gln Ala Gln
            20                  25                  30

Glu Gln Gln Gly Gly Gly Ser Asn Cys Ser Ile Met Ile Asp Glu Ile
        35                  40                  45

Ile His His Leu Lys Arg Pro Pro Ala Pro Leu Leu Asp Pro Asn Asn
    50                  55                  60

Leu Asn Asp Glu Asp Val Ser Ile Leu Met Asp Arg Asn Leu Arg Leu
65                  70                  75                  80

Pro Asn Leu Glu Ser Phe Val Arg Ala Val Lys Asn Leu Glu Asn Ala
                85                  90                  95

Ser Gly Ile Glu Ala Ile Leu Arg Asn Leu Gln Pro Cys Leu Pro Ser
            100                 105                 110

Ala Thr Ala Tyr Val Glu Gly Gly Gly Ser Pro Gly Glu Pro Ser
        115                 120                 125

Gly Pro Ile Ser Thr Ile Asn Pro Ser Pro Ser Lys Glu Ser His
    130                 135                 140

Lys Ser Pro Asn Met Ala Thr Gln Gly Ala Met Pro Ala Phe Ala Ser
145                 150                 155                 160

Ala Phe Gln Arg Arg Ala Gly Gly Val Leu Val Ala Ser His Leu Gln
                165                 170                 175

Ser Phe Leu Glu Val Ser Tyr Arg Val Leu Arg His Leu Ala Gln Pro
            180                 185                 190

Ser Gly Gly Ser Gly Gly Ser Gln Ser Phe Leu Leu Lys Ser Leu Glu
        195                 200                 205

Gln Val Arg Lys Ile Gln Gly Asp Gly Ala Ala Leu Gln Glu Lys Leu
    210                 215                 220

Cys Ala Thr Tyr Lys Leu Cys His Pro Glu Glu Leu Val Leu Leu Gly
225                 230                 235                 240

His Ser Leu Gly Ile Pro Trp Ala Pro Leu Ser Ser Cys Pro Ser Gln
                245                 250                 255

Ala Leu Gln Leu Ala Gly Cys Leu Ser Gln Leu His Ser Gly Leu Phe
            260                 265                 270

Leu Tyr Gln Gly Leu Leu Gln Ala Leu Glu Gly Ile Ser Pro Glu Leu
        275                 280                 285

Gly Pro Thr Leu Asp Thr Leu Gln Leu Asp Val Ala Asp Phe Ala Thr
    290                 295                 300

Thr Ile Trp Gln Gln Met Glu Glu Leu Gly Met Ala Pro Ala Leu Gln
```

```
305                 310                 315                 320
Pro (2) INFORMATION FOR SEQ ID NO:189:

(i) SEQUENCE CHARACTERISTICS:
        (A) LENGTH: 321 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:189:

Ala Gly Asp Trp Gln Glu Phe Arg Glu Lys Leu Thr Phe Tyr Leu Val
1               5                   10                  15

Thr Leu Glu Gln Ala Gln Glu Gln Gln Gly Gly Ser Asn Cys Ser
            20                  25                  30

Ile Met Ile Asp Glu Ile Ile His His Leu Lys Arg Pro Pro Ala Pro
            35                  40                  45

Leu Leu Asp Pro Asn Asn Leu Asn Asp Glu Asp Val Ser Ile Leu Met
        50                  55                  60

Asp Arg Asn Leu Arg Leu Pro Asn Leu Glu Ser Phe Val Arg Ala Val
65                  70                  75                  80

Lys Asn Leu Glu Asn Ala Ser Gly Ile Glu Ala Ile Leu Arg Asn Leu
            85                  90                  95

Gln Pro Cys Leu Pro Ser Ala Thr Ala Ala Pro Ser Arg His Pro Ile
            100                 105                 110

Ile Ile Lys Tyr Val Glu Gly Gly Gly Ser Pro Gly Glu Pro Ser
            115                 120                 125

Gly Pro Ile Ser Thr Ile Asn Pro Ser Pro Pro Ser Lys Glu Ser His
        130                 135                 140

Lys Ser Pro Asn Met Ala Thr Gln Gly Ala Met Pro Ala Phe Ala Ser
145                 150                 155                 160

Ala Phe Gln Arg Arg Ala Gly Gly Val Leu Val Ala Ser His Leu Gln
                165                 170                 175

Ser Phe Leu Glu Val Ser Tyr Arg Val Leu Arg His Leu Ala Gln Pro
            180                 185                 190

Ser Gly Gly Ser Gly Gly Ser Gln Ser Phe Leu Leu Lys Ser Leu Glu
            195                 200                 205

Gln Val Arg Lys Ile Gln Gly Asp Gly Ala Ala Leu Gln Glu Lys Leu
        210                 215                 220

Cys Ala Thr Tyr Lys Leu Cys His Pro Glu Glu Leu Val Leu Leu Gly
225                 230                 235                 240

His Ser Leu Gly Ile Pro Trp Ala Pro Leu Ser Ser Cys Pro Ser Gln
                245                 250                 255

Ala Leu Gln Leu Ala Gly Cys Leu Ser Gln Leu His Ser Gly Leu Phe
            260                 265                 270

Leu Tyr Gln Gly Leu Leu Gln Ala Leu Glu Gly Ile Ser Pro Glu Leu
        275                 280                 285

Gly Pro Thr Leu Asp Thr Leu Gln Leu Asp Val Ala Asp Phe Ala Thr
        290                 295                 300

Thr Ile Trp Gln Gln Met Glu Glu Leu Gly Met Ala Pro Ala Leu Gln
305                 310                 315                 320

Pro
```

(2) INFORMATION FOR SEQ ID NO:190:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:190:

```
Leu Asp Pro Asn Asn Leu Asn Asp Glu Asp Val Ser Ile Leu Met Asp
  1               5                  10                  15

Arg Asn Leu Arg Leu Pro Asn Leu Glu Ser Phe Val Arg Ala Val Lys
             20                  25                  30

Asn Leu Glu Asn Ala Ser Gly Ile Glu Ala Ile Leu Arg Asn Leu Gln
         35                  40                  45

Pro Cys Leu Pro Ser Ala Thr Ala Ala Pro Ser Arg His Pro Ile Ile
 50                  55                  60

Ile Lys Ala Gly Asp Trp Gln Glu Phe Arg Glu Lys Leu Thr Phe Tyr
 65                  70                  75                  80

Leu Val Thr Leu Glu Gln Ala Gln Glu Gln Gln Gly Gly Gly Ser Gly
                 85                  90                  95

Gly Gly Ser Gly Gly Gly Ser Asn Cys Ser Ile Met Ile Asp Glu Ile
                100                 105                 110

Ile His His Leu Lys Arg Pro Pro Ala Pro Leu Tyr Val Glu Gly Gly
            115                 120                 125

Gly Gly Ser Pro Gly Glu Pro Ser Gly Pro Ile Ser Thr Ile Asn Pro
        130                 135                 140

Ser Pro Pro Ser Lys Glu Ser His Lys Ser Pro Asn Met Ala Thr Gln
145                 150                 155                 160

Gly Ala Met Pro Ala Phe Ala Ser Ala Phe Gln Arg Arg Ala Gly Gly
                165                 170                 175

Val Leu Val Ala Ser His Leu Gln Ser Phe Leu Glu Val Ser Tyr Arg
            180                 185                 190

Val Leu Arg His Leu Ala Gln Pro Ser Gly Gly Ser Gly Gly Ser Gln
        195                 200                 205

Ser Phe Leu Leu Lys Ser Leu Glu Gln Val Arg Lys Ile Gln Gly Asp
210                 215                 220

Gly Ala Ala Leu Gln Glu Lys Leu Cys Ala Thr Tyr Lys Leu Cys His
225                 230                 235                 240

Pro Glu Glu Leu Val Leu Leu Gly His Ser Leu Gly Ile Pro Trp Ala
                245                 250                 255

Pro Leu Ser Ser Cys Pro Ser Gln Ala Leu Gln Leu Ala Gly Cys Leu
            260                 265                 270

Ser Gln Leu His Ser Gly Leu Phe Leu Tyr Gln Gly Leu Leu Gln Ala
        275                 280                 285

Leu Glu Gly Ile Ser Pro Glu Leu Gly Pro Thr Leu Asp Thr Leu Gln
290                 295                 300

Leu Asp Val Ala Asp Phe Ala Thr Thr Ile Trp Gln Gln Met Glu Glu
305                 310                 315                 320

Leu Gly Met Ala Pro Ala Leu Gln Pro
                325
```

(2) INFORMATION FOR SEQ ID NO:191:

(i) SEQUENCE CHARACTERISTICS:
            (A) LENGTH: 329 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:191:

Asn Ala Ser Gly Ile Glu Ala Ile Leu Arg Asn Leu Gln Pro Cys Leu
1               5                   10                  15

Pro Ser Ala Thr Ala Ala Pro Ser Arg His Pro Ile Ile Ile Lys Ala
            20                  25                  30

Gly Asp Trp Gln Glu Phe Arg Glu Lys Leu Thr Phe Tyr Leu Val Thr
            35                  40                  45

Leu Glu Gln Ala Gln Glu Gln Gly Gly Ser Gly Gly Gly Ser
    50                  55                  60

Gly Gly Gly Ser Asn Cys Ser Ile Met Ile Asp Glu Ile Ile His His
65                  70                  75                  80

Leu Lys Arg Pro Pro Ala Pro Leu Leu Asp Pro Asn Asn Leu Asn Asp
                85                  90                  95

Glu Asp Val Ser Ile Leu Met Asp Arg Asn Leu Arg Leu Pro Asn Leu
            100                 105                 110

Glu Ser Phe Val Arg Ala Val Lys Asn Leu Glu Tyr Val Glu Gly Gly
            115                 120                 125

Gly Gly Ser Pro Gly Glu Pro Ser Gly Pro Ile Ser Thr Ile Asn Pro
130                 135                 140

Ser Pro Pro Ser Lys Glu Ser His Lys Ser Pro Asn Met Ala Thr Gln
145                 150                 155                 160

Gly Ala Met Pro Ala Phe Ala Ser Ala Phe Gln Arg Arg Ala Gly Gly
                165                 170                 175

Val Leu Val Ala Ser His Leu Gln Ser Phe Leu Glu Val Ser Tyr Arg
                180                 185                 190

Val Leu Arg His Leu Ala Gln Pro Ser Gly Ser Gly Gly Ser Gln
                195                 200                 205

Ser Phe Leu Leu Lys Ser Leu Glu Gln Val Arg Lys Ile Gln Gly Asp
210                 215                 220

Gly Ala Ala Leu Gln Glu Lys Leu Cys Ala Thr Tyr Lys Leu Cys His
225                 230                 235                 240

Pro Glu Glu Leu Val Leu Leu Gly His Ser Leu Gly Ile Pro Trp Ala
                245                 250                 255

Pro Leu Ser Ser Cys Pro Ser Gln Ala Leu Gln Leu Ala Gly Cys Leu
            260                 265                 270

Ser Gln Leu His Ser Gly Leu Phe Leu Tyr Gln Gly Leu Leu Gln Ala
                275                 280                 285

Leu Glu Gly Ile Ser Pro Glu Leu Gly Pro Thr Leu Asp Thr Leu Gln
    290                 295                 300

Leu Asp Val Ala Asp Phe Ala Thr Thr Ile Trp Gln Gln Met Glu Glu
305                 310                 315                 320

Leu Gly Met Ala Pro Ala Leu Gln Pro
                325

(2) INFORMATION FOR SEQ ID NO:192:

(i) SEQUENCE CHARACTERISTICS:
            (A) LENGTH: 329 amino acids
            (B) TYPE: amino acid (C) STRANDEDNESS: unknown
        (D) TOPOLOGY: unknown (ii) MOLECULE TYPE: peptide (xi) SEQUENCE DESCRIPTION: SEQ ID NO:192:

Ala Pro Ser Arg His Pro Ile Ile Ile Lys Ala Gly Asp Trp Gln Glu
1               5                   10                  15

Phe Arg Glu Lys Leu Thr Phe Tyr Leu Val Thr Leu Glu Gln Ala Gln
            20                  25                  30

Glu Gln Gln Gly Gly Gly Ser Gly Gly Ser Gly Gly Gly Ser Asn
        35                  40                  45

Cys Ser Ile Met Ile Asp Glu Ile Ile His His Leu Lys Arg Pro Pro
50                      55                  60

Ala Pro Leu Leu Asp Pro Asn Asn Leu Asn Asp Glu Asp Val Ser Ile
65                  70                  75                  80

Leu Met Asp Arg Asn Leu Arg Leu Pro Asn Leu Glu Ser Phe Val Arg
                85                  90                  95

Ala Val Lys Asn Leu Glu Asn Ala Ser Gly Ile Glu Ala Ile Leu Arg
                100                 105                 110

Asn Leu Gln Pro Cys Leu Pro Ser Ala Thr Ala Tyr Val Glu Gly Gly
                115                 120                 125

Gly Gly Ser Pro Gly Glu Pro Ser Gly Pro Ile Ser Thr Ile Asn Pro
130                 135                 140

Ser Pro Pro Ser Lys Glu Ser His Lys Ser Pro Asn Met Ala Thr Gln
145                 150                 155                 160

Gly Ala Met Pro Ala Phe Ala Ser Ala Phe Gln Arg Arg Ala Gly Gly
                165                 170                 175

Val Leu Val Ala Ser His Leu Gln Ser Phe Leu Glu Val Ser Tyr Arg
                180                 185                 190

Val Leu Arg His Leu Ala Gln Pro Ser Gly Ser Gly Gly Ser Gln
                195                 200                 205

Ser Phe Leu Leu Lys Ser Leu Glu Gln Val Arg Lys Ile Gln Gly Asp
                210                 215                 220

Gly Ala Ala Leu Gln Glu Lys Leu Cys Ala Thr Tyr Lys Leu Cys His
225                 230                 235                 240

Pro Glu Glu Leu Val Leu Leu Gly His Ser Leu Gly Ile Pro Trp Ala
                245                 250                 255

Pro Leu Ser Ser Cys Pro Ser Gln Ala Leu Gln Leu Ala Gly Cys Leu
                260                 265                 270

Ser Gln Leu His Ser Gly Leu Phe Leu Tyr Gln Gly Leu Leu Gln Ala
                275                 280                 285

Leu Glu Gly Ile Ser Pro Glu Leu Gly Pro Thr Leu Asp Thr Leu Gln
                290                 295                 300

Leu Asp Val Ala Asp Phe Ala Thr Thr Ile Trp Gln Gln Met Glu Glu
305                 310                 315                 320

Leu Gly Met Ala Pro Ala Leu Gln Pro
                325

(2) INFORMATION FOR SEQ ID NO:193:

(i) SEQUENCE CHARACTERISTICS:
        (A) LENGTH: 299 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:193:

```
Gly Gly Ser Gly Gly Ser Asn Cys Ser Ile Met Ile Asp Glu Ile
1               5                   10                  15

Ile His His Leu Lys Arg Pro Pro Ala Pro Leu Leu Asp Pro Asn Asn
                20                  25                  30

Leu Asn Asp Glu Asp Val Ser Ile Leu Met Asp Arg Asn Leu Arg Leu
            35                  40                  45

Pro Asn Leu Glu Ser Phe Val Arg Ala Val Lys Asn Leu Glu Asn Ala
    50                  55                  60

Ser Gly Ile Glu Ala Ile Leu Arg Asn Leu Gln Pro Cys Leu Pro Ser
65                  70                  75                  80

Ala Thr Ala Ala Pro Ser Arg His Pro Ile Ile Ile Lys Tyr Val Glu
                85                  90                  95

Gly Gly Gly Gly Ser Pro Gly Glu Pro Ser Gly Pro Ile Ser Thr Ile
                100                 105                 110

Asn Pro Ser Pro Pro Ser Lys Glu Ser His Lys Ser Pro Asn Met Ala
        115                 120                 125

Thr Gln Gly Ala Met Pro Ala Phe Ala Ser Ala Phe Gln Arg Arg Ala
    130                 135                 140

Gly Gly Val Leu Val Ala Ser His Leu Gln Ser Phe Leu Glu Val Ser
145                 150                 155                 160

Tyr Arg Val Leu Arg His Leu Ala Gln Pro Ser Gly Ser Gly Gly
                165                 170                 175

Ser Gln Ser Phe Leu Leu Lys Ser Leu Glu Gln Val Arg Lys Ile Gln
            180                 185                 190

Gly Asp Gly Ala Ala Leu Gln Glu Lys Leu Cys Ala Thr Tyr Lys Leu
        195                 200                 205

Cys His Pro Glu Glu Leu Val Leu Leu Gly His Ser Leu Gly Ile Pro
    210                 215                 220

Trp Ala Pro Leu Ser Ser Cys Pro Ser Gln Ala Leu Gln Leu Ala Gly
225                 230                 235                 240

Cys Leu Ser Gln Leu His Ser Gly Leu Phe Leu Tyr Gln Gly Leu Leu
                245                 250                 255

Gln Ala Leu Glu Gly Ile Ser Pro Glu Leu Gly Pro Thr Leu Asp Thr
            260                 265                 270

Leu Gln Leu Asp Val Ala Asp Phe Ala Thr Thr Ile Trp Gln Gln Met
        275                 280                 285

Glu Glu Leu Gly Met Ala Pro Ala Leu Gln Pro
    290                 295
```

(2) INFORMATION FOR SEQ ID NO:194:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:194:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30
```

```
Val Ser Ile Leu Met Asp Arg Asn Leu Arg Leu Pro Asn Leu Glu Ser
         35                  40                  45

Phe Val Arg Ala Val Lys Asn Leu Glu Asn Ala Ser Gly Ile Glu Ala
         50                  55                  60

Ile Leu Arg Asn Leu Gln Pro Cys Leu Pro Ser Ala Thr Ala Ala Pro
 65                  70                  75                  80

Ser Arg His Pro Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
             100                 105                 110

Gln Tyr Val Glu Gly Gly Gly Ser Pro Gly Glu Pro Ser Gly Pro
             115                 120                 125

Ile Ser Thr Ile Asn Pro Ser Pro Pro Ser Lys Glu Ser His Lys Ser
            130                 135                 140

Pro Asn Met Ala Tyr Lys Leu Cys His Pro Glu Glu Leu Val Leu Leu
145                 150                 155                 160

Gly His Ser Leu Gly Ile Pro Trp Ala Pro Leu Ser Ser Cys Pro Ser
                165                 170                 175

Gln Ala Leu Gln Leu Ala Gly Cys Leu Ser Gln Leu His Ser Gly Leu
                180                 185                 190

Phe Leu Tyr Gln Gly Leu Leu Gln Ala Leu Glu Gly Ile Ser Pro Glu
            195                 200                 205

Leu Gly Pro Thr Leu Asp Thr Leu Gln Leu Asp Val Ala Asp Phe Ala
210                 215                 220

Thr Thr Ile Trp Gln Gln Met Glu Glu Leu Gly Met Ala Pro Ala Leu
225                 230                 235                 240

Gln Pro Thr Gln Gly Ala Met Pro Ala Phe Ala Ser Ala Phe Gln Arg
                245                 250                 255

Arg Ala Gly Gly Val Leu Val Ala Ser His Leu Gln Ser Phe Leu Glu
                260                 265                 270

Val Ser Tyr Arg Val Leu Arg His Leu Ala Gln Pro Gly Gly Gly Ser
            275                 280                 285

Asp Met Ala Thr Pro Leu Gly Pro Ala Ser Ser Leu Pro Gln Ser Phe
290                 295                 300

Leu Leu Lys Ser Leu Glu Gln Val Arg Lys Ile Gln Gly Asp Gly Ala
305                 310                 315                 320

Ala Leu Gln Glu Lys Leu Cys Ala Thr
                325

(2) INFORMATION FOR SEQ ID NO:195:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:195:

Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
             35                  40                  45
```

-continued

```
Phe Val Arg Ala Val Lys Asn Leu Glu Asn Ala Ser Gly Ile Glu Ala
     50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
             115                 120                 125

Ile Ser Thr Ile Asn Pro Ser Pro Pro Ser Lys Glu Ser His Lys Ser
    130                 135                 140

Pro Asn Met Ala Pro Glu Leu Gly Pro Thr Leu Asp Thr Leu Gln Leu
145                 150                 155                 160

Asp Val Ala Asp Phe Ala Thr Thr Ile Trp Gln Gln Met Glu Glu Leu
                165                 170                 175

Gly Met Ala Pro Ala Leu Gln Pro Thr Gln Gly Ala Met Pro Ala Phe
            180                 185                 190

Ala Ser Ala Phe Gln Arg Arg Ala Gly Gly Val Leu Val Ala Ser His
        195                 200                 205

Leu Gln Ser Phe Leu Glu Val Ser Tyr Arg Val Leu Arg His Leu Ala
    210                 215                 220

Gln Pro Gly Gly Gly Ser Asp Met Ala Thr Pro Leu Gly Pro Ala Ser
225                 230                 235                 240

Ser Leu Pro Gln Ser Phe Leu Leu Lys Ser Leu Glu Gln Val Arg Lys
                245                 250                 255

Ile Gln Gly Asp Gly Ala Ala Leu Gln Glu Lys Leu Cys Ala Thr Tyr
            260                 265                 270

Lys Leu Cys His Pro Glu Glu Leu Val Leu Leu Gly His Ser Leu Gly
        275                 280                 285

Ile Pro Trp Ala Pro Leu Ser Ser Cys Pro Ser Gln Ala Leu Gln Leu
    290                 295                 300

Ala Gly Cys Leu Ser Gln Leu His Ser Gly Leu Phe Leu Tyr Gln Gly
305                 310                 315                 320

Leu Leu Gln Ala Leu Glu Gly Ile Ser
                325

(2) INFORMATION FOR SEQ ID NO:196:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:196:

Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Asp Glu Asp
             20                  25                  30

Val Ser Ile Leu Met Asp Arg Asn Leu Arg Leu Pro Asn Leu Glu Ser
         35                  40                  45

Phe Val Arg Ala Val Lys Asn Leu Glu Asn Ala Ser Gly Ile Glu Ala
     50                  55                  60
```

```
Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Ser Lys Glu Ser His Lys Ser
    130                 135                 140

Pro Asn Met Ala Ser Ala Phe Gln Arg Arg Ala Gly Gly Val Leu Val
145                 150                 155                 160

Ala Ser His Leu Gln Ser Phe Leu Glu Val Ser Tyr Arg Val Leu Arg
                165                 170                 175

His Leu Ala Gln Pro Gly Gly Gly Ser Asp Met Ala Thr Pro Leu Gly
                180                 185                 190

Pro Ala Ser Ser Leu Pro Gln Ser Phe Leu Leu Lys Ser Leu Glu Gln
                195                 200                 205

Val Arg Lys Ile Gln Gly Asp Gly Ala Ala Leu Gln Glu Lys Leu Cys
210                 215                 220

Ala Thr Tyr Lys Leu Cys His Pro Glu Glu Leu Val Leu Leu Gly His
225                 230                 235                 240

Ser Leu Gly Ile Pro Trp Ala Pro Leu Ser Ser Cys Pro Ser Gln Ala
                245                 250                 255

Leu Gln Leu Ala Gly Cys Leu Ser Gln Leu His Ser Gly Leu Phe Leu
                260                 265                 270

Tyr Gln Gly Leu Leu Gln Ala Leu Glu Gly Ile Ser Pro Glu Leu Gly
                275                 280                 285

Pro Thr Leu Asp Thr Leu Gln Leu Asp Val Ala Asp Phe Ala Thr Thr
                290                 295                 300

Ile Trp Gln Gln Met Glu Glu Leu Gly Met Ala Pro Ala Leu Gln Pro
305                 310                 315                 320

Thr Gln Gly Ala Met Pro Ala Phe Ala
                325

(2) INFORMATION FOR SEQ ID NO:197:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:197:

Met Ala Asn Cys Ser Ile Met Ile Asp Glu Ile Ile His His Leu Lys
  1               5                  10                  15

Arg Pro Pro Ala Pro Leu Leu Asp Pro Asn Asn Leu Asn Asp Glu Asp
                 20                  25                  30

Val Ser Ile Leu Met Asp Arg Asn Leu Arg Leu Pro Asn Leu Glu Ser
             35                  40                  45

Phe Val Arg Ala Val Lys Asn Leu Glu Asn Ala Ser Gly Ile Glu Ala
             50                  55                  60

Ile Leu Arg Asn Leu Gln Pro Cys Leu Pro Ser Ala Thr Ala Ala Pro
 65                  70                  75                  80
```

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
130                 135                 140

Pro Asn Met Ala Met Ala Pro Ala Leu Gln Pro Thr Gln Gly Ala Met
145                 150                 155                 160

Pro Ala Phe Ala Ser Ala Phe Gln Arg Arg Ala Gly Gly Val Leu Val
                165                 170                 175

Ala Ser His Leu Gln Ser Phe Leu Glu Val Ser Tyr Arg Val Leu Arg
                180                 185                 190

His Leu Ala Gln Pro Gly Gly Gly Ser Asp Met Ala Thr Pro Leu Gly
                195                 200                 205

Pro Ala Ser Ser Leu Pro Gln Ser Phe Leu Leu Lys Ser Leu Glu Gln
210                 215                 220

Val Arg Lys Ile Gln Gly Asp Gly Ala Ala Leu Gln Glu Lys Leu Cys
225                 230                 235                 240

Ala Thr Tyr Lys Leu Cys His Pro Glu Glu Leu Val Leu Leu Gly His
                245                 250                 255

Ser Leu Gly Ile Pro Trp Ala Pro Leu Ser Ser Cys Pro Ser Gln Ala
                260                 265                 270

Leu Gln Leu Ala Gly Cys Leu Ser Gln Leu His Ser Gly Leu Phe Leu
                275                 280                 285

Tyr Gln Gly Leu Leu Gln Ala Leu Glu Gly Ile Ser Pro Glu Leu Gly
290                 295                 300

Pro Thr Leu Asp Thr Leu Gln Leu Asp Val Ala Asp Phe Ala Thr Thr
305                 310                 315                 320

Ile Trp Gln Gln Met Glu Glu Leu Gly
                325

(2) INFORMATION FOR SEQ ID NO:198:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:198:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95
```

```
Glu Lys Leu Thr Phe Tyr Leu Val Thr Leu Gln Ala Gln Glu Gln
                100                 105                 110

Gln Tyr Val Glu Gly Gly Gly Ser Pro Gly Glu Pro Ser Gly Pro
            115                 120                 125

Ile Ser Thr Ile Asn Pro Ser Pro Ser Lys Glu Ser His Lys Ser
            130                 135                 140

Pro Asn Met Ala Thr Gln Gly Ala Met Pro Ala Phe Ala Ser Ala Phe
145                 150                 155                 160

Gln Arg Arg Ala Gly Gly Val Leu Val Ala Ser His Leu Gln Ser Phe
                165                 170                 175

Leu Glu Val Ser Tyr Arg Val Leu Arg His Leu Ala Gln Pro Gly Gly
                180                 185                 190

Gly Ser Asp Met Ala Thr Pro Leu Gly Pro Ala Ser Ser Leu Pro Gln
            195                 200                 205

Ser Phe Leu Leu Lys Ser Leu Glu Gln Val Arg Lys Ile Gln Gly Asp
            210                 215                 220

Gly Ala Ala Leu Gln Glu Lys Leu Cys Ala Thr Tyr Lys Leu Cys His
225                 230                 235                 240

Pro Glu Glu Leu Val Leu Leu Gly His Ser Leu Gly Ile Pro Trp Ala
                245                 250                 255

Pro Leu Ser Ser Cys Pro Ser Gln Ala Leu Gln Leu Ala Gly Cys Leu
                260                 265                 270

Ser Gln Leu His Ser Gly Leu Phe Leu Tyr Gln Gly Leu Leu Gln Ala
            275                 280                 285

Leu Glu Gly Ile Ser Pro Glu Leu Gly Pro Thr Leu Asp Thr Leu Gln
            290                 295                 300

Leu Asp Val Ala Asp Phe Ala Thr Thr Ile Trp Gln Gln Met Glu Glu
305                 310                 315                 320

Leu Gly Met Ala Pro Ala Leu Gln Pro
                325

(2) INFORMATION FOR SEQ ID NO:199:

(i) SEQUENCE CHARACTERISTICS:
        (A) LENGTH: 319 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:199:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Asp Asn Asn Leu Arg Arg Pro Asn Leu Glu Ala
            35                  40                  45

Phe Asn Arg Ala Val Lys Ser Leu Gln Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110
```

```
Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
    130                 135                 140

Pro Asn Met Ala Thr Gln Gly Ala Met Pro Ala Phe Ala Ser Ala Phe
145                 150                 155                 160

Gln Arg Arg Ala Gly Gly Val Leu Val Ala Ser His Leu Gln Ser Phe
                165                 170                 175

Leu Glu Val Ser Tyr Arg Val Leu Arg His Leu Ala Gln Pro Ser Gly
            180                 185                 190

Gly Ser Gly Gly Ser Gln Ser Phe Leu Leu Lys Ser Leu Glu Gln Val
            195                 200                 205

Arg Lys Ile Gln Gly Asp Gly Ala Ala Leu Gln Glu Lys Leu Cys Ala
            210                 215                 220

Thr Tyr Lys Leu Cys His Pro Glu Glu Leu Val Leu Leu Gly His Ser
225                 230                 235                 240

Leu Gly Ile Pro Trp Ala Pro Leu Ser Ser Cys Pro Ser Gln Ala Leu
                245                 250                 255

Gln Leu Ala Gly Cys Leu Ser Gln Leu His Ser Gly Leu Phe Leu Tyr
                260                 265                 270

Gln Gly Leu Leu Gln Ala Leu Glu Gly Ile Ser Pro Glu Leu Gly Pro
            275                 280                 285

Thr Leu Asp Thr Leu Gln Leu Asp Val Ala Asp Phe Ala Thr Thr Ile
            290                 295                 300

Trp Gln Gln Met Glu Glu Leu Gly Met Ala Pro Ala Leu Gln Pro
305                 310                 315

(2) INFORMATION FOR SEQ ID NO:200:

(i) SEQUENCE CHARACTERISTICS:
        (A) LENGTH: 322 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:200:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Ala Ile Glu Ser
50                  55                  60

Ile Leu Lys Asn Leu Leu Pro Cys Leu Pro Leu Ala Thr Ala Ala Pro
65                  70                  75                  80

Thr Arg His Pro Ile Ile Ile Arg Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110

Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
    130                 135                 140
```

```
Pro Asn Met Ala Thr Gln Gly Ala Met Pro Ala Phe Ala Ser Ala Phe
145                 150                 155                 160

Gln Arg Arg Ala Gly Gly Val Leu Val Ala Ser His Leu Gln Ser Phe
            165                 170                 175

Leu Glu Val Ser Tyr Arg Val Leu Arg His Leu Ala Gln Pro Thr Pro
                180                 185                 190

Leu Gly Pro Ala Ser Ser Leu Pro Gln Ser Phe Leu Leu Lys Ser Leu
            195                 200                 205

Glu Gln Val Arg Lys Ile Gln Gly Asp Gly Ala Ala Leu Gln Glu Lys
        210                 215                 220

Leu Cys Ala Thr Tyr Lys Leu Cys His Pro Glu Glu Leu Val Leu Leu
225                 230                 235                 240

Gly His Ser Leu Gly Ile Pro Trp Ala Pro Leu Ser Ser Cys Pro Ser
                245                 250                 255

Gln Ala Leu Gln Leu Ala Gly Cys Leu Ser Gln Leu His Ser Gly Leu
            260                 265                 270

Phe Leu Tyr Gln Gly Leu Leu Gln Ala Leu Glu Gly Ile Ser Pro Glu
        275                 280                 285

Leu Gly Pro Thr Leu Asp Thr Leu Gln Leu Asp Val Ala Asp Phe Ala
        290                 295                 300

Thr Thr Ile Trp Gln Gln Met Glu Glu Leu Gly Met Ala Pro Ala Leu
305                 310                 315                 320

Gln Pro (2) INFORMATION FOR SEQ ID NO:201:

(i) SEQUENCE CHARACTERISTICS:
        (A) LENGTH: 319 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:201:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
            20                  25                  30

Gln Asp Ile Leu Met Glu Asn Asn Leu Arg Arg Pro Asn Leu Glu Ala
        35                  40                  45

Phe Asn Arg Ala Val Lys Ser Leu Gln Asn Ala Ser Ala Ile Glu Ser
50                  55                  60

Ile Leu Lys Asn Leu Leu Pro Cys Leu Pro Leu Ala Thr Ala Ala Pro
65                  70                  75                  80

Thr Arg His Pro Ile Ile Ile Arg Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Ser Lys Glu Ser His Lys Ser
        130                 135                 140

Pro Asn Met Ala Thr Gln Gly Ala Met Pro Ala Phe Ala Ser Ala Phe
145                 150                 155                 160
```

-continued

```
Gln Arg Arg Ala Gly Gly Val Leu Val Ala Ser His Leu Gln Ser Phe
                165                 170                 175

Leu Glu Val Ser Tyr Arg Val Leu Arg His Leu Ala Gln Pro Ser Gly
                180                 185                 190

Gly Ser Gly Gly Ser Gln Ser Phe Leu Leu Lys Ser Leu Glu Gln Val
                195                 200                 205

Arg Lys Ile Gln Gly Asp Gly Ala Ala Leu Gln Glu Lys Leu Cys Ala
    210                 215                 220

Thr Tyr Lys Leu Cys His Pro Glu Leu Val Leu Leu Gly His Ser
225                 230                 235                 240

Leu Gly Ile Pro Trp Ala Pro Leu Ser Ser Cys Pro Ser Gln Ala Leu
                245                 250                 255

Gln Leu Ala Gly Cys Leu Ser Gln Leu His Ser Gly Leu Phe Leu Tyr
                260                 265                 270

Gln Gly Leu Leu Gln Ala Leu Glu Gly Ile Ser Pro Glu Leu Gly Pro
                275                 280                 285

Thr Leu Asp Thr Leu Gln Leu Asp Val Ala Asp Phe Ala Thr Thr Ile
                290                 295                 300

Trp Gln Gln Met Glu Glu Leu Gly Met Ala Pro Ala Leu Gln Pro
305                 310                 315
```

(2) INFORMATION FOR SEQ ID NO:202:

(i) SEQUENCE CHARACTERISTICS:
        (A) LENGTH: 322 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:202:

```
Met Ala Asn Cys Ser Asn Met Ile Asp Glu Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Asp Asn Asn Leu Arg Arg Pro Asn Leu Glu Ala
                35                  40                  45

Phe Asn Arg Ala Val Lys Ser Leu Gln Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110

Gln Tyr Val Glu Gly Gly Gly Ser Pro Gly Glu Pro Ser Gly Pro
    115                 120                 125

Ile Ser Thr Ile Asn Pro Ser Pro Ser Lys Glu Ser His Lys Ser
    130                 135                 140

Pro Asn Met Ala Thr Gln Gly Ala Met Pro Ala Phe Ala Ser Ala Phe
145                 150                 155                 160

Gln Arg Arg Ala Gly Gly Val Leu Val Ala Ser His Leu Gln Ser Phe
                165                 170                 175

Leu Glu Val Ser Tyr Arg Val Leu Arg His Leu Ala Gln Pro Thr Pro
                180                 185                 190
```

```
Leu Gly Pro Ala Ser Ser Leu Pro Gln Ser Phe Leu Leu Lys Ser Leu
            195                 200                 205

Glu Gln Val Arg Lys Ile Gln Gly Asp Gly Ala Ala Leu Gln Glu Lys
            210                 215                 220

Leu Cys Ala Thr Tyr Lys Leu Cys His Pro Glu Glu Leu Val Leu Leu
225                 230                 235                 240

Gly His Ser Leu Gly Ile Pro Trp Ala Pro Leu Ser Ser Cys Pro Ser
                245                 250                 255

Gln Ala Leu Gln Leu Ala Gly Cys Leu Ser Gln Leu His Ser Gly Leu
            260                 265                 270

Phe Leu Tyr Gln Gly Leu Leu Gln Ala Leu Glu Gly Ile Ser Pro Glu
            275                 280                 285

Leu Gly Pro Thr Leu Asp Thr Leu Gln Leu Asp Val Ala Asp Phe Ala
290                 295                 300

Thr Thr Ile Trp Gln Gln Met Glu Glu Leu Gly Met Ala Pro Ala Leu
305                 310                 315                 320

Gln Pro (2) INFORMATION FOR SEQ ID NO:203:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:203:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
            50                  55                  60

Leu Arg Asn Leu Gln Pro Cys Leu Pro Ser Ala Thr Ala Ala Pro Ser
65                  70                  75                  80

Arg His Pro Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
            130                 135                 140

Asn Met Glu Val His Pro Leu Pro Thr Pro Val Leu Leu Pro Ala Val
145                 150                 155                 160

Asp Phe Ser Leu Gly Glu Trp Lys Thr Gln Met Glu Glu Thr Lys Ala
                165                 170                 175

Gln Asp Ile Leu Gly Ala Val Thr Leu Leu Leu Glu Gly Val Met Ala
            180                 185                 190

Ala Arg Gly Gln Leu Gly Pro Thr Cys Leu Ser Ser Leu Leu Gly Gln
            195                 200                 205

Leu Ser Gly Gln Val Arg Leu Leu Leu Gly Ala Leu Gln Ser Leu Leu
```

```
            210                 215                 220
Gly Thr Gln Leu Pro Pro Gln Gly Arg Thr Thr Ala His Lys Asp Pro
225                 230                 235                 240

Asn Ala Ile Phe Leu Ser Phe Gln His Leu Leu Arg Gly Lys Val Arg
                245                 250                 255

Phe Leu Met Leu Val Gly Gly Ser Thr Leu Cys Val Arg Glu Phe Gly
                260                 265                 270

Gly Asn Met Ala Ser Pro Ala Pro Pro Ala Cys Asp Leu Arg Val Leu
                275                 280                 285

Ser Lys Leu Leu Arg Asp Ser His Val Leu His Ser Arg Leu Ser Gln
290                 295                 300

Cys Pro
305

(2) INFORMATION FOR SEQ ID NO:204:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:204:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
                35                  40                  45

Val Arg Ala Val Lys Asn Leu Glu Asn Ala Ser Gly Ile Glu Ala Ile
            50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Leu Pro Thr Pro Val Leu Leu Pro Ala Val Asp Phe Ser Leu
145                 150                 155                 160

Gly Glu Trp Lys Thr Gln Met Glu Glu Thr Lys Ala Gln Asp Ile Leu
                165                 170                 175

Gly Ala Val Thr Leu Leu Leu Glu Gly Val Met Ala Ala Arg Gly Gln
                180                 185                 190

Leu Gly Pro Thr Cys Leu Ser Ser Leu Leu Gly Gln Leu Ser Gly Gln
            195                 200                 205

Val Arg Leu Leu Leu Gly Ala Leu Gln Ser Leu Leu Gly Thr Gln Leu
            210                 215                 220

Pro Pro Gln Gly Arg Thr Thr Ala His Lys Asp Pro Asn Ala Ile Phe
225                 230                 235                 240

Leu Ser Phe Gln His Leu Leu Arg Gly Lys Val Arg Phe Leu Met Leu
```

-continued

```
                245                 250                 255
Val Gly Gly Ser Thr Leu Cys Val Arg Glu Phe Gly Gly Asn Met Ala
            260                 265                 270

Ser Pro Ala Pro Pro Ala Cys Asp Leu Arg Val Leu Ser Lys Leu Leu
        275                 280                 285

Arg Asp Ser His Val Leu His Ser Arg Leu Ser Gln Cys Pro Glu Val
    290                 295                 300

His Pro
305

(2) INFORMATION FOR SEQ ID NO:205:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:205:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
    130                 135                 140

Asn Met Val Leu Leu Pro Ala Val Asp Phe Ser Leu Gly Glu Trp Lys
145                 150                 155                 160

Thr Gln Met Glu Glu Thr Lys Ala Gln Asp Ile Leu Gly Ala Val Thr
                165                 170                 175

Leu Leu Leu Glu Gly Val Met Ala Ala Arg Gly Gln Leu Gly Pro Thr
            180                 185                 190

Cys Leu Ser Ser Leu Leu Gly Gln Leu Ser Gly Gln Val Arg Leu Leu
        195                 200                 205

Leu Gly Ala Leu Gln Ser Leu Leu Gly Thr Gln Leu Pro Pro Gln Gly
    210                 215                 220

Arg Thr Thr Ala His Lys Asp Pro Asn Ala Ile Phe Leu Ser Phe Gln
225                 230                 235                 240

His Leu Leu Arg Gly Lys Val Arg Phe Leu Met Leu Val Gly Gly Ser
                245                 250                 255

Thr Leu Cys Val Arg Glu Phe Gly Gly Asn Met Ala Ser Pro Ala Pro
            260                 265                 270

Pro Ala Cys Asp Leu Arg Val Leu Ser Lys Leu Leu Arg Asp Ser His
```

```
                275                 280                 285
Val Leu His Ser Arg Leu Ser Gln Cys Pro Glu Val His Pro Leu Pro
        290                 295                 300

Thr Pro
305

(2) INFORMATION FOR SEQ ID NO:206:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:206:

Ala Asn Cys Ser Ile Met Ile Asp Glu Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Ala Val Asp Phe Ser Leu Gly Glu Trp Lys Thr Gln Met Glu
145                 150                 155                 160

Glu Thr Lys Ala Gln Asp Ile Leu Gly Ala Val Thr Leu Leu Leu Glu
            165                 170                 175

Gly Val Met Ala Ala Arg Gly Gln Leu Gly Pro Thr Cys Leu Ser Ser
            180                 185                 190

Leu Leu Gly Gln Leu Ser Gly Gln Val Arg Leu Leu Leu Gly Ala Leu
            195                 200                 205

Gln Ser Leu Leu Gly Thr Gln Leu Pro Pro Gln Gly Arg Thr Thr Ala
210                 215                 220

His Lys Asp Pro Asn Ala Ile Phe Leu Ser Phe Gln His Leu Leu Arg
225                 230                 235                 240

Gly Lys Val Arg Phe Leu Met Leu Val Gly Gly Ser Thr Leu Cys Val
            245                 250                 255

Arg Glu Phe Gly Gly Asn Met Ala Ser Pro Ala Pro Ala Cys Asp
            260                 265                 270

Leu Arg Val Leu Ser Lys Leu Leu Arg Asp Ser His Val Leu His Ser
            275                 280                 285

Arg Leu Ser Gln Cys Pro Glu Val His Pro Leu Pro Thr Pro Val Leu
            290                 295                 300

Leu Pro
```

305

(2) INFORMATION FOR SEQ ID NO:207:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:207:

```
Ala Asn Cys Ser Ile Met Ile Asp Glu Ile Ile His His Leu Lys Arg
 1               5                  10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
130                 135                 140

Asn Met Asp Phe Ser Leu Gly Glu Trp Lys Thr Gln Met Glu Glu Thr
145                 150                 155                 160

Lys Ala Gln Asp Ile Leu Gly Ala Val Thr Leu Leu Leu Glu Gly Val
                165                 170                 175

Met Ala Ala Arg Gly Gln Leu Gly Pro Thr Cys Leu Ser Ser Leu Leu
            180                 185                 190

Gly Gln Leu Ser Gly Gln Val Arg Leu Leu Leu Gly Ala Leu Gln Ser
        195                 200                 205

Leu Leu Gly Thr Gln Leu Pro Pro Gln Gly Arg Thr Thr Ala His Lys
210                 215                 220

Asp Pro Asn Ala Ile Phe Leu Ser Phe Gln His Leu Leu Arg Gly Lys
225                 230                 235                 240

Val Arg Phe Leu Met Leu Val Gly Gly Ser Thr Leu Cys Val Arg Glu
                245                 250                 255

Phe Gly Gly Asn Met Ala Ser Pro Ala Pro Ala Cys Asp Leu Arg
            260                 265                 270

Val Leu Ser Lys Leu Leu Arg Asp Ser His Val Leu His Ser Arg Leu
        275                 280                 285

Ser Gln Cys Pro Glu Val His Pro Leu Pro Thr Pro Val Leu Leu Pro
290                 295                 300

Ala Val
305
```

(2) INFORMATION FOR SEQ ID NO:208:

(i) SEQUENCE CHARACTERISTICS:

(A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:208:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
50                      55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Gly Glu Trp Lys Thr Gln Met Glu Glu Thr Lys Ala Gln Asp
145                 150                 155                 160

Ile Leu Gly Ala Val Thr Leu Leu Leu Glu Gly Val Met Ala Ala Arg
                165                 170                 175

Gly Gln Leu Gly Pro Thr Cys Leu Ser Ser Leu Leu Gly Gln Leu Ser
            180                 185                 190

Gly Gln Val Arg Leu Leu Leu Gly Ala Leu Gln Ser Leu Leu Gly Thr
            195                 200                 205

Gln Leu Pro Pro Gln Gly Arg Thr Thr Ala His Lys Asp Pro Asn Ala
210                 215                 220

Ile Phe Leu Ser Phe Gln His Leu Leu Arg Gly Lys Val Arg Phe Leu
225                 230                 235                 240

Met Leu Val Gly Gly Ser Thr Leu Cys Val Arg Glu Phe Gly Gly Asn
                245                 250                 255

Met Ala Ser Pro Ala Pro Pro Ala Cys Asp Leu Arg Val Leu Ser Lys
            260                 265                 270

Leu Leu Arg Asp Ser His Val Leu His Ser Arg Leu Ser Gln Cys Pro
            275                 280                 285

Glu Val His Pro Leu Pro Thr Pro Val Leu Leu Pro Ala Val Asp Phe
            290                 295                 300

Ser Leu
305

(2) INFORMATION FOR SEQ ID NO:209:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:209:

```
Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
                115                 120                 125

Ser Thr Ile Asn Pro Ser Pro Pro Ser Lys Glu Ser His Lys Ser Pro
    130                 135                 140

Asn Met Gly Pro Thr Cys Leu Ser Ser Leu Leu Gly Gln Leu Ser Gly
145                 150                 155                 160

Gln Val Arg Leu Leu Leu Gly Ala Leu Gln Ser Leu Leu Gly Thr Gln
                165                 170                 175

Leu Pro Pro Gln Gly Arg Thr Thr Ala His Lys Asp Pro Asn Ala Ile
                180                 185                 190

Phe Leu Ser Phe Gln His Leu Leu Arg Gly Lys Val Arg Phe Leu Met
                195                 200                 205

Leu Val Gly Gly Ser Thr Leu Cys Val Arg Glu Phe Gly Gly Asn Met
    210                 215                 220

Ala Ser Pro Ala Pro Ala Cys Asp Leu Arg Val Leu Ser Lys Leu
225                 230                 235                 240

Leu Arg Asp Ser His Val Leu His Ser Arg Leu Ser Gln Cys Pro Glu
                245                 250                 255

Val His Pro Leu Pro Thr Pro Val Leu Leu Pro Ala Val Asp Phe Ser
                260                 265                 270

Leu Gly Glu Trp Lys Thr Gln Met Glu Glu Thr Lys Ala Gln Asp Ile
                275                 280                 285

Leu Gly Ala Val Thr Leu Leu Leu Glu Gly Val Met Ala Ala Arg Gly
                290                 295                 300

Gln Leu
305
```

(2) INFORMATION FOR SEQ ID NO:210:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:210:

```
Ala Asn Cys Ser Ile Met Ile Asp Glu Ile Ile His His Leu Lys Arg
1               5                   10                  15
```

-continued

```
Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
            50                  55                  60

Leu Arg Asn Leu Gln Pro Cys Leu Pro Ser Ala Thr Ala Ala Pro Ser
 65                  70                  75                  80

Arg His Pro Ile Ile Ile Lys Ala Gly Asp Trp Gln Glu Phe Arg Glu
                     85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
                115                 120                 125

Ser Thr Ile Asn Pro Ser Pro Pro Ser Lys Glu Ser His Lys Ser Pro
            130                 135                 140

Asn Met Gly Thr Gln Leu Pro Pro Gln Gly Arg Thr Thr Ala His Lys
145                 150                 155                 160

Asp Pro Asn Ala Ile Phe Leu Ser Phe Gln His Leu Leu Arg Gly Lys
                165                 170                 175

Val Arg Phe Leu Met Leu Val Gly Gly Ser Thr Leu Cys Val Arg Glu
            180                 185                 190

Phe Gly Gly Asn Met Ala Ser Pro Ala Pro Ala Cys Asp Leu Arg
            195                 200                 205

Val Leu Ser Lys Leu Leu Arg Asp Ser His Val Leu His Ser Arg Leu
            210                 215                 220

Ser Gln Cys Pro Glu Val His Pro Leu Pro Thr Pro Val Leu Leu Pro
225                 230                 235                 240

Ala Val Asp Phe Ser Leu Gly Glu Trp Lys Thr Gln Met Glu Glu Thr
                245                 250                 255

Lys Ala Gln Asp Ile Leu Gly Ala Val Thr Leu Leu Leu Glu Gly Val
                260                 265                 270

Met Ala Ala Arg Gly Gln Leu Gly Pro Thr Cys Leu Ser Ser Leu Leu
            275                 280                 285

Gly Gln Leu Ser Gly Gln Val Arg Leu Leu Leu Gly Ala Leu Gln Ser
            290                 295                 300

Leu Leu
305
```

(2) INFORMATION FOR SEQ ID NO:211:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:211:

```
Ala Asn Cys Ser Ile Met Ile Asp Glu Ile Ile His His Leu Lys Arg
 1               5                  10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45
```

```
Val Arg Ala Val Lys Asn Leu Glu Asn Ala Ser Gly Ile Glu Ala Ile
 50                  55                  60

Leu Arg Asn Leu Gln Pro Cys Leu Pro Ser Ala Thr Ala Ala Pro Ser
 65                  70                  75                  80

Arg His Pro Ile Ile Ile Lys Ala Gly Asp Trp Gln Glu Phe Arg Glu
                 85                  90                  95

Lys Leu Thr Phe Tyr Leu Val Thr Leu Glu Gln Ala Gln Glu Gln Gln
            100                 105                 110

Tyr Val Glu Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
130                 135                 140

Asn Met Gly Arg Thr Thr Ala His Lys Asp Pro Asn Ala Ile Phe Leu
145                 150                 155                 160

Ser Phe Gln His Leu Leu Arg Gly Lys Val Arg Phe Leu Met Leu Val
                165                 170                 175

Gly Gly Ser Thr Leu Cys Val Arg Glu Phe Gly Gly Asn Met Ala Ser
            180                 185                 190

Pro Ala Pro Pro Ala Cys Asp Leu Arg Val Leu Ser Lys Leu Leu Arg
        195                 200                 205

Asp Ser His Val Leu His Ser Arg Leu Ser Gln Cys Pro Glu Val His
        210                 215                 220

Pro Leu Pro Thr Pro Val Leu Leu Pro Ala Val Asp Phe Ser Leu Gly
225                 230                 235                 240

Glu Trp Lys Thr Gln Met Glu Glu Thr Lys Ala Gln Asp Ile Leu Gly
                245                 250                 255

Ala Val Thr Leu Leu Leu Glu Gly Val Met Ala Ala Arg Gly Gln Leu
            260                 265                 270

Gly Pro Thr Cys Leu Ser Ser Leu Leu Gly Gln Leu Ser Gly Gln Val
        275                 280                 285

Arg Leu Leu Leu Gly Ala Leu Gln Ser Leu Leu Gly Thr Gln Leu Pro
290                 295                 300

Pro Gln
305

(2) INFORMATION FOR SEQ ID NO:212:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:212:

Ala Asn Cys Ser Ile Met Ile Asp Glu Ile Ile His His Leu Lys Arg
 1               5                  10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
             35                  40                  45

Val Arg Ala Val Lys Asn Leu Glu Asn Ala Ser Gly Ile Glu Ala Ile
         50                  55                  60

Leu Arg Asn Leu Gln Pro Cys Leu Pro Ser Ala Thr Ala Ala Pro Ser
 65                  70                  75                  80
```

```
Arg His Pro Ile Ile Ile Lys Ala Gly Asp Trp Gln Glu Phe Arg Glu
                    85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
            115                 120                 125

Ser Thr Ile Asn Pro Ser Pro Ser Lys Glu Ser His Lys Ser Pro
    130                 135                 140

Asn Met Ala His Lys Asp Pro Asn Ala Ile Phe Leu Ser Phe Gln His
145                 150                 155                 160

Leu Leu Arg Gly Lys Val Arg Phe Leu Met Leu Val Gly Gly Ser Thr
                165                 170                 175

Leu Cys Val Arg Glu Phe Gly Gly Asn Met Ala Ser Pro Ala Pro Pro
                180                 185                 190

Ala Cys Asp Leu Arg Val Leu Ser Lys Leu Leu Arg Asp Ser His Val
            195                 200                 205

Leu His Ser Arg Leu Ser Gln Cys Pro Glu Val His Pro Leu Pro Thr
    210                 215                 220

Pro Val Leu Leu Pro Ala Val Asp Phe Ser Leu Gly Glu Trp Lys Thr
225                 230                 235                 240

Gln Met Glu Glu Thr Lys Ala Gln Asp Ile Leu Gly Ala Val Thr Leu
                245                 250                 255

Leu Leu Glu Gly Val Met Ala Ala Arg Gly Gln Leu Gly Pro Thr Cys
                260                 265                 270

Leu Ser Ser Leu Leu Gly Gln Leu Ser Gly Gln Val Arg Leu Leu Leu
            275                 280                 285

Gly Ala Leu Gln Ser Leu Leu Gly Thr Gln Leu Pro Pro Gln Gly Arg
            290                 295                 300

Thr Thr
305

(2) INFORMATION FOR SEQ ID NO:213:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:213:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
        50                  55                  60

Leu Arg Asn Leu Gln Pro Cys Leu Pro Ser Ala Thr Ala Ala Pro Ser
65              70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110
```

```
Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
130                 135                 140

Asn Met Asp Pro Asn Ala Ile Phe Leu Ser Phe Gln His Leu Leu Arg
145                 150                 155                 160

Gly Lys Val Arg Phe Leu Met Leu Val Gly Gly Ser Thr Leu Cys Val
                165                 170                 175

Arg Glu Phe Gly Gly Asn Met Ala Ser Pro Ala Pro Ala Cys Asp
                180                 185                 190

Leu Arg Val Leu Ser Lys Leu Leu Arg Asp Ser His Val Leu His Ser
        195                 200                 205

Arg Leu Ser Gln Cys Pro Glu Val His Pro Leu Pro Thr Pro Val Leu
        210                 215                 220

Leu Pro Ala Val Asp Phe Ser Leu Gly Glu Trp Lys Thr Gln Met Glu
225                 230                 235                 240

Glu Thr Lys Ala Gln Asp Ile Leu Gly Ala Val Thr Leu Leu Leu Glu
                245                 250                 255

Gly Val Met Ala Ala Arg Gly Gln Leu Gly Pro Thr Cys Leu Ser Ser
                260                 265                 270

Leu Leu Gly Gln Leu Ser Gly Gln Val Arg Leu Leu Gly Ala Leu
        275                 280                 285

Gln Ser Leu Leu Gly Thr Gln Leu Pro Pro Gln Gly Arg Thr Thr Ala
290                 295                 300

His Lys
305

(2) INFORMATION FOR SEQ ID NO:214:

(i) SEQUENCE CHARACTERISTICS:
        (A) LENGTH: 306 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:214:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
                35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
130                 135                 140
```

```
Asn Met Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Glu Phe
                165                 170                 175

Gly Gly Asn Met Ala Ser Pro Ala Pro Ala Cys Asp Leu Arg Val
            180                 185                 190

Leu Ser Lys Leu Leu Arg Asp Ser His Val Leu His Ser Arg Leu Ser
        195                 200                 205

Gln Cys Pro Glu Val His Pro Leu Pro Thr Pro Val Leu Leu Pro Ala
    210                 215                 220

Val Asp Phe Ser Leu Gly Glu Trp Lys Thr Gln Met Glu Glu Thr Lys
225                 230                 235                 240

Ala Gln Asp Ile Leu Gly Ala Val Thr Leu Leu Glu Leu Gly Val Met
                245                 250                 255

Ala Ala Arg Gly Gln Leu Gly Pro Thr Cys Leu Ser Ser Leu Leu Gly
            260                 265                 270

Gln Leu Ser Gly Gln Val Arg Leu Leu Leu Gly Ala Leu Gln Ser Leu
        275                 280                 285

Leu Gly Thr Gln Leu Pro Pro Gln Gly Arg Thr Thr Ala His Lys Asp
290                 295                 300

Pro Asn
305

(2) INFORMATION FOR SEQ ID NO:215:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:215:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Pro Ser Gly Pro Ile
            115                 120                 125

Ser Thr Ile Asn Pro Ser Pro Ser Lys Glu Ser His Lys Ser Pro
130                 135                 140

Asn Met Glu Val His Pro Leu Pro Thr Pro Val Leu Leu Pro Ala Val
145                 150                 155                 160

Asp Phe Ser Leu Gly Glu Trp Lys Thr Gln Met Glu Glu Thr Lys Ala
                165                 170                 175
```

```
Gln Asp Ile Leu Gly Ala Val Thr Leu Leu Glu Gly Val Met Ala
            180                 185                 190

Ala Arg Gly Gln Leu Gly Pro Thr Cys Leu Ser Ser Leu Leu Gly Gln
        195                 200                 205

Leu Ser Gly Gln Val Arg Leu Leu Gly Ala Leu Gln Ser Leu Leu
    210                 215                 220

Gly Thr Gln Leu Pro Pro Gln Gly Arg Thr Thr Ala His Lys Asp Pro
225                 230                 235                 240

Asn Ala Ile Phe Leu Ser Phe Gln His Leu Leu Arg Gly Lys Val Arg
                245                 250                 255

Phe Leu Met Leu Val Gly Gly Ser Thr Leu Cys Val Arg Glu Phe Gly
                260                 265                 270

Asn Met Ala Ser Pro Ala Pro Pro Ala Cys Asp Leu Arg Val Leu Ser
            275                 280                 285

Lys Leu Leu Arg Asp Ser His Val Leu His Ser Arg Leu Ser Gln Cys
290                 295                 300

Pro
305

(2) INFORMATION FOR SEQ ID NO:216:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:216:

Ala Asn Cys Ser Ile Met Ile Asp Glu Ile Ile His His Leu Lys Arg
1               5                   10                  15

Pro Pro Ala Pro Leu Leu Asp Pro Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
    130                 135                 140

Asn Met Leu Pro Thr Pro Val Leu Pro Ala Val Asp Phe Ser Leu
145                 150                 155                 160

Gly Glu Trp Lys Thr Gln Met Glu Glu Thr Lys Ala Gln Asp Ile Leu
                165                 170                 175

Gly Ala Val Thr Leu Leu Glu Gly Val Met Ala Ala Arg Gly Gln
            180                 185                 190

Leu Gly Pro Thr Cys Leu Ser Ser Leu Leu Gly Gln Leu Ser Gly Gln
        195                 200                 205
```

```
Val Arg Leu Leu Leu Gly Ala Leu Gln Ser Leu Leu Gly Thr Gln Leu
    210                 215                 220

Pro Pro Gln Gly Arg Thr Thr Ala His Lys Asp Pro Asn Ala Ile Phe
225                 230                 235                 240

Leu Ser Phe Gln His Leu Leu Arg Gly Lys Val Arg Phe Leu Met Leu
                245                 250                 255

Val Gly Gly Ser Thr Leu Cys Val Arg Glu Phe Gly Asn Met Ala Ser
                260                 265                 270

Pro Ala Pro Pro Ala Cys Asp Leu Arg Val Leu Ser Lys Leu Leu Arg
                275                 280                 285

Asp Ser His Val Leu His Ser Arg Leu Ser Gln Cys Pro Glu Val His
                290                 295                 300

Pro
305

(2) INFORMATION FOR SEQ ID NO:217:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:217:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
                35                  40                  45

Val Arg Ala Val Lys Asn Leu Glu Asn Ala Ser Gly Ile Glu Ala Ile
            50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Val Leu Leu Pro Ala Val Asp Phe Ser Leu Gly Glu Trp Lys
145                 150                 155                 160

Thr Gln Met Glu Glu Thr Lys Ala Gln Asp Ile Leu Gly Ala Val Thr
                165                 170                 175

Leu Leu Leu Glu Gly Val Met Ala Ala Arg Gly Gln Leu Gly Pro Thr
                180                 185                 190

Cys Leu Ser Ser Leu Leu Gly Gln Leu Ser Gly Gln Val Arg Leu Leu
            195                 200                 205

Leu Gly Ala Leu Gln Ser Leu Leu Gly Thr Gln Leu Pro Pro Gln Gly
    210                 215                 220

Arg Thr Thr Ala His Lys Asp Pro Asn Ala Ile Phe Leu Ser Phe Gln
225                 230                 235                 240
```

```
His Leu Leu Arg Gly Lys Val Arg Phe Leu Met Leu Val Gly Gly Ser
                245                 250                 255

Thr Leu Cys Val Arg Glu Phe Gly Asn Met Ala Ser Pro Ala Pro Pro
            260                 265                 270

Ala Cys Asp Leu Arg Val Leu Ser Lys Leu Leu Arg Asp Ser His Val
        275                 280                 285

Leu His Ser Arg Leu Ser Gln Cys Pro Glu Val His Pro Leu Pro Thr
    290                 295                 300

Pro
305

(2) INFORMATION FOR SEQ ID NO:218:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:218:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
    130                 135                 140

Asn Met Ala Val Asp Phe Ser Leu Gly Trp Lys Thr Gln Met Glu
145                 150                 155                 160

Glu Thr Lys Ala Gln Asp Ile Leu Gly Ala Val Thr Leu Leu Leu Glu
            165                 170                 175

Gly Val Met Ala Ala Arg Gly Gln Leu Gly Pro Thr Cys Leu Ser Ser
        180                 185                 190

Leu Leu Gly Gln Leu Ser Gly Gln Val Arg Leu Leu Leu Gly Ala Leu
    195                 200                 205

Gln Ser Leu Leu Gly Thr Gln Leu Pro Pro Gln Gly Arg Thr Thr Ala
210                 215                 220

His Lys Asp Pro Asn Ala Ile Phe Leu Ser Phe Gln His Leu Leu Arg
225                 230                 235                 240

Gly Lys Val Arg Phe Leu Met Leu Val Gly Gly Ser Thr Leu Cys Val
            245                 250                 255

Arg Glu Phe Gly Asn Met Ala Ser Pro Ala Pro Ala Cys Asp Leu
        260                 265                 270
```

```
Arg Val Leu Ser Lys Leu Leu Arg Asp Ser His Val Leu His Ser Arg
            275                 280                 285

Leu Ser Gln Cys Pro Glu Val His Pro Leu Pro Thr Pro Val Leu Leu
            290                 295                 300

Pro
305

(2) INFORMATION FOR SEQ ID NO:219:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:219:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
        50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
            85                  90                  95

Lys Leu Thr Phe Tyr Leu Val Thr Leu Glu Gln Ala Gln Glu Gln Gln
            100                 105                 110

Tyr Val Glu Gly Gly Gly Ser Gly Glu Pro Ser Gly Pro Ile
            115                 120                 125

Ser Thr Ile Asn Pro Ser Pro Ser Lys Glu Ser His Lys Ser Pro
            130                 135                 140

Asn Met Asp Phe Ser Leu Gly Glu Trp Lys Thr Gln Met Glu Glu Thr
145                 150                 155                 160

Lys Ala Gln Asp Ile Leu Gly Ala Val Thr Leu Leu Leu Glu Gly Val
            165                 170                 175

Met Ala Ala Arg Gly Gln Leu Gly Pro Thr Cys Leu Ser Ser Leu Leu
            180                 185                 190

Gly Gln Leu Ser Gly Gln Val Arg Leu Leu Gly Ala Leu Gln Ser
            195                 200                 205

Leu Leu Gly Thr Gln Leu Pro Pro Gln Gly Arg Thr Thr Ala His Lys
            210                 215                 220

Asp Pro Asn Ala Ile Phe Leu Ser Phe Gln His Leu Leu Arg Gly Lys
225                 230                 235                 240

Val Arg Phe Leu Met Leu Val Gly Gly Ser Thr Leu Cys Val Arg Glu
            245                 250                 255

Phe Gly Asn Met Ala Ser Pro Ala Pro Pro Ala Cys Asp Leu Arg Val
            260                 265                 270

Leu Ser Lys Leu Leu Arg Asp Ser His Val Leu His Ser Arg Leu Ser
            275                 280                 285

Gln Cys Pro Glu Val His Pro Leu Pro Thr Pro Val Leu Leu Pro Ala
            290                 295                 300
```

```
Val
305

(2) INFORMATION FOR SEQ ID NO:220:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:220:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
    130                 135                 140

Asn Met Gly Glu Trp Lys Thr Gln Met Glu Glu Thr Lys Ala Gln Asp
145                 150                 155                 160

Ile Leu Gly Ala Val Thr Leu Leu Glu Gly Val Met Ala Ala Arg
                165                 170                 175

Gly Gln Leu Gly Pro Thr Cys Leu Ser Ser Leu Leu Gly Gln Leu Ser
                180                 185                 190

Gly Gln Val Arg Leu Leu Leu Gly Ala Leu Gln Ser Leu Leu Gly Thr
            195                 200                 205

Gln Leu Pro Pro Gln Gly Arg Thr Thr Ala His Lys Asp Pro Asn Ala
        210                 215                 220

Ile Phe Leu Ser Phe Gln His Leu Leu Arg Gly Lys Val Arg Phe Leu
225                 230                 235                 240

Met Leu Val Gly Gly Ser Thr Leu Cys Val Arg Glu Phe Gly Asn Met
                245                 250                 255

Ala Ser Pro Ala Pro Pro Ala Cys Asp Leu Arg Val Leu Ser Lys Leu
            260                 265                 270

Leu Arg Asp Ser His Val Leu His Ser Arg Leu Ser Gln Cys Pro Glu
        275                 280                 285

Val His Pro Leu Pro Thr Pro Val Leu Leu Pro Ala Val Asp Phe Ser
    290                 295                 300

Leu
305

(2) INFORMATION FOR SEQ ID NO:221:
```

(i) SEQUENCE CHARACTERISTICS:
            (A) LENGTH: 305 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:221:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
            115                 120                 125

Ser Thr Ile Asn Pro Ser Pro Ser Lys Glu Ser His Lys Ser Pro
130                 135                 140

Asn Met Gly Pro Thr Cys Leu Ser Ser Leu Leu Gly Gln Leu Ser Gly
145                 150                 155                 160

Gln Val Arg Leu Leu Leu Gly Ala Leu Gln Ser Leu Leu Gly Thr Gln
            165                 170                 175

Leu Pro Pro Gln Gly Arg Thr Thr Ala His Lys Asp Pro Asn Ala Ile
            180                 185                 190

Phe Leu Ser Phe Gln His Leu Leu Arg Gly Lys Val Arg Phe Leu Met
            195                 200                 205

Leu Val Gly Gly Ser Thr Leu Cys Val Arg Glu Phe Gly Asn Met Ala
210                 215                 220

Ser Pro Ala Pro Pro Ala Cys Asp Leu Arg Val Leu Ser Lys Leu Leu
225                 230                 235                 240

Arg Asp Ser His Val Leu His Ser Arg Leu Ser Gln Cys Pro Glu Val
                245                 250                 255

His Pro Leu Pro Thr Pro Val Leu Leu Pro Ala Val Asp Phe Ser Leu
            260                 265                 270

Gly Glu Trp Lys Thr Gln Met Glu Glu Thr Lys Ala Gln Asp Ile Leu
            275                 280                 285

Gly Ala Val Thr Leu Leu Leu Glu Gly Val Met Ala Ala Arg Gly Gln
            290                 295                 300

Leu
305

(2) INFORMATION FOR SEQ ID NO:222:

(i) SEQUENCE CHARACTERISTICS:
            (A) LENGTH: 305 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:222:

| | | | | | | | | | | | | | | |
|---|---|---|---|---|---|---|---|---|---|---|---|---|---|---|
| Ala | Asn | Cys | Ser | Ile | Met | Ile | Asp | Glu | Ile | Ile | His | His | Leu | Lys | Arg |
| 1 | | | | 5 | | | | | 10 | | | | | 15 | |

```
Ala Asn Cys Ser Ile Met Ile Asp Glu Ile Ile His His Leu Lys Arg
1               5                   10                  15
Pro Pro Ala Pro Leu Leu Asp Pro Asn Asn Leu Asn Asp Glu Asp Val
                20                  25                  30
Ser Ile Leu Met Asp Arg Asn Leu Arg Leu Pro Asn Leu Glu Ser Phe
                35                  40                  45
Val Arg Ala Val Lys Asn Leu Glu Asn Ala Ser Gly Ile Glu Ala Ile
 50                  55                  60
Leu Arg Asn Leu Gln Pro Cys Leu Pro Ser Ala Thr Ala Ala Pro Ser
 65                  70                  75                  80
Arg His Pro Ile Ile Ile Lys Ala Gly Asp Trp Gln Glu Phe Arg Glu
                 85                  90                  95
Lys Leu Thr Phe Tyr Leu Val Thr Leu Glu Gln Ala Gln Glu Gln Gln
                100                 105                 110
Tyr Val Glu Gly Gly Gly Ser Pro Gly Glu Pro Ser Gly Pro Ile
                115                 120                 125
Ser Thr Ile Asn Pro Ser Pro Pro Ser Lys Glu Ser His Lys Ser Pro
130                 135                 140
Asn Met Gly Thr Gln Leu Pro Pro Gln Gly Arg Thr Thr Ala His Lys
145                 150                 155                 160
Asp Pro Asn Ala Ile Phe Leu Ser Phe Gln His Leu Leu Arg Gly Lys
                165                 170                 175
Val Arg Phe Leu Met Leu Val Gly Gly Ser Thr Leu Cys Val Arg Glu
                180                 185                 190
Phe Gly Asn Met Ala Ser Pro Ala Pro Pro Ala Cys Asp Leu Arg Val
                195                 200                 205
Leu Ser Lys Leu Leu Arg Asp Ser His Val Leu His Ser Arg Leu Ser
                210                 215                 220
Gln Cys Pro Glu Val His Pro Leu Pro Thr Pro Val Leu Leu Pro Ala
225                 230                 235                 240
Val Asp Phe Ser Leu Gly Glu Trp Lys Thr Gln Met Glu Glu Thr Lys
                245                 250                 255
Ala Gln Asp Ile Leu Gly Ala Val Thr Leu Leu Glu Gly Val Met
                260                 265                 270
Ala Ala Arg Gly Gln Leu Gly Pro Thr Cys Leu Ser Ser Leu Leu Gly
                275                 280                 285
Gln Leu Ser Gly Gln Val Arg Leu Leu Leu Gly Ala Leu Gln Ser Leu
290                 295                 300
Leu
305
```

(2) INFORMATION FOR SEQ ID NO:223:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:223:

```
Ala Asn Cys Ser Ile Met Ile Asp Glu Ile Ile His His Leu Lys Arg
1               5                   10                  15
```

```
Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Ser Pro Gly Glu Pro Ser Gly Pro Ile
            115                 120                 125

Ser Thr Ile Asn Pro Ser Pro Ser Lys Glu Ser His Lys Ser Pro
            130                 135                 140

Asn Met Gly Arg Thr Thr Ala His Lys Asp Pro Asn Ala Ile Phe Leu
145                 150                 155                 160

Ser Phe Gln His Leu Leu Arg Gly Lys Val Arg Phe Leu Met Leu Val
            165                 170                 175

Gly Gly Ser Thr Leu Cys Val Arg Glu Phe Gly Asn Met Ala Ser Pro
            180                 185                 190

Ala Pro Pro Ala Cys Asp Leu Arg Val Leu Ser Lys Leu Leu Arg Asp
            195                 200                 205

Ser His Val Leu His Ser Arg Leu Ser Gln Cys Pro Glu Val His Pro
210                 215                 220

Leu Pro Thr Pro Val Leu Leu Pro Ala Val Asp Phe Ser Leu Gly Glu
225                 230                 235                 240

Trp Lys Thr Gln Met Glu Glu Thr Lys Ala Gln Asp Ile Leu Gly Ala
            245                 250                 255

Val Thr Leu Leu Leu Glu Gly Val Met Ala Ala Arg Gly Gln Leu Gly
            260                 265                 270

Pro Thr Cys Leu Ser Ser Leu Leu Gly Gln Leu Ser Gly Gln Val Arg
            275                 280                 285

Leu Leu Leu Gly Ala Leu Gln Ser Leu Leu Gly Thr Gln Leu Pro Pro
    290                 295                 300

Gln
305

(2) INFORMATION FOR SEQ ID NO:224:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:224:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45
```

-continued

```
Val Arg Ala Val Lys Asn Leu Glu Asn Ala Ser Gly Ile Glu Ala Ile
     50                  55                  60

Leu Arg Asn Leu Gln Pro Cys Leu Pro Ser Ala Thr Ala Ala Pro Ser
 65                  70                  75                  80

Arg His Pro Ile Ile Ile Lys Ala Gly Asp Trp Gln Glu Phe Arg Glu
                     85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Pro Ser Gly Pro Ile
                115                 120                 125

Ser Thr Ile Asn Pro Ser Pro Pro Ser Lys Glu Ser His Lys Ser Pro
    130                 135                 140

Asn Met Gly Arg Thr Thr Ala His Lys Asp Pro Asn Ala Ile Phe Leu
145                 150                 155                 160

Ser Phe Gln His Leu Leu Arg Gly Lys Val Arg Phe Leu Met Leu Val
                165                 170                 175

Gly Gly Ser Thr Leu Cys Val Arg Glu Phe Gly Asn Met Ala Ser Pro
                180                 185                 190

Ala Pro Pro Ala Cys Asp Leu Arg Val Leu Ser Lys Leu Leu Arg Asp
                195                 200                 205

Ser His Val Leu His Ser Arg Leu Ser Gln Cys Pro Glu Val His Pro
    210                 215                 220

Leu Pro Thr Pro Val Leu Leu Pro Ala Val Asp Phe Ser Leu Gly Glu
225                 230                 235                 240

Trp Lys Thr Gln Met Glu Glu Thr Lys Ala Gln Asp Ile Leu Gly Ala
                245                 250                 255

Val Thr Leu Leu Leu Glu Gly Val Met Ala Ala Arg Gly Gln Leu Gly
                260                 265                 270

Pro Thr Cys Leu Ser Ser Leu Leu Gly Gln Leu Ser Gly Gln Val Arg
                275                 280                 285

Leu Leu Leu Gly Ala Leu Gln Ser Leu Leu Gly Thr Gln Leu Pro Pro
        290                 295                 300

Gln
305
```

(2) INFORMATION FOR SEQ ID NO:225:

(i) SEQUENCE CHARACTERISTICS:
  (A) LENGTH: 305 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:225:

```
Ala Asn Cys Ser Ile Met Ile Asp Glu Ile Ile His His Leu Lys Arg
 1               5                  10                  15

Pro Pro Ala Pro Leu Leu Asp Pro Asn Asn Leu Asn Asp Glu Asp Val
                 20                  25                  30

Ser Ile Leu Met Asp Arg Asn Leu Arg Leu Pro Asn Leu Glu Ser Phe
             35                  40                  45

Val Arg Ala Val Lys Asn Leu Glu Asn Ala Ser Gly Ile Glu Ala Ile
     50                  55                  60

Leu Arg Asn Leu Gln Pro Cys Leu Pro Ser Ala Thr Ala Ala Pro Ser
 65                  70                  75                  80
```

-continued

```
Arg His Pro Ile Ile Ile Lys Ala Gly Asp Trp Gln Glu Phe Arg Glu
                85                  90                  95
Lys Leu Thr Phe Tyr Leu Val Thr Leu Glu Gln Ala Gln Glu Gln Gln
            100                 105                 110
Tyr Val Glu Gly Gly Gly Ser Pro Gly Glu Pro Ser Gly Pro Ile
        115                 120                 125
Ser Thr Ile Asn Pro Ser Pro Ser Lys Glu Ser His Lys Ser Pro
    130                 135                 140
Asn Met Asp Pro Asn Ala Ile Phe Leu Ser Phe Gln His Leu Leu Arg
145                 150                 155                 160
Gly Lys Val Arg Phe Leu Met Leu Val Gly Gly Ser Thr Leu Cys Val
                165                 170                 175
Arg Glu Phe Gly Asn Met Ala Ser Pro Ala Pro Pro Ala Cys Asp Leu
                180                 185                 190
Arg Val Leu Ser Lys Leu Leu Arg Asp Ser His Val Leu His Ser Arg
            195                 200                 205
Leu Ser Gln Cys Pro Glu Val His Pro Leu Pro Thr Pro Val Leu Leu
    210                 215                 220
Pro Ala Val Asp Phe Ser Leu Gly Glu Trp Lys Thr Gln Met Glu Glu
225                 230                 235                 240
Thr Lys Ala Gln Asp Ile Leu Gly Ala Val Thr Leu Leu Leu Glu Gly
                245                 250                 255
Val Met Ala Ala Arg Gly Gln Leu Gly Pro Thr Cys Leu Ser Ser Leu
                260                 265                 270
Leu Gly Gln Leu Ser Gly Gln Val Arg Leu Leu Leu Gly Ala Leu Gln
            275                 280                 285
Ser Leu Leu Gly Thr Gln Leu Pro Pro Gln Gly Arg Thr Thr Ala His
    290                 295                 300
Lys
305
```

(2) INFORMATION FOR SEQ ID NO:226:

(i) SEQUENCE CHARACTERISTICS:
        (A) LENGTH: 305 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:226:

```
Ala Asn Cys Ser Ile Met Ile Asp Glu Ile Ile His His Leu Lys Arg
1               5                   10                  15
Pro Pro Ala Pro Leu Leu Asp Pro Asn Asn Leu Asn Asp Glu Asp Val
            20                  25                  30
Ser Ile Leu Met Asp Arg Asn Leu Arg Leu Pro Asn Leu Glu Ser Phe
        35                  40                  45
Val Arg Ala Val Lys Asn Leu Glu Asn Ala Ser Gly Ile Glu Ala Ile
    50                  55                  60
Leu Arg Asn Leu Gln Pro Cys Leu Pro Ser Ala Thr Ala Ala Pro Ser
65                  70                  75                  80
Arg His Pro Ile Ile Ile Lys Ala Gly Asp Trp Gln Glu Phe Arg Glu
                85                  90                  95
Lys Leu Thr Phe Tyr Leu Val Thr Leu Glu Gln Ala Gln Glu Gln Gln
            100                 105                 110
```

```
Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
        130                 135                 140

Asn Met Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Glu Phe
                165                 170                 175

Gly Asn Met Ala Ser Pro Ala Pro Pro Ala Cys Asp Leu Arg Val Leu
            180                 185                 190

Ser Lys Leu Leu Arg Asp Ser His Val Leu His Ser Arg Leu Ser Gln
        195                 200                 205

Cys Pro Glu Val His Pro Leu Pro Thr Pro Val Leu Leu Pro Ala Val
        210                 215                 220

Asp Phe Ser Leu Gly Glu Trp Lys Thr Gln Met Glu Glu Thr Lys Ala
225                 230                 235                 240

Gln Asp Ile Leu Gly Ala Val Thr Leu Leu Leu Glu Gly Val Met Ala
                245                 250                 255

Ala Arg Gly Gln Leu Gly Pro Thr Cys Leu Ser Ser Leu Leu Gly Gln
            260                 265                 270

Leu Ser Gly Gln Val Arg Leu Leu Leu Gly Ala Leu Gln Ser Leu Leu
        275                 280                 285

Gly Thr Gln Leu Pro Pro Gln Gly Arg Thr Thr Ala His Lys Asp Pro
        290                 295                 300

Asn
305

(2) INFORMATION FOR SEQ ID NO:227:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:227:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
        130                 135                 140
```

```
Asn Met Leu Pro Thr Pro Val Leu Leu Pro Ala Val Asp Phe Ser Leu
145                 150                 155                 160

Gly Glu Trp Lys Thr Gln Met Glu Gly Thr Lys Ala Gln Asp Ile Leu
                165                 170                 175

Gly Ala Val Thr Leu Leu Glu Gly Val Met Ala Ala Arg Gly Gln
                180                 185                 190

Leu Gly Pro Thr Cys Leu Ser Ser Leu Leu Gly Gln Leu Ser Gly Gln
                195                 200                 205

Val Arg Leu Leu Leu Gly Ala Leu Gln Ser Leu Leu Gly Thr Gln Leu
        210                 215                 220

Pro Pro Gln Gly Arg Thr Thr Ala His Lys Asp Pro Asn Ala Ile Phe
225                 230                 235                 240

Leu Ser Phe Gln His Leu Leu Arg Gly Lys Val Arg Phe Leu Met Leu
                245                 250                 255

Val Gly Gly Ser Thr Leu Cys Val Arg Glu Phe Gly Gly Asn Gly Gly
                260                 265                 270

Asn Met Ala Ser Pro Ala Pro Pro Ala Cys Asp Leu Arg Val Leu Ser
        275                 280                 285

Lys Leu Leu Arg Asp Ser His Val Leu His Ser Arg Leu Ser Gln Cys
290                 295                 300

Pro Glu Val His Pro
305

(2) INFORMATION FOR SEQ ID NO:228:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:228:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
                35                  40                  45

Val Arg Ala Val Lys Asn Leu Glu Asn Ala Ser Gly Ile Glu Ala Ile
        50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
                115                 120                 125

Ser Thr Ile Asn Pro Ser Pro Pro Ser Lys Glu Ser His Lys Ser Pro
        130                 135                 140

Asn Met Leu Pro Thr Pro Val Leu Leu Pro Ala Val Asp Phe Ser Leu
145                 150                 155                 160

Gly Glu Trp Lys Thr Gln Met Glu Gly Thr Lys Ala Gln Asp Ile Leu
                165                 170                 175
```

```
Gly Ala Val Thr Leu Leu Leu Glu Gly Val Met Ala Ala Arg Gly Gln
            180                 185                 190

Leu Gly Pro Thr Cys Leu Ser Ser Leu Leu Gly Gln Leu Ser Gly Gln
            195                 200                 205

Val Arg Leu Leu Leu Gly Ala Leu Gln Ser Leu Leu Gly Thr Gln Leu
            210                 215                 220

Pro Pro Gln Gly Arg Thr Thr Ala His Lys Asp Pro Asn Ala Ile Phe
225                 230                 235                 240

Leu Ser Phe Gln His Leu Leu Arg Gly Lys Val Arg Phe Leu Met Leu
            245                 250                 255

Val Gly Gly Ser Thr Leu Cys Val Arg Glu Phe Gly Gly Asn Gly Gly
            260                 265                 270

Asn Met Ala Ser Pro Ala Pro Pro Ala Cys Asp Leu Arg Val Leu Ser
            275                 280                 285

Lys Leu Leu Arg Asp Ser His Val Leu His Ser Arg Leu Ser Gln Cys
            290                 295                 300

Pro Glu Val His Pro
305
```

(2) INFORMATION FOR SEQ ID NO:229:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:229:

```
Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
            50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
            85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
            130                 135                 140

Asn Met Val Leu Leu Pro Ala Val Asp Phe Ser Leu Gly Glu Trp Lys
145                 150                 155                 160

Thr Gln Met Glu Glu Thr Lys Ala Gln Asp Ile Leu Gly Ala Val Thr
            165                 170                 175

Leu Leu Leu Glu Gly Val Met Ala Ala Arg Gly Gln Leu Gly Pro Thr
            180                 185                 190

Cys Leu Ser Ser Leu Leu Gly Gln Leu Ser Gly Gln Val Arg Leu Leu
            195                 200                 205
```

```
Leu Gly Ala Leu Gln Ser Leu Leu Gly Thr Gln Leu Pro Pro Gln Gly
    210                 215                 220

Arg Thr Thr Ala His Lys Asp Pro Asn Ala Ile Phe Leu Ser Phe Gln
225                 230                 235                 240

His Leu Leu Arg Gly Lys Val Arg Phe Leu Met Leu Val Gly Gly Ser
                245                 250                 255

Thr Leu Cys Val Arg Glu Phe Gly Gly Asn Gly Gly Asn Met Ala Ser
            260                 265                 270

Pro Ala Pro Pro Ala Cys Asp Leu Arg Val Leu Ser Lys Leu Leu Arg
                275                 280                 285

Asp Ser His Val Leu His Ser Arg Leu Ser Gln Cys Pro Glu Val His
    290                 295                 300

Pro Leu Pro Thr Pro
305
```

(2) INFORMATION FOR SEQ ID NO:230:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:230:

```
Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
    115                 120                 125

Ser Thr Ile Asn Pro Ser Pro Ser Lys Glu Ser His Lys Ser Pro
    130                 135                 140

Asn Met Ala Val Asp Phe Ser Leu Gly Glu Trp Lys Thr Gln Met Glu
145                 150                 155                 160

Glu Thr Lys Ala Gln Asp Ile Leu Gly Ala Val Thr Leu Leu Leu Glu
                165                 170                 175

Gly Val Met Ala Ala Arg Gly Gln Gly Pro Thr Cys Leu Ser Ser
                180                 185                 190

Leu Leu Gly Gln Leu Ser Gly Gln Val Arg Leu Leu Gly Ala Leu
            195                 200                 205

Gln Ser Leu Leu Gly Thr Gln Leu Pro Pro Gln Gly Arg Thr Thr Ala
    210                 215                 220

His Lys Asp Pro Asn Ala Ile Phe Leu Ser Phe Gln His Leu Leu Arg
225                 230                 235                 240
```

```
Gly Lys Val Arg Phe Leu Met Leu Val Gly Gly Ser Thr Leu Cys Val
                245                 250                 255

Arg Glu Phe Gly Gly Asn Gly Gly Asn Met Ala Ser Pro Ala Pro Pro
            260                 265                 270

Ala Cys Asp Leu Arg Val Leu Ser Lys Leu Leu Arg Asp Ser His Val
        275                 280                 285

Leu His Ser Arg Leu Ser Gln Cys Pro Glu Val His Pro Leu Pro Thr
    290                 295                 300

Pro Val Leu Leu Pro
305
```

(2) INFORMATION FOR SEQ ID NO:231:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:231:

```
Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
130                 135                 140

Asn Met Asp Phe Ser Leu Gly Glu Trp Lys Thr Gln Met Glu Glu Thr
145                 150                 155                 160

Lys Ala Gln Asp Ile Leu Gly Ala Val Thr Leu Leu Glu Gly Val
                165                 170                 175

Met Ala Ala Arg Gly Gln Leu Gly Pro Thr Cys Leu Ser Ser Leu Leu
            180                 185                 190

Gly Gln Leu Ser Gly Gln Val Arg Leu Leu Leu Gly Ala Leu Gln Ser
        195                 200                 205

Leu Leu Gly Thr Gln Leu Pro Pro Gln Gly Arg Thr Thr Ala His Lys
    210                 215                 220

Asp Pro Asn Ala Ile Phe Leu Ser Phe Gln His Leu Leu Arg Gly Lys
225                 230                 235                 240

Val Arg Phe Leu Met Leu Val Gly Gly Ser Thr Leu Cys Val Arg Glu
                245                 250                 255

Phe Gly Gly Asn Gly Gly Asn Met Ala Ser Pro Ala Pro Pro Ala Cys
            260                 265                 270
```

```
Asp Leu Arg Val Leu Ser Lys Leu Leu Arg Asp Ser His Val Leu His
            275                 280                 285

Ser Arg Leu Ser Gln Cys Pro Glu Val His Pro Leu Pro Thr Pro Val
            290                 295                 300

Leu Leu Pro Ala Val
305
```

(2) INFORMATION FOR SEQ ID NO:232:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:232:

```
Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
 50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Ser Pro Gly Glu Pro Ser Gly Pro Ile
            115                 120                 125

Ser Thr Ile Asn Pro Ser Pro Ser Lys Glu Ser His Lys Ser Pro
            130                 135                 140

Asn Met Gly Glu Trp Lys Thr Gln Met Glu Glu Thr Lys Ala Gln Asp
145                 150                 155                 160

Ile Leu Gly Ala Val Thr Leu Leu Glu Gly Val Met Ala Ala Arg
                165                 170                 175

Gly Gln Leu Gly Pro Thr Cys Leu Ser Ser Leu Leu Gly Gln Leu Ser
            180                 185                 190

Gly Gln Val Arg Leu Leu Leu Gly Ala Leu Gln Ser Leu Leu Gly Thr
            195                 200                 205

Gln Leu Pro Pro Gln Gly Arg Thr Thr Ala His Lys Asp Pro Asn Ala
            210                 215                 220

Ile Phe Leu Ser Phe Gln His Leu Leu Arg Gly Lys Val Arg Phe Leu
225                 230                 235                 240

Met Leu Val Gly Gly Ser Thr Leu Cys Val Arg Glu Phe Gly Gly Asn
                245                 250                 255

Gly Gly Asn Met Ala Ser Pro Ala Pro Pro Ala Cys Asp Leu Arg Val
            260                 265                 270

Leu Ser Lys Leu Leu Arg Asp Ser His Val Leu His Ser Arg Leu Ser
            275                 280                 285

Gln Cys Pro Glu Val His Pro Leu Pro Thr Pro Val Leu Leu Pro Ala
            290                 295                 300
```

```
Val Asp Phe Ser Leu
305

(2) INFORMATION FOR SEQ ID NO:233:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:233:

Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
                35                  40                  45

Val Arg Ala Val Lys Asn Leu Glu Asn Ala Ser Gly Ile Glu Ala Ile
50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
                100                 105                 110

Tyr Val Glu Gly Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Gly Pro Thr Cys Leu Ser Ser Leu Leu Gly Gln Leu Ser Gly
145                 150                 155                 160

Gln Val Arg Leu Leu Leu Gly Ala Leu Gln Ser Leu Leu Gly Thr Gln
                165                 170                 175

Leu Pro Pro Gln Gly Arg Thr Thr Ala His Lys Asp Pro Asn Ala Ile
            180                 185                 190

Phe Leu Ser Phe Gln His Leu Leu Arg Gly Lys Val Arg Phe Leu Met
            195                 200                 205

Leu Val Gly Gly Ser Thr Leu Cys Val Arg Glu Phe Gly Gly Asn Gly
210                 215                 220

Gly Asn Met Ala Ser Pro Ala Pro Pro Ala Cys Asp Leu Arg Val Leu
225                 230                 235                 240

Ser Lys Leu Leu Arg Asp Ser His Val Leu His Ser Arg Leu Ser Gln
                245                 250                 255

Cys Pro Glu Val His Pro Leu Pro Thr Pro Val Leu Leu Pro Ala Val
            260                 265                 270

Asp Phe Ser Leu Gly Glu Trp Lys Thr Gln Met Glu Glu Thr Lys Ala
            275                 280                 285

Gln Asp Ile Leu Gly Ala Val Thr Leu Leu Leu Glu Gly Val Met Ala
            290                 295                 300

Ala Arg Gly Gln Leu
305

(2) INFORMATION FOR SEQ ID NO:234:
```

(i) SEQUENCE CHARACTERISTICS:
    (A) LENGTH: 309 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:234:

```
Ala Asn Cys Ser Ile Met Ile Asp Glu Ile Ile His His Leu Lys Arg
1               5                   10                  15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
        35                  40                  45

Val Arg Ala Val Lys Asn Leu Glu Asn Ala Ser Gly Ile Glu Ala Ile
    50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                85                  90                  95

Lys Leu Thr Phe Tyr Leu Val Thr Leu Glu Gln Ala Gln Glu Gln Gln
            100                 105                 110

Tyr Val Glu Gly Gly Gly Gly Ser Pro Gly Glu Pro Ser Gly Pro Ile
        115                 120                 125

Ser Thr Ile Asn Pro Ser Pro Pro Ser Lys Glu Ser His Lys Ser Pro
130                 135                 140

Asn Met Gly Thr Gln Leu Pro Pro Gln Gly Arg Thr Thr Ala His Lys
145                 150                 155                 160

Asp Pro Asn Ala Ile Phe Leu Ser Phe Gln His Leu Leu Arg Gly Lys
                165                 170                 175

Val Arg Phe Leu Met Leu Val Gly Gly Ser Thr Leu Cys Val Arg Glu
            180                 185                 190

Phe Gly Gly Asn Gly Gly Asn Met Ala Ser Pro Ala Pro Pro Ala Cys
        195                 200                 205

Asp Leu Arg Val Leu Ser Lys Leu Leu Arg Asp Ser His Val Leu His
210                 215                 220

Ser Arg Leu Ser Gln Cys Pro Glu Val His Pro Leu Pro Thr Pro Val
225                 230                 235                 240

Leu Leu Pro Ala Val Asp Phe Ser Leu Gly Glu Trp Lys Thr Gln Met
                245                 250                 255

Glu Glu Thr Lys Ala Gln Asp Ile Leu Gly Ala Val Thr Leu Leu Leu
            260                 265                 270

Glu Gly Val Met Ala Ala Arg Gly Gln Leu Gly Pro Thr Cys Leu Ser
        275                 280                 285

Ser Leu Leu Gly Gln Leu Ser Gly Gln Val Arg Leu Leu Leu Gly Ala
290                 295                 300

Leu Gln Ser Leu Leu
305
```

(2) INFORMATION FOR SEQ ID NO:235:

(i) SEQUENCE CHARACTERISTICS:
    (A) LENGTH: 309 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:235:

| Ala | Asn | Cys | Ser | Ile | Met | Ile | Asp | Glu | Ile | Ile | His | His | Leu | Lys | Arg |
|---|---|---|---|---|---|---|---|---|---|---|---|---|---|---|---|
| 1 | | | | 5 | | | | | 10 | | | | | 15 | |

| Pro | Pro | Ala | Pro | Leu | Leu | Asp | Pro | Asn | Asn | Leu | Asn | Asp | Glu | Asp | Val |
| | | | 20 | | | | | 25 | | | | | 30 | | |

| Ser | Ile | Leu | Met | Asp | Arg | Asn | Leu | Arg | Leu | Pro | Asn | Leu | Glu | Ser | Phe |
| | | | 35 | | | | | 40 | | | | | 45 | | |

| Val | Arg | Ala | Val | Lys | Asn | Leu | Glu | Asn | Ala | Ser | Gly | Ile | Glu | Ala | Ile |
| | 50 | | | | | 55 | | | | | 60 | | | | |

| Leu | Arg | Asn | Leu | Gln | Pro | Cys | Leu | Pro | Ser | Ala | Thr | Ala | Ala | Pro | Ser |
| 65 | | | | | 70 | | | | | 75 | | | | | 80 |

| Arg | His | Pro | Ile | Ile | Ile | Lys | Ala | Gly | Asp | Trp | Gln | Glu | Phe | Arg | Glu |
| | | | | 85 | | | | | 90 | | | | | 95 | |

| Lys | Leu | Thr | Phe | Tyr | Leu | Val | Thr | Leu | Glu | Gln | Ala | Gln | Glu | Gln | Gln |
| | | | 100 | | | | | 105 | | | | | 110 | | |

| Tyr | Val | Glu | Gly | Gly | Gly | Ser | Pro | Gly | Glu | Pro | Ser | Gly | Pro | Ile |
| | | 115 | | | | | 120 | | | | | 125 | | |

| Ser | Thr | Ile | Asn | Pro | Ser | Pro | Pro | Ser | Lys | Glu | Ser | His | Lys | Ser | Pro |
| | 130 | | | | | 135 | | | | | 140 | | | | |

| Asn | Met | Gly | Arg | Thr | Thr | Ala | His | Lys | Asp | Pro | Asn | Ala | Ile | Phe | Leu |
| 145 | | | | | 150 | | | | | 155 | | | | | 160 |

| Ser | Phe | Gln | His | Leu | Leu | Arg | Gly | Lys | Val | Arg | Phe | Leu | Met | Leu | Val |
| | | | | 165 | | | | | 170 | | | | | 175 | |

| Gly | Gly | Ser | Thr | Leu | Cys | Val | Arg | Glu | Phe | Gly | Asn | Gly | Gly | Asn |
| | | | 180 | | | | | 185 | | | | | 190 | | |

| Met | Ala | Ser | Pro | Ala | Pro | Pro | Ala | Cys | Asp | Leu | Arg | Val | Leu | Ser | Lys |
| | | | 195 | | | | | 200 | | | | | 205 | | |

| Leu | Leu | Arg | Asp | Ser | His | Val | Leu | His | Ser | Arg | Leu | Ser | Gln | Cys | Pro |
| | 210 | | | | | 215 | | | | | 220 | | | | |

| Glu | Val | His | Pro | Leu | Pro | Thr | Pro | Val | Leu | Leu | Pro | Ala | Val | Asp | Phe |
| 225 | | | | | 230 | | | | | 235 | | | | | 240 |

| Ser | Leu | Gly | Glu | Trp | Lys | Thr | Gln | Met | Glu | Glu | Thr | Lys | Ala | Gln | Asp |
| | | | | 245 | | | | | 250 | | | | | 255 | |

| Ile | Leu | Gly | Ala | Val | Thr | Leu | Leu | Glu | Gly | Val | Met | Ala | Ala | Arg |
| | | | 260 | | | | | 265 | | | | | 270 | | |

| Gly | Gln | Leu | Gly | Pro | Thr | Cys | Leu | Ser | Ser | Leu | Leu | Gly | Gln | Leu | Ser |
| | | 275 | | | | | 280 | | | | | 285 | | | |

| Gly | Gln | Val | Arg | Leu | Leu | Leu | Gly | Ala | Leu | Gln | Ser | Leu | Leu | Gly | Thr |
| | 290 | | | | | 295 | | | | | 300 | | | | |

| Gln | Leu | Pro | Pro | Gln |
| 305 | | | | |

(2) INFORMATION FOR SEQ ID NO:236:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:236:

Ala Asn Cys Ser Ile Met Ile Asp Glu Ile Ile His His Leu Lys Arg

```
 1               5                  10                 15
Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
 50                  55                  60

Leu Arg Asn Leu Gln Pro Cys Leu Pro Ser Ala Thr Ala Ala Pro Ser
 65                  70                  75                  80

Arg His Pro Ile Ile Ile Lys Ala Gly Asp Trp Gln Glu Phe Arg Glu
                 85                  90                  95

Lys Leu Thr Phe Tyr Leu Val Thr Leu Glu Gln Ala Gln Glu Gln Gln
            100                 105                 110

Tyr Val Glu Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Ala His Lys Asp Pro Asn Ala Ile Phe Leu Ser Phe Gln His
145                 150                 155                 160

Leu Leu Arg Gly Lys Val Arg Phe Leu Met Leu Val Gly Gly Ser Thr
                165                 170                 175

Leu Cys Val Arg Glu Phe Gly Gly Asn Gly Gly Asn Met Ala Ser Pro
            180                 185                 190

Ala Pro Pro Ala Cys Asp Leu Arg Val Leu Ser Lys Leu Leu Arg Asp
            195                 200                 205

Ser His Val Leu His Ser Arg Leu Ser Gln Cys Pro Glu Val His Pro
210                 215                 220

Leu Pro Thr Pro Val Leu Leu Pro Ala Val Asp Phe Ser Leu Gly Glu
225                 230                 235                 240

Trp Lys Thr Gln Met Glu Glu Thr Lys Ala Gln Asp Ile Leu Gly Ala
                245                 250                 255

Val Thr Leu Leu Leu Glu Gly Val Met Ala Ala Arg Gly Gln Leu Gly
                260                 265                 270

Pro Thr Cys Leu Ser Ser Leu Leu Gly Gln Leu Ser Gly Gln Val Arg
            275                 280                 285

Leu Leu Leu Gly Ala Leu Gln Ser Leu Leu Gly Thr Gln Leu Pro Pro
            290                 295                 300

Gln Gly Arg Thr Thr
305

(2) INFORMATION FOR SEQ ID NO:237:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:237:

Ala Asn Cys Ser Ile Met Ile Asp Glu Ile Ile His His Leu Lys Arg
 1               5                  10                 15

Pro Pro Ala Pro Leu Leu Asp Pro Asn Asn Leu Asn Asp Glu Asp Val
            20                  25                  30

Ser Ile Leu Met Asp Arg Asn Leu Arg Leu Pro Asn Leu Glu Ser Phe
```

```
                35                  40                  45
Val Arg Ala Val Lys Asn Leu Glu Asn Ala Ser Gly Ile Glu Ala Ile
 50                  55                  60

Leu Arg Asn Leu Gln Pro Cys Leu Pro Ser Ala Thr Ala Ala Pro Ser
 65                  70                  75                  80

Arg His Pro Ile Ile Ile Lys Ala Gly Asp Trp Gln Glu Phe Arg Glu
                     85                  90                  95

Lys Leu Thr Phe Tyr Leu Val Thr Leu Glu Gln Ala Gln Glu Gln Gln
                    100                 105                 110

Tyr Val Glu Gly Gly Gly Ser Pro Gly Glu Pro Ser Gly Pro Ile
                115                 120                 125

Ser Thr Ile Asn Pro Ser Pro Pro Ser Lys Glu Ser His Lys Ser Pro
130                 135                 140

Asn Met Asp Pro Asn Ala Ile Phe Leu Ser Phe Gln His Leu Leu Arg
145                 150                 155                 160

Gly Lys Val Arg Phe Leu Met Leu Val Gly Gly Ser Thr Leu Cys Val
                165                 170                 175

Arg Glu Phe Gly Gly Asn Gly Gly Asn Met Ala Ser Pro Ala Pro Pro
                180                 185                 190

Ala Cys Asp Leu Arg Val Leu Ser Lys Leu Leu Arg Asp Ser His Val
                195                 200                 205

Leu His Ser Arg Leu Ser Gln Cys Pro Glu Val His Pro Leu Pro Thr
210                 215                 220

Pro Val Leu Leu Pro Ala Val Asp Phe Ser Leu Gly Glu Trp Lys Thr
225                 230                 235                 240

Gln Met Glu Glu Thr Lys Ala Gln Asp Ile Leu Gly Ala Val Thr Leu
                245                 250                 255

Leu Leu Glu Gly Val Met Ala Ala Arg Gly Gln Leu Gly Pro Thr Cys
                260                 265                 270

Leu Ser Ser Leu Leu Gly Gln Leu Ser Gly Gln Val Arg Leu Leu Leu
                275                 280                 285

Gly Ala Leu Gln Ser Leu Leu Gly Thr Gln Leu Pro Pro Gln Gly Arg
                290                 295                 300

Thr Thr Ala His Lys
305

(2) INFORMATION FOR SEQ ID NO:238:

(i) SEQUENCE CHARACTERISTICS:
        (A) LENGTH: 309 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:238:

Ala Asn Cys Ser Ile Met Ile Asp Glu Ile Ile His His Leu Lys Arg
 1                   5                  10                  15

Pro Pro Ala Pro Leu Leu Asp Pro Asn Asn Leu Asn Asp Glu Asp Val
                     20                  25                  30

Ser Ile Leu Met Asp Arg Asn Leu Arg Leu Pro Asn Leu Glu Ser Phe
                 35                  40                  45

Val Arg Ala Val Lys Asn Leu Glu Asn Ala Ser Gly Ile Glu Ala Ile
 50                  55                  60

Leu Arg Asn Leu Gln Pro Cys Leu Pro Ser Ala Thr Ala Ala Pro Ser
```

```
                65                  70                  75                  80
Arg His Pro Ile Ile Ile Lys Ala Gly Asp Trp Gln Glu Phe Arg Glu
                        85                  90                  95

Lys Leu Thr Phe Tyr Leu Val Thr Leu Glu Gln Ala Gln Glu Gln Gln
                100                 105                 110

Tyr Val Glu Gly Gly Gly Ser Pro Gly Glu Pro Ser Gly Pro Ile
            115                 120                 125

Ser Thr Ile Asn Pro Ser Pro Pro Ser Lys Glu Ser His Lys Ser Pro
130                 135                 140

Asn Met Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Glu Phe
                165                 170                 175

Gly Gly Asn Gly Gly Asn Met Ala Ser Pro Ala Pro Pro Ala Cys Asp
                180                 185                 190

Leu Arg Val Leu Ser Lys Leu Leu Arg Asp Ser His Val Leu His Ser
            195                 200                 205

Arg Leu Ser Gln Cys Pro Glu Val His Pro Leu Pro Thr Pro Val Leu
210                 215                 220

Leu Pro Ala Val Asp Phe Ser Leu Gly Glu Trp Lys Thr Gln Met Glu
225                 230                 235                 240

Glu Thr Lys Ala Gln Asp Ile Leu Gly Ala Val Thr Leu Leu Leu Glu
                245                 250                 255

Gly Val Met Ala Ala Arg Gly Gln Leu Gly Pro Thr Cys Leu Ser Ser
                260                 265                 270

Leu Leu Gly Gln Leu Ser Gly Gln Val Arg Leu Leu Leu Gly Ala Leu
                275                 280                 285

Gln Ser Leu Leu Gly Thr Gln Leu Pro Pro Gln Gly Arg Thr Thr Ala
290                 295                 300

His Lys Asp Pro Asn
305

(2) INFORMATION FOR SEQ ID NO:239:

(i) SEQUENCE CHARACTERISTICS:
        (A) LENGTH: 302 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:239:

Ala Asn Cys Ser Ile Met Ile Asp Glu Ile His His Leu Lys Arg
1               5                   10                  15

Pro Pro Ala Pro Leu Leu Asp Pro Asn Asn Leu Asn Asp Glu Asp Val
                20                  25                  30

Ser Ile Leu Met Asp Arg Asn Leu Arg Leu Pro Asn Leu Glu Ser Phe
            35                  40                  45

Val Arg Ala Val Lys Asn Leu Glu Asn Ala Ser Gly Ile Glu Ala Ile
        50                  55                  60

Leu Arg Asn Leu Gln Pro Cys Leu Pro Ser Ala Thr Ala Ala Pro Ser
65                  70                  75                  80

Arg His Pro Ile Ile Ile Lys Ala Gly Asp Trp Gln Glu Phe Arg Glu
                        85                  90                  95

Lys Leu Thr Phe Tyr Leu Val Thr Leu Glu Gln Ala Gln Glu Gln Gln
```

-continued

```
                100                 105                 110
Tyr Val Glu Gly Gly Gly Ser Pro Gly Glu Pro Ser Gly Pro Ile
            115                 120                 125

Ser Thr Ile Asn Pro Ser Pro Ser Lys Glu Ser His Lys Ser Pro
    130                 135                 140

Asn Met Asp Pro Asn Ala Ile Phe Leu Ser Phe Gln His Leu Arg
145                 150                 155                 160

Gly Lys Val Arg Phe Leu Met Leu Val Gly Ser Thr Leu Cys Val
                165                 170                 175

Arg Glu Phe Gly Gly Asn Met Ala Ser Pro Ala Pro Ala Cys Asp
            180                 185                 190

Leu Arg Val Leu Ser Lys Leu Leu Arg Asp Ser His Val Leu His Ser
        195                 200                 205

Arg Leu Ser Gln Cys Pro Glu Val His Pro Leu Pro Thr Pro Val Leu
    210                 215                 220

Leu Pro Ala Val Asp Phe Ser Leu Gly Glu Trp Lys Thr Gln Met Glu
225                 230                 235                 240

Glu Thr Lys Ala Gln Asp Ile Leu Gly Ala Val Thr Leu Leu Leu Glu
                245                 250                 255

Gly Val Met Ala Ala Arg Gly Gln Leu Gly Pro Thr Cys Leu Ser Ser
            260                 265                 270

Leu Leu Gly Gln Leu Ser Gly Gln Val Arg Leu Leu Leu Gly Ala Leu
        275                 280                 285

Gln Ser Leu Leu Gly Thr Gln Gly Arg Thr Thr Ala His Lys
    290                 295                 300
```

(2) INFORMATION FOR SEQ ID NO:240:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:240:

```
AATTCCGTCG TAAACTGACC TTCTATCTGA AAACCTTGGA GAACGCGCAG GCTCAACAGT    60

ACGTAGAGGG CGGTGGAGGC TCC                                           83
```

(2) INFORMATION FOR SEQ ID NO:241:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:241:

```
CCGGGGAGCC TCCACCGCCC TCTACGTACT GTTGAGCCTG CGCGTTCTCC AAGGTTTTCA    60

GATAGAAGGT CAGTTTACGA CGG                                           83
```

(2) INFORMATION FOR SEQ ID NO:242:

(i) SEQUENCE CHARACTERISTICS:
        (A) LENGTH: 8 amino acids (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:242:

Gly Gly Gly Ser Gly Gly Gly Ser
1               5

(2) INFORMATION FOR SEQ ID NO:243:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:243:

Gly Gly Gly Ser Gly Gly Gly Ser Gly Gly Gly Ser
1               5                   10

(2) INFORMATION FOR SEQ ID NO:244:

(i) SEQUENCE CHARACTERISTICS:
            (A) LENGTH: 7 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:244:

Ser Gly Gly Ser Gly Gly Ser
1               5

(2) INFORMATION FOR SEQ ID NO:245:

(i) SEQUENCE CHARACTERISTICS:
            (A) LENGTH: 6 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:245:

Glu Phe Gly Asn Met Ala
1               5

(2) INFORMATION FOR SEQ ID NO:246:

(i) SEQUENCE CHARACTERISTICS:
            (A) LENGTH: 7 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:246:

Glu Phe Gly Gly Asn Met Ala
1               5

(2) INFORMATION FOR SEQ ID NO:247:

(i) SEQUENCE CHARACTERISTICS:

(A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:247:

Glu Phe Gly Gly Asn Gly Gly Asn Met Ala
1               5                   10

(2) INFORMATION FOR SEQ ID NO:248:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:248:

Gly Gly Ser Asp Met Ala Gly
1               5

(2) INFORMATION FOR SEQ ID NO:249:

(i) SEQUENCE CHARACTERISTICS:
        (A) LENGTH: 459 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:249:

TCTCCCGCTC CGCCTGCTTG TGACCTCCGA GTCCTCAGTA AACTGCTTCG TGACTCCCAT     60

GTCCTTCACA GCAGACTGAG CCAGTGCCCA GAGGTTCACC CTTTGCCTAC ACCTGTCCTG    120

CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

CTGGGACCCA CTTGCCTCTC ATCCCTCCTG GGGCAGCTTT CTGGACAGGT CCGTCTCCTC    300

CTTGGGGCCC TGCAGAGCCT CCTTGGAACC CAGCTTCCTC CACAGGGCAG GACCACAGCT    360

CACAAGGATC CCAATGCCAT CTTCCTGAGC TTCAACACC TGCTCCGAGG AAAGGTGCGT     420

TTCCTGATGC TTGTAGGAGG GTCCACCCTC TGCGTCAGG                           459

(2) INFORMATION FOR SEQ ID NO:250:

(i) SEQUENCE CHARACTERISTICS:
        (A) LENGTH: 447 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:250:

TCTCCCGCTC CGCCTGCTTG TGACCTCCGA GTCCTCAGTA AACTGCTTCG TGACTCCCAT     60

GTCCTTCACA GCAGACTGAG CCAGTGCCCA GAGGTTCACC CTTTGCCTAC ACCTGTCCTG    120

CTGCCTGCTG TGGACTTTAG CTTGGGAGAA TGGAAAACCC AGATGGAGGA GACCAAGGCA    180

CAGGACATTC TGGGAGCAGT GACCCTTCTG CTGGAGGGAG TGATGGCAGC ACGGGGACAA    240

```
CTGGGACCCA CTTGCCTCTC ATCCCTCCTG GGGCAGCTTT CTGGACAGGT CCGTCTCCTC        300

CTTGGGGCCC TGCAGAGCCT CCTTGGAACC CAGGGCAGGA CCACAGCTCA CAAGGATCCC        360

AATGCCATCT TCCTGAGCTT CCAACACCTG CTCCGAGGAA AGGTGCGTTT CCTGATGCTT        420

GTAGGAGGGT CCACCCTCTG CGTCAGG                                           447
```

(2) INFORMATION FOR SEQ ID NO:251:

(i) SEQUENCE CHARACTERISTICS:
        (A) LENGTH: 459 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:251:

```
TCCCCAGCGC CGCCTGCTTG TGACCTCCGA GTCCTCAGTA AACTGCTTCG TGACTCCCAT         60

GTCCTTCACA GCAGACTGAG CCAGTGCCCA GAGGTTCACC CTTTGCCTAC ACCTGTCCTG        120

CTGCCTGCTG TGGACTTTAG CTTGGGAGAA TGGAAAACCC AGATGGAGGA GACCAAGGCA        180

CAGGACATTC TGGGAGCAGT GACCCTTCTG CTGGAGGGAG TGATGGCAGC ACGGGGACAA        240

CTGGGACCCA CTTGCCTCTC ATCCCTCCTG GGGCAGCTTT CTGGACAGGT CCGTCTCCTC        300

CTTGGGGCCC TGCAGAGCCT CCTTGGAACC CAGCTTCCTC CACAGGGCAG GACCACAGCT        360

CACAAGGATC CCAATGCCAT CTTCCTGAGC TTCCAACACC TGCTCCGAGG AAAGGTGCGT        420

TTCCTGATGC TTGTAGGAGG GTCCACCCTC TGCGTCAGG                              459
```

(2) INFORMATION FOR SEQ ID NO:252:

(i) SEQUENCE CHARACTERISTICS:
        (A) LENGTH: 153 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:252:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
        130                 135                 140
```

Val Gly Gly Ser Thr Leu Cys Val Arg
145                 150

(2) INFORMATION FOR SEQ ID NO:253:

(i) SEQUENCE CHARACTERISTICS:
        (A) LENGTH: 149 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:253:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Gly
                100                 105                 110

Arg Thr Thr Ala His Lys Asp Pro Asn Ala Ile Phe Leu Ser Phe Gln
            115                 120                 125

His Leu Leu Arg Gly Lys Val Arg Phe Leu Met Leu Val Gly Gly Ser
130                 135                 140

Thr Leu Cys Val Arg
145

(2) INFORMATION FOR SEQ ID NO:254:

(i) SEQUENCE CHARACTERISTICS:
        (A) LENGTH: 153 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:254:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

```
Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
        130                 135                 140

Val Gly Gly Ser Thr Leu Cys Val Arg
145                 150
```

(2) INFORMATION FOR SEQ ID NO:255:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:255:

```
GGATCCACCA TGAGCCGCCT GCCCGTCCTG CTCCTGCTCC AACTCCTGGT CCGCCCCGCC    60

ATGG                                                                 64
```

(2) INFORMATION FOR SEQ ID NO:256:

(i) SEQUENCE CHARACTERISTICS:
        (A) LENGTH: 153 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Modified-site
        (B) LOCATION: 112
        (D) OTHER INFORMATION: /note= "position 112 is deleted or
            Leu, Ala,VAl, Ile, Pro, Phe, Trp or Met"

(ix) FEATURE:
        (A) NAME/KEY: Modified-site
        (B) LOCATION: 113
        (D) OTHER INFORMATION: /note= "positoin 113 is deleted or
            Pro, Phe, Ala, Val, Leu, Ile, Trp or Met"

(ix) FEATURE:
        (A) NAME/KEY: Modified-site
        (B) LOCATION: 114
        (D) OTHER INFORMATION: /note= "position 114 is deleted or
            Pro, Phe, Ala, Val, Leu, Ile, Trp or Met"

(ix) FEATURE:
        (A) NAME/KEY: Modified-site
        (B) LOCATION: 115
        (D) OTHER INFORMATION: /note= "positon 115 is deleted or
            Gln, Gly, Ser, Thr, Tyr, or Asn"

(xi) SEQUENCE DESCRIPTION: SEQ ID NO:256:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80
```

```
Leu Gly Pro Thr Cys Leu Ser Ser Leu Leu Gln Leu Ser Gly Gln
                85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg
145                 150

(2) INFORMATION FOR SEQ ID NO:257:

(i) SEQUENCE CHARACTERISTICS:
        (A) LENGTH: 464 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:257:

CCATGGCTAA CTGCTCTATA ATGATCGATG AAATTATACA TCACTTAAAG AGACCACCTG      60

CACCTTTGCT GGACCCGAAC AACCTCAATG ACGAAGACGT CTCTATCCTG ATGGATCGAA     120

ACCTTCGACT TCCAAACCTG GAGAGCTTCG TAAGGGCTGT CAAGAACTTA GAAAATGCAT     180

CAGGTATTGA GGCAATTCTT CGTAATCTCC AACCATGTCT GCCCTCTGCC ACGGCCGCAC     240

CCTCTCGACA TCCAATCATC ATCAAGGCAG GTGACTGGCA AGAATTCCGG GAAAAACTGA     300

CGTTCTATCT GGTTACCCTT GAGCAAGCGC AGGAACAACA GTACGTAGAG GGCGGTGGAG     360

GCTCCCCGGG TGAACCGTCT GGTCCAATCT CTACTATCAA CCCGTCTCCT CCGTCTAAAG     420

AATCTCATAA ATCTCCAAAC ATGTAAGGTA CCGCATGCAA GCTT                      464

(2) INFORMATION FOR SEQ ID NO:258:

(i) SEQUENCE CHARACTERISTICS:
        (A) LENGTH: 100 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "SYNTHETIC"

(xi) SEQUENCE DESCRIPTION: SEQ ID NO:258:

AAAACAAGAA GAAAGGCGAT AAAAAGGTTG TGGTAAGAGA AATGGATAAA AAGGGGTCGG      60

GGAAGGAAGG TGGGAGTTAA AAAAGAGGAA GTAGGTCAAG                          100

(2) INFORMATION FOR SEQ ID NO:259:

(i) SEQUENCE CHARACTERISTICS:
        (A) LENGTH: 11808 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:259:

ACGTACTCCA TGGCTAACTG CTCTATAATG ATCGATGAAA TTATACATCA CTTAAAGAGA      60
```

```
CCACCTGCAC CTTTGCTGGA CCCGAACAAC CTCAATGACG AAGACGTCTC TATCCTGATG      120

GATCGAAACC TTCGACTTCC AAACCTGGAG AGCTTCGTAA GGGCTGTCAA GAACTTAGAA      180

AATGCATCAG GTATTGAGGC AATTCTTCGT AATCTCCAAC CATGTCTGCC CTCTGCCACG      240

GCCGCACCCT CTCGACATCC AATCATCATC AAGGCAGGTG ACTGGCAAGA ATTCCGGGAA      300

AAACTGACGT TCTATCTGGT TACCCTTGAG CAAGCGCAGG AACAACAGTA CGTAGAGGGC      360

GGTGGAGGCT CCCCGGGTGA ACCGTCTGGT CCAATCTCTA CTATCAACCC GTCTCCTCCG      420

TCTAAAGAAT CTCATAAATC TCCAAACATG GCTTTAGGCC CTGCCAGCTC CCTGCCCCAG      480

AGCTTCCTGC TCAAGTCTTT AGAGCAAGTG AGGAAGATCC AGGGCGATGG CGCAGCGCTC      540

CAGGAGAAGC TGTGTGCCAC CTACAAGCTG TGCCACCCCG AGGAGCTGGT GCTGCTCGGA      600

CACTCTCTGG GCATCCCCTG GCTCCCCTG AGCTCCTGCC CCAGCCAGGC CTGCAGCTG       660

GCAGGCTGCT TGAGCCAACT CCATAGCGGC CTTTTCCTCT ACCAGGGGCT CCTGCAGGCC      720

CTGGAAGGGA TATCCCCCGA GTTGGGTCCC ACCTTGGACA CACTGCAGCT GGACGTCGCC      780

GACTTTGCCA CCACCATCTG GCAGCAGATG GAAGAACTGG GAATGGCCCC TGCCCTGCAG      840

CCCACCCAGG GTGCCATGCC GGCCTTCGCC TCTGCTTTCC AGCGCCGGGC AGGAGGGGTC      900

CTGGTTGCTA GCCATCTGCA GAGCTTCCTG GAGGTGTCGT ACCGCGTTCT ACGCCACCTT      960

GCGCAGCCCG ACATGGCTAC ACCAACGTAC TCCATGGCTA ACTGCTCTAT AATGATCGAT     1020

GAAATTATAC ATCACTTAAA GAGACCACCT GCACCTTTGC TGGACCCGAA CAACCTCAAT     1080

GACGAAGACG TCTCTATCCT GATGGATCGA AACCTTCGAC TTCCAAACCT GGAGAGCTTC     1140

GTAAGGGCTG TCAAGAACTT AGAAAATGCA TCAGGTATTG AGGCAATTCT TCGTAATCTC     1200

CAACCATGTC TGCCCTCTGC CACGGCCGCA CCCTCTCGAC ATCCAATCAT CATCAAGGCA     1260

GGTGACTGGC AAGAATTCCG GGAAAAACTG ACGTTCTATC TGGTTACCCT TGAGCAAGCG     1320

CAGGAACAAC AGTACGTAGA GGGCGGTGGA GGCTCCCCGG GTGAACCGTC TGGTCCAATC     1380

TCTACTATCA ACCCGTCTCC TCCGTCTAAA GAATCTCATA AATCTCCAAA CATGGCTCAG     1440

AGCTTCCTGC TCAAGTCTTT AGAGCAAGTG AGGAAGATCC AGGGCGATGG CGCAGCGCTC     1500

CAGGAGAAGC TGTGTGCCAC CTACAAGCTG TGCCACCCCG AGGAGCTGGT GCTGCTCGGA     1560

CACTCTCTGG GCATCCCCTG GCTCCCCTG AGCTCCTGCC CCAGCCAGGC CTGCAGCTG      1620

GCAGGCTGCT TGAGCCAACT CCATAGCGGC CTTTTCCTCT ACCAGGGGCT CCTGCAGGCC     1680

CTGGAAGGGA TATCCCCCGA GTTGGGTCCC ACCTTGGACA CACTGCAGCT GGACGTCGCC     1740

GACTTTGCCA CCACCATCTG GCAGCAGATG GAAGAACTGG GAATGGCCCC TGCCCTGCAG     1800

CCCACCCAGG GTGCCATGCC GGCCTTCGCC TCTGCTTTCC AGCGCCGGGC AGGAGGGGTC     1860

CTGGTTGCTA GCCATCTGCA GAGCTTCCTG GAGGTGTCGT ACCGCGTTCT ACGCCACCTT     1920

GCGCAGCCCG ACATGGCTAC ACCATTAGGC CCTGCCAGCT CCCTGCCCAC GTACTCCATG     1980

GCTAACTGCT CTATAATGAT CGATGAAATT ATACATCACT TAAAGAGACC ACCTGCACCT     2040

TTGCTGGACC CGAACAACCT CAATGACGAA GACGTCTCTA TCCTGATGGA TCGAAACCTT     2100

CGACTTCCAA ACCTGGAGAG CTTCGTAAGG GCTGTCAAGA ACTTAGAAAA TGCATCAGGT     2160

ATTGAGGCAA TTCTTCGTAA TCTCCAACCA TGTCTGCCCT CTGCCACGGC CGCACCCTCT     2220

CGACATCCAA TCATCATCAA GGCAGGTGAC TGGCAAGAAT TCCGGGAAAA ACTGACGTTC     2280

TATCTGGTTA CCCTTGAGCA AGCGCAGGAA CAACAGTACG TAGAGGGCGG TGGAGGCTCC     2340

CCGGGTGAAC CGTCTGGTCC AATCTCTACT ATCAACCCGT CTCCTCCGTC TAAAGAATCT     2400
```

```
CATAAATCTC CAAACATGGC TTTCCTGCTC AAGTCTTTAG AGCAAGTGAG GAAGATCCAG    2460

GGCGATGGCG CAGCGCTCCA GGAGAAGCTG TGTGCCACCT ACAAGCTGTG CCACCCCGAG    2520

GAGCTGGTGC TGCTCGGACA CTCTCTGGGC ATCCCCTGGG CTCCCCTGAG CTCCTGCCCC    2580

AGCCAGGCCC TGCAGCTGGC AGGCTGCTTG AGCCAACTCC ATAGCGGCCT TTTCCTCTAC    2640

CAGGGGCTCC TGCAGGCCCT GGAAGGGATA TCCCCCGAGT TGGGTCCCAC CTTGGACACA    2700

CTGCAGCTGG ACGTCGCCGA CTTTGCCACC ACCATCTGGC AGCAGATGGA AGAACTGGGA    2760

ATGGCCCCTG CCCTGCAGCC CACCCAGGGT GCCATGCCGG CCTTCGCCTC TGCTTTCCAG    2820

CGCCGGGCAG GAGGGGTCCT GGTTGCTAGC CATCTGCAGA GCTTCCTGGA GGTGTCGTAC    2880

CGCGTTCTAC GCCACCTTGC GCAGCCCGAC ATGGCTACAC CATTAGGCCC TGCCAGCTCC    2940

CTGCCCCAGA GCACGTACTC CATGGCTAAC TGCTCTATAA TGATCGATGA AATTATACAT    3000

CACTTAAAGA GACCACCTGC ACCTTTGCTG GACCCGAACA ACCTCAATGA CGAAGACGTC    3060

TCTATCCTGA TGGATCGAAA CCTTCGACTT CCAAACCTGG AGAGCTTCGT AAGGGCTGTC    3120

AAGAACTTAG AAAATGCATC AGGTATTGAG GCAATTCTTC GTAATCTCCA ACCATGTCTG    3180

CCCTCTGCCA CGGCCGCACC CTCTCGACAT CCAATCATCA TCAAGGCAGG TGACTGGCAA    3240

GAATTCCGGG AAAAACTGAC GTTCTATCTG GTTACCCTTG AGCAAGCGCA GGAACAACAG    3300

TACGTAGAGG GCGGTGGAGG CTCCCCGGGT GAACCGTCTG GTCCAATCTC TACTATCAAC    3360

CCGTCTCCTC CGTCTAAAGA ATCTCATAAA TCTCCAAACA TGGCTGAGCA AGTGAGGAAG    3420

ATCCAGGGCG ATGGCGCAGC GCTCCAGGAG AAGCTGTGTG CCACCTACAA GCTGTGCCAC    3480

CCCGAGGAGC TGGTGCTGCT CGGACACTCT CTGGGCATCC CCTGGGCTCC CCTGAGCTCC    3540

TGCCCCAGCC AGGCCCTGCA GCTGGCAGGC TGCTTGAGCC AACTCCATAG CGGCCTTTTC    3600

CTCTACCAGG GGCTCCTGCA GGCCCTGGAA GGGATATCCC CCGAGTTGGG TCCCACCTTG    3660

GACACACTGC AGCTGGACGT CGCCGACTTT GCCACCACCA TCTGGCAGCA GATGGAAGAA    3720

CTGGGAATGG CCCCTGCCCT GCAGCCCACC CAGGGTGCCA TGCCGGCCTT CGCCTCTGCT    3780

TTCCAGCGCC GGGCAGGAGG GGTCCTGGTT GCTAGCCATC TGCAGAGCTT CCTGGAGGTG    3840

TCGTACCGCG TTCTACGCCA CCTTGCGCAG CCCGACATGG CTACACCATT AGGCCCTGCC    3900

AGCTCCCTGC CCCAGAGCTT CCTGCTCAAG TCTTTAACGT ACTCCATGGC TAACTGCTCT    3960

ATAATGATCG ATGAAATTAT ACATCACTTA AAGAGACCAC CTGCACCTTT GCTGGACCCG    4020

AACAACCTCA ATGACGAAGA CGTCTCTATC CTGATGGATC GAAACCTTCG ACTTCCAAAC    4080

CTGGAGAGCT TCGTAAGGGC TGTCAAGAAC TTAGAAAATG CATCAGGTAT TGAGGCAATT    4140

CTTCGTAATC TCCAACCATG TCTGCCCTCT GCCACGGCCG CACCCTCTCG ACATCCAATC    4200

ATCATCAAGG CAGGTGACTG GCAAGAATTC CGGGAAAAAC TGACGTTCTA TCTGGTTACC    4260

CTTGAGCAAG CGCAGGAACA ACAGTACGTA GAGGGCGGTG GAGGCTCCCC GGGTGAACCG    4320

TCTGGTCCAA TCTCTACTAT CAACCCGTCT CCTCCGTCTA AAGAATCTCA TAAATCTCCA    4380

AACATGGCTC TGCTCGGACA CTCTCTGGGC ATCCCCTGGG CTCCCCTGAG CTCCTGCCCC    4440

AGCCAGGCCC TGCAGCTGGC AGGCTGCTTG AGCCAACTCC ATAGCGGCCT TTTCCTCTAC    4500

CAGGGGCTCC TGCAGGCCCT GGAAGGGATA TCCCCCGAGT TGGGTCCCAC CTTGGACACA    4560

CTGCAGCTGG ACGTCGCCGA CTTTGCCACC ACCATCTGGC AGCAGATGGA AGAACTGGGA    4620

ATGGCCCCTG CCCTGCAGCC CACCCAGGGT GCCATGCCGG CCTTCGCCTC TGCTTTCCAG    4680

CGCCGGGCAG GAGGGGTCCT GGTTGCTAGC CATCTGCAGA GCTTCCTGGA GGTGTCGTAC    4740

CGCGTTCTAC GCCACCTTGC GCAGCCCGAC ATGGCTACAC CATTAGGCCC TGCCAGCTCC    4800
```

```
CTGCCCCAGA GCTTCCTGCT CAAGTCTTTA GAGCAAGTGA GGAAGATCCA GGGCGATGGC    4860

GCAGCGCTCC AGGAGAAGCT GTGTGCCACC TACAAGCTGT GCCACCCCGA GGAGCTGGTG    4920

ACGTACTCCA TGGCTAACTG CTCTATAATG ATCGATGAAA TTATACATCA CTTAAAGAGA    4980

CCACCTGCAC CTTTGCTGGA CCCGAACAAC CTCAATGACG AAGACGTCTC TATCCTGATG    5040

GATCGAAACC TTCGACTTCC AAACCTGGAG AGCTTCGTAA GGGCTGTCAA GAACTTAGAA    5100

AATGCATCAG GTATTGAGGC AATTCTTCGT AATCTCCAAC CATGTCTGCC CTCTGCCACG    5160

GCCGCACCCT CTCGACATCC AATCATCATC AAGGCAGGTG ACTGGCAAGA ATTCCGGGAA    5220

AAACTGACGT TCTATCTGGT TACCCTTGAG CAAGCGCAGG AACAACAGTA CGTAGAGGGC    5280

GGTGGAGGCT CCCCGGGTGA ACCGTCTGGT CCAATCTCTA CTATCAACCC GTCTCCTCCG    5340

TCTAAAGAAT CTCATAAATC TCCAAACATG GCTCCCCTGA GCTCCTGCCC CAGCCAGGCC    5400

CTGCAGCTGG CAGGCTGCTT GAGCCAACTC CATAGCGGCC TTTTCCTCTA CCAGGGGCTC    5460

CTGCAGGCCC TGGAAGGGAT ATCCCCCGAG TTGGGTCCCA CCTTGGACAC ACTGCAGCTG    5520

GACGTCGCCG ACTTTGCCAC CACCATCTGG CAGCAGATGG AAGAACTGGG AATGCCCCT    5580

GCCCTGCAGC CCACCCAGGG TGCCATGCCG GCCTTCGCCT CTGCTTTCCA GCGCCGGGCA    5640

GGAGGGGTCC TGGTTGCTAG CCATCTGCAG AGCTTCCTGG AGGTGTCGTA CCGCGTTCTA    5700

CGCCACCTTG CGCAGCCCGA CATGGCTACA CCATTAGGCC CTGCCAGCTC CCTGCCCCAG    5760

AGCTTCCTGC TCAAGTCTTT AGAGCAAGTG AGGAAGATCC AGGGCGATGG CGCAGCGCTC    5820

CAGGAGAAGC TGTGTGCCAC CTACAAGCTG TGCCACCCCG AGGAGCTGGT GCTGCTCGGA    5880

CACTCTCTGG GCATCCCCTG GCTACGTAC TCCATGGCTA ACTGCTCTAT AATGATCGAT    5940

GAAATTATAC ATCACTTAAA GAGACCACCT GCACCTTTGC TGGACCCGAA CAACCTCAAT    6000

GACGAAGACG TCTCTATCCT GATGGATCGA AACCTTCGAC TTCCAAACCT GGAGAGCTTC    6060

GTAAGGGCTG TCAAGAACTT AGAAAATGCA TCAGGTATTG AGGCAATTCT TCGTAATCTC    6120

CAACCATGTC TGCCCTCTGC CACGGCCGCA CCCTCTCGAC ATCCAATCAT CATCAAGGCA    6180

GGTGACTGGC AAGAATTCCG GGAAAAACTG ACGTTCTATC TGGTTACCCT TGAGCAAGCG    6240

CAGGAACAAC AGTACGTAGA GGGCGGTGGA GGCTCCCCGG GTGAACCGTC TGGTCCAATC    6300

TCTACTATCA ACCCGTCTCC TCCGTCTAAA GAATCTCATA AATCTCCAAA CATGGCTCAG    6360

GCCCTGCAGC TGGCAGGCTG CTTGAGCCAA CTCCATAGCG GCCTTTTCCT CTACCAGGGG    6420

CTCCTGCAGG CCCTGGAAGG GATATCCCCC GAGTTGGGTC CCACCTTGGA CACACTGCAG    6480

CTGGACGTCG CCGACTTTGC CACCACCATC TGGCAGCAGA TGGAAGAACT GGGAATGGCC    6540

CCTGCCCTGC AGCCCACCCA GGGTGCCATG CCGGCCTTCG CCTCTGCTTT CCAGCGCCGG    6600

GCAGGAGGGG TCCTGGTTGC TAGCCATCTG CAGAGCTTCC TGGAGGTGTC GTACCGCGTT    6660

CTACGCCACC TTGCGCAGCC CGACATGGCT ACACCATTAG GCCCTGCCAG CTCCCTGCCC    6720

CAGAGCTTCC TGCTCAAGTC TTTAGAGCAA GTGAGGAAGA TCCAGGGCGA TGGCGCAGCG    6780

CTCCAGGAGA AGCTGTGTGC CACCTACAAG CTGTGCCACC CCGAGGAGCT GGTGCTGCTC    6840

GGACACTCTC TGGGCATCCC CTGGGCTCCC CTGAGCTCCT GCCCCAGCAC GTACTCCATG    6900

GCTAACTGCT CTATAATGAT CGATGAAATT ATACATCACT TAAAGAGACC ACCTGCACCT    6960

TTGCTGGACC CGAACAACCT CAATGACGAA GACGTCTCTA TCCTGATGGA TCGAAACCTT    7020

CGACTTCCAA ACCTGGAGAG CTTCGTAAGG GCTGTCAAGA ACTTAGAAAA TGCATCAGGT    7080

ATTGAGGCAA TTCTTCGTAA TCTCCAACCA TGTCTGCCCT CTGCCACGGC CGCACCCTCT    7140
```

-continued

```
CGACATCCAA TCATCATCAA GGCAGGTGAC TGGCAAGAAT TCCGGGAAAA ACTGACGTTC    7200

TATCTGGTTA CCCTTGAGCA AGCGCAGGAA CAACAGTACG TAGAGGGCGG TGGAGGCTCC    7260

CCGGGTGAAC CGTCTGGTCC AATCTCTACT ATCAACCCGT CTCCTCCGTC TAAAGAATCT    7320

CATAAATCTC CAAACATGGC TCTGCAGCTG GCAGGCTGCT TGAGCCAACT CCATAGCGGC    7380

CTTTTCCTCT ACCAGGGGCT CCTGCAGGCC CTGGAAGGGA TATCCCCCGA GTTGGGTCCC    7440

ACCTTGGACA CACTGCAGCT GGACGTCGCC GACTTTGCCA CCACCATCTG GCAGCAGATG    7500

GAAGAACTGG GAATGGCCCC TGCCCTGCAG CCCACCCAGG GTGCCATGCC GGCCTTCGCC    7560

TCTGCTTTCC AGCGCCGGGC AGGAGGGGTC CTGGTTGCTA GCCATCTGCA GAGCTTCCTG    7620

GAGGTGTCGT ACCGCGTTCT ACGCCACCTT GCGCAGCCCG ACATGGCTAC ACCATTAGGC    7680

CCTGCCAGCT CCCTGCCCCA GAGCTTCCTG CTCAAGTCTT TAGAGCAAGT GAGGAAGATC    7740

CAGGGCGATG GCGCAGCGCT CCAGGAGAAG CTGTGTGCCA CCTACAAGCT GTGCCACCCC    7800

GAGGAGCTGG TGCTGCTCGG ACACTCTCTG GGCATCCCCT GGGCTCCCCT GAGCTCCTGC    7860

CCCAGCCAGG CCACGTACTC CATGGCTAAC TGCTCTATAA TGATCGATGA AATTATACAT    7920

CACTTAAAGA GACCACCTGC ACCTTTGCTG GACCCGAACA ACCTCAATGA CGAAGACGTC    7980

TCTATCCTGA TGGATCGAAA CCTTCGACTT CCAAACCTGG AGAGCTTCGT AAGGGCTGTC    8040

AAGAACTTAG AAAATGCATC AGGTATTGAG GCAATTCTTC GTAATCTCCA ACCATGTCTG    8100

CCCTCTGCCA CGGCCGCACC CTCTCGACAT CCAATCATCA TCAAGGCAGG TGACTGGCAA    8160

GAATTCCGGG AAAAACTGAC GTTCTATCTG GTTACCCTTG AGCAAGCGCA GGAACAACAG    8220

TACGTAGAGG GCGGTGGAGG CTCCCCGGGT GAACCGTCTG GTCCAATCTC TACTATCAAC    8280

CCGTCTCCTC CGTCTAAAGA ATCTCATAAA TCTCCAAACA TGGCTCTGGC AGGCTGCTTG    8340

AGCCAACTCC ATAGCGGCCT TTTCCTCTAC CAGGGGCTCC TGCAGGCCCT GGAAGGGATA    8400

TCCCCCGAGT TGGGTCCCAC CTTGGACACA CTGCAGCTGG ACGTCGCCGA CTTTGCCACC    8460

ACCATCTGGC AGCAGATGGA AGAACTGGGA ATGGCCCCTG CCCTGCAGCC CACCCAGGGT    8520

GCCATGCCGG CCTTCGCCTC TGCTTTCCAG CGCCGGGCAG GAGGGGTCCT GGTTGCTAGC    8580

CATCTGCAGA GCTTCCTGGA GGTGTCGTAC CGCGTTCTAC GCCACCTTGC GCAGCCCGAC    8640

ATGGCTACAC CATTAGGCCC TGCCAGCTCC CTGCCCCAGA GCTTCCTGCT CAAGTCTTTA    8700

GAGCAAGTGA GGAAGATCCA GGGCGATGGC GCAGCGCTCC AGGAGAAGCT GTGTGCCACC    8760

TACAAGCTGT GCCACCCCGA GGAGCTGGTG CTGCTCGGAC ACTCTCTGGG CATCCCCTGG    8820

GCTCCCCTGA GCTCCTGCCC CAGCCAGGCC CTGCAGACGT ACTCCATGGC TAACTGCTCT    8880

ATAATGATCG ATGAAATTAT ACATCACTTA AAGAGACCAC CTGCACCTTT GCTGGACCCG    8940

AACAACCTCA ATGACGAAGA CGTCTCTATC CTGATGGATC GAAACCTTCG ACTTCCAAAC    9000

CTGGAGAGCT TCGTAAGGGC TGTCAAGAAC TTAGAAAATG CATCAGGTAT TGAGGCAATT    9060

CTTCGTAATC TCCAACCATG TCTGCCCTCT GCCACGGCCG CACCCTCTCG ACATCCAATC    9120

ATCATCAAGG CAGGTGACTG GCAAGAATTC CGGGAAAAAC TGACGTTCTA TCTGGTTACC    9180

CTTGAGCAAG CGCAGGAACA ACAGTACGTA GAGGGCGGTG GAGGCTCCCC GGGTGAACCG    9240

TCTGGTCCAA TCTCTACTAT CAACCCGTCT CCTCCGTCTA AAGAATCTCA TAAATCTCCA    9300

AACATGGCTG AACTGGGAAT GGCCCCTGCC CTGCAGCCCA CCCAGGGTGC CATGCCGGCC    9360

TTCGCCTCTG CTTTCCAGCG CCGGGCAGGA GGGGTCCTGG TTGCTAGCCA TCTGCAGAGC    9420

TTCCTGGAGG TGTCGTACCG CGTTCTACGC CACCTTGCGC AGCCCGACAT GGCTACACCA    9480

TTAGGCCCTG CCAGCTCCCT GCCCCAGAGC TTCCTGCTCA AGTCTTTAGA GCAAGTGAGG    9540
```

```
AAGATCCAGG GCGATGGCGC AGCGCTCCAG GAGAAGCTGT GTGCCACCTA CAAGCTGTGC    9600

CACCCCGAGG AGCTGGTGCT GCTCGGACAC TCTCTGGGCA TCCCCTGGGC TCCCCTGAGC    9660

TCCTGCCCCA GCCAGGCCCT GCAGCTGGCA GGCTGCTTGA GCCAACTCCA TAGCGGCCTT    9720

TTCCTCTACC AGGGGCTCCT GCAGGCCCTG GAAGGGATAT CCCCCGAGTT GGGTCCCACC    9780

TTGGACACAC TGCAGCTGGA CGTCGCCGAC TTTGCCACCA CCATCTGGCA GCAGATGGAA    9840

ACGTACTCCA TGGCTAACTG CTCTATAATG ATCGATGAAA TTATACATCA CTTAAAGAGA    9900

CCACCTGCAC CTTTGCTGGA CCCGAACAAC CTCAATGACG AAGACGTCTC TATCCTGATG    9960

GATCGAAACC TTCGACTTCC AAACCTGGAG AGCTTCGTAA GGGCTGTCAA GAACTTAGAA   10020

AATGCATCAG GTATTGAGGC AATTCTTCGT AATCTCCAAC CATGTCTGCC CTCTGCCACG   10080

GCCGCACCCT CTCGACATCC AATCATCATC AAGGCAGGTG ACTGGCAAGA ATTCCGGGAA   10140

AAACTGACGT TCTATCTGGT TACCCTTGAG CAAGCGCAGG AACAACAGTA CGTAGAGGGC   10200

GGTGGAGGCT CCCCGGGTGA ACCGTCTGGT CCAATCTCTA CTATCAACCC GTCTCCTCCG   10260

TCTAAAGAAT CTCATAAATC TCCAAACATG GCTGGAATGG CCCCTGCCCT GCAGCCCACC   10320

CAGGGTGCCA TGCCGGCCTT CGCCTCTGCT TTCCAGCGCC GGGCAGGAGG GGTCCTGGTT   10380

GCTAGCCATC TGCAGAGCTT CCTGGAGGTG TCGTACCGCG TTCTACGCCA CCTTGCGCAG   10440

CCCGACATGG CTACACCATT AGGCCCTGCC AGCTCCCTGC CCCAGAGCTT CCTGCTCAAG   10500

TCTTTAGAGC AAGTGAGGAA GATCCAGGGC GATGGCGCAG CGCTCAGGA GAAGCTGTGT    10560

GCCACCTACA AGCTGTGCCA CCCCGAGGAG CTGGTGCTGC TCGGACACTC TCTGGGCATC   10620

CCCTGGGCTC CCCTGAGCTC CTGCCCCAGC CAGGCCCTGC AGCTGGCAGG CTGCTTGAGC   10680

CAACTCCATA GCGGCCTTTT CCTCTACCAG GGGCTCCTGC AGGCCCTGGA AGGGATATCC   10740

CCCGAGTTGG GTCCCACCTT GGACACACTG CAGCTGGACG TCGCCGACTT TGCCACCACC   10800

ATCTGGCAGC AGATGGAAGA ACTGACGTAC TCCATGGCTA ACTGCTCTAT AATGATCGAT   10860

GAAATTATAC ATCACTTAAA GAGACCACCT GCACCTTTGC TGGACCCGAA CAACCTCAAT   10920

GACGAAGACG TCTCTATCCT GATGGATCGA AACCTTCGAC TTCCAAACCT GGAGAGCTTC   10980

GTAAGGGCTG TCAAGAACTT AGAAAATGCA TCAGGTATTG AGGCAATTCT TCGTAATCTC   11040

CAACCATGTC TGCCCTCTGC CACGGCCGCA CCCTCTCGAC ATCCAATCAT CATCAAGGCA   11100

GGTGACTGGC AAGAATTCCG GGAAAAACTG ACGTTCTATC TGGTTACCCT TGAGCAAGCG   11160

CAGGAACAAC AGTACGTAGA GGGCGGTGGA GGCTCCCCGG GTGAACCGTC TGGTCCAATC   11220

TCTACTATCA ACCCGTCTCC TCCGTCTAAA GAATCTCATA AATCTCCAAA CATGGCTAGC   11280

TTCCTGGAGG TGTCGTACCG CGTTCTACGC CACCTTGCGC AGCCCGACAT GGCTACACCA   11340

TTAGGCCCTG CCAGCTCCCT GCCCCAGAGC TTCCTGCTCA AGTCTTTAGA GCAAGTGAGG   11400

AAGATCCAGG GCGATGGCGC AGCGCTCCAG GAGAAGCTGT GTGCCACCTA CAAGCTGTGC   11460

CACCCCGAGG AGCTGGTGCT GCTCGGACAC TCTCTGGGCA TCCCCTGGGC TCCCCTGAGC   11520

TCCTGCCCCA GCCAGGCCCT GCAGCTGGCA GGCTGCTTGA GCCAACTCCA TAGCGGCCTT   11580

TTCCTCTACC AGGGGCTCCT GCAGGCCCTG GAAGGGATAT CCCCCGAGTT GGGTCCCACC   11640

TTGGACACAC TGCAGCTGGA CGTCGCCGAC TTTGCCACCA CCATCTGGCA GCAGATGGAA   11700

GAACTGGGAA TGGCCCCTGC CCTGCAGCCC ACCCAGGGTG CCATGCCGGC CTTCGCCTCT   11760

GCTTTCCAGC GCCGGGCAGG AGGGGTCCTG GTTGCTAGCC ATCTGCAG               11808
```

(2) INFORMATION FOR SEQ ID NO:260:

```
    (i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:260:

ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCT CTATCCTGAT GGATCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAGT ACGTAGAGGG CGGTGGAGGC       360

TCCCCGGGTG AACCGTCTGG TCCAATCTCT ACTATCAACC CGTCTCCTCC GTCTAAAGAA       420

TCTCATAAAT CTCCAAACAT GGCTCAGAGC TTCCTGCTCA AGTCTTTAGA GCAAGTGAGG       480

AAGATCCAGG GCGATGGCGC AGCGCTCCAG GAGAAGCTGT GTGCCACCTA CAAGCTGTGC       540

CACCCCGAGG AGCTGGTGCT GCTCGGACAC TCTCTGGGCA TCCCCTGGGC TCCCCTGAGC       600

TCCTGCCCCA GCCAGGCCCT GCAGCTGGCA GGCTGCTTGA GCCAACTCCA TAGCGGCCTT       660

TTCCTCTACC AGGGGCTCCT GCAGGCCCTG GAAGGGATAT CCCCCGAGTT GGGTCCCACC       720

TTGGACACAC TGCAGCTGGA CGTCGCCGAC TTTGCCACCA CCATCTGGCA GCAGATGGAA       780

GAACTGGGAA TGGCCCCTGC CCTGCAGCCC ACCCAGGGTG CCATGCCGGC CTTCGCCTCT       840

GCTTTCCAGC GCCGGGCAGG AGGGGTCCTG GTTGCTAGCC ATCTGCAGAG CTTCCTGGAG       900

GTGTCGTACC GCGTTCTACG CCACCTTGCG CAGCCCGACA TGGCTACACC ATTAGGCCCT       960

GCCAGCTCCC TGCCC                                                       975

(2) INFORMATION FOR SEQ ID NO:261:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:261:

ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCT CTATCCTGAT GGATCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAGT ACGTAGAGGG CGGTGGAGGC       360

TCCCCGGGTG AACCGTCTGG TCCAATCTCT ACTATCAACC CGTCTCCTCC GTCTAAAGAA       420

TCTCATAAAT CTCCAAACAT GGCTCAGAGC TTCCTGCTCA AGTCTTTAGA GCAAGTGAGG       480

AAGATCCAGG GCGATGGCGC AGCGCTCCAG GAGAAGCTGT GTGCCACCTA CAAGCTGTGC       540

CACCCCGAGG AGCTGGTGCT GCTCGGACAC TCTCTGGGCA TCCCCTGGGC TCCCCTGAGC       600
```

```
TCCTGCCCCA GCCAGGCCCT GCAGCTGGCA GGCTGCTTGA GCCAACTCCA TAGCGGCCTT    660

TTCCTCTACC AGGGGCTCCT GCAGGCCCTG GAAGGGATAT CCCCCGAGTT GGGTCCCACC    720

TTGGACACAC TGCAGCTGGA CGTCGCCGAC TTTGCCACCA CCATCTGGCA GCAGATGGAA    780

GAACTGGGAA TGGCCCCTGC CCTGCAGCCC ACCCAGGGTG CCATGCCGGC CTTCGCCTCT    840

GCTTTCCAGC GCCGGGCAGG AGGGGTCCTG GTTGCTAGCC ATCTGCAGAG CTTCCTGGAG    900

GTGTCGTACC GCGTTCTACG CCACCTTGCG CAGCCCGACA TGGCTACACC ATTAGGCCCT    960

GCCAGCTCCC TGCCC                                                     975

(2) INFORMATION FOR SEQ ID NO:262:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:262:

ATGGCTAACT GCTCTATAAT GATCGATGAA ATTATACATC ACTTAAAGAG ACCACCTGCA     60

CCTTTGCTGG ACCCGAACAA CCTCAATGAC GAAGACGTCT CTATCCTGAT GGATCGAAAC    120

CTTCGACTTC CAAACCTGGA GAGCTTCGTA AGGGCTGTCA AGAACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAGAGGG CGGTGGAGGC    360

TCCCCGGGTG AACCGTCTGG TCCAATCTCT ACTATCAACC CGTCTCCTCC GTCTAAAGAA    420

TCTCATAAAT CTCCAAACAT GGCTGAGCAA GTGAGGAAGA TCCAGGGCGA TGGCGCAGCG    480

CTCCAGGAGA AGCTGTGTGC CACCTACAAG CTGTGCCACC CCGAGGAGCT GGTGCTGCTC    540

GGACACTCTC TGGGCATCCC CTGGGCTCCC CTGAGCTCCT GCCCCAGCCA GGCCCTGCAG    600

CTGGCAGGCT GCTTGAGCCA ACTCCATAGC GGCCTTTTCC TCTACCAGGG GCTCCTGCAG    660

GCCCTGGAAG GGATATCCCC CGAGTTGGGT CCCACCTTGG ACACACTGCA GCTGGACGTC    720

GCCGACTTTG CCACCACCAT CTGGCAGCAG ATGGAAGAAC TGGGAATGGC CCCTGCCCTG    780

CAGCCCACCC AGGGTGCCAT GCCGGCCTTC GCCTCTGCTT TCCAGCGCCG GGCAGGAGGG    840

GTCCTGGTTG CTAGCCATCT GCAGAGCTTC CTGGAGGTGT CGTACCGCGT TCTACGCCAC    900

CTTGCGCAGC CCGACATGGC TACACCATTA GGCCCTGCCA GCTCCCTGCC CCAGAGCTTC    960

CTGCTCAAGT CTTTA                                                     975

(2) INFORMATION FOR SEQ ID NO:263:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:263:

ATGGCTAACT GCTCTATAAT GATCGATGAA ATTATACATC ACTTAAAGAG ACCACCTGCA     60
```

```
CCTTTGCTGG ACCCGAACAA CCTCAATGAC GAAGACGTCT CTATCCTGAT GGATCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTCTGCTC GGACACTCTC TGGGCATCCC CTGGGCTCCC      480

CTGAGCTCCT GCCCCAGCCA GGCCCTGCAG CTGGCAGGCT GCTTGAGCCA ACTCCATAGC      540

GGCCTTTTCC TCTACCAGGG GCTCCTGCAG GCCCTGGAAG GGATATCCCC CGAGTTGGGT      600

CCCACCTTGG ACACACTGCA GCTGGACGTC GCCGACTTTG CCACCACCAT CTGGCAGCAG      660

ATGGAAGAAC TGGGAATGGC CCCTGCCCTG CAGCCCACCC AGGGTGCCAT GCCGGCCTTC      720

GCCTCTGCTT TCCAGCGCCG GCAGGAGGG GTCCTGGTTG CTAGCCATCT GCAGAGCTTC      780

CTGGAGGTGT CGTACCGCGT TCTACGCCAC CTTGCGCAGC CCGACATGGC TACACCATTA      840

GGCCCTGCCA GCTCCCTGCC CCAGAGCTTC CTGCTCAAGT CTTTAGAGCA AGTGAGGAAG      900

ATCCAGGGCG ATGGCGCAGC GCTCCAGGAG AAGCTGTGTG CCACCTACAA GCTGTGCCAC      960

CCCGAGGAGC TGGTG                                                     975

(2) INFORMATION FOR SEQ ID NO:264:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
         (A) DESCRIPTION: /desc = "synthetic"

(xi) SEQUENCE DESCRIPTION: SEQ ID NO:264:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGATCGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTCCCCTG AGCTCCTGCC CCAGCCAGGC CCTGCAGCTG      480

GCAGGCTGCT TGAGCCAACT CCATAGCGGC CTTTTCCTCT ACCAGGGGCT CCTGCAGGCC      540

CTGGAAGGGA TATCCCCCGA GTTGGGTCCC ACCTTGGACA CACTGCAGCT GGACGTCGCC      600

GACTTTGCCA CCACCATCTG GCAGCAGATG GAAGAACTGG GAATGGCCCC TGCCCTGCAG      660

CCCACCCAGG GTGCCATGCC GGCCTTCGCC TCTGCTTTCC AGCGCCGGGC AGGAGGGGTC      720

CTGGTTGCTA GCCATCTGCA GAGCTTCCTG GAGGTGTCGT ACCGCGTTCT ACGCCACCTT      780

GCGCAGCCCG ACATGGCTAC ACCATTAGGC CCTGCCAGCT CCCTGCCCCA GAGCTTCCTG      840

CTCAAGTCTT TAGAGCAAGT GAGGAAGATC AGGGCGATG GCGCAGCGCT CCAGGAGAAG      900

CTGTGTGCCA CCTACAAGCT GTGCCACCCC GAGGAGCTGG TGCTGCTCGG ACACTCTCTG      960

GGCATCCCCT GGGCT                                                     975
```

(2) INFORMATION FOR SEQ ID NO:265:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:265:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGATCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GGCTCAGGCC CTGCAGCTGG CAGGCTGCTT GAGCCAACTC     480

CATAGCGGCC TTTTCCTCTA CCAGGGGCTC CTGCAGGCCC TGGAAGGGAT ATCCCCCGAG     540

TTGGGTCCCA CCTTGGACAC ACTGCAGCTG GACGTCGCCG ACTTTGCCAC CACCATCTGG     600

CAGCAGATGG AAGAACTGGG AATGGCCCCT GCCCTGCAGC CCACCCAGGG TGCCATGCCG     660

GCCTTCGCCT CTGCTTTCCA GCGCCGGGCA GGAGGGGTCC TGGTTGCTAG CCATCTGCAG     720

AGCTTCCTGG AGGTGTCGTA CCGCGTTCTA CGCCACCTTG CGCAGCCCGA CATGGCTACA     780

CCATTAGGCC CTGCCAGCTC CCTGCCCCAG AGCTTCCTGC TCAAGTCTTT AGAGCAAGTG     840

AGGAAGATCC AGGGCGATGG CGCAGCGCTC CAGGAGAAGC TGTGTGCCAC CTACAAGCTG     900

TGCCACCCCG AGGAGCTGGT GCTGCTCGGA CACTCTCTGG GCATCCCCTG GGCTCCCCTG     960

AGCTCCTGCC CCAGC                                                     975
```

(2) INFORMATION FOR SEQ ID NO:266:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:266:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGATCGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG AACCGTCTGG TCCAATCTCT ACTATCAACC CGTCTCCTCC GTCTAAAGAA     420

TCTCATAAAT CTCCAAACAT GGCTCTGCAG CTGGCAGGCT GCTTGAGCCA ACTCCATAGC     480
```

```
GGCCTTTTCC TCTACCAGGG GCTCCTGCAG GCCCTGGAAG GGATATCCCC CGAGTTGGGT        540

CCCACCTTGG ACACACTGCA GCTGGACGTC GCCGACTTTG CCACCACCAT CTGGCAGCAG        600

ATGGAAGAAC TGGGAATGGC CCCTGCCCTG CAGCCCACCC AGGGTGCCAT GCCGGCCTTC        660

GCCTCTGCTT TCCAGCGCCG GGCAGGAGGG GTCCTGGTTG CTAGCCATCT GCAGAGCTTC        720

CTGGAGGTGT CGTACCGCGT TCTACGCCAC CTTGCGCAGC CCGACATGGC TACACCATTA        780

GGCCCTGCCA GCTCCCTGCC CCAGAGCTTC CTGCTCAAGT CTTTAGAGCA AGTGAGGAAG        840

ATCCAGGGCG ATGGCGCAGC GCTCCAGGAG AAGCTGTGTG CCACCTACAA GCTGTGCCAC        900

CCCGAGGAGC TGGTGCTGCT CGGACACTCT CTGGGCATCC CCTGGGCTCC CCTGAGCTCC        960

TGCCCCAGCC AGGCC                                                        975

(2) INFORMATION FOR SEQ ID NO:267:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:267:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACGTCT CTATCCTGAT GGATCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAGAGGG CGGTGGAGGC        360

TCCCCGGGTG AACCGTCTGG TCCAATCTCT ACTATCAACC CGTCTCCTCC GTCTAAAGAA        420

TCTCATAAAT CTCCAAACAT GGCTCTGGCA GGCTGCTTGA GCCAACTCCA TAGCGGCCTT        480

TTCCTCTACC AGGGGCTCCT GCAGGCCCTG GAAGGGATAT CCCCCGAGTT GGGTCCCACC        540

TTGGACACAC TGCAGCTGGA CGTCGCCGAC TTTGCCACCA CCATCTGGCA GCAGATGGAA        600

GAACTGGGAA TGGCCCCTGC CCTGCAGCCC ACCCAGGGTG CCATGCCGGC CTTCGCCTCT        660

GCTTTCCAGC GCCGGGCAGG AGGGGTCCTG GTTGCTAGCC ATCTGCAGAG CTTCCTGGAG        720

GTGTCGTACC GCGTTCTACG CCACCTTGCG CAGCCCGACA TGGCTACACC ATTAGGCCCT        780

GCCAGCTCCC TGCCCCAGAG CTTCCTGCTC AAGTCTTTAG AGCAAGTGAG GAAGATCCAG        840

GGCGATGGCG CAGCGCTCCA GGAGAAGCTG TGTGCCACCT ACAAGCTGTG CCACCCCGAG        900

GAGCTGGTGC TGCTCGGACA CTCTCTGGGC ATCCCCTGGG CTCCCCTGAG CTCCTGCCCC        960

AGCCAGGCCC TGCAG                                                        975

(2) INFORMATION FOR SEQ ID NO:268:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO:268:
```

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGATCGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTGAACTG GGAATGGCCC CTGCCCTGCA GCCCACCCAG | 480 |
| GGTGCCATGC CGGCCTTCGC CTCTGCTTTC AGCGCCGGG CAGGAGGGGT CCTGGTTGCT | 540 |
| AGCCATCTGC AGAGCTTCCT GGAGGTGTCG TACCGCGTTC TACGCCACCT TGCGCAGCCC | 600 |
| GACATGGCTA CACCATTAGG CCCTGCCAGC TCCCTGCCCC AGAGCTTCCT GCTCAAGTCT | 660 |
| TTAGAGCAAG TGAGGAAGAT CCAGGGCGAT GGCGCAGCGC TCCAGGAGAA GCTGTGTGCC | 720 |
| ACCTACAAGC TGTGCCACCC CGAGGAGCTG GTGCTGCTCG ACACTCTCT GGGCATCCCC | 780 |
| TGGGCTCCCC TGAGCTCCTG CCCCAGCCAG GCCCTGCAGC TGGCAGGCTG CTTGAGCCAA | 840 |
| CTCCATAGCG GCCTTTTCCT CTACCAGGGG CTCCTGCAGG CCCTGGAAGG GATATCCCCC | 900 |
| GAGTTGGGTC CCACCTTGGA CACACTGCAG CTGGACGTCG CCGACTTTGC CACCACCATC | 960 |
| TGGCAGCAGA TGGAA | 975 |

(2) INFORMATION FOR SEQ ID NO:269:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:269:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGATCGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTGGAATG CCCCTGCCC TGCAGCCCAC CCAGGGTGCC | 480 |
| ATGCCGGCCT TCGCCTCTGC TTTCCAGCGC CGGGCAGGAG GGTCCTGGT TGCTAGCCAT | 540 |
| CTGCAGAGCT TCCTGGAGGT GTCGTACCGC GTTCTACGCC ACCTTGCGCA GCCCGACATG | 600 |
| GCTACACCAT TAGGCCCTGC CAGCTCCCTG CCCCAGAGCT TCCTGCTCAA GTCTTTAGAG | 660 |
| CAAGTGAGGA AGATCCAGGG CGATGGCGCA GCGCTCCAGG AGAAGCTGTG TGCCACCTAC | 720 |
| AAGCTGTGCC ACCCCGAGGA GCTGGTGCTG CTCGGACACT CTCTGGGCAT CCCCTGGGCT | 780 |
| CCCCTGAGCT CCTGCCCCAG CCAGGCCCTG CAGCTGGCAG GCTGCTTGAG CCAACTCCAT | 840 |
| AGCGGCCTTT TCCTCTACCA GGGGCTCCTG CAGGCCCTGG AAGGGATATC CCCCGAGTTG | 900 |

```
GGTCCCACCT TGGACACACT GCAGCTGGAC GTCGCCGACT TTGCCACCAC CATCTGGCAG    960

CAGATGGAAG AACTG                                                    975
```

(2) INFORMATION FOR SEQ ID NO:270:

(i) SEQUENCE CHARACTERISTICS:
       (A) LENGTH: 975 base pairs
       (B) TYPE: nucleic acid
       (C) STRANDEDNESS: unknown
       (D) TOPOLOGY: unknown (ii) MOLECULE TYPE: other nucleic acid
       (A) DESCRIPTION: /desc = "synthetic"

(xi) SEQUENCE DESCRIPTION: SEQ ID NO:270:

```
ATGGCTAACT GCTCTATAAT GATCGATGAA ATTATACATC ACTTAAAGAG ACCACCTGCA     60

CCTTTGCTGG ACCCGAACAA CCTCAATGAC GAAGACGTCT CTATCCTGAT GGATCGAAAC    120

CTTCGACTTC CAAACCTGGA GAGCTTCGTA AGGGCTGTCA AGAACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAGAGGG CGGTGGAGGC    360

TCCCCGGGTG AACCGTCTGG TCCAATCTCT ACTATCAACC CGTCTCCTCC GTCTAAAGAA    420

TCTCATAAAT CTCCAAACAT GGCTAGCTTC CTGGAGGTGT CGTACCGCGT TCTACGCCAC    480

CTTGCGCAGC CCGACATGGC TACACCATTA GGCCCTGCCA GCTCCCTGCC CCAGAGCTTC    540

CTGCTCAAGT CTTTAGAGCA AGTGAGGAAG ATCCAGGGCG ATGGCGCAGC GCTCCAGGAG    600

AAGCTGTGTG CCACCTACAA GCTGTGCCAC CCCGAGGAGC TGGTGCTGCT CGGACACTCT    660

CTGGGCATCC CCTGGGCTCC CCTGAGCTCC TGCCCCAGCC AGGCCCTGCA GCTGGCAGGC    720

TGCTTGAGCC AACTCCATAG CGGCCTTTTC CTCTACCAGG GCTCCTGCA GGCCCTGGAA    780

GGGATATCCC CCGAGTTGGG TCCCACCTTG ACACACTGC AGCTGGACGT CGCCGACTTT    840

GCCACCACCA TCTGGCAGCA GATGGAAGAA CTGGGAATGG CCCCTGCCCT GCAGCCCACC    900

CAGGGTGCCA TGCCGGCCTT CGCCTCTGCT TTCCAGCGCC GGGCAGGAGG GGTCCTGGTT    960

GCTAGCCATC TGCAG                                                    975
```

(2) INFORMATION FOR SEQ ID NO:271:

(i) SEQUENCE CHARACTERISTICS:
       (A) LENGTH: 325 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:271:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80
```

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Pro Ser Lys Glu Ser His Lys Ser
        130                 135                 140

Pro Asn Met Ala Leu Gly Pro Ala Ser Ser Leu Pro Gln Ser Phe Leu
145                 150                 155                 160

Leu Lys Ser Leu Glu Gln Val Arg Lys Ile Gln Gly Asp Gly Ala Ala
                165                 170                 175

Leu Gln Glu Lys Leu Cys Ala Thr Tyr Lys Leu Cys His Pro Glu Glu
            180                 185                 190

Leu Val Leu Leu Gly His Ser Leu Gly Ile Pro Trp Ala Pro Leu Ser
                195                 200                 205

Ser Cys Pro Ser Gln Ala Leu Gln Leu Ala Gly Cys Leu Ser Gln Leu
        210                 215                 220

His Ser Gly Leu Phe Leu Tyr Gln Gly Leu Leu Gln Ala Leu Glu Gly
225                 230                 235                 240

Ile Ser Pro Glu Leu Gly Pro Thr Leu Asp Thr Leu Gln Leu Asp Val
                245                 250                 255

Ala Asp Phe Ala Thr Thr Ile Trp Gln Gln Met Glu Glu Leu Gly Met
            260                 265                 270

Ala Pro Ala Leu Gln Pro Thr Gln Gly Ala Met Pro Ala Phe Ala Ser
        275                 280                 285

Ala Phe Gln Arg Arg Ala Gly Gly Val Leu Val Ala Ser His Leu Gln
290                 295                 300

Ser Phe Leu Glu Val Ser Tyr Arg Val Leu Arg His Leu Ala Gln Pro
305                 310                 315                 320

Asp Met Ala Thr Pro
            325

(2) INFORMATION FOR SEQ ID NO:272:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:272:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95
```

```
Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Pro Ser Lys Glu Ser His Lys Ser
            130                 135                 140

Pro Asn Met Ala Leu Gly Pro Ala Ser Ser Leu Pro Gln Ser Phe Leu
145                 150                 155                 160

Leu Lys Ser Leu Glu Gln Val Arg Lys Ile Gln Gly Asp Gly Ala Ala
                165                 170                 175

Leu Gln Glu Lys Leu Cys Ala Thr Tyr Lys Leu Cys His Pro Glu Glu
            180                 185                 190

Leu Val Leu Leu Gly His Ser Leu Gly Ile Pro Trp Ala Pro Leu Ser
            195                 200                 205

Ser Cys Pro Ser Gln Ala Leu Gln Leu Ala Gly Cys Leu Ser Gln Leu
            210                 215                 220

His Ser Gly Leu Phe Leu Tyr Gln Gly Leu Leu Gln Ala Leu Glu Gly
225                 230                 235                 240

Ile Ser Pro Glu Leu Gly Pro Thr Leu Asp Thr Leu Gln Leu Asp Val
            245                 250                 255

Ala Asp Phe Ala Thr Thr Ile Trp Gln Gln Met Glu Glu Leu Gly Met
            260                 265                 270

Ala Pro Ala Leu Gln Pro Thr Gln Gly Ala Met Pro Ala Phe Ala Ser
            275                 280                 285

Ala Phe Gln Arg Arg Ala Gly Gly Val Leu Val Ala Ser His Leu Gln
            290                 295                 300

Ser Phe Leu Glu Val Ser Tyr Arg Val Leu Arg His Leu Ala Gln Pro
305                 310                 315                 320

Asp Met Ala Thr Pro
                325

(2) INFORMATION FOR SEQ ID NO:273:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:273:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110
```

```
Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
    130                 135                 140

Pro Asn Met Ala Phe Leu Leu Lys Ser Leu Glu Gln Val Arg Lys Ile
145                 150                 155                 160

Gln Gly Asp Gly Ala Ala Leu Gln Glu Lys Leu Cys Ala Thr Tyr Lys
                165                 170                 175

Leu Cys His Pro Glu Glu Leu Val Leu Leu Gly His Ser Leu Gly Ile
            180                 185                 190

Pro Trp Ala Pro Leu Ser Ser Cys Pro Ser Gln Ala Leu Gln Leu Ala
            195                 200                 205

Gly Cys Leu Ser Gln Leu His Ser Gly Leu Phe Leu Tyr Gln Gly Leu
    210                 215                 220

Leu Gln Ala Leu Glu Gly Ile Ser Pro Glu Leu Gly Pro Thr Leu Asp
225                 230                 235                 240

Thr Leu Gln Leu Asp Val Ala Asp Phe Ala Thr Thr Ile Trp Gln Gln
                245                 250                 255

Met Glu Glu Leu Gly Met Ala Pro Ala Leu Gln Pro Thr Gln Gly Ala
            260                 265                 270

Met Pro Ala Phe Ala Ser Ala Phe Gln Arg Arg Ala Gly Gly Val Leu
            275                 280                 285

Val Ala Ser His Leu Gln Ser Phe Leu Glu Val Ser Tyr Arg Val Leu
    290                 295                 300

Arg His Leu Ala Gln Pro Asp Met Ala Thr Pro Leu Gly Pro Ala Ser
305                 310                 315                 320

Ser Leu Pro Gln Ser
                325

(2) INFORMATION FOR SEQ ID NO:274:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:274:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
            115                 120                 125
```

```
Ile Ser Thr Ile Asn Pro Ser Pro Ser Lys Glu Ser His Lys Ser
    130                 135                 140

Pro Asn Met Ala Glu Gln Val Arg Lys Ile Gln Gly Asp Gly Ala Ala
145                 150                 155                 160

Leu Gln Glu Lys Leu Cys Ala Thr Tyr Lys Leu Cys His Pro Glu Glu
                165                 170                 175

Leu Val Leu Leu Gly His Ser Leu Gly Ile Pro Trp Ala Pro Leu Ser
                180                 185                 190

Ser Cys Pro Ser Gln Ala Leu Gln Leu Ala Gly Cys Leu Ser Gln Leu
                195                 200                 205

His Ser Gly Leu Phe Leu Tyr Gln Gly Leu Leu Gln Ala Leu Glu Gly
    210                 215                 220

Ile Ser Pro Glu Leu Gly Pro Thr Leu Asp Thr Leu Gln Leu Asp Val
225                 230                 235                 240

Ala Asp Phe Ala Thr Thr Ile Trp Gln Gln Met Glu Glu Leu Gly Met
                245                 250                 255

Ala Pro Ala Leu Gln Pro Thr Gln Gly Ala Met Pro Ala Phe Ala Ser
                260                 265                 270

Ala Phe Gln Arg Arg Ala Gly Gly Val Leu Val Ala Ser His Leu Gln
                275                 280                 285

Ser Phe Leu Glu Val Ser Tyr Arg Val Leu Arg His Leu Ala Gln Pro
    290                 295                 300

Asp Met Ala Thr Pro Leu Gly Pro Ala Ser Ser Leu Pro Gln Ser Phe
305                 310                 315                 320

Leu Leu Lys Ser Leu
                325

(2) INFORMATION FOR SEQ ID NO:275:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:275:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
            115                 120                 125

Ile Ser Thr Ile Asn Pro Ser Pro Ser Lys Glu Ser His Lys Ser
    130                 135                 140
```

```
Pro Asn Met Ala Leu Leu Gly His Ser Leu Gly Ile Pro Trp Ala Pro
145                 150                 155                 160

Leu Ser Ser Cys Pro Ser Gln Ala Leu Gln Leu Ala Gly Cys Leu Ser
            165                 170                 175

Gln Leu His Ser Gly Leu Phe Leu Tyr Gln Gly Leu Leu Gln Ala Leu
            180                 185                 190

Glu Gly Ile Ser Pro Glu Leu Gly Pro Thr Leu Asp Thr Leu Gln Leu
            195                 200                 205

Asp Val Ala Asp Phe Ala Thr Thr Ile Trp Gln Gln Met Glu Glu Leu
210                 215                 220

Gly Met Ala Pro Ala Leu Gln Pro Thr Gln Gly Ala Met Pro Ala Phe
225                 230                 235                 240

Ala Ser Ala Phe Gln Arg Arg Ala Gly Gly Val Leu Val Ala Ser His
            245                 250                 255

Leu Gln Ser Phe Leu Glu Val Ser Tyr Arg Val Leu Arg His Leu Ala
            260                 265                 270

Gln Pro Asp Met Ala Thr Pro Leu Gly Pro Ala Ser Ser Leu Pro Gln
            275                 280                 285

Ser Phe Leu Leu Lys Ser Leu Glu Gln Val Arg Lys Ile Gln Gly Asp
290                 295                 300

Gly Ala Ala Leu Gln Glu Lys Leu Cys Ala Thr Tyr Lys Leu Cys His
305                 310                 315                 320

Pro Glu Glu Leu Val
            325

(2) INFORMATION FOR SEQ ID NO:276:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:276:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
            85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
            115                 120                 125

Ile Ser Thr Ile Asn Pro Ser Pro Ser Lys Glu Ser His Lys Ser
            130                 135                 140

Pro Asn Met Ala Pro Leu Ser Ser Cys Pro Ser Gln Ala Leu Gln Leu
145                 150                 155                 160
```

```
Ala Gly Cys Leu Ser Gln Leu His Ser Gly Leu Phe Leu Tyr Gln Gly
                165                 170                 175

Leu Leu Gln Ala Leu Glu Gly Ile Ser Pro Glu Leu Gly Pro Thr Leu
            180                 185                 190

Asp Thr Leu Gln Leu Asp Val Ala Asp Phe Ala Thr Thr Ile Trp Gln
        195                 200                 205

Gln Met Glu Glu Leu Gly Met Ala Pro Ala Leu Gln Pro Thr Gln Gly
    210                 215                 220

Ala Met Pro Ala Phe Ala Ser Ala Phe Gln Arg Arg Ala Gly Gly Val
225                 230                 235                 240

Leu Val Ala Ser His Leu Gln Ser Phe Leu Glu Val Ser Tyr Arg Val
                245                 250                 255

Leu Arg His Leu Ala Gln Pro Asp Met Ala Thr Pro Leu Gly Pro Ala
            260                 265                 270

Ser Ser Leu Pro Gln Ser Phe Leu Leu Lys Ser Leu Glu Gln Val Arg
        275                 280                 285

Lys Ile Gln Gly Asp Gly Ala Ala Leu Gln Glu Lys Leu Cys Ala Thr
290                 295                 300

Tyr Lys Leu Cys His Pro Glu Glu Leu Val Leu Leu Gly His Ser Leu
305                 310                 315                 320

Gly Ile Pro Trp Ala
                325

(2) INFORMATION FOR SEQ ID NO:277:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:277:

Met Ala Asn Cys Ser Ile Met Ile Asp Glu Ile Ile His His Leu Lys
1               5                   10                  15

Arg Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Ser Lys Glu Ser His Lys Ser
        130                 135                 140

Pro Asn Met Ala Gln Ala Leu Gln Leu Ala Gly Cys Leu Ser Gln Leu
145                 150                 155                 160

His Ser Gly Leu Phe Leu Tyr Gln Gly Leu Leu Gln Ala Leu Glu Gly
                165                 170                 175
```

```
Ile Ser Pro Glu Leu Gly Pro Thr Leu Asp Thr Leu Gln Leu Asp Val
            180                 185                 190

Ala Asp Phe Ala Thr Thr Ile Trp Gln Gln Met Glu Glu Leu Gly Met
        195                 200                 205

Ala Pro Ala Leu Gln Pro Thr Gln Gly Ala Met Pro Ala Phe Ala Ser
        210                 215                 220

Ala Phe Gln Arg Arg Ala Gly Gly Val Leu Val Ala Ser His Leu Gln
225                 230                 235                 240

Ser Phe Leu Glu Val Ser Tyr Arg Val Leu Arg His Leu Ala Gln Pro
                245                 250                 255

Asp Met Ala Thr Pro Leu Gly Pro Ala Ser Ser Leu Pro Gln Ser Phe
            260                 265                 270

Leu Leu Lys Ser Leu Glu Gln Val Arg Lys Ile Gln Gly Asp Gly Ala
        275                 280                 285

Ala Leu Gln Glu Lys Leu Cys Ala Thr Tyr Lys Leu Cys His Pro Glu
        290                 295                 300

Glu Leu Val Leu Leu Gly His Ser Leu Gly Ile Pro Trp Ala Pro Leu
305                 310                 315                 320

Ser Ser Cys Pro Ser
                325

(2) INFORMATION FOR SEQ ID NO:278:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:278:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Pro Ser Lys Glu Ser His Lys Ser
        130                 135                 140

Pro Asn Met Ala Leu Gln Leu Ala Gly Cys Leu Ser Gln Leu His Ser
145                 150                 155                 160

Gly Leu Phe Leu Tyr Gln Gly Leu Leu Gln Ala Leu Glu Gly Ile Ser
                165                 170                 175

Pro Glu Leu Gly Pro Thr Leu Asp Thr Leu Gln Leu Asp Val Ala Asp
            180                 185                 190
```

```
Phe Ala Thr Thr Ile Trp Gln Gln Met Glu Glu Leu Gly Met Ala Pro
        195                 200                 205

Ala Leu Gln Pro Thr Gln Gly Ala Met Pro Ala Phe Ala Ser Ala Phe
    210                 215                 220

Gln Arg Arg Ala Gly Gly Val Leu Val Ala Ser His Leu Gln Ser Phe
225                 230                 235                 240

Leu Glu Val Ser Tyr Arg Val Leu Arg His Leu Ala Gln Pro Asp Met
                245                 250                 255

Ala Thr Pro Leu Gly Pro Ala Ser Ser Leu Pro Gln Ser Phe Leu Leu
            260                 265                 270

Lys Ser Leu Glu Gln Val Arg Lys Ile Gln Gly Asp Gly Ala Ala Leu
        275                 280                 285

Gln Glu Lys Leu Cys Ala Thr Tyr Lys Leu Cys His Pro Glu Glu Leu
290                 295                 300

Val Leu Leu Gly His Ser Leu Gly Ile Pro Trp Ala Pro Leu Ser Ser
305                 310                 315                 320

Cys Pro Ser Gln Ala
            325

(2) INFORMATION FOR SEQ ID NO:279:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:279:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
        115                 120                 125

Ile Ser Thr Ile Asn Pro Ser Pro Ser Lys Glu Ser His Lys Ser
130                 135                 140

Pro Asn Met Ala Leu Ala Gly Cys Leu Ser Gln Leu His Ser Gly Leu
145                 150                 155                 160

Phe Leu Tyr Gln Gly Leu Leu Gln Ala Leu Glu Gly Ile Ser Pro Glu
                165                 170                 175

Leu Gly Pro Thr Leu Asp Thr Leu Gln Leu Asp Val Ala Asp Phe Ala
            180                 185                 190

Thr Thr Ile Trp Gln Gln Met Glu Glu Leu Gly Met Ala Pro Ala Leu
        195                 200                 205
```

```
Gln Pro Thr Gln Gly Ala Met Pro Ala Phe Ala Ser Ala Phe Gln Arg
    210                 215                 220

Arg Ala Gly Gly Val Leu Val Ala Ser His Leu Gln Ser Phe Leu Glu
225                 230                 235                 240

Val Ser Tyr Arg Val Leu Arg His Leu Ala Gln Pro Asp Met Ala Thr
                245                 250                 255

Pro Leu Gly Pro Ala Ser Ser Leu Pro Gln Ser Phe Leu Leu Lys Ser
                260                 265                 270

Leu Glu Gln Val Arg Lys Ile Gln Gly Asp Gly Ala Ala Leu Gln Glu
            275                 280                 285

Lys Leu Cys Ala Thr Tyr Lys Leu Cys His Pro Glu Glu Leu Val Leu
290                 295                 300

Leu Gly His Ser Leu Gly Ile Pro Trp Ala Pro Leu Ser Ser Cys Pro
305                 310                 315                 320

Ser Gln Ala Leu Gln
            325

(2) INFORMATION FOR SEQ ID NO:280:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:280:

Met Ala Asn Cys Ser Ile Met Ile Asp Glu Ile Ile His His Leu Lys
1               5                   10                  15

Arg Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
130                 135                 140

Pro Asn Met Ala Glu Leu Gly Met Ala Pro Ala Leu Gln Pro Thr Gln
145                 150                 155                 160

Gly Ala Met Pro Ala Phe Ala Ser Ala Phe Gln Arg Arg Ala Gly Gly
                165                 170                 175

Val Leu Val Ala Ser His Leu Gln Ser Phe Leu Glu Val Ser Tyr Arg
            180                 185                 190

Val Leu Arg His Leu Ala Gln Pro Asp Met Ala Thr Pro Leu Gly Pro
            195                 200                 205

Ala Ser Ser Leu Pro Gln Ser Phe Leu Leu Lys Ser Leu Glu Gln Val
210                 215                 220
```

```
Arg Lys Ile Gln Gly Asp Gly Ala Ala Leu Gln Glu Lys Leu Cys Ala
225                 230                 235                 240

Thr Tyr Lys Leu Cys His Pro Glu Glu Leu Val Leu Leu Gly His Ser
            245                 250                 255

Leu Gly Ile Pro Trp Ala Pro Leu Ser Ser Cys Pro Ser Gln Ala Leu
            260                 265                 270

Gln Leu Ala Gly Cys Leu Ser Gln Leu His Ser Gly Leu Phe Leu Tyr
            275                 280                 285

Gln Gly Leu Leu Gln Ala Leu Glu Gly Ile Ser Pro Glu Leu Gly Pro
290                 295                 300

Thr Leu Asp Thr Leu Gln Leu Asp Val Ala Asp Phe Ala Thr Thr Ile
305                 310                 315                 320

Trp Gln Gln Met Glu
                325

(2) INFORMATION FOR SEQ ID NO:281:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:281:

Met Ala Asn Cys Ser Ile Met Ile Asp Glu Ile Ile His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
            115                 120                 125

Ile Ser Thr Ile Asn Pro Ser Pro Ser Lys Glu Ser His Lys Ser
            130                 135                 140

Pro Asn Met Ala Gly Met Ala Pro Ala Leu Gln Pro Thr Gln Gly Ala
145                 150                 155                 160

Met Pro Ala Phe Ala Ser Ala Phe Gln Arg Arg Ala Gly Gly Val Leu
                165                 170                 175

Val Ala Ser His Leu Gln Ser Phe Leu Glu Val Ser Tyr Arg Val Leu
            180                 185                 190

Arg His Leu Ala Gln Pro Asp Met Ala Thr Pro Leu Gly Pro Ala Ser
        195                 200                 205

Ser Leu Pro Gln Ser Phe Leu Leu Lys Ser Leu Glu Gln Val Arg Lys
            210                 215                 220

Ile Gln Gly Asp Gly Ala Ala Leu Gln Glu Lys Leu Cys Ala Thr Tyr
225                 230                 235                 240
```

```
Lys Leu Cys His Pro Glu Glu Leu Val Leu Leu Gly His Ser Leu Gly
                245                 250                 255

Ile Pro Trp Ala Pro Leu Ser Ser Cys Pro Ser Gln Ala Leu Gln Leu
                260                 265                 270

Ala Gly Cys Leu Ser Gln Leu His Ser Gly Leu Phe Leu Tyr Gln Gly
                275                 280                 285

Leu Leu Gln Ala Leu Glu Gly Ile Ser Pro Glu Leu Gly Pro Thr Leu
                290                 295                 300

Asp Thr Leu Gln Leu Asp Val Ala Asp Phe Ala Thr Thr Ile Trp Gln
305                 310                 315                 320

Gln Met Glu Glu Leu
                325

(2) INFORMATION FOR SEQ ID NO:282:

(i) SEQUENCE CHARACTERISTICS:
        (A) LENGTH: 325 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:282:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
                35                  40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65              70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
                115                 120                 125

Ile Ser Thr Ile Asn Pro Ser Pro Pro Ser Lys Glu Ser His Lys Ser
                130                 135                 140

Pro Asn Met Ala Ser Phe Leu Glu Val Ser Tyr Arg Val Leu Arg His
145                 150                 155                 160

Leu Ala Gln Pro Asp Met Ala Thr Pro Leu Gly Pro Ala Ser Ser Leu
                165                 170                 175

Pro Gln Ser Phe Leu Leu Lys Ser Leu Glu Gln Val Arg Lys Ile Gln
                180                 185                 190

Gly Asp Gly Ala Ala Leu Gln Glu Leu Cys Ala Thr Tyr Lys Leu
                195                 200                 205

Cys His Pro Glu Glu Leu Val Leu Leu Gly His Ser Leu Gly Ile Pro
                210                 215                 220

Trp Ala Pro Leu Ser Ser Cys Pro Ser Gln Ala Leu Gln Leu Ala Gly
225                 230                 235                 240

Cys Leu Ser Gln Leu His Ser Gly Leu Phe Leu Tyr Gln Gly Leu Leu
                245                 250                 255
```

```
Gln Ala Leu Glu Gly Ile Ser Pro Glu Leu Gly Pro Thr Leu Asp Thr
            260                 265                 270

Leu Gln Leu Asp Val Ala Asp Phe Ala Thr Thr Ile Trp Gln Gln Met
        275                 280                 285

Glu Glu Leu Gly Met Ala Pro Ala Leu Gln Pro Thr Gln Gly Ala Met
        290                 295                 300

Pro Ala Phe Ala Ser Ala Phe Gln Arg Arg Ala Gly Gly Val Leu Val
305                 310                 315                 320

Ala Ser His Leu Gln
            325
```

(2) INFORMATION FOR SEQ ID NO:283:

(i) SEQUENCE CHARACTERISTICS:
        (A) LENGTH: 153 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 7
        (D) OTHER INFORMATION: /note= "Xaa at position 7 is Ser or
            Ala;"

(ix) FEATURE:
        (A) NAME/KEY: Modified-site
        (B) LOCATION: 112
        (D) OTHER INFORMATION: /note= "Xaa at position 112 is
            deleted or Leu, Ala, Val, Ile, Pro, Phe, Trp, or Met;"

(ix) FEATURE:
        (A) NAME/KEY: Modified-site
        (B) LOCATION: 113
        (D) OTHER INFORMATION: /note= "Xaa at position 113 is
            deleted or Pro, Phe, Ala, Val, Leu, Ile, Trp, or Met;"

(ix) FEATURE:
        (A) NAME/KEY: Modified-site
        (B) LOCATION: 114
        (D) OTHER INFORMATION: /note= "Xaa at position 114 is
            deleted or Pro, Phe, Ala, Val, Leu, Ile, Trp, or Met;"

(ix) FEATURE:
        (A) NAME/KEY: Modified-site
        (B) LOCATION: 115
        (D) OTHER INFORMATION: /note= "Xaa at position 115 is
            deleted or Gln, Gly, Ser, Thr, Tyr, or Asn;"

(ix) FEATURE:
        (A) NAME/KEY: Modified-site
        (B) LOCATION: 151
        (D) OTHER INFORMATION: /note= "Xaa at position 151 is Ser
            or Ala;"

(xi) SEQUENCE DESCRIPTION: SEQ ID NO:283:

```
Ser Pro Ala Pro Pro Ala Xaa Asp Leu Arg Val Leu Ser Lys Leu Leu
1                   5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80
```

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Xaa
            100                 105                 110

Xaa Xaa Xaa Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Xaa Val Arg
145                 150

(2) INFORMATION FOR SEQ ID NO:284:

(i) SEQUENCE CHARACTERISTICS:
        (A) LENGTH: 162 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:284:

Met Ala Gly Arg Thr Thr Ala His Lys Asp Pro Asn Ala Ile Phe Leu
1               5                   10                  15

Ser Phe Gln His Leu Leu Arg Gly Lys Val Arg Phe Leu Met Leu Val
                20                  25                  30

Gly Gly Ser Thr Leu Ala Val Arg Glu Phe Gly Gly Asn Met Ala Ser
            35                  40                  45

Pro Ala Pro Ala Ala Asp Leu Arg Val Leu Ser Lys Leu Leu Arg
    50                  55                  60

Asp Ser His Val Leu His Ser Arg Leu Ser Gln Cys Pro Glu Val His
65                  70                  75                  80

Pro Leu Pro Thr Pro Val Leu Leu Pro Ala Val Asp Phe Ser Leu Gly
                85                  90                  95

Glu Trp Lys Thr Gln Met Glu Glu Thr Lys Ala Gln Asp Ile Leu Gly
                100                 105                 110

Ala Val Thr Leu Leu Leu Glu Gly Val Met Ala Ala Arg Gly Gln Leu
            115                 120                 125

Gly Pro Thr Cys Leu Ser Ser Leu Leu Gly Gln Leu Ser Gly Gln Val
    130                 135                 140

Arg Leu Leu Leu Gly Ala Leu Gln Ser Leu Leu Gly Thr Gln Leu Pro
145                 150                 155                 160

Pro Gln (2) INFORMATION FOR SEQ ID NO:285:

(i) SEQUENCE CHARACTERISTICS:
        (A) LENGTH: 162 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:285:

Met Ala Gly Pro Thr Cys Leu Ser Ser Leu Leu Gly Gln Leu Ser Gly
1               5                   10                  15

Gln Val Arg Leu Leu Leu Gly Ala Leu Gln Ser Leu Leu Gly Thr Gln
                20                  25                  30

```
Leu Pro Pro Gln Gly Arg Thr Thr Ala His Lys Asp Pro Asn Ala Ile
         35                  40                  45

Phe Leu Ser Phe Gln His Leu Leu Arg Gly Lys Val Arg Phe Leu Met
 50                  55                  60

Leu Val Gly Gly Ser Thr Leu Ala Val Arg Glu Phe Gly Gly Asn Met
 65                  70                  75                  80

Ala Ser Pro Ala Pro Ala Ala Asp Leu Arg Val Leu Ser Lys Leu
                 85                  90                  95

Leu Arg Asp Ser His Val Leu His Ser Arg Leu Ser Gln Cys Pro Glu
                100                 105                 110

Val His Pro Leu Pro Thr Pro Val Leu Leu Pro Ala Val Asp Phe Ser
                115                 120                 125

Leu Gly Glu Trp Lys Thr Gln Met Glu Glu Thr Lys Ala Gln Asp Ile
                130                 135                 140

Leu Gly Ala Val Thr Leu Leu Leu Glu Gly Val Met Ala Ala Arg Gly
145                 150                 155                 160

Gln Leu (2) INFORMATION FOR SEQ ID NO:286:

(i) SEQUENCE CHARACTERISTICS:
        (A) LENGTH: 180 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:286:

Ala Thr Gly Gly Cys Thr Gly Gly Ala Cys Cys Cys Ala Cys Thr Thr
 1               5                  10                  15

Gly Cys Cys Thr Cys Thr Cys Ala Thr Cys Cys Cys Thr Cys Cys Thr
                 20                  25                  30

Gly Gly Gly Gly Cys Ala Gly Cys Thr Thr Cys Thr Gly Gly Ala
             35                  40                  45

Cys Ala Gly Gly Thr Cys Cys Gly Thr Cys Thr Cys Thr Cys Cys
 50                  55                  60

Thr Thr Gly Gly Gly Cys Cys Thr Gly Cys Ala Gly Ala Gly
 65                  70                  75                  80

Cys Cys Thr Cys Cys Thr Thr Gly Gly Ala Ala Cys Cys Cys Ala Gly
                 85                  90                  95

Cys Thr Thr Cys Cys Thr Cys Ala Cys Ala Gly Gly Gly Cys Ala
                100                 105                 110

Gly Gly Ala Cys Cys Ala Cys Ala Gly Cys Thr Cys Ala Cys Ala Ala
                115                 120                 125

Gly Gly Ala Thr Cys Cys Cys Ala Ala Thr Gly Cys Cys Ala Thr Cys
                130                 135                 140

Thr Thr Cys Cys Thr Gly Ala Gly Cys Thr Thr Cys Cys Ala Ala Cys
145                 150                 155                 160

Ala Cys Cys Thr Gly Cys Thr Cys Cys Gly Ala Gly Gly Ala Ala Ala
                165                 170                 175

Gly Gly Thr Gly
                180

(2) INFORMATION FOR SEQ ID NO:287:
```

(i) SEQUENCE CHARACTERISTICS:
        (A) LENGTH: 486 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:287:

| | | | | | |
|---|---|---|---|---|---|
| ATGGCTGGCA | GGACCACAGC | TCACAAGGAT | CCCAATGCCA | TCTTCCTGAG | CTTCCAACAC | 60 |
| CTGCTCCGAG | GAAAGGTGCG | TTTCCTGATG | CTTGTAGGAG | GGTCCACCCT | CGCCGTCAGG | 120 |
| GAATTCGGCG | GCAACATGGC | GTCTCCGGCG | CCGCCTGCTG | CTGACCTCCG | AGTCCTCAGT | 180 |
| AAACTGCTTC | GTGACTCCCA | TGTCCTTCAC | AGCAGACTGA | GCCAGTGCCC | AGAGGTTCAC | 240 |
| CCTTTGCCTA | CACCTGTCCT | GCTGCCTGCT | GTGGACTTTA | GCTTGGGAGA | ATGGAAAACC | 300 |
| CAGATGGAGG | AGACCAAGGC | ACAGGACATT | CTGGGAGCAG | TGACCCTTCT | GCTGGAGGGA | 360 |
| GTGATGGCAG | CACGGGGACA | ACTGGGACCC | ACTTGCCTCT | CATCCCTCCT | GGGGCAGCTT | 420 |
| TCTGGACAGG | TCCGTCTCCT | CCTTGGGGCC | CTGCAGAGCC | TCCTTGGAAC | CCAGCTTCCT | 480 |
| CCACAG | | | | | | 486 |

(2) INFORMATION FOR SEQ ID NO:288:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:288:

| | | | | | |
|---|---|---|---|---|---|
| CAGAGCTTCC | TGCTCAAGTC | TTTAGAGCAA | GTGAGGAAGA | TCCAGGGCGA | TGGCGCAGCG | 60 |
| CTCCAGGAGA | AGCTGTGTGC | CACCTACAAG | CTGTGCCACC | CCGAGGAGCT | GGTGCTGCTC | 120 |
| GGACACTCTC | TGGGCATCCC | CTGGGCTCCC | CTGAGCTCCT | GCCCCAGCCA | GGCCCTGCAG | 180 |
| CTGGCAGGCT | GCTTGAGCCA | ACTCCATAGC | GGCCTTTTCC | TCTACCAGGG | GCTCCTGCAG | 240 |
| GCCCTGGAAG | GGATATCCCC | CGAGTTGGGT | CCCACCTTGG | ACACACTGCA | GCTGGACGTC | 300 |
| GCCGACTTTG | CCACCACCAT | CTGGCAGCAG | ATGGAAGAAC | TGGGAATGGC | CCCTGCCCTG | 360 |
| CAGCCCACCC | AGGGTGCCAT | GCCGGCCTTC | GCCTCTGCTT | TCCAGCGCCG | GGCAGGAGGG | 420 |
| GTCCTGGTTG | CTAGCCATCT | GCAGAGCTTC | CTGGAGGTGT | CGTACCGCGT | TCTACGCCAC | 480 |
| CTTGCGCAGC | CCGACATGGC | TACACCATTA | GGCCCTGCCA | GCTCCCTGCC | C | 531 |

(2) INFORMATION FOR SEQ ID NO:289:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:289:

| | | | | | |
|---|---|---|---|---|---|
| GAACTGGGAA | TGGCCCCTGC | CCTGCAGCCC | ACCCAGGGTG | CCATGCCGGC | CTTCGCCTCT | 60 |
| GCTTTCCAGC | GCCGGGCAGG | AGGGGTCCTG | GTTGCTAGCC | ATCTGCAGAG | CTTCCTGGAG | 120 |

```
GTGTCGTACC GCGTTCTACG CCACCTTGCG CAGCCCGACA TGGCTACACC ATTAGGCCCT      180

GCCAGCTCCC TGCCCCAGAG CTTCCTGCTC AAGTCTTTAG AGCAAGTGAG GAAGATCCAG      240

GGCGATGGCG CAGCGCTCCA GGAGAAGCTG TGTGCCACCT ACAAGCTGTG CCACCCCGAG      300

GAGCTGGTGC TGCTCGGACA CTCTCTGGGC ATCCCCTGGG CTCCCCTGAG CTCCTGCCCC      360

AGCCAGGCCC TGCAGCTGGC AGGCTGCTTG AGCCAACTCC ATAGCGGCCT TTTCCTCTAC      420

CAGGGGCTCC TGCAGGCCCT GGAAGGGATA TCCCCCGAGT TGGGTCCCAC CTTGGACACA      480

CTGCAGCTGG ACGTCGCCGA CTTTGCCACC ACCATCTGGC AGCAGATGGA A               531

(2) INFORMATION FOR SEQ ID NO:290:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:290:

GGAATGGCCC CTGCCCTGCA GCCCACCCAG GGTGCCATGC CGGCCTTCGC CTCTGCTTTC       60

CAGCGCCGGG CAGGAGGGGT CCTGGTTGCT AGCCATCTGC AGAGCTTCCT GGAGGTGTCG      120

TACCGCGTTC TACGCCACCT TGCGCAGCCC GACATGGCTA CACCATTAGG CCCTGCCAGC      180

TCCCTGCCCC AGAGCTTCCT GCTCAAGTCT TTAGAGCAAG TGAGGAAGAT CCAGGGCGAT      240

GGCGCAGCGC TCCAGGAGAA GCTGTGTGCC ACCTACAAGC TGTGCCACCC CGAGGAGCTG      300

GTGCTGCTCG GACACTCTCT GGGCATCCCC TGGGCTCCCC TGAGCTCCTG CCCCAGCCAG      360

GCCCTGCAGC TGGCAGGCTG CTTGAGCCAA CTCCATAGCG GCCTTTTCCT CTACCAGGGG      420

CTCCTGCAGG CCCTGGAAGG GATATCCCCC GAGTTGGGTC CCACCTTGGA CACACTGCAG      480

CTGGACGTCG CCGACTTTGC CACCACCATC TGGCAGCAGA TGGAAGAACT G               531

(2) INFORMATION FOR SEQ ID NO:291:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:291:

TTCCTGCTCA AGTCTTTAGA GCAAGTGAGG AAGATCCAGG GCGATGGCGC AGCGCTCCAG       60

GAGAAGCTGT GTGCCACCTA CAAGCTGTGC CACCCCGAGG AGCTGGTGCT GCTCGGACAC      120

TCTCTGGGCA TCCCCTGGGC TCCCCTGAGC TCCTGCCCCA GCCAGGCCCT GCAGCTGGCA      180

GGCTGCTTGA GCCAACTCCA TAGCGGCCTT TTCCTCTACC AGGGGCTCCT GCAGGCCCTG      240

GAAGGGATAT CCCCCGAGTT GGGTCCCACC TTGGACACAC TGCAGCTGGA CGTCGCCGAC      300

TTTGCCACCA CCATCTGGCA GCAGATGGAA GAACTGGGAA TGGCCCCTGC CCTGCAGCCC      360

ACCCAGGGTG CCATGCCGGC CTTCGCCTCT GCTTTCCAGC GCCGGGCAGG AGGGGTCCTG      420

GTTGCTAGCC ATCTGCAGAG CTTCCTGGAG GTGTCGTACC GCGTTCTACG CCACCTTGCG      480

CAGCCCGACA TGGCTACACC ATTAGGCCCT GCCAGCTCCC TGCCCCAGAG C               531
```

(2) INFORMATION FOR SEQ ID NO:292:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:292:

```
AGCTTCCTGG AGGTGTCGTA CCGCGTTCTA CGCCACCTTG CGCAGCCCGA CATGGCTACA      60

CCATTAGGCC CTGCCAGCTC CCTGCCCCAG AGCTTCCTGC TCAAGTCTTT AGAGCAAGTG     120

AGGAAGATCC AGGGCGATGG CGCAGCGCTC CAGGAGAAGC TGTGTGCCAC CTACAAGCTG     180

TGCCACCCCG AGGAGCTGGT GCTGCTCGGA CACTCTCTGG GCATCCCCTG GGCTCCCCTG     240

AGCTCCTGCC CCAGCCAGGC CCTGCAGCTG GCAGGCTGCT TGAGCCAACT CCATAGCGGC     300

CTTTTCCTCT ACCAGGGGCT CCTGCAGGCC CTGGAAGGGA TATCCCCCGA GTTGGGTCCC     360

ACCTTGGACA CACTGCAGCT GGACGTCGCC GACTTTGCCA CCACCATCTG GCAGCAGATG     420

GAAGAACTGG GAATGGCCCC TGCCCTGCAG CCCACCCAGG GTGCCATGCC GGCCTTCGCC     480

TCTGCTTTCC AGCGCCGGGC AGGAGGGGTC CTGGTTGCTA GCCATCTGCA G              531
```

(2) INFORMATION FOR SEQ ID NO:293:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:293:

```
AGCTTCCTGG AGGTGTCGTA CCGCGTTCTA CGCCACCTTG CGCAGCCCGA CATGGCTACA      60

CCATTAGGCC CTGCCAGCTC CCTGCCCCAG AGCTTCCTGC TCAAGTCTTT AGAGCAAGTG     120

AGGAAGATCC AGGGCGATGG CGCAGCGCTC CAGGAGAAGC TGTGTGCCAC CTACAAGCTG     180

TGCCACCCCG AGGAGCTGGT GCTGCTCGGA CACTCTCTGG GCATCCCCTG GGCTCCCCTG     240

AGCTCCTGCC CCAGCCAGGC CCTGCAGCTG GCAGGCTGCT TGAGCCAACT CCATAGCGGC     300

CTTTTCCTCT ACCAGGGGCT CCTGCAGGCC CTGGAAGGGA TATCCCCCGA GTTGGGTCCC     360

ACCTTGGACA CACTGCAGCT GGACGTCGCC GACTTTGCCA CCACCATCTG GCAGCAGATG     420

GAAGAACTGG GAATGGCCCC TGCCCTGCAG CCCACCCAGG GTGCCATGCC GGCCTTCGCC     480

TCTGCTTTCC AGCGCCGGGC AGGAGGGGTC CTGGTTGCTA GCCATCTGCA G              531
```

(2) INFORMATION FOR SEQ ID NO:294:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:294:

```
TTAGGCCCTG CCAGCTCCCT GCCCCAGAGC TTCCTGCTCA AGTCTTTAGA GCAAGTGAGG      60
```

```
AAGATCCAGG GCGATGGCGC AGCGCTCCAG GAGAAGCTGT GTGCCACCTA CAAGCTGTGC    120

CACCCCGAGG AGCTGGTGCT GCTCGGACAC TCTCTGGGCA TCCCCTGGGC TCCCCTGAGC    180

TCCTGCCCCA GCCAGGCCCT GCAGCTGGCA GGCTGCTTGA GCCAACTCCA TAGCGGCCTT    240

TTCCTCTACC AGGGGCTCCT GCAGGCCCTG GAAGGGATAT CCCCCGAGTT GGGTCCCACC    300

TTGGACACAC TGCAGCTGGA CGTCGCCGAC TTTGCCACCA CCATCTGGCA GCAGATGGAA    360

GAACTGGGAA TGGCCCCTGC CCTGCAGCCC ACCCAGGGTG CCATGCCGGC CTTCGCCTCT    420

GCTTTCCAGC GCCGGGCAGG AGGGGTCCTG GTTGCTAGCC ATCTGCAGAG CTTCCTGGAG    480

GTGTCGTACC GCGTTCTACG CCACCTTGCG CAGCCCGACA TGGCTACACC A             531
```

(2) INFORMATION FOR SEQ ID NO:295:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:295:

```
CTGCTCGGAC ACTCTCTGGG CATCCCCTGG GCTCCCCTGA GCTCCTGCCC CAGCCAGGCC     60

CTGCAGCTGG CAGGCTGCTT GAGCCAACTC CATAGCGGCC TTTTCCTCTA CCAGGGGCTC    120

CTGCAGGCCC TGGAAGGGAT ATCCCCCGAG TTGGGTCCCA CCTTGGACAC ACTGCAGCTG    180

GACGTCGCCG ACTTTGCCAC CACCATCTGG CAGCAGATGG AAGAACTGGG AATGGCCCCT    240

GCCCTGCAGC CCACCCAGGG TGCCATGCCG GCCTTCGCCT CTGCTTTCCA GCGCCGGGCA    300

GGAGGGGTCC TGGTTGCTAG CCATCTGCAG AGCTTCCTGG AGGTGTCGTA CCGCGTTCTA    360

CGCCACCTTG CGCAGCCCGA CATGGCTACA CCATTAGGCC CTGCCAGCTC CCTGCCCCAG    420

AGCTTCCTGC TCAAGTCTTT AGAGCAAGTG AGGAAGATCC AGGGCGATGG CGCAGCGCTC    480

CAGGAGAAGC TGTGTGCCAC CTACAAGCTG TGCCACCCCG AGGAGCTGGT G             531
```

(2) INFORMATION FOR SEQ ID NO:296:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:296:

```
CCCCTGAGCT CCTGCCCCAG CCAGGCCCTG CAGCTGGCAG GCTGCTTGAG CCAACTCCAT     60

AGCGGCCTTT TCCTCTACCA GGGGCTCCTG CAGGCCCTGG AAGGGATATC CCCCGAGTTG    120

GGTCCCACCT TGGACACACT GCAGCTGGAC GTCGCCGACT TTGCCACCAC CATCTGGCAG    180

CAGATGGAAG AACTGGGAAT GGCCCCTGCC CTGCAGCCCA CCCAGGGTGC CATGCCGGCC    240

TTCGCCTCTG CTTTCCAGCG CCGGGCAGGA GGGGTCCTGG TTGCTAGCCA TCTGCAGAGC    300

TTCCTGGAGG TGTCGTACCG CGTTCTACGC CACCTTGCGC AGCCCGACAT GGCTACACCA    360

TTAGGCCCTG CCAGCTCCCT GCCCCAGAGC TTCCTGCTCA AGTCTTTAGA GCAAGTGAGG    420

AAGATCCAGG GCGATGGCGC AGCGCTCCAG GAGAAGCTGT GTGCCACCTA CAAGCTGTGC    480
```

```
CACCCCGAGG AGCTGGTGCT GCTCGGACAC TCTCTGGGCA TCCCCTGGGC T                531
```

(2) INFORMATION FOR SEQ ID NO:297:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:297:

```
CAGGCCCTGC AGCTGGCAGG CTGCTTGAGC CAACTCCATA GCGGCCTTTT CCTCTACCAG         60

GGGCTCCTGC AGGCCCTGGA AGGGATATCC CCCGAGTTGG GTCCCACCTT GGACACACTG        120

CAGCTGGACG TCGCCGACTT TGCCACCACC ATCTGGCAGC AGATGGAAGA ACTGGGAATG        180

GCCCCTGCCC TGCAGCCCAC CCAGGGTGCC ATGCCGGCCT TCGCCTCTGC TTTCCAGCGC        240

CGGGCAGGAG GGTCCTGGT TGCTAGCCAT CTGCAGAGCT TCCTGGAGGT GTCGTACCGC         300

GTTCTACGCC ACCTTGCGCA GCCCGACATG GCTACACCAT TAGGCCCTGC CAGCTCCCTG        360

CCCCAGAGCT TCCTGCTCAA GTCTTTAGAG CAAGTGAGGA AGATCCAGGG CGATGGCGCA        420

GCGCTCCAGG AGAAGCTGTG TGCCACCTAC AAGCTGTGCC ACCCCGAGGA GCTGGTGCTG        480

CTCGGACACT CTCTGGGCAT CCCCTGGGCT CCCCTGAGCT CCTGCCCCAG C                531
```

(2) INFORMATION FOR SEQ ID NO:298:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:298:

```
CTGCAGCTGG CAGGCTGCTT GAGCCAACTC CATAGCGGCC TTTTCCTCTA CCAGGGGCTC         60

CTGCAGGCCC TGGAAGGGAT ATCCCCCGAG TTGGGTCCCA CCTTGGACAC ACTGCAGCTG        120

GACGTCGCCG ACTTTGCCAC CACCATCTGG CAGCAGATGG AAGAACTGGG AATGGCCCCT        180

GCCCTGCAGC CCACCCAGGG TGCCATGCCG GCCTTCGCCT CTGCTTTCCA GCGCGGGCA         240

GGAGGGGTCC TGGTTGCTAG CCATCTGCAG AGCTTCCTGG AGGTGTCGTA CCGCGTTCTA        300

CGCCACCTTG CGCAGCCCGA CATGGCTACA CCATTAGGCC CTGCCAGCTC CCTGCCCCAG        360

AGCTTCCTGC TCAAGTCTTT AGAGCAAGTG AGGAAGATCC AGGGCGATGG CGCAGCGCTC        420

CAGGAGAAGC TGTGTGCCAC CTACAAGCTG TGCCACCCCG AGGAGCTGGT GCTGCTCGGA        480

CACTCTCTGG GCATCCCCTG GCTCCCCTG AGCTCCTGCC CAGCCAGGC C                   531
```

(2) INFORMATION FOR SEQ ID NO:299:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:299:

```
CTGGCAGGCT GCTTGAGCCA ACTCCATAGC GGCCTTTTCC TCTACCAGGG GCTCCTGCAG        60

GCCCTGGAAG GGATATCCCC CGAGTTGGGT CCCACCTTGG ACACACTGCA GCTGGACGTC       120

GCCGACTTTG CCACCACCAT CTGGCAGCAG ATGGAAGAAC TGGGAATGGC CCCTGCCCTG       180

CAGCCCACCC AGGGTGCCAT GCCGGCCTTC GCCTCTGCTT TCCAGCGCCG GGCAGGAGGG       240

GTCCTGGTTG CTAGCCATCT GCAGAGCTTC CTGGAGGTGT CGTACCGCGT TCTACGCCAC       300

CTTGCGCAGC CCGACATGGC TACACCATTA GGCCCTGCCA GCTCCCTGCC CCAGAGCTTC       360

CTGCTCAAGT CTTTAGAGCA AGTGAGGAAG ATCCAGGGCG ATGGCGCAGC GCTCCAGGAG       420

AAGCTGTGTG CCACCTACAA GCTGTGCCAC CCCGAGGAGC TGGTGCTGCT CGGACACTCT       480

CTGGGCATCC CCTGGGCTCC CCTGAGCTCC TGCCCCAGCC AGGCCCTGCA G               531
```

(2) INFORMATION FOR SEQ ID NO:300:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:300:

```
Gln Ser Phe Leu Leu Lys Ser Leu Glu Gln Val Arg Lys Ile Gln Gly
1               5                   10                  15

Asp Gly Ala Ala Leu Gln Glu Lys Leu Cys Ala Thr Tyr Lys Leu Cys
                20                  25                  30

His Pro Glu Glu Leu Val Leu Leu Gly His Ser Leu Gly Ile Pro Trp
            35                  40                  45

Ala Pro Leu Ser Ser Cys Pro Ser Gln Ala Leu Gln Leu Ala Gly Cys
        50                  55                  60

Leu Ser Gln Leu His Ser Gly Leu Phe Leu Tyr Gln Gly Leu Leu Gln
65                  70                  75                  80

Ala Leu Glu Gly Ile Ser Pro Glu Leu Gly Pro Thr Leu Asp Thr Leu
                85                  90                  95

Gln Leu Asp Val Ala Asp Phe Ala Thr Thr Ile Trp Gln Gln Met Glu
            100                 105                 110

Glu Leu Gly Met Ala Pro Ala Leu Gln Pro Thr Gln Gly Ala Met Pro
        115                 120                 125

Ala Phe Ala Ser Ala Phe Gln Arg Arg Ala Gly Gly Val Leu Val Ala
    130                 135                 140

Ser His Leu Gln Ser Phe Leu Glu Val Ser Tyr Arg Val Leu Arg His
145                 150                 155                 160

Leu Ala Gln Pro Asp Met Ala Thr Pro Leu Gly Pro Ala Ser Ser Leu
                165                 170                 175

Pro
```

(2) INFORMATION FOR SEQ ID NO:301:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:301:

```
Glu Leu Gly Met Ala Pro Ala Leu Gln Pro Thr Gln Gly Ala Met Pro
1               5                   10                  15

Ala Phe Ala Ser Ala Phe Gln Arg Arg Ala Gly Gly Val Leu Val Ala
                20                  25                  30

Ser His Leu Gln Ser Phe Leu Glu Val Ser Tyr Arg Val Leu Arg His
            35                  40                  45

Leu Ala Gln Pro Asp Met Ala Thr Pro Leu Gly Pro Ala Ser Ser Leu
        50                  55                  60

Pro Gln Ser Phe Leu Leu Lys Ser Leu Glu Gln Val Arg Lys Ile Gln
65                  70                  75                  80

Gly Asp Gly Ala Ala Leu Gln Glu Lys Leu Cys Ala Thr Tyr Lys Leu
                85                  90                  95

Cys His Pro Glu Glu Leu Val Leu Leu Gly His Ser Leu Gly Ile Pro
            100                 105                 110

Trp Ala Pro Leu Ser Ser Cys Pro Ser Gln Ala Leu Gln Leu Ala Gly
        115                 120                 125

Cys Leu Ser Gln Leu His Ser Gly Leu Phe Leu Tyr Gln Gly Leu Leu
130                 135                 140

Gln Ala Leu Glu Gly Ile Ser Pro Glu Leu Gly Pro Thr Leu Asp Thr
145                 150                 155                 160

Leu Gln Leu Asp Val Ala Asp Phe Ala Thr Thr Ile Trp Gln Gln Met
                165                 170                 175

Glu (2) INFORMATION FOR SEQ ID NO:302:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:302:

Gly Met Ala Pro Ala Leu Gln Pro Thr Gln Gly Ala Met Pro Ala Phe
1               5                   10                  15

Ala Ser Ala Phe Gln Arg Arg Ala Gly Gly Val Leu Val Ala Ser His
                20                  25                  30

Leu Gln Ser Phe Leu Glu Val Ser Tyr Arg Val Leu Arg His Leu Ala
            35                  40                  45

Gln Pro Asp Met Ala Thr Pro Leu Gly Pro Ala Ser Ser Leu Pro Gln
        50                  55                  60

Ser Phe Leu Leu Lys Ser Leu Glu Gln Val Arg Lys Ile Gln Gly Asp
65                  70                  75                  80

Gly Ala Ala Leu Gln Glu Lys Leu Cys Ala Thr Tyr Lys Leu Cys His
                85                  90                  95

Pro Glu Glu Leu Val Leu Leu Gly His Ser Leu Gly Ile Pro Trp Ala
            100                 105                 110

Pro Leu Ser Ser Cys Pro Ser Gln Ala Leu Gln Leu Ala Gly Cys Leu
        115                 120                 125

Ser Gln Leu His Ser Gly Leu Phe Leu Tyr Gln Gly Leu Leu Gln Ala
130                 135                 140

Leu Glu Gly Ile Ser Pro Glu Leu Gly Pro Thr Leu Asp Thr Leu Gln
145                 150                 155                 160
```

```
Leu Asp Val Ala Asp Phe Ala Thr Thr Ile Trp Gln Gln Met Glu Glu
                165                 170                 175

Leu (2) INFORMATION FOR SEQ ID NO:303:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:303:

Phe Leu Leu Lys Ser Leu Glu Gln Val Arg Lys Ile Gln Gly Asp Gly
1               5                   10                  15

Ala Ala Leu Gln Glu Lys Leu Cys Ala Thr Tyr Lys Leu Cys His Pro
            20                  25                  30

Glu Glu Leu Val Leu Leu Gly His Ser Leu Gly Ile Pro Trp Ala Pro
        35                  40                  45

Leu Ser Ser Cys Pro Ser Gln Ala Leu Gln Leu Ala Gly Cys Leu Ser
50                  55                  60

Gln Leu His Ser Gly Leu Phe Leu Tyr Gln Gly Leu Leu Gln Ala Leu
65                  70                  75                  80

Glu Gly Ile Ser Pro Glu Leu Gly Pro Thr Leu Asp Thr Leu Gln Leu
                85                  90                  95

Asp Val Ala Asp Phe Ala Thr Thr Ile Trp Gln Gln Met Glu Glu Leu
                100                 105                 110

Gly Met Ala Pro Ala Leu Gln Pro Thr Gln Gly Ala Met Pro Ala Phe
            115                 120                 125

Ala Ser Ala Phe Gln Arg Arg Ala Gly Gly Val Leu Val Ala Ser His
        130                 135                 140

Leu Gln Ser Phe Leu Glu Val Ser Tyr Arg Val Leu Arg His Leu Ala
145                 150                 155                 160

Gln Pro Asp Met Ala Thr Pro Leu Gly Pro Ala Ser Ser Leu Pro Gln
                165                 170                 175

Ser (2) INFORMATION FOR SEQ ID NO:304:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:304:

Ser Phe Leu Glu Val Ser Tyr Arg Val Leu Arg His Leu Ala Gln Pro
1               5                   10                  15

Asp Met Ala Thr Pro Leu Gly Pro Ala Ser Ser Leu Pro Gln Ser Phe
            20                  25                  30

Leu Leu Lys Ser Leu Glu Gln Val Arg Lys Ile Gln Gly Asp Gly Ala
        35                  40                  45

Ala Leu Gln Glu Lys Leu Cys Ala Thr Tyr Lys Leu Cys His Pro Glu
50                  55                  60

Glu Leu Val Leu Leu Gly His Ser Leu Gly Ile Pro Trp Ala Pro Leu
```

-continued

```
65                  70                  75                  80
Ser Ser Cys Pro Ser Gln Ala Leu Gln Leu Ala Gly Cys Leu Ser Gln
                85                  90                  95

Leu His Ser Gly Leu Phe Leu Tyr Gln Gly Leu Leu Gln Ala Leu Glu
                100                 105                 110

Gly Ile Ser Pro Glu Leu Gly Pro Thr Leu Asp Thr Leu Gln Leu Asp
                115                 120                 125

Val Ala Asp Phe Ala Thr Thr Ile Trp Gln Gln Met Glu Glu Leu Gly
            130                 135                 140

Met Ala Pro Ala Leu Gln Pro Thr Gln Gly Ala Met Pro Ala Phe Ala
145                 150                 155                 160

Ser Ala Phe Gln Arg Arg Ala Gly Gly Val Leu Val Ala Ser His Leu
                165                 170                 175

Gln
```

(2) INFORMATION FOR SEQ ID NO:305:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:305:

```
Glu Gln Val Arg Lys Ile Gln Gly Asp Gly Ala Ala Leu Gln Glu Lys
1               5                   10                  15

Leu Cys Ala Thr Tyr Lys Leu Cys His Pro Glu Glu Leu Val Leu Leu
                20                  25                  30

Gly His Ser Leu Gly Ile Pro Trp Ala Pro Leu Ser Ser Cys Pro Ser
                35                  40                  45

Gln Ala Leu Gln Leu Ala Gly Cys Leu Ser Gln Leu His Ser Gly Leu
            50                  55                  60

Phe Leu Tyr Gln Gly Leu Leu Gln Ala Leu Glu Gly Ile Ser Pro Glu
65                  70                  75                  80

Leu Gly Pro Thr Leu Asp Thr Leu Gln Leu Asp Val Ala Asp Phe Ala
                85                  90                  95

Thr Thr Ile Trp Gln Gln Met Glu Glu Leu Gly Met Ala Pro Ala Leu
                100                 105                 110

Gln Pro Thr Gln Gly Ala Met Pro Ala Phe Ala Ser Ala Phe Gln Arg
                115                 120                 125

Arg Ala Gly Gly Val Leu Val Ala Ser His Leu Gln Ser Phe Leu Glu
            130                 135                 140

Val Ser Tyr Arg Val Leu Arg His Leu Ala Gln Pro Asp Met Ala Thr
145                 150                 155                 160

Pro Leu Gly Pro Ala Ser Ser Leu Pro Gln Ser Phe Leu Leu Lys Ser
                165                 170                 175

Leu
```

(2) INFORMATION FOR SEQ ID NO:306:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:306:

| Leu | Gly | Pro | Ala | Ser | Ser | Leu | Pro | Gln | Ser | Phe | Leu | Leu | Lys | Ser | Leu |
|---|---|---|---|---|---|---|---|---|---|---|---|---|---|---|---|
| 1 | | | | 5 | | | | | 10 | | | | | 15 | |

| Glu | Gln | Val | Arg | Lys | Ile | Gln | Gly | Asp | Gly | Ala | Ala | Leu | Gln | Glu | Lys |
|---|---|---|---|---|---|---|---|---|---|---|---|---|---|---|---|
| | | | 20 | | | | | 25 | | | | | 30 | | |

| Leu | Cys | Ala | Thr | Tyr | Lys | Leu | Cys | His | Pro | Glu | Glu | Leu | Val | Leu | Leu |
|---|---|---|---|---|---|---|---|---|---|---|---|---|---|---|---|
| | | | 35 | | | | | 40 | | | | | 45 | | |

| Gly | His | Ser | Leu | Gly | Ile | Pro | Trp | Ala | Pro | Leu | Ser | Ser | Cys | Pro | Ser |
|---|---|---|---|---|---|---|---|---|---|---|---|---|---|---|---|
| | 50 | | | | | 55 | | | | | 60 | | | | |

| Gln | Ala | Leu | Gln | Leu | Ala | Gly | Cys | Leu | Ser | Gln | Leu | His | Ser | Gly | Leu |
|---|---|---|---|---|---|---|---|---|---|---|---|---|---|---|---|
| 65 | | | | | 70 | | | | | 75 | | | | | 80 |

| Phe | Leu | Tyr | Gln | Gly | Leu | Leu | Gln | Ala | Leu | Glu | Gly | Ile | Ser | Pro | Glu |
|---|---|---|---|---|---|---|---|---|---|---|---|---|---|---|---|
| | | | | 85 | | | | | 90 | | | | | 95 | |

| Leu | Gly | Pro | Thr | Leu | Asp | Thr | Leu | Gln | Leu | Asp | Val | Ala | Asp | Phe | Ala |
|---|---|---|---|---|---|---|---|---|---|---|---|---|---|---|---|
| | | | 100 | | | | | 105 | | | | | 110 | | |

| Thr | Thr | Ile | Trp | Gln | Gln | Met | Glu | Glu | Leu | Gly | Met | Ala | Pro | Ala | Leu |
|---|---|---|---|---|---|---|---|---|---|---|---|---|---|---|---|
| | | | 115 | | | | | 120 | | | | | 125 | | |

| Gln | Pro | Thr | Gln | Gly | Ala | Met | Pro | Ala | Phe | Ala | Ser | Ala | Phe | Gln | Arg |
|---|---|---|---|---|---|---|---|---|---|---|---|---|---|---|---|
| | | 130 | | | | | 135 | | | | | 140 | | | |

| Arg | Ala | Gly | Gly | Val | Leu | Val | Ala | Ser | His | Leu | Gln | Ser | Phe | Leu | Glu |
|---|---|---|---|---|---|---|---|---|---|---|---|---|---|---|---|
| 145 | | | | | 150 | | | | | 155 | | | | | 160 |

| Val | Ser | Tyr | Arg | Val | Leu | Arg | His | Leu | Ala | Gln | Pro | Asp | Met | Ala | Thr |
|---|---|---|---|---|---|---|---|---|---|---|---|---|---|---|---|
| | | | 165 | | | | | 170 | | | | | 175 | | |

Pro (2) INFORMATION FOR SEQ ID NO:307:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:307:

| Leu | Leu | Gly | His | Ser | Leu | Gly | Ile | Pro | Trp | Ala | Pro | Leu | Ser | Ser | Cys |
|---|---|---|---|---|---|---|---|---|---|---|---|---|---|---|---|
| 1 | | | | 5 | | | | | 10 | | | | | 15 | |

| Pro | Ser | Gln | Ala | Leu | Gln | Leu | Ala | Gly | Cys | Leu | Ser | Gln | Leu | His | Ser |
|---|---|---|---|---|---|---|---|---|---|---|---|---|---|---|---|
| | | | 20 | | | | | 25 | | | | | 30 | | |

| Gly | Leu | Phe | Leu | Tyr | Gln | Gly | Leu | Leu | Gln | Ala | Leu | Glu | Gly | Ile | Ser |
|---|---|---|---|---|---|---|---|---|---|---|---|---|---|---|---|
| | | | 35 | | | | | 40 | | | | | 45 | | |

| Pro | Glu | Leu | Gly | Pro | Thr | Leu | Asp | Thr | Leu | Gln | Leu | Asp | Val | Ala | Asp |
|---|---|---|---|---|---|---|---|---|---|---|---|---|---|---|---|
| | 50 | | | | | 55 | | | | | 60 | | | | |

| Phe | Ala | Thr | Thr | Ile | Trp | Gln | Gln | Met | Glu | Glu | Leu | Gly | Met | Ala | Pro |
|---|---|---|---|---|---|---|---|---|---|---|---|---|---|---|---|
| 65 | | | | | 70 | | | | | 75 | | | | | 80 |

| Ala | Leu | Gln | Pro | Thr | Gln | Gly | Ala | Met | Pro | Ala | Phe | Ala | Ser | Ala | Phe |
|---|---|---|---|---|---|---|---|---|---|---|---|---|---|---|---|
| | | | | 85 | | | | | 90 | | | | | 95 | |

| Gln | Arg | Arg | Ala | Gly | Gly | Val | Leu | Val | Ala | Ser | His | Leu | Gln | Ser | Phe |
|---|---|---|---|---|---|---|---|---|---|---|---|---|---|---|---|
| | | | 100 | | | | | 105 | | | | | 110 | | |

| Leu | Glu | Val | Ser | Tyr | Arg | Val | Leu | Arg | His | Leu | Ala | Gln | Pro | Asp | Met |
|---|---|---|---|---|---|---|---|---|---|---|---|---|---|---|---|
| | | | 115 | | | | | 120 | | | | | 125 | | |

| Ala | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| | | 130 | | | | | 135 | | | | | 140 | | | |

```
Lys Ser Leu Glu Gln Val Arg Lys Ile Gln Gly Asp Gly Ala Ala Leu
145                 150                 155                 160

Gln Glu Lys Leu Cys Ala Thr Tyr Lys Leu Cys His Pro Glu Glu Leu
                165                 170                 175

Val (2) INFORMATION FOR SEQ ID NO:308:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:308:

Pro Leu Ser Ser Cys Pro Ser Gln Ala Leu Gln Leu Ala Gly Cys Leu
1               5                   10                  15

Ser Gln Leu His Ser Gly Leu Phe Leu Tyr Gln Gly Leu Leu Gln Ala
                20                  25                  30

Leu Glu Gly Ile Ser Pro Glu Leu Gly Pro Thr Leu Asp Thr Leu Gln
            35                  40                  45

Leu Asp Val Ala Asp Phe Ala Thr Thr Ile Trp Gln Gln Met Glu Glu
50                  55                  60

Leu Gly Met Ala Pro Ala Leu Gln Pro Thr Gln Gly Ala Met Pro Ala
65                  70                  75                  80

Phe Ala Ser Ala Phe Gln Arg Arg Ala Gly Gly Val Leu Val Ala Ser
                85                  90                  95

His Leu Gln Ser Phe Leu Glu Val Ser Tyr Arg Val Leu Arg His Leu
                100                 105                 110

Ala Gln Pro Asp Met Ala Thr Pro Leu Gly Pro Ala Ser Ser Leu Pro
            115                 120                 125

Gln Ser Phe Leu Leu Lys Ser Leu Glu Gln Val Arg Lys Ile Gln Gly
130                 135                 140

Asp Gly Ala Ala Leu Gln Glu Lys Leu Cys Ala Thr Tyr Lys Leu Cys
145                 150                 155                 160

His Pro Glu Glu Leu Val Leu Leu Gly His Ser Leu Gly Ile Pro Trp
                165                 170                 175

Ala (2) INFORMATION FOR SEQ ID NO:309:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:309:

Gln Ala Leu Gln Leu Ala Gly Cys Leu Ser Gln Leu His Ser Gly Leu
1               5                   10                  15

Phe Leu Tyr Gln Gly Leu Leu Gln Ala Leu Glu Gly Ile Ser Pro Glu
                20                  25                  30

Leu Gly Pro Thr Leu Asp Thr Leu Gln Leu Asp Val Ala Asp Phe Ala
            35                  40                  45

Thr Thr Ile Trp Gln Gln Met Glu Glu Leu Gly Met Ala Pro Ala Leu
```

-continued

```
                50                  55                  60
Gln Pro Thr Gln Gly Ala Met Pro Ala Phe Ala Ser Ala Phe Gln Arg
 65                  70                  75                  80

Arg Ala Gly Gly Val Leu Val Ala Ser His Leu Gln Ser Phe Leu Glu
                 85                  90                  95

Val Ser Tyr Arg Val Leu Arg His Leu Ala Gln Pro Asp Met Ala Thr
                100                 105                 110

Pro Leu Gly Pro Ala Ser Ser Leu Pro Gln Ser Phe Leu Leu Lys Ser
                115                 120                 125

Leu Glu Gln Val Arg Lys Ile Gln Gly Asp Gly Ala Ala Leu Gln Glu
                130                 135                 140

Lys Leu Cys Ala Thr Tyr Lys Leu Cys His Pro Glu Glu Leu Val Leu
145                 150                 155                 160

Leu Gly His Ser Leu Gly Ile Pro Trp Ala Pro Leu Ser Ser Cys Pro
                165                 170                 175

Ser
```

(2) INFORMATION FOR SEQ ID NO:310:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:310:

```
Leu Gln Leu Ala Gly Cys Leu Ser Gln Leu His Ser Gly Leu Phe Leu
 1               5                  10                  15

Tyr Gln Gly Leu Leu Gln Ala Leu Glu Gly Ile Ser Pro Glu Leu Gly
                20                  25                  30

Pro Thr Leu Asp Thr Leu Gln Leu Asp Val Ala Asp Phe Ala Thr Thr
                35                  40                  45

Ile Trp Gln Gln Met Glu Glu Leu Gly Met Ala Pro Ala Leu Gln Pro
 50                  55                  60

Thr Gln Gly Ala Met Pro Ala Phe Ala Ser Ala Phe Gln Arg Arg Ala
 65                  70                  75                  80

Gly Gly Val Leu Val Ala Ser His Leu Gln Ser Phe Leu Glu Val Ser
                 85                  90                  95

Tyr Arg Val Leu Arg His Leu Ala Gln Pro Asp Met Ala Thr Pro Leu
                100                 105                 110

Gly Pro Ala Ser Ser Leu Pro Gln Ser Phe Leu Leu Lys Ser Leu Glu
                115                 120                 125

Gln Val Arg Lys Ile Gln Gly Asp Gly Ala Ala Leu Gln Glu Lys Leu
                130                 135                 140

Cys Ala Thr Tyr Lys Leu Cys His Pro Glu Glu Leu Val Leu Leu Gly
145                 150                 155                 160

His Ser Leu Gly Ile Pro Trp Ala Pro Leu Ser Ser Cys Pro Ser Gln
                165                 170                 175

Ala
```

(2) INFORMATION FOR SEQ ID NO:311:

(i) SEQUENCE CHARACTERISTICS:
        (A) LENGTH: 177 amino acids
        (B) TYPE: amino acid (C) STRANDEDNESS: unknown
        (D) TOPOLOGY: unknown (ii) MOLECULE TYPE: peptide (xi) SEQUENCE DESCRIPTION: SEQ ID NO:311:

Leu Ala Gly Cys Leu Ser Gln Leu His Ser Gly Leu Phe Leu Tyr Gln
1               5                   10                  15

Gly Leu Leu Gln Ala Leu Glu Gly Ile Ser Pro Glu Leu Gly Pro Thr
                20                  25                  30

Leu Asp Thr Leu Gln Leu Asp Val Ala Asp Phe Ala Thr Thr Ile Trp
            35                  40                  45

Gln Gln Met Glu Glu Leu Gly Met Ala Pro Ala Leu Gln Pro Thr Gln
        50                  55                  60

Gly Ala Met Pro Ala Phe Ala Ser Ala Phe Gln Arg Arg Ala Gly Gly
65                  70                  75                  80

Val Leu Val Ala Ser His Leu Gln Ser Phe Leu Glu Val Ser Tyr Arg
                85                  90                  95

Val Leu Arg His Leu Ala Gln Pro Asp Met Ala Thr Pro Leu Gly Pro
                100                 105                 110

Ala Ser Ser Leu Pro Gln Ser Phe Leu Leu Lys Ser Leu Glu Gln Val
                115                 120                 125

Arg Lys Ile Gln Gly Asp Gly Ala Ala Leu Gln Glu Lys Leu Cys Ala
130                 135                 140

Thr Tyr Lys Leu Cys His Pro Glu Glu Leu Val Leu Leu Gly His Ser
145                 150                 155                 160

Leu Gly Ile Pro Trp Ala Pro Leu Ser Ser Cys Pro Ser Gln Ala Leu
                165                 170                 175

Gln (2) INFORMATION FOR SEQ ID NO:312:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:312:

His Leu Ala Gln Pro Asp Met Ala Thr Pro Leu Gly Pro Ala Ser Ser
1               5                   10                  15

Leu Pro Gln Ser Phe Leu Leu Lys Ser Leu Glu Gln Val Arg Lys Ile
                20                  25                  30

Gln Gly Asp Gly Ala Ala Leu Gln Glu Lys Leu Cys Ala Thr Tyr Lys
            35                  40                  45

Leu Cys His Pro Glu Glu Leu Val Leu Leu Gly His Ser Leu Gly Ile
        50                  55                  60

Pro Trp Ala Pro Leu Ser Ser Cys Pro Ser Gln Ala Leu Gln Leu Ala
65                  70                  75                  80

Gly Cys Leu Ser Gln Leu His Ser Gly Leu Phe Leu Tyr Gln Gly Leu
                85                  90                  95

Leu Gln Ala Leu Glu Gly Ile Ser Pro Glu Leu Gly Pro Thr Leu Asp
                100                 105                 110

Thr Leu Gln Leu Asp Val Ala Asp Phe Ala Thr Thr Ile Trp Gln Gln
                115                 120                 125

-continued

```
Met Glu Glu Leu Gly Met Ala Pro Ala Leu Gln Pro Thr Gln Gly Ala
    130             135             140

Met Pro Ala Phe Ala Ser Ala Phe Gln Arg Arg Ala Gly Gly Val Leu
145             150              155                  160

Val Ala Ser His Leu Gln Ser Phe Leu Glu Val Ser Tyr Arg Val Leu
                165             170                 175

Arg
```

(2) INFORMATION FOR SEQ ID NO:313:

(i) SEQUENCE CHARACTERISTICS:
       (A) LENGTH: 531 base pairs
       (B) TYPE: nucleic acid
       (C) STRANDEDNESS: unknown
       (D) TOPOLOGY: unknown (ii) MOLECULE TYPE: other nucleic acid
       (A) DESCRIPTION: /desc = "synthetic"

(xi) SEQUENCE DESCRIPTION: SEQ ID NO:313:

```
CACCTTGCGC AGCCCGACAT GGCTACACCA TTAGGCCCTG CCAGCTCCCT GCCCCAGAGC    60

TTCCTGCTCA AGTCTTTAGA GCAAGTGAGG AAGATCCAGG GCGATGGCGC AGCGCTCCAG   120

GAGAAGCTGT GTGCCACCTA CAAGCTGTGC CACCCCGAGG AGCTGGTGCT GCTCGGACAC   180

TCTCTGGGCA TCCCCTGGGC TCCCCTGAGC TCCTGCCCCA GCCAGGCCCT GCAGCTGGCA   240

GGCTGCTTGA GCCAACTCCA TAGCGGCCTT TTCCTCTACC AGGGGCTCCT GCAGGCCCTG   300

GAAGGGATAT CCCCCGAGTT GGGTCCCACC TTGGACACAC TGCAGCTGGA CGTCGCCGAC   360

TTTGCCACCA CCATCTGGCA GCAGATGGAA GAACTGGGAA TGGCCCCTGC CCTGCAGCCC   420

ACCCAGGGTG CCATGCCGGC CTTCGCCTCT GCTTTCCAGC GCCGGGCAGG AGGGGTCCTG   480

GTTGCTAGCC ATCTGCAGAG CTTCCTGGAG GTGTCGTACC GCGTTCTACG C           531
```

MULTI-FUNCTIONAL HEMATOPOIETIC FUSION PROTEINS BETWEEN SEQUENCE REARRANGED C-MPL RECEPTOR AGONISTS AND OTHER HEMATOPOIETIC FACTORS

The present application is a Continuation-in-Part of PCT/US 96/15774 filed Oct. 4, 1996 which claims priority under 35 USC §119(e) of U.S. provisional application Serial No. 60/004,834 filed Oct. 5, 1995.

FIELD OF THE INVENTION

The present invention relates to multi-functional hematopoietic receptor agonists.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively, while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies.

U.S. Pat. No. 4,877,729 and U.S. Pat. No. 4,959,455 disclose human IL-3 and gibbon IL-3 cDNAs and the protein sequences for which they code. The hIL-3 disclosed has serine rather than proline at position 8 in the protein sequence.

International Patent Application (PCT) WO 88/00598 discloses gibbon- and human-like IL-3. The hIL-3 contains a $Ser^8$->$Pro^8$ replacement. Suggestions are made to replace Cys by Ser, thereby breaking the disulfide bridge, and to replace one or more amino acids at the glycosylation sites.

U.S. Pat. No. 4,810,643 discloses the DNA sequence encoding human G-CSF.

WO 91/02754 discloses a fusion protein comprised of GM-CSF and IL-3 which has increased biological activity compared to GM-CSF or IL-3 alone. Also disclosed are nonglycosylated IL-3 and GM-CSF analog proteins as components of the multi-functional hematopoietic receptor agonist.

WO 92/04455 discloses fusion proteins composed of IL-3 fused to a lymphokine selected from the group consisting of IL-3, IL-6, IL-7, IL-9, IL-11, EPO and G-CSF.

WO 95/21197 and WO 95/21254 disclose fusion proteins capable of broad multi-functional hematopoietic properties.

GB 2,285,446 relates to the c-mpl ligand (thrombopoietin) and various forms of thrombopoietin which are shown to influence the replication, differentiation and maturation of megakaryocytes and megakaryocytes progenitors which may be used for the treatment of thrombocytopenia.

EP 675,201 A1 relates to the c-mpl ligand (Megakaryocyte growth and development factor (MGDF), allelic variations of c-mpl ligand and c-mpl ligand attached to water soluble polymers such as polyethylene glycol.

WO 95/21920 provides the murine and human c-mpl ligand and polypeptide fragments thereof. The proteins are useful for in vivo and ex vivo therapy for stimulating platelet production.

Rearrangement of Protein Sequences

In evolution, rearrangements of DNA sequences serve an important role in generating a diversity of protein structure and function. Gene duplication and exon shuffling provide an important mechanism to rapidly generate diversity and thereby provide organisms with a competitive advantage, especially since the basal mutation rate is low (Doolittle, *Protein Science* 1: 191–200, 1992).

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., *Proc. Natl. Acad. Sci. U.S.A.* 76: 3218–3222, 1979; Teather & Erfle, *J. Bacteriol.* 172: 3837–3841, 1990; Schimming et al., *Eur. J. Biochem.* 204: 13–19, 1992; Yamiuchi and Minamikawa, *FEBS Lett.* 260: 127–130, 1991; MacGregor et al., *FEBS Lett.* 378: 263–266). The first in vitro application of this type of rearrangement to proteins was described by Goldenberg and Creighton (*J. Mol. Biol.* 165: 407–413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain.

This approach has been applied to proteins which range in size from 58 to 462 amino acids (Goldenberg & Creighton, *J. Mol. Biol.* 165: 407–413, 1983; Li & Coffino, *Mol. Cell. Biol.* 13: 2377–2383, 1993). The proteins examined have represented a broad range of structural classes, including proteins that contain predominantly α-helix (interleukin-4; Kreitman et al., *Cytokine* 7: 311–318, 1995), β-sheet (interleukin-1; Horlick et al., *Protein Eng.* 5: 427–431, 1992), or mixtures of the two (yeast phosphoribosyl anthranilate isomerase; Luger et al., *Science* 243: 206–210, 1989). Broad categories of protein function are represented in these sequence reorganization studies:

Enzymes

T4 lysozyme Zhang et al., *Biochemistry* 32: 12311–12318, 1993; Zhang et al., *Nature Struct. Biol.* 1: 434–438 (1995)

dihydrofolate reductase Buchwalder et al., *Biochemistry* 31: 1621–1630, 1994; Protasova et al., *Prot. Eng.* 7: 1373–1377, 1995)

ribonuclease T1 Mullins et al., *J. Am. Chem. Soc.* 116: 5529–5533, 1994; Garrett et al., *Protein Science* 5: 204–211, 1996)

Bacillus β-glucanse Hahn et al., *Proc. Natl. Acad. Sci. U.S.A.* 91: 10417–10421, 1994)

aspartate transcarbamoylase Yang & Schachman, *Proc. Natl. Acad. Sci. U.S.A.* 90: 11980–11984, 1993)

phosphoribosyl anthranilate isomerase Luger et al., *Science* 243: 206–210 (1989; Luger et al., *Prot. Eng.* 3: 249–258, 1990)

pepsin/pepsinogen Lin et al., *Protein Science* 4: 159–166, 1995)

glyceraldehyde-3-phosphate dehydrogenase Vignais et al., *Protein Science* 4: 994–1000, 1995)

ornithine decarboxylase Li & Coffino, *Mol. Cell. Biol.* 13: 2377–2383, 1993)

yeast phosphoglycerate dehydrogenase Ritco-Vonsovici et al., *Biochemistry* 34: 16543–16551, 1995)

Enzyme Inhibitor basic pancreatic trypsin inhibitor Goldenberg & Creighton, *J. Mol. Biol.* 165: 407–413, 1983)

Cytokines interleukin-1β Horlick et al., *Protein Eng.* 5: 427–431, 1992)
interleukin-4 Kreitman et al., *Cytokine* 7: 311–318, 1995)

Tyrosine Kinase Recognition Domain

α-spectrin SH3 domain Viguera, et al., *J. Mol. Biol.* 247: 670–681, 1995)

Transmembrane Protein omp A Koebnik & Kramer, *J. Mol. Biol.* 250: 617–626, 1995)

Chimeric Protein interleukin-4-Pseudomonas exotoxin Kreitman et al., *Proc. Natl. Acad. Sci. U.S.A.* 91: 6889–6893, 1994).

The results of these studies have been highly variable. In many cases substantially lower activity, solubility or thermodynamic stability were observed (*E. coli* dihydrofolate reductase, aspartate transcarbamoylase, phosphoribosyl anthranilate isomerase, glyceraldehyde-3-phosphate dehydrogenase, ornithine decarboxylase, omp A, yeast phosphoglycerate dehydrogenase). In other cases, the sequence rearranged protein appeared to have many nearly identical properties as its natural counterpart (basic pancreatic trypsin inhibitor, T4 lysozyme, ribonuclease T1, Bacillus β-glucanase, interleukin-1β, α-spectrin SH3 domain, pepsinogen, interleukin-4). In exceptional cases, an unexpected improvement over some properties of the natural sequence was observed, e.g., the solubility and refolding rate for rearranged α-spectrin SH3 domain sequences, and the receptor affinity and anti-tumor activity of transposed interleukin-4-Pseudomonas exotoxin fusion molecule (Kreitman et al., *Proc. Natl. Acad. Sci. U.S.A.* 91: 6889–6893, 1994; Kreitman et al., *Cancer Res.* 55: 3357–3363, 1995).

The primary motivation for these types of studies has been to study the role of short-range and long-range interactions in protein folding and stability. Sequence rearrangements of this type convert a subset of interactions that are long-range in the original sequence into short-range interactions in the new sequence, and vice versa. The fact that many of these sequence rearrangements are able to attain a conformation with at least some activity is persuasive evidence that protein folding occurs by multiple folding pathways (Viguera, et al., *J. Mol. Biol.* 247: 670–681, 1995). In the case of the SH3 domain of a-spectrin, choosing new termini at locations that corresponded to β-hairpin turns resulted in proteins with slightly less stability, but which were nevertheless able to fold.

The positions of the internal breakpoints used in the studies cited here are found exclusively on the surface of proteins, and are distributed throughout the linear sequence without any obvious bias towards the ends or the middle (the variation in the relative distance from the original N-terminus to the breakpoint is ca. 10 to 80% of the total sequence length). The linkers connecting the original N- and C-termini in these studies have ranged from 0 to 9 residues. In one case (Yang & Schachman, *Proc. Natl. Acad. Sci. U.S.A.* 90: 11980–11984, 1993), a portion of sequence has been deleted from the original C-terminal segment, and the connection made from the truncated C-terminus to the original N-terminus. Flexible hydrophilic residues such as Gly and Ser are frequently used in the linkers. Viguera, et al. (*J. Mol. Biol.* 247: 670–681, 1995) compared joining the original N- and C-termini with 3- or 4-residue linkers; the 3-residue linker was less thermodynamically stable. Protasova et al. (*Protein Eng.* 7: 1373–1377, 1994) used 3- or 5-residue linkers in connecting the original N-termini of *E. coli* dihydrofolate reductase; only the 3-residue linker produced protein in good yield.

SUMMARY OF THE INVENTION

Novel hematopoietic proteins of this invention are represented by the formulas:

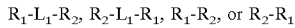

wherein $R_1$ and $R_2$ are independently selected from the group consisting of;

(I) A polypeptide comprising; a modified human G-CSF amino acid sequence of the formula:

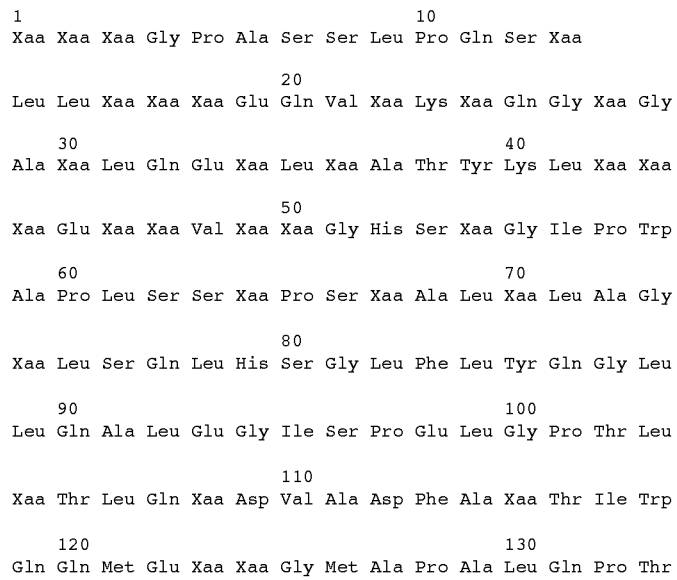

-continued

```
                    140
Gln Gly Ala Met Pro Ala Phe Ala Ser Ala Xaa Gln Xaa Xaa Ala 150                                 160
Gly Gly Val Leu Val Ala Ser Xaa Leu Gln Xaa Phe Leu Xaa Xaa

170
Ser Tyr Arg Val Leu Xaa Xaa Leu Ala Gln Pro (SEQ ID NO:1)
``` wherein
Xaa at position 1 is Thr, Ser, Arg, Tyr or Gly;
Xaa at position 2 is Pro or Leu;
Xaa at position 3 is Leu, Arg, Tyr or Ser;
Xaa at position 13 is Phe, Ser, His, Thr or Pro;
Xaa at position 16 is Lys, Pro, Ser, Thr or His;
Xaa at position 17 is Cys, Ser, Gly, Ala, Ile, Tyr or Arg;
Xaa at position 18 is Leu, Thr, Pro, His, Ile or Cys;
Xaa at position 22 is Arg, Tyr, Ser, Thr or Ala;
Xaa at position 24 is Ile, Pro, Tyr or Leu;
Xaa at position 27 is Asp, or Gly;
Xaa at position 30 is Ala, Ile, Leu or Gly;
Xaa at position 34 is Lys or Ser;
Xaa at position 36 is Cys or Ser;
Xaa at position 42 is Cys or Ser;
Xaa at position 43 is His, Thr, Gly, Val, Lys, Trp, Ala, Arg, Cys, or Leu;
Xaa at position 44 is Pro, Gly, Arg, Asp, Val, Ala, His, Trp, Gln, or Thr;
Xaa at position 46 is Glu, Arg, Phe, Arg, Ile or Ala;
Xaa at position 47 is Leu or Thr;
Xaa at position 49 is Leu, Phe, Arg or Ser;
Xaa at position 50 is Leu, Ile, His, Pro or Tyr;
Xaa at position 54 is Leu or His;
Xaa at position 64 is Cys or Ser;
Xaa at position 67 is Gln, Lys, Leu or Cys;
Xaa at position 70 is Gln, Pro, Leu, Arg or Ser;
Xaa at position 74 is Cys or Ser;
Xaa at position 104 is Asp, Gly or Val;
Xaa at position 108 is Leu, Ala, Val, Arg, Trp, Gln or Gly;
Xaa at position 115 is Thr, His, Leu or Ala;
Xaa at position 120 is Gln, Gly, Arg, Lys or His;
Xaa at position 123 is Glu, Arg, Phe or Thr;
Xaa at position 144 is Phe, His, Arg, Pro, Leu, Gln or Glu;
Xaa at position 146 is Arg or Gln;
Xaa at position 147 is Arg or Gln;
Xaa at position 156 is His, Gly or Ser;
Xaa at position 159 is Ser, Arg, Thr, Tyr, Val or Gly;
Xaa at position 162 is Glu, Leu, Gly or Trp;
Xaa at position 163 is Val, Gly, Arg or Ala;
Xaa at position 169 is Arg, Ser, Leu, Arg or Cys;
Xaa at position 170 is His, Arg or Ser;
wherein optionally 1–11 amino acids from the N-terminus and 1–5 from the C-terminus can be deleted; and
wherein the N-terminus is joined to the C-terminus directly or through a linker capable of joining the N-terminus to the C-terminus and having new C- and N-termini at amino acids;

| | | |
|---|---|---|
| 39–40

```
                        -continued
Xaa Xaa Xaa Xaa Xaa Xaa Xaa Xaa Xaa Xaa Xaa Xaa Xaa Xaa Xaa
                95                  100                 105

Xaa Phe Xaa Xaa Xaa Xaa Xaa Xaa Xaa Xaa Xaa Xaa Xaa Xaa
                110                 115                 120

Xaa Xaa Xaa Gln Gln Thr Thr Leu Ser Leu Ala Ile Phe
                125                 130    (SEQ ID NO:2);
``` wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Gly, Trp, Lys, Phe, Leu, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp, Pro, Met, Lys, His, Thr, Val, Tyr, Glu, Asn, Ser, Ala, Gly, Ile, Leu, or Gln;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein optionally from 1 to 14 amino acids can be deleted from the N-terminus and/or from 1 to 15 amino acids can be deleted from the C-terminus; and wherein from 0 to 44 of the amino acids designated by Xaa are different from the corresponding amino acids of native (1–133) human interleukin-3; and wherein the N-terminus is joined to the C-terminus directly or through a linker ($L_2$) capable of joining the N-terminus to the C-terminus and having new C- and N-termini at amino acids;

| | | |
|---|---|---|
| 26–27 | 49–50 | 83–84 |
| 27–28 | 50–51 | 84–85 |
| 28–29 | 51–52 | 85–86 |
| 29–30 | 52–53 | 86–87 |
| 30–31 | 53–54 | 87–88 |
| 31–32 | 54–55 | 88–89 |
| 32–33 | 64–65 | 89–90 |
| 33–34 | 65–66 | 90–91 |
| 34–35 | 66–67 | 91–92 |
| 35–36 | 67–68 | 92–93 |
| 36–37 | 68–69 | 97–98 |
| 37–38 | 69–70 | 98–99 |
| 38–39 | 70–71 | 99–100 |
| 39–40 | 71–72 | 100–101 |
| 40–41 | 72–73 | 101–102 |
| 41–42 | 82–83 | 102–103 |
| | | or 103–104; | or (III) A polypeptide comprising; a modified human c-mpl ligand amino acid sequence of the formula:

```
SerProAlaProProAlaCysAspLeuArgValLeuSerLysLeuLeuArgAspSer
1           5                10               15

HisValLeuHisSerArgLeuSerGlnCysProGluValHisProLeuProThrPro
20              25               30               35

ValLeuLeuProAlaValAspPheSerLeuGlyGluTrpLysThrGlnMetGluGlu
   40              45               50               55

ThrLysAlaGlnAspIleLeuGlyAlaValThrLeuLeuLeuGluGlyValMetAla
      60              65               70               75

AlaArgGlyGlnLeuGlyProThrCysLeuSerSerLeuLeuGlyGlnLeuSerGly
         80              85               90               95

GlnValArgLeuLeuLeuGlyAlaLeuGlnSerLeuLeuGlyThrGlnXaaXaaXaa
            100             105              110

XaaGlyArgThrThrAlaHisLysAspProAsnAlaIlePheLeuSerPheGlnHis
115            120              125              130

LeuLeuArgGlyLysValArgPheLeuMetLeuValGlyGlySerThrLeuCysVal
   135             140              145              150

ArgArgAlaProProThrThrAlaValProSerArgThrSerLeuValLeuThrLeu
      155             160              165              170

AsnGluLeuProAsnArgThrSerGlyLeuLeuGluThrAsnPheThrAlaSerAla
         175             180              185              190
```

-continued
```
ArgThrThrGlySerGlyLeuLeuLysTrpGlnGlnGlyPheArgAlaLysIlePro
            195                 200                 205

GlyLeuLeuAsnGlnThrSerArgSerLeuAspGlnIleProGlyTyrLeuAsnArg
210             215                 220                 225

IleHisGluLeuLeuAsnGlyThrArgGlyLeuPheProGlyProSerArgArgThr
    230             235                 240                 245

LeuGlyAlaProAspIleSerSerGlyThrSerAspThrGlySerLeuProProAsn
        250             255                 260             265

LeuGlnProGlyTyrSerProSerProThrHisProProThrGlyGlnTyrThrLeu
            270             275                 280             285

PheProLeuProProThrLeuProThrProValValGlnLeuHisProLeuLeuPro
            290                 295             300

AspProSerAlaProThrProThrProThrSerProLeuLeuAsnThrSerTyrThr
305             310                 315             320

HisSerGlnAsnLeuSerGlnGluGly  (SEQ ID NO:3)
    325             330     332
153
``` wherein;
Xaa at position 112 is deleted or Leu, Ala, Val, Ile, Pro, Phe, Trp, or Met;
Xaa at position 113 is deleted or Pro, Phe, Ala, Val, Leu, Ile, Trp, or Met;
Xaa at position 114 is deleted or Pro, Phe, Ala, Val, Leu, Ile, Trp, or Met;
Xaa at position 115 is deleted or Gln, Gly, Ser, Thr, Tyr, or Asn; and
wherein the N-terminus is joined to the C-terminus directly or through a linker ($L_2$) capable of joining the N-terminus to the C-terminus and having new C- and N-termini at amino acids;

| | | |
|---|---|---|
| 26–27 | 51–52 | 108–109 |
| 27–28 | 52–53 | 109–110 |
| 28–29 | 53–54 | 110–111 |
| 29–30 | 54–55 | 111–112 |
| 30–31 | 55–56 | 112–113 |
| 32–33 | 56–57 | 113–114 |
| 33–34 | 57–58 | 114–115 |
| 34–35 | 58–59 | 115–116 |
| 36–37 | 59–60 | 116–117 |
| 37–38 | 78–79 | 117–118 |
| 38–39 | 79–80 | 118–119 |
| 40–41 | 80–81 | 119–120 |
| 41–42 | 81–82 | 120–121 |
| 42–43 | 82–83 | 121–122 |
| 43–44 | 83–84 | 122–123 |
| 44–45 | 84–85 | 123–124 |
| 46–47 | 85–86 | 124–125 |
| 47–48 | 86–87 | 125–126 |
| 48–49 | 87–88 | 126–127 |
| 50–51 | 88–89 | or 127–128; | or (IV) A polypeptide comprising; a modified hIL-3 amino acid sequence of the formula:

```
Ala Pro Met Thr Gln Thr Thr Ser Leu Lys Thr Ser Trp Val Asn
1               5                   10                  15

Cys Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Asn Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa Xaa
                65                  70                  75

Xaa Xaa Xaa Xaa Xaa Xaa Xaa Xaa Xaa Xaa Xaa Xaa Xaa Xaa Xaa
                80                  85                  90

Xaa Xaa Xaa Xaa Xaa Xaa Xaa Xaa Xaa Xaa Xaa Xaa Xaa Xaa Xaa
                95                  100                 105

Xaa Phe Xaa Xaa Xaa Xaa Xaa Xaa Xaa Xaa Xaa Xaa Xaa Xaa Xaa
                110                 115                 120

Xaa Xaa Xaa Gln Gln Thr Thr Leu Ser Leu Ala Ile Phe
                125                 130  (SEQ ID NO:2)
``` wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Gly, Trp, Lys, Phe, Leu, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;

Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein optionally from 1 to 14 amino acids can be deleted from the N-terminus and/or from 1 to 15 amino acids can be deleted from the C-terminus; and wherein from 1 to 44 of the amino acids designated by Xaa are different from the corresponding amino acids of native (1–133) human interleukin-3; or
(V) a colony stimulating factor;
and wherein $L_1$ is a linker capable of linking $R_1$ to $R_2$;
with the proviso that at least $R_1$ or $R_2$ is selected from the polypeptide of formula (I), (II), or (III); and
said hematopoietic protein can optionally be immediately preceded by (methionine$^{-1}$), (alanine$^{-1}$) or (methionine$^{-2}$, alanine$^{-1}$).

The more preferred breakpoints at which new C-terminus and N-terminus can be made in the polypeptide (I) above are; 38-39, 39-40, 40-41, 41-42, 48-49, 53-54, 54-55, 55-56, 56-57, 57-58, 58-59, 59-60, 60-61, 61-62, 62-63, 64-65, 65-66, 66-67, 67-68, 68-69, 69-70, 96-97, 125-126, 126-127, 127-128, 128-129, 129-130, 130-131, 131-132, 132-133, 133-134, 134-135, 135-136, 136-137, 137-138, 138-139, 139-140, 140-141 and 141-142.

The most preferred breakpoints at which new C-terminus and N-terminus can be made in the polypeptide (I) above are; 38-39, 48-49, 96-97, 125-126, 132-133 and 141-142.

The more preferred breakpoints at which new C-terminus and N-terminus can be made in the polypeptide (II) above are; 28-29, 29-30, 30-31, 31-32, 32-33, 33-34, 34-35, 35-36, 36-37, 37-38, 38-39, 39-40, 66-67, 67-68, 68-69, 69-70, 70-71, 84-85, 85-86, 86-87, 87-88, 88-89, 89-90, 90-91, 98-99, 99-100, 100-101 and 101-102.

The most preferred breakpoints at which new C-terminus and N-terminus can be made in the polypeptide (II) above are; 34-35, 69-70 and 90-91.

The more preferred breakpoints at which new C-terminus and N-terminus can be made in the polypeptide (III) above or the amino acid sequence of (SEQ ID NO:256) are; 80-81, 81-82, 82-83, 83-84, 84-85, 85-86, 86-87, 108-109, 109-110, 110-111, 111-112, 112-113, 113-114, 114-115, 115-116, 116-117, 117-118, 118-119, 119-120, 120-121, 121-122, 122-123, 123-124, 124-125, 125-126 and 126-127.

The most preferred breakpoints at which new C-terminus and N-terminus can be made in the polypeptide (III) above or the amino acid sequence of (SEQ ID NO:256) are; 81-82, 108-109, 115-116, 119-120, 122-123 and 125-126.

The invention is also intended to include multifunctional receptor agonists which comprises a sequence rearranged c-mpl receptor agonist in which the cysteine at position 7 and/or 151 are substituted with another amino acid. Preferably, the substitution at position 7 and 151 is Ser, Ala, Gly, His, Asn, Asp, Thr, Phe or Thr. More preferably, the substitution at position 7 and 151 is Ser, Ala, Gly, His or Asn.

The multifunctional receptor agonist of the present invention can also be represented by the following formula:

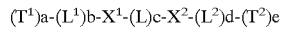

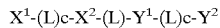

in which:
$X^1$ is a peptide comprising an amino acid sequence corresponding to the sequence of residues n+1 through J of the original protein having amino acids residues numbered sequentially 1 through J with an amino terminus at residue 1;

L is an optional linker;

$X^2$ is a peptide comprising an amino acid sequence of residues 1 through n of the original protein;

$Y^1$ is a peptide comprising an amino acid sequence corresponding to the sequence of residues n=1 through K of the original protein having amino acids residues numbered sequentially 1 through K with an amino terminus at residue 1;

$Y^2$ is a peptide comprising an amino acid sequence of residues 1 through n of the original protein;

$L^1$ and $L^2$ are optional peptide spacers:

n is an integer ranging from 1 to J–1;

b, c, and d are each independently 0 or 1;

a and e are either 0 or 1, provided that both a and e cannot both be 0; and $T^1$ and $T^2$ are proteins.

Additionally, the present invention relates to recombinant expression vectors comprising nucleotide sequences encoding the multi-functional hematopoietic receptor agonists, related microbial expression systems, and processes for making the multi-functional hematopoietic receptor agonists. The invention also relates to pharmaceutical compositions containing the multi-functional hematopoietic receptor agonists, and methods for using the multi-functional hematopoietic receptor agonists.

In addition to the use of the multi-functional hematopoietic receptor agonists of the present invention in vivo, it is envisioned that in vitro uses would include the ability to stimulate bone marrow and blood cell activation and growth before infusion into patients.

BRIEF DESCRIPTION OF THE FIGURES

FIG. 4 shows a schematic of Method III, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to amino acid 1 through a linker region and a new C-terminus created at amino acid 96 of the original sequence.

DETAILED DESCRIPTION OF THE INVENTION

Figure 1:
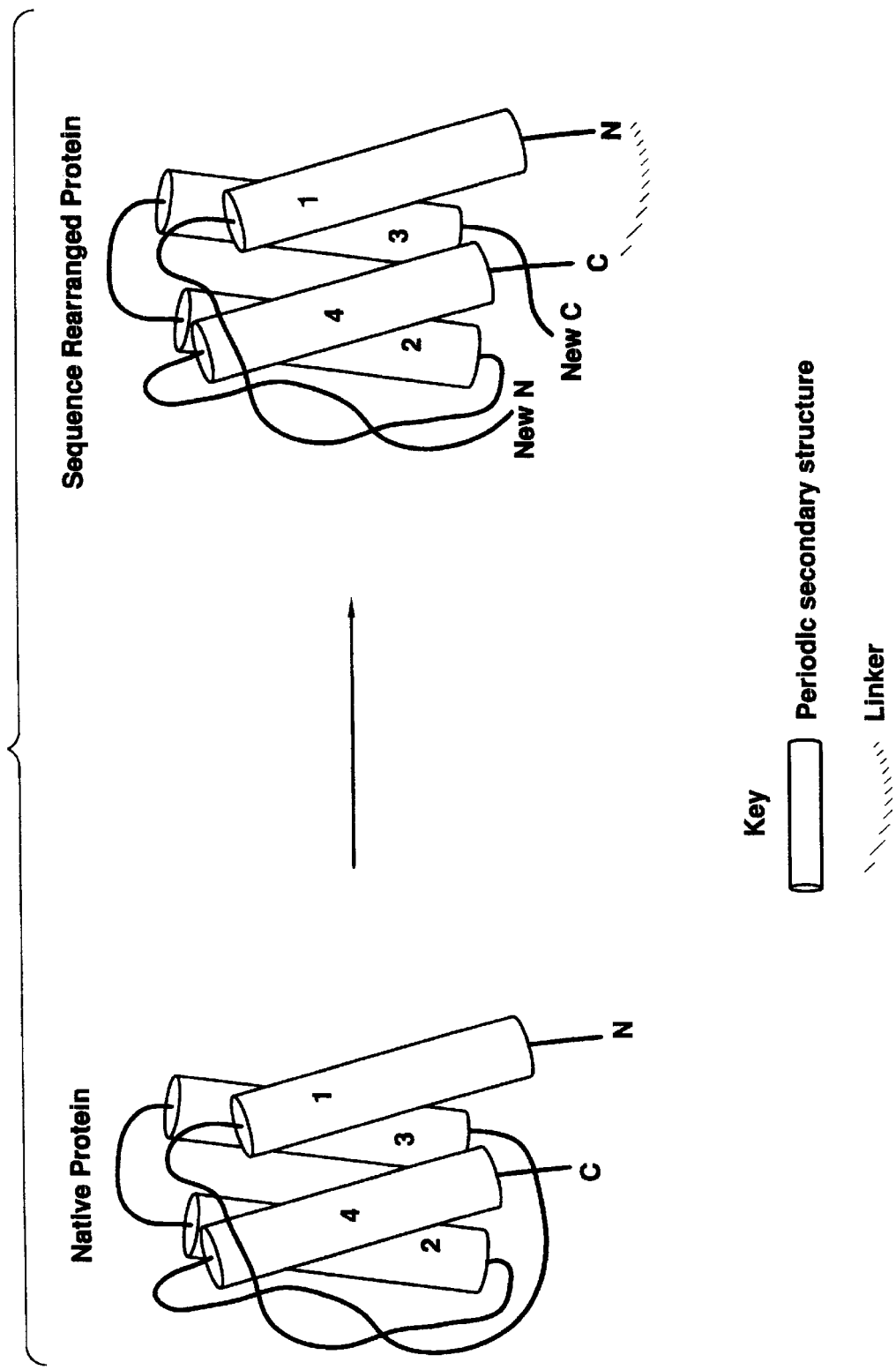
FIG. 1 schematically illustrates the sequence rearrangement of a protein. The N-terminus (N) and the C-terminus (C) of the native protein are joined through a linker, or joined directly. The protein is opened at a breakpoint creating a new N-terminus (new N) and a new C-terminus (new-C) resulting in a protein with a new linear amino acid sequence. A rearranged molecule may be synthesized de novo as linear molecule and not go through the steps of joining the original N-terminus and the C-terminus and opening of the protein at the breakpoint.

The present invention encompasses multi-functional hematopoietic receptor agonists formed from covalently linked polypeptides, each of which may act through a different and specific cell receptor to initiate complementary biological activities. Hematopoiesis requires a complex series of cellular events in which stem cells generate continuously into large populations of maturing cells in all major lineages. There are currently at least 20 known regulators with hematopoietic proliferative activity. Most of these proliferative regulators can only stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, *Nature* 339: 27, 1989). Other mechanisms could explain synergy. For example, if one signaling pathway is limited by an intermediate activation of an additional signaling pathway which is caused by a second factor, then this may result in a super additive response. In some cases, activation of one receptor type can induce an enhanced expression of other receptors (Metcalf, *Blood* 82: 3515–3523, 1993). Two or more factors may result in a different pattern of cell lineages than from a single factor. The use of multi-functional hematopoietic receptor agonists may have a potential clinical advantage resulting from a proliferative response that is not possible by any single factor.

The receptors of hematopoietic and other growth factors can be grouped into two distinct families of related proteins: (1) tyrosine kinase receptors, including those for epidermal growth factor, M-CSF (Sherr, *Blood* 75: 1, 1990) and SCF (Yarden et al., *EMBO J.* 6: 3341, 1987): and (2) hematopoietic receptors, not containing a tyrosine kinase domain, but exhibiting obvious homology in their extracellular domain (Bazan, *PNAS USA* 87: 6934–6938, 1990). Included in this latter group are erythropoietin (EPO) (D'Andrea et al., *Cell* 57: 277, 1989), GM-CSF (Gearing et al., *EMBO J.* 8: 3667, 1989), IL-3 (Kitamura et al., *Cell* 66: 1165, 1991), G-CSF (Fukunaga et al., *J. Bio. Chem.* 265: 14008–15, 1990), IL-4 (Harada et al., *PNAS USA* 87: 857, 1990), IL-5 (Takaki et al., *EMBO J.* 9: 4367, 1990), IL-6 (Yamasaki et al., *Science* 241: 825, 1988), IL-7 (Goodwin et al., *Cell* 60: 941–51, 1990), LIF (Gearing et al., *EMBO J.* 10: 2839, 1991) and IL-2 (Cosman et al., *Mol-Immunol.* 23: 935–94, 1986). Most of the latter group of receptors exists in a high-affinity form as heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Kitamura et al., *Cell* 66: 1165, 1991), Takaki et al., *EMBO J.* 10: 2833–8, 1991) and receptor complexes for IL-6, LIF and IL-11 share a common β-chain (gp130) (Taga et al., *Cell* 58: 573–81, 1989; Gearing et al., *Science* 255: 1434–7, 1992). The receptor complexes of IL-2, IL-4, IL-7, IL-9 and IL-15 share a common γ-chain (Kondo et al., *Science* 262: 1874, 1993; Russell et al., *Science* 266: 1042–1045, 1993; Noguchi et al., *Science* 262: 1877, 1993; Giri et al., *EMBO J.* 13: 2822–2830, 1994).

The use of a multiply acting hematopoietic factor may also have a potential advantage by reducing the demands placed on factor-producing cells and their induction systems. If there are limitations in the ability of a cell to produce a factor, then by lowering the required concentrations of each of the factors, and using them in combination may usefully reduce demands on the factor-producing cells. The use of a multiply acting hematopoietic factor may lower the amount of the factors that would be needed, probably reducing the likelihood of adverse side-effects.

Novel compounds of this invention are represented by a formula selected from the group consisting of:

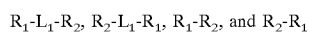

$R_1$-$L_1$-$R_2$, $R_2$-$L_1$-$R_1$, $R_1$-$R_2$, and $R_2$-$R_1$

Where $R_1$ and $R_2$ are as defined above. $R_2$ is preferably a colony stimulating factor with a different but complementary activity than $R_1$. By complementary activity is meant activity which enhances or changes the response to another cell modulator. The $R_1$ polypeptide is joined either directly or through a linker segment to the $R_2$ polypeptide. The term "directly" defines multi-functional hematopoietic receptor agonists in which the polypeptides are joined without a peptide linker. Thus $L_1$ represents a chemical bond or polypeptide segment to which both $R_1$ and $R_2$ are joined in frame, most commonly $L_1$ is a linear peptide to which $R_1$ and $R_2$ are joined by amide bonds linking the carboxy terminus of $R_1$ to the amino terminus of $L_1$ and carboxy terminus of $L_1$ to the amino terminus of $R_2$. By "joined in frame" is meant that there is no translation termination or disruption between the reading frames of the DNA encoding $R_1$ and $R_2$.

A non-exclusive list of other growth factors, i.e. colony stimulating factors (CSFs), are cytokines, lymphokines, interleukins, hematopoietic growth factors which can be joined to (I), (II) or (III) include GM-CSF, G-CSF, c-mpl ligand (also known as TPO or MGDF), M-CSF, erythropoietin (EPO), IL-1, IL-4, IL-2, IL-3, IL-5, IL 6, IL-7, IL-8, IL-9, IL-10, IL-11, IL-12, IL-13, IL-15, LIF, flt3 ligand, human growth hormone, and stem cell factor (SCF) also known as steel factor or c-kit ligand. Additionally, this invention encompasses the use of modified $R_1$ or $R_2$ molecules or mutated or modified DNA sequences encoding these $R_1$ or $R_2$ molecules. The present invention also includes multi-functional hematopoietic receptor agonists in which $R_1$ or $R_2$ is an hIL-3 variant, c-mpl ligand variant, or G-CSF variant. A "hIL-3 variant" is defined as a hIL-3 molecule which has amino acid substitutions and/or portions of hIL-3 deleted as disclosed in WO 94/12638, WO 94/12639 and WO 95/00646, as well as other variants known in the art. A "c-mpl ligand variant" is defined an c-mpl ligand molecule which has amino acid substitutions and/or portions of c-mpl ligand deleted, disclosed in U.S. application Ser. No. 08/383,035 as well as other variants known in the art. A "G-CSF variant" is defined an G-CSF molecule which has amino acid substitutions and/or portions of G-CSF deleted, as disclosed herein, as well as other variants known in the art.

The linking group (Li) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic characteristics which could interact with the functional protein domains and (4) provide steric separation of $R_1$ and $R_2$ such that $R_1$ and $R_2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the multi-functional hematopoietic receptor agonists.

Preferred $L_1$ linkers of the present invention include sequences selected from the group of formulas: $(Gly^3Ser)^n$ (SEQ ID NO:4), $(Gly^4Ser)^n$ (SEQ ID NO:5), $(Gly^5Ser)^n$ (SEQ ID NO:6), $(Gly^nSer)^n$ (SEQ ID NO:7) or $(AlaGlySer)^n$ (SEQ ID NO:8).

One example of a highly-flexible linker is the glycine and serine-rich spacer region present within the pIII protein of the filamentous bacteriophages, e.g. bacteriophages M13 or fd (Schaller et al., *PNAS USA* 72: 737–741, 1975). This region provides a long, flexible spacer region between two domains of the pIII surface protein. The spacer region consists of the amino acid sequence:

GlyGlyGlySerGlyGlyGlySerGlyG-
   lyGlySerGluGlyGlyGlySerGluG-
   lyGlyGlySerGluGlyGlyGlySerGluGlyGlyGly-
   SerGlyGlyGlySer            (SEQ ID NO:9).

The present invention also includes linkers in which an endopeptidase recognition sequence is included. Such a cleavage site may be valuable to separate the individual components of the multi-functional hematopoietic receptor agonist to determine if they are properly folded and active in vitro. Examples of various endopeptidases include, but are not limited to, plasmin, enterokinase, kallikrein, urokinase, tissue plasminogen activator, clostripain, chymosin, collagenase, Russell's viper venom protease, postproline cleavage enzyme, V8 protease, Thrombin and factor Xa.

Peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Preferred linkers of the present invention include sequences derived from murine IgG gamma 2b hinge region in which the cysteines have been changed to serines. These linkers may also include an endopeptidase cleavage site. Examples of such linkers include the following sequences:

IleSerGluProSerGlyProIleSerThrIleAsnProSerProProSerLysGlu-
   SerHisLysSerPro            (SEQ ID NO:10)

and

IleGluGlyArgIleSerGluProSerGlyProIleSerThrIleAsnProSerProPro-
   SerLysGluSerHisLysSerPro            (SEQ ID NO:11).

The present invention is, however, not limited by the form, size or number of linker sequences employed and the only requirement of the linker is that functionally it does not interfere with the folding and function of the individual molecules of the multi-functional hematopoietic receptor agonist.

One aspect of the invention includes multi-functional hematopoietic receptor agonists which comprise a sequence rearranged c-mpl receptor agonist in which the cysteine(s) at position 7 and 151 of c-mpl ligand, have been substituted with another amino acid. Kaushansky et al. (*Blood* 86: 255a Abstract 1008, 1995) teaches that all four of the cysteines at positions 7, 29, 85, and 151 are required for bioactivity. The presence of cysteines in a protein can cause problems in processing when the protein is being produced recombinantly in a bacterial host. Microbially produced cysteine-containing proteins may tend to form multimers which greatly complicate purification of the protein product. Several additional purification steps, such as reduction and reoxidation of the recombinant protein may be required to obtain the protein in the proper confirmation. Removal of one of the cysteine residues, with concurrent replacement by a chemically equivalent neutral amino acid, would be desirable, in order to simplify the isolation and purification of the molecule. However, the successful removal of cysteines from biologically active molecules is unpredictable, in that the tertiary structure in the absence of the normally formed disulfide bridges, can be substantially altered. A molecule in which a pair of cysteines at positions 7 and 151 are substituted with another amino acid may have one or more advantages including, but not limited to: 1) increased folding efficiency of the heterologously expressed protein; 2) elimination of mispaired disulfides, 3) use of milder refold conditions (ie. Guanidine vs. Urea); 4) increased purification yields, 5) increased protein solubility; and 6) increased protein stability.

Determination of the Linker $L_2$

The length of the amino acid sequence of the linker $L_2$ to be used in $R_1$ and/or $R_2$ can be selected empirically or with guidance from structural information, or by using a combination of the two approaches.

When no structural information is available, a small series of linkers can be prepared for testing using a design whose length is varied in order to span a range from 0 to 50 Å and whose sequence is chosen in order to be consistent with surface exposure (hydrophilicity, Hopp & Woods, *Mol. Immunol.* 20: 483–489, 1983), Kyte & Doolittle, *J. Mol. Biol.* 157: 105–132; solvent exposed surface area, Lee & Richards, *J. Mol. Biol.* 55: 379–400, 1971) and the ability to adopt the necessary conformation with out deranging the conformation of $R^1$ or $R^2$ (conformationally flexible; Karplus & Schulz, *Naturwissenschaften* 72: 212–213, 1985). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser (SEQ ID NO:12) repeated n times, where n is 1, 2, 3 or 4. Those skilled in the art will recognize that there are many such sequences that vary in length or composition that can serve as linkers with the primary consideration being that they be neither excessively long nor short (cf., Sandhu, *Critical Rev. Biotech.* 12: 437–462, 1992); if they are too long, entropy effects will likely destabilize the three-dimensional fold, and may also make folding kinetically impractical, and if they are too short, they will likely destabilize the molecule because of torsional or steric strain.

Those skilled in the analysis of protein structural information will recognize that using the distance between the chain ends, defined as the distance between the c-alpha carbons, can be used to define the length of the sequence to be used, or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser (SEQ ID NO:12) cassette approach mentioned above; or optionally a combination of the original sequence and new sequence having the appropriate total length may be used.

Determination of the Amino and Carboxyl Termini of $R_1$ and $R_2$

Sequences of $R_1$ and $R_2$ capable of folding to biologically active states can be prepared by appropriate selection of the beginning (amino terminus) and ending (carboxyl terminus) positions from within the original polypeptide chain while using the linker sequence $L_2$ as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence.

It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein crystals or nuclear magnetic resonance spectroscopy of protein solutions. Examples of structural information that are relevant to the identification of breakpoint regions include the location and type of protein secondary structure (alpha and 3–10 helices, parallel and anti-parallel beta sheets, chain reversals and turns, and loops; Kabsch & Sander, *Biopolymers* 22: 2577–2637, 1983), the degree of solvent exposure of amino acid residues, the extent and type of interactions of residues with one another (Chothia, *Ann. Rev. Biochem.* 53: 537–572, 1984) and the static and dynamic distribution of conformations along the polypeptide chain (Alber & Mathews, *Methods Enzymol.* 154: 511–533, 1987). In some cases additional information is known about solvent exposure of residues; one example is a site of post-translational attachment of carbohydrate which is necessarily on the surface of the protein. When experimental structural information is not available, or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile & Salvatore, *Eur. J. Biochem.* 218: 603–621, 1993) Thus using either the experimentally derived structural information or predictive methods (e.g., Srinivisan & Rose *Proteins: Struct., Funct. & Genetics,* 22: 81–99, 1995) the parental amino acid sequence is inspected to classify regions according to whether or not they are integral to the maintenance of secondary and tertiary structure. The occurrence of sequences within regions that are known to be involved in periodic secondary structure (alpha and 3–10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region.

Non-covalent Multifunctional hematopoietic growth factors

An alternative method for connecting two hematopoietic growth factors is by means of a non-covalent interaction. Such complexed proteins can be described by one of the formulae:

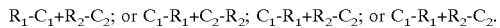

$R_1$ and $R_2$ are as is defined above. Domains $C_1$ and $C_2$ are either identical or non-identical chemical structures, typically proteinaceous, which can form a non-covalent, specific association. Complexes between $C_1$ and $C_2$ result in a one-to-one stoichiometric relationship between $R_1$ and $R_2$ for each complex. Examples of domains which associate are "leucine zipper" domains of transcription factors, dimerization domains of bacterial transcription repressors and immunoglobulin constant domains. Covalent bonds link $R_1$ and $C_1$, and $R_2$ and $C_2$, respectively. As indicated in the formulae, the domains $C_1$ and $C_2$ can be present either at the N-terminus or C-terminus of their corresponding hematopoietic growth factor (R). These multimerization domains ($C_1$ and $C_2$) include those derived from the bZIP family of proteins (Abel et al., *Nature* 341: 24–25, 1989; Landshulz et al., *Science* 240: 1759–1764, 1988; Pu et al., *Nuc. Acid Res.* 21: 4348–4355, 1993; Kozarides et al., *Nature* 336: 646–651, 1988), as well as multimerization domains of the helix-loop-helix family of proteins (Abel et al., *Nature* 341: 24–25, 1989; Murre et al., *Cell* 56: 777–783, 1989; Tapscott et al., *Science* 242: 405–411, 1988; Fisher et al., *Genes & Dev.* 5: 2342–2352, 1991). Preferred multi-functional hematopoietic receptor agonists of the present invention include colony stimulating factors dimerized by virtue of their incorporation as translational multi-functional hematopoietic receptor agonists with the leucine zipper dimerization domains of the bZIP family proteins Fos and Jun. The leucine zipper domain of Jun is capable of interacting with identical domains. On the other hand, the leucine zipper domain of Fos interacts with the Jun leucine zipper domain, but does not interact with other Fos leucine zipper domains. Mixtures of Fos and Jun predominantly result in formation of Fos-Jun heterodimers. Consequently, when joined to colony stimulating factors, the Jun domain can be used to direct the formation of either homo- or heterodimers. Preferential formation of heterodimers can be achieved if one of the colony stimulating factor partners is engineered to possess the Jun leucine zipper domain while the other is engineered to possess the Fos zipper.

Additional peptide sequences may also be added to facilitate purification or identification of multi-functional hematopoietic receptor agonist proteins (e.g., poly-His). A highly antigenic peptide may also be added that would enable rapid assay and facile purification of the multi-functional hematopoietic receptor agonist protein by a specific monoclonal antibody.

"Mutant amino acid sequence," "mutant protein", "variant protein", "mutein", or "mutant polypeptide" refers to a polypeptide having an amino acid sequence which varies from a native sequence due to amino acid deletions, substitutions, or both, or is encoded by a nucleotide sequence intentionally made variant from a native sequence. "Native sequence" refers to an amino acid or nucleic acid sequence which is identical to a wild-type or native form of a gene or protein.

Hematopoietic growth factors can be characterized by their ability to stimulate colony formation by human hematopoietic progenitor cells. The colonies formed include erythroid, granulocyte, megakaryocyte, granulocytic macrophages and mixtures thereof. Many of the hematopoietic growth factors have demonstrated the ability to restore bone marrow function and peripheral blood cell populations to therapeutically beneficial levels in studies performed initially in primates and subsequently in humans. Many or all of these biological activities of hematopoietic growth factors involve signal transduction and high affinity receptor binding. Multi-functional hematopoietic receptor agonists of the present invention may exhibit useful properties such as having similar or greater biological activity when compared to a single factor or by having improved half-life or decreased adverse side effects, or a combination of these properties.

Multi-functional hematopoietic receptor agonists which have little or no agonist activity maybe useful as antagonists, as antigens for the production of antibodies for use in immunology or immunotherapy, as genetic probes or as intermediates used to construct other useful hIL-3 muteins.

Biological activity of the multi-functional hematopoietic receptor agonist proteins of the present invention can be determined by DNA synthesis in factor-dependent cell lines or by counting the colony forming units in an in vitro bone marrow assay.

The multi-functional hematopoietic receptor agonists of the present invention may have an improved therapeutic profile as compared to single acting hematopoietic agonists. For example, some multi-functional hematopoietic receptor agonists of the present invention may have a similar or more potent growth factor activity relative to other hematopoietic agonists without having a similar or corresponding increase in side-effects.

The present invention also includes the DNA sequences which code for the multi-functional hematopoietic receptor agonist proteins, DNA sequences which are substantially similar and perform substantially the same function, and DNA sequences which differ from the DNAs encoding the multi-functional hematopoietic receptor agonists of the invention only due to the degeneracy of the genetic code. Also included in the present invention are the oligonucleotide intermediates used to construct the mutant DNAs and the polypeptides coded for by these oligonucleotides.

Genetic engineering techniques now standard in the art (U.S. Pat. No. 4,935,233 and Sambrook et al., "Molecular Cloning A Laboratory Manual", Cold Spring Harbor Laboratory, 1989) may be used in the construction of the DNA sequences of the present invention. One such method is cassette mutagenesis (Wells et al., *Gene* 34: 315–323, 1985) in which a portion of the coding sequence in a plasmid is replaced with synthetic oligonucleotides that encode the desired amino acid substitutions in a portion of the gene between two restriction sites.

Pairs of complementary synthetic oligonucleotides encoding the desired gene can be made and annealed to each other. The DNA sequence of the oligonucleotide would encode sequence for amino acids of desired gene with the exception of those substituted and/or deleted from the sequence.

Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with the desired genes.

Cloning of the DNA sequences of the novel multifunctional hematopoietic agonists wherein at least one of the with the DNA sequence of the other colony stimulating factor may be accomplished by the use of intermediate vectors. Alternatively one gene can be cloned directly into a vector containing the other gene. Linkers and adapters can be used for joining the DNA sequences, as well as replacing lost sequences, where a restriction site was internal to the region of interest. Thus genetic material (DNA) encoding one polypeptide, peptide linker, and the other polypeptide is inserted into a suitable expression vector which is used to transform bacteria, yeast, insect cells or mammalian cells. The transformed organism is grown and the protein isolated by standard techniques. The resulting product is therefore a new protein which has a colony stimulating factor joined by a linker region to a second colony stimulating factor.

Another aspect of the present invention provides plasmid DNA vectors for use in the expression of these novel multi-functional hematopoietic receptor agonists. These vectors contain the novel DNA sequences described above which code for the novel polypeptides of the invention. Appropriate vectors which can transform microorganisms capable of expressing the multi-functional hematopoietic receptor agonists include expression vectors comprising nucleotide sequences coding for the multi-functional hematopoietic receptor agonists joined to transcriptional and translational regulatory sequences which are selected according to the host cells used.

Vectors incorporating modified sequences as described above are included in the present invention and are useful in the production of the multi-functional hematopoietic receptor agonist polypeptides. The vector employed in the method also contains selected regulatory sequences in operative association with the DNA coding sequences of the invention and which are capable of directing the replication and expression thereof in selected host cells.

As another aspect of the present invention, there is provided a method for producing the novel multi-functional hematopoietic receptor agonists. The method of the present invention involves culturing suitable cells or cell line, which has been transformed with a vector containing a DNA sequence coding for expression of a novel multi-functional hematopoietic receptor agonist. Suitable cells or cell lines may be bacterial cells. For example, the various strains of *E. coli* are well-known as host cells in the field of biotechnology. Examples of such strains include *E. coli* strains JM101 (Yanish-Perron et al. *Gene* 33: 103–119, 1985) and MON105 (Obukowicz et al., *Applied Environmental Microbiology* 58: 1511–1523, 1992). Also included in the present invention is the expression of the multi-functional hematopoietic receptor agonist protein utilizing a chromosomal expression vector for *E. coli* based on the bacteriophage Mu (Weinberg et al., *Gene* 126: 25–33, 1993). Various strains of *B. subtilis* may also be employed in this method. Many strains of yeast cells known to those skilled in the art are also available as host cells for expression of the polypeptides of the present invention. When expressed in the *E. coli* cytoplasm, the gene encoding the multi-functional hematopoietic receptor agonists of the present invention may also be constructed such that at the 5' end of the gene codons are added to encode $Met^{-2}$-$Ala^{-1}$- or $Met^{-1}$ at the N-terminus of the protein. The N termini of proteins made in the cytoplasm of *E. coli* are affected by post-translational processing by methionine aminopeptidase (Ben Bassat et al., *J. Bac.* 169: 751–757, 1987) and possibly by other peptidases so that upon expression the methionine is cleaved off the N-terminus. The multi-functional hematopoietic receptor agonists of the present invention may include multi-functional hematopoietic receptor agonist polypeptides having $Met^{-1}$, $Ala^{-1}$ or $Met^{-2}$-$Ala^{-1}$ at the N-terminus. These mutant multi-functional hematopoietic receptor agonists may also be expressed in *E. coli* by fusing a secretion signal peptide to the N-terminus. This signal peptide is cleaved from the polypeptide as part of the secretion process.

Also suitable for use in the present invention are mammalian cells, such as Chinese hamster ovary cells (CHO). General methods for expression of foreign genes in mammalian cells are reviewed in Kaufman, R. J., 1987) Genetic Engineering, Principles and Methods, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally joined to the coding region for the multi-functional hematopoietic receptor agonist. For example, plasmids such as pcDNA I/Neo, pRc/RSV, and pRc/CMV (obtained from Invitrogen Corp., San Diego, Calif.) can be used. The eukaryotic secretion signal peptide coding region can be from the gene itself or it can be from another secreted mammalian protein (Bayne, M. L. et al., *Proc. Natl. Acad. Sci. USA* 84: 2638–2642, 1987). After construction of the vector containing the gene, the vector DNA is transfected into mammalian cells. Such cells can be, for example, the COS7, HeLa, BHK, CHO, or mouse L lines. The cells can be cultured, for example, in DMEM media (JRH Scientific). The polypeptide secreted into the media can be recovered by standard biochemical approaches following transient expression for 24–72 hours after transfection of the cells or after establishment of stable cell lines following selection for antibiotic resistance. The selection of suitable mammalian host cells and methods for transformation, culture, amplification, screening and product production and purification are known in the art. See, e.g., Gething and Sambrook, *Nature*, 293: 620–625, 1981), or alternatively, Kaufman et al, *Mol. Cell. Biol.,* 5 (7): 1750–1759, 1985) or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g., Miller et al., *Genetic Engineering*, 8: 277–298 (Plenum Press 1986) and references cited therein. In addition, general methods for expression of foreign genes in insect cells using Baculovirus vectors are described in: Summers, M. D. and Smith, G. E., 1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally joined to the coding region for the multi-functional hematopoietic receptor agonist polypeptide. For example, the plasmid pVL1392 (obtained from Invitrogen Corp., San Diego, Calif.) can be used. After construction of the vector carrying the gene encoding the multi-functional hematopoietic receptor agonist polypeptide, two micrograms of this DNA is co-transfected with one microgram of Baculovirus DNA (see Summers & Smith, 1987) into insect cells, strain SF9. Pure recombinant Baculovirus carrying the multi-functional hematopoietic receptor agonist is used to infect cells cultured, for example, in Excell 401 serum-free medium (JRH Biosciences, Lenexa, Kans.). The multi-functional hematopoietic receptor agonist secreted into the medium can be recovered by standard biochemical approaches. Supernatants from mammalian or insect cells expressing the multi-functional hematopoietic receptor agonist protein can be first concentrated using any of a number of commercial concentration units.

The multi-functional hematopoietic receptor agonists of the present invention may be useful in the treatment of diseases characterized by decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these multi-functional hematopoietic receptor agonists of the present invention may avoid undesirable side effects caused by treatment with presently available drugs.

The multi-functional hematopoietic receptor agonists of the present invention may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

The multi-functional hematopoietic receptor agonist of the present invention may be useful in the treatment or prevention of thrombocytopenia. Currently the only therapy for thrombocytopenia is platelet transfusion which are costly and carry the significant risks of infection (HIV, HBV) and alloimmunization. The multi-functional hematopoietic receptor agonist may alleviate or diminish the need for platelet transfusion. Severe thrombocytopenia may result from genetic defects such as Fanconi's Anemia, Wiscott-Aldrich, or May Hegglin syndromes. Acquired. thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis.

The multi-functional hematopoietic receptor agonists of the present invention may be useful in the mobilization of hematopoietic progenitors and stem cells in peripheral blood. Peripheral blood derived progenitors have been shown to be effective in reconstituting patients in the setting of autologous marrow transplantation. Hematopoietic growth factors including G-CSF and GM-CSF have been shown to enhance the number of circulating progenitors and stem cells in the peripheral blood. This has simplified the procedure for peripheral stem cell collection and dramatically decreased the cost of the procedure by decreasing the number of pheresis required. The multi-functional hematopoietic receptor agonist may be useful in mobilization of stem cells and further enhance the efficacy of peripheral stem cell transplantation.

The multi-functional hematopoietic receptor agonists of the present invention may also be useful in the ex vivo expansion of hematopoietic progenitors and stem cells.

Colony stimulating factors (CSFs), such as hIL-3, have been administered alone, co-administered with other CSFs, or in combination with bone marrow transplants subsequent to high dose chemotherapy to treat the neutropenia and thrombocytopenia which are often the result of such treatment. However the period of severe neutropenia and thrombocytopenia may not be totally eliminated. The myeloid lineage, which is comprised of monocytes (macrophages), granulocytes (including neutrophils) and megakaryocytes, is critical in preventing infections and bleeding which can be life-threatening. Neutropenia and thrombocytopenia may also be the result of disease, genetic disorders, drugs, toxins, radiation and many therapeutic treatments such as conventional oncology therapy.

Bone marrow transplants have been used to treat this patient population. However, several problems are associated with the use of bone marrow to reconstitute a compromised hematopoietic system including: 1) the number of stem cells in bone marrow, spleen, or peripheral blood is limited, 2) Graft Versus Host Disease, 3) graft rejection and 4) possible contamination with tumor cells. Stem cells make up a very small percentage of the nucleated cells in the bone marrow, spleen and peripheral blood. It is clear that a dose response exists such that a greater number of stem cells will enhance hematopoietic recovery. Therefore, the in vitro expansion of stem cells should enhance hematopoietic recovery and patient survival. Bone marrow from an allogeneic donor has been used to provide bone marrow for transplant. However, Graft Versus Host Disease and graft rejection limit bone marrow transplantation even in recipients with HLA-matched sibling donors. An alternative to allogeneic bone marrow transplants is autologous bone marrow transplants. In autologous bone marrow transplants, some of the patient's own marrow is harvested prior to myeloablative therapy, e.g. high dose chemotherapy, and is transplanted back into the patient afterwards. Autologous transplants eliminate the risk of Graft Versus Host Disease and graft rejection. However, autologous bone marrow transplants still present problems in terms of the limited number of stems cells in the marrow and possible contamination with tumor cells. The limited number of stem cells may be overcome by ex-vivo expansion of the stem cells. In addition, stem cells can be specifically isolated, based on the presence of specific surface antigens such as CD34+ in order to decrease tumor cell contamination of the marrow graft.

The following patents contain further details on separating stem cells, CD34+ cells, culturing the cells with hematopoietic factors, the use of the cells for the treatment of patients with hematopoietic disorders and the use of hematopoietic factors for cell expansion and gene therapy.

U.S. Pat. No. 5,061,620 relates to compositions comprising human hematopoietic stem cells provided by separating the stem cells from dedicated cells.

U.S. Pat. No. 5,199,942 describes a method for autologous hematopoietic cell transplantation comprising: (1) obtaining hematopoietic progenitor cells from a patient; (2) ex-vivo expansion of cells with a growth factor selected from the group consisting of IL-3, flt3 ligand, c-kit ligand, GM-CSF, IL-1, GM-CSF/IL-3 fusion protein and combinations thereof; (3) administering cellular preparation to a patient.

U.S. Pat. No. 5,240,856 relates to a cell separator that includes an apparatus for automatically controlling the cell separation process.

WO 91/16116 describes devices and methods for selectively isolating and separating target cells from a mixture of cells.

WO 91/18972 describes methods for in vitro culturing of bone marrow, by incubating suspension of bone marrow cells, using a hollow fiber bioreactor.

WO 92/18615 relates to a process for maintaining and expanding bone marrow cells, in a culture medium containing specific mixtures of cytokines, for use in transplants.

WO 93/08268 describes a method for selectively expanding stem cells, comprising the steps of (a) separating CD34+ stem cells from other cells and (b) incubating the separated cells in a selective medium, such that the stem cells are selectively expanded.

WO 93/18136 describes a process for in vitro support of mammalian cells derived from peripheral blood.

WO 93/18648 relates to a composition comprising human neutrophil precursor cells with a high content of myeloblasts and promyelocytes for treating genetic or acquired neutropenia.

WO 94/08039 describes a method of enrichment for human hematopoietic stem cells by selection for cells which express c-kit protein.

WO 94/11493 describes a stem cell population that are CD34+ and small in size, which are isolated using a counterflow elutriation method.

WO 94/27698 relates to a method combining immunoaffinity separation and continuous flow centrifugal separation for the selective separation of a nucleated heterogeneous cell population from a heterogeneous cell mixture.

WO 94/25848 describes a cell separation apparatus for collection and manipulation of target cells.

The long term culturing of highly enriched CD34+ precursors of hematopoietic progenitor cells from human bone marrow in cultures containing IL-1a, IL-3, IL-6 or GM-CSF is discussed in Brandt et al *J. Clin. Invest.* 86: 932–941, 1990).

One aspect of the present invention provides a method for selective ex-vivo expansion of stem cells. The term "stem cell" refers to the totipotent hematopoietic stem cells as well as early precursors and progenitor cells which can be isolated from bone marrow, spleen or peripheral blood. The term "expansion" refers to the differentiation and proliferation of the cells. The present invention provides a method for selective ex-vivo expansion of stem cells, comprising the steps of: (a) separating stem cells from other cells, (b) culturing said separated stem cells with a selective media which contains multi-functional hematopoietic receptor agonist protein(s) and (c) harvesting said stems cells. Stem cells, as well as committed progenitor cells destined to become neutrophils, erythrocytes, platelets, etc. may be distinguished from most other cells by the presence or absence of particular progenitor marker antigens, such as D34, that are present on the surface of these cells nd/or by morphological characteristics. The phenotype for a highly enriched human stem cell fraction is reported as CD34+, Thy-1+ and lin–, but it is to be understood that the present invention is not limited to the expansion of this stem cell population. The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several sub-populations characterized by the presence or absence of co-expression of different lineage associated cell surface associated molecules. The most immature progenitor cells do not express any known lineage associated markers, such as HLA-DR or CD38, but they may express CD90(thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various colony stimulating factors may be utilized in order to selectively expand cells. Representative factors that have been utilized for ex-vivo expansion of bone marrow include, c-kit ligand, IL-3, G-CSF, GM-CSF, IL-1, IL-6, IL-11, flt-3 ligand or combinations thereof. The proliferation of the stem cells can be monitored by enumerating the number of stem cells and other cells, by standard techniques (e.g. hemacytometer, CFU, LTCIC) or by flow cytometry prior and subsequent to incubation.

Several methods for ex-vivo expansion of stem cells have been reported utilizing a number of selection methods and expansion using various colony stimulating factors including c-kit ligand (Brandt et al., *Blood* 83: 1507–1514 [1994], McKenna et al., *Blood* 86: 3413–3420 [1995]), IL-3 (Brandt et al., *Blood* 83: 1507–1514 [1994], Sato et al., *Blood* 82: 3600–3609 [1993]), G-CSF (Sato et al., *Blood* 82: 3600–3609 [1993]), GM-CSF (Sato et al., *Blood* 82: 3600–3609 [1993]), IL-1 (Muench et al., *Blood* 81: 3463–3473 [1993]), IL-6 (Sato et al., *Blood* 82: 3600–3609 [1993]), IL-11 (Lemoli et al., *Exp. Hem.* 21: 1668–1672 [1993], Sato et al., *Blood* 82: 3600–3609 [1993]), flt-3 ligand (McKenna et al., *Blood* 86: 3413 3420 [1995]) and/or combinations thereof (Brandt et al., *Blood* 83: 1507 1514 [1994], Haylock et al., *Blood* 80: 1405–1412 [1992], Koller et al., *Biotechnology* 11: 358–363 [1993], (Lemoli et al., *Exp. Hem.* 21: 1668–1672 [1993]), McKenna et al., *Blood* 86: 3413–3420 [1995], Muench et al., *Blood* 81: 3463–3473 [1993], Patchen et al., *Biotherapy* 7: 13–26 [1994], Sato et al., *Blood* 82: 3600–3609 [1993], Smith et al., *Exp. Hem.* 21: 870–877 [1993], Steen et al., *Stem Cells* 12: 214–224 [1994], Tsujino et al., *Exp. Hem.* 21: 1379–1386 [1993]). Among the individual colony stimulating factors, hIL-3 has been shown to be one of the most potent in expanding peripheral blood CD34+ cells (Sato et al., *Blood* 82: 3600–3609 [1993], Kobayashi et al., *Blood* 73: 1836–1841 [1989]). However, no single factor has been shown to be as effective as the combination of multiple factors. The present invention provides methods for ex vivo expansion that utilize multi-functional hematopoietic receptor agonists that are more effective than a single factor alone.

Another aspect of the invention provides methods of sustaining and/or expanding hematopoietic precursor cells which includes inoculating the cells into a culture vessel which contains a culture medium that has been conditioned by exposure to a stromal cell line such as HS-5 (WO 96/02662, Roecklein and Torok-Strob, *Blood* 85: 997–1105, 1995) that has been supplemented with a multi-functional hematopoietic receptor agonist of the present invention.

Another projected clinical use of growth factors has been in the in vitro activation of hematopoietic progenitors and stem cells for gene therapy. Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, *Science* 270: 404–410 [1995]) include; 1) the treatment of many congenital metabolic disorders and immunodeficiencies (Kay and Woo, *Trends Genet.* 10: 253–257 [1994]), 2) neurological disorders (Friedmann, *Trends Genet.* 10: 210–214 [1994]), 3) cancer (Culver and Blaese, *Trends Genet.* 10: 174–178 [1994]) and 4) infectious diseases (Gilboa and Smith, *Trends Genet.* 10: 139–144 [1994]).

There are a variety of methods, known to those with skill in the art, for introducing genetic material into a host cell. A number of vectors, both viral and non-viral have been developed for transferring therapeutic genes into primary cells. Viral based vectors include; 1) replication deficient recombinant retrovirus (Boris-Lawrie and Temin, *Curr. Opin. Genet. Dev.* 3: 102–109 [1993], Boris-Lawrie and Temin, Annal. New York Acad. Sci. 716: 59–71 [1994], Miller, *Current Top. Microbiol. Immunol.* 158: 1–24 [1992]) and replication-deficient recombinant adenovirus (Berkner, *BioTechniques* 6: 616–629 [1988], Berkner, *Current Top. Microbiol. Immunol.* 158: 39–66 [1992], Brody and Crystal, Annal. New York Acad. Sci. 716: 90–103 [1994]). Non-viral based vectors include protein/DNA complexes (Cristiano et al., *PNAS USA.* 90: 2122–2126 [1993], Curiel et al., *PNAS USA* 88: 8850–8854 [1991], Curiel, Annal. New York Acad. Sci. 716: 36–58 [1994]), electroporation and liposome mediated delivery such as cationic liposomes (Farhood et al., Annal. New York Acad. Sci. 716: 23–35 [1994]).

The present invention provides an improvement to the existing methods of expanding hematopoietic cells, which new genetic material has been introduced, in that it provides methods utilizing multi-functional hematopoietic receptor agonist proteins that have improved biological activity, including an activity not seen by any single colony stimulation factor.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti-convulsants such as phenytoin or carbamazepine, antithyroids such as propylthiouracil and methimazole and diuretics. The multi-functional hematopoietic receptor agonists of the present invention may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. The multi-functional hematopoietic receptor agonists of the present invention may be useful in treating such hematopoietic deficiencies.

The treatment of hematopoietic deficiency may include administration of a pharmaceutical composition containing the multi-functional hematopoietic receptor agonists to a patient. The multi-functional hematopoietic receptor agonists of the present invention may also be useful for the activation and amplification of hematopoietic precursor cells by treating these cells in vitro with the multi-functional hematopoietic receptor agonist proteins of the present invention prior to injecting the cells into a patient.

Various immunodeficiencies, e.g., in T and/or B lymphocytes, or immune disorders, e.g., rheumatoid arthritis, may also be beneficially affected by treatment with the multi-functional hematopoietic receptor agonists of the present invention. Immunodeficiencies may be the result of viral infections, e.g., HTLVI, HTLVII, HTLVIII, severe exposure to radiation, cancer therapy or the result of other medical treatment. The multi-functional hematopoietic receptor agonists of the present invention may also be employed, alone or in combination with other colony stimulating factors, in the treatment of other blood cell deficiencies, including thrombocytopenia (platelet deficiency), or anemia. Other uses for these novel polypeptides are the in vivo and ex vivo treatment of patients recovering from bone marrow transplants, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the multi-functional hematopoietic receptor agonists of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g., the condition, body weight, sex and diet of the patient, the severity of any infection, time of administration and other clinical factors. Generally, a daily regimen may be in the range of 0.2–150 $\mu$g/kg of multi-functional hematopoietic receptor agonist protein per kilogram of body weight. Dosages would be adjusted relative to the activity of a given multi-functional hematopoietic receptor agonist protein and it would not be unreasonable to note that dosage regimens may include doses as low as 0.1 microgram and as high as 1 milligram per kilogram of body weight per day. In addition, there may exist specific circumstances where dosages of multi-functional hematopoietic receptor agonist would be adjusted higher or lower than the range of 0.2–150 micrograms per kilogram of body weight. These include co-administration with other colony stimulating factors or IL-3 variants or growth factors; co-administration with chemotherapeutic drugs and/or radiation; the use of glycosylated multi-functional hematopoietic receptor agonist protein; and various patient-related issues mentioned earlier in this section. As indicated above, the therapeutic method and compositions may also include co-administration with other human factors. A non-exclusive list of other appropriate colony stimulating factors (CSFs), cytokines, lymphokines, hematopoietic growth factors and interleukins for simultaneous or serial co-administration with the polypeptides of the present invention includes GM-CSF, G-CSF, c-mpl ligand (also known as TPO or MGDF), M-CSF, erythropoietin (EPO), IL-1, IL-4, IL-2, IL-3, IL-5, IL-6, IL-7, IL-8, IL-9, IL-10, IL-11, IL-12, IL-13, IL-15, IL-16, LIF, flt3 ligand, and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

Materials and Methods

Unless noted otherwise, all specialty chemicals were obtained from Sigma, Co. (St. Louis, Mo.). Restriction endonucleases and T4 DNA ligase were obtained from New England Biolabs (Beverly, Mass.) or Boehringer Mannheim (Indianapolis, Ind.).

Transformation of E. coli strains

E. coli strains, such as DH5α™ (Life Technologies, Gaithersburg, Md.) and TG1 (Amersham Corp., Arlington Heights, Ill.) are used for transformation of ligation reactions and are the source of plasmid DNA for transfecting mammalian cells. E. coli strains, such as JM101 (Yanisch-Perron, et al., Gene, 33: 103–119, 1985) and MON105 (Obukowicz, et al., Appl. and Envir. Micr., 58: 1511–1523, 1992) can be used for expressing the multi-functional hematopoietic receptor agonist of the present invention in the cytoplasm or periplasmic space.

MON105 ATCC#55204: F−, lambda−,IN(rrnD, rrE)1, rpoD+, rpoH358

DH5α™: F−, phi80dlacZdeltaM15, delta(lacZYA-argF) U169, deoR, recA1, endA1, hsdR17(rk−,mk+), phoA, supE44lamda−, thi-1, gyrA96, relA1

TG1: delta(lac-pro), supE, thi-1, hsdD5/F'(traD36, proA+ B+, lacIq, lacZdeltaM15)

JM101 ATCC#33876: delta (pro lac), supE, thi, F'(traD36, proA+B+, lacIq, lacZdeltaM15)

DH5α™ Subcloning efficiency cells are purchased as competent cells and are ready for transformation using the manufacturer's protocol, while both E. coli strains TG1 and MON105 are rendered competent to take up DNA using a $CaCl_2$ method. Typically, 20 to 50 mL of cells are grown in LB medium (1% bacto-tryptone, 0.5% bacto-yeast extract, 150 mM NaCl) to a density of approximately 1.0 optical density unit at 600 nanometers (OD600) as measured by a Baush & Lomb Spectronic spectrophotometer (Rochester, N.Y.). The cells are collected by centrifugation and resuspended in one-fifth culture volume of $CaCl_2$ solution (50 mM $CaCl_2$, 10 mM Tris-Cl, pH7.4) and are held at 4° C. for 30 minutes. The cells are again collected by centrifugation and resuspended in one-tenth culture volume of $CaCl_2$ solution. Ligated DNA is added to 0.2 mL of these cells, and the samples are held at 4° C. for 30–60 minutes. The samples are shifted to 42° C. for two minutes and 1.0 mL of LB is added prior to shaking the samples at 37° C. for one hour. Cells from these samples are spread on plates (LB medium plus 1.5% bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C. Colonies are picked and inoculated into LB plus appropriate antibiotic (100 ug/mL ampicillin or 75 ug/mL spectinomycin) and are grown at 37° C. while shaking.

Methods for creation of genes with new N-terminus/C-terminus

Method I. Creation of genes with new N-terminus/C-terminus which contain a linker region ($L_2$).

Figure 2:
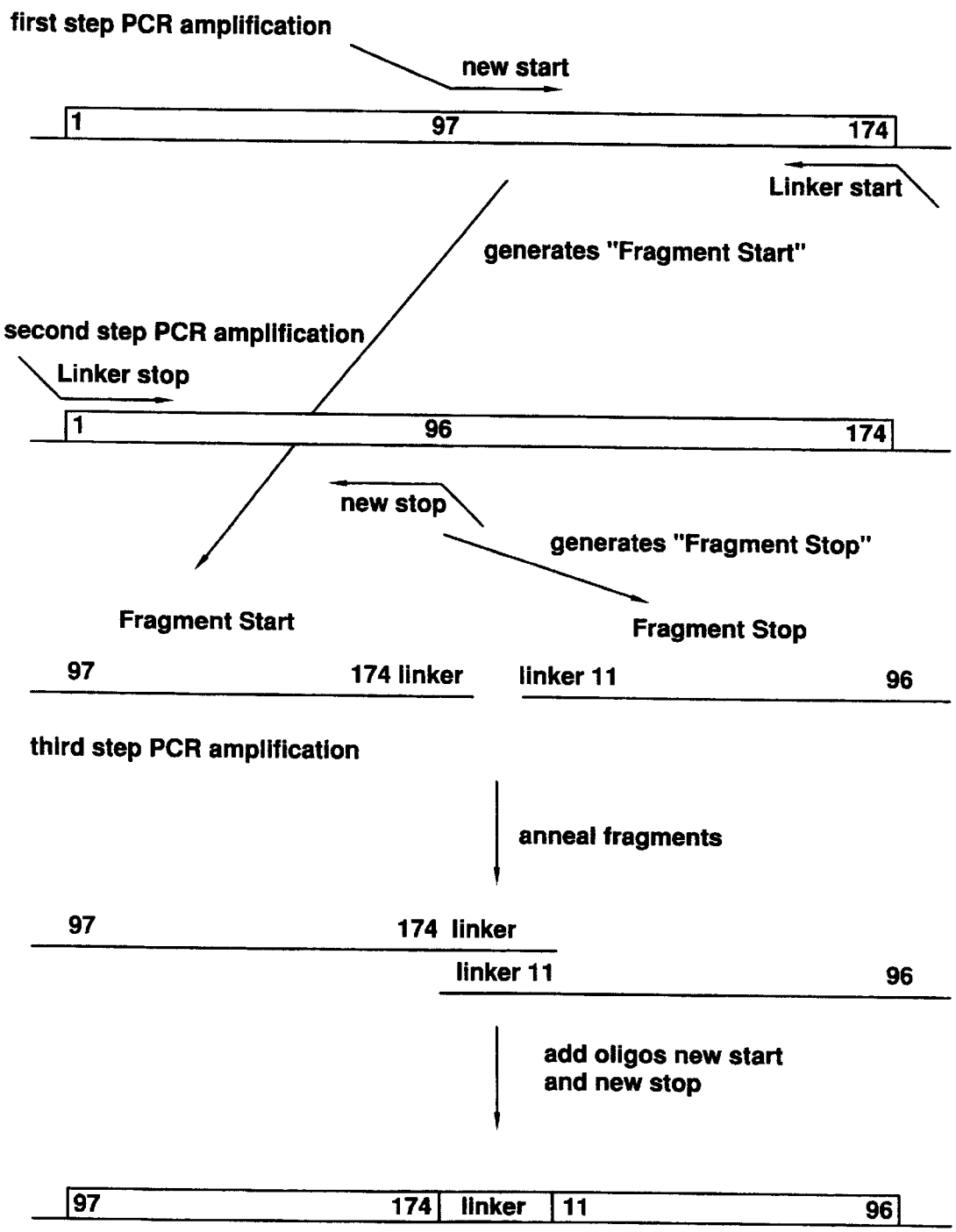
FIG. 2 shows a schematic of Method I, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the amino acid 11 (a.a. 1–10 are deleted) through a linker region and a new C-terminus created at amino acid 96 of the original sequence.

Genes with new N-terminus/C-terminus which contain a linker region ($L_2$) separating the original C-terminus and N-terminus can be made essentially following the method described in L. S. Mullins, et al J. Am. Chem. Soc. 116, 5529–5533, 1994). Multiple steps of polymerase chain reaction (PCR) amplifications are used to rearrange the DNA sequence encoding the primary amino acid sequence of the protein. The steps are illustrated in FIG. 2.

In the first step, the first primer set ("new start" and "linker start") is used to create and amplify, from the original gene sequence, the DNA fragment ("Fragment Start") that contains the sequence encoding the new N-terminal portion of the new protein followed by the linker ($L_2$) that connects the C-terminal and N-terminal ends of the original protein. In the second step, the second primer set ("new stop" and "linker stop") is used to create and amplify, from the original gene sequence, the DNA fragment ("Fragment Stop") that encodes the same linker as used above, followed by the new C-terminal portion of the new protein. The "new start" and "new stop" primers are designed to include the appropriate restriction sites which allow cloning of the new gene into expression plasmids. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and one ug of template DNA; and 1× PCR buffer, 200 uM dGTP, 200 uM DATP, 200 uM dTTP, 200 uM dCTP, 2.5 units AmpliTaq DNA polymerase and 2 mM MgCl2. PCR reactions are performed in a Model 480 DNA thermal cycler (Perkin Elmer Corporation, Norwalk, Conn.).

"Fragment Start" and "Fragment Stop", which have complementary sequence in the linker region and the coding sequence for the two amino acids on both sides of the linker, are joined together in a third PCR step to make the full-length gene encoding the new protein. The DNA fragments "Fragment Start" and "Fragment Stop" are resolved on a 1% TAE gel, stained with ethidium bromide and isolated using a Qiaex Gel Extraction kit (Qiagen). These fragments are combined in equimolar quantities, heated at 70° C. for ten minutes and slow cooled to allow annealing through their shared sequence in "linker start" and "linker stop". In the third PCR step, primers "new start" and "new stop" are added to the annealed fragments to create and amplify the full-length new N-terminus/C-terminus gene. Typical PCR conditions are one cycle 95° C. melting for two minutes; 25 cycles 94° C. denaturation for one minute, 60° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and approximately 0.5 ug of DNA; and 1× PCR buffer, 200 uM dGTP, 200 uM dATP, 200 uM dTTP, 200 uM dCTP, 2.5 units AmpliTaq DNA polymerase and 2 mM MgCl2. PCR reactions are purified using a Wizard PCR Preps kit (Promega).

Method II. Creation of genes with new N-terminus/C-terminus without a linker region.

Figure 3:
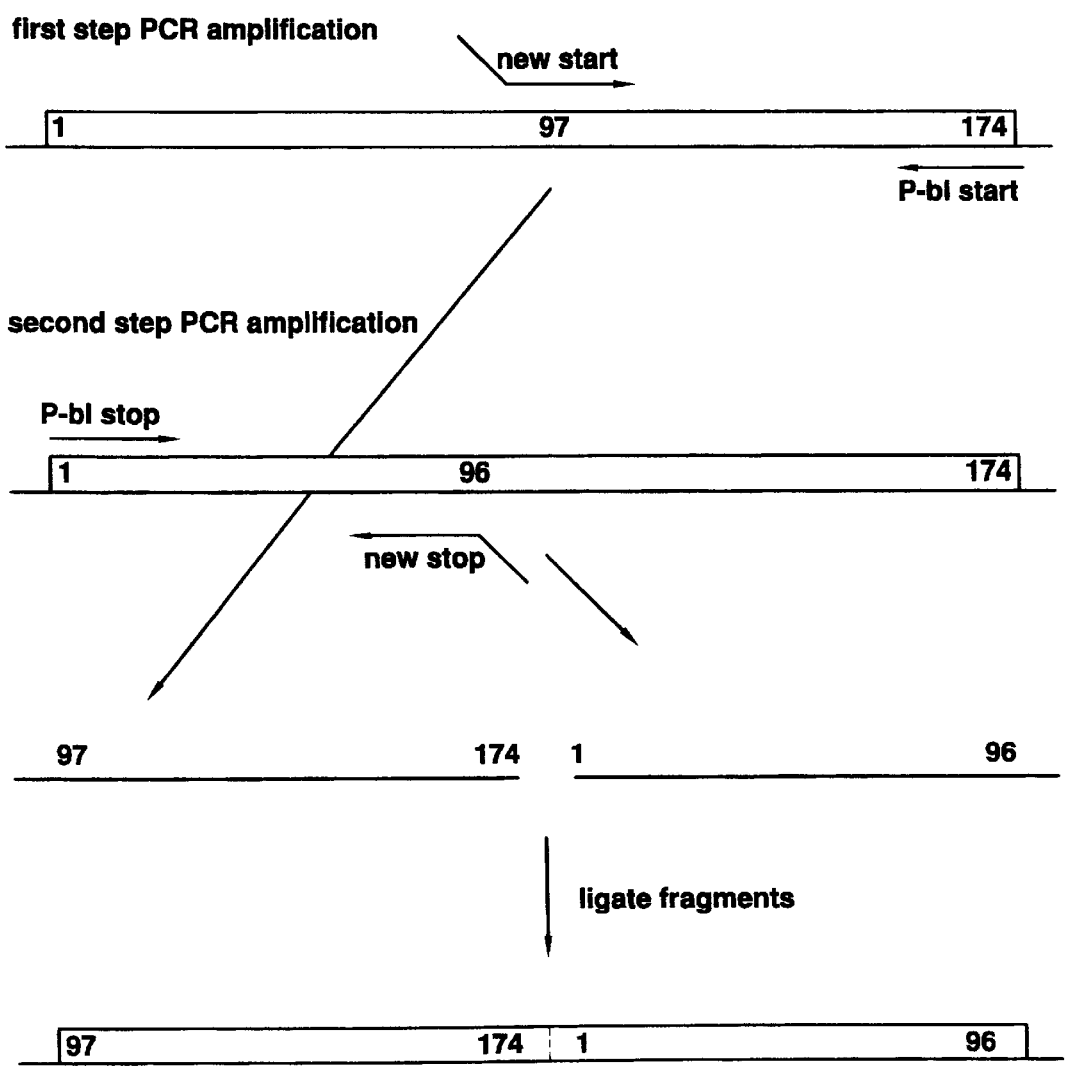
FIG. 3 shows a schematic of Method II, for creating new proteins in which the original N-terminus and C-terminus of the native protein are joined without a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the original N-terminus and a new C-terminus created at amino acid 96 of the original sequence.

New N-terminus/C-terminus genes without a linker joining the original N-terminus and C-terminus can be made using two steps of PCR amplification and a blunt end ligation. The steps are illustrated in FIG. 3. In the first step, the primer set ("new start" and "P-bl start") is used to create and amplify, from the original gene sequence, the DNA fragment ("Fragment Start") that contains the sequence encoding the new N-terminal portion of the new protein. In the second step, the primer set ("new stop" and "P-bl stop") is used to create and amplify, from gene sequence, the DNA fragment ("Fragment Stop") that contains the sequence encoding the new C-terminal portion of the new protein. The "new start" and "new stop" primers are designed to include appropriate restriction sites which allow cloning of the new gene into expression vectors. Typical PCR conditions are one cycle 95° C. melting for two minutes; 25 cycles 94° C. denaturation for one minute, 50° C. annealing for 45 seconds and 72° C. extension for 45 seconds. Deep Vent polymerase (New England Biolabs) is used to reduce the occurrence of overhangs in conditions recommended by the manufacturer. The "P-bl start" and "P-bl stop" primers are phosphorylated at the 5' end to aid in the subsequent blunt end ligation of "Fragment Start" and "Fragment Stop" to each other. A 100 ul reaction contained 150 pmole of each primer and one ug of template DNA; and 1× Vent buffer (New England Biolabs), 300 uM dGTP, 300 uM DATP, 300 uM dTTP, 300 uM dCTP, and 1 unit Deep Vent polymerase. PCR reactions are performed in a Model 480 DNA thermal cycler (Perkin Elmer Corporation, Norwalk, Conn.). PCR reaction products are purified using a Wizard PCR Preps kit (Promega).

The primers are designed to include appropriate restriction sites which allow for the cloning of the new gene into expression vectors. Typically "Fragment Start" is designed to create NcoI restriction site, and "Fragment Stop" is designed to create a HindIII restriction site. Restriction digest reactions are purified using a Magic DNA Clean-up System kit (Promega). Fragments Start and Stop are resolved on a 1% TAE gel, stained with ethidium bromide and isolated using a Qiaex Gel Extraction kit (Qiagen). These fragments are combined with and annealed to the ends of the ~3800 base pair NcoI/HindIII vector fragment of pMON3934 by heating at 50° C. for ten minutes and allowed to slow cool. The three fragments are ligated together using T4 DNA ligase (Boehringer Mannheim). The result is a plasmid containing the full-length new N-terminus/C-terminus gene. A portion of the ligation reaction is used to transform *E. coli* strain DH5a cells (Life Technologies, Gaithersburg, Md.). Plasmid DNA is purified and sequence confirmed as below.

Method III. Creation of new N-terminus/C-terminus genes by tandem-duplication method New N-terminus/C-terminus genes can be made based on the method described in R. A. Horlick, et al *Protein Eng.* 5: 427–431, 1992). Polymerase chain reaction (PCR) amplification of the new N-terminus/C-terminus genes is performed using a tandemly duplicated template DNA. The steps are illustrated in FIG. 3.

The tandemly-duplicated template DNA is created by cloning and contains two copies of the gene separated by DNA sequence encoding a linker connecting the original C- and N-terminal ends of the two copies of the gene. Specific primer sets are used to create and amplify a full-length new N terminus/C-terminus gene from the tandemly-duplicated template DNA. These primers are designed to include appropriate restriction sites which allow for the cloning of the new gene into expression vectors. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer Gene-Amp PCR Core Reagents kit (Perkin Elmer Corporation, Norwalk, Conn.) is used. A 100 ul reaction contains 100 pmole of each primer and one ug of template DNA; and 1× PCR buffer, 200 uM dGTP, 200 uM DATP, 200 uM dTTP, 200 uM dCTP, 2.5 units AmpliTaq DNA polymerase and 2 mM $MgCl_2$. PCR reactions are performed in a Model 480 DNA thermal cycler (Perkin Elmer Corporation, Norwalk, Conn.). PCR reactions are purified using a Wizard PCR Preps kit (Promega).

Cloning of new N-terminus/C-terminus genes into multi-functional receptor agonist expression vectors The new N-terminus/C-terminus gene is digested with restriction endonucleases to create ends that are compatible to insertion into an expression vector containing another colony stimulating factor gene. This expression vector is likewise digested with restriction endonucleases to form compatible ends. After purification, the gene and the vector DNAs are combined and ligated using T4 DNA ligase. A portion of the ligation reaction is used to transform *E. coli*. Plasmid DNA is purified and sequenced to confirm the correct insert. The correct clones are grown for protein expression.

DNA isolation and characterization

Plasmid DNA can be isolated by a number of different methods and using commercially available kits known to those skilled in the art. A few such methods are shown herein. Plasmid DNA is isolated using the Promega Wizard™ Miniprep kit (Madison, Wis.), the Qiagen QIAwell Plasmid isolation kits (Chatsworth, Calif.) or Qiagen Plasmid Midi kit. These kits follow the same general procedure for plasmid DNA isolation. Briefly, cells are pelleted by centrifugation (5000×g), plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted with TE. After screening for the colonies with the plasmid of interest, the *E. coli* cells are inoculated into 50–100 mls of LB plus appropriate antibiotic for overnight growth at 37° C. in an air incubator while shaking. The purified plasmid DNA is used for DNA sequencing, further restriction enzyme digestion, additional subcloning of DNA fragments and transfection into mammalian, *E. coli* or other cells.

Sequence confirmation

Purified plasmid DNA is resuspended in $dH_2O$ and quantitated by measuring the absorbance at 260/280 nm in a Bausch and Lomb Spectronic 601 UV spectrometer. DNA samples are sequenced using ABI PRISM™ DyeDeoxy™ terminator sequencing chemistry (Applied Biosystems Division of Perkin Elmer Corporation, Lincoln City, Calif.) kits (Part Number 401388 or 402078) according to the manufacturers suggested protocol usually modified by the addition of 5% DMSO to the sequencing mixture. Sequencing reactions are performed in a Model 480 DNA thermal cycler (Perkin Elmer Corporation, Norwalk, Conn.) following the recommended amplification conditions. Samples are purified to remove excess dye terminators with Centri-Sep™ spin columns (Princeton Separations, Adelphia, N.J.) and lyophilized. Fluorescent dye labeled sequencing reactions are resuspended in deionized formamide, and sequenced on denaturing 4.75% polyacrylamide-8M urea gels using an ABI Model 373A automated DNA sequencer. Overlapping DNA sequence fragments are analyzed and assembled into master DNA contigs using Sequencher v2.1 DNA analysis software (Gene Codes Corporation, Ann Arbor, Mich.).

Expression of multi-functional receptor agonists in mammalian cells

Mammalian Cell Transfection/Production of Conditioned Media

The BHK-21 cell line can be obtained from the ATCC (Rockville, Md.). The cells are cultured in Dulbecco's modified Eagle media (DMEM/high-glucose), supplemented to 2 mM (mM) L-glutamine and 10% fetal bovine serum (FBS). This formulation is designated BHK growth media. Selective media is BHK growth media supplemented with 453 units/mL hygromycin B (Calbiochem, San Diego, Calif.). The BHK-21 cell line was previously stably transfected with the HSV transactivating protein VP16, which transactivates the IE110 promoter found on the plasmid pMON3359 (See Hippenmeyer et al., *Bio/Technology,* pp.1037–1041, 1993). The VP16 protein drives expression of genes inserted behind the IE110 promoter. BHK-21 cells expressing the transactivating protein VP16 are designated BHK-VP16. The plasmid pMON1118 (See Highkin et al., *Poultry Sci.,* 70: 970–981, 1991) expresses the hygromycin resistance gene from the SV40 promoter. A similar plasmid is available from ATCC, pSV2-hph.

BHK-VP16 cells are seeded into a 60 millimeter (mm) tissue culture dish at $3×10^5$ cells per dish 24 hours prior to transfection. Cells are transfected for 16 hours in 3 mL of "OPTIMEM"™ (Gibco-BRL, Gaithersburg, Md.) containing 10 ug of plasmid DNA containing the gene of interest, 3 ug hygromycin resistance plasmid, pMON1118, and 80 ug of Gibco-BRL "LIPOFECTAMINE"™ per dish. The media is subsequently aspirated and replaced with 3 mL of growth media. At 48 hours post-transfection, media from each dish is collected and assayed for activity (transient conditioned media). The cells are removed from the dish by trypsin-EDTA, diluted 1:10 and transferred to 100 mm tissue culture dishes containing 10 mL of selective media. After approximately 7 days in selective media, resistant cells grow into colonies several millimeters in diameter. The colonies are removed from the dish with filter paper (cut to approximately the same size as the colonies and soaked in trypsin/EDTA) and transferred to individual wells of a 24 well plate containing 1 mL of selective media. After the clones are grown to confluence, the conditioned media is re-assayed, and positive clones are expanded into growth media.

Expression of multi-functional receptor agonists in E. coli

E. coli strain MON105 or JM101 harboring the plasmid of interest are grown at 37° C. in M9 plus casamino acids medium with shaking in a air incubator Model G25 from New Brunswick Scientific (Edison, N.J.). Growth is monitored at OD600 until it reaches a value of 1.0 at which time Nalidixic acid (10 milligrams/mL) in 0.1 N NaOH is added to a final concentration of 50 µg/mL. The cultures are then shaken at 37° C. for three to four additional hours. A high degree of aeration is maintained throughout culture period in order to achieve maximal production of the desired gene product. The cells are examined under a light microscope for the presence of inclusion bodies (IB). One mL aliquots of the culture are removed for analysis of protein content by boiling the pelleted cells, treating them with reducing buffer and electrophoresis via SDS-PAGE (see Maniatis et al. Molecular Cloning: A Laboratory Manual, 1982). The culture is centrifuged (5000×g) to pellet the cells.

Inclusion Body preparation, Extraction, Refolding, Dialysis, DEAE Chromatography, and Characterization of the multi-functional hematopoietic receptor agonists which accumulate as inclusion bodies in E. coli Isolation of Inclusion Bodies The cell pellet from a 330 mL E. coli culture is resuspended in 15 mL of sonication buffer (10 mM 2-amino-2-(hydroxymethyl) 1,3-propanediol hydrochloride (Tris-HCl), pH 8.0+1 mM ethylenediaminetetraacetic acid (EDTA). These resuspended cells are sonicated using the microtip probe of a Sonicator Cell Disruptor (Model W-375, Heat Systems-Ultrasonics, Inc., Farmingdale, N.Y.). Three rounds of sonication in sonication buffer followed by centrifugation are employed to disrupt the cells and wash the inclusion bodies (IB). The first round of sonication is a 3 minute burst followed by a 1 minute burst, and the final two rounds of sonication are for 1 minute each.

Extraction and refolding of proteins from inclusion body pellets

Following the final centrifugation step, the IB pellet is resuspended in 10 mL of 50 mM Tris-HCl, pH 9.5, 8 M urea and 5 mM dithiothreitol (DTT) and stirred at room temperature for approximately 45 minutes to allow for denaturation of the expressed protein.

The extraction solution is transferred to a beaker containing 70 mL of 5 mM Tris-HCl, pH 9.5 and 2.3 M urea and gently stirred while exposed to air at 4° C. for 18 to 48 hours to allow the proteins to refold. Refolding is monitored by analysis on a Vydac (Hesperia, Calif.) C18 reversed phase high pressure liquid chromatography (RP-HPLC) column (0.46×25 cm). A linear gradient of 40% to 65% acetonitrile, containing 0.1% trifluoroacetic acid (TFA), is employed to monitor the refold. This gradient is developed over 30 minutes at a flow rate of 1.5 mL per minute. Denatured proteins generally elute later in the gradient than the refolded proteins.

Purification

Following the refold, contaminating E. coli proteins are removed by acid precipitation. The pH of the refold solution is titrated to between pH 5.0 and pH 5.2 using 15% (v/v) acetic acid (HOAc). This solution is stirred at 4° C. for 2 hours and then centrifuged for 20 minutes at 12,000×g to pellet any insoluble protein.

The supernatant from the acid precipitation step is dialyzed using a Spectra/Por 3 membrane with a molecular weight cut off (MWCO) of 3,500 daltons. The dialysis is against 2 changes of 4 liters (a 50-fold excess) of 10 mM Tris-HCl, pH 8.0 for a total of 18 hours. Dialysis lowers the sample conductivity and removes urea prior to DEAE chromatography. The sample is then centrifuged (20 minutes at 12,000×g) to pellet any insoluble protein following dialysis.

A Bio-Rad Bio-Scale DEAE2 column (7×52 mm) is used for ion exchange chromatography. The column is equilibrated in a buffer containing 10 mM Tris-HCl, pH 8.0, and a 0-to-500 mM sodium chloride (NaCl) gradient, in equilibration buffer, over 45 column volumes is used to elute the protein. A flow rate of 1.0 mL per minute is used throughout the run. Column fractions (2.0 mL per fraction) are collected across the gradient and analyzed by RP HPLC on a Vydac (Hesperia, Calif.) C18 column (0.46×25 cm). A linear gradient of 40% to 65% acetonitrile, containing 0.1% trifluoroacetic acid (TFA), is employed. This gradient is developed over 30 minutes at a flow rate of 1.5 mL per minute. Pooled fractions are then dialyzed against 2 changes of 4 liters (50-to-500-fold excess) of 10 mM ammonium acetate (NH4Ac), pH 4.0 for a total of 18 hours. Dialysis is performed using a Spectra/Por 3 membrane with a MWCO of 3,500 daltons. Finally, the sample is sterile filtered using a 0.22 µm syringe filter (µStar LB syringe filter, Costar, Cambridge, Mass.), and stored at 4° C.

In some cases the folded proteins can be affinity purified using affinity reagents such as mAbs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

These and other protein purification methods are described in detail in Methods in Enzymology, Volume 182 'Guide to Protein Purification' edited by Murray Deutscher, Academic Press, San Diego, Calif. (1990).

Protein Characterization

The purified protein is analyzed by RP-HPLC, electrospray mass spectrometry, and SDS-PAGE. The protein quantitation is done by amino acid composition, RP-HPLC, and Bradford protein determination. In some cases tryptic peptide mapping is performed in conjunction with electrospray mass spectrometry to confirm the identity of the protein.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM-CSF supplemented medium (Lange, B., et al., Blood 70: 192, 1987; Valtieri, M., et al., J. Immunol. 138: 4042, 1987). The ability of AML 193 cells to proliferate in the presence of human IL-3 has also been documented. (Santoli, D., et al., J. Immunol. 139: 348, 1987). A cell line variant was used, AML 193 1.3, which was adapted for long term growth in IL-3 by washing out the growth factors and starving the cytokine dependent AML 193 cells for growth factors for 24 hours. The cells are then replated at $1\times10^5$ cells/well in a 24 well plate in media containing 100 U/mL IL-3. It took approximately 2 months for the cells to grow rapidly in IL-3. These cells are maintained as AML 193 1.3 thereafter by supplementing tissue culture medium (see below) with human IL-3.

AML 193 1.3 cells are washed 6 times in cold Hanks balanced salt solution (HBSS, Gibco, Grand Island, N.Y.) by centrifuging cell suspensions at 250×g for 10 minutes followed by decantation of the supernatant. Pelleted cells are resuspended in HBSS and the procedure is repeated until six wash cycles are completed. Cells washed six times by this procedure are resuspended in tissue culture medium at a density ranging from $2\times10^5$ to $5\times10^5$ viable cells/mL. This medium is prepared by supplementing Iscove's modified Dulbecco's Medium (IMDM, Hazelton, Lenexa, Kans.) with albumin, transferrin, lipids and 2-mercaptoethanol. Bovine albumin (Boehringer-Mannheim, Indianapolis, Ind.) is added at 500 µg/mL; human transferrin (Boehringer-Mannheim, Indianapolis, Ind.) is added at 100 µg/mL; soybean lipid (Boehringer-Mannheim, Indianapolis, Ind.) is added at 50 µg/mL; and 2-mercaptoethanol (Sigma, St. Louis, Mo.) is added at $5\times10^{-5}$ M.

Serial dilutions of human interleukin-3 or multi-functional hematopoietic receptor agonist proteins are made in triplicate series in tissue culture medium supplemented as stated above in 96 well Costar 3596 tissue culture plates. Each well contained 50 µl of medium containing interleukin-3 or multi-functional hematopoietic receptor agonist proteins once serial dilutions are completed. Control wells contained tissue culture medium alone (negative control). AML 193 1.3 cell suspensions prepared as above are added to each well by pipetting 50 µl ($2.5\times10^4$ cells) into each well. Tissue culture plates are incubated at 37° C. with 5% $CO_2$ in humidified air for 3 days. On day 3, 0.5 µCi $^3$H-thymidine (2 Ci/mM, New England Nuclear, Boston, Mass.) is added in 50 µl of tissue culture medium. Cultures are incubated at 37° C. with 5% $CO_2$ in humidified air for 18–24 hours. Cellular DNA is harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats are allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) is added. Beta emissions of samples from individual tissue culture wells are counted in a LKB BetaPlate model 1205 scintillation counter (Pharmacia LKB, Gaithersburg, Md.) and data is expressed as counts per minute of $^3$H-thymidine incorporated into cells from each tissue culture well. Activity of each human interleukin-3 preparation or multi-functional hematopoietic receptor agonist protein preparation is quantitated by measuring cell proliferation ($^3$H-thymidine incorporation) induced by graded concentrations of interleukin-3 or multi-functional hematopoietic receptor agonist. Typically, concentration ranges from 0.05 pM–$10^5$ pM are quantitated in these assays. Activity is determined by measuring the dose of interleukin-3 or multi-functional hematopoietic receptor agonist protein which provides 50% of maximal proliferation ($EC_{50}$=0.5×(maximum average counts per minute of $^3$H-thymidine incorporated per well among triplicate cultures of all concentrations of interleukin-3 tested—background proliferation measured by $^3$H-thymidine incorporation observed in triplicate cultures lacking interleukin-3). This $EC_{50}$ value is also equivalent to 1 unit of bioactivity. Every assay is performed with native interleukin-3 as a reference standard so that relative activity levels could be assigned.

Typically, the multi-functional hematopoietic receptor agonist proteins were tested in a concentration range of 2000 pM to 0.06 pM titrated in serial 2 fold dilutions.

Activity for each sample was determined by the concentration which gave 50% of the maximal response by fitting a four-parameter logistic model to the data. It was observed that the upper plateau (maximal response) for the sample and the standard with which it was compared did not differ. Therefore relative potency calculation for each sample was determined from $EC_{50}$ estimations for the sample and the standard as indicated above. AML 193.1.3 cells proliferate in response to hIL-3, hGM-CSF and hG-CSF. Therefore the following additional assays were performed for some samples to demonstrate that the G-CSF receptor agonist portion of the multi-functional hematopoietic receptor agonist proteins was active. The proliferation assay was performed with the multi-functional hematopoietic receptor agonist plus and minus neutralizing monoclonal antibodies to the hIL-3 receptor agonist portion. In addition, a fusion molecule with the factor Xa cleavage site was cleaved then purified and the halves of the molecule were assayed for proliferative activity. These experiments showed that both components of the multi-functional hematopoietic receptor agonist proteins were active.

TF1 c-mpl ligand dependent proliferation assay

The c-mpl ligand proliferative activity can be assayed using a subclone of the pluripotential human cell line TF1 (Kitamura et al., J. Cell Physiol 140: 323–334. [1989]). TF1 cells are maintained in h-IL3 (100 U/mL). To establish a sub-clone responsive to c-mpl ligand, cells are maintained in passage media containing 10% supernatant from BHK cells transfected with the gene expressing the 1–153 form of c-mpl ligand (pMON26448). Most of the cells die, but a subset of cells survive. After dilution cloning, a c-mpl ligand responsive clone is selected, and these cells are split into passage media to a density of $0.3\times10^6$ cells/mL the day prior to assay set-up. Passage media for these cells is the following: RPMI 1640 (Gibco), 10% FBS (Harlan, Lot #91206), 10% c-mpl ligand supernatant from transfected BHK cells, 1 mM sodium pyruvate (Gibco), 2 mM glutamine (Gibco), and 100 ug/mL penicillin-streptomycin (Gibco). The next day, cells are harvested and washed twice in RPMI or IMDM media with a final wash in the ATL, or assay media. ATL medium consists of the following: IMDM (Gibco), 500 ug/mL of bovine serum albumin, 100 ug/mL of human transferrin, 50 ug/mL soybean lipids, $4\times10-8$M beta-mercaptoethanol and 2 mL of A9909 (Sigma, antibiotic solution) per 1000 mL of ATL. Cells are diluted in assay media to a final density of $0.25\times10^6$ cells/mL in a 96-well low evaporation plate (Costar) to a final volume of 50 ul. Transient supernatants (conditioned media) from transfected clones are added at a volume of 50 ul as duplicate samples at a final concentration of 50% and diluted three-fold to a final dilution of 1.8%. Triplicate samples of a dose curve of IL-3 variant pMON13288 starting at 1 ng/mL and diluted using three-fold dilutions to 0.0014 ng/mL is included as a positive control. Plates are incubated at 5% $CO_2$ and 37° C. At day six of culture, the plate is pulsed with 0.5 Ci of 3H/well (NEN) in a volume of 20 ul/well and allowed to incubate at 5% $CO_2$ and 37° C. for four hours. The plate is harvested and counted on a Betaplate counter.

Other in vitro cell based proliferation assays

Other in vitro cell based assays, known to those skilled in the art, may also be useful to determine the activity of the multi-functional hematopoietic receptor agonists depending on the factors that comprise the molecule in a similar manner as described in the AML 193.1.3 cell proliferation assay. The following are examples of other useful assays.

TF1 proliferation assay: TF1 is a pluripotential human cell line (Kitamura et al., J. Cell Physiol 140: 323–334. [1989]) that responds to hIL-3.

32D proliferation assay: 32D is a murine IL-3 dependent cell line which does not respond to human IL-3 but does respond to human G-CSF which is not species restricted.

Baf/3 proliferation assay: Baf/3 is a murine IL-3 dependent cell line which does not respond to human IL-3 or human c-mpl ligand but does respond to human G-CSF which is not species restricted.

T1165 proliferation assay: T1165 cells are a IL-6 dependent murine cell line (Nordan et al., 1986) which respond to IL-6 and IL-11.

Human Plasma Clot meg-CSF Assay: Used to assay megakaryocyte colony formation activity (Mazur et al., 1981).

Transfected cell lines

Cell lines such as the murine Baf/3 cell line can be transfected with a colony stimulating factor receptor, such as the human G-CSF receptor or human c-mpl receptor, which the cell line does not have. These transfected cell lines can be used to determine the activity of the ligand for which the receptor has been transfected into the cell line.

One such transfected Baf/3 cell line was made by cloning the cDNA encoding c-mpl from a library made from a c-mpl responsive cell line and cloned into the multiple cloning site of the plasmid pcDNA3 (Invitrogen, San Diego Calif.). Baf/3 cells were transfected with the plasmid via electroporation. The cells were grown under G418 selection in the presence of mouse IL-3 in Wehi conditioned media. Clones were established through limited dilution.

In a similar manner the human G-CSF receptor can be transfected into the Baf/3 cell line and used to determine the bioactivity of the multi-functional hematopoietic receptor agoinsts.

Analysis of c-mpl ligand proliferative activity

Methods

1. Bone marrow proliferation assay a. CD34+ Cell Purification

Bone marrow aspirates (15–20 mL) were obtained from normal allogeneic marrow donors after informed consent. Cells were diluted 1:3 in phosphate buffered saline (PBS, Gibco-BRL), 30 mL were layered over 15 mL Histopaque-1077 (Sigma) and centrifuged for 30 minutes at 300 RCF. The mononuclear interface layer was collected and washed in PBS. CD34+ cells were enriched from the mononuclear cell preparation using an affinity column per manufacturers instructions (CellPro, Inc, Bothell Wash.). After enrichment, the purity of CD34+ cells was 70% on average as determined by using flow cytometric analysis using anti-CD34 monoclonal antibody conjugated to fluorescein and anti-CD38 conjugated to phycoerythrin (Becton Dickinson, San Jose Calif.).

Cells were resuspended at 40,000 cells/mL in X-Vivo 10 media (Bio-Whittaker, Walkersville, Md.) and 1 mL was plated in 12-well tissue culture plates (Costar). The growth factor rhIL-3 was added at 100 ng/mL (pMON5873) was added to some wells. hIL3 variants were used at 10 ng/mL to 100 ng/mL. Conditioned media from BHK cells transfected with plasmid encoding c-mpl ligand or multi-functional hematopoietic receptor agonists were tested by addition of 100 µl of supernatant added to 1 mL cultures (approximately a 10% dilution). Cells were incubated at 37° C. for 8–14 days at 5% $CO_2$ in a 37° C. humidified incubator.

b. Cell Harvest and Analysis

At the end of the culture period a total cell count was obtained for each condition. For fluorescence analysis and ploidy determination cells were washed in megakaryocyte buffer (MK buffer, 13.6 mM sodium citrate, 1 mM theophylline, 2.2 µm PGE1, 11 mM glucose, 3% w/v BSA, in PBS, pH 7.4,) (Tomer et al., Blood 70: 1735–1742, 1987) resuspended in 500 µl of MK buffer containing anti-CD41a FITC antibody (1:200, AMAC, Westbrook, Me.) and washed in MK buffer. For DNA analysis cells were permeablized in MK buffer containing 0.5% Tween 20 (Fisher, Fair Lawn N.J.) for 20 min. on ice followed by fixation in 0.5% Tween-20 and 1% paraformaldehyde (Fisher Chemical) for 30 minutes followed by incubation in propidium iodide (Calbiochem , La Jolla Calif.) (50 µg/mL) with RNA-ase (400 U/mL) in 55% v/v MK buffer (200 mOsm) for 1–2 hours on ice. Cells were analyzed on a FACScan or Vantage flow cytometer (Becton Dickinson, San Jose, Calif.). Green fluorescence (CD41a-FITC) was collected along with linear and log signals for red fluorescence (PI) to determine DNA ploidy. All cells were collected to determine the percent of cells that were CD41+. Data analysis was performed using software by LYSIS (Becton Dickinson, San Jose, Calif.). Percent of cells expressing the CD41 antigen was obtained from flow cytometry analysis (Percent). Absolute (Abs) number of CD41+ cells/mL was calculated by: (Abs)=(Cell Count)*(Percent)/100.

2. Megakaryocyte fibrin clot assay

CD34+ enriched population were isolated as described above. Cells were suspended at 25,000 cells/mL with or without cytokine(s) in a media consisting of a base Iscoves IMDM media supplemented with 0.3% BSA, 0.4 mg/mL apo-transferrin, 6.67 µM $FeCl_2$, 25 µg/mL $CaCl_2$, 25 µg/mL L-asparagine, 500 µg/mL ε-amino-n-caproic acid and penicillin/streptomycin. Prior to plating into 35 mm plates, thrombin was added (0.25 Units/mL) to initiate clot formation. Cells were incubated at 37° C. for 13 days at 5% $CO_2$ in a 37° C. humidified incubator.

At the end of the culture period plates were fixed with methanol:acetone (1:3), air dried and stored at −200° C. until staining. A peroxidase immunocytochemistry staining procedure was used (Zymed, Histostain-SP. San Francisco, Calif.) using a cocktail of primary monoclonal antibodies consisting of anti-CD41a, CD42 and CD61. Colonies were counted after staining and classified as negative, CFU-MK (small colonies, 1–2 foci and less that approx. 25 cells), BFU-MK (large, multi-foci colonies with >25 cells) or mixed colonies (mixture of both positive and negative cells.

Methylcellulose Assay

This assay reflects the ability of colony stimulating factors to stimulate normal bone marrow cells to produce different types of hematopoietic colonies in vitro (Bradley et al.,Aust. Exp Biol. Sci. 44: 287–300, 1966), Pluznik et al., J. Cell Comp. Physio 66: 319–324, 1965).

Methods

Approximately 30 mL of fresh, normal, healthy bone marrow aspirate are obtained from individuals following informed consent. Under sterile conditions samples are diluted 1:5 with a 1× PBS (#14040.059 Life Technologies, Gaithersburg, Md.) solution in a 50 mL conical tube (#25339-50 Corning, Corning Md.). Ficoll (Histopaque 1077 Sigma H-8889) is layered under the diluted sample and centrifuged, 300×g for 30 min. The mononuclear cell band is removed and washed two times in 1× PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen.

Cultures are set up in triplicate with a final volume of 1.0 mL in a 35×10 mm petri dish (Nunc#174926). Culture medium is purchased from Terry Fox Labs. (HCC-4230 medium (Terry Fox Labs, Vancouver, B.C., Canada) and erythropoietin (Amgen, Thousand Oaks, Calif.) is added to the culture media. 3,000–10,000 CD34+ cells are added per dish. Recombinant IL-3, purified from mammalian cells or E. coli, and multi-functional hematopoietic receptor agonist proteins, in conditioned media from transfected mammalian cells or purified from conditioned media from transfected mammalian cells or E. coli, are added to give final concentrations ranging from 0.001 nM to 10 nM. Recombinant hIL-3, GM-CSF, c-mpl ligand and multi-functional hematopoietic receptor agonist are supplied in house. G-CSF (Neupogen) is from Amgen (Thousand Oaks Calf.). Cultures are resuspended using a 3 cc syringe and 1.0 mL is dispensed per dish. Control (baseline response) cultures received no colony stimulating factors. Positive control cultures received conditioned media (PHA stimulated human cells: Terry Fox Lab. H2400). Cultures are incubated at 37° C., 5% $CO_2$ in humidified air. Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

Human Cord Blood Hemopoietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., *PNAS USA* 89: 4109–113, 1992; Mayani et al., *Blood* 81: 3252–3258, 1993). In contrast to bone marrow, cord blood is more readily available on a regular basis. There is also a potential to reduce assay variability by pooling cells obtained fresh from several donors, or to create a bank of cryopreserved cells for this purpose. By modifying the culture conditions, and/or analyzing for lineage specific markers, it is be possible to assay specifically for granulocyte/macrophage colonies (CFU-GM), for megakaryocyte CSF activity, or for high proliferative potential colony forming cell (HPP-CFC) activity.

Methods

Mononuclear cells (MNC) are isolated from cord blood within 24 hr. of collection, using a standard density gradient (1.077 g/mL Histopaque). Cord blood MNC have been further enriched for stem cells and progenitors by several procedures, including immunomagnetic selection for CD14−, CD34+ cells; panning for SBA−, CD34+ fraction using coated flasks from Applied Immune Science (Santa Clara, Calif.); and CD34+ selection using a CellPro (Bothell, Wash.) avidin column. Either freshly isolated or cryopreserved CD34+ cell enriched fractions are used for the assay. Duplicate cultures for each serial dilution of sample (concentration range from 1 pM to 1204 pM) are #prepared with 1×104 cells in 1 ml of 0.9% methycellulose containing medium without additional growth factors (Methocult H4230 from Stem Cell Technologies, Vancouver, BC.). In some experiments, Methocult H4330 containing erythropoietin (EPO) was used instead of Methocult H4230, or Stem Cell Factor (SCF), 50 ng/mL (Biosource International, Camarillo, Calif.) was added. After culturing for 7–9 days, colonies containing >30 cells are counted. In order to rule out subjective bias in scoring, assays are scored blind.

Additional details about recombinant DNA methods which may be used to create the variants, express them in bacteria, mammalian cells or insect cells, purification and refold of the desired proteins and assays for determining the bioactivity of the proteins may be found in co-filed Applications WO 95/00646, WO 94/12639, WO 94/12638, WO 95/20976, WO 95/21197, WO 95/20977, WO 95/21254 and US 08/383,035 which are hereby incorporated by reference in their entirety.

Further details known to those skilled in the art may be found in T. Maniatis, et al., *Molecular Cloning, A Laboratory Manual*, Cold Spring Harbor Laboratory, 1982) and references cited therein, incorporated herein by reference; and in J. Sambrook, et al., *Molecular Cloning, A Laboratory Manual*, 2nd edition, Cold Spring Harbor Laboratory, 1989) and references cited therein, incorporated herein by reference.

TABLE 1

OLIGONUCLEOTIDES c-mplNcoI
    ACGTCCATGGCNTCNCCNGCNCCNCCTGCTTGTGCACTCCGAGTC
    (SEQ ID NO:13)
N = A, C, G or T Ecompl      ATGCACGAATTCCCTGACGCAGAGGGTGGA
             (SEQ ID NO:14)

c-mplHindIII  TGACAAGCTTACCTGACGCAGAGGGTGGACCCT
             (SEQ ID NO:15)

4L-5'         AATTCGGCAA (SEQ ID NO:16)

4L-3'         CATGTTGCCG (SEQ ID NO:17)

5L-5'         AATTCGGCGGCAA (SEQ ID NO:18)

5L-3'         CATGTTGCCGCCG (SEQ ID NO:19)

8L-5'         AATTCGGCGGCAACGGCGGCAA (SEQ ID NO:20)

TABLE 1-continued

| | OLIGONUCLEOTIDES |
|---|---|
| 8L-3' | CATGTTGCCGCCGTTGCCGCCG (SEQ ID NO:21) |
| 31-5' | CGATCCATGGAGGTTCACCCTTTGCCT (SEQ ID NO:22) |
| 31-3' | GATCAAGCTTATGGGCACTGGCTCAGTCT (SEQ ID NO:23) |
| 35-5' | CGATACATGTTGCCTACACCTGTCCTG (SEQ ID NO:24) |
| 35-3' | GATCAAGCTTAAGGGTGAACCTCTGGGCA (SEQ ID NO:25) |
| 39-5' | CGATCCATGGTCCTGCTGCCTGCTGTG (SEQ ID NO:26) |
| 39-3' | GATCAAGCTTAAGGTGTAGGCAAAGGGTG (SEQ ID NO:27) |
| 43-5' | CGATCCATGGCTGTGGACTTTAGCTTGGGA (SEQ ID NO:28) |
| 43-3' | GATCAAGCTTAAGGCAGCAGGACAGGTGT (SEQ ID NO:29) |
| 45-5' | CGATCCATGGACTTTAGCTTGGGAGAA (SEQ ID NO:30) |
| 45-3' | GATCAAGCTTACACAGCAGGCAGCAGGAC (SEQ ID NO:31) |
| 49-5' | CGATCCATGGGAGAATGGAAAACCCAG (SEQ ID NO:32) |
| 49-3' | GATCAAGCTTACAAGCTAAAGTCCACAGC (SEQ ID NO:33) |
| 82-5' | CGATCCATGGGACCCACTTGCCTCTCA (SEQ ID NO:34) |
| 82-3' | GATCAAGCTTACAGTTGTCCCCGTGCTGC (SEQ ID NO:35) |
| 109-5' | CAGTCCATGGGAACCCAGCTTCCTCCA (SEQ ID NO: 36) |
| 109-3' | GATCAAGCTTAAAGGAGGCTCTGCAGGGC (SEQ ID NO:37) |
| 116-5' | CGATCCATGGGCAGGACCACAGCTCAC (SEQ ID NO:38) |
| 116-3' | GATCAAGCTTACTGTGGAGGAAGCTGGGTT (SEQ ID NO: 39) |
| 120-5' | CGATCCATGGCTCACAAGGATCCCAATGCC (SEQ ID NO:40) |
| 120-3' | GATCAAGCTTATGTGGTCCTGCCCTGTGG (SEQ ID NO:41) |
| 123-5' | CGATCCATGGATCCCAATGCCATCTTCCTG (SEQ ID NO:42) |
| 123-3' | GATCAAGCTTACTTGTGAGCTGTGGTCCT (SEQ ID NO:43) |
| 126-5' | CGATCCATGGCCATCTTCCTGAGCTTCCAA (SEQ ID NO:44) |
| 126-3' | GATCAAGCTTAATTGGGATCCTTGTGAGCTGT (SEQ ID NO:45) |
| SYNNOXA1.REQ | AATTCCGTCG TAAACTGACC TTCTATCTGA AAACCTTGGA GAACGCGCAG GCTCAACAGT ACGTAGAGGG CGGTGGAGGC TCC (SEQ ID NO:46) |
| SYNNOXA2.REQ | CCGGGGAGCC TCCACCGCCC TCTACGTACT GTTGAGCCTG CGCGTTCTCC AAGGTTTTCA GATAGAAGGT CAGTTTACGA CGG (SEQ ID NO:47) |
| L1syn.for | GTTACCCTTG AGCAAGCGCA GGAACAACAG GGTGGTGGCT CTAACTGCTC TATAATGAT (SEQ ID NO:48) |
| L1syn.rev | CGATCATTAT AGAGCAGTTA GAGCCACCAC CCTGTTGTTC CTGCGCTTGC TCAAGG (SEQ ID NO:49) |
| L3syn.for | GTTACCCTTG AGCAAGCGCA GGAACAACAG GGTGGTGGCT CTGGCGGTGG CAGCGGCGGC GGTTCTAACT GCTCTATAAT GAT (SEQ ID NO:50) |
| L3syn.rev | CGATCATTAT AGAGCAGTTA GAACCGCCGC CGCTGCCACC GCCAGAGCCA CCACCCTGTT GTTCCTGCGC TTGCTCAAGG (SEQ ID NO:51) |
| 35start.seq | GATCGACCAT GGCTCTGGAC CCGAACAACC TC (SEQ ID NO:52) |

TABLE 1-continued

| OLIGONUCLEOTIDES | |
|---|---|
| 34rev.seq | CTCGATTACG TACAAAGGTG CAGGTGGT (SEQ ID NO:53) |
| 70start.seq | GATCGACCAT GGCTAATGCA TCAGGTATTG AG (SEQ ID NO:54) |
| 69rev.seq | CTCGATTACG TATTCTAAGT TCTTGACA (SEQ ID NO:55) |
| 91start.seq | GATCGACCAT GGCTGCACCC TCTCGACATC CA (SEQ ID NO:56) |
| 90rev.seq | CTCGATTACG TAGGCCGTGG CAGAGGGC (SEQ ID NO:57) |
| 101start.seq | GATCGACCAT GGCTGCAGGT GACTGGCAAG AA (SEQ ID NO:58) |
| 100rev.seq | CTCGATTACG TACTTGATGA TGATTGGA (SEQ ID NO:59) |
| L-11start.seq | GCTCTGAGAG CCGCCAGAGC CGCCAGAGGG CTGCGCAAGG TGGCGTAGAA CGCG (SEQ ID NO:60) |
| L-11stop.seq | CAGCCCTCTG GCGGCTCTGG CGGCTCTCAG AGCTTCCTGC TCAAGTCTTT AGAG (SEQ ID NO:61) |
| P-b1start.seq | GGGCTGCGCA AGGTGGCG (SEQ ID NO:62) |
| P-b1stop.seq | ACACCATTGG GCCCTGCCAG C (SEQ ID NO:63) |
| 39start.seq | GATCGACCAT GGCTTACAAG CTGTGCCACC CC (SEQ ID NO:64) |
| 38stop.Seq | CGATCGAAGC TTATTAGGTG GCACACAGCT TCTCCT (SEQ ID NO:65) |
| 97start.seq | GATCGACCAT GGCTCCCGAG TTGGGTCCCA CC (SEQ ID NO:66) |
| 96stop.Seq | CGATCGAAGC TTATTAGGAT ATCCCTTCCA GGGCCT (SEQ ID NO:67) |
| 126start.seq | GATCGACCAT GGCTATGGCC CCTGCCCTGC AG (SEQ ID NO:68) |
| 125stop.Seq | CGATCGAAGC TTATTATCCC AGTTCTTCCA TCTGCT (SEQ ID NO:69) |
| 133start.seq | GATCGACCAT GGCTACCCAG GGTGCCATGC CG (SEQ ID NO:70) |
| 132stop.seq | CGATCGAAGC TTATTAGGGC TGCAGGGCAG GGGCCA (SEQ ID NO:71) |
| 142start.seq | GATCGACCAT GGCTTCTGCT TTCCAGCGCC GG (SEQ ID NO:72) |
| 141stop.Seq | CGATCGAAGC TTATTAGGCG AAGGCCGGCA TGGCAC (SEQ ID NO:73) |
| GLYXA1 | GTAGAGGGCG GTGGAGGCTC C (SEQ ID NO:74) |
| GLYXA2 | CCGGGGAGCC TCCACCGCCC TCTAC (SEQ ID NO:75) |
| 1GGGSfor | TTCTACGCCA CCTTGCGCAG CCCGGCGGCG GCTCTGACAT GTCTACACCA TTG (SEQ ID NO:76) |
| 1GGGSrev | CAATGGTGTA GACATGTCAG AGCCGCCGCC GGGCTGCGCA AGGTGGCGTA GAA (SEQ ID NO:77) |
| Synnoxa1.req | AATTCCGTCG TAAACTGACC TTCTATCTGA AAACCTTGGA GAACGCGCAG GCTCAACAGT ACGTAGAGGG CGGTGGAGGC TCC (SEQ ID NO:240) |
| Synnoxa2.req | CCGGGGAGCC TCCACCGCCC TCTACGTACT GTTGAGCCTG CGCGTTCTCC AAGGTTTTCA GATAGAAGGT CAGTTTACGA CGG (SEQ ID NO:241) |

TABLE 2

GENE SEQUENCES pMON30304

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGT (SEQ ID NO:78)

pMON26458

TCCCCAGCTCCACCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGGGAATTC
(SEQ ID NO:79)

pMON28548

TCCCCAGCTCCACCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGGGAATTCGGCG
GCAACATGGCGTCTCCCGCTCCGCCTGCTTGTGACCTCCGAGTCCTCAGTAAACTGCTTCGTGACTC
CCATGTCCTTCACAGCAGACTGAGCCAGTGCCCAGAGGTTCACCCTTTGCCTACACCTGTCCTGCTG
CCTGCTGTGGACTTTAGCTTGGGAGAATGGAAAACCCAGATGGAGGAGACCAAGGCACAGGACATTC
TGGGAGCAGTGACCCTTCTGCTGGAGGGAGTGATGGCAGCACGGGACAACTGGGACCCACTTGCCT
CTCATCCCTCCTGGGGCAGCTTTCTGGACAGGTCCGTCTCCTCCTTGGGGCCCTGCAGAGCCTCCTT
GGAACCCAGGGCAGGACCACAGCTCACAAGGATCCCAATGCCATCTTCCTGAGCTTCCAACACCTGC
TCCGAGGAAAGGTGCGTTTCCTGATGCTTGTAGGAGGGTCCACCCTCTGCGTCAGG
(SEQ ID NO:80)

pMON28500

TCCCCAGCTCCACCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGGGAATTCGGCA
ACATGGCGTCTCCCGCTCCGCCTGCTTGTGACCTCCGAGTCCTCAGTAAACTGCTTCGTGACTCCCA
TGTCCTTCACAGCAGACTGAGCCAGTGCCCAGAGGTTCACCCTTTGCCTACACCTGTCCTGCTGCCT
GCTGTGGACTTTAGCTTGGGAGAATGGAAAACCCAGATGGAGGAGACCAAGGCACAGGACATTCTGG
GAGCAGTGACCCTTCTGCTGGAGGGAGTGATGGCAGCACGGGACAACTGGGACCCACTTGCCTCTC
ATCCCTCCTGGGGCAGCTTTCTGGACAGGTCCGTCTCCTCCTTGGGGCCCTGCAGAGCCTCCTTGGA
ACCCAGCTTCCTCCACAGGGCAGGACCACAGCTCACAAGGATCCCAATGCCATCTTCCTGAGCTTCC
AACACCTGCTCCGAGGAAAGGTGCGTTTCCTGATGCTTGTAGGAGGGTCCACCCTCTGCGTCAGG
(SEQ ID NO:81)

pMON28501

TCCCCAGCTCCACCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGGGAATTCGGCG
GCAACATGGCGTCTCCCGCTCCGCCTGCTTGTGACCTCCGAGTCCTCAGTAAACTGCTTCGTGACTC
CCATGTCCTTCACAGCAGACTGAGCCAGTGCCCAGAGGTTCACCCTTTGCCTACACCTGTCCTGCTG
CCTGCTGTGGACTTTAGCTTGGGAGAATGGAAAACCCAGATGGAGGAGACCAAGGCACAGGACATTC
TGGGAGCAGTGACCCTTCTGCTGGAGGGAGTGATGGCAGCACGGGACAACTGGGACCCACTTGCCT
CTCATCCCTCCTGGGGCAGCTTTCTGGACAGGTCCGTCTCCTCCTTGGGGCCCTGCAGAGCCTCCTT
GGAACCCAGCTTCCTCCACAGGGCAGGACCACAGCTCACAAGGATCCCAATGCCATCTTCCTGAGCT
TCCAACACCTGCTCCGAGGAAAGGTGCGTTTCCTGATGCTTGTAGGAGGGTCCACCCTCTGCGTCAG
G (SEQ ID NO:82)

pMON28502

TCCCCAGCGCCGCCTGCTTGTGACCTCCGAGTCCTCAGTAAACTGCTTCGTGACTCCCATGTCCTTC

TABLE 2-continued

GENE SEQUENCES

ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGGGAATTCGGCG
GCAACGGCGGCAACATGGCGTCCCAGCGCCGCCTGCTTGTGACCTCCGAGTCCTCAGTAAACTGCT
TCGTGACTCCCATGTCCTTCACAGCAGACTGAGCCAGTGCCCAGAGGTTCACCCTTTGCCTACACCT
GTCCTGCTGCCTGCTGTGGACTTTAGCTTGGGAGAATGGAAAACCCAGATGGAGGAGACCAAGGCAC
AGGACATTCTGGGAGCAGTGACCCTTCTGCTGGAGGGAGTGATGGCAGCACGGGACAACTGGGACC
CACTTGCCTCTCATCCCTCCTGGGGCAGCTTTCTGGACAGGTCCGTCTCCTCCTTGGGGCCCTGCAG
AGCCTCCTTGGAACCCAGCTTCCTCCACAGGGCAGGACCACAGCTCACAAGGATCCCAATGCCATCT
TCCTGAGCTTCCAACACCTGCTCCGAGGAAAGGTGCGTTTCCTGATGCTTGTAGGAGGGTCCACCCT
CTGCGTCAGG (SEQ ID NO:83)

Syntan1

1 CATGGCTAAC TGCTCTATAA TGATCGATGA AATTATACAT CACTTAAAGA
     51 GACCACCTGC ACCTTTGCTG GACCCGAACA ACCTCAATGA CGAAGACGTC
    101 TCTATCCTGA TGGACCGAAA CCTTCGACTT CCAAACCTGG AGAGCTTCGT
    151 AAGGGCTGTC AAGAACTTAG AAAATGCATC AGGTATTGAG GCAATTCTTC
    201 GTAATCTCCA ACCATGTCTG CCCTCTGCCA CGGCCGCACC CTCTCGACAT
    251 CCAATCATCA TCAAGGCAGG TGACTGGCAA GAATTCCGGG AAAAACTGAC
    301 GTTCTATCTG GTTACCCTTG AGCAAGCGCA GGAACAACAG GGTGGTGGCT
    351 CTAACTGCTC TATAATGATC GATGAAATTA TACATCACTT AAAGAGACCA
    401 CCTGCACCTT TGCTGGACCC GAACAACCTC AATGACGAAG ACGTCTCTAT
    451 CCTGATGGAC CGAAACCTTC GACTTCCAAA CCTGGAGAGC TTCGTAAGGG
    501 CTGTCAAGAA CTTAGAAAAT GCATCAGGTA TTGAGGCAAT TCTTCGTAAT
    551 CTCCAACCAT GTCTGCCCTC TGCCACGGCC GCACCCTCTC GACATCCAAT
    601 CATCATCAAG GCAGGTGACT GGCAAGAATT CCGGGAAAAA CTGACGTTCT
    651 ATCTGGTTAC CCTTGAGCAA GCGCAGGAAC AACAGTAC (SEQ ID NO:84)

Syntan3

1 CATGGCTAAC TGCTCTATAA TGATCGATGA AATTATACAT CACTTAAAGA
     51 GACCACCTGC ACCTTTGCTG GACCCGAACA ACCTCAATGA CGAAGACGTC
    101 TCTATCCTGA TGGACCGAAA CCTTCGACTT CCAAACCTGG AGAGCTTCGT
    151 AAGGGCTGTC AAGAACTTAG AAAATGCATC AGGTATTGAG GCAATTCTTC
    201 GTAATCTCCA ACCATGTCTG CCCTCTGCCA CGGCCGCACC CTCTCGACAT
    251 CCAATCATCA TCAAGGCAGG TGACTGGCAA GAATTCCGGG AAAAACTGAC
    301 GTTCTATCTG GTTACCCTTG AGCAAGCGCA GGAACAACAG GGTGGTGGCT
    351 CTGGCGGTGG CAGCGGCGGC GGTTCTAACT GCTCTATAAT GATCGATGAA
    401 ATTATACATC ACTTAAAGAG ACCACCTGCA CCTTTGCTGG ACCCGAACAA
    451 CCTCAATGAC GAAGACGTCT CTATCCTGAT GGACCGAAAC CTTCGACTTC
    501 CAAACCTGGA GAGCTTCGTA AGGGCTGTCA AGAACTTAGA AAATGCATCA
    551 GGTATTGAGG CAATTCTTCG TAATCTCCAA CCATGTCTGC CCTCTGCCAC
    601 GGCCGCACCC TCTCGACATC CAATCATCAT CAAGGCAGGT GACTGGCAAG
    651 AATTCCGGGA AAAACTGACG TTCTATCTGG TTACCCTTGA GCAAGCGCAG
    701 GAACAACAGT AC (SEQ ID NO:85)

pMON31104

1 ATGGCTCTGG ACCCGAACAA CCTCAATGAC GAAGACGTCT CTATCCTGAT
     51 GGACCGAAAC CTTCGACTTC CAAACCTGGA GAGCTTCGTA AGGGCTGTCA
    101 AGAACTTAGA AAATGCATCA GGTATTGAGG CAATTCTTCG TAATCTCCAA
    151 CCATGTCTGC CCTCTGCCAC GGCCGCACCC TCTCGACATC CAATCATCAT
    201 CAAGGCAGGT GACTGGCAAG AATTCCGGGA AAAACTGACG TTCTATCTGG
    251 TTACCCTTGA GCAAGCGCAG GAACAACAGG GTGGTGGCTC TAACTGCTCT
    301 ATAATGATCG ATGAAATTAT ACATCACTTA AAGAGACCAC CTGCACCCTTT
    351 GTACGTAGAG GGCGGTGGAG GCTCCCCGGG TGAACCGTCT GGTCCAATCT
    401 CTACTATCAA CCCGTCTCCT CCGTCTAAAG AATCTCATAA ATCTCCAAAC
    451 ATGGCTACCC AGGGTGCCAT GCCGGCCTTC GCCTCTGCTT TCCAGCGCCG
    501 GGCAGGAGGG GTCCTGGTTG CTAGCCATCT GCAGAGCTTC CTGGAGGTGT
    551 CGTACCGCGT TCTACGCCAC CTTGCGCAGC CCTCTGGCGG CTCTGGCGGC
    601 TCTCAGAGCT TCCTGCTCAA GTCTTTAGAG CAAGTGAGAA AGATCCAGGG
    651 CGATGGCGCA GCGCTCCAGG AGAAGCTGTG TGCCACCTAC AAGCTGTGCC
    701 ACCCCGAGGA GCTGGTGCTG CTCGGACACT CTCTGGGCAT CCCCTGGGCT
    751 CCCCTGAGCT CCTGCCCCAG CCAGGCCCTG CAGCTGGCAG GCTGCTTGAG
    801 CCAACTCCAT AGCGGCCTTT TCCTCTACCA GGGGCTCCTG CAGGCCCTGG
    851 AAGGGATATC CCCCGAGTTG GGTCCCACCT TGGACACACT GCAGCTGGAC
    901 GTCGCCGACT TTGCCACCAC CATCTGGCAG CAGATGGAAG AACTGGGAAT
    951 GGCCCCTGCC CTGCAGCCCT AATAA (SEQ ID NO:86)

pMON31105

1 ATGGCTAATG CATCAGGTAT TGAGGCAATT CTTCGTAATC TCCAACCATG
     51 TCTGCCCTCT GCCACGGCCG CACCCTCTCG ACATCCAATC ATCATCAAGG

TABLE 2-continued

GENE SEQUENCES

```
101 CAGGTGACTG GCAAGAATTC CGGGAAAAAC TGACGTTCTA TCTGGTTACC
151 CTTGAGCAAG CGCAGGAACA ACAGGGTGGT GGCTCTAACT GCTCTATAAT
201 GATCGATGAA ATTATACATC ACTTAAAGAG ACCACCTGCA CCTTTGCTGG
251 ACCCGAACAA CCTCAATGAC GAAGACGTCT CTATCCTGAT GGACCGAAAC
301 CTTCGACTTC CAAACCTGGA GAGCTTCGTA AGGGCTGTCA AGAACTTAGA
351 ATACGTAGAG GGCGGTGGAG GCTCCCCGGG TGAACCGTCT GGTCCAATCT
401 CTACTATCAA CCCGTCTCCT CCGTCTAAAG AATCTCATAA ATCTCCAAAC
451 ATGGCTACCC AGGGTGCCAT GCCGGCCTTC GCCTCTGCTT TCCAGCGCCG
501 GGCAGGAGGG GTCCTGGTTG CTAGCCATCT GCAGAGCTTC CTGGAGGTGT
551 CGTACCGCGT TCTACGCCAC CTTGCGCAGC CCTCTGGCGG CTCTGGCGGC
601 TCTCAGAGCT TCCTGCTCAA GTCTTTAGAG CAAGTGAGAA AGATCCAGGG
651 CGATGGCGCA GCGCTCCAGG AGAAGCTGTG TGCCACCTAC AAGCTGTGCC
701 ACCCCGAGGA GCTGGTGCTG CTCGGACACT CTCTGGGCAT CCCCTGGGCT
751 CCCCTGAGCT CCTGCCCCAG CCAGGCCCTG CAGCTGGCAG GCTGCTTGAG
801 CCAACTCCAT AGCGGCCTTT TCCTCTACCA GGGGCTCCTG CAGGCCCTGG
851 AAGGGATATC CCCCGAGTTG GGTCCCACCT TGGACACACT GCAGCTGGAC
901 GTCGCCGACT TGCCACCAC CATCTGGCAG CAGATGGAAG AACTGGGAAT
951 GGCCCCTGCC CTGCAGCCCT AATAA (SEQ ID NO:87)
``` pMON31106

```
  1 ATGGCTGCAC CCTCTCGACA TCCAATCATC ATCAAGGCAG GTGACTGGCA
 51 AGAATTCCGG GAAAAACTGA CGTTCTATCT GGTTACCCTT GAGCAAGCGC
101 AGGAACAACA GGGTGGTGGC TCTAACTGCT CTATAATGAT CGATGAAATT
151 ATACATCACT TAAAGAGACC ACCTGCACCT TTGCTGGACC CGAACAACCT
201 CAATGACGAA GACGTCTCTA TCCTGATGGA CCGAAACCTT CGACTTCCAA
251 ACCTGGAGAG CTTCGTAAGG CTGTCAAGA ACTTAGAAAA TGCATCAGGT
301 ATTGAGGCAA TTCTTCGTAA TCTCCAACCA TGTCTGCCCT CTGCCACGGC
351 CTACGTAGAG GGCGGTGGAG GCTCCCCGGG TGAACCGTCT GGTCCAATCT
401 CTACTATCAA CCCGTCTCCT CCGTCTAAAG AATCTCATAA ATCTCCAAAC
451 ATGGCTACCC AGGGTGCCAT GCCGGCCTTC GCCTCTGCTT TCCAGCGCCG
501 GGCAGGAGGG GTCCTGGTTG CTAGCCATCT GCAGAGCTTC CTGGAGGTGT
551 CGTACCGCGT TCTACGCCAC CTTGCGCAGC CCTCTGGCGG CTCTGGCGGC
601 TCTCAGAGCT TCCTGCTCAA GTCTTTAGAG CAAGTGAGAA AGATCCAGGG
651 CGATGGCGCA GCGCTCCAGG AGAAGCTGTG TGCCACCTAC AAGCTGTGCC
701 ACCCCGAGGA GCTGGTGCTG CTCGGACACT CTCTGGGCAT CCCCTGGGCT
751 CCCCTGAGCT CCTGCCCCAG CCAGGCCCTG CAGCTGGCAG GCTGCTTGAG
801 CCAACTCCAT AGCGGCCTTT TCCTCTACCA GGGGCTCCTG CAGGCCCTGG
851 AAGGGATATC CCCCGAGTTG GGTCCCACCT TGGACACACT GCAGCTGGAC
901 GTCGCCGACT TGCCACCAC CATCTGGCAG CAGATGGAAG AACTGGGAAT
951 GGCCCCTGCC CTGCAGCCCT AATAA (SEQ ID NO:88)
``` pMON31107

```
  1 ATGGCTGCAG GTGACTGGCA AGAATTCCGG GAAAAACTGA CGTTCTATCT
 51 GGTTACCCTT GAGCAAGCGC AGGAACAACA GGGTGGTGGC TCTAACTGCT
101 CTATAATGAT CGATGAAATT ATACATCACT TAAAGAGACC ACCTGCACCT
151 TTGCTGGACC CGAACAACCT CAATGACGAA GACGTCTCTA TCCTGATGGA
201 CCGAAACCTT CGACTTCCAA ACCTGGAGAG CTTCGTAAGG CTGTCAAGA
251 ACTTAGAAAA TGCATCAGGT ATTGAGGCAA TTCTTCGTAA TCTCCAACCA
301 TGTCTGCCCT CTGCCACGGC CGCACCCTCT CGACATCCAA TCATCATCAA
351 GTACGTAGAG GGCGGTGGAG GCTCCCCGGG TGAACCGTCT GGTCCAATCT
401 CTACTATCAA CCCGTCTCCT CCGTCTAAAG AATCTCATAA ATCTCCAAAC
451 ATGGCTACCC AGGGTGCCAT GCCGGCCTTC GCCTCTGCTT TCCAGCGCCG
501 GGCAGGAGGG GTCCTGGTTG CTAGCCATCT GCAGAGCTTC CTGGAGGTGT
551 CGTACCGCGT TCTACGCCAC CTTGCGCAGC CCTCTGGCGG CTCTGGCGGC
601 TCTCAGAGCT TCCTGCTCAA GTCTTTAGAG CAAGTGAGAA AGATCCAGGG
651 CGATGGCGCA GCGCTCCAGG AGAAGCTGTG TGCCACCTAC AAGCTGTGCC
701 ACCCCGAGGA GCTGGTGCTG CTCGGACACT CTCTGGGCAT CCCCTGGGCT
751 CCCCTGAGCT CCTGCCCCAG CCAGGCCCTG CAGCTGGCAG GCTGCTTGAG
801 CCAACTCCAT AGCGGCCTTT TCCTCTACCA GGGGCTCCTG CAGGCCCTGG
851 AAGGGATATC CCCCGAGTTG GGTCCCACCT TGGACACACT GCAGCTGGAC
901 GTCGCCGACT TGCCACCAC CATCTGGCAG CAGATGGAAG AACTGGGAAT
951 GGCCCCTGCC CTGCAGCCCT AATAA (SEQ ID NO:89)
``` pMON31108

```
  1 ATGGCTCTGG ACCCGAACAA CCTCAATGAC GAAGACGTCT CTATCCTGAT
 51 GGACCGAAAC CTTCGACTTC CAAACCTGGA GAGCTTCGTA AGGGCTGTCA
101 AGAACTTAGA AAATGCATCA GGTATTGAGG CAATTCTTCG TAATCTCCAA
151 CCATGTCTGC CCTCTGCCAC GGCCGCACCC TCTCGACATC CAATCATCAT
201 CAAGGCAGGT GACTGGCAAG AATTCCGGGA AAAACTGACG TTCTATCTGG
251 TTACCCTTGA GCAAGCGCAG GAACAACAGG GTGGTGGCTC TGGCGGTGGC
301 AGCGGCGGCG GTTCTAACTG CTCTATAATG ATCGATGAAA TTATACATCA
351 CTTAAAGAGA CCACCTGCAC CTTTGTACGT AGAGGGCGGT GGAGGCTCCC
401 CGGGTGAACC GTCTGGTCCA ATCTCTACTA TCAACCCGTC TCCTCCGTCT
451 AAAGAATCTC ATAAATCTCC AAACATGGCT ACCCAGGGTG CCATGCCGGC
```

TABLE 2-continued

GENE SEQUENCES

```
501 CTTCGCCTCT GCTTTCCAGC GCCGGGCAGG AGGGGTCCTG GTTGCTAGCC
551 ATCTGCAGAG CTTCCTGGAG GTGTCGTACC GCGTTCTACG CCACCTTGCG
601 CAGCCCTCTG GCGGCTCTGG CGGCTCTCAG AGCTTCCTGC TCAAGTCTTT
651 AGAGCAAGTG AGAAAGATCC AGGGCGATGG CGCAGCGCTC CAGGAGAAGC
701 TGTGTGCCAC CTACAAGCTG TGCCACCCCG AGGAGCTGGT GCTGCTCGGA
751 CACTCTCTGG GCATCCCCTG GCTCCCCTG AGCTCCTGCC CCAGCCAGGC
801 CCTGCAGCTG GCAGGCTGCT TGAGCCAACT CCATAGCGGC CTTTTCCTCT
851 ACCAGGGGCT CCTGCAGGCC CTGGAAGGGA TATCCCCCGA GTTGGGTCCC
901 ACCTTGGACA CACTGCAGCT GGACGTCGCC GACTTTGCCA CCACCATCTG
951 GCAGCAGATG GAAGAACTGG GAATGGCCCC TGCCCTGCAG CCCTAATAA
    (SEQ ID NO:90)
``` pMON31109

```
  1 ATGGCTAATG CATCAGGTAT TGAGGCAATT CTTCGTAATC TCCAACCATG
 51 TCTGCCCTCT GCCACGGCCG CACCCTCTCG ACATCCAATC ATCATCAAGG
101 CAGGTGACTG GCAAGAATTC CGGGAAAAAC TGACGTTCTA TCTGGTTACC
151 CTTGAGCAAG CGCAGGAACA ACAGGGTGGT GGCTCTGGCG GTGGCAGCGG
201 CGGCGGTTCT AACTGCTCTA TAATGATCGA TGAAATTATA CATCACTTAA
251 AGAGACCACC TGCACCTTTG CTGGACCCGA ACAACCTCAA TGACGAAGAC
301 GTCTCTATCC TGATGGACCG AAACCTTCGA CTTCCAAACC TGGAGAGCTT
351 CGTAAGGGCT GTCAAGAACT TAGAATACGT AGAGGGCGGT GGAGGCTCCC
401 CGGGTGAACC GTCTGGTCCA ATCTCTACTA TCAACCCGTC TCCTCCGTCT
451 AAAGAATCTC ATAAATCTCC AAACATGGCT ACCCAGGGTG CCATGCCGGC
501 CTTCGCCTCT GCTTTCCAGC GCCGGGCAGG AGGGGTCCTG GTTGCTAGCC
551 ATCTGCAGAG CTTCCTGGAG GTGTCGTACC GCGTTCTACG CCACCTTGCG
601 CAGCCCTCTG GCGGCTCTGG CGGCTCTCAG AGCTTCCTGC TCAAGTCTTT
651 AGAGCAAGTG AGAAAGATCC AGGGCGATGG CGCAGCGCTC CAGGAGAAGC
701 TGTGTGCCAC CTACAAGCTG TGCCACCCCG AGGAGCTGGT GCTGCTCGGA
751 CACTCTCTGG GCATCCCCTG GCTCCCCTG AGCTCCTGCC CCAGCCAGGC
801 CCTGCAGCTG GCAGGCTGCT TGAGCCAACT CCATAGCGGC CTTTTCCTCT
851 ACCAGGGGCT CCTGCAGGCC CTGGAAGGGA TATCCCCCGA GTTGGGTCCC
901 ACCTTGGACA CACTGCAGCT GGACGTCGCC GACTTTGCCA CCACCATCTG
951 GCAGCAGATG GAAGAACTGG GAATGGCCCC TGCCCTGCAG CCCTAATAA
    (SEQ ID NO:91)
``` pMON31110

```
  1 ATGGCTGCAC CCTCTCGACA TCCAATCATC ATCAAGGCAG GTGACTGGCA
 51 AGAATTCCGG GAAAAACTGA CGTTCTATCT GGTTACCCTT GAGCAAGCGC
101 AGGAACAACA GGGTGGTGGC TCTGGCGGTG GCAGCGGCGG CGGTTCTAAC
151 TGCTCTATAA TGATCGATGA AATTATACAT CACTTAAAGA GACCACCTGC
201 ACCTTTGCTG ACCCGAACA ACCTCAATGA CGAAGACGTC TCTATCCTGA
251 TGGACCGAAA CCTTCGACTT CCAAACCTGG AGAGCTTCGT AAGGGCTGTC
301 AAGAACTTAG AAAATGCATC AGGTATTGAG GCAATTCTTC GTAATCTCCA
351 ACCATGTCTG CCCTCTGCCA CGGCCTACGT AGAGGGCGGT GGAGGCTCCC
401 CGGGTGAACC GTCTGGTCCA ATCTCTACTA TCAACCCGTC TCCTCCGTCT
451 AAAGAATCTC ATAAATCTCC AAACATGGCT ACCCAGGGTG CCATGCCGGC
501 CTTCGCCTCT GCTTTCCAGC GCCGGGCAGG AGGGGTCCTG GTTGCTAGCC
551 ATCTGCAGAG CTTCCTGGAG GTGTCGTACC GCGTTCTACG CCACCTTGCG
601 CAGCCCTCTG GCGGCTCTGG CGGCTCTCAG AGCTTCCTGC TCAAGTCTTT
651 AGAGCAAGTG AGAAAGATCC AGGGCGATGG CGCAGCGCTC CAGGAGAAGC
701 TGTGTGCCAC CTACAAGCTG TGCCACCCCG AGGAGCTGGT GCTGCTCGGA
751 CACTCTCTGG GCATCCCCTG GCTCCCCTG AGCTCCTGCC CCAGCCAGGC
801 CCTGCAGCTG GCAGGCTGCT TGAGCCAACT CCATAGCGGC CTTTTCCTCT
851 ACCAGGGGCT CCTGCAGGCC CTGGAAGGGA TATCCCCCGA GTTGGGTCCC
901 ACCTTGGACA CACTGCAGCT GGACGTCGCC GACTTTGCCA CCACCATCTG
951 GCAGCAGATG GAAGAACTGG GAATGGCCCC TGCCCTGCAG CCCTAATAA
    (SEQ ID NO:92)
``` pMON31111

```
  1 ATGGCTGCAG GTGACTGGCA AGAATTCCGG GAAAAACTGA CGTTCTATCT
 51 GGTTACCCTT GAGCAAGCGC AGGAACAACA GGGTGGTGGC TCTGGCGGTG
101 GCAGCGGCGG CGGTTCTAAC TGCTCTATAA TGATCGATGA AATTATACAT
151 CACTTAAAGA GACCACCTGC ACCTTTGCTG ACCCGAACA ACCTCAATGA
201 CGAAGACGTC TCTATCCTGA TGGACCGAAA CCTTCGACTT CCAAACCTGG
251 AGAGCTTCGT AAGGGCTGTC AAGAACTTAG AAAATGCATC AGGTATTGAG
301 GCAATTCTTC GTAATCTCCA ACCATGTCTG CCCTCTGCCA CGGCCGCACC
351 CTCTCGACAT CCAATCATCA TCAAGTACGT AGAGGGCGGT GGAGGCTCCC
401 CGGGTGAACC GTCTGGTCCA ATCTCTACTA TCAACCCGTC TCCTCCGTCT
451 AAAGAATCTC ATAAATCTCC AAACATGGCT ACCCAGGGTG CCATGCCGGC
501 CTTCGCCTCT GCTTTCCAGC GCCGGGCAGG AGGGGTCCTG GTTGCTAGCC
551 ATCTGCAGAG CTTCCTGGAG GTGTCGTACC GCGTTCTACG CCACCTTGCG
601 CAGCCCTCTG GCGGCTCTGG CGGCTCTCAG AGCTTCCTGC TCAAGTCTTT
651 AGAGCAAGTG AGAAAGATCC AGGGCGATGG CGCAGCGCTC CAGGAGAAGC
701 TGTGTGCCAC CTACAAGCTG TGCCACCCCG AGGAGCTGGT GCTGCTCGGA
```

TABLE 2-continued

GENE SEQUENCES

```
751 CACTCTCTGG GCATCCCCTG GGCTCCCCTG AGCTCCTGCC CCAGCCAGGC
801 CCTGCAGCTG GCAGGCTGCT TGAGCCAACT CCATAGCGGC CTTTTCCTCT
851 ACCAGGGGCT CCTGCAGGCC CTGGAAGGGA TATCCCCCGA GTTGGGTCCC
901 ACCTTGGACA CACTGCAGCT GGACGTCGCC GACTTTGCCA CCACCATCTG
951 GCAGCAGATG GAAGAACTGG GAATGGCCCC TGCCCTGCAG CCCTAATAA
    (SEQ ID NO:93)
``` pMON13182

```
  1 ATGGCTAACTGCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTT
401 ACAAGCTGTG CCACCCCGAG GAGCTGGTGC TGCTCGGACA CTCTCTGGGC
451 ATCCCCTGGG CTCCCCTGAG CTCCTGCCCC AGCCAGGCCC TGCAGCTGGC
501 AGGCTGCTTG AGCCAACTCC ATAGCGGCCT TTTCCTCTAC CAGGGGCTCC
551 TGCAGGCCCT GGAAGGGATA TCCCCCGAGT TGGGTCCCAC CTTGGACACA
601 CTGCAGCTGG ACGTCGCCGA CTTTGCCACC ACCATCTGGC AGCAGATGGA
651 AGAACTGGGA ATGGCCCCTG CCCTGCAGCC CACCCAGGGT GCCATGCCGG
701 CCTTCGCCTC TGCTTTCCAG CGCCGGGCAG GAGGGGTCCT GGTTGCTAGC
751 CATCTGCAGA GCTTCCTGGA GGTGTCGTAC CGCGTTCTAC GCCACCTTGC
801 GCAGCCCTCT GGCGGCTCTG GCGGCTCTCA GAGCTTCCTG CTCAAGTCTT
851 TAGAGCAAGT GAGAAAGATC CAGGGCGATG GCGCAGCGCT CCAGGAGAAG
901 CTGTGTGCCA CCTAATAA (SEQ ID NO:94)
``` pMON13183

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTTACAAG
451 CTGTGCCACC CCGAGGAGCT GGTGCTGCTC GGACACTCTC TGGGCATCCC
501 CTGGGCTCCC CTGAGCTCCT GCCCCAGCCA GGCCCTGCAG CTGGCAGGCT
551 GCTTGAGCCA ACTCCATAGC GGCCTTTTCC TCTACCAGGG GCTCCTGCAG
601 GCCCTGGAAG GGATATCCCC CGAGTTGGGT CCCACCTTGG ACACACTGCA
651 GCTGGACGTC GCCGACTTTG CCACCACCAT CTGGCAGCAG ATGGAAGAAC
701 TGGGAATGGC CCCTGCCCTG CAGCCCACCC AGGGTGCCAT GCCGGCCTTC
751 GCCTCTGCTT TCCAGCGCCG GGCAGGAGGG GTCCTGGTTG CTAGCCATCT
801 GCAGAGCTTC CTGGAGGTGT CGTACCGCGT TCTACGCCAC CTTGCGCAGC
851 CCTCTGGCGG CTCTGGCGGC TCTCAGAGCT TCCTGCTCAA GTCTTTAGAG
901 CAAGTGAGAA AGATCCAGGG CGATGGCGCA GCGCTCCAGG AGAAGCTGTG
951 TGCCACCTAA TAA (SEQ ID NO:95)
``` pMON13184

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTC
401 CCGAGTTGGG TCCCACCTTG GACACACTGC AGCTGGACGT CGCCGACTTT
451 GCCACCACCA TCTGGCAGCA GATGGAAGAA CTGGGAATGG CCCCTGCCCT
501 GCAGCCCACC CAGGGTGCCA TGCCGGCCTT CGCCTCTGCT TTCCAGCGCC
551 GGGCAGGAGG GGTCCTGGTT GCTAGCCATC TGCAGAGCTT CCTGGAGGTG
601 TCGTACCGCG TTCTACGCCA CCTTGCGCAG CCCTCTGGCG GCTCTGGCGG
651 CTCTCAGAGC TTCCTGCTCA AGTCTTTAGA GCAAGTGAGA AGATCCAGG
701 GCGATGGCGC AGCGCTCCAG GAGAAGCTGT GTGCCACCTA AGCTGTGC
751 CACCCCGAGG AGCTGGTGCT GCTCGGACAC TCTCTGGGCA TCCCCTGGGC
801 TCCCCTGAGC TCCTGCCCCA GCCAGGCCCT GCAGCTGGCA GGCTGCTTGA
851 GCCAACTCCA TAGCGGCCTT TTCCTCTACC AGGGGCTCCT GCAGGCCCTG
901 GAAGGGATAT CCTAATAA (SEQ ID NO:96)
``` pMON13185

```
  1 ATGGCTAACT GCTCTATAAT GATCGATGAA ATTATACATC ACTTAAAGAG
```

TABLE 2-continued

GENE SEQUENCES

```
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCCCGAG
451 TTGGGTCCCA CCTTGGACAC ACTGCAGCTG GACGTCGCCG ACTTTGCCAC
501 CACCATCTGG CAGCAGATGG AAGAACTGGG AATGGCCCCT GCCCTGCAGC
551 CCACCCAGGG TGCCATGCCG GCCTTCGCCT CTGCTTTCCA GCGCGGGGCA
601 GGAGGGGTCC TGGTTGCTAG CCATCTGCAG AGCTTCCTGG AGGTGTCGTA
651 CCGCGTTCTA CGCCACCTTG CGCAGCCCTC TGGCGGCTCT GGCGGCTCTC
701 AGAGCTTCCT GCTCAAGTCT TTAGAGCAAG TGAGAAAGAT CCAGGGCGAT
751 GGCGCAGCGC TCCAGGAGAA GCTGTGTGCC ACCTACAAGC TGTGCCACCC
801 CGAGGAGCTG GTGCTGCTCG ACACTCTCT GGGCATCCCC TGGGCTCCCC
851 TGAGCTCCTG CCCCAGCCAG GCCCTGCAGC TGGCAGGCTG CTTGAGCCAA
901 CTCCATAGCG GCCTTTTCCT CTACCAGGGG CTCCTGCAGG CCCTGGAAGG
951 GATATCCTAA TAA (SEQ ID NO:97)
``` pMON13186

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTA
401 TGGCCCCTGC CCTGCAGCCC ACCCAGGGTG CCATGCCGGC CTTCGCCTCT
451 GCTTTCCAGC GCGGGCAGG AGGGGTCCTG GTTGCTAGCC ATCTGCAGAG
501 CTTCCTGGAG GTGTCGTACC GCGTTCTACG CCACCTTGCG CAGCCCTCTG
551 GCGGCTCTGG CGGCTCTCAG AGCTTCCTGC TCAAGTCTTT AGAGCAAGTG
601 AGAAAGATCC AGGGCGATGG CGCAGCGCTC CAGGAGAAGC TGTGTGCCAC
651 CTACAAGCTG TGCCACCCCG AGGAGCTGGT GCTGCTCGGA CACTCTCTGG
701 GCATCCCCTG GGCTCCCCTG AGCTCCTGCC CAGCCAGGC CCTGCAGCTG
751 GCAGGCTGCT TGAGCCAACT CCATAGCGGC CTTTTCCTCT ACCAGGGGCT
801 CCTGCAGGCC CTGGAAGGGA TATCCCCCGA GTTGGGTCCC ACCTTGGACA
851 CACTGCAGCT GGACGTCGCC GACTTTGCCA CCACCATCTG GCAGCAGATG
901 GAAGAACTGG GATAATAA (SEQ ID NO:98)
``` pMON13187

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTATGGCC
451 CCTGCCCTGC AGCCCACCCA GGGTGCCATG CCGGCCTTCG CCTCTGCTTT
501 CCAGCGCCGG GCAGGAGGGG TCCTGGTTGC TAGCCATCTG CAGAGCTTCC
551 TGGAGGTGTC GTACCGCGTT CTACGCCACC TTGCGCAGCC CTCTGGCGGC
601 TCTGGCGGCT CTCAGAGCTT CCTGCTCAAG TCTTTAGAGC AAGTGAGAAA
651 GATCCAGGGC GATGGCGCAG CGCTCCAGGA GAAGCTGTGT GCCACCTACA
701 AGCTGTGCCA CCCCGAGGAG CTGGTGCTGC TCGGACACTC TCTGGGCATC
751 CCCTGGGCTC CCCTGAGCTC CTGCCCCAGC CAGGCCCTGC AGCTGGCAGG
801 CTGCTTGAGC CAACTCCATA GCGGCCTTTT CCTCTACCAG GGGCTCCTGC
851 AGGCCCTGGA AGGGATATCC CCGAGTTGG GTCCCACCTT GGACACACTG
901 CAGCTGGACG TCGCCGACTT TGCCACCACC ATCTGGCAGC AGATGGAAGA
951 ACTGGGATAA TAA (SEQ ID NO:99)
``` pMON13188

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTA
401 CCCAGGGTGC CATGCCGGCC TTCGCCTCTG CTTTCCAGCG CCGGGCAGGA
451 GGGGTCCTGG TTGCTAGCCA TCTGCAGAGC TTCCTGGAGG TGTCGTACCG
```

TABLE 2-continued

GENE SEQUENCES

501 CGTTCTACGC CACCTTGCGC AGCCCTCTGG CGGCTCTGGC GGCTCTCAGA
551 GCTTCCTGCT CAAGTCTTTA GAGCAAGTGA GAAAGATCCA GGGCGATGGC
601 GCAGCGCTCC AGGAGAAGCT GTGTGCCACC TACAAGCTGT GCCACCCCGA
651 GGAGCTGGTG CTGCTCGGAC ACTCTCTGGG CATCCCCTGG GCTCCCCTGA
701 GCTCCTGCCC CAGCCAGGCC CTGCAGCTGG CAGGCTGCTT GAGCCAACTC
751 CATAGCGGCC TTTTCCTCTA CCAGGGGCTC CTGCAGGCCC TGGAAGGGAT
801 ATCCCCCGAG TTGGGTCCCA CCTTGGACAC ACTGCAGCTG GACGTCGCCG
851 ACTTTGCCAC CACCATCTGG CAGCAGATGG AAGAACTGGG AATGGCCCCT
901 GCCCTGCAGC CCTAATAA (SEQ ID NO:100)

pMON13189

1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTACCCAG
451 GGTGCCATGC CGGCCTTCGC CTCTGCTTTC CAGCGCCGGG CAGGAGGGGT
501 CCTGGTTGCT AGCCATCTGC AGAGCTTCCT GGAGGTGTCG TACCGCGTTC
551 TACGCCACCT TGCGCAGCCC TCTGGCGGCT CTGGCGGCTC TCAGAGCTTC
601 CTGCTCAAGT CTTTAGAGCA AGTGAGAAAG ATCCAGGGCG ATGGCGCAGC
651 GCTCCAGGAG AAGCTGTGTG CCACCTACAA GCTGTGCCAC CCCGAGGAGC
701 TGGTGCTGCT CGGACACTCT CTGGGCATCC CCTGGGCTCC CCTGAGCTCC
751 TGCCCCAGCC AGGCCCTGCA GCTGGCAGGC TGCTTGAGCC AACTCCATAG
801 CGGCCTTTTC CTCTACCAGG GGCTCCTGCA GGCCCTGGAA GGGATATCCC
851 CCGAGTTGGG TCCCACCTTG GACACACTGC AGCTGGACGT CGCCGACTTT
901 GCCACCACCA TCTGGCAGCA GATGGAAGAA CTGGGAATGG CCCCTGCCCT
951 GCAGCCCTAA TAA (SEQ ID NO:101)

pMON13190

1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTT
401 CTGCTTTCCA GCGCCGGGCA GGAGGGGTCC TGGTTGCTAG CCATCTGCAG
451 AGCTTCCTGG AGGTGTCGTA CCGCGTTCTA CGCCACCTTG CGCAGCCCTC
501 TGGCGGCTCT GGCGGCTCTC AGAGCTTCCT GCTCAAGTCT TTAGAGCAAG
551 TGAGAAAGAT CCAGGGCGAT GGCGCAGCGC TCCAGGAGAA GCTGTGTGCC
601 ACCTACAAGC TGTGCCACCC CGAGGAGCTG GTGCTGCTCG GACACTCTCT
651 GGGCATCCCC TGGGCTCCCC TGAGCTCCTG CCCCAGCCAG GCCCTGCAGC
701 TGGCAGGCTG CTTGAGCCAA CTCCATAGCG GCCTTTTCCT CTACCAGGGG
751 CTCCTGCAGG CCCTGGAAGG GATATCCCCC GAGTTGGGTC CCACCTTGGA
801 CACACTGCAG CTGGACGTCG CCGACTTTGC CACCACCATC TGGCAGCAGA
851 TGGAAGAACT GGGAATGGCC CCTGCCCTGC AGCCCACCCA GGGTGCCATG
901 CCGGCCTTCG CCTAATAA (SEQ ID NO:102)

pMON13191

1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTTCTGCT
451 TTCCAGCGCC GGGCAGGAGG GGTCCTGGTT GCTAGCCATC TGCAGAGCTT
501 CCTGGAGGTG TCGTACCGCG TTCTACGCCA CCTTGCGCAG CCCTCTGGCG

TABLE 2-continued

GENE SEQUENCES

```
551 GCTCTGGCGG CTCTCAGAGC TTCCTGCTCA AGTCTTTAGA GCAAGTGAGA
601 AAGATCCAGG GCGATGGCGC AGCGCTCCAG GAGAAGCTGT GTGCCACCTA
651 CAAGCTGTGC CACCCCGAGG AGCTGGTGCT GCTCGGACAC TCTCTGGGCA
701 TCCCCTGGGC TCCCCTGAGC TCCTGCCCCA GCCAGGCCCT GCAGCTGGCA
751 GGCTGCTTGA GCCAACTCCA TAGCGGCCTT TTCCTCTACC AGGGGCTCCT
801 GCAGGCCCTG GAAGGGATAT CCCCCGAGTT GGGTCCCACC TTGGACACAC
851 TGCAGCTGGA CGTCGCCGAC TTTGCCACCA CCATCTGGCA GCAGATGGAA
901 GAACTGGGAA TGGCCCCTGC CCTGCAGCCC ACCCAGGGTG CCATGCCGGC
951 CTTCGCCTAA TAA (SEQ ID NO:103)
``` pMON13192

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTT
401 ACAAGCTGTG CCACCCCGAG GAGCTGGTGC TGCTCGGACA CTCTCTGGGC
451 ATCCCCTGGG CTCCCCTGAG CTCCTGCCCC AGCCAGGCCC TGCAGCTGGC
501 AGGCTGCTTG AGCCAACTCC ATAGCGGCCT TTTCCTCTAC CAGGGGCTCC
551 TGCAGGCCCT GGAAGGGATA TCCCCCGAGT TGGGTCCCAC CTTGGACACA
601 CTGCAGCTGG ACGTCGCCGA CTTTGCCACC ACCATCTGGC AGCAGATGGA
651 AGAACTGGGA ATGGCCCCTG CCCTGCAGCC CACCCAGGGT GCCATGCCGG
701 CCTTCGCCTC TGCTTTCCAG CGCCGGGCAG GAGGGGTCCT GGTTGCTAGC
751 CATCTGCAGA GCTTCCTGGA GGTGTCGTAC CGCGTTCTAC GCCACCTTGC
801 GCAGCCCACA CCATTGGGCC CTGCCAGCTC CCTGCCCCAG AGCTTCCTGC
851 TCAAGTCTTT AGAGCAAGTG AGAAAGATCC AGGGCGATGG CGCAGCGCTC
901 CAGGAGAAGC TGTGTGCCAC CTAATAA (SEQ ID NO:104)
``` pMON13193

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTTACAAG
451 CTGTGCCACC CCGAGGAGCT GGTGCTGCTC GGACACTCTC TGGGCATCCC
501 CTGGGCTCCC CTGAGCTCCT GCCCCAGCCA GGCCCTGCAG CTGGCAGGCT
551 GCTTGAGCCA ACTCCATAGC GGCCTTTTCC TCTACCAGGG GCTCCTGCAG
601 GCCCTGGAAG GGATATCCCC CGAGTTGGGT CCCACCTTGG ACACACTGCA
651 GCTGGACGTC GCCGACTTTG CCACCACCAT CTGGCAGCAG ATGGAAGAAC
701 TGGGAATGGC CCCTGCCCTG CAGCCCACCC AGGGTGCCAT GCCGGCCTTC
751 GCCTCTGCTT TCCAGCGCCG GGCAGGAGGG GTCCTGGTTG CTAGCCATCT
801 GCAGAGCTTC CTGGAGGTGT CGTACCGCGT TCTACGCCAC CTTGCGCAGC
851 CCACACCATT GGGCCCTGCC AGCTCCCTGC CCCAGAGCTT CCTGCTCAAG
901 TCTTTAGAGC AAGTGAGAAA GATCCAGGGC GATGGCGCAG CGCTCCAGGA
951 GAAGCTGTGT GCCACCTAAT AA (SEQ ID NO:105)
``` pMON25190

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTC
401 CCGAGTTGGG TCCCACCTTG ACACACTGC AGCTGGACGT CGCCGACTTT
451 GCCACCACCA TCTGGCAGCA GATGGAAGAA CTGGGAATGG CCCCTGCCCT
501 GCAGCCCACC CAGGGTGCCA TGCCGGCCTT CGCCTCTGCT TTCCAGCGCC
551 GGGCAGGAGG GGTCCTGGTT GCTAGCCATC TGCAGAGCTT CCTGGAGGTG
601 TCGTACCGCG TTCTACGCCA CCTTGCGCAG CCCACACCAT GGGCCCTGC
651 CAGCTCCCTG CCCCAGAGCT TCCTGCTCAA GTCTTTAGAG CAAGTGAGAA
701 AGATCCAGGG CGATGGCGCA GCGCTCCAGG AGAAGCTGTG TGCCACCTAC
751 AAGCTGTGCC ACCCCGAGGA GCTGGTGCTG CTCGGACACT CTCTGGGCAT
801 CCCCTGGGCT CCCCTGAGCT CCTGCCCCAG CCAGGCCCTG CAGCTGGCAG
851 GCTGCTTGAG CCAACTCCAT AGCGGCCTTT TCCTCTACCA GGGGCTCCTG
901 CAGGCCCTGG AAGGGATATC CTAATAA (SEQ ID NO:106)
```

TABLE 2-continued

GENE SEQUENCES pMON25191

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCCCGAG
451 TTGGGTCCCA CCTTGGACAC ACTGCAGCTG GACGTCGCCG ACTTTGCCAC
501 CACCATCTGG CAGCAGATGG AAGAACTGGG AATGGCCCCT GCCCTGCAGC
551 CCACCCAGGG TGCCATGCCG GCCTTCGCCT CTGCTTTCCA GCGCCGGGCA
601 GGAGGGGTCC TGGTTGCTAG CCATCTGCAG AGCTTCCTGG AGGTGTCGTA
651 CCGCGTTCTA CGCCACCTTG CGCAGCCCAC ACCATTGGGC CCTGCCAGCT
701 CCCTGCCCCA GAGCTTCCTG CTCAAGTCTT TAGAGCAAGT GAGAAAGATC
751 CAGGGCGATG CGCAGCGCT  CCAGGAGAAG CTGTGTGCCA CCTACAAGCT
801 GTGCCACCCC GAGGAGCTGG TGCTGCTCGG ACACTCTCTG GGCATCCCCT
851 GGGCTCCCCT GAGCTCCTGC CCAGCCAGG  CCCTGCAGCT GGCAGGCTGC
901 TTGAGCCAAC TCCATAGCGG CCTTTTCCTC TACCAGGGGC TCCTGCAGGC
951 CCTGGAAGGG ATATCCTAAT AA (SEQ ID NO:107)
``` pMON13194

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTA
401 TGGCCCCTGC CCTGCAGCCC ACCCAGGGTG CCATGCCGGC CTTCGCCTCT
451 GCTTTCCAGC GCCGGGCAGG AGGGGTCCTG GTTGCTAGCC ATCTGCAGAG
501 CTTCCTGGAG GTGTCGTACC GCGTTCTACG CCACCTTGCG CAGCCCACAC
551 CATTGGGCCC TGCCAGCTCC CTGCCCCAGA GCTTCCTGCT CAAGTCTTTA
601 GAGCAAGTGA GAAAGATCCA GGGCGATGGC GCAGCGCTCC AGGAGAAGCT
651 GTGTGCCACC TAqAAGCTGT GCCACCCCGA GGAGCTGGTG CTGCTCGGAC
701 ACTCTCTGGG CATCCCCTGG GCTCCCCTGA GCTCCTGCCC CAGCCAGGCC
751 CTGCAGCTGG CAGGCTGCTT GAGCCAACTC CATAGCGGCC TTTTCCTCTA
801 CCAGGGGCTC CTGCAGGCCC TGGAAGGGAT ATCCCCGAGC TTGGGTCCCA
851 CCTTGGACAC ACTGCAGCTG GACGTCGCCG ACTTTGCCAC CACCATCTGG
901 CAGCAGATGG AAGAACTGGG ATAATAA (SEQ ID NO:108)
``` pMON13195

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTATGGCC
451 CCTGCCCTGC AGCCCACCCA GGGTGCCATG CCGGCCTTCG CCTCTGCTTT
501 CCAGCGCCGG GCAGGAGGGG TCCTGGTTGC TAGCCATCTG CAGAGCTTCC
551 TGGAGGTGTC GTACCGCGTT CTACGCCACC TTGCGCAGCC CACACCATTG
601 GGCCCTGCCA GCTCCCTGCC CCAGAGCTTC CTGCTCAAGT CTTTAGAGCA
651 AGTGAGAAAG ATCCAGGGCG ATGGCGCAGC GCTCCAGGAG AAGCTGTGTG
701 CCACCTACAA GCTGTGCCAC CCCGAGGAGC TGGTGCTGCT CGGACACTCT
751 CTGGGCATCC CCTGGGCTCC CCTGAGCTCC TGCCCCAGCC AGGCCCTGCA
801 GCTGGCAGGC TGCTTGAGCC AACTCCATAG CGGCCTTTTC CTCTACCAGG
851 GGCTCCTGCA GGCCCTGGAA GGGATATCCC CGAGTTGGGT CCCACCTTG
901 GACACACTGC AGCTGGACGT CGCCGACTTT GCCACCACCA TCTGGCAGCA
951 GATGGAAGAA CTGGGATAAT AA (SEQ ID NO:109)
``` pMON13196

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
```

TABLE 2-continued

GENE SEQUENCES

```
351 CGGTGGAGGC TCCCCGGGTG GTGGTTCTGG CGGCGGCTCC AACATGGCTA
401 CCCAGGGTGC CATGCCGGCC TTCGCCTCTG CTTTCCAGCC CCGGGCAGGA
451 GGGGTCCTGG TTGCTAGCCA TCTGCAGAGC TTCCTGGAGG TGTCGTACCG
501 CGTTCTACGC CACCTTGCGC AGCCCACACC ATTGGGCCCT GCCAGCTCCC
551 TGCCCCAGAG CTTCCTGCTC AAGTCTTTAG AGCAAGTGAG AAAGATCCAG
601 GGCCGATGGCG CAGCGCTCCA GGAGAAGCTG TGTGCCACCT ACAAGCTGTG
651 CCACCCCGAG GAGCTGGTGC TGCTCGGACA CTCTCTGGGC ATCCCCTGGG
701 CTCCCCTGAG CTCCTGCCCC AGCCAGGCCC TGCAGCTGGC AGGCTGCTTG
751 AGCCAACTCC ATAGCGGCCT TTTCCTCTAC CAGGGGCTCC TGCAGGCCCT
801 GGAAGGGATA TCCCCCGAGT TGGGTCCCAC CTTGGACACA CTGCAGCCTGG
851 ACGTCGCCGA CTTTGCCACC ACCATCTGGC AGCAGATGGA AGAACTGGGA
901 ATGGCCCCTG CCCTGCAGCC CTAATAA (SEQ ID NO:110)
``` pMON13197

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC AAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTACCCAG
451 GGTGCCATGC CGGCCTTCGC CTCTGCTTTC CAGCGCCGGG CAGGAGGGGT
501 CCTGGTTGCT AGCCATCTGC AGAGCTTCCT GGAGGTGTCG TACCGCGTTC
551 TACGCCACCT TGCGCAGCCC ACACCATTGG GCCCTGCCAG CTCCCTGCCC
601 CAGAGCTTCC TGCTCAAGTC TTTAGAGCAA GTGAGAAAGA TCCAGGGCGA
651 TGGCGCAGCG CTCCAGGAGA AGCTGTGTGC CACCTACAAG CTGTGCCACC
701 CCGAGGAGCT GGTGCTGCTC GGACACTCTC TGGGCATCCC CTGGGCTCCC
751 CTGAGCTCCT GCCCCAGCCA GGCCCTGCAG CTGGCAGGCT GCTTGAGCCA
801 ACTCCATAGC GGCCTTTTCC TCTACCAGGG GCTCCTGCAG GCCCTGGAAG
851 GGATATCCCC CGAGTTGGGT CCCACCTTGG ACACACTGCA GCTGGACGTC
901 GCCGACTTTG CCACCACCAT CTGGCAGCAG ATGGAAGAAC TGGGAATGGC
951 CCCTGCCCTG CAGCCCTAAT AA (SEQ ID NO:111)
``` pMON13198

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC AAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG GTGGTTCTGG CGGCGGCTCC AACATGGCTT
401 CTGCTTTCCA GCGCCGGGCA GGAGGGGTCC TGGTTGCTAG CCATCTGCAG
451 AGCTTCCTGG AGGTGTCGTA CCGCGTTCTA CGCCACCTTG CGCAGCCCAC
501 ACCATTGGGC CCTGCCAGCT CCCTGCCCCA GAGCTTCCTG CTCAAGTCTT
551 TAGAGCAAGT GAGAAAGATC CAGGGCGATG GCGCAGCGCT CCAGGAGAAG
601 CTGTGTGCCA CCTACAAGCT GTGCCACCCC GAGGAGCTGG TGCTGCTCGG
651 ACACTCTCTG GGCATCCCCT GGGCTCCCCT GAGCTCCTGC CCCAGCCAGG
701 CCCTGCAGCT GGCAGGCTGC TTGAGCCAAC TCCATAGCGG CCTTTTCCTC
751 TACCAGGGGC TCCTGCAGGC CCTGGAAGGG ATATCCCCCG AGTTGGGTCC
801 CACCTTGGAC ACACTGCAGC TGGACGTCGC CGACTTTGCC ACCACCATCT
851 GGCAGCAGAT GGAAGAACTG GGAATGGCCC CTGCCCTGCA GCCCACCCAG
901 GGTGCCATGC CGGCCTTCGC CTAATAA (SEQ ID NO:112)
``` pMON13199

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGACCGAAAC CTTCGACTTC AAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTTCTGCT
451 TTCCAGCGCC GGGCAGGAGG GGTCCTGGTT GCTAGCCATC TGCAGAGCTT
501 CCTGGAGGTG TCGTACCGCG TTCTACGCCA CCTTGCGCAG CCCACACCAT
551 TGGGCCCTGC CAGCTCCCTG CCCCAGAGCT TCCTGCTCAA GTCTTTAGAG
601 CAAGTGAGAA AGATCCAGGG CGATGGCGCA GCGCTCCAGG AGAAGCTGTG
651 TGCCACCTAC AAGCTGTGCC ACCCCGAGGA GCTGGTGCTG CTCGGACACT
701 CTCTGGGCAT CCCCTGGGCT CCCCTGAGCT CCTGCCCCAG CCAGGCCCTG
751 CAGCTGGCAG GCTGCTTGAG CCAACTCCAT AGCGGCCTTT TCCTCTACCA
801 GGGGCTCCTG CAGGCCCTGG AAGGGATATC CCCCGAGTTG GGTCCCACCT
```

TABLE 2-continued

GENE SEQUENCES

```
    851 TGGACACACT GCAGCTGGAC GTCGCCGACT TTGCCACCAC CATCTGGCAG
    901 CAGATGGAAG AACTGGGAAT GGCCCCTGCC CTGCAGCCCA CCCAGGGTGC
    951 CATGCCGGCC TTCGCCTAAT AA (SEQ ID NO:113)

pMON31112

1 ATGGCTAACT GCTCTAACAT GATCGATGAA ATCATCACCC ACCTGAAGCA
     51 GCCACCGCTG CCGCTGCTGG ACTTCAACAA CCTCAATGGT GAAGACCAAG
    101 ATATCCTAAT GGACAATAAC CTTCGTCGTC CAAACCTCGA GGCATTCAAC
    151 CGTGCTGTCA AGTCTCTGCA GAATGCATCA GCAATTGAGA GCATTCTTAA
    201 AAATCTCCTG CCATGTCTGC CGCTAGCCAC GGCCGCACCC ACGCGACATC
    251 CAATCCATAT CAAGGACGGT GACTGGAATG AATTCCGTCG TAAACTGACC
    301 TTCTATCTGA AAACCTTGGA GAACGCGCAG GCTCAACAGT ACGTAGAGGG
    351 CGGTGGAGGC TCCCCGGGTG AACCGTCTGG TCCAATCTCT ACTATCAACC
    401 CGTCTCCTCC GTCTAAAGAA TCTCATAAAT CTCCAAACAT GGCTACCCAG
    451 GGTGCCATGC CGGCCTTCGC CTCTGCTTTC CAGCGCCGGG CAGGAGGGGT
    501 CCTGGTTGCT AGCCATCTGC AGAGCTTCCT GGAGGTGTCG TACCGCGTTC
    551 TACGCCACCT TGCGCAGCCC TCTGGCGGCT CTGGCGGCTC TCAGAGCTTC
    601 CTGCTCAAGT CTTTAGAGCA AGTGAGAAAG ATCCAGGGCG ATGGCGCAGC
    651 GCTCCAGGAG AAGCTGTGTG CCACCTACAA GCTGTGCCAC CCCGAGGAGC
    701 TGGTGCTGCT CGGACACTCT CTGGGCATCC CTGGGCTCC CCTGAGCTCC
    751 TGCCCCAGCC AGGCCCTGCA GCTGGCAGGC TGCTTGAGCC AACTCCATAG
    801 CGGCCTTTTC CTCTACCAGG GGCTCCTGCA GGCCCTGGAA GGGATATCCC
    851 CCGAGTTGGG TCCCACCTTG GACACACTGC AGCTGGACGT CGCCGACTTT
    901 GCCACCACCA TCTGGCAGCA GATGGAAGAA CTGGGAATGG CCCCTGCCCT
    951 GCAGCCCTAA TAA (SEQ ID NO:114)

pMON31113

1 ATGGCTAACT GCTCTAACAT GATCGATGAA ATCATCACCC ACCTGAAGCA
     51 GCCACCGCTG CCGCTGCTGG ACTTCAACAA CCTCAATGGT GAAGACCAAG
    101 ATATCCTGAT GGAAAATAAC CTTCGTCGTC CAAACCTCGA GGCATTCAAC
    151 CGTGCTGTCA AGTCTCTGCA GAATGCATCA GCAATTGAGA GCATTCTTAA
    201 AAATCTCCTG CCATGTCTGC CCTGGCCAC GGCCGCACCC ACGCGACATC
    251 CAATCATCAT CCGTGACGGT GACTGGAATG AATTCCGTCG TAAACTGACC
    301 TTCTATCTGA AAACCTTGGA GAACGCGCAG GCTCAACAGT ACGTAGAGGG
    351 CGGTGGAGGC TCCCCGGGTG AACCGTCTGG TCCAATCTCT ACTATCAACC
    401 CGTCTCCTCC GTCTAAAGAA TCTCATAAAT CTCCAAACAT GGCTACCCAG
    451 GGTGCCATGC CGGCCTTCGC CTCTGCTTTC CAGCGCCGGG CAGGAGGGGT
    501 CCTGGTTGCT AGCCATCTGC AGAGCTTCCT GGAGGTGTCG TACCGCGTTC
    551 TACGCCACCT TGCGCAGCCC ACACCATTGG GCCCTGCCAG CTCCCTGCCC
    601 CAGAGCTTCC TGCTCAAGTC TTTAGAGCAA GTGAGAAAGA TCCAGGGCGA
    651 TGGCGCAGCG CTCCAGGAGA AGCTGTGTGC CACCTACAAG CTGTGCCACC
    701 CCGAGGAGCT GGTGCTGCTC GGACACTCTC TGGGCATCCC CTGGGCTCCC
    751 CTGAGCTCCT GCCCCAGCCA GGCCCTGCAG CTGGCAGGCT GCTTGAGCCA
    801 ACTCCATAGC GGCCTTTTCC TCTACCAGGG GCTCCTGCAG GCCCTGGAAG
    851 GGATATCCCC CGAGTTGGGT CCCACCTTGG ACACACTGC AGCTGGACGTC
    901 GCCGACTTTG CCACCACCAT CTGGCAGCAG ATGGAAGAAC TGGGAATGGC
    951 CCCTGCCCTG CAGCCCTAAT AA (SEQ ID NO:115)

pMON31114

1 ATGGCTAACT GCTCTAACAT GATCGATGAA ATCATCACCC ACCTGAAGCA
     51 GCCACCGCTG CCGCTGCTGG ACTTCAACAA CCTCAATGGT GAAGACCAAG
    101 ATATCCTGAT GGAAAATAAC CTTCGTCGTC CAAACCTCGA GGCATTCAAC
    151 CGTGCTGTCA AGTCTCTGCA GAATGCATCA GCAATTGAGA GCATTCTTAA
    201 AAATCTCCTG CCATGTCTGC CCTGGCCAC GGCCGCACCC ACGCGACATC
    251 CAATCATCAT CCGTGACGGT GACTGGAATG AATTCCGTCG TAAACTGACC
    301 TTCTATCTGA AAACCTTGGA GAACGCGCAG GCTCAACAGT ACGTAGAGGG
    351 CGGTGGAGGC TCCCCGGGTG AACCGTCTGG TCCAATCTCT ACTATCAACC
    401 CGTCTCCTCC GTCTAAAGAA TCTCATAAAT CTCCAAACAT GGCTACCCAG
    451 GGTGCCATGC CGGCCTTCGC CTCTGCTTTC CAGCGCCGGG CAGGAGGGGT
    501 CCTGGTTGCT AGCCATCTGC AGAGCTTCCT GGAGGTGTCG TACCGCGTTC
    551 TACGCCACCT TGCGCAGCCC TCTGGCGGCT CTGGCGGCTC TCAGAGCTTC
    601 CTGCTCAAGT CTTTAGAGCA AGTGAGAAAG ATCCAGGGCG ATGGCGCAGC
    651 GCTCCAGGAG AAGCTGTGTG CCACCTACAA GCTGTGCCAC CCCGAGGAGC
    701 TGGTGCTGCT CGGACACTCT CTGGGCATCC CTGGGCTCC CCTGAGCTCC
    751 TGCCCCAGCC AGGCCCTGCA GCTGGCAGGC TGCTTGAGCC AACTCCATAG
    801 CGGCCTTTTC CTCTACCAGG GGCTCCTGCA GGCCCTGGAA GGGATATCCC
    851 CCGAGTTGGG TCCCACCTTG GACACACTGC AGCTGGACGT CGCCGACTTT
    901 GCCACCACCA TCTGGCAGCA GATGGAAGAA CTGGGAATGG CCCCTGCCCT
    951 GCAGCCCTAA TAA (SEQ ID NO:116)

pMON31115

1 ATGGCTAACT GCTCTAACAT GATCGATGAA ATCATCACCC ACCTGAAGCA
     51 GCCACCGCTG CCGCTGCTGG ACTTCAACAA CCTCAATGGT GAAGACCAAG
```

TABLE 2-continued

GENE SEQUENCES

```
101 ATATCCTAAT GGACAATAAC CTTCGTCGTC CAAACCTCGA GGCATTCAAC
151 CGTGCTGTCA AGTCTCTGCA GAATGCATCA GCAATTGAGA GCATTCTTAA
201 AAATCTCCTG CCATGTCTGC CGCTAGCCAC GGCCGCACCC ACGCGACATC
251 CAATCCATAT CAAGGACGGT GACTGGAATG AATTCCGTCG TAAACTGACC
301 TTCTATCTGA AAACCTTGGA GAACGCGCAG GCTCAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTACCCAG
451 GGTGCCATGC CGGCCTTCGC CTCTGCTTTC CAGCGCCGGG CAGGAGGGGT
501 CCTGGTTGCT AGCCATCTGC AGAGCTTCCT GGAGGTGTCG TACCGCGTTC
551 TACGCCACCT TGCGCAGCCC ACACCATTGG GCCCTGCCAG CTCCCTGCCC
601 CAGAGCTTCC TGCTCAAGTC TTTAGAGCAA GTGAGAAAGA TCCAGGGCGA
651 TGGCGCAGCG CTCCAGGAGA AGCTGTGTGC CACCTACAAG CTGTGCCACC
701 CCGAGGAGCT GGTGCTGCTC GGACACTCTC TGGGCATCCC CTGGGCTCCC
751 CTGAGCTCCT GCCCCAGCCA GGCCCTGCAG CTGGCAGGCT GCTTGAGCCA
801 ACTCCATAGC GGCCTTTTCC TCTACCAGGG GCTCCTGCAG GCCCTGGAAG
851 GGATATCCCC CGAGTTGGGT CCCACCTTGG ACACACTGCA GCTGGACGTC
901 GCCGACTTTG CCACCACCAT CTGGCAGCAG ATGGAAGAAC TGGGAATGGC
951 CCCTGCCCTG CAGCCCTAAT AA (SEQ ID NO:117)
``` pMON28505

```
GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGAGGTTCACCCTTTGCCTACACCTGTCCTGC
TGCCTGCTGTGGACTTTAGCTTGGGAGAATGGAAAACCCAGATGGAGGAGACCAAGGCACAGGACAT
TCTGGGAGCAGTGACCCTTCTGCTGGAGGGAGTGATGGCAGCACGGGACAACTGGGACCCACTTGC
CTCTCATCCCTCCTGGGGCAGCTTTCTGGACAGGTCCGTCTCCTCCTTGGGGCCCTGCAGAGCCTCC
TTGGAACCCAGCTTCCTCCACAGGGCAGGACCACAGCTCACAAGGATCCCAATGCCATCTTCCTGAG
CTTCCAACACCTGCTCCGAGGAAAGGTGCGTTTCCTGATGCTTGTAGGAGGGTCCACCCTCTGCGTC
AGGGAATTCGGCGGCAACATGGCGTCTCCCGCTCCGCCTGCTTGTGACCTCCGAGTCCTCAGTAAAC
TGCTTCGTGACTCCCATGTCCTTCACAGCAGACTGAGCCAGTGCCCA (SEQ ID NO:118)
``` pMON28506

```
GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCAATCTCTACTATCAACCCGTCT
CCTCCGTCTAAAGAATCTCATAAATCTCCAAACATGTTGCCTACACCTGTCCTGCTGCCTGCTGTGG
ACTTTAGCTTGGGAGAATGGAAAACCCAGATGGAGGAGACCAAGGCACAGGACATTCTGGGAGCAGT
GACCCTTCTGCTGGAGGGAGTGATGGCAGCACGGGACAACTGGGACCCACTTGCCTCTCATCCCTC
CTGGGGCAGCTTTCTGGACAGGTCCGTCTCCTCCTTGGGGCCCTGCAGAGCCTCCTTGGAACCCAGC
TTCCTCCACAGGGCAGGACCACAGCTCACAAGGATCCCAATGCCATCTTCCTGAGCTTCCAACACCT
GCTCCGAGGAAAGGTGCGTTTCCTGATGCTTGTAGGAGGGTCCACCCTCTGCGTCAGGGAATTCGGC
GGCAACATGGCGTCTCCCGCTCCGCCTGCTTGTGACCTCCGAGTCCTCAGTAAACTGCTTCGTGACT
CCCATGTCCTTCACAGCAGACTGAGCCAGTGCCCAGAGGTTCACCCT (SEQ ID NO:119)
``` pMON28507

```
GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCAATCTCTACTATCAACCCGTCT
CCTCCGTCTAAAGAATCTCATAAATCTCCAAACATGGTCCTGCTGCCTGCTGTGGACTTTAGCTTGG
GAGAATGGAAAACCCAGATGGAGGAGACCAAGGCACAGGACATTCTGGGAGCAGTGACCCTTCTGCT
GGAGGGAGTGATGGCAGCACGGGACAACTGGGACCCACTTGCCTCTCATCCCTCCTGGGGCAGCTT
TCTGGACAGGTCCGTCTCCTCCTTGGGGCCCTGCAGAGCCTCCTTGGAACCCAGCTTCCTCCACAGG
GCAGGACCACAGCTCACAAGGATCCCAATGCCATCTTCCTGAGCTTCCAACACCTGCTCCGAGGAAA
GGTGCGTTTCCTGATGCTTGTAGGAGGGTCCACCCTCTGCGTCAGGGAATTCGGCGGCAACATGGCG
TCTCCCGCTCCGCCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCT (SEQ ID NO:120)
``` pMON28508

```
GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
```

TABLE 2-continued

GENE SEQUENCES

GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCTGTGGACTTTAGCTTGGGAGAATGGAAAA
CCCAGATGGAGGAGACCAAGGCACAGGACATTCTGGGAGCAGTGACCCTTCTGCTGGAGGGAGTGAT
GGCAGCACGGGACAACTGGGACCCACTTGCCTCTCATCCCTCCTGGGGCAGCTTTCTGGACAGGTC
CGTCTCCTCCTTGGGGCCCTGCAGAGCCTCCTTGGAACCCAGCTTCCTCCACAGGGCAGGACCACAG
CTCACAAGGATCCCAATGCCATCTTCCTGAGCTTCCAACACCTGCTCCGAGGAAAGGTGCGTTTCCT
GATGCTTGTAGGAGGGTCCACCCTCTGCGTCAGGGAATTCGGCGGCAACATGGCGTCTCCCGCTCCG
CCTGCTTGTGACCTCCGAGTCCTCAGTAAACTGCTTCGTGACTCCCATGTCCTTCACAGCAGACTGA
GCCAGTGCCCAGAGGTTCACCCTTTGCCTACACCTGTCCTGCTGCCT (SEQ ID NO:121)

pMON28509

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGACTTTAGCTTGGGAGAATGGAAAACCCAGA
TGGAGGAGACCAAGGCACAGGACATTCTGGGAGCAGTGACCCTTCTGCTGGAGGGAGTGATGGCAGC
ACGGGGACAACTGGGACCCACTTGCCTCTCATCCCTCCTGGGGCAGCTTTCTGGACAGGTCCGTCTC
CTCCTTGGGGCCCTGCAGAGCCTCCTTGGAACCCAGCTTCCTCCACAGGGCAGGACCACAGCTCACA
AGGATCCCAATGCCATCTTCCTGAGCTTCCAACACCTGCTCCGAGGAAAGGTGCGTTTCCTGATGCT
TGTAGGAGGGTCCACCCTCTGCGTCAGGGAATTCGGCGGCAACATGGCGTCTCCCGCTCCGCCTGCT
TGTGACCTCCGAGTCCTCAGTAAACTGCTTCGTGACTCCCATGTCCTTCACAGCAGACTGAGCCAGT
GCCCAGAGGTTCACCCTTTGCCTACACCTGTCCTGCTGCCTGCTGTG (SEQ ID NO:122)

pMON28510
GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCGGTTACCCTTGAGCAAGCGCAGGAACAACAG
TACGTAGAGGGCGGTGGAGGCTCCCCGGGGAACCGTCTGGTCCAATCTCTACTATCAACCCGTCTCC
TCCGTCTAAAGAATCTCATAAACTCCAAACATGGAGAATGGAAAACCCAGATGGAGGAGACCAAGG
CACAGGACATTCTGGAGCAGTGACCCTTCTGCTGGAGGGAGTGATGGCAGCACGGGGACAACTGGGA
CCCACTTGCTCTCATCCCTCCTGGGGCAGCTTTCTGGACAGGTCCGTCTCCTCCTTGGGGCCCTGCA
GGCCTCCTTGGAACCCAGCTTCCTCCACAGGGCAGGACCACAGCTCACAAGGATCCCAATGCCATCT
TCCTGAGCTTCCAACACCTGCTCCGAGGAAAGGTGCGTTTCCTGATGCTTGTAGGGGGTCCACCCTCT
GCGTCAGGGAATTCGGCGGCAACATGGCGTCTCCCGCTCCGCCTGCTGTGACCTCCGAGTCCTCAGT
AAACTGCTTCGTGACTCCCATGTCCTTCACAGCAGACTGACCAGTGCCCAGAGGTTCACCCTTTGCC
TACACCTGTCCTGCTGCCTGCTGTGGACTTTAGTTG (SEQ ID NO:123)

pMON28511

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGACCCACTTGCCTCTCATCCCTCCTGGGGC
AGCTTTCTGGACAGGTCCGTCTCCTCCTTGGGGCCCTGCAGAGCCTCCTTGGAACCCAGCTTCCTCC
ACAGGGCAGGACCACAGCTCACAAGGATCCCAATGCCATCTTCCTGAGCTTCCAACACCTGCTCCGA
GGAAAGGTGCGTTTCCTGATGCTTGTAGGAGGGTCCACCCTCTGCGTCAGGGAATTCGGCGGCAACA
TGGCGTCTCCCGCTCCGCCTGCTTGTGACCTCCGAGTCCTCAGTAAACTGCTTCGTGACTCCCATGT
CCTTCACAGCAGACTGAGCCAGTGCCCAGAGGTTCACCCTTTGCCTACACCTGTCCTGCTGCCTGCT
GTGGACTTTAGCTTGGGAGAATGGAAAACCCAGATGGAGGAGACCAAGGCACAGGACATTCTGGGAG
CAGTGACCCTTCTGCTGGAGGGAGTGATGGCAGCACGGGACAACTG (SEQ ID NO:124)

pMON28512

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGAACCCAGCTTCCTCCACAGGGCAGGACCA
CAGCTCACAAGGATCCCAATGCCATCTTCCTGAGCTTCCAACACCTGCTCCGAGGAAAGGTGCGTTT
CCTGATGCTTGTAGGAGGGTCCACCCTCTGCGTCAGGGAATTCGGCGGCAACATGGCGTCTCCCGCT
CCGCCTGCTTGTGACCTCCGAGTCCTCAGTAAACTGCTTCGTGACTCCCATGTCCTTCACAGCAGAC
TGAGCCAGTGCCCAGAGGTTCACCCTTTGCCTACACCTGTCCTGCTGCCTGCTGTGGACTTTAGCTT
GGGAGAATGGAAAACCCAGATGGAGGAGACCAAGGCACAGGACATTCTGGGAGCAGTGACCCTTCTG
CTGGAGGGAGTGATGGCAGCACGGGACAACTGGGACCCACTTGCCTCTCATCCCTCCTGGGGCAGC
TTTCTGGACAGGTCCGTCTCCTCCTTGGGGCCCTGCAGAGCCTCCTT (SEQ ID NO:125)

TABLE 2-continued

GENE SEQUENCES pMON28513

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGCAGGACCACAGCTCACAAGGATCCCAATG
CCATCTTCCTGAGCTTCCAACACCTGCTCCGAGGAAAGGTGCGTTTCCTGATGCTTGTAGGAGGGTC
CACCCTCTGCGTCAGGGAATTCGGCGGCAACATGGCGTCTCCCGCTCCGCTGCTTGTGACCTCCGA
GTCCTCAGTAAACTGCTTCGTGACTCCCATGTCCTTCACAGCAGACTGAGCCAGTGCCCAGAGGTTC
ACCCTTTGCCTACACCTGTCCTGCTGCCTGCTGTGGACTTTAGCTTGGGAGAATGGAAAACCCAGAT
GGAGGAGACCAAGGCACAGGACATTCTGGGAGCAGTGACCCTTCTGCTGGAGGGAGTGATGGCAGCA
CGGGGACAACTGGGACCCACTTGCCTCTCATCCCTCCTGGGGCAGCTTTCTGGACAGGTCCGTCTCC
TCCTTGGGGCCCTGCAGAGCCTCCTTGGAACCCAGCTTCCTCCACAG (SEQ ID NO:126)

pMON28514

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCTCACAAGGATCCCAATGCCATCTTCCTGA
GCTTCCAACACCTGCTCCGAGGAAAGGTGCGTTTCCTGATGCTTGTAGGAGGGTCCACCCTCTGCGT
CAGGGAATTCGGCGGCAACATGGCGTCTCCCGCTCCGCTGCTTGTGACCTCCGAGTCCTCAGTAAA
CTGCTTCGTGACTCCCATGTCCTTCACAGCAGACTGAGCCAGTGCCCAGAGGTTCACCCTTTGCCTA
CACCTGTCCTGCTGCCTGCTGTGGACTTTAGCTTGGGAGAATGGAAAACCCAGATGGAGGAGACCAA
GGCACAGGACATTCTGGGAGCAGTGACCCTTCTGCTGGAGGGAGTGATGGCAGCACGGGGACAACTG
GGACCCACTTGCCTCTCATCCCTCCTGGGGCAGCTTTCTGGACAGGTCCGTCTCCTCCTTGGGGCCC
TGCAGAGCCTCCTTGGAACCCAGCTTCCTCCACAGGGCAGGACCACA (SEQ ID NO:127)

pMON28515

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGATCCCAATGCCATCTTCCTGAGCTTCCAAC
ACCTGCTCCGAGGAAAGGTGCGTTTCCTGATGCTTGTAGGAGGGTCCACCCTCTGCGTCAGGGAATT
CGGCGGCAACATGGCGTCTCCCGCTCCGCTGCTTGTGACCTCCGAGTCCTCAGTAAACTGCTTCGT
GACTCCCATGTCCTTCACAGCAGACTGAGCCAGTGCCCAGAGGTTCACCCTTTGCCTACACCTGTCC
TGCTGCCTGCTGTGGACTTTAGCTTGGGAGAATGGAAAACCCAGATGGAGGAGACCAAGGCACAGGA
CATTCTGGGAGCAGTGACCCTTCTGCTGGAGGGAGTGATGGCAGCACGGGGACAACTGGGACCCACT
TGCCTCTCATCCCTCCTGGGGCAGCTTTCTGGACAGGTCCGTCTCCTCCTTGGGGCCCTGCAGAGCC
TCCTTGGAACCCAGCTTCCTCCACAGGGCAGGACCACAGCTCACAAG (SEQ ID NO:128)

pMON28516

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCCATCTTCCTGAGCTTCCAACACCTGCTCC
GAGGAAAGGTGCGTTTCCTGATGCTTGTAGGAGGGTCCACCCTCTGCGTCAGGGAATTCGGCGGCAA
CATGGCGTCTCCCGCTCCGCTGCTTGTGACCTCCGAGTCCTCAGTAAACTGCTTCGTGACTCCCAT
GTCCTTCACAGCAGACTGAGCCAGTGCCCAGAGGTTCACCCTTTGCCTACACCTGTCCTGCTGCCTG
CTGTGGACTTTAGCTTGGGAGAATGGAAAACCCAGATGGAGGAGACCAAGGCACAGGACATTCTGGG
AGCAGTGACCCTTCTGCTGGAGGGAGTGATGGCAGCACGGGGACAACTGGGACCCACTTGCCTCTCA
TCCCTCCTGGGGCAGCTTTCTGGACAGGTCCGTCTCCTCCTTGGGGCCCTGCAGAGCCTCCTTGGAA
CCCAGCTTCCTCCACAGGGCAGGACCACAGCTCACAAGGATCCCAAT (SEQ ID NO:129)

pMON28519

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGAGGTTCACCCTTTGCCTACACCTGTCCTGC

TABLE 2-continued

GENE SEQUENCES

TGCCTGCTGTGGACTTTAGCTTGGGAGAATGGAAAACCCAGATGGAGGAGACCAAGGCACAGGACAT
TCTGGGAGCAGTGACCCTTCTGCTGGAGGGAGTGATGGCAGCACGGGGACAACTGGGACCCACTTGC
CTCTCATCCCTCCTGGGGCAGCTTTCTGGACAGGTCCGTCTCCTCCTTGGGGCCCTGCAGAGCCTCC
TTGGAACCCAGCTTCCTCCACAGGGCAGGACCACAGCTCACAAGGATCCCAATGCCATCTTCCTGAG
CTTCCAACACCTGCTCCGAGGAAAGGTGCGTTTCCTGATGCTTGTAGGAGGGTCCACCCTCTGCGTC
AGGGAATTCGGCAACATGGCGTCTCCCGCTCCGCCTGCTTGTGACCTCCGAGTCCTCAGTAAACTGC
TTCGTGACTCCCATGTCCTTCACAGCAGACTGAGCCAGTGCCCA (SEQ ID NO:130)

pMON28520

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGTTGCCTACACCTGTCCTGCTGCCTGCTGTGG
ACTTTAGCTTGGGAGAATGGAAAACCCAGATGGAGGAGACCAAGGCACAGGACATTCTGGGAGCAGT
GACCCTTCTGCTGGAGGGAGTGATGGCAGCACGGGGACAACTGGGACCCACTTGCCTCTCATCCCTC
CTGGGGCAGCTTTCTGGACAGGTCCGTCTCCTCCTTGGGGCCCTGCAGAGCCTCCTTGGAACCCAGC
TTCCTCCACAGGGCAGGACCACAGCTCACAAGGATCCCAATGCCATCTTCCTGAGCTTCCAACACCT
GCTCCGAGGAAAGGTGCGTTTCCTGATGCTTGTAGGAGGGTCCACCCTCTGCGTCAGGGAATTCGGC
AACATGGCGTCTCCCGCTCCGCCTGCTTGTGACCTCCGAGTCCTCAGTAAACTGCTTCGTGACTCCC
ATGTCCTTCACAGCAGACTGAGCCAGTGCCCAGAGGTTCACCCT (SEQ ID NO:131)

pMON28521

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGTCCTGCTGCCTGCTGTGGACTTTAGCTTGG
GAGAATGGAAAACCCAGATGGAGGAGACCAAGGCACAGGACATTCTGGGAGCAGTGACCCTTCTGCT
GGAGGGAGTGATGGCAGCACGGGGACAACTGGGACCCACTTGCCTCTCATCCCTCCTGGGGCAGCTT
TCTGGACAGGTCCGTCTCCTCCTTGGGGCCCTGCAGAGCCTCCTTGGAACCCAGCTTCCTCCACAGG
GCAGGACCACAGCTCACAAGGATCCCAATGCCATCTTCCTGAGCTTCCAACACCTGCTCCGAGGAAA
GGTGCGTTTCCTGATGCTTGTAGGAGGGTCCACCCTCTGCGTCAGGGAATTCGGCAACATGGCGTCT
CCCGCTCCGCCTGCTTGTGACCTCCGAGTCCTCAGTAAACTGCTTCGTGACTCCCATGTCCTTCACA
GCAGACTGAGCCAGTGCCCAGAGGTTCACCCTTTGCCTACACCT (SEQ ID NO:132)

pMON28522

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCTTTAGCTTGGGAGAATGGAAAA
CCCAGATGGAGGAGACCAAGGCACAGGACATTCTGGGAGCAGTGACCCTTCTGCTGGAGGGAGTGAT
GGCAGCACGGGGACAACTGGGACCCACTTGCCTCTCATCCCTCCTGGGGCAGCTTTCTGGACAGGTC
CGTCTCCTCCTTGGGGCCCTGCAGAGCCTCCTTGGAACCCAGCTTCCTCCACAGGGCAGGACCACAG
CTCACAAGGATCCCAATGCCATCTTCCTGAGCTTCCAACACCTGCTCCGAGGAAAGGTGCGTTTCCT
GATGCTTGTAGGAGGGTCCACCCTCTGCGTCAGGGAATTCGGCAACATGGCGTCTCCCGCTCCGCCT
GCTTGTGACCTCCGAGTCCTCAGTAAACTGCTTCGTGACTCCCATGTCCTTCACAGCAGACTGAGCC
AGTGCCCAGAGGTTCACCCTTTGCCTACACCTGTCCTGCTGCCT (SEQ ID NO:133)

pMON28523

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGACTTTAGCTTGGGAGAATGGAAAACCCAGA
TGGAGGAGACCAAGGCACAGGACATTCTGGGAGCAGTGACCCTTCTGCTGGAGGGAGTGATGGCAGC
ACGGGGACAACTGGGACCCACTTGCCTCTCATCCCTCCTGGGGCAGCTTTCTGGACAGGTCCGTCTC
CTCCTTGGGGCCCTGCAGAGCCTCCTTGGAACCCAGCTTCCTCCACAGGGCAGGACCACAGCTCACA
AGGATCCCAATGCCATCTTCCTGAGCTTCCAACACCTGCTCCGAGGAAAGGTGCGTTTCCTGATGCT
TGTAGGAGGGTCCACCCTCTGCGTCAGGGAATTCGGCAACATGGCGTCTCCCGCTCCGCCTGCTTGT
GACCTCCGAGTCCTCAGTAAACTGCTTCGTGACTCCCATGTCCTTCACAGCAGACTGAGCCAGTGCC
CAGAGGTTCACCCTTTGCCTACACCTGTCCTGCTGCCTGCTGTG (SEQ ID NO:134)

TABLE 2-continued

GENE SEQUENCES pMON28524

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGGAGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGAGACCACCACCAGATGGAGGAGACCA
AGGCACAGGACATTCTGGGAGCAGTGACCCTTCTGCTGGAGGGAGTGATGGCAGCACGGGGACAACT
GGGACCCACTTGCCTCTCATCCCTCCTGGGGCAGCTTTCTGGACAGGTCCGTCTCCTCCTTGGGGCC
CTGCAGAGCCTCCTTGGAACCCAGCTTCCTCCACAGGGCAGGACCACAGCTCACAAGGATCCCAATG
CCATCTTCCTGAGCTTCCAACACCTGCTCCGAGGAAAGGTGCGTTTCCTGATGCTTGTAGGAGGGTC
CACCCTCTGCGTCAGGGAATTCGGCAACATGGCGTCTCCCGCTCCGCCTGCTTGTGACCTCCGAGTC
CTCAGTAAACTGCTTCGTGACTCCCATGTCCTTCACAGCAGACTGAGCCAGTGCCCAGAGGTTCACC
CTTTGCCTACACCTGTCCTGCTGCCTGCTGTGGACTTTAGCTTG (SEQ ID NO:135)

pMON28525

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGACCCACTTGCCTCTCATCCCTCCTGGGGC
AGCTTTCTGGACAGGTCCGTCTCCTCCTTGGGGCCCTGCAGAGCCTCCTTGGAACCCAGCTTCCTCC
ACAGGGCAGGACCACAGCTCACAAGGATCCCAATGCCATCTTCCTGAGCTTCCAACACCTGCTCCGA
GGAAAGGTGCGTTTCCTGATGCTTGTAGGAGGGTCCACCCTCTGCGTCAGGGAATTCGGCAACATGG
CGTCTCCCGCTCCGCCTGCTTGTGACCTCCGAGTCCTCAGTAAACTGCTTCGTGACTCCCATGTCCT
TCACAGCAGACTGAGCCAGTGCCCAGAGGTTCACCCTTTGCCTACACCTGTCCTGCTGCCTGCTGTG
GACTTTAGCTTGGGAGAATGGAAAACCCAGATGGAGGAGACCAAGGCACAGGACATTCTGGGAGCAG
TGACCCTTCTGCTGGAGGGAGTGATGGCAGCACGGGGACAACTG (SEQ ID NO:136)

pMON28526

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGAACCCAGCTTCCTCCACAGGGCAGGACCA
CAGCTCACAAGGATCCCAATGCCATCTTCCTGAGCTTCCAACACCTGCTCCGAGGAAAGGTGCGTTT
CCTGATGCTTGTAGGAGGGTCCACCCTCTGCGTCAGGGAATTCGGCAACATGGCGTCTCCCGCTCCG
CCTGCTTGTGACCTCCGAGTCCTCAGTAAACTGCTTCGTGACTCCCATGTCCTTCACAGCAGACTGA
GCCAGTGCCCAGAGGTTCACCCTTTGCCTACACCTGTCCTGCTGCCTGCTGTGGACTTTAGCTTGGG
AGAATGGAAAACCCAGATGGAGGAGACCAAGGCACAGGACATTCTGGGAGCAGTGACCCTTCTGCTG
GAGGGAGTGATGGCAGCACGGGGACAACTGGGACCCACTTGCCTCTCATCCCTCCTGGGGCAGCTTT
CTGGACAGGTCCGTCTCCTCCTTGGGGCCCTGCAGAGCCTCCTT (SEQ ID NO:137)

pMON28527

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGCAGGACCACAGCTCACAAGGATCCCAATG
CCATCTTCCTGAGCTTCCAACACCTGCTCCGAGGAAAGGTGCGTTTCCTGATGCTTGTAGGAGGGTC
CACCCTCTGCGTCAGGGAATTCGGCAACATGGCGTCTCCCGCTCCGCCTGCTTGTGACCTCCGAGTC
CTCAGTAAACTGCTTCGTGACTCCCATGTCCTTCACAGCAGACTGAGCCAGTGCCCAGAGGTTCACC
CTTTGCCTACACCTGTCCTGCTGCCTGCTGTGGACTTTAGCTTGGGAGAATGGAAAACCCAGATGGA
GGAGACCAAGGCACAGGACATTCTGGGAGCAGTGACCCTTCTGCTGGAGGGAGTGATGGCAGCACGG
GGACAACTGGGACCCACTTGCCTCTCATCCCTCCTGGGGCAGCTTTCTGGACAGGTCCGTCTCCTCC
TTGGGGCCCTGCAGAGCCTCCTTGGAACCCAGCTTCCTCCACAG (SEQ ID NO:138)

pMON28528

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCTCACAAGGATCCCAATGCCATCTTCCTGA

TABLE 2-continued

GENE SEQUENCES

GCTTCCAACACCTGCTCCGAGGAAAGGTGCGTTTCCTGATGCTTGTAGGAGGGTCCACCCTCTGCGT
CAGGGAATTCGGCAACATGGCGTCTCCCGCTCCGCCTGCTTGTGACCTCCGAGTCCTCAGTAAACTG
CTTCGTGACTCCCATGTCCTTCACAGCAGACTGAGCCAGTGCCCAGAGGTTCACCCTTTGCCTACAC
CTGTCCTGCTGCCTGCTGTGGACTTTAGCTTGGGAGAATGGAAAACCCAGATGGAGGAGACCAAGGC
ACAGGACATTCTGGGAGCAGTGACCCTTCTGCTGGAGGGAGTGATGGCAGCACGGGGACAACTGGGA
CCCACTTGCCTCTCATCCCTCCTGGGGCAGCTTTCTGGACAGGTCCGTCTCCTCCTTGGGGCCCTGC
AGAGCCTCCTTGGAACCCAGCTTCCTCCACAGGGCAGGACCACA (SEQ ID NO:139)

pMON28529

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGATCCCAATGCCATCTTCCTGAGCTTCCAAC
ACCTGCTCCGAGGAAAGGTGCGTTTCCTGATGCTTGTAGGAGGGTCCACCCTCTGCGTCAGGGAATT
CGGCAACATGGCGTCTCCCGCTCCGCCTGCTTGTGACCTCCGAGTCCTCAGTAAACTGCTTCGTGAC
TCCCATGTCCTTCACAGCAGACTGAGCCAGTGCCCAGAGGTTCACCCTTTGCCTACACCTGTCCTGC
TGCCTGCTGTGGACTTTAGCTTGGGAGAATGGAAAACCCAGATGGAGGAGACCAAGGCACAGGACAT
TCTGGGAGCAGTGACCCTTCTGCTGGAGGGAGTGATGGCAGCACGGGGACAACTGGGACCCACTTGC
CTCTCATCCCTCCTGGGGCAGCTTTCTGGACAGGTCCGTCTCCTCCTTGGGGCCCTGCAGAGCCTCC
TTGGAACCCAGCTTCCTCCACAGGGCAGGACCACAGCTCACAAG (SEQ ID NO:140)

pMON28530

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCCATCTTCCTGAGCTTCCAACACCTGCTCC
GAGGAAAGGTGCGTTTCCTGATGCTTGTAGGAGGGTCCACCCTCTGCGTCAGGGAATTCGGCAACAT
GGCGTCTCCCGCTCCGCCTGCTTGTGACCTCCGAGTCCTCAGTAAACTGCTTCGTGACTCCCATGTC
CTTCACAGCAGACTGAGCCAGTGCCCAGAGGTTCACCCTTTGCCTACACCTGTCCTGCTGCCTGCTG
TGGACTTTAGCTTGGGAGAATGGAAAACCCAGATGGAGGAGACCAAGGCACAGGACATTCTGGGAGC
AGTGACCCTTCTGCTGGAGGGAGTGATGGCAGCACGGGGACAACTGGGACCCACTTGCCTCTCATCC
CTCCTGGGGCAGCTTTCTGGACAGGTCCGTCTCCTCCTTGGGGCCCTGCAGAGCCTCCTTGGAACCC
AGCTTCCTCCACAGGGCAGGACCACAGCTCACAAGGATCCCAAT (SEQ ID NO:141)

pMON28533

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCTG
GAGAGCTTCGTAAGGGCTGTCAAGAACTTAGAAAATGCATCAGGTATGAGGCAATTCTTCGTAATCT
CCAACCATGTCTGCCCTCTGCCACGGCCGCACCCTCTCGCATCCAATCATCATCAAGGCAGGTGACT
GGCAAGAATTCCGGGAAAAACTGACGTTCTATTGGTTACCCTTGAGCAAGCGCAGGAACAACAGTAC
GTAGAGGGCGGTGGAGGCTCCCCGGTAACCGTCTGGTCCAATCTCTACTATCAACCCGTCTCCTCCG
TCTAAAGAATCTCATAAATCTCCAAACATGGAGGTTCACCCTTTGCCTACACCTGTCCTGCTGCCTG
CTGTGGACTTTAGCTTGGGAGAATGGAAAACCCAGATGGAGGAGACCAAGGCACAGGACATTCTGGG
AGCAGTGACCCTTCTGCTGGAGGGAGTGATGGCAGCACGGGGACAACTGGGACCCACTTGCCTCTCA
TCCCTCCTGGGGCAGCTTTCTGGACAGGTCCGTCTCCTCCTTGGGGCCCTGCAGAGCCTCCTTGGAA
CCCAGCTTCCTCCACAGGGCAGGACCACAGCTCACAAGGATCCCATCTTCCTGAGCTTCCA
ACACCTGCTCCGAGGAAAGGTGCGTTTCCTGATGCTTGTAGGAGGGTCCACCCTCTGCGTCAGGGAA
TTCGGCGGCAACGGCGGCAACATGGCGTCCCCAGCGCCGCCTGCTTGTGACCTCCGAGTCCTCAGTA
AACTGCTTCGTGACTCCCATGTCCTTCACAGCAGACTGAGCCAGTGCCCA (SEQ ID NO:142)

pMON28534

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGTTGCCTACACCTGTCCTGCTGCCTGCTGTGG
ACTTTAGCTTGGGAGAATGGAAAACCCAGATGGAGGAGACCAAGGCACAGGACATTCTGGGAGCAGT
GACCCTTCTGCTGGAGGGAGTGATGGCAGCACGGGGACAACTGGGACCCACTTGCCTCTCATCCCTC
CTGGGGCAGCTTTCTGGACAGGTCCGTCTCCTCCTTGGGGCCCTGCAGAGCCTCCTTGGAACCCAGC
TTCCTCCACAGGGCAGGACCACAGCTCACAAGGATCCCATCTTCCTGAGCTTCCAACACCT
GCTCCGAGGAAAGGTGCGTTTCCTGATGCTTGTAGGAGGGTCCACCCTCTGCGTCAGGGAATTCGGC
GGCAACGGCGGCAACATGGCGTCCCCAGCGCCGCCTGCTTGTGACCTCCGAGTCCTCAGTAAACTGC
TTCGTGACTCCCATGTCCTTCACAGCAGACTGAGCCAGTGCCCAGAGGTTCACCCT (SEQ ID NO:143)

TABLE 2-continued

GENE SEQUENCES pMON28535

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGTCCTGCTGCCTGCTGTGGACTTTAGCTTGG
GAGAATGGAAAACCCAGATGGAGGAGACCAAGGCACAGGACATTCTGGGAGCAGTGACCCTTCTGCT
GGAGGGAGTGATGGCAGCACGGGGACAACTGGGACCCACTTGCCTCTCATCCCTCCTGGGGCAGCTT
TCTGGACAGGTCCGTCTCCTCCTTGGGGCCCTGCAGAGCCTCCTTGGAACCCAGCTTCCTCCACAGG
GCAGGACCACAGCTCACAAGGATCCCAATGCCATCTTCCTGAGCTTCCAACACCTGCTCCGAGGAAA
GGTGCGTTTCCTGATGCTTGTAGGAGGGTCCACCCTCTGCGTCAGGGAATTCGGCGGCAACGGCGGC
AACATGGCGTCCCCAGCGCCGCCTGCTTGTGACCTCCGAGTCCTCAGTAAACTGCTTCGTGACTCCC
ATGTCCTTCACAGCAGACTGAGCCAGTGCCCAGAGGTTCACCCTTTGCCTACACCT (SEQ ID
NO:144)

pMON28536

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCTGTGGACTTTAGCTTGGGAGAATGGAAAA
CCCAGATGGAGGAGACCAAGGCACAGGACATTCTGGGAGCAGTGACCCTTCTGCTGGAGGGAGTGAT
GGCAGCACGGGGACAACTGGGACCCACTTGCCTCTCATCCCTCCTGGGGCAGCTTTCTGGACAGGTC
CGTCTCCTCCTTGGGGCCCTGCAGAGCCTCCTTGGAACCCAGCTTCCTCCACAGGGCAGGACCACAG
CTCACAAGGATCCCAATGCCATCTTCCTGAGCTTCCAACACCTGCTCCGAGGAAAGGTGCGTTTCCT
GATGCTTGTAGGAGGGTCCACCCTCTGCGTCAGGGAATTCGGCGGCAACGGCGGCAACATGGCGTCC
CCAGCGCCGCCTGCTTGTGACCTCCGAGTCCTCAGTAAACTGCTTCGTGACTCCCATGTCCTTCACA
GCAGACTGAGCCAGTGCCCAGAGGTTCACCCTTTGCCTACACCTGTCCTGCTGCCT
(SEQ ID NO:145)

pMON28537

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGACTTTAGCTTGGGAGAATGGAAAACCCAGA
TGGAGGAGACCAAGGCACAGGACATTCTGGGAGCAGTGACCCTTCTGCTGGAGGGAGTGATGGCAGC
ACGGGGACAACTGGGACCCACTTGCCTCTCATCCCTCCTGGGGCAGCTTTCTGGACAGGTCCGTCTC
CTCCTTGGGGCCCTGCAGAGCCTCCTTGGAACCCAGCTTCCTCCACAGGGCAGGACCACAGCTCACA
AGGATCCCAATGCCATCTTCCTGAGCTTCCAACACCTGCTCCGAGGAAAGGTGCGTTTCCTGATGCT
TGTAGGAGGGTCCACCCTCTGCGTCAGGGAATTCGGCGGCAACGGCGGCAACATGGCGTCCCCAGCG
CCGCCTGCTTGTGACCTCCGAGTCCTCAGTAAACTGCTTCGTGACTCCCATGTCCTTCACAGCAGAC
TGAGCCAGTGCCCAGAGGTTCACCCTTTGCCTACACCTGTCCTGCTGCCTGCTGTG
(SEQ ID NO:146)

pMON28538

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGAGAATGGAAAACCCAGATGGAGGAGACCA
AGGCACAGGACATTCTGGGAGCAGTGACCCTTCTGCTGGAGGGAGTGATGGCAGCACGGGGACAACT
GGGACCCACTTGCCTCTCATCCCTCCTGGGGCAGCTTTCTGGACAGGTCCGTCTCCTCCTTGGGGCC
CTGCAGAGCCTCCTTGGAACCCAGCTTCCTCCACAGGGCAGGACCACAGCTCACAAGGATCCCAATG
CCATCTTCCTGAGCTTCCAACACCTGCTCCGAGGAAAGGTGCGTTTCCTGATGCTTGTAGGAGGGTC
CACCCTCTGCGTCAGGGAATTCGGCGGCAACGGCGGCAACATGGCGTCCCCAGCGCCGCCTGCTTGT
GACCTCCGAGTCCTCAGTAAACTGCTTCGTGACTCCCATGTCCTTCACAGCAGACTGAGCCAGTGCC
CAGAGGTTCACCCTTTGCCTACACCTGTCCTGCTGCCTGCTGTGGACTTTAGCTTG
(SEQ ID NO:147)

pMON28539

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT

TABLE 2-continued

GENE SEQUENCES

CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGACCCACTTGCCTCTCATCCCTCCTGGGGC
AGCTTTCTGGACAGGTCCGTCTCCTCCTTGGGGCCCTGCAGAGCCTCCTTGGAACCCAGCTTCCTCC
ACAGGGCAGGACCACAGCTCACAAGGATCCCAATGCCATCTTCCTGAGCTTCCAACACCTGCTCCGA
GGAAAGGTGCGTTTCCTGATGCTTGTAGGAGGGTCCACCCTCTGCGTCAGGGAATTCGGCGGCAACG
GCGGCAACATGGCGTCCCCAGCGCCGCCTGCTTGTGACCTCCGAGTCCTCAGTAAACTGCTTCGTGA
CTCCCATGTCCTTCACAGCAGACTGAGCCAGTGCCCAGAGGTTCACCCTTTGCCTACACCTGTCCTG
CTGCCTGCTGTGGACTTTAGCTTGGGAGAATGGAAAACCCAGATGGAGGAGACCAAGGCACAGGACA
TTCTGGGAGCAGTGACCCTTCTGCTGGAGGGAGTGATGGCAGCACGGGGACAACTG
(SEQ ID NO:148)

pMON28540

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGAACCCAGCTTCCTCCACAGGGCAGGACCA
CAGCTCACAAGGATCCCAATGCCATCTTCCTGAGCTTCCAACACCTGCTCCGAGGAAAGGTGCGTTT
CCTGATGCTTGTAGGAGGGTCCACCCTCTGCGTCAGGGAATTCGGCGGCAACGGCGGCAACATGGCG
TCCCCAGCGCCGCCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGGACAACTGGGACCCACTTGCCTCTCATCCCTCC
TGGGGCAGCTTTCTGGACAGGTCCGTCTCCTCCTTGGGGCCCTGCAGAGCCTCCTT
(SEQ ID NO:149)

pMON28541

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGGCAGGACCACAGCTCACAAGGATCCCAATG
CCATCTTCCTGAGCTTCCAACACCTGCTCCGAGGAAAGGTGCGTTTCCTGATGCTTGTAGGAGGGTC
CACCCTCTGCGTCAGGGAATTCGGCGGCAACGGCGGCAACATGGCGTCCCCAGCGCCGCCTGCTTGT
GACCTCCGAGTCCTCAGTAAACTGCTTCGTGACTCCCATGTCCTTCACAGqAGACTGAGCCAGTGCC
CAGAGGTTCACCCTTTGCCTACACCTGTCCTGCTGCCTGCTGTGGACTTTAGCTTGGGAGAATGGAA
AACCCAGATGGAGGAGACCAAGGCACAGGACATTCTGGGAGCAGTGACCCTTCTGCTGGAGGGAGTG
ATGGCAGCACGGGGACAACTGGGACCCACTTGCCTCTCATCCCTCCTGGGGCAGCTTTCTGGACAGG
TCCGTCTCCTCCTTGGGGCCCTGCAGAGCCTCCTTGGAACCCAGCTTCCTCCACAG
(SEQ ID NO:150)

pMON28542

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCTCACAAGGATCCCAATGCCATCTTCCTGA
GCTTCCAACACCTGCTCCGAGGAAAGGTGCGTTTCCTGATGCTTGTAGGAGGGTCCACCCTCTGCGT
CAGGGAATTCGGCGGCAACGGCGGCAACATGGCGTCCCCAGCGCCGCCTGCTTGTGACCTCCGAGTC
CTCAGTAAACTGCTTCGTGACTCCCATGTCCTTCACAGCAGACTGAGCCAGTGCCCAGAGGTTCACC
CTTTGCCTACACCTGTCCTGCTGCCTGCTGTGGACTTTAGCTTGGGAGAATGGAAAACCCAGATGGA
GGAGACCAAGGCACAGGACATTCTGGGAGCAGTGACCCTTCTGCTGGAGGGAGTGATGGCAGCACGG
GGACAACTGGGACCCACTTGCCTCTCATCCCTCCTGGGGCAGCTTTCTGGACAGGTCCGTCTCCTCC
TTGGGGCCCTGCAGAGCCTCCTTGGAACCCAGCTTCCTCCACAGGGCAGGACCACA
(SEQ ID NO:151)

pMON28543

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGATCCCAATGCCATCTTCCTGAGCTTCCAAC
ACCTGCTCCGAGGAAAGGTGCGTTTCCTGATGCTTGTAGGAGGGTCCACCCTCTGCGTCAGGGAATT

TABLE 2-continued

GENE SEQUENCES

CGGCGGCAACGGCGGCAACATGGCGTCCCCAGCGCCGCCTGCTTGTGACCTCCGAGTCCTCAGTAAA
CTGCTTCGTGACTCCCATGTCCTTCACAGCAGACTGAGCCAGTGCCCAGAGGTTCACCCTTTGCCTA
CACCTGTCCTGCTGCCTGCTGTGGACTTTAGCTTGGGAGAATGGAAAACCCAGATGGAGGAGACCAA
GGCACAGGACATTCTGGGAGCAGTGACCCTTCTGCTGGAGGGAGTGATGGCAGCACGGGGACAACTG
GGACCCACTTGCCTCTCATCCCTCCTGGGGCAGCTTTCTGGACAGGTCCGTCTCCTCCTTGGGGCCC
TGCAGAGCCTCCTTGGAACCCAGCTTCCTCCACAGGGCAGGACCACAGCTCACAAG
(SEQ ID NO:152)

pMON28544

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGCCATCTTCCTGAGCTTCCAACACCTGCTCC
GAGGAAAGGTGCGTTTCCTGATGCTTGTAGGAGGGTCCACCCTCTGCGTCAGGGAATTCGGCGGCAA
CGGCGGCAACATGGCGTCCCCAGCGCCGCCTGCTTGTGACCTCCGAGTCCTCAGTAAACTGCTTCGT
GACTCCCATGTCCTTCACAGCAGACTGAGCCAGTGCCCAGAGGTTCACCCTTTGCCTACACCTGTCC
TGCTGCCTGCTGTGGACTTTAGCTTGGGAGAATGGAAAACCCAGATGGAGGAGACCAAGGCACAGGA
CATTCTGGGAGCAGTGACCCTTCTGCTGGAGGGAGTGATGGCAGCACGGGGACAACTGGGACCCACT
TGCCTCTCATCCCTCCTGGGGCAGCTTTCTGGACAGGTCCGTCTCCTCCTTGGGGCCCTGCAGAGCC
TCCTTGGAACCCAGCTTCCTCCACAGGGCAGGACCACAGCTCACAAGGATCCCAAT
(SEQ ID NO:153)

pMON28545

GCTAACTGCTCTATAATGATCGATGAAATTATACATCACTTAAAGAGACCACCTGCACCTTTGCTGG
ACCCGAACAACCTCAATGACGAAGACGTCTCTATCCTGATGGACCGAAACCTTCGACTTCCAAACCT
GGAGAGCTTCGTAAGGGCTGTCAAGAACTTAGAAAATGCATCAGGTATTGAGGCAATTCTTCGTAAT
CTCCAACCATGTCTGCCCTCTGCCACGGCCGCACCCTCTCGACATCCAATCATCATCAAGGCAGGTG
ACTGGCAAGAATTCCGGGAAAAACTGACGTTCTATCTGGTTACCCTTGAGCAAGCGCAGGAACAACA
GTACGTAGAGGGCGGTGGAGGCTCCCCGGGTGAACCGTCTGGTCCAATCTCTACTATCAACCCGTCT
CCTCCGTCTAAAGAATCTCATAAATCTCCAAACATGGATCCCAATGCCATCTTCCTGAGCTTCCAAC
ACCTGCTCCGAGGAAAGGTGCGTTTCCTGATGCTTGTAGGAGGGTCCACCCTCTGCGTCAGGGAATT
CGGCGGCAACATGGCGTCTCCCGCTCCGCCTGCTTGTGACCTCCGAGTCCTCAGTAAACTGCTTCGT
GACTCCCATGTCCTTCACAGCAGACTGAGCCAGTGCCCAGAGGTTCACCCTTTGCCTACACCTGTCC
TGCTGCCTGCTGTGGACTTTAGCTTGGGAGAATGGAAAACCCAGATGGAGGAGACCAAGGCACAGGA
CATTCTGGGAGCAGTGACCCTTCTGCTGGAGGGAGTGATGGCAGCACGGGGACAACTGGGACCCACT
TGCCTCTCATCCCTCCTGGGGCAGCTTTCTGGACAGGTCCGTCTCCTCCTTGGGGCCCTGCAGAGCC
TCCTTGGAACCCAGGGCAGGACCACAGCTCACAAG (SEQ ID NO:154)

pMON15981

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GTCTTACAAG
451 CTGTGCCACC CCGAGGAGCT GGTGCTGCTC GGACACTCTC TGGGCATCCC
501 CTGGGCTCCC CTGAGCTCCT GCCCCAGCCA GGCCCTGCAG CTGGCAGGCT
551 GCTTGAGCCA ACTCCATAGC GGCCTTTTCC TCTACCAGGG GCTCCTGCAG
601 GCCCTGGAAG GGATATCCCC CGAGTTGGGT CCCACCTTGG ACACACTGCA
651 GCTGGACGTC GCCGACTTTG CCACCACCAT CTGGCAGCAG ATGGAAGAAC
701 TGGGAATGGC CCCTGCCCTG CAGCCCACCC AGGGTGCCAT GCCGGCCTTC
751 GCCTCTGCTT TCCAGCGCCG GGCAGGAGGG GTCCTGGTTG CTAGCCATCT
801 GCAGAGCTTC CTGGAGGTGT CGTACCGCGT TCTACGCCAC CTTGCGCAGC
851 CCGGCGGCGG CTCTGACATG GCTACACCAT TAGGCCCTGC CAGCTCCCTG
901 CCCCAGAGCT TCCTGCTCAA GTCTTTAGAG CAAGTGAGGA AGATCCAGGG
951 CGATGGCGCA GCGCTCCAGG AGAAGCTGTG TGCCACCTAA TAA;
       (SEQ ID NO:155)
``` pMON15982

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GTCTCCCGAG
```

TABLE 2-continued

GENE SEQUENCES

```
451 TTGGGTCCCA CCTTGGACAC ACTGCAGCTG GACGTCGCCG ACTTTGCCAC
501 CACCATCTGG CAGCAGATGG AAGAACTGGG AATGGCCCCT GCCCTGCAGC
551 CCACCCAGGG TGCCATGCCG GCCTTCGCCT CTGCTTTCCA GCGCCGGGCA
601 GGAGGGGTCC TGGTTGCTAG CCATCTGCAG AGCTTCCTGG AGGTGTCGTA
651 CCGCGTTCTA CGCCACCTTG CGCAGCCCqG CGGCGGCTCT GACATGGCTA
701 CACCATTAGG CCCTGCCAGC TCCCTGCCCC AGAGCTTCCT GCTCAAGTCT
751 TTAGAGCAAG TGAGGAAGAT CCAGGGCGAT GGCGCAGCGC TCCAGGAGAA
801 GCTGTGTGCC ACCTACAAGC TGTGCCACCC CGAGGAGCTG GTGCTGCTCG
851 GACACTCTCT GGGCATCCCC TGGGCTCCCC TGAGCTCCTG CCCCAGCCAG
901 GCCCTGCAGC TGGCAGGCTG CTTGAGCCAA CTCCATAGCG GCCTTTTCCT
951 CTACCAGGGG CTCCTGCAGG CCCTGGAAGG GATATCCTAA TAA;
      (SEQ ID NO:156)

pMON15965

1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GTCTTCTGCT
451 TTCCAGCGCC GGGCAGGAGG GGTCCTGGTT GCTAGCCATC TGCAGAGCTT
501 CCTGGAGGTG TCGTACCGCG TTCTACGCCA CCTTGCGCAG CCCGGCGGCG
551 GCTCTGACAT GGCTACACCA TTAGGCCCTG CCAGCTCCCT GCCCCAGAGC
601 TTCCTGCTCA AGTCTTTAGA GCAAGTGAGG AAGATCCAGG GCGATGGCGC
651 AGCGCTCCAG GAGAAGCTGT GTGCCACCTA CAAGCTGTGC CACCCCGAGG
701 AGCTGGTGCT GCTCGGACAC TCTCTGGGCA TCCCCTGGGC TCCCCTGAGC
751 TCCTGCCCCA GCCAGGCCCT GCAGCTGGCA GGCTGCTTGA GCCAACTCCA
801 TAGCGGCCTT TTCCTCTACC AGGGGCTCCT GCAGGCCCTG GAAGGGATAT
851 CCCCCGAGTT GGGTCCCACC TTGGACACAC TGCAGCTGGA CGTCGCCGAC
901 TTTGCCACCA CCATCTGGCA GCAGATGGAA GAACTGGGAA TGGCCCCTGC
951 CCTGCAGCCC ACCCAGGGTG CCATGCCGGC CTTCGCCTAA TAA
      (SEQ ID NO:157)

pMON15966

1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GTCTATGGCC
451 CCTGCCCTGC AGCCCACCCA GGGTGCCATG CCGGCCTTCG CCTCTGCTTT
501 CCAGCGCCGG GCAGGAGGGG TCCTGGTTGC TAGCCATCTG CAGAGCTTCC
551 TGGAGGTGTC GTACCGCGTT CTACGCCACC TTGCGCAGCC CGGCGGCGGC
601 TCTGACATGG CTACACCATT AGGCCCTGCC AGCTCCCTGC CCCAGAGCTT
651 CCTGCTCAAG TCTTTAGAGC AAGTGAGGAA GATCCAGGGC GATGGCGCAG
701 CGCTCCAGGA GAAGCTGTGT GCCACCTACA GCTGTGCCA CCCCGAGGAG
751 CTGGTGCTGC TCGGACACTC TCTGGGCATC CCCTGGGCTC CCCTGAGCTC
801 CTGCCCCAGC CAGGCCCTGC AGCTGGCAGG CTGCTTGAGC CAACTCCATA
851 GCGGCCTTTT CCTCTACCAG GGGCTCCTGC AGGCCCTGGA AGGGATATCC
901 CCCGAGTTGG GTCCCACCTT GGACACACTG CAGCTGGACG TCGCCGACTT
951 TGCCACCACC ATCTGGCAGC AGATGGAAGA ACTGGGATAA TAA
      (SEQ ID NO:158)

pMON15967

1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GTCTACCCAG
451 GGTGCCATGC CGGCCTTCGC CTCTGCTTTC CAGCGCCGGG CAGGAGGGGT
501 CCTGGTTGCT AGCCATCTGC AGAGCTTCCT GGAGGTGTCG TACCGCGTTC
551 TACGCCACCT TGCGCAGCCC GGCGGCGGCT CTGACATGGC TACACCATTA
601 GGCCCTGCCA GCTCCCTGCC CCAGAGCTTC CTGCTCAAGT CTTTAGAGCA
651 AGTGAGGAAG ATCCAGGGCG ATGGCGCAGC GCTCCAGGAG AAGCTGTGTG
```

TABLE 2-continued

GENE SEQUENCES

```
701 CCACCTACAA GCTGTGCCAC CCCGAGGAGC TGGTGCTGCT CGGACACTCT
751 CTGGGCATCC CCTGGGCTCC CCTGAGCTCC TGCCCCAGCC AGGCCCTGCA
801 GCTGGCAGGC TGCTTGAGCC AACTCCATAG CGGCCTTTTC CTCTACCAGG
851 GGCTCCTGCA GGCCCTGGAA GGGATATCCC CCGAGTTGGG TCCCACCTTG
901 GACACACTGC AGCTGGACGT CGCCGACTTT GCCACCACCA TCTGGCAGCA
951 GATGGAAGAA CTGGGAATGG CCCCTGCCCT GCAGCCCTAA TAA
     (SEQ ID NO:159)
``` pMON15960

```
   1 ATGGCTACAC CATTGGGCCC TGCCAGCTCC CTGCCCCAGA GCTTCCTGCT
  51 CAAGTCTTTA GAGCAAGTGA GGAAGATCCA GGGCGATGGC GCAGCGCTCC
 101 AGGAGAAGCT GTGTGCCACC TACAAGCTGT GCCACCCCGA GGAGCTGGTG
 151 CTGCTCGGAC ACTCTCTGGG CATCCCCTGG GCTCCCCTGA GCTCCTGCCC
 201 CAGCCAGGCC CTGCAGCTGG CAGGCTGCTT GAGCCAACTC CATAGCGGCC
 251 TTTTCCTCTA CCAGGGGCTC CTGCAGGCCC TGGAAGGGAT ATCCCCCGAG
 301 TTGGGTCCCA CCTTGGACAC ACTGCAGCTG GACGTCGCCG ACTTTGCCAC
 351 CACCATCTGG CAGCAGATGG AAGAACTGGG AATGGCCCCT GCCCTGCAGC
 401 CCACCCAGGG TGCCATGCCG GCCTTCGCCT CTGCTTTCCA GCGCCGGGCA
 451 GGAGGGGTCC TGGTTGCTAG CCATCTGCAG AGCTTCCTGG AGGTGTCGTA
 501 CCGCGTTCTA CGCCACCTTG CGCAGCCCGG CGGCGGCTCT GACATGGCTA
 551 CACCATTGGG CCCTGCCAGC TCCCTGCCCC AGAGCTTCCT GCTCAAGTCT
 601 TTAGAGCAAG TGAGGAAGAT CCAGGGCGAT GGCGCAGCGC TCCAGGAGAA
 651 GCTGTGTGCC ACCTACAAGC TGTGCCACCC CGAGGAGCTG GTGCTGCTCG
 701 GACACTCTCT GGGCATCCCC TGGGCTCCCC TGAGCTCCTG CCCCAGCCAG
 751 GCCCTGCAGC TGGCAGGCTG CTTGAGCCAA CTCCATAGCG GCCTTTTCCT
 801 CTACCAGGGG CTCCTGCAGG CCCTGGAAGG GATATCCCCC GAGTTGGGTC
 851 CCACCTTGGA CACACTGCAG CTGGACGTCG CCGACTTTGC CACCACCATC
 901 TGGCAGCAGA TGGAAGAACT GGGAATGGCC CCTGCCCTGC AGCCCACCCA
 951 TCCTGGTTGC TAGCCATCTG CAGAGCTTCC TGGAGGTGTC GTACCGCGTT
1051 CTACGCCACC TTGCGCAGCC CTGATAA (SEQ ID NO:160)
```

PM0N32132

```
TCTCCCGCTCCGCCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGG
(SEQ ID NO:249)
```

PMON32133

```
TCTCCCGCTCCGCCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGGG
CAGGACCACAGCTCACAAGGATCCCAATGCCATCTTCCTGAGCTTCCAACACCTGCTCCGAGGAAAG
GTGCGTTTCCTGATGCTTGTAGGAGGGTCCACCCTCTGCGTCAGG (SEQ ID NO:250)
``` pMON32134

```
TCCCCAGCGCCGCCTGCTTGTGACCTCCGAGTCCTCAGTAAACTGCTTCGTGACTCCCATGTCCTTC
ACAGCAGACTGAGCCAGTGCCCAGAGGTTCACCCTTTGCCTACACCTGTCCTGCTGCCTGCTGTGGA
CTTTAGCTTGGGAGAATGGAAAACCCAGATGGAGGAGACCAAGGCACAGGACATTCTGGGAGCAGTG
ACCCTTCTGCTGGAGGGAGTGATGGCAGCACGGGACAACTGGGACCCACTTGCCTCTCATCCCTCC
TGGGGCAGCTTTCTGGACAGGTCCGTCTCCTCCTTGGGGCCCTGCAGAGCCTCCTTGGAACCCAGCT
TCCTCCACAGGGCAGGACCACAGCTCACAAGGATCCCAATGCCATCTTCCTGAGCTTCCAACACCTG
CTCCGAGGAAAGGTGCGTTTCCTGATGCTTGTAGGAGGGTCCACCCTCTGCGTCAGG
(SEQ ID NO:251)
```

Pmon13181

```
   1 CCATGGCTAA CTGCTCTATA ATGATCGATG AAATTATACA TCACTTAAAG
  51 AGACCACCTG CACCTTTGCT GGACCCGAAC AACCTCAATG ACGAAGACGT
 101 CTCTATCCTG ATGGATCGAA ACCTTCGACT TCCAAACCTG GAGAGCTTCG
 151 TAAGGGCTGT CAAGAACTTA GAAAATGCAT CAGGTATTGA GGCAATTCTT
 201 CGTAATCTCC AACCATGTCT GCCCTCTGCC ACGGCCGCAC CCTCTCGACA
 251 TCCAATCATC ATCAAGGCAG GTGACTGGCA AGAATTCCGG GAAAAACTGA
 301 CGTTCTATCT GGTTACCCTT GAGCAAGCGC AGGAACAACA GTACGTAgag
 351 ggcggtggag gctcCCCGGG TGAACCGTCT GGTCCAATCT CTACTATCAA
 401 CCCGTCTCCT CCGTCTAAAG AATCTCATAA ATCTCCAAAC ATGTAAGGTA
 451 CCGCATGCAA GCTT (SEQ ID NO:257)
```

TABLE 2-continued

GENE SEQUENCES

Pmon13180.Seq

```
  1 CCATGGCTAA CTGCTCTATA ATGATCGATG AAATTATACA TCACTTAAAG
 51 AGACCACCTG CACCTTTGCT GGACCCGAAC AACCTCAATG ACGAAGACGT
101 CTCTATCCTG ATGGATCGAA ACCTTCGACT TCCAAACCTG GAGAGCTTCG
151 TAAGGGCTGT CAAGAACTTA GAAAATGCAT CAGGTATTGA GGCAATTCTT
201 CGTAATCTCC AACCATGTCT GCCCTCTGCC ACGGCCGCAC CCTCTCGACA
251 TCCAATCATC ATCAAGGCAG GTGACTGGCA AGAATTCCGG GAAAAACTGA
301 CGTTCTATCT GGTTACCCTT GAGCAAGCGC AGGAACAACA GTACGTAgag
351 ggcggtggag gctcCCCGGG TGGTGGTTCT GGCGGCGGCT CCAACATGTA
401 AGGTACCGCA TGCAAGCTT (SEQ ID NO:258)
``` pmon16017.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTTTAGGC
451 CCTGCCAGCT CCCTGCCCCA GAGCTTCCTG CTCAAGTCTT TAGAGCAAGT
501 GAGGAAGATC CAGGGCGATG GCGCAGCGCT CCAGGAGAAG CTGTGTGCCA
551 CCTACAAGCT GTGCCACCCC GAGGAGCTGG TGCTGCTCGG ACACTCTCTG
601 GGCATCCCCT GGGCTCCCCT GAGCTCCTGC CCCAGCCAGG CCCTGCAGCT
651 GGCAGGCTGC TTGAGCCAAC TCCATAGCGG CCTTTTCCTC TACCAGGGGC
701 TCCTGCAGGC CCTGGAAGGG ATATCCCCCG AGTTGGGTCC CACCTTGGAC
751 ACACTGCAGC TGGACGTCGC CGACTTTGCC ACCACCATCT GGCAGCAGAT
801 GGAAGAACTG GGAATGGCCC CTGCCCTGCA GCCCACCCAG GGTGCCATGC
851 CGGCCTTCGC CTCTGCTTTC CAGCGCCGGG CAGGAGGGGT CCTGGTTGCT
901 AGCCATCTGC AGAGCTTCCT GGAGGTGTCG TACCGCGTTC TACGCCACCT
951 TGCGCAGCCC GACATGGCTA CACCA (SEQ ID NO:259)
``` pmon16018.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCAGAGC
451 TTCCTGCTCA AGTCTTTAGA GCAAGTGAGG AAGATCCAGG GCGATGGCGC
501 AGCGCTCCAG GAGAAGCTGT GTGCCACCTA CAAGCTGTGC CACCCCGAGG
551 AGCTGGTGCT GCTCGGACAC TCTCTGGGCA TCCCCTGGGC TCCCCTGAGC
601 TCCTGCCCCA GCCAGGCCCT GCAGCTGGCA GGCTGCTTGA GCCAACTCCA
651 TAGCGGCCTT TTCCTCTACC AGGGGCTCCT GCAGGCCCTG GAAGGGATAT
701 CCCCCGAGTT GGGTCCCACC TTGGACACAC TGCAGCTGGA CGTCGCCGAC
751 TTTGCCACCA CCATCTGGCA GCAGATGGAA GAACTGGGAA TGGCCCCTGC
801 CCTGCAGCCC ACCCAGGGTG CCATGCCGGC CTTCGCCTCT GCTTTCCAGC
851 GCCGGGCAGG AGGGGTCCTG GTTGCTAGCC ATCTGCAGAG CTTCCTGGAG
901 GTGTCGTACC GCGTTCTACG CCACCTTGCG CAGCCCGACA TGGCTACACC
951 ATTAGGCCCT GCCAGCTCCC TGCCC (SEQ ID NO:260)
``` pmon16019.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTTTCCTG
451 CTCAAGTCTT TAGAGCAAGT GAGGAAGATC CAGGGCGATG GCGCAGCGCT
501 CCAGGAGAAG CTGTGTGCCA CCTACAAGCT GTGCCACCCC GAGGAGCTGG
551 TGCTGCTCGG ACACTCTCTG GGCATCCCCT GGGCTCCCCT GAGCTCCTGC
601 CCCAGCCAGG CCCTGCAGCT GGCAGGCTGC TTGAGCCAAC TCCATAGCGG
651 CCTTTTCCTC TACCAGGGGC TCCTGCAGGC CCTGGAAGGG ATATCCCCCG
701 AGTTGGGTCC CACCTTGGAC ACACTGCAGC TGGACGTCGC CGACTTTGCC
751 ACCACCATCT GGCAGCAGAT GGAAGAACTG GGAATGGCCC CTGCCCTGCA
801 GCCCACCCAG GGTGCCATGC CGGCCTTCGC CTCTGCTTTC CAGCGCCGGG
851 CAGGAGGGGT CCTGGTTGCT AGCCATCTGC AGAGCTTCCT GGAGGTGTCG
901 TACCGCGTTC TACGCCACCT TGCGCAGCCC GACATGGCTA CACCATTAGG
```

TABLE 2-continued

GENE SEQUENCES

```
951 CCCTGCCAGC TCCCTGCCCC AGAGC (SEQ ID NO:261)
``` pmon16020.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTGAGCAA
451 GTGAGGAAGA TCCAGGGCGA TGGCGCAGCG CTCCAGGAGA AGCTGTGTGC
501 CACCTACAAG CTGTGCCACC CCGAGGAGCT GGTGCTGCTC GGACACTCTC
551 TGGGCATCCC CTGGGCTCCC CTGAGCTCCT GCCCCAGCCA GGCCCTGCAG
601 CTGGCAGGCT GCTTGAGCCA ACTCCATAGC GGCCTTTTCC TCTACCAGGG
651 GCTCCTGCAG GCCCTGGAAG GATATCCCC CGAGTTGGGT CCCACCTTGG
701 ACACACTGCA GCTGGACGTC GCCGACTTTG CCACCACCAT CTGGCAGCAG
751 ATGGAAGAAC TGGGAATGGC CCCTGCCCTG CAGCCCACCC AGGGTGCCAT
801 GCCGGCCTTC GCCTCTGCTT TCCAGCGCCG GGCAGGAGGG GTCCTGGTTG
851 CTAGCCATCT GCAGAGCTTC CTGGAGGTGT CGTACCGCGT TCTACGCCAC
901 CTTGCGCAGC CCGACATGGC TACACCATTA GGCCCTGCCA GCTCCCTGCC
951 CCAGAGCTTC CTGCTCAAGT CTTTA (SEQ ID NO:262)
``` pmon16021.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCTGCTC
451 GGACACTCTC TGGGCATCCC CTGGGCTCCC CTGAGCTCCT GCCCCAGCCA
501 GGCCCTGCAG CTGGCAGGCT GCTTGAGCCA ACTCCATAGC GGCCTTTTCC
551 TCTACCAGGG GCTCCTGCAG GCCCTGGAAG GATATCCCC CGAGTTGGGT
601 CCCACCTTGG ACACACTGCA GCTGGACGTC GCCGACTTTG CCACCACCAT
651 CTGGCAGCAG ATGGAAGAAC TGGGAATGGC CCCTGCCCTG CAGCCCACCC
701 AGGGTGCCAT GCCGGCCTTC GCCTCTGCTT TCCAGCGCCG GGCAGGAGGG
751 GTCCTGGTTG CTAGCCATCT GCAGAGCTTC CTGGAGGTGT CGTACCGCGT
801 TCTACGCCAC CTTGCGCAGC CCGACATGGC TACACCATTA GGCCCTGCCA
851 GCTCCCTGCC CCAGAGCTTC CTGCTCAAGT CTTTAGAGCA AGTGAGGAAG
901 ATCCAGGGCG ATGGCGCAGC GCTCCAGGAG AAGCTGTGTG CCACCTACAA
951 GCTGTGCCAC CCCGAGGAGC TGGTG (SEQ ID NO:263)
``` pmon16022.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT CTCCCCCTG
451 AGCTCCTGCC CCAGCCAGGC CCTGCAGCTG GCAGGCTGCT TGAGCCAACT
501 CCATAGCGGC CTTTTCCTCT ACCAGGGGCT CCTGCAGGCC CTGGAAGGGA
551 TATCCCCCGA GTTGGGTCCC ACCTTGGACA CACTGCAGCT GGACGTCGCC
601 GACTTTGCCA CCACCATCTG GCAGCAGATG GAAGAACTGG GAATGGCCCC
651 TGCCCTGCAG CCCACCCAGG GTGCCATGCC GGCCTTCGCC TCTGCTTTCC
701 AGCGCCGGGC AGGAGGGGTC CTGGTTGCTA GCCATCTGCA GAGCTTCCTG
751 GAGGTGTCGT ACCGCGTTCT ACGCCACCTT GCGCAGCCCG ACATGGCTAC
801 ACCATTAGGC CCTGCCAGCT CCCTGCCCCA GAGCTTCCTG CTCAAGTCTT
851 TAGAGCAAGT GAGGAAGATC CAGGGCGATG GCGCAGCGCT CCAGGAGAAG
901 CTGTGTGCCA CCTACAAGCT GTGCCACCCC GAGGAGCTGG TGCTGCTCGG
951 ACACTCTCTG GGCATCCCCT GGGCT (SEQ ID NO:264)
``` pmon16023.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
```

TABLE 2-continued

GENE SEQUENCES

```
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCAGGCC
451 CTGCAGCTGG CAGGCTGCTT GAGCCAACTC CATAGCGGCC TTTTCCTCTA
501 CCAGGGGCTC CTGCAGGCCC TGGAAGGGAT ATCCCCCGAG TTGGGTCCCA
551 CCTTGGACAC ACTGCAGCTG GACGTCGCCG ACTTTGCCAC CACCATCTGG
601 CAGCAGATGG AAGAACTGGG AATGGCCCCT GCCCTGCAGC CCACCCAGGG
651 TGCCATGCCG GCCTTCGCCT CTGCTTTCCA GCGCCGGGCA GGAGGGGTCC
701 TGGTTGCTAG CCATCTGCAG AGCTTCCTGG AGGTGTCGTA CCGCGTTCTA
751 CGCCACCTTG CGCAGCCCGA CATGGCTACA CCATTAGGCC CTGCCAGCTC
801 CCTGCCCCAG AGCTTCCTGC TCAAGTCTTT AGAGCAAGTG AGGAAGATCC
851 AGGGCGATGG CGCAGCGCTC CAGGAGAAGC TGTGTGCCAC CTACAAGCTG
901 TGCCACCCCG AGGAGCTGGT GCTGCTCGGA CACTCTCTGG GCATCCCCTG
951 GGCTCCCCTG AGCTCCTGCC CCAGC (SEQ ID NO:265)
``` pmon16024.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCTGCAG
451 CTGGCAGGCT GCTTGAGCCA ACTCCATAGC GGCCTTTTCC TCTACCAGGG
501 GCTCCTGCAG GCCCTGGAAG GGATATCCCC CGAGTTGGGT CCCACCTTGG
551 ACACACTGCA GCTGGACGTC GCCGACTTTG CCACCACCAT CTGGCAGCAG
601 ATGGAAGAAC TGGGAATGGC CCCTGCCCTG CAGCCCACCC AGGGTGCCAT
651 GCCGGCCTTC GCCTCTGCTT TCCAGCGCCG GGCAGGAGGG GTCCTGGTTG
701 CTAGCCATCT GCAGAGCTTC CTGGAGGTGT CGTACCGCGT TCTACGCCAC
751 CTTGCGCAGC CCGACATGGC TACACCATTA GGCCCTGCCA GCTCCCTGCC
801 CCAGAGCTTC CTGCTCAAGT CTTTAGAGCA AGTGAGGAAG ATCCAGGGCG
851 ATGGCGCAGC GCTCCAGGAG AAGCTGTGTG CCACCTACAA GCTGTGCCAC
901 CCCGAGGAGC TGGTGCTGCT CGGACACTCT CTGGGCATCC CCTGGGCTCC
951 CCTGAGCTCC TGCCCCAGCC AGGCC (SEQ ID NO:266)
``` pmon16025.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTCTGGCA
451 GGCTGCTTGA GCCAACTCCA TAGCGGCCTT TTCCTCTACC AGGGGCTCCT
501 GCAGGCCCTG GAAGGGATAT CCCCCGAGTT GGGTCCCACC TTGGACACAC
551 TGCAGCTGGA CGTCGCCGAC TTTGCCACCA CCATCTGGCA GCAGATGGAA
601 GAACTGGGAA TGGCCCCTGC CCTGCAGCCC ACCCAGGGTG CCATGCCGGC
651 CTTCGCCTCT GCTTTCCAGC GCCGGGCAGG AGGGGTCCTG GTTGCTAGCC
701 ATCTGCAGAG CTTCCTGGAG GTGTCGTACC GCGTTCTACG CCACCTTGCG
751 CAGCCCGACA TGGCTACACC ATTAGGCCCT GCCAGCTCCC TGCCCCAGAG
801 CTTCCTGCTC AAGTCTTTAG AGCAAGTGAG GAAGATCCAG GGCGATGGCG
851 CAGCGCTCCA GGAGAAGCTG TGTGCCACCT ACAAGCTGTG CCACCCCGAG
901 GAGCTGGTGC TGCTCGGACA CTCTCTGGGC ATCCCCTGGG CTCCCCTGAG
951 CTCCTGCCCC AGCCAGGCCC TGCAG (SEQ ID NO:267)
``` pmon16026.seq

```
  1 ATGGCTAACT GCTCTATAAT GATCGATGAA ATTATACATC ACTTAAAGAG
 51 ACCACCTGCA CCTTTGCTGG ACCCGAACAA CCTCAATGAC GAAGACGTCT
101 CTATCCTGAT GGATCGAAAC CTTCGACTTC CAAACCTGGA GAGCTTCGTA
151 AGGGCTGTCA AGAACTTAGA AAATGCATCA GGTATTGAGG CAATTCTTCG
201 TAATCTCCAA CCATGTCTGC CCTCTGCCAC GGCCGCACCC TCTCGACATC
251 CAATCATCAT CAAGGCAGGT GACTGGCAAG AATTCCGGGA AAAACTGACG
301 TTCTATCTGG TTACCCTTGA GCAAGCGCAG GAACAACAGT ACGTAGAGGG
351 CGGTGGAGGC TCCCCGGGTG AACCGTCTGG TCCAATCTCT ACTATCAACC
401 CGTCTCCTCC GTCTAAAGAA TCTCATAAAT CTCCAAACAT GGCTGAACTG
451 GGAATGGCCC CTGCCCTGCA GCCCACCCAG GGTGCCATGC CGGCCTTCGC
501 CTCTGCTTTC AGCGCCGGG CAGGAGGGGT CCTGGTTGCT AGCCATCTGC
551 AGAGCTTCCT GGAGGTGTCG TACCGCGTTC TACGCCACCT TGCGCAGCCC
601 GACATGGCTA CACCATTAGG CCCTGCCAGC TCCCTGCCCC AGAGCTTCCT
651 GCTCAAGTCT TTAGAGCAAG TGAGGAAGAT CCAGGGCGAT GGCGCAGCGC
```

TABLE 2-continued

GENE SEQUENCES

```
  701 TCCAGGAGAA GCTGTGTGCC ACCTACAAGC TGTGCCACCC CGAGGAGCTG
  751 GTGCTGCTCG GACACTCTCT GGGCATCCCC TGGGCTCCCC TGAGCTCCTG
  801 CCCCAGCCAG GCCCTGCAGC TGGCAGGCTG CTTGAGCCAA CTCCATAGCG
  851 GCCTTTTCCT CTACCAGGGG CTCCTGCAGG CCCTGGAAGG GATATCCCCC
  901 GAGTTGGGTC CCACCTTGGA CACACTGCAG CTGGACGTCG CCGACTTTGC
  951 CACCACCATC TGGCAGCAGA TGGAA (SEQ ID NO:268)

pmon16027.seq
    1 ATGGCTAACT GCTCTATAAT GATCGATGAA ATTATACATC ACTTAAAGAG
   51 ACCACCTGCA CCTTTGCTGG ACCCGAACAA CCTCAATGAC GAAGACGTCT
  101 CTATCCTGAT GGATCGAAAC CTTCGACTTC CAAACCTGGA GAGCTTCGTA
  151 AGGGCTGTCA AGAACTTAGA AAATGCATCA GGTATTGAGG CAATTCTTCG
  201 TAATCTCCAA CCATGTCTGC CCTCTGCCAC GGCCGCACCC TCTCGACATC
  251 CAATCATCAT CAAGGCAGGT GACTGGCAAG AATTCCGGGA AAAACTGACG
  301 TTCTATCTGG TTACCCTTGA GCAAGCGCAG GAACAACAGT ACGTAGAGGG
  351 CGGTGGAGGC TCCCCGGGTG AACCGTCTGG TCCAATCTCT ACTATCAACC
  401 CGTCTCCTCC GTCTAAAGAA TCTCATAAAT CTCCAAACAT GGCTGGAATG
  451 GCCCCTGCCC TGCAGCCCAC CCAGGGTGCC ATGCCGGCCT TCGCCTCTGC
  501 TTTCCAGCGC CGGGCAGGAG GGGTCCTGGT TGCTAGCCAT CTGCAGAGCT
  551 TCCTGGAGGT GTCGTACCGC GTTCTACGCC ACCTTGCGCA GCCCGACATG
  601 GCTACACCAT TAGGCCCTGC CAGCTCCCTG CCCCAGAGCT TCCTGCTCAA
  651 GTCTTTAGAG CAAGTGAGGA AGATCCAGGG CGATGGCGCA GCGCTCCAGG
  701 AGAAGCTGTG TGCCACCTAC AAGCTGTGCC ACCCCGAGGA GCTGGTGCTG
  751 CTCGGACACT CTCTGGGCAT CCCCTGGGCT CCCCTGAGCT CCTGCCCCAG
  801 CCAGGCCCTG CAGCTGGCAG GCTGCTTGAG CCAACTCCAT AGCGGCCTTT
  851 TCCTCTACCA GGGGCTCCTG CAGGCCCTGG AAGGGATATC CCCGAGTTG
  901 GGTCCCACCT TGGACACACT GCAGCTGGAC GTCGCCGACT TTGCCACCAC
  951 CATCTGGCAG CAGATGGAAG AACTG (SEQ ID NO:269)

pmon16028.seq

1 ATGGCTAACT GCTCTATAAT GATCGATGAA ATTATACATC ACTTAAAGAG
   51 ACCACCTGCA CCTTTGCTGG ACCCGAACAA CCTCAATGAC GAAGACGTCT
  101 CTATCCTGAT GGATCGAAAC CTTCGACTTC CAAACCTGGA GAGCTTCGTA
  151 AGGGCTGTCA AGAACTTAGA AAATGCATCA GGTATTGAGG CAATTCTTCG
  201 TAATCTCCAA CCATGTCTGC CCTCTGCCAC GGCCGCACCC TCTCGACATC
  251 CAATCATCAT CAAGGCAGGT GACTGGCAAG AATTCCGGGA AAAACTGACG
  301 TTCTATCTGG TTACCCTTGA GCAAGCGCAG GAACAACAGT ACGTAGAGGG
  351 CGGTGGAGGC TCCCCGGGTG AACCGTCTGG TCCAATCTCT ACTATCAACC
  401 CGTCTCCTCC GTCTAAAGAA TCTCATAAAT CTCCAAACAT GGCTAGCTTC
  451 CTGGAGGTGT CGTACCGCGT TCTACGCCAC CTTGCGCAGC CCGACATGGC
  501 TACACCATTA GGCCCTGCCA GCTCCCTGCC CCAGAGCTTC CTGCTCAAGT
  551 CTTTAGAGCA AGTGAGGAAG ATCCAGGGCG ATGGCGCAGC GCTCCAGGAG
  601 AAGCTGTGTG CCACCTACAA GCTGTGCCAC CCCGAGGAGC TGGTGCTGCT
  651 CGGACACTCT CTGGGCATCC CCTGGGCTCC CCTGAGCTCC TGCCCCAGCC
  701 AGGCCCTGCA GCTGGCAGGC TGCTTGAGCC AACTCCATAG CGGCCTTTTC
  751 CTCTACCAGG GGCTCCTGCA GGCCCTGGAA GGGATATCCC CCGAGTTGGG
  801 TCCCACCTTG GACACACTGC AGCTGGACGT CGCCGACTTT GCCACCACCA
  851 TCTGGCAGCA GATGGAAGAA CTGGGAATGG CCCCTGCCCT GCAGCCCACC
  901 CAGGGTGCCA TGCCGGCCTT CGCCTCTGCT TTCCAGCGCC GGGCAGGAGG
  951 GGTCCTGGTT GCTAGCCATC TGCAG (SEQ ID NO:270)

1 ATGGCTGGAC CCACTTGCCT CTCATCCCTC CTGGGGCAGC TTTCTGGACA
   51 GGTCCGTCTC CTCCTTGGGG CCCTGCAGAG CCTCCTTGGA ACCCAGCTTC
  101 CTCCACAGGG CAGGACCACA GCTCACAAGG ATCCCAATGC CATCTTCCTG
  151 AGCTTCCAAC ACCTGCTCCG AGGAAAGGTG CGTTTCCTGA TGCTTGTAGG
  201 AGGGTCCACC CTCGCCGTCA GGGAATTCGG CGGCAACATG GCGTCTCCGG
  251 CGCCGCCTGC TGCTGACCTC CGAGTCCTCA GTAAACTGCT TCGTGACTCC
  301 CATGTCCTTC ACAGCAGACT GAGCCAGTGC CCAGAGGTTC ACCCTTTGCC
  351 TACACCTGTC CTGCTGCCTG CTGTGGACTT TAGCTTGGGA GAATGGAAAA
  401 CCCAGATGGA GGAGACCAAG GCACAGGACA TTCTGGGAGC AGTGACCCTT
  451 CTGCTGGAGG GAGTGATGGC AGCACGGGGA CAACTG
      (SEQ ID NO:286)

1 ATGGCTGGCA GGACCACAGC TCACAAGGAT CCCAATGCCA TCTTCCTGAG
   51 CTTCCAACAC CTGCTCCGAG GAAAGGTGCG TTTCCTGATG CTTGTAGGAG
  101 GGTCCACCCT CGCCGTCAGG GAATTCGGCG GCAACATGGC GTCTCCGGCG
  151 CCGCCTGCTG CTGACCTCCG AGTCCTCAGT AAACTGCTTC GTGACTCCCA
  201 TGTCCTTCAC AGCAGACTGA GCCAGTGCCC AGAGGTTCAC CCTTTGCCTA
  251 CACCTGTCCT GCTGCCTGCT GTGGACTTTA GCTTGGGAGA ATGGAAACC
  301 CAGATGGAGG AGACCAAGGC ACAGGACATT CTGGGAGCAG TGACCCTTCT
  351 GCTGGAGGGA GTGATGGCAG CACGGGGACA ACTGGGACCC ACTTGCCTCT
  401 CATCCCTCCT GGGGCAGCTT TCTGGACAGG TCCGTCTCCT CCTTGGGGCC
  451 CTGCAGAGCC TCCTTGGAAC CCAGCTTCCT CCACAG
      (SEQ ID NO:287)
```

TABLE 3

PROTEIN SEQUENCES pMON26458pep

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg
PheLeuMetLeuValGlyGlySerThrLeuCysValArgGluPhe
(SEQ ID NO:161)

pMON28548pep

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg
PheLeuMetLeuValGlyGlySerThrLeuCysValArgGluPheGlyAsnMetAla
SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnGlyArgThrThrAlaHisLysAspPro
AsnAlaIlePheLeuSerPheGlnHisLeuLeuArgGlyLysValArgPheLeuMetLeu
ValGlyGlySerThrLeuCysValArg (SEQ ID NO:162)

pMON28500

SerProAlaProProAlaCysAspLeuArgValLeuSerLysLeuLeuArgAspSerHisValLeu
HisSerArgLeuSerGlnCysProGluValHisProLeuProThrProValLeuLeuProAlaVal
AspPheSerLeuGlyGluTrpLysThrGlnMetGluGluThrLysAlaGlnAspIleLeuGlyAla
ValThrLeuLeuLeuGluGlyValMetAlaAlaArgGlyGlnLeuGlyProThrCysLeuSerSer
LeuLeuGlyGlnLeuSerGlyGlnValArgLeuLeuLeuGlyAlaLeuGlnSerLeuLeuGlyThr
GlnLeuProProGlnGlyArgThrThrAlaHisLysAspProAsnAlaIlePheLeuSerPheGln
HisLeuLeuArgGlyLysValArgPheLeuMetLeuValGlyGlySerThrLeuCysValArgGlu
PheGlyAsnMetAlaSerProAlaProProAlaCysAspLeuArgValLeuSerLysLeuLeuArg
AspSerHisValLeuHisSerArgLeuSerGlnCysProGluValHisProLeuProThrProVal
LeuLeuProAlaValAspPheSerLeuGlyGluTrpLysThrGlnMetGluGluThrLysAlaGln
AspIleLeuGlyAlaValThrLeuLeuLeuGluGlyValMetAlaAlaArgGlyGlnLeuGlyPro
ThrCysLeuSerSerLeuLeuGlyGlnLeuSerGlyGlnValArgLeuLeuLeuGlyAlaLeuGln
SerLeuLeuGlyThrGlnLeuProProGlnGlyArgThrThrAlaHisLysAspProAsnAlaIle
PheLeuSerPheGlnHisLeuLeuArgGlyLysValArgPheLeuMetLeuValGlyGlySerThr
LeuCysValArg (SEQ ID NO:163)

pMON28501

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg
PheLeuMetLeuValGlyGlySerThrLeuCysValArgGluPheGlyAsnMetAla
SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg
PheLeuMetLeuValGlyGlySerThrLeuCysValArg (SEQ ID NO:164)

pMON28502

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg

TABLE 3-continued

PROTEIN SEQUENCES

PheLeuMetLeuValGlyGlySerThrLeuCysValArgGluPheGlyGlyAsnGlyGly
AsnMetAlaSerProAlaProProAlaCysAspLeuArgValLeuSerLysLeuLeuArg
AspSerHisValLeuHisSerArgLeuSerGlnCysProGluValHisProLeuProThr
ProValLeuLeuProAlaValAspPheSerLeuGlyGluTrpLysThrGlnMetGluGlu
ThrLysAlaGlnAspIleLeuGlyAlaValThrLeuLeuLeuGlyValMetAlaAla
ArgGlyGlnLeuGlyProThrCysLeuSerSerLeuLeuGlyGlnLeuSerGlyGlnVal
ArgLeuLeuLeuGlyAlaLeuGlnSerLeuLeuGlyThrGlnLeuProProGlnGlyArg
ThrThrAlaHisLysAspProAsnAlaIlePheLeuSerPheGlnHisLeuLeuArgGly
LysValArgPheLeuMetLeuValGlyGlySerThrLeuCysValArg
(SEQ ID NO:165)

13182.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Ser Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr (SEQ ID NO:166)

13183.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr (SEQ ID NO:167)

13184.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Ser Asn Met Ala Pro Glu Leu Gly
Pro Thr Leu Asp Thr Leu Gln Leu Asp Val Ala Asp Phe Ala Leu
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu

TABLE 3-continued

PROTEIN SEQUENCES

```
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser (SEQ ID NO:168)
```

13185.Pept

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser (SEQ ID NO:169)
```

13186.Pept

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Ser Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Ser Gly Gly Ser Gly Gly Ser Gln Ser Phe Leu Leu Lys Ser Leu
Glu Gln Val Arg Lys Ile Gln Gly Asp Gly Ala Ala Leu Gln Glu
Lys Leu Cys Ala Thr Tyr Lys Leu Cys His Pro Glu Glu Leu Val
Leu Leu Gly His Ser Leu Gly Ile Pro Trp Ala Pro Leu Ser Ser
Cys Pro Ser Gln Ala Leu Gln Leu Ala Gly Cys Leu Ser Gln Leu
His Ser Gly Leu Phe Leu Tyr Gln Gly Leu Leu Gln Ala Leu Glu
Gly Ile Ser Pro Glu Leu Gly Pro Thr Leu Asp Thr Leu Gln Leu
Asp Val Ala Asp Phe Ala Thr Thr Ile Trp Gln Gln Met Glu Glu
Leu Gly (SEQ ID NO:170)
```

13187.Pept

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Ser Gly Gly Ser Gly Gly Ser Gln Ser Phe Leu Leu Lys Ser Leu
Glu Gln Val Arg Lys Ile Gln Gly Asp Gly Ala Ala Leu Gln Glu
Lys Leu Cys Ala Thr Tyr Lys Leu Cys His Pro Glu Glu Leu Val
Leu Leu Gly His Ser Leu Gly Ile Pro Trp Ala Pro Leu Ser Ser
Cys Pro Ser Gln Ala Leu Gln Leu Ala Gly Cys Leu Ser Gln Leu
His Ser Gly Leu Phe Leu Tyr Gln Gly Leu Leu Gln Ala Leu Glu
```

TABLE 3-continued

PROTEIN SEQUENCES

Gly Ile Ser Pro Glu Leu Gly Pro Thr Leu Asp Thr Leu Gln Leu
Asp Val Ala Asp Phe Ala Thr Thr Ile Trp Gln Gln Met Glu Glu
Leu Gly (SEQ ID NO:171)

13188.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Ser Gly Gly Ser Gly Gly Ser
Gln Ser Phe Leu Leu Lys Ser Leu Glu Gln Val Arg Lys Ile Gln
Gly Asp Gly Ala Ala Leu Gln Glu Lys Leu Cys Ala Thr Tyr Lys
Leu Cys His Pro Glu Glu Leu Val Leu Leu Gly His Ser Leu Gly
Ile Pro Trp Ala Pro Leu Ser Ser Cys Pro Ser Gln Ala Leu Gln
Leu Ala Gly Cys Leu Ser Gln Leu His Ser Gly Leu Phe Leu Tyr
Gln Gly Leu Leu Gln Ala Leu Glu Gly Ile Ser Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro (SEQ ID NO:172)

13189.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Ser Gly Gly Ser Gly Gly Ser
Gln Ser Phe Leu Leu Lys Ser Leu Glu Gln Val Arg Lys Ile Gln
Gly Asp Gly Ala Ala Leu Gln Glu Lys Leu Cys Ala Thr Tyr Lys
Leu Cys His Pro Glu Glu Leu Val Leu Leu Gly His Ser Leu Gly
Ile Pro Trp Ala Pro Leu Ser Ser Cys Pro Ser Gln Ala Leu Gln
Leu Ala Gly Cys Leu Ser Gln Leu His Ser Gly Leu Phe Leu Tyr
Gln Gly Leu Leu Gln Ala Leu Glu Gly Ile Ser Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro (SEQ ID NO:173)

13190.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser Pro Glu Leu Gly Pro Thr Leu Asp Thr Leu Gln Leu Asp
Val Ala Asp Phe Ala Thr Thr Ile Trp Gln Gln Met Glu Glu Leu
Gly Met Ala Pro Ala Leu Gln Pro Thr Gln Gly Ala Met Pro Ala
Phe Ala (SEQ ID NO:174)

TABLE 3-continued

PROTEIN SEQUENCES

13191.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser Pro Glu Leu Gly Pro Thr Leu Asp Thr Leu Gln Leu Asp
Val Ala Asp Phe Ala Thr Thr Ile Trp Gln Gln Met Glu Glu Leu
Gly Met Ala Pro Ala Leu Gln Pro Thr Gln Gly Ala Met Pro Ala
Phe Ala (SEQ ID NO:175)

13192.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Thr Pro Leu
Gly Pro Ala Ser Ser Leu Pro Gln Ser Phe Leu Leu Lys Ser Leu
Glu Gln Val Arg Lys Ile Gln Gly Asp Gly Ala Ala Leu Gln Glu
Lys Leu Cys Ala Thr (SEQ ID NO:176)

13193.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Thr Pro Leu
Gly Pro Ala Ser Ser Leu Pro Gln Ser Phe Leu Leu Lys Ser Leu
Glu Gln Val Arg Lys Ile Gln Gly Asp Gly Ala Ala Leu Gln Glu
Lys Leu Cys Ala Thr (SEQ ID NO:177)

25190.Pept

Asn Cys Ser Ile Met Ile Asp Glu Ile Ile His His Leu Lys Arg

TABLE 3-continued

PROTEIN SEQUENCES

Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser (SEQ ID NO:178)

pMON25191.Pep

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser (SEQ ID NO:179)

13194.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Thr Pro Leu Gly Pro Ala Ser Ser Leu Pro Gln Ser Phe Leu Leu
Lys Ser Leu Glu Gln Val Arg Lys Ile Gln Gly Asp Gly Ala Ala
Leu Gln Glu Lys Leu Cys Ala Thr Tyr Lys Leu Cys His Pro Glu
Glu Leu Val Leu Leu Gly His Ser Leu Gly Ile Pro Trp Ala Pro
Leu Ser Ser Cys Pro Ser Gln Ala Leu Gln Leu Ala Gly Cys Leu
Ser Gln Leu His Ser Gly Leu Phe Leu Tyr Gln Gly Leu Leu Gln
Ala Leu Glu Gly Ile Ser Pro Glu Leu Gly Pro Thr Leu Asp Thr
Leu Gln Leu Asp Val Ala Asp Phe Ala Thr Thr Ile Trp Gln Gln
Met Glu Glu Leu Gly (SEQ ID NO:180)

13195.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr

TABLE 3-continued

PROTEIN SEQUENCES

Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Thr Pro Leu Gly Pro Ala Ser Ser Leu Pro Gln Ser Phe Leu Leu
Lys Ser Leu Glu Gln Val Arg Lys Ile Gln Gly Asp Gly Ala Ala
Leu Gln Glu Lys Leu Cys Ala Thr Tyr Lys Leu Cys His Pro Glu
Glu Leu Val Leu Leu Gly His Ser Leu Gly Ile Pro Trp Ala Pro
Leu Ser Ser Cys Pro Ser Gln Ala Leu Gln Leu Ala Gly Cys Leu
Ser Gln Leu His Ser Gly Leu Phe Leu Tyr Gln Gly Leu Leu Gln
Ala Leu Glu Gly Ile Ser Pro Glu Leu Gly Pro Thr Leu Asp Thr
Leu Gln Leu Asp Val Ala Asp Phe Ala Thr Thr Ile Trp Gln Gln
Met Glu Glu Leu Gly (SEQ ID NO:181)

13196.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Thr Pro Leu Gly Pro Ala Ser
Ser Leu Pro Gln Ser Phe Leu Leu Lys Ser Leu Glu Gln Val Arg
Lys Ile Gln Gly Asp Gly Ala Ala Leu Gln Glu Lys Leu Cys Ala
Thr Tyr Lys Leu Cys His Pro Glu Glu Leu Val Leu Leu Gly His
Ser Leu Gly Ile Pro Trp Ala Pro Leu Ser Ser Cys Pro Ser Gln
Ala Leu Gln Leu Ala Gly Cys Leu Ser Gln Leu His Ser Gly Leu
Phe Leu Tyr Gln Gly Leu Leu Gln Ala Leu Glu Gly Ile Ser Pro
Glu Leu Gly Pro Thr Leu Asp Thr Leu Gln Leu Asp Val Ala Asp
Phe Ala Thr Thr Ile Trp Gln Gln Met Glu Glu Leu Gly Met Ala
Pro Ala Leu Gln Pro (SEQ ID NO:182)

13197.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Thr Pro Leu Gly Pro Ala Ser
Ser Leu Pro Gln Ser Phe Leu Leu Lys Ser Leu Glu Gln Val Arg
Lys Ile Gln Gly Asp Gly Ala Ala Leu Gln Glu Lys Leu Cys Ala
Thr Tyr Lys Leu Cys His Pro Glu Glu Leu Val Leu Leu Gly His
Ser Leu Gly Ile Pro Trp Ala Pro Leu Ser Ser Cys Pro Ser Gln
Ala Leu Gln Leu Ala Gly Cys Leu Ser Gln Leu His Ser Gly Leu
Phe Leu Tyr Gln Gly Leu Leu Gln Ala Leu Glu Gly Ile Ser Pro
Glu Leu Gly Pro Thr Leu Asp Thr Leu Gln Leu Asp Val Ala Asp
Phe Ala Thr Thr Ile Trp Gln Gln Met Glu Glu Leu Gly Met Ala
Pro Ala Leu Gln Pro (SEQ ID NO:183)

13198.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro

TABLE 3-continued

PROTEIN SEQUENCES

Gly Gly Gly Ser Gly Gly Gly Ser Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser Pro Glu Leu Gly Pro Thr Leu Asp Thr Leu
Gln Leu Asp Val Ala Asp Phe Ala Thr Thr Ile Trp Gln Gln Met
Glu Glu Leu Gly Met Ala Pro Ala Leu Gln Pro Thr Gln Gly Ala
Met Pro Ala Phe Ala (SEQ ID NO:184)

13199.Pept

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser Pro Glu Leu Gly Pro Thr Leu Asp Thr Leu
Gln Leu Asp Val Ala Asp Phe Ala Thr Thr Ile Trp Gln Gln Met
Glu Glu Leu Gly Met Ala Pro Ala Leu Gln Pro Thr Gln Gly Ala
Met Pro Ala Phe Ala (SEQ ID NO:185)

31104.Pep

Leu Asp Pro Asn Asn Leu Asn Asp Glu Asp Val Ser Ile Leu Met
Asp Arg Asn Leu Arg Leu Pro Asn Leu Glu Ser Phe Val Arg Ala
Val Lys Asn Leu Glu Asn Ala Ser Gly Ile Glu Ala Ile Leu Arg
Asn Leu Gln Pro Cys Leu Pro Ser Ala Thr Ala Ala Pro Ser Arg
His Pro Ile Ile Ile Lys Ala Gly Asp Trp Gln Glu Phe Arg Glu
Lys Leu Thr Phe Tyr Leu Val Thr Leu Glu Gln Ala Gln Glu Gln
Gln Gly Gly Gly Ser Asn Cys Ser Ile Met Ile Asp Glu Ile Ile
His His Leu Lys Arg Pro Pro Ala Pro Leu Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Glu Leu Gly Met
Ala Pro Ala Leu Gln Pro (SEQ ID NO:186)

31105.Pep

Asn Ala Ser Gly Ile Glu Ala Ile Leu Arg Asn Leu Gln Pro Cys
Leu Pro Ser Ala Thr Ala Ala Pro Ser Arg His Pro Ile Ile Ile
Lys Ala Gly Asp Trp Gln Glu Phe Arg Glu Lys Leu Thr Phe Tyr
Leu Val Thr Leu Glu Gln Ala Gln Glu Gln Gln Gly Gly Gly Ser
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg

TABLE 3-continued

PROTEIN SEQUENCES

Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Leu Gly Met
Ala Pro Ala Leu Gln Pro (SEQ ID NO:187)

31106.Pep

Ala Pro Ser Arg His Pro Ile Ile Ile Lys Ala Gly Asp Trp Gln
Glu Phe Arg Glu Lys Leu Thr Phe Tyr Leu Val Thr Leu Glu Gln
Ala Gln Glu Gln Gln Gly Gly Gly Ser Asn Cys Ser Ile Met Ile
Asp Glu Ile Ile His His Leu Lys Arg Pro Pro Ala Pro Leu Leu
Asp Pro Asn Asn Leu Asn Asp Glu Asp Val Ser Ile Leu Met Asp
Arg Asn Leu Arg Leu Pro Asn Leu Glu Ser Phe Val Arg Ala Val
Lys Asn Leu Glu Asn Ala Ser Gly Ile Glu Ala Ile Leu Arg Asn
Leu Gln Pro Cys Leu Pro Ser Ala Thr Ala Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Leu Gly Met
Ala Pro Ala Leu Gln Pro (SEQ ID NO:188)

31107.Pep

Ala Gly Asp Trp Gln Glu Phe Arg Glu Lys Leu Thr Phe Tyr Leu
Val Thr Leu Glu Gln Ala Gln Glu Gln Gln Gly Gly Gly Ser Asn
Cys Ser Ile Met Ile Asp Glu Ile Ile His His Leu Lys Arg Pro
Pro Ala Pro Leu Leu Asp Pro Asn Asn Leu Asn Asp Glu Asp Val
Ser Ile Leu Met Asp Arg Asn Leu Arg Leu Pro Asn Leu Glu Ser
Phe Val Arg Ala Val Lys Asn Leu Glu Asn Ala Ser Gly Ile Glu
Ala Ile Leu Arg Asn Leu Gln Pro Cys Leu Pro Ser Ala Thr Ala
Ala Pro Ser Arg His Pro Ile Ile Ile Lys Thr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Leu Gly Met
Ala Pro Ala Leu Gln Pro (SEQ ID NO:189)

31108.Pep

Leu Asp Pro Asn Asn Leu Asn Asp Glu Asp Val Ser Ile Leu Met
Asp Arg Asn Leu Arg Leu Pro Asn Leu Glu Ser Phe Val Arg Ala
Val Lys Asn Leu Glu Asn Ala Ser Gly Ile Glu Ala Ile Leu Arg
Asn Leu Gln Pro Cys Leu Pro Ser Ala Thr Ala Ala Pro Ser Arg
His Pro Ile Ile Ile Lys Ala Gly Asp Trp Gln Glu Phe Arg Glu
Lys Leu Thr Phe Tyr Leu Val Thr Leu Glu Gln Ala Gln Glu Gln
Gln Gly Gly Gly Ser Gly Gly Gly Ser Gly Gly Ser Asn Cys
Ser Ile Met Ile Asp Glu Ile Ile His His Leu Lys Arg Pro Pro
Ala Pro Leu Tyr Val Glu Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg

TABLE 3-continued

PROTEIN SEQUENCES

His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:190)

31109.Pep

Asn Ala Ser Gly Ile Glu Ala Ile Leu Arg Asn Leu Gln Pro Cys
Leu Pro Ser Ala Thr Ala Ala Pro Ser Arg His Pro Ile Ile Ile
Lys Ala Gly Asp Trp Gln Glu Phe Arg Glu Lys Leu Thr Phe Tyr
Leu Val Thr Leu Glu Gln Ala Gln Glu Gln Gln Gly Gly Gly Ser
Gly Gly Gly Ser Gly Gly Gly Ser Asn Cys Ser Ile Met Ile Asp
Glu Ile Ile His His Leu Lys Arg Pro Pro Ala Pro Leu Leu Asp
Pro Asn Asn Leu Asn Asp Glu Asp Val Ser Ile Leu Met Asp Arg
Asn Leu Arg Leu Pro Asn Leu Glu Ser Phe Val Arg Ala Val Lys
Asn Leu Glu Tyr Val Glu Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:191)

31110.Pep

Ala Pro Ser Arg His Pro Ile Ile Ile Lys Ala Gly Asp Trp Gln
Glu Phe Arg Glu Lys Leu Thr Phe Tyr Leu Val Thr Leu Glu Gln
Ala Gln Glu Gln Gln Gly Gly Gly Ser Gly Gly Gly Ser Gly Gly
Gly Ser Asn Cys Ser Ile Met Ile Asp Glu Ile Ile His His Leu
Lys Arg Pro Pro Ala Pro Leu Leu Asp Pro Asn Asn Leu Asn Asp
Glu Asp Val Ser Ile Leu Met Asp Arg Asn Leu Arg Leu Pro Asn
Leu Glu Ser Phe Val Arg Ala Val Lys Asn Leu Glu Asn Ala Ser
Gly Ile Glu Ala Ile Leu Arg Asn Leu Gln Pro Cys Leu Pro Ser
Ala Thr Ala Tyr Val Glu Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:192)

31111.Pep

Ala Gly Asp Trp Gln Glu Phe Arg Glu Lys Leu Thr Phe Tyr Leu
Val Thr Leu Glu Gln Ala Gln Glu Gln Gln Gly Gly Gly Ser Gly
Gly Gly Ser Gly Gly Gly Ser Asn Cys Ser Ile Met Ile Asp Glu
Ile Ile His His Leu Lys Arg Pro Pro Ala Pro Leu Leu Asp Pro
Asn Asn Leu Asn Asp Glu Asp Val Ser Ile Leu Met Asp Arg Asn
Leu Arg Leu Pro Asn Leu Glu Ser Phe Val Arg Ala Val Lys Asn
Leu Glu Asn Ala Ser Gly Ile Glu Ala Ile Leu Arg Asn Leu Gln
Pro Cys Leu Pro Ser Ala Thr Ala Ala Pro Ser Arg His Pro Ile
Ile Ile Lys Tyr Val Glu Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala

TABLE 3-continued

PROTEIN SEQUENCES

Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:193)

pMON15981

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaTyrLysLeuCysHisProGluGluLeuValLeuLeu
GlyHisSerLeuGlyIleProTrpAlaProLeuSerSerCysProSerGlnAlaLeuGln
LeuAlaGlyCysLeuSerGlnLeuHisSerGlyLeuPheLeuTyrGlnGlyLeuLeuGln
AlaLeuGluGlyIleSerProGluLeuGlyProThrLeuAspThrLeuGlnLeuAspVal
AlaAspPheAlaThrThrIleTrpGlnGlnMetGluGluLeuGlyMetAlaProAlaLeu
GlnProThrGlnGlyAlaMetProAlaPheAlaSerAlaPheGlnArgArgAlaGlyGly
ValLeuValAlaSerHisLeuGlnSerPheLeuGluValSerTyrArgValLeuArgHis
LeuAlaGlnProGlyGlyGlySerAspMetAlaThrProLeuGlyProAlaSerSerLeu
ProGlnSerPheLeuLeuLysSerLeuGluGlnValArgLysIleGlnGlyAspGlyAla
AlaLeuGlnGluLysLeuCysAlaThr (SEQ ID NO:194)

pMON15982

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaProGluLeuGlyProThrLeuAspThrLeuGlnLeu
AspValAlaAspPheAlaThrThrIleTrpGlnGlnMetGluGluLeuGlyMetAlaPro
AlaLeuGlnProThrGlnGlyAlaMetProAlaPheAlaSerAlaPheGlnArgArgAla
GlyGlyValLeuValAlaSerHisLeuGlnSerPheLeuGluValSerTyrArgValLeu
ArgHisLeuAlaGlnProGlyGlyGlySerAspMetAlaThrProLeuGlyProAlaSer
SerLeuProGlnSerPheLeuLeuLysSerLeuGluGlnValArgLysIleGlnGlyAsp
GlyAlaAlaLeuGlnGluLysLeuCysAlaThrTyrLysLeuCysHisProGluGluLeu
ValLeuLeuGlyHisSerLeuGlyIleProTrpAlaProLeuSerSerCysProSerGln
AlaLeuGlnLeuAlaGlyCysLeuSerGlnLeuHisSerGlyLeuPheLeuTyrGlnGly
LeuLeuGlnAlaLeuGluGlyIleSer (SEQ ID NO:195)

pMON15965

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaSerAlaPheGlnArgArgAlaGlyGlyValLeuVal
AlaSerHisLeuGlnSerPheLeuGluValSerTyrArgValLeuArgHisLeuAlaGln
ProGlyGlyGlySerAspMetAlaThrProLeuGlyProAlaSerSerLeuProGlnSer
PheLeuLeuLysSerLeuGluGlnValArgLysIleGlnGlyAspGlyAlaAlaLeuGln
GluLysLeuCysAlaThrTyrLysLeuCysHisProGluGluLeuValLeuLeuGlyHis
SerLeuGlyIleProTrpAlaProLeuSerSerCysProSerGlnAlaLeuGlnLeuAla
GlyCysLeuSerGlnLeuHisSerGlyLeuPheLeuTyrGlnGlyLeuLeuGlnAlaLeu
GluGlyIleSerProGluLeuGlyProThrLeuAspThrLeuGlnLeuAspValAlaAsp
PheAlaThrThrIleTrpGlnGlnMetGluGluLeuGlyMetAlaProAlaLeuGlnPro
ThrGlnGlyAlaMetProAlaPheAla (SEQ ID NO:196)

pMON15966

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer

TABLE 3-continued

PROTEIN SEQUENCES

GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaMetAlaProAlaLeuGlnProThrGlnGlyAlaMet
ProAlaPheAlaSerAlaPheGlnArgArgAlaGlyGlyValLeuValAlaSerHisLeu
GlnSerPheLeuGluValSerTyrArgValLeuArgHisLeuAlaGlnProGlyGlyGly
SerAspMetAlaThrProLeuGlyProAlaSerSerLeuProGlnSerPheLeuLeuLys
SerLeuGluValArgLysIleGlnGlyAspGlyAlaAlaLeuGlnGluLysLeuCys
AlaThrTyrLysLeuCysHisProGluGluLeuValLeuLeuGlyHisSerLeuGlyIle
ProTrpAlaProLeuSerSerCysProSerGlnAlaLeuGlnLeuAlaGlyCysLeuSer
GlnLeuHisSerGlyLeuPheLeuTyrGlnGlyLeuLeuGlnAlaLeuGluGlyIleSer
ProGluLeuGlyProThrLeuAspThrLeuGlnLeuAspValAlaAspPheAlaThrThr
IleTrpGlnGlnMetGluGluLeuGly (SEQ ID NO:197)

pMON15967

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaThrGlnGlyAlaMetProAlaPheAlaSerAlaPhe
GlnArgArgAlaGlyGlyValLeuValAlaSerHisLeuGlnSerPheLeuGluValSer
TyrArgValLeuArgHisLeuAlaGlnProGlyGlyGlySerAspMetAlaThrProLeu
GlyProAlaSerSerLeuProGlnSerPheLeuLeuLysSerLeuGluGlnValArgLys
IleGlnGlyAspGlyAlaAlaLeuGlnGluLysLeuCysAlaThrTyrLysLeuCysHis
ProGluGluLeuValLeuLeuGlyHisSerLeuGlyIleProTrpAlaProLeuSerSer
CysProSerGlnAlaLeuGlnLeuAlaGlyCysLeuSerGlnLeuHisSerGlyLeuPhe
LeuTyrGlnGlyLeuLeuGlnAlaLeuGluGlyIleSerProGluLeuGlyProThrLeu
AspThrLeuGlnLeuAspValAlaAspPheAlaThrThrIleTrpGlnGlnMetGluGlu
LeuGlyMetAlaProAlaLeuGlnPro (SEQ ID NO:198)

pMON31112.pep

MetAlaAsnCysSerAsnMetIleAspGluIleIleThrHisLeuLysGlnProProLeu
ProLeuLeuAspPheAsnAsnLeuAsnGlyGluAspGlnAspIleLeuMetAspAsnAsn
LeuArgArgProAsnLeuGluAlaPheAsnArgAlaValLysSerLeuGlnAsnAlaSer
AlaIleGluSerIleLeuLysAsnLeuLeuProCysLeuProLeuAlaThrAlaAlaPro
ThrArgHisProIleHisIleLysAspGlyAspTrpAsnGluPheArgArgLysLeuThr
PheTyrLeuLysThrLeuGluAsnAlaGlnAlaGlnGlnTyrValGluGlyGlyGlyGly
SerProGlyGluProSerGlyProIleSerThrIleAsnProSerProProSerLysGlu
SerHisLysSerProAsnMetAlaThrGlnGlyAlaMetProAlaPheAlaSerAlaPhe
GlnArgArgAlaGlyGlyValLeuValAlaSerHisLeuGlnSerPheLeuGluValSer
TyrArgValLeuArgHisLeuAlaGlnProSerGlyGlySerGlyGlySerGlnSerPhe
LeuLeuLysSerLeuGluGlnValArgLysIleGlnGlyAspGlyAlaAlaLeuGlnLeu
LysLeuCysAlaThrTyrLysLeuCysHisProGluGluLeuValLeuLeuGlyHisSer
LeuGlyIleProTrpAlaProLeuSerSerCysProSerGlnAlaLeuGlnLeuAlaGly
CysLeuSerGlnLeuHisSerGlyLeuPheLeuTyrGlnGlyLeuLeuGlnAlaLeuGlu
GlyIleSerProGluLeuGlyProThrLeuAspThrLeuGlnLeuAspValAlaAspPhe
AlaThrThrIleTrpGlnGlnMetGluGluLeuGlyMetAlaProAlaLeuGlnPro
(SEQ ID NO:199)

pMON31113.pep

MetAlaAsnCysSerAsnMetIleAspGluIleIleThrHisLeuLysGlnProProLeu
ProLeuLeuAspPheAsnAsnLeuAsnGlyGluAspGlnAspIleLeuMetGluAsnAsn
LeuArgArgProAsnLeuGluAlaPheAsnArgAlaValLysSerLeuGlnAsnAlaSer
AlaIleGluSerIleLeuLysAsnLeuLeuProCysLeuProLeuAlaThrAlaAlaPro
ThrArgHisProIleIleIleArgAspGlyAspTrpAsnGluPheArgArgLysLeuThr
PheTyrLeuLysThrLeuGluAsnAlaGlnAlaGlnGlnTyrValGluLysGlyGlyGly
SerProGlyGluProSerGlyProIleSerThrIleAsnProSerProProSerLysGlu
SerHisLysSerProAsnMetAlaThrGlnGlyAlaMetProAlaPheAlaSerAlaPhe
GlnArgArgAlaGlyGlyValLeuValAlaSerHisLeuGlnSerPheLeuGluValSer
TyrArgValLeuArgHisLeuAlaGlnProThrProLeuGlyProAlaSerSerLeuPro
GlnSerPheLeuLeuLysSerLeuGluGlnValArgLysIleGlnGlyAspGlyAlaAla
LeuGlnGluLysLeuCysAlaThrTyrLysLeuCysHisProGluGluLeuValLeuLeu
GlyHisSerLeuGlyIleProTrpAlaProLeuSerSerCysProSerGlnAlaLeuGln
LeuAlaGlyCysLeuSerGlnLeuHisSerGlyLeuPheLeuTyrGlnGlyLeuLeuGln
AlaLeuGluGlyIleSerProGluLeuGlyProThrLeuAspThrLeuGlnLeuAspVal
AlaAspPheAlaThrThrIleTrpGlnGlnMetGluGluLeuGlyMetAlaProAlaLeu
GlnPro (SEQ ID NO:200)

TABLE 3-continued

PROTEIN SEQUENCES pMON31114.pep

MetAlaAsnCysSerAsnMetIleAspGluIleIleThrHisLeuLysGlnProProLeu
ProLeuLeuAspPheAsnAsnLeuAsnGlyGluAspGlnAspIleLeuMetGluAsnAsn
LeuArgArgProAsnLeuGluAlaPheAsnArgAlaValLysSerLeuGlnAsnAlaSer
AlaIleGluSerIleLeuLysAsnLeuLeuProCysLeuProLeuAlaThrAlaAlaPro
ThrArgHisProIleIleArgAspGlyAspTrpAsnGluPheArgArgLysLeuThr
PheTyrLeuLysThrLeuGluAsnAlaGlnAlaGlnGlnTyrValGluGlyGlyGlyGly
SerProGlyGluProSerGlyProIleSerThrIleAsnProSerProProSerLysGlu
SerHisLysSerProAsnMetAlaThrGlnGlyAlaMetProAlaPheAlaSerAlaPhe
GlnArgArgAlaGlyGlyValLeuValAlaSerHisLeuGlnSerPheLeuGluValSer
TyrArgValLeuArgHisLeuAlaGlnProSerGlyGlySerGlyGlySerGlnSerPhe
LeuLeuLysSerLeuGluGlnValArgLysIleGlnGlyAspGlyAlaAlaLeuGlnGlu
LysLeuCysAlaThrTyrLysLeuCysHisProGluGluLeuValLeuLeuGlyHisSer
LeuGlyIleProTrpAlaProLeuSerSerCysProSerGlnAlaLeuGlnLeuAlaGly
CysLeuSerGlnLeuHisSerGlyLeuPheLeuTyrGlnGlyLeuLeuGlnAlaLeuGlu
GlyIleSerProGluLeuGlyProThrLeuAspThrLeuGlnLeuAspValAlaAspPhe
AlaThrThrIleTrpGlnGlnMetGluGluLeuGlyMetAlaProAlaLeuGlnPro
(SEQ ID NO:201)

pMON31115.pep

MetAlaAsnCysSerAsnMetIleAspGluIleIleThrHisLeuLysGlnProProLeu
ProLeuLeuAspPheAsnAsnLeuAsnGlyGluAspGlnAspIleLeuMetAspAsnAsn
LeuArgArgProAsnLeuGluAlaPheAsnArgAlaValLysSerLeuGlnAsnAlaSer
AlaIleGluSerIleLeuLysAsnLeuLeuProCysLeuProLeuAlaThrAlaAlaPro
ThrArgHisProIleHisIleLysAspGlyAspTrpAsnGluPheArgArgLysLeuThr
PheTyrLeuLysThrLeuGluAsnAlaGlnAlaGlnGlnTyrValGluGlyGlyGlyGly
SerProGlyGluProSerGlyProIleSerThrIleAsnProSerProProSerLysGlu
SerHisLysSerProAsnMetAlaThrGlnGlyAlaMetProAlaPheAlaSerAlaPhe
GlnArgArgAlaGlyGlyValLeuValAlaSerHisLeuGlnSerPheLeuGluValSer
TyrArgValLeuArgHisLeuAlaGlnProThrProLeuGlyProAlaSerSerLeuPro
GlnSerPheLeuLeuLysSerLeuGluGlnValArgLysIleGlnGlyAspGlyAlaAla
LeuGlnGluLysLeuCysAlaThrTyrLysLeuCysHisProGluGluLeuValLeuLeu
GlyHisSerLeuGlyIleProTrpAlaProLeuSerSerCysProSerGluAlaLeuGln
LeuAlaGlyCysLeuSerGlnLeuHisSerGlyLeuPheLeuTyrGlnGlyLeuLeuGln
AlaLeuGluGlyIleSerProGluLeuGlyProThrLeuAspThrLeuGlnLeuAspVal
AlaAspPheAlaThrThrIleTrpGlnGlnMetGluGluLeuGlyMetAlaProAlaLeu
GlnPro (SEQ ID NO:202)

pMON28505

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGluAlaGlnGluGlnGlnTyrValGluGlyGlyGlyGlySer
ProGlyGluProSerGlyProIleSerThrIleAsnProSerProProSerLysGluSer
HisLysSerProAsnMetGluValHisProLeuProThrProValLeuLeuProAlaVal
AspPheSerLeuGlyGluTrpLysThrGlnMetGluGluThrLysAlaGluAspIleLeu
GlyAlaValThrLeuLeuLeuGluGlyValMetAlaAlaArgGlyGlnLeuGlyProThr
CysLeuSerSerLeuLeuGlyGlnLeuSerGlyGlnValArgLeuLeuLeuGlyAlaLeu
GlnSerLeuLeuGlyThrGlnLeuProProGlnGlyArgThrThrAlaHisLysAspPro
AsnAlaIlePheLeuSerPheGlnHisLeuLeuArgGlyLysValArgPheLeuMetLeu
ValGlyGlySerThrLeuCysValArgGluPheGlyGlyAsnMetAlaSerProAlaPro
ProAlaCysAspLeuArgValLeuSerLysLeuLeuArgAspSerHisValLeuHisSer
ArgLeuSerGlnCysPro (SEQ ID NO:203)

pMON28506

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGluAlaGlnGluGlnGlnTyrValGluGlyGlyGlyGlySer
ProGlyGluProSerGlyProIleSerThrIleAsnProSerProProSerLysGluSer
HisLysSerProAsnMetLeuProThrProValLeuLeuProAlaValAspPheSerLeu
GlyGluTrpLysThrGlnMetGluGluThrLysAlaGluAspIleLeuGlyAlaValThr
LeuLeuLeuGluGlyValMetAlaAlaArgGlyGlnLeuGlyProThrCysLeuSerSer
LeuLeuGlyGlnLeuSerGlyGlnValArgLeuLeuLeuGlyAlaLeuGlnSerLeuLeu
GlyThrGlnLeuProProGlnGlyArgThrThrAlaHisLysAspProAsnAlaIlePhe
LeuSerPheGlnHisLeuLeuArgGlyLysValArgPheLeuMetLeuValGlyGlySer
ThrLeuCysValArgGluPheGlyGlyAsnMetAlaSerProAlaProProAlaCysAsp
LeuArgValLeuSerLysLeuLeuArgAspSerHisValLeuHisSerArgLeuSerGln
CysProGluValHisPro (SEQ ID NO:204)

TABLE 3-continued

PROTEIN SEQUENCES pMON28507

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetValLeuLeuProAlaValAspPheSerLeuGlyGluTrpLys
ThrGlnMetGluGluThrLysAlaGlnAspIleLeuGlyAlaValThrLeuLeuLeuGlu
GlyValMetAlaAlaArgGlyGlnLeuGlyProThrCysLeuSerSerLeuLeuGlyGln
LeuSerGlyGlnValArgLeuLeuLeuGlyAlaLeuGlnSerLeuLeuGlyThrGlnLeu
ProProGlnGlyArgThrThrAlaHisLysAspProAsnAlaIlePheLeuSerPheGln
HisLeuLeuArgGlyLysValArgPheLeuMetLeuValGlyGlySerThrLeuCysVal
ArgGluPheGlyGlyAsnMetAlaSerProAlaProProAlaCysAspLeuArgValLeu
SerLysLeuLeuArgAspSerHisValLeuHisSerArgLeuSerGlnCysProGluVal
HisProLeuProThrPro (SEQ ID NO:205)

pMON28508

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGluAlaGlnGluGlnGlnTyrValGluGlyGlyGlyGlySer
ProGlyGluProSerGlyProIleSerThrIleAsnProSerProProSerLysGluSer
HisLysSerProAsnMetAlaValAspPheSerLeuGlyGluTrpLysThrGlnMetGlu
GluThrLysAlaGlnAspIleLeuGlyAlaValThrLeuLeuLeuGluGlyValMetAla
AlaArgGlyGlnLeuGlyProThrCysLeuSerSerLeuLeuGlyGlnLeuSerGlyGln
ValArgLeuLeuLeuGlyAlaLeuGlnSerLeuLeuGlyThrGlnLeuProProGlnGly
ArgThrThrAlaHisLysAspProAsnAlaIlePheLeuSerPheGlnHisLeuLeuArg
GlyLysValArgPheLeuMetLeuValGlyGlySerThrLeuCysValArgGluPheGly
GlyAsnMetAlaSerProAlaProProAlaCysAspLeuArgValLeuSerLysLeuLeu
ArgAspSerHisValLeuHisSerArgLeuSerGlnCysProGluValHisProLeuPro
ThrProValLeuLeuPro (SEQ ID NO:206)

pMON28509

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGluAlaGlnGluGlnGlnTyrValGluGlyGlyGlyGlySer
ProGlyGluProSerGlyProIleSerThrIleAsnProSerProProSerLysGluSer
HisLysSerProAsnMetAspPheSerLeuGlyGluTrpLysThrGlnMetGluGluThr
LysAlaGluAspIleLeuGlyAlaValThrLeuLeuLeuGluGlyValMetAlaAlaArg
GlyGlnLeuGlyProThrCysLeuSerSerLeuLeuGlyGlnLeuSerGlyGlnValArg
LeuLeuLeuGlyAlaLeuGlnSerLeuLeuGlyThrGlnLeuProProGlnGlyArgThr
ThrAlaHisLysAspProAsnAlaIlePheLeuSerPheGlnHisLeuLeuArgGlyLys
ValArgPheLeuMetLeuValGlyGlySerThrLeuCysValArgGluPheGlyGlyAsn
MetAlaSerProAlaProProAlaCysAspLeuArgValLeuSerLysLeuLeuArgAsp
SerHisValLeuHisSerArgLeuSerGlnCysProGluValHisProLeuProThrPro
ValLeuLeuProAlaVal (SEQ ID NO:207)

pMON28510

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyGluTrpLysThrGlnMetGluGluThrLysAlaGlnAsp
IleLeuGlyAlaValThrLeuLeuLeuGluGlyValMetAlaAlaArgGlyGlnLeuGly
ProThrCysLeuSerSerLeuLeuGlyGlnLeuSerGlyGlnValArgLeuLeuLeuGly
AlaLeuGlnSerLeuLeuGlyThrGlnLeuProProGlnGlyArgThrThrAlaHisLys
AspProAsnAlaIlePheLeuSerPheGlnHisLeuLeuArgGlyLysValArgPheLeu
MetLeuValGlyGlySerThrLeuCysValArgGluPheGlyGlyAsnMetAlaSerPro
AlaProProAlaCysAspLeuArgValLeuSerLysLeuLeuArgAspSerHisValLeu
HisSerArgLeuSerGlnCysProGluValHisProLeuProThrProValLeuLeuPro
AlaValAspPheSerLeu (SEQ ID NO:208)

TABLE 3-continued

PROTEIN SEQUENCES pMON28511

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyProThrCysLeuSerSerLeuLeuGlyGlnLeuSerGly
GlnValArgLeuLeuLeuGlyAlaLeuGlnSerLeuLeuGlyThrGlnLeuProProGln
GlyArgThrThrAlaHisLysAspProAsnAlaIlePheLeuSerPheGlnHisLeuLeu
ArgGlyLysValArgPheLeuMetLeuValGlyGlySerThrLeuCysValArgGluPhe
GlyGlyAsnMetAlaSerProAlaProProAlaCysAspLeuArgValLeuSerLysLeu
LeuArgAspSerHisValLeuHisSerArgLeuSerGlnCysProGluValHisProLeu
ProThrProValLeuLeuProAlaValAspPheSerLeuGlyGluTrpLysThrGlnMet
GluGluThrLysAlaGlnAspIleLeuGlyAlaValThrLeuLeuLeuGluGlyValMet
AlaAlaArgGlyGlnLeu (SEQ ID NO:209)

pMON28512

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyThrGlnLeuProProGlnGlyArgThrThrAlaHisLys
AspProAsnAlaIlePheLeuSerPheGlnHisLeuLeuArgGlyLysValArgPheLeu
MetLeuValGlyGlySerThrLeuCysValArgGluPheGlyGlyAsnMetAlaSerPro
AlaProProAlaCysAspLeuArgValLeuSerLysLeuLeuArgAspSerHisValLeu
HisSerArgLeuSerGlnCysProGluValHisProLeuProThrProValLeuLeuPro
AlaValAspPheSerLeuGlyGluTrpLysThrGlnMetGluGluThrLysAlaGlnAsp
IleLeuGlyAlaValThrLeuLeuLeuGluGlyValMetAlaAlaArgGlyGlnLeuGly
ProThrCysLeuSerSerLeuLeuGlyGlnLeuSerGlyGlnValArgLeuLeuLeuGly
AlaLeuGlnSerLeuLeu (SEQ ID NO:210)

pMON28513

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyArgThrThrAlaHisLysAspProAsnAlaIlePheLeu
SerPheGlnHisLeuLeuArgGlyLysValArgPheLeuMetLeuValGlyGlySerThr
LeuCysValArgGluPheGlyGlyAsnMetAlaSerProAlaProProAlaCysAspLeu
ArgValLeuSerLysLeuLeuArgAspSerHisValLeuHisSerArgLeuSerGlnCys
ProGluValHisProLeuProThrProValLeuLeuProAlaValAspPheSerLeuGly
GluTrpLysThrGlnMetGluGluThrLysAlaGlnAspIleLeuGlyAlaValThrLeu
LeuLeuGluGlyValMetAlaAlaArgGlyGlnLeuGlyProThrCysLeuSerSerLeu
LeuGlyGlnLeuSerGlyGlnValArgLeuLeuLeuGlyAlaLeuGlnSerLeuLeuGly
ThrGlnLeuProProGln (SEQ ID NO:211)

pMON28514

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaHisLysAspProAsnAlaIlePheLeuSerPheGlnHis
LeuLeuArgGlyLysValArgPheLeuMetLeuValGlyGlySerThrLeuCysValArg
GluPheGlyGlyAsnMetAlaSerProAlaProProAlaCysAspLeuArgValLeuSer
LysLeuLeuArgAspSerHisValLeuHisSerArgLeuSerGlnCysProGluValHis
ProLeuProThrProValLeuLeuProAlaValAspPheSerLeuGlyGluTrpLysThr
GlnMetGluGluThrLysAlaGlnAspIleLeuGlyAlaValThrLeuLeuLeuGluGly
ValMetAlaAlaArgGlyGlnLeuGlyProThrCysLeuSerSerLeuLeuGlyGlnLeu
SerGlyGlnValArgLeuLeuLeuGlyAlaLeuGlnSerLeuLeuGlyThrGlnLeuPro
ProGlnGlyArgThrThr (SEQ ID NO:212)

TABLE 3-continued

PROTEIN SEQUENCES pMON28515

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAspProAsnAlaIlePheLeuSerPheGlnHisLeuLeuArg
GlyLysValArgPheLeuMetLeuValGlyGlySerThrLeuCysValArgGluPheGly
GlyAsnMetAlaSerProAlaProProAlaCysAspLeuArgValLeuSerLysLeuLeu
ArgAspSerHisValLeuHisSerArgLeuSerGlnCysProGluValHisProLeuPro
ThrProValLeuLeuProAlaValAspPheSerLeuGlyGluTrpLysThrGlnMetGlu
GluThrLysAlaGluAspIleLeuGlyAlaValThrLeuLeuLeuGluGlyValMetAla
AlaArgGlyGlnLeuGlyProThrCysLeuSerSerLeuLeuGlyGlnLeuSerGlyGln
ValArgLeuLeuLeuGlyAlaLeuGlnSerLeuLeuGlyThrGlnLeuProProGlnGly
ArgThrThrAlaHisLys (SEQ ID NO:213)

pMON28516

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaIlePheLeuSerPheGlnHisLeuLeuArgGlyLysVal
ArgPheLeuMetLeuValGlyGlySerThrLeuCysValArgGluPheGlyGlyAsnMet
AlaSerProAlaProProAlaCysAspLeuArgValLeuSerLysLeuLeuArgAspSer
HisValLeuHisSerArgLeuSerGlnCysProGluValHisProLeuProThrProVal
LeuLeuProAlaValAspPheSerLeuGlyGluTrpLysThrGlnMetGluGluThrLys
AlaGlnAspIleLeuGlyAlaValThrLeuLeuLeuGluGlyValMetAlaAlaArgGly
GlnLeuGlyProThrCysLeuSerSerLeuLeuGlyGlnLeuSerGlyGlnValArgLeu
LeuLeuGlyAlaLeuGlnSerLeuLeuGlyThrGlnLeuProProGlnGlyArgThrThr
AlaHisLysAspProAsn (SEQ ID NO:214)

pMON28519

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGluValHisProLeuProThrProValLeuLeuProAlaVal
AspPheSerLeuGlyGluTrpLysThrGlnMetGluGluThrLysAlaGlnAspIleLeu
GlyAlaValThrLeuLeuLeuGluGlyValMetAlaAlaArgGlyGlnLeuGlyProThr
CysLeuSerSerLeuLeuGlyGlnLeuSerGlyGlnValArgLeuLeuLeuGlyAlaLeu
GlnSerLeuLeuGlyThrGlnLeuProProGlnGlyArgThrThrAlaHisLysAspPro
AsnAlaIlePheLeuSerPheGlnHisLeuLeuArgGlyLysValArgPheLeuMetLeu
ValGlyGlySerThrLeuCysValArgGluPheGlyGlyAsnMetAlaSerProAlaPro
ProAlaCysAspLeuArgValLeuSerLysLeuLeuArgAspSerHisValLeuHisSerArg
LeuSerGlnCysPro (SEQ ID NO:215)

pMON28520

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetLeuProThrProValLeuLeuProAlaValAspPheSerLeu
GlyGluTrpLysThrGlnMetGluGluThrLysAlaGlnAspIleLeuGlyAlaValThr
LeuLeuLeuGluGlyValMetAlaAlaArgGlyGlnLeuGlyProThrCysLeuSerSer
LeuLeuGlyGlnLeuSerGlyGlnValArgLeuLeuLeuGlyAlaLeuGlnSerLeuLeu
GlyThrGlnLeuProProGlnGlyArgThrThrAlaHisLysAspProAsnAlaIlePhe
LeuSerPheGlnHisLeuLeuArgGlyLysValArgPheLeuMetLeuValGlyGlySer
ThrLeuCysValArgGluPheGlyGlyAsnMetAlaSerProAlaProProAlaCysAspLeu
ArgValLeuSerLysLeuLeuArgAspSerHisValLeuHisSerArgLeuSerGlnCys
ProGluValHisPro (SEQ ID NO:216)

TABLE 3-continued

PROTEIN SEQUENCES pMON28521

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetValLeuLeuProAlaValAspPheSerLeuGlyGluTrpLys
ThrGlnMetGluGluThrLysAlaGlnAspIleLeuGlyAlaValThrLeuLeuLeuGlu
GlyValMetAlaAlaArgGlyGlnLeuGlyProThrCysLeuSerSerLeuLeuGlyGln
LeuSerGlyGlnValArgLeuLeuLeuGlyAlaLeuGlnSerLeuLeuGlyThrGlnLeu
ProProGlnGlyArgThrThrAlaHisLysAspProAsnAlaIlePheLeuSerPheGln
HisLeuLeuArgGlyLysValArgPheLeuMetLeuValGlyGlySerThrLeuCysVal
ArgGluPheGlyAsnMetAlaSerProAlaProProAlaCysAspLeuArgValLeuSer
LysLeuLeuArgAspSerHisValLeuHisSerArgLeuSerGlnCysProGluValHis
ProLeuProThrPro (SEQ ID NO:217)

pMON28522

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaValAspPheSerLeuGlyGluTrpLysThrGlnMetGlu
GluThrLysAlaGlnAspIleLeuGlyAlaValThrLeuLeuLeuGluGlyValMetAla
AlaArgGlyGlnLeuGlyProThrCysLeuSerSerLeuLeuGlyGlnLeuSerGlyGln
ValArgLeuLeuLeuGlyAlaLeuGlnSerLeuLeuGlyThrGlnLeuProProGlnGly
ArgThrThrAlaHisLysAspProAsnAlaIlePheLeuSerPheGlnHisLeuLeuArg
GlyLysValArgPheLeuMetLeuValGlyGlySerThrLeuCysValArgGluPheGly
AsnMetAlaSerProAlaProProAlaCysAspLeuArgValLeuSerLysLeuLeuArg
AspSerHisValLeuHisSerArgLeuSerGlnCysProGluValHisProLeuProThr
ProValLeuLeuPro (SEQ ID NO:218)

pMON28523

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAspPheSerLeuGlyGluTrpLysThrGlnMetGluGluThr
LysAlaGlnAspIleLeuGlyAlaValThrLeuLeuLeuGluGlyValMetAlaAlaArg
GlyGlnLeuGlyProThrCysLeuSerSerLeuLeuGlyGlnLeuSerGlyGlnValArg
LeuLeuLeuGlyAlaLeuGlnSerLeuLeuGlyThrGlnLeuProProGlnGlyArgThr
ThrAlaHisLysAspProAsnAlaIlePheLeuSerPheGlnHisLeuLeuArgGlyLys
ValArgPheLeuMetLeuValGlyGlySerThrLeuCysValArgGluPheGlyAsnMet
AlaSerProAlaProProAlaCysAspLeuArgValLeuSerLysLeuLeuArgAspSer
HisValLeuHisSerArgLeuSerGlnCysProGluValHisProLeuProThrProVal
LeuLeuProAlaVal (SEQ ID NO:219)

pMON28524

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyGluTrpLysThrGlnMetGluGluThrLysAlaGlnAsp
IleLeuGlyAlaValThrLeuLeuLeuGluGlyValMetAlaAlaArgGlyGlnLeuGly
ProThrCysLeuSerSerLeuLeuGlyGlnLeuSerGlyGlnValArgLeuLeuLeuGly
AlaLeuGlnSerLeuLeuGlyThrGlnLeuProProGlnGlyArgThrThrAlaHisLys
AspProAsnAlaIlePheLeuSerPheGlnHisLeuLeuArgGlyLysValArgPheLeu
MetLeuValGlyGlySerThrLeuCysValArgGluPheGlyAsnMetAlaSerProAla
ProProAlaCysAspLeuArgValLeuSerLysLeuLeuArgAspSerHisValLeuHis
SerArgLeuSerGlnCysProGluValHisProLeuProThrProValLeuLeuProAla
ValAspPheSerLeu (SEQ ID NO:220)

TABLE 3-continued

PROTEIN SEQUENCES pMON28525

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyProThrCysLeuSerSerLeuLeuGlyGlnLeuSerGly
GlnValArgLeuLeuLeuGlyAlaLeuGlnSerLeuLeuGlyThrGlnLeuProProGln
GlyArgThrThrAlaHisLysAspProAsnAlaIlePheLeuSerPheGlnHisLeuLeu
ArgGlyLysValArgPheLeuMetLeuValGlyGlySerThrLeuCysValArgGluPhe
GlyAsnMetAlaSerProAlaProProAlaCysAspLeuArgValLeuSerLysLeuLeu
ArgAspSerHisValLeuHisSerArgLeuSerGlnCysProGluValHisProLeuPro
ThrProValLeuLeuProAlaValAspPheSerLeuGlyGluTrpLysThrGlnMetGlu
GluThrLysAlaGlnAspIleLeuGlyAlaValThrLeuLeuLeuGluGlyValMetAla
AlaArgGlyGlnLeu (SEQ ID NO:221)

pMON28526

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyThrGlnLeuProProGlnGlyArgThrThrAlaHisLys
AspProAsnAlaIlePheLeuSerPheGlnHisLeuLeuArgGlyLysValArgPheLeu
MetLeuValGlyGlySerThrLeuCysValArgGluPheGlyAsnMetAlaSerProAla
ProProAlaCysAspLeuArgValLeuSerLysLeuLeuArgAspSerHisValLeuHis
SerArgLeuSerGlnCysProGluValHisProLeuProThrProValLeuLeuProAla
ValAspPheSerLeuGlyGluTrpLysThrGlnMetGluGluThrLysAlaGlnAspIle
LeuGlyAlaValThrLeuLeuLeuGluGlyValMetAlaAlaArgGlyGlnLeuGlyPro
ThrCysLeuSerSerLeuLeuGlyGlnLeuSerGlyGlnValArgLeuLeuLeuGlyAla
LeuGlnSerLeuLeu (SEQ ID NO:222)

pMON28527

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyArgThrThrAlaHisLysAspProAsnAlaIlePheLeu
SerPheGlnHisLeuLeuArgGlyLysValArgPheLeuMetLeuValGlyGlySerThr
LeuCysValArgGluPheGlyAsnMetAlaSerProAlaProProAlaCysAspLeuArg
ValLeuSerLysLeuLeuArgAspSerHisValLeuHisSerArgLeuSerGlnCysPro
GluValHisProLeuProThrProValLeuLeuProAlaValAspPheSerLeuGlyGlu
TrpLysThrGlnMetGluGluThrLysAlaGlnAspIleLeuGlyAlaValThrLeuLeu
LeuGluGlyValMetAlaAlaArgGlyGlnLeuGlyProThrCysLeuSerSerLeuLeu
GlyGlnLeuSerGlyGlnValArgLeuLeuLeuGlyAlaLeuGlnSerLeuLeuGlyThr
GlnLeuProProGln (SEQ ID NO:223)

pMON28528

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaHisLysAspProAsnAlaIlePheLeuSerPheGlnHis
LeuLeuArgGlyLysValArgPheLeuMetLeuValGlyGlySerThrLeuCysValArg
GluPheGlyAsnMetAlaSerProAlaProProAlaCysAspLeuArgValLeuSerLys
LeuLeuArgAspSerHisValLeuHisSerArgLeuSerGlnCysProGluValHisPro
LeuProThrProValLeuLeuProAlaValAspPheSerLeuGlyGluTrpLysThrGln
MetGluGluThrLysAlaGlnAspIleLeuGlyAlaValThrLeuLeuLeuGluGlyVal
MetAlaAlaArgGlyGlnLeuGlyProThrCysLeuSerSerLeuLeuGlyGlnLeuSer
GlyGlnValArgLeuLeuLeuGlyAlaLeuGlnSerLeuLeuGlyThrGlnLeuProPro
GlnGlyArgThrThr (SEQ ID NO:224)

TABLE 3-continued

PROTEIN SEQUENCES pMON28529

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAspProAsnAlaIlePheLeuSerPheGlnHisLeuLeuArg
GlyLysValArgPheLeuMetLeuValGlyGlySerThrLeuCysValArgGluPheGly
AsnMetAlaSerProAlaProProAlaCysAspLeuArgValLeuSerLysLeuLeuArg
AspSerHisValLeuHisSerArgLeuSerGlnCysProGluValHisProLeuProThr
ProValLeuLeuProAlaValAspPheSerLeuGlyGluTrpLysThrGlnMetGluGlu
ThrLysAlaGlnAspIleLeuGlyAlaValThrLeuLeuLeuGluGlyValMetAlaAla
ArgGlyGlnLeuGlyProThrCysLeuSerSerLeuLeuGlyGlnLeuSerGlyGlnVal
ArgLeuLeuLeuGlyAlaLeuGlnSerLeuLeuGlyThrGlnLeuProProGlnGlyArg
ThrThrAlaHisLys (SEQ ID NO:225)

pMON28530

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaIlePheLeuSerPheGlnHisLeuLeuArgGlyLysVal
ArgPheLeuMetLeuValGlyGlySerThrLeuCysValArgGluPheGlyAsnMetAla
SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsn (SEQ ID NO:226)

pMON28533

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGluValHisProLeuProThrProValLeuLeuProAlaVal
AspPheSerLeuGlyGluTrpLysThrGlnMetGluGluThrLysAlaGlnAspIleLeu
GlyAlaValThrLeuLeuLeuGluGlyValMetAlaAlaArgGlyGlnLeuGlyProThr
CysLeuSerSerLeuLeuGlyGlnLeuSerGlyGlnValArgLeuLeuLeuGlyAlaLeu
GlnSerLeuLeuGlyThrGlnLeuProProGlnGlyArgThrThrAlaHisLysAspPro
AsnAlaIlePheLeuSerPheGlnHisLeuLeuArgGlyLysValArgPheLeuMetLeu
ValGlyGlySerThrLeuCysValArgGluPheGlyGlyAsnGlyGlyAsnMetAlaSer
ProAlaProProAlaCysAspLeuArgValLeuSerLysLeuLeuArgAspSerHisVal
LeuHisSerArgLeuSerGlnCysPro (SEQ ID NO:227)

pMON28534

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetLeuProThrProValLeuLeuProAlaValAspPheSerLeu
GlyGluTrpLysThrGlnMetGluGluThrLysAlaGlnAspIleLeuGlyAlaValThr
LeuLeuLeuGluGlyValMetAlaAlaArgGlyGlnLeuGlyProThrCysLeuSerSer
LeuLeuGlyGlnLeuSerGlyGlnValArgLeuLeuLeuGlyAlaLeuGlnSerLeuLeu
GlyThrGlnLeuProProGlnGlyArgThrThrAlaHisLysAspProAsnAlaIlePhe
LeuSerPheGlnHisLeuLeuArgGlyLysValArgPheLeuMetLeuValGlyGlySer
ThrLeuCysValArgGluPheGlyGlyAsnGlyGlyAsnMetAlaSerProAlaProPro
AlaCysAspLeuArgValLeuSerLysLeuLeuArgAspSerHisValLeuHisSerArg
LeuSerGlnCysProGluValHisPro (SEQ ID NO:228)

TABLE 3-continued

PROTEIN SEQUENCES pMON28535

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetValLeuLeuProAlaValAspPheSerLeuGlyGluTrpLys
ThrGlnMetGluGluThrLysAlaGluAspIleLeuGlyAlaValThrLeuLeuLeuGlu
GlyValMetAlaAlaArgGlyGlnLeuGlyProThrCysLeuSerSerLeuLeuGlyGln
LeuSerGlyGlnValArgLeuLeuLeuGlyAlaLeuGlnSerLeuLeuGlyThrGlnLeu
ProProGlnGlyArgThrThrAlaHisLysAspProAsnAlaIlePheLeuSerPheGln
HisLeuLeuArgGlyLysValArgPheLeuMetLeuValGlyGlySerThrLeuCysVal
ArgGluPheGlyGlyAsnGlyGlyAsnMetAlaSerProAlaProProAlaCysAspLeu
ArgValLeuSerLysLeuLeuArgAspSerHisValLeuHisSerArgLeuSerGlnCys
ProGluValHisProLeuProThrPro (SEQ ID NO:229)

pMON28536

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaValAspPheSerLeuGlyGluTrpLysThrGlnMetGlu
GluThrLysAlaGluAspIleLeuGlyAlaValThrLeuLeuLeuGluGlyValMetAla
AlaArgGlyGlnLeuGlyProThrCysLeuSerSerLeuLeuGlyGlnLeuSerGlyGln
ValArgLeuLeuLeuGlyAlaLeuGlnSerLeuLeuGlyThrGlnLeuProProGlnGly
ArgThrThrAlaHisLysAspProAsnAlaIlePheLeuSerPheGlnHisLeuLeuArg
GlyLysValArgPheLeuMetLeuValGlyGlySerThrLeuCysValArgGluPheGly
GlyAsnGlyGlyAsnMetAlaSerProAlaProProAlaCysAspLeuArgValLeuSer
LysLeuLeuArgAspSerHisValLeuHisSerArgLeuSerGlnCysProGluValHis
ProLeuProThrProValLeuLeuPro (SEQ ID NO:230)

pMON28537

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAspPheSerLeuGlyGluTrpLysThrGlnMetGluGluThr
LysAlaGlnAspIleLeuGlyAlaValThrLeuLeuLeuGluGlyValMetAlaAlaArg
GlyGlnLeuGlyProThrCysLeuSerSerLeuLeuGlyGlnLeuSerGlyGlnValArg
LeuLeuLeuGlyAlaLeuGlnSerLeuLeuGlyThrGlnLeuProProGlnGlyArgThr
ThrAlaHisLysAspProAsnAlaIlePheLeuSerPheGlnHisLeuLeuArgGlyLys
ValArgPheLeuMetLeuValGlyGlySerThrLeuCysValArgGluPheGlyGlyAsn
GlyGlyAsnMetAlaSerProAlaProProAlaCysAspLeuArgValLeuSerLysLeu
LeuArgAspSerHisValLeuHisSerArgLeuSerGlnCysProGluValHisProLeu
ProThrProValLeuLeuProAlaVal (SEQ ID NO:231)

pMON28538

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPh&ArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyGluTrpLysThrGlnMetGluGluThrLysAlaGluAsp
IleLeuGlyAlaValThrLeuLeuLeuGluGlyValMetAlaAlaArgGlyGlnLeuGly
ProThrCysLeuSerSerLeuLeuGlyGlnLeuSerGlyGlnValArgLeuLeuLeuGly
AlaLeuGlnSerLeuLeuGlyThrGlnLeuProProGlnGlyArgThrThrAlaHisLys
AspProAsnAlaIlePheLeuSerPheGlnHisLeuLeuArgGlyLysValArgPheLeu
MetLeuValGlyGlySerThrLeuCysValArgGluPheGlyGlyAsnGlyGlyAsnMet
AlaSerProAlaProProAlaCysAspLeuArgValLeuSerLysLeuLeuArgAspSer
HisValLeuHisSerArgLeuSerGlnCysProGluValHisProLeuProThrProVal
LeuLeuProAlaValAspPheSerLeu (SEQ ID NO:232)

TABLE 3-continued

PROTEIN SEQUENCES pMON28539

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGluAlaGlnGluGlnGlnTyrValGluGlyGlyGlyGlySer
ProGlyGluProSerGlyProIleSerThrIleAsnProSerProProSerLysGluSer
HisLysSerProAsnMetGlyProThrCysLeuSerSerLeuLeuGlyGlnLeuSerGly
GlnValArgLeuLeuLeuGlyAlaLeuGlnSerLeuLeuGlyThrGlnLeuProProGln
GlyArgThrThrAlaHisLysAspProAsnAlaIlePheLeuSerPheGlnHisLeuLeu
ArgGlyLysValArgPheLeuMetLeuValGlyGlySerThrLeuCysValArgGluPhe
GlyGlyAsnGlyGlyAsnMetAlaSerProAlaProProAlaCysAspLeuArgValLeu
SerLysLeuLeuArgAspSerHisValLeuHisSerArgLeuSerGlnCysProGluVal
HisProLeuProThrProValLeuLeuProAlaValAspPheSerLeuGlyGluTrpLys
ThrGlnMetGluGluThrLysAlaGluAspIleLeuGlyAlaValThrLeuLeuLeuGlu
GlyValMetAlaAlaArgGlyGlnLeu (SEQ ID NO:233)

pMON28540

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyThrGlnLeuProProGlnGlyArgThrThrAlaHisLys
AspProAsnAlaIlePheLeuSerPheGlnHisLeuLeuArgGlyLysValArgPheLeu
MetLeuValGlyGlySerThrLeuCysValArgGluPheGlyGlyAsnGlyGlyAsnMet
AlaSerProAlaProProAlaCysAspLeuArgValLeuSerLysLeuLeuArgAspSer
HisValLeuHisSerArgLeuSerGlnCysProGluValHisProLeuProThrProVal
LeuLeuProAlaValAspPheSerLeuGlyGluTrpLysThrGlnMetGluGluThrLys
AlaGlnAspIleLeuGlyAlaValThrLeuLeuLeuGluGlyValMetAlaAlaArgGly
GlnLeuGlyProThrCysLeuSerSerLeuLeuGlyGlnLeuSerGlyGlnValArgLeu
LeuLeuGlyAlaLeuGlnSerLeuLeu (SEQ ID NO:234)

pMON28541

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetGlyArgThrThrAlaHisLysAspProAsnAlaIlePheLeu
SerPheGlnHisLeuLeuArgGlyLysValArgPheLeuMetLeuValGlyGlySerThr
LeuCysValArgGluPheGlyGlyAsnGlyGlyAsnMetAlaSerProAlaProProAla
CysAspLeuArgValLeuSerLysLeuLeuArgAspSerHisValLeuHisSerArgLeu
SerGlnCysProGluValHisProLeuProThrProValLeuLeuProAlaValAspPhe
SerLeuGlyGluTrpLysThrGlnMetGluGluThrLysAlaGlnAspIleLeuGlyAla
ValThrLeuLeuLeuGluGlyValMetAlaAlaArgGlyGlnLeuGlyProThrCysLeu
SerSerLeuLeuGlyGlnLeuSerGlyGlnValArgLeuLeuLeuGlyAlaLeuGlnSer
LeuLeuGlyThrGlnLeuProProGln (SEQ ID NO:235)

pMON28542

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaHisLysAspProAsnAlaIlePheLeuSerPheGlnHis
LeuLeuArgGlyLysValArgPheLeuMetLeuValGlyGlySerThrLeuCysValArg
GluPheGlyGlyAsnGlyGlyAsnMetAlaSerProAlaProProAlaCysAspLeuArg
ValLeuSerLysLeuLeuArgAspSerHisValLeuHisSerArgLeuSerGlnCysPro
GluValHisProLeuProThrProValLeuLeuProAlaValAspPheSerLeuGlyGlu
TrpLysThrGlnMetGluGluThrLysAlaGlnAspIleLeuGlyAlaValThrLeuLeu
LeuGluGlyValMetAlaAlaArgGlyGlnLeuGlyProThrCysLeuSerSerLeuLeu
GlyGlnLeuSerGlyGlnValArgLeuLeuLeuGlyAlaLeuGlnSerLeuLeuGlyThr
GlnLeuProProGlnGlyArgThrThr (SEQ ID NO:236)

TABLE 3-continued

PROTEIN SEQUENCES pMON28543

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGluAlaGlnGluGlnGlnTyrValGluGlyGlyGlyGlySer
ProGlyGluProSerGlyProIleSerThrIleAsnProSerProProSerLysGluSer
HisLysSerProAsnMetAspProAsnAlaIlePheLeuSerPheGlnHisLeuLeuArg
GlyLysValArgPheLeuMetLeuValGlyGlySerThrLeuCysValArgGluPheGly
GlyAsnGlyGlyAsnMetAlaSerProAlaProProAlaCysAspLeuArgValLeuSer
LysLeuLeuArgAspSerHisValLeuHisSerArgLeuSerGlnCysProGluValHis
ProLeuProThrProValLeuLeuProAlaValAspPheSerLeuGlyGluTrpLysThr
GlnMetGluGluThrLysAlaGlnAspIleLeuGlyAlaValThrLeuLeuLeuGluGly
ValMetAlaAlaArgGlyGlnLeuGlyProThrCysLeuSerSerLeuLeuGlyGlnLeu
SerGlyGlnValArgLeuLeuLeuGlyAlaLeuGlnSerLeuLeuGlyThrGlnLeuPro
ProGlnGlyArgThrThrAlaHisLys (SEQ ID NO: 237)

pMON28544

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAlaIlePheLeuSerPheGlnHisLeuLeuArgGlyLysVal
ArgPheLeuMetLeuValGlyGlySerThrLeuCysValArgGluPheGlyGlyAsnGly
GlyAsnMetAlaSerProAlaProProAlaCysAspLeuArgValLeuSerLysLeuLeu
ArgAspSerHisValLeuHisSerArgLeuSerGlnCysProGluValHisProLeuPro
ThrProValLeuLeuProAlaValAspPheSerLeuGlyGluTrpLysThrGlnMetGlu
GluThrLysAlaGlnAspIleLeuGlyAlaValThrLeuLeuLeuGluGlyValMetAla
AlaArgGlyGlnLeuGlyProThrCysLeuSerSerLeuLeuGlyGlnLeuSerGlyGln
ValArgLeuLeuLeuGlyAlaLeuGlnSerLeuLeuGlyThrGlnLeuProProGlnGly
ArgThrThrAlaHisLysAspProAsn (SEQ ID NO: 238)

pMON28545

AlaAsnCysSerIleMetIleAspGluIleIleHisHisLeuLysArgProProAlaPro
LeuLeuAspProAsnAsnLeuAsnAspGluAspValSerIleLeuMetAspArgAsnLeu
ArgLeuProAsnLeuGluSerPheValArgAlaValLysAsnLeuGluAsnAlaSerGly
IleGluAlaIleLeuArgAsnLeuGlnProCysLeuProSerAlaThrAlaAlaProSer
ArgHisProIleIleIleLysAlaGlyAspTrpGlnGluPheArgGluLysLeuThrPhe
TyrLeuValThrLeuGluGlnAlaGlnGluGlnGlnTyrValGluGlyGlyGlyGlySer
ProGlyGluProSerGlyProIleSerThrIleAsnProSerProProSerLysGluSer
HisLysSerProAsnMetAspProAsnAlaIlePheLeuSerPheGlnHisLeuLeuArg
GlyLysValArgPheLeuMetLeuValGlyGlySerThrLeuCysValArgGluPheGly
GlyAsnMetAlaSerProAlaProProAlaCysAspLeuArgValLeuSerLysLeuLeu
ArgAspSerHisValLeuHisSerArgLeuSerGlnCysProGluValHisProLeuPro
ThrProValLeuLeuProAlaValAspPheSerLeuGlyGluTrpLysThrGlnMetGlu
GluThrLysAlaGlnAspIleLeuGlyAlaValThrLeuLeuLeuGluGlyValMetAla
AlaArgGlyGlnLeuGlyProThrCysLeuSerSerLeuLeuGlyGlnLeuSerGlyGln
ValArgLeuLeuLeuGlyAlaLeuGlnSerLeuLeuGlyThrGlnGlyArgThrThrAla
HisLys (SEQ ID NO:239)

pMON32132

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg
PheLeuMetLeuValGlyGlySerThrLeuCysValArg (SEQ ID NO: 252)

PMON32133

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuLeuGlyGlnLeuSerGlyGlnValArgLeuLeu
LeuGlyAlaLeuGlnSerLeuLeuGlyThrGlnGlyArgThrThrAlaHisLysAspPro
AsnAlaIlePheLeuSerPheGlnHisLeuLeuArgGlyLysValArgPheLeuMetLeu

TABLE 3-continued

PROTEIN SEQUENCES

ValGlyGlySerThrLeuCysValArg (SEQ ID NO:253)

PMON32134

SerProAlaProProAlaCysAspLeuArgValLeuSerLysLeuLeuArgAspSerHis
ValLeuHisSerArgLeuSerGlnCysProGluValHisProLeuProThrProValLeu
LeuProAlaValAspPheSerLeuGlyGluTrpLysThrGlnMetGluGluThrLysAla
GlnAspIleLeuGlyAlaValThrLeuLeuLeuGluGlyValMetAlaAlaArgGlyGln
LeuGlyProThrCysLeuSerSerLeuGlyGlnLeuSerGlyGlnValArgLeuLeu
LeuGlyAlaLeuGlnSerLeuLeuGlyThrGlnLeuProProGlnGlyArgThrThrAla
HisLysAspProAsnAlaIlePheLeuSerPheGlnHisLeuLeuArgGlyLysValArg
PheLeuMetLeuValGlyGlySerThrLeuCysValArg (SEQ ID NO:254)

pmon16017.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Leu Gly
151 Pro Ala Ser Ser Leu Pro Gln Ser Phe Leu Leu Lys Ser Leu Glu
166 Gln Val Arg Lys Ile Gln Gly Asp Gly Ala Ala Leu Gln Glu Lys
181 Leu Cys Ala Thr Tyr Lys Leu Cys His Pro Glu Glu Leu Val Leu
196 Leu Gly His Ser Leu Gly Ile Pro Trp Ala Pro Leu Ser Ser Cys
211 Pro Ser Gln Ala Leu Gln Leu Ala Gly Cys Leu Ser Gln Leu His
226 Ser Gly Leu Phe Leu Tyr Gln Gly Leu Leu Gln Ala Leu Glu Gly
241 Ile Ser Pro Glu Leu Gly Pro Thr Leu Asp Thr Leu Gln Leu Asp
256 Val Ala Asp Phe Ala Thr Thr Ile Trp Gln Gln Met Glu Glu Leu
271 Gly Met Ala Pro Ala Leu Gln Pro Thr Gln Gly Ala Met Pro Ala
286 Phe Ala Ser Ala Phe Gln Arg Arg Ala Gly Gly Val Leu Val Ala
301 Ser His Leu Gln Ser Phe Leu Glu Val Ser Tyr Arg Val Leu Arg
316 His Leu Ala Gln Pro Asp Met Ala Thr Pro (SEQ ID NO:271)
``` pmon16018.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 31 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Leu Gly
151 Pro Ala Ser Ser Leu Pro Gln Ser Phe Leu Leu Lys Ser Leu Glu
176 Gln Val Arg Lys Ile Gln Gly Asp Gly Ala Ala Leu Gln Glu Lys
191 Leu Cys Ala Thr Tyr Lys Leu Cys His Pro Glu Glu Leu Val Leu
206 Leu Gly His Ser Leu Gly Ile Pro Trp Ala Pro Leu Ser Ser Cys
221 Pro Ser Gln Ala Leu Gln Leu Ala Gly Cys Leu Ser Gln Leu His
236 Ser Gly Leu Phe Leu Tyr Gln Gly Leu Leu Gln Ala Leu Glu Gly
251 Ile Ser Pro Glu Leu Gly Pro Thr Leu Asp Thr Leu Gln Leu Asp
266 Val Ala Asp Phe Ala Thr Thr Ile Trp Gln Gln Met Glu Glu Leu
281 Gly Met Ala Pro Ala Leu Gln Pro Thr Gln Gly Ala Met Pro Ala
296 Phe Ala Ser Ala Phe Gln Arg Arg Ala Gly Gly Val Leu Val Ala
311 Ser His Leu Gln Ser Phe Leu Glu Val Ser Tyr Arg Val Leu Arg
326 His Leu Ala Gln Pro Asp Met Ala Thr Pro (SEQ ID NO:272)
``` pmon16019.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Phe Leu
151 Leu Lys Ser Leu Glu Gln Val Arg Lys Ile Gln Gly Asp Gly Ala
166 Ala Leu Gln Glu Lys Leu Cys Ala Thr Tyr Lys Leu Cys His Pro
```

TABLE 3-continued

PROTEIN SEQUENCES

```
181 Glu Glu Leu Val Leu Leu Gly His Ser Leu Gly Ile Pro Trp Ala
196 Pro Leu Ser Ser Cys Pro Ser Gln Ala Leu Gln Leu Ala Gly Cys
211 Leu Ser Gln Leu His Ser Gly Leu Phe Leu Tyr Gln Gly Leu Leu
226 Gln Ala Leu Glu Gly Ile Ser Pro Glu Leu Gly Pro Thr Leu Asp
241 Thr Leu Gln Leu Asp Val Ala Asp Phe Ala Thr Thr Ile Trp Gln
256 Gln Met Glu Glu Leu Gly Met Ala Pro Ala Leu Gln Pro Thr Gln
271 Gly Ala Met Pro Ala Phe Ala Ser Ala Phe Gln Arg Arg Ala Gly
286 Gly Val Leu Val Ala Ser His Leu Gln Ser Phe Leu Glu Val Ser
301 Tyr Arg Val Leu Arg His Leu Ala Gln Pro Asp Met Ala Thr Pro
316 Leu Gly Pro Ala Ser Ser Leu Pro Gln Ser (SEQ ID NO:273)
``` pmon16020.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Glu Gln
151 Val Arg Lys Ile Gln Gly Asp Gly Ala Ala Leu Gln Glu Lys Leu
166 Cys Ala Thr Tyr Lys Leu Cys His Pro Glu Glu Leu Val Leu Leu
181 Gly His Ser Leu Gly Ile Pro Trp Ala Pro Leu Ser Ser Cys Pro
196 Ser Gln Ala Leu Gln Leu Ala Gly Cys Leu Ser Gln Leu His Ser
211 Gly Leu Phe Leu Tyr Gln Gly Leu Leu Gln Ala Leu Glu Gly Ile
226 Ser Pro Glu Leu Gly Pro Thr Leu Asp Thr Leu Gln Leu Asp Val
241 Ala Asp Phe Ala Thr Thr Ile Trp Gln Gln Met Glu Glu Leu Gly
256 Met Ala Pro Ala Leu Gln Pro Thr Gln Gly Ala Met Pro Ala Phe
271 Ala Ser Ala Phe Gln Arg Arg Ala Gly Gly Val Leu Val Ala Ser
286 His Leu Gln Ser Phe Leu Glu Val Ser Tyr Arg Val Leu Arg His
301 Leu Ala Gln Pro Asp Met Ala Thr Pro Leu Gly Pro Ala Ser Ser
316 Leu Pro Gln Ser Phe Leu Leu Lys Ser Leu (SEQ ID NO:274)
``` pmon16021.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Leu Leu
151 Gly His Ser Leu Gly Ile Pro Trp Ala Pro Leu Ser Ser Cys Pro
166 Ser Gln Ala Leu Gln Leu Ala Gly Cys Leu Ser Gln Leu His Ser
181 Gly Leu Phe Leu Tyr Gln Gly Leu Leu Gln Ala Leu Glu Gly Ile
196 Ser Pro Glu Leu Gly Pro Thr Leu Asp Thr Leu Gln Leu Asp Val
211 Ala Asp Phe Ala Thr Thr Ile Trp Gln Gln Met Glu Glu Leu Gly
226 Met Ala Pro Ala Leu Gln Pro Thr Gln Gly Ala Met Pro Ala Phe
241 Ala Ser Ala Phe Gln Arg Arg Ala Gly Gly Val Leu Val Ala Ser
256 His Leu Gln Ser Phe Leu Glu Val Ser Tyr Arg Val Leu Arg His
271 Leu Ala Gln Pro Asp Met Ala Thr Pro Leu Gly Pro Ala Ser Ser
286 Leu Pro Gln Ser Phe Leu Leu Lys Ser Leu Glu Gln Val Arg Lys
301 Ile Gln Gly Asp Gly Ala Ala Leu Gln Glu Lys Leu Cys Ala Thr
316 Tyr Lys Leu Cys His Pro Glu Glu Leu Val (SEQ ID NO:275)
``` pmon16022.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Pro Leu
151 Ser Ser Cys Pro Ser Gln Ala Leu Gln Leu Ala Gly Cys Leu Ser
166 Gln Leu His Ser Gly Leu Phe Leu Tyr Gln Gly Leu Leu Gln Ala
181 Leu Glu Gly Ile Ser Pro Glu Leu Gly Pro Thr Leu Asp Thr Leu
196 Gln Leu Asp Val Ala Asp Phe Ala Thr Thr Ile Trp Gln Gln Met
```

TABLE 3-continued

PROTEIN SEQUENCES

```
211 Glu Glu Leu Gly Met Ala Pro Ala Leu Gln Pro Thr Gln Gly Ala
226 Met Pro Ala Phe Ala Ser Ala Phe Gln Arg Arg Ala Gly Gly Val
241 Leu Val Ala Ser His Leu Gln Ser Phe Leu Glu Val Ser Tyr Arg
256 Val Leu Arg His Leu Ala Gln Pro Asp Met Ala Thr Pro Leu Gly
271 Pro Ala Ser Ser Leu Pro Gln Ser Phe Leu Leu Lys Ser Leu Glu
286 Gln Val Arg Lys Ile Gln Gly Asp Gly Ala Ala Leu Gln Glu Lys
301 Leu Cys Ala Thr Tyr Lys Leu Cys His Pro Glu Glu Leu Val Leu
316 Leu Gly His Ser Leu Gly Ile Pro Trp Ala (SEQ ID NO:276)
``` pmon16023.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Leu Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Gln Ala
151 Leu Gln Leu Ala Gly Cys Leu Ser Gln Leu His Ser Gly Leu Phe
166 Leu Tyr Gln Gly Leu Leu Gln Ala Leu Glu Gly Ile Ser Pro Glu
181 Leu Gly Pro Thr Leu Asp Thr Leu Gln Leu Asp Val Ala Asp Phe
196 Ala Thr Thr Ile Trp Gln Gln Met Glu Glu Leu Gly Met Ala Pro
211 Ala Leu Gln Pro Thr Gln Gly Ala Met Pro Ala Phe Ala Ser Ala
226 Phe Gln Arg Arg Ala Gly Gly Val Leu Val Ala Ser His Leu Gln
241 Ser Phe Leu Glu Val Ser Tyr Arg Val Leu Arg His Leu Ala Gln
256 Pro Asp Met Ala Thr Pro Leu Gly Pro Ala Ser Ser Leu Pro Gln
271 Ser Phe Leu Leu Lys Ser Leu Glu Gln Val Arg Lys Ile Gln Gly
286 Asp Gly Ala Ala Leu Gln Glu Lys Leu Cys Ala Thr Tyr Lys Leu
301 Cys His Pro Glu Glu Leu Val Leu Leu Gly His Ser Leu Gly Ile
316 Pro Trp Ala Pro Leu Ser Ser Cys Pro Ser (SEQ ID NO:277)
``` pmon16024.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Leu Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Leu Gln
151 Leu Ala Gly Cys Leu Ser Gln Leu His Ser Gly Leu Phe Leu Tyr
166 Gln Gly Leu Leu Gln Ala Leu Glu Gly Ile Ser Pro Glu Leu Gly
181 Pro Thr Leu Asp Thr Leu Gln Leu Asp Val Ala Asp Phe Ala Thr
196 Thr Ile Trp Gln Gln Met Glu Glu Leu Gly Met Ala Pro Ala Leu
211 Gln Pro Thr Gln Gly Ala Met Pro Ala Phe Ala Ser Ala Phe Gln
226 Arg Arg Ala Gly Gly Valleu Val Ala Ser His Leu Gln Ser Phe
241 Leu Glu Val Ser Tyr Arg Val Leu Arg His Leu Ala Gln Pro Asp
256 Met Ala Thr Pro Leu Gly Pro Ala Ser Ser Leu Pro Gln Ser Phe
271 Leu Leu Lys Ser Leu Glu Gln Val Arg Lys Ile Gln Gly Asp Gly
286 Ala Ala Leu Gln Glu Lys Leu Cys Ala Thr Tyr Lys Leu Cys His
301 Pro Glu Glu Leu Val Leu Leu Gly His Ser Leu Gly Ile Pro Trp
316 Ala Pro Leu Ser Ser Cys Pro Ser Gln Ala (SEQ ID NO:278)
``` pmon16025.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Leu Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Leu Ala
151 Gly Cys Leu Ser Gln Leu His Ser Gly Leu Phe Leu Tyr Gln Gly
166 Leu Leu Gln Ala Leu Glu Gly Ile Ser Pro Glu Leu Gly Pro Thr
181 Leu Asp Thr Leu Gln Leu Asp Val Ala Asp Phe Ala Thr Thr Ile
196 Trp Gln Gln Met Glu Glu Leu Gly Met Ala Pro Ala Leu Gln Pro
211 Thr Gly Ala Met Pro Ala Phe Ala Ser Ala Phe Gln Arg Arg
226 Ala Gly Gly Val Leu Val Ala Ser His Leu Gln Ser Phe Leu Glu
```

TABLE 3-continued

PROTEIN SEQUENCES

```
241 Val Ser Tyr Arg Val Leu Arg His Leu Ala Gln Pro Asp Met Ala
256 Thr Pro Leu Gly Pro Ala Ser Ser Leu Pro Gln Ser Phe Leu Leu
271 Lys Ser Leu Glu Gln Val Arg Lys Ile Gln Gly Asp Gly Ala Ala
286 Leu Gln Glu Lys Leu Cys Ala Thr Tyr Lys Leu Cys His Pro Glu
301 Glu Leu Val Leu Leu Gly His Ser Leu Gly Ile Pro Trp Ala Pro
316 Leu Ser Ser Cys Pro Ser Gln Ala Leu Gln (SEQ ID NO:279)
``` pmon16026.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Glu Leu
151 Gly Met Ala Pro Ala Leu Gln Pro Thr Gln Gly Ala Met Pro Ala
166 Phe Ala Ser Ala Phe Gln Arg Arg Ala Gly Gly Val Leu Val Ala
181 Ser His Leu Gln Ser Phe Leu Glu Val Ser Tyr Arg Val Leu Arg
196 His Leu Ala Gln Pro Asp Met Ala Thr Pro Leu Gly Pro Ala Ser
211 Ser Leu Pro Gln Ser Phe Leu Leu Lys Ser Leu Glu Gln Val Arg
226 Lys Ile Gln Gly Asp Gly Ala Ala Leu Gln Glu Lys Leu Cys Ala
241 Thr Tyr Lys Leu Cys His Pro Glu Glu Leu Val Leu Leu Gly His
256 Ser Leu Gly Ile Pro Trp Ala Pro Leu Ser Ser Cys Pro Ser Gln
271 Ala Leu Gln Leu Ala Gly Cys Leu Ser Gln Leu His Ser Gly Leu
286 Phe Leu Tyr Gln Gly Leu Leu Gln Ala Leu Glu Gly Ile Ser Pro
301 Glu Leu Gly Pro Thr Leu Asp Thr Leu Gln Leu Asp Val Ala Asp
316 Phe Ala Thr Thr Ile Trp Gln Gln Met Glu (SEQ ID NO:280)
``` pmon16027.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Gly Met
151 Ala Pro Ala Leu Gln Pro Thr Gln Gly Ala Met Pro Ala Phe Ala
166 Ser Ala Phe Gln Arg Arg Ala Gly Gly Val Leu Val Ala Ser His
181 Leu Gln Ser Phe Leu Glu Val Ser Tyr Arg Val Leu Arg His Leu
196 Ala Gln Pro Asp Met Ala Thr Pro Leu Gly Pro Ala Ser Ser Leu
211 Pro Gln Ser Phe Leu Leu Lys Ser Leu Glu Gln Val Arg Lys Ile
226 Gln Gly Asp Gly Ala Ala Leu Gln Glu Lys Leu Cys Ala Thr Tyr
241 Lys Leu Cys His Pro Glu Glu Leu Val Leu Leu Gly His Ser Leu
256 Gly Ile Pro Trp Ala Pro Leu Ser Ser Cys Pro Ser Gln Ala Leu
271 Gln Leu Ala Gly Cys Leu Ser Gln Leu His Ser Gly Leu Phe Leu
286 Tyr Gln Gly Leu Leu Gln Ala Leu Glu Gly Ile Ser Pro Glu Leu
301 Gly Pro Thr Leu Asp Thr Leu Gln Leu Asp Val Ala Asp Phe Ala
316 Thr Thr Ile Trp Gln Gln Met Glu Glu Leu (SEQ ID NO:281)
``` pmon16028.pep

```
  1 Met Ala Asn Cys Ser Ile Met Ile Asp Glu Ile Ile His His Leu
 16 Lys Arg Pro Pro Ala Pro Leu Leu Asp Pro Asn Asn Leu Asn Asp
 31 Glu Asp Val Ser Ile Leu Met Asp Arg Asn Leu Arg Leu Pro Asn
 46 Leu Glu Ser Phe Val Arg Ala Val Lys Asn Leu Glu Asn Ala Ser
 61 Gly Ile Glu Ala Ile Leu Arg Asn Leu Gln Pro Cys Leu Pro Ser
 76 Ala Thr Ala Ala Pro Ser Arg His Pro Ile Ile Ile Lys Ala Gly
 91 Asp Trp Gln Glu Phe Arg Glu Lys Leu Thr Phe Tyr Leu Val Thr
106 Leu Glu Gln Ala Gln Glu Gln Gln Tyr Val Glu Gly Gly Gly Gly
121 Ser Pro Gly Glu Pro Ser Gly Pro Ile Ser Thr Ile Asn Pro Ser
136 Pro Pro Ser Lys Glu Ser His Lys Ser Pro Asn Met Ala Ser Phe
151 Leu Glu Val Ser Tyr Arg Val Leu Arg His Leu Ala Gln Pro Asp
166 Met Ala Thr Pro Leu Gly Pro Ala Ser Ser Leu Pro Gln Ser Phe
181 Leu Leu Lys Ser Leu Glu Gln Val Arg Lys Ile Gln Gly Asp Gly
196 Ala Ala Leu Gln Glu Lys Leu Cys Ala Thr Tyr Lys Leu Cys His
211 Pro Glu Glu Leu Val Leu Leu Gly His Ser Leu Gly Ile Pro Trp
226 Ala Pro Leu Ser Ser Cys Pro Ser Gln Ala Leu Gln Leu Ala Gly
241 Cys Leu Ser Gln Leu His Ser Gly Leu Phe Leu Tyr Gln Gly Leu
256 Leu Gln Ala Leu Glu Gly Ile Ser Pro Glu Leu Gly Pro Thr Leu
271 Asp Thr Leu Gln Leu Asp Val Ala Asp Phe Ala Thr Thr Ile Trp
```

TABLE 3-continued

PROTEIN SEQUENCES

```
286 Gln Gln Met Glu Glu Leu Gly Met Ala Pro Ala Leu Gln Pro Thr
301 Gln Gly Ala Met Pro Ala Phe Ala Ser Ala Phe Gln Arg Arg Ala
316 Gly Gly Val Leu Val Ala Ser His Leu Gln (SEQ ID NO:282)

MetAlaGlyArgThrThrAlaHisLysAspProAsnAlaIlePheLeuSerPheGlnHis
LeuLeuArgGlyLysValArgPheLeuMetLeuValGlyGlySerThrLeuAlaValArg
GluPheGlyGlyAsnMetAlaSerProAlaProProAlaAlaAspLeuArgValLeuSer
LysLeuLeuArgAspSerHisValLeuHisSerArgLeuSerGlnCysProGluValHis
ProLeuProThrProValLeuLeuProAlaValAspPheSerLeuGlyGluTrpLysThr
GlnMetGluGluThrLysAlaGlnAspIleLeuGlyAlaValThrLeuLeuLeuGluGly
ValMetAlaAlaArgGlyGlnLeuGlyProThrCysLeuSerSerLeuLeuGlyGlnLeu
SerGlyGlnValArgLeuLeuLeuGlyAlaLeuGlnSerLeuLeuGlyThrGlnLeuPro
ProGln (SEQ ID NO:284);

MetAlaGlyProThrCysLeuSerSerLeuLeuGlyGlnLeuSerGlyGlnValArgLeu
LeuLeuGlyAlaLeuGlnSerLeuLeuGlyThrGlnLeuProProGlnGlyArgThrThr
AlaHisLysAspProAsnAlaIlePheLeuSerPheGlnHisLeuLeuArgGlyLysVal
ArgPheLeuMetLeuValGlyGlySerThrLeuAlaValArgGluPheGlyGlyAsnMet
AlaSerProAlaProProAlaAlaAspLeuArgValLeuSerLysLeuLeuArgAspSer
HisValLeuHisSerArgLeuSerGlnCysProGluValHisProLeuProThrProVal
LeuLeuProAlaValAspPheSerLeuGlyGluTrpLysThrGlnMetGluGluThrLys
AlaGlnAspIleLeuGlyAlaValThrLeuLeuLeuGluGlyValMetAlaAlaArgGly
GlnLeu (SEQ ID NO:285)
```

The following examples will illustrate the invention in greater detail although it will be understood that the invention is not limited to these specific examples.

EXAMPLE 1

Construction of Parental BHK Expression Vector

A. Removal of AflIII site from mammalian expression plasmid.

A new mammalian expression vector was constructed to accept NcoI-HindIII or AflIII-HindIII gene fragments in-frame and 3' to the hIL-3 receptor agonist pMON13146 (WO 94/12638) gene and a mouse IgG2b linker fragment. First, the single AflIII site was removed from pMON3934, which is a derivative of pMON3359. pMON3359 is a pUC18-based vector containing a mammalian expression cassette. The cassette includes a herpes simplex viral promoter IE110 (-800 to +120) followed by a modified human IL-3 signal peptide sequence and an SV40 late polyadenylation (poly-A) signal which has been subcloned into the pUC18 polylinker (See Hippenmeyer et al., Bio/Technology, 1993, pp.1037–1041). The modified human IL-3 signal sequence, which facilitates secretion of gene products outside of the cell, is flanked by a BamHI site on the 5' end and a unique NcoI site on the 3' end. A unique HindIII site is 3' to the NcoI site and 5' to the poly-A sequence. The DNA sequence encoding the signal peptide is shown below (restriction enzyme sites are indicated above). The ATG (methionine) codon within the NcoI site is in-frame with the initiator ATG of the signal peptide (underlined); BamHI NcoI 5'GGATCCACC ATGAGCCTGCCCGTCCTGCTCCTGCTCCAACTCCT-GGTCCGCCCCGCCATGG (SEQ ID NO:255)

The single AflIII site was removed from pMON3934 by digestion with AflIII followed by filling in the overhangs by addition of a DNA polymerase and nucleotides. The digested DNA fragment was purified via Magic PCR Clean up kit (Promega) and ligated with T4 DNA ligase. The ligation reaction was transformed into DH5α ™ and the cells were plated onto LB-agar plus ampicillin. Individual colonies were screened for the loss of the AflIII site by restriction analysis with AflIII and HindIII which results in a single fragment if the AflIII site was removed. The resulting plasmid was designated pMON30275.

B. Transfer of hIL-3 receptor agonist pMON13416/IgG2b cassette into pMON30275.

The NcoI-HindIII fragment (ca. 425 bp) from pMON30245 was ligated to the NcoI-HindIII fragment (ca. 3800 bp) of the pMON30275. pMON30245 (WO 94/12638) contains the gene coding for hIL-3 receptor agonist pMON13416 joined to a mouse IgG2b hinge fragment. Immediately 3' to the IgG2b hinge and 5' to the HindIII site is an AflIII site. Genes can be cloned into the AflIII-HindIII sites as NcoI-HindIII or AflIII-HindIII fragments in frame with the hIL-3 variant pMON13416/IgG2b hinge to create novel chimeras. The NcoI site and the AflIII site have compatible overhangs and will ligate but both recognition sites are lost. The plasmid, pMON30304 containing the DNA sequence of (SEQ ID NO:78), coding for hIL-3 variant pMON13416 joined with a mouse IgG2b hinge region, was a result of this cloning.

EXAMPLE 2

Construction of an intermediate plasmid containing one copy of the c-mpl ligand (1–153) gene of the dimer template In order to generate a plasmid DNA with the coding sequence of c-mpl (1–153) ligand followed by a unique EcoRI restriction site, the gene is isolated via reverse transcriptase/polymerase chain reaction (RT/PCR). Human fetal (lot #38130) and adult liver (lot #46018) A+RNA are obtained from Clontech (Palo Alto, Calif.) for source of c-mpl ligand messenger RNA (mRNA). The first strand cDNA reactions are carried out using a cDNA Cycle™ Kit obtained from Invitrogen (San Diego, Calif.). In the RT reaction, random primers and oligo dT primer are used to generate cDNA from a combination of human and fetal liver mRNA. For amplification of c-mpl ligand gene fragment encoding amino acids 1–153, the RT product serves as the template for PCR with a combination of the primers, Forward primer: c-mplNcoI (SEQ ID NO:13) and Reverse primer: Ecompl. The c-mplNcoI primer anneals to the c-mpl ligand gene (bases #279–311 based on c-mpl ligand sequence from Gene bank accession #L33410 or de Sauvage et al., Nature 369: 533–538 (1994)) and encodes a NcoI restriction enzyme site immediately 5' to the first codon (Ser+1) of c-mpl ligand. The NcoI restriction enzyme site codes for methionine and alanine codons prior to Ser+1 and includes codon degeneracy for the Ala codon and the first four codons (Ser, Pro, Ala, & Pro) of c-mpl ligand. The Ecompl primer anneals to bases #720–737 of c-mpl ligand and encodes an EcoRI site (GAATTC) in-frame with the c-mpl ligand gene immediately following Arg-153. The EcoRI site creates Glu and Phe codons following Arg-153. The ca. 480 bp PCR product was purified, digested with NcoI and EcoRI and ligated to the NcoI-EcoRI vector fragment of pMON3993 (ca. 4550 bp.). pMON3993 was a derivative of pMON3359 (described in Example 1). The human IL-3 signal peptide sequence, which had been subcloned as a BamHI fragment into the unique BamHI site between the IE110 promoter and poly-A signal, contains an NcoI site at its 3' end and is followed by a unique EcoRI site. The plasmid, pMON26458 containing the DNA sequence of (SEQ ID NO:79), coding for c-mpl ligand amino acids 1–153 (SEQ ID NO:161), was the result of this cloning.

EXAMPLE 3

Construction of the parental plasmids containing the second genes of the dimer templates For amplification of c-mpl ligand gene fragments starting at amino acid 1 (Ser) with a termination codon following amino acid 153 (Arg), the RT reaction from Example 2 serves as the template for PCR with a combination of the following primers; c-mplNcoI (SEQ ID NO:13) (forward primer) and c-mplHindIII (SEQ ID NO:15) (reverse primer). The c-mplNcoI (SEQ ID NO:13) primer is described in Example 2. The c-mplHindIII (SEQ ID NO:15) primer, which anneals to bases #716–737 of c-mpl ligand, adds both a termination codon and a HindIII restriction enzyme site immediately following the final codon, Arg$^{153}$.

Two types of PCR products are generated from the RT cDNA samples, one with a deletion of the codons for amino acids 112–115 and one without the deletion of these codons. The c-mpl ligand PCR products (ca. 480 bp) are digested with NcoI and HindIII restriction enzymes for transfer to a mammalian expression vector, pMON3934. pMON3934 is digested with NcoI and HindIII (ca. 3800 bp) and will accept the PCR products.

Plasmid, pMON32132 (SEQ ID NO:249), coding for c-mpl ligand amino acids 1–153 (SEQ ID NO:252) was a result of this cloning. Plasmid, pMON32134 (SEQ ID NO:250), coding for c-mpl ligand amino acids 1–153 (SEQ ID NO:253) was a result of this cloning. Plasmid, pMON32133 (SEQ ID NO:251), coding for c-mpl ligand amino acids 1–153 with a deletion of codons 112–115 (Δ112–115) (SEQ ID NO:254) was also a result of this cloning.

EXAMPLE 4

Generation of PCR dimer template 5L with a Δ112–115 deletion in the second c-mpl ligand gene A PCR template for generating novel forms of c-mpl ligand is constructed by ligating the 3.7 Kbp BstXI/EcoRI fragment of pMON26458 to the 1 Kbp NcoI/BstXI fragment from pMON32133 (containing a deletion of amino acids 112–115) along with the EcoRI/AflIII 5L synthetic oligonucleotide linker 5L-5' (SEQ ID NO:18) and 5L-3' (SEQ ID NO:19).

The EcoRI end of the linker will ligate to the EcoRI end of pMON26458. The AflIII end of the linker will ligate to the NcoI site of pMON32133, and neither restriction site will be retained upon ligation. The BstXI sites of pMON26458 and pMON32133 will ligate as well. Plasmid, pMON28548, is a result of the cloning and contains the DNA sequence of (SEQ ID NO:80) which encodes amino acids 1–153 c-mpl ligand fused via a GluPheGlyGlyAsnMetAla (SEQ ID NO:222) linker to amino acids 1–153 c-mpl ligand that contains a deletion of amino acids 112–115 (SEQ ID NO:162).

EXAMPLE 5

Generation of PCR Dimer Template 4L

A PCR template for generating novel forms of c-mpl ligand is constructed by ligating the 3.7 Kbp BstXI/EcoRI fragment of pMON26458 to the 1 Kbp NcoI/BstXI fragment from pMON32132 along with the EcoRI/AflIII 4L synthetic oligonucleotide linker 4L-5' (SEQ ID NO:16) and 4L-3' (SEQ ID NO:17).

The EcoRI end of the linker will ligate to the EcoRI end of pMON26458. The AflIII end of the linker will ligate to the NcoI site of pMON32132, and neither restriction site will be retained upon ligation. The BstXI sites of pMON26458 and pMON32132 will ligate as well. The plasmid, pMON28500, is a result of the cloning and contains the DNA sequence of (SEQ ID NO:82) which encodes amino acids 1–153 c-mpl ligand fused via a GluPheGlyAsnMetAla (SEQ ID NO:223) linker (4L) to amino acids 1–153 c-mpl ligand (SEQ ID NO:163).

EXAMPLE 6

Generation of PCR Dimer Template 5L

A PCR template for generating novel forms of c-mpl ligand is constructed by ligating the 3.7 Kbp BstXI/EcoRI fragment of pMON26458 to the 1 Kbp NcoI/BstXI fragment from pMON32132 along with the EcoRI/AflIII 5L synthetic oligonucleotide linker 5L-5' (SEQ ID NO:18) and 5L-3' (SEQ ID NO:19).

The EcoRI end of the linker will ligate to the EcoRI end of pMON26458. The AflIII end of the linker will ligate to the NcoI site of pMON32132, and neither restriction site will be retained upon ligation. The BstXI sites of pMON26458 and pMON32132 will ligate as well. Plasmid, pMON28501 is a result of the cloning and contains the DNA sequence of (SEQ ID NO: 82) which encodes amino acids 1–153 c-mpl ligand fused via a GluPheGlyGlyAsnMetAla (SEQ ID NO:222) linker (5L) to amino acids 1–153 c-mpl ligand (SEQ ID NO:164).

EXAMPLE 7

Generation of PCR Dimer Templates 8L

A PCR template for generating novel forms of c-mpl ligand is constructed by ligating the 3.7 Kbp BstXI/EcoRI fragment of pMON26458 to the 1 Kbp NcoI/BstXI fragment from pMON32134 along with the EcoRI/AflIII 8L synthetic oligonucleotide linker 8L-5' (SEQ ID NO:20) and 8L-3' (SEQ ID NO:21).

The EcoRI end of the linker will ligate to the EcoRI end of pMON26458. The AflIII end of the linker will ligate to the NcoI site of pMON32134, and neither restriction site will be retained upon ligation. The BstXI sites of pMON26458 and pMON32134 will ligate as well. Plasmid, pMON28502 is a result of the cloning which contains the DNA sequence of (SEQ ID NO:83) and encodes amino acids 1–153 c-mpl ligand fused via a GluPheGlyGlyAsnGlyGlyAsnMetAla (SEQ ID NO:224) linker (8L) to amino acids 1–153 c-mpl ligand (SEQ ID NO:165).

EXAMPLES 8–44

Generation of novel c-mpl ligand genes with new N-terminus and C-terminus

A. PCR generation of genes encoding novel c-mpl ligand receptor agonists.

Genes encoding novel c-mpl ligand receptor agonists were generated using Method III (Horlick et al., *Prot. Eng.* 5:427–433, 1992). The PCR reactions were carried out using dimer templates, pMONs 28500, 28501, 28502 or 28548 and one of the sets of synthetic primer sets below (The first number refers to the position of the first amino acid in the original sequence. For example, the 31-5' and 31-3' refers to the 5' and 3' oligo primers, receptively, for the sequence beginning at the codon corresponding to residue 31 of the original sequence.).

B. Subcloning of novel c-mpl receptor agonist gene products into mammalian expression vector for generation of chimeras.

The c-mpl receptor agonist gene PCR products were digested with NcoI and HindIII or AflIII and HindIII restriction enzymes (ca. 470 bp) for transfer to a mammalian expression vector. The expression vector, pMON30304, was digested with NcoI and HindIII (ca. 4200 bp) and accepts the PCR products as NcoI-HindIII or AflIII-HindIII fragments. The restriction digest of the PCR product and the resulting plasmids are shown in Table 4.

TABLE 4

| Example # | PCR template | PCR Product Primer set | PCR Product Restriction Digest | Linker | Resulting Plasmid pMON | Breakpoint in c-mpl ligand |
|---|---|---|---|---|---|---|
| Example 8 | pMON28501 | 31 | NcoI/HindIII | 5L | 28505 | 30–31 |
| Example 9 | pMON28501 | 35 | AflIII/HindIII | 5L | 28506 | 34–35 |
| Example 10 | pMON28501 | 39 | NcoI/HindIII | 5L | 28507 | 38–39 |
| Example 11 | pMON28501 | 43 | NcoI/HindIII | 5L | 28508 | 42–43 |
| Example 12 | pMON28501 | 45 | NcoI/HindIII | 5L | 28509 | 44–45 |
| Example 13 | pMON28501 | 49 | NcoI/HindIII | 5L | 28510 | 48–49 |
| Example 14 | pMON28501 | 82 | NcoI/HindIII | 5L | 28511 | 81–82 |
| Example 15 | PMON28501 | 109 | NcoI/HindIII | 5L | 28512 | 108–109 |
| Example 16 | PMON28501 | 116 | NcoI/HindIII | 5L | 28513 | 115–116 |
| Example 17 | pMON28501 | 120 | NcoI/HindIII | 5L | 28514 | 119–120 |
| Example 18 | pMON28501 | 123 | NcoI/HindIII | 5L | 28515 | 122–123 |
| Example 19 | PMON28501 | 126 | NcoI/HindIII | 5L | 28516 | 125–126 |
| Example 20 | pMON28500 | 31 | NcoI/HindIII | 4L | 28519 | 30–31 |
| Example 21 | pMON28500 | 35 | AflIII/HindIII | 4L | 28520 | 34–35 |
| Example 22 | pMON28500 | 39 | NcoI/HindIII | 4L | 28521 | 38–39 |
| Example 23 | pMON28500 | 43 | NcoI/HindIII | 4L | 28522 | 42–43 |
| Example 24 | pMON28500 | 45 | NcoI/HindIII | 4L | 28523 | 44–45 |
| Example 25 | pMON28500 | 49 | NcoI/HindIII | 4L | 28524 | 48–49 |
| Example 26 | PMON28500 | 82 | NcoI/HindIII | 4L | 28525 | 81–82 |
| Example 27 | pMON28500 | 109 | NcoI/HindIII | 4L | 28526 | 108–109 |
| Example 28 | pMON28500 | 116 | NcoI/HindIII | 4L | 28527 | 115–116 |
| Example 29 | pMON28500 | 120 | NcoI/HindIII | 4L | 28528 | 119–120 |
| Example 30 | pMON28500 | 123 | NcoI/HindIII | 4L | 28529 | 122–123 |
| Example 31 | pMON28500 | 126 | NcoI/HindIII | 4L | 28530 | 125–126 |
| Example 32 | pMON28502 | 31 | NcoIIHindIII | 8L | 28533 | 30–31 |
| Example 33 | pMON28502 | 35 | AflIII/HindIII | 8L | 28534 | 34–35 |
| Example 34 | pMON28502 | 39 | NcoI/HindIII | 8L | 28535 | 38–39 |
| Example 35 | pMON28502 | 43 | NcoI/HindIII | 8L | 28536 | 42–43 |
| Example 36 | pMON28502 | 45 | NcoI/HindIII | 8L | 28537 | 44–45 |
| Example 37 | pMON28502 | 49 | NcoI/HindIII | 8L | 28538 | 48–49 |
| Example 38 | pMON28502 | 82 | NcoI/HindIII | 8L | 28539 | 81–82 |
| Example 39 | pMON28502 | 109 | NcoI/HindIII | 8L | 28540 | 108–109 |
| Example 40 | pMON28502 | 116 | NcoI/HindIII | 8L | 28541 | 115–116 |
| EXAMPLE 41 | pMON28502 | 120 | NcoI/HindIII | 8L | 28542 | 119–120 |
| Example 42 | pMON28502 | 123 | NcoI/HindIII | 8L | 28543 | 122–123 |
| Example 43 | pMON28502 | 126 | NcoI/HindIII | 8L | 28544 | 125–126 |
| Example 44 | pMON28548 | 123 | NcoI/HindIII | 5L | 28545 | 122–123 |

31-5' (SEQ ID NO:22) and 31-3' (SEQ ID NO:23), 35-5' (SEQ ID NO:24) and 35-3' (SEQ ID NO:25), 39-5' (SEQ ID NO:26) and 39-3' (SEQ ID NO:27), 43-5' (SEQ ID NO:28) and 43-3' (SEQ ID NO:29), 45-5' (SEQ ID NO:30) and 45-3' (SEQ ID NO:31), 49-5' (SEQ ID NO:32) and 49-3' (SEQ ID NO:33), 82-5' (SEQ ID NO:34) and 82-3' (SEQ ID NO:35), 109-5' (SEQ ID NO:36) and 109-3' (SEQ ID NO:37), 115-5' (SEQ ID NO:38) and 115-3' (SEQ ID NO:39), 120-5' (SEQ ID NO:40) and 120-3' (SEQ ID NO:41), 123-5' (SEQ ID NO:42) and 123-3' (SEQ ID NO:43), 126-5' (SEQ ID NO:44) and 126-3' (SEQ ID NO:45).

The templates and oligonucleotide sets used in the PCR reactions are shown in Table 4. The products that were generated were about 480 bp and were purified via Magic PCR Clean up kits (Promega).

EXAMPLE 45

Construction of pMON15960

Construction of pMON15960, an intermediate plasmid used for constructing plasmids containing DNA sequences encoding G-CSF Ser$^{17}$ with a new N-terminus and C-terminus. Plasmid pACYC177 (Chang, A. C. Y. and Cohen, S. N. *J. Bacteriol.* 134:1141–1156, 1978) DNA was digested with restriction enzymes HindIII and BamHI, resulting in a 3092 base pair HindIII, BamHI fragment. Plasmid, pMON13037 (WO 95/21254), DNA was digested with BglII and FspI, resulting in a 616 base pair BglII, FspI fragment. A second sample of plasmid, pMON13037, DNA was digested with NcoI and HindIII, resulting in a 556 base pair NcoI, HindIII fragment. The synthetic DNA oligonucleotides 1GGGSfor (SEQ ID NO:76) and 1GGGSrev (SEQ ID NO:77) were annealed to each other, and then digested with AflIII and FspI, resulting in a 21 base pair AflIII, FspI fragment. The restriction fragments were ligated, and the ligation reaction mixture was used to transform *E. coli* K-12 strain JM101. Transformant bacteria were selected on ampicillin-containing plates. Plasmid DNA was isolated and analyzed by restriction analysis to confirm the correct insert.

EXAMPLE 46

Construction of pMON15981

Construction of pMON15981, a plasmid containing DNA sequences encoding a multi-functional hematopoietic receptor agonist. Plasmid, pMON15960, DNA was digested with restriction enzyme SmaI and used as template in a PCR reaction using synthetic DNA oligonucleotides 38 stop (SEQ ID NO:65) and 39 start (SEQ ID NO:64) as primers, resulting in the amplification of a DNA fragment of 576 base pairs. The amplified fragment was digested with restriction enzymes HindIII and NcoI, resulting in a HindIII, NcoI fragment of 558 base pairs. Plasmid, pMON13181, DNA was digested with HindIII and AflIII, resulting in a HindIII, AflIII fragment of 4068 base pairs. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON15981, contains the DNA sequence of (SEQ ID NO:155) which encodes the following amino acid sequence:

```
MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaTyrLysLeuCysHisProGluGluLeuValLeuLeu
GlyHisSerLeuGlyIleProTrpAlaProLeuSerSerCysProSerGlnAlaLeuGln
LeuAlaGlyCysLeuSerGlnLeuHisSerGlyLeuPheLeuTyrGlnGlyLeuLeuGln
AlaLeuGluGlyIleSerProGluLeuGlyProThrLeuAspThrLeuGlnLeuAspVal
AlaAspPheAlaThrThrIleTrpGlnGlnMetGluGluLeuGlyMetAlaProAlaLeu
GlnProThrGlnGlyAlaMetProAlaPheAlaSerAlaPheGlnArgArgAlaGlyGly
ValLeuValAlaSerHisLeuGlnSerPheLeuGluValSerTyrArgValLeuArgHis
LeuAlaGlnProGlyGlyGlySerAspMetAlaThrProLeuGlyProAlaSerSerLeu
ProGlnSerPheLeuLeuLysSerLeuGluGlnValArgLysIleGlnGlyAspGlyAla
AlaLeuGlnGluLysLeuCysAlaThr      (SEQ ID NO:195)
```

EXAMPLE 47

Construction of pMON15982

Construction of pMON15982, a plasmid containing DNA sequences encoding a multi-functional hematopoietic receptor agonist. Plasmid, pMON15960, DNA was digested with restriction enzyme SmaI and used as template in a PCR reaction using synthetic DNA oligonucleotides 96 stop (SEQ ID NO:67) and 97 start (SEQ ID NO:66) as primers, resulting in the amplification of a DNA fragment of 576 base pairs. The amplified fragment was digested with restriction enzymes HindIII and NcoI, resulting in a HindIII, NcoI fragment of 558 base pairs. Plasmid, pMON13181, DNA was digested with HindIII and AflIII, resulting in a HindIII, AflIII fragment of 4068 base pairs. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON15982, contains the DNA sequence of (SEQ ID NO:157) which encodes the following amino acid sequence:

```
MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaProGluLeuGlyProThrLeuAspThrLeuGlnLeu
```

-continued
```
AspValAlaAspPheAlaThrThrIleTrpGlnGlnMetGluGluLeuGlyMetAlaPro
AlaLeuGlnProThrGlnGlyAlaMetProAlaPheAlaSerAlaPheGlnArgArgAla
GlyGlyValLeuValAlaSerHisLeuGlnSerPheLeuGluValSerTyrArgValLeu
ArgHisLeuAlaGlnProGlyGlyGlySerAspMetAlaThrProLeuGlyProAlaSer
SerLeuProGlnSerPheLeuLeuLysSerLeuGluGlnValArgLysIleGlnGlyAsp
GlyAlaAlaLeuGlnGluLysLeuCysAlaThrTyrLysLeuCysHisProGluGluLeu
ValLeuLeuGlyHisSerLeuGlyIleProTrpAlaProLeuSerSerCysProSerGln
AlaLeuGlnLeuAlaGlyCysLeuSerGlnLeuHisSerGlyLeuPheLeuTyrGlnGly
LeuLeuGlnAlaLeuGluGlyIleSer    (SEQ ID NO:196)
```

EXAMPLE 48

Construction of pMON15965

Construction of pMON15965, a plasmid containing DNA sequences encoding a multi-functional hematopoietic receptor agonist. Plasmid, pMON15960, DNA was digested with restriction enzyme SmaI and used as template in a PCR reaction using synthetic DNA oligonucleotides 142 stop (SEQ ID NO:73) and 141 start (SEQ ID NO:72) as primers, resulting in the amplification of a DNA fragment of 576 base pairs. The amplified fragment was digested with restriction enzymes HindIII and NcoI, resulting in a HindIII, NcoI fragment of 558 base pairs. Plasmid, pMON13181, DNA was digested with HindIII and AflIII, resulting in a HindIII, AflIII fragment of 4068 base pairs. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON15965, contains the DNA sequence of (SEQ ID NO:157) which encodes the following amino acid sequence:

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaSerAlaPheGlnArgArgAlaGlyGlyValLeuVal
AlaSerHisLeuGlnSerPheLeuGluValSerTyrArgValLeuArgHisLeuAlaGln
ProGlyGlyGlySerAspMetAlaThrProLeuGlyProAlaSerSerLeuProGlnSer
PheLeuLeuLysSerLeuGluGlnValArgLysIleGlnGlyAspGlyAlaAlaLeuGln
GluLysLeuCysAlaThrTyrLysLeuCysHisProGluGluLeuValLeuLeuGlyHis
SerLeuGlyIleProTrpAlaProLeuSerSerCysProSerGluAlaLeuGlnLeuAla
GlyCysLeuSerGlnLeuHisSerGlyLeuPheLeuTyrGlnGlyLeuLeuGlnAlaLeu
GluGlyIleSerProGluLeuGlyProThrLeuAspThrLeuGlnLeuAspValAlaAsp
PheAlaThrThrIleTrpGlnGlnMetGluGluLeuGlyMetAlaProAlaLeuGlnPro
ThrGlnGlyAlaMetProAlaPheAla (SEQ ID NO:196)

EXAMPLE 49

Construction of pMON15966

Construction of pMON15966, a plasmid containing DNA sequences encoding a multi-functional hematopoietic receptor agonist. Plasmid, pMON15960, DNA was digested with restriction enzyme SmaI and used as template in a PCR reaction using synthetic DNA oligonucleotides 126 stop (SEQ ID NO:68) and 125 start (SEQ ID NO:69) as primers, resulting in the amplification of a DNA fragment of 576 base pairs. The amplified fragment was digested with restriction enzymes HindIII and NcoI, resulting in a HindIII, NcoI fragment of 558 base pairs. Plasmid, pMON13181, DNA was digested with HindIII and AflIII, resulting in a HindIII, AflIII fragment of 4068 base pairs. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON15966, contains the DNA sequence of (SEQ ID NO:158) which encodes the following amino acid sequence:

```
MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaMetAlaProAlaLeuGlnProThrGlnGlyAlaMet
ProAlaPheAlaSerAlaPheGlnArgArgAlaGlyGlyValLeuValAlaSerHisLeu
GlnSerPheLeuGluValSerTyrArgValLeuArgHisLeuAlaGlnProGlyGlyGly
SerAspMetAlaThrProLeuGlyProAlaSerSerLeuProGlnSerPheLeuLeuLys
SerLeuGluGlnValArgLysIleGlnGlyAspGlyAlaAlaLeuGlnGluLysLeuCys
AlaThrTyrLysLeuCysHisProGluGluLeuValLeuLeuGlyHisSerLeuGlyIle
ProTrpAlaProLeuSerSerCysProSerGlnAlaLeuGlnLeuAlaGlyCysLeuSer
GlnLeuHisSerGlyLeuPheLeuTyrGlnGlyLeuLeuGlnAlaLeuGluGlyIleSer
ProGluLeuGlyProThrLeuAspThrLeuGlnLeuAspValAlaAspPheAlaThrThr
IleTrpGlnGlnMetGluGluLeuGly (SEQ ID NO:197)
```

EXAMPLE 50

Construction of pMON15967

Construction of pMON15967, a plasmid containing DNA sequences encoding a multi-functional hematopoietic receptor agonist. Plasmid, pMON15960, DNA was digested with restriction enzyme SmaI and used as template in a PCR reaction using synthetic DNA oligonucleotides 132 stop (SEQ ID NO:71) and 133 start (SEQ ID NO:70) as primers, resulting in the amplification of a DNA fragment of 576 base pairs. The amplified fragment was digested with restriction enzymes HindIII and NcoI, resulting in a HindIII, NcoI fragment of 558 base pairs. Plasmid, pMON13181, DNA was digested with HindIII and AflIII, resulting in a HindIII, AflIII fragment of 4068 base pairs. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON15967, contains the DNA sequence of (SEQ ID NO: 159) which encodes the following amino acid sequence:

MetAlaAsnCysSerIleMetIleAspGluIleIleHisHisLeuLysArgProProAla
ProLeuLeuAspProAsnAsnLeuAsnAspGluAspValSerIleLeuMetAspArgAsn
LeuArgLeuProAsnLeuGluSerPheValArgAlaValLysAsnLeuGluAsnAlaSer
GlyIleGluAlaIleLeuArgAsnLeuGlnProCysLeuProSerAlaThrAlaAlaPro
SerArgHisProIleIleIleLysAlaGlyAspTrpGlnGluPheArgGluLysLeuThr
PheTyrLeuValThrLeuGluGlnAlaGlnGluGlnGlnTyrValGluGlyGlyGlyGly
SerProGlyGluProSerGlyProIleSerThrIleAsnProSerProProSerLysGlu
SerHisLysSerProAsnMetAlaThrGlnGlyAlaMetProAlaPheAlaSerAlaPhe
GlnArgArgAlaGlyGlyValLeuValAlaSerHisLeuGlnSerPheLeuGluValSer
TyrArgValLeuArgHisLeuAlaGlnProGlyGlyGlySerAspMetAlaThrProLeu
GlyProAlaSerSerLeuProGlnSerPheLeuLeuLysSerLeuGluGlnValArgLys
IleGlnGlyAspGlyAlaAlaLeuGlnGluLysLeuCysAlaThrTyrLysLeuCysHis
ProGluGluLeuValLeuLeuGlyHisSerLeuGlyIleProTrpAlaProLeuSerSer
CysProSerGlnAlaLeuGlnLeuAlaGlyCysLeuSerGlnLeuHisSerGlyLeuPhe
LeuTyrGlnGlyLeuLeuGlnAlaLeuGluGlyIleSerProGluLeuGlyProThrLeu
AspThrLeuGlnLeuAspValAlaAspPheAlaThrThrIleTrpGlnGlnMetGluGlu
LeuGlyMetAlaProAlaLeuGlnPro SEQ ID NO:198

EXAMPLE 51

Construction of pMON13180, an intermediate plasmid used for constructing Dlasmids that contain DNA sequence encoding multi-functional hematopoietic receptor agonists.

Plasmid, pMON13046 (WO 95/21254), DNA was digested with restriction endonucleases XmaI and SnaBI, resulting in a 4018 base pair vector fragment. The 4018 base pair XmaI-SnaBI fragment was purified using a Magic DNA Clean-up System kit (Promega, Madison, Wis.) in which the 25 base pair XmaI-SnaBI insert fragment is not retained. The complimentary pair of synthetic oligonucleotides, glyxal (SEQ ID NO:74) and glyxa2 (SEQ ID NO:75), were designed to remove sequence encoding a factor Xa cleavage site. When properly assembled these oligonucleotides also result in XmaI and SnaBI ends. The primers, Glyxa1 and glyxa2, were annealed in annealing buffer (20 mM Tris-HCl pH7.5, 10 mM $MgCl_2$, 50 mM NaCl) by heating at 70° C. for ten minutes and allowed to slow cool. The 4018 base pair XmaI-SnaBI fragment from pMON13046 was ligated with the assembled oligonucleotides using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated from the transformants and analyzed using a PCR based assay. Plasmid DNA from selected transformants was sequenced to confirm the correct insertion of the oligonucleotides. The resulting plasmid was designated pMON13180 and contains the DNA sequence of (SEQ ID NO:258).

EXAMPLE 52

Construction of pMON13181. an intermediate plasmid used for constructing plasmids that contain DNA sequences encoding multi-functional hematopoietic receptor agonists.

Plasmid, pMON13047 (WO 95/21254), DNA was digested with restriction endonucleases XmaI and SnaBI, resulting in a 4063 base pair vector fragment. The 4063 base pair XmaI-SnaBI fragment was purified using a Magic DNA Clean-up System kit (Promega, Madison, Wis.) in which the 25 base pair XmaI-SnaBI insert fragment is not retained. The complimentary pair of synthetic oligonucleotides, glyxal (SEQ ID NO:74) and glyxa2 (SEQ ID NO:75), were designed to remove sequence encoding the factor Xa cleavage site. When properly assembled these oligonucleotides also result in XmaI and SnaBI ends. Glyxal and glyxa2 were annealed in annealing buffer by heating at 70° C. for ten minutes and allowed to slow cool. The 4063 base pair XmaI-SnaBI fragment from pMON13047 was ligated with the assembled oligonucleotides using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated from the transformants and analyzed using a PCR based assay. Plasmid DNA from selected transformants was sequenced to confirm the correct insertion of the oligonucleotides. The resulting plasmid was designated pMON13181 and contains the DNA sequence of (SEQ ID NO:257).

EXAMPLE 53

Construction of pMON13182

The new N-terminus/C-terminus gene in pMON13182 was created using Method I as described in Materials and Methods. Fragment Start was created and amplified from G-CSF Ser[17] sequence in pMON13037 using the primer set, 39 start (SEQ ID NO:64) and L-11 start (SEQ ID NO:60). Fragment Stop was created and amplified from G-CSF Ser[17] sequence in pMON13037 using the primer set, 38 stop (SEQ ID NO:65) and L-11 stop (SEQ ID NO:61). The full-length new N terminus/C-terminus G-CSF Ser[17] gene was created and amplified from the annealed Fragments Start and Stop using primers 39 start and 38 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13182.

*E. coli* strain JM101 was transformed with pMON13182 for protein expression and protein isolation from inclusion bodies.

The plasmid, pMON13182, contains the DNA sequence of (SEQ ID NO:94) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr (SEQ ID NO:166)
```

EXAMPLE 54

Construction of pMON13183

The new N-terminus/C-terminus gene in pMON13183 was created using Method I as described in Materials and Methods. "Fragment Start" was created and amplified from G-CSF Ser[17] sequence in pMON13037 using the primer set, 39 start (SEQ ID NO:64) and L-11 start (SEQ ID NO:60). Fragment Stop was created and amplified from G-CSF Ser17 sequence in pMON13037 using the primer set, 38 stop (SEQ ID NO:65) and L-11 stop (SEQ ID NO:61). The full-length new N terminus/C-terminus G-CSF Ser$^{17}$ gene was created and amplified from the annealed Fragments Start and Stop using 39 start and 38 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13183.

E. coli strain JM101 was transformed with pMON13183 for protein expression and protein isolation from inclusion bodies.

The plasmid, pMON13183, contains the DNA sequence of (SEQ ID NO:95) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr    (SEQ ID NO:167)
```

EXAMPLE 55

Construction of pMON13184

The new N-terminus/C-terminus gene in pMON13184 was created using Method I as described in Materials and Methods. Fragment Start was created and amplified from G-CSF Ser$^{17}$ sequence in pMON13037 using the primer set, 97 start (SEQ ID NO:66) and L-11 start (SEQ ID NO:60). Fragment Stop was created and amplified from G-CSF Ser$^{17}$ sequence in pMON13037 using the primer set, 96 stop (SEQ ID NO:67) and L-11 stop (SEQ ID NO:61). The full-length new N terminus/C-terminus G-CSF Ser$^{17}$ gene was created and amplified from the annealed Fragments Start and Stop using 97 start and 96 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13184.

E. coli strain JM101 was transformed with pMON13184 for protein expression and protein isolation from inclusion bodies.

The plasmid, pMON13184, contains the DNA sequence of (SEQ ID NO:96) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Ser Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser (SEQ ID NO:168)
```

EXAMPLE 56

Construction of pMON13185

The new N-terminus/C-terminus gene in pMON13185 was created using Method I as described in Materials and Methods. Fragment Start was created and amplified from G-CSF Ser[17] sequence in pMON13037 using the primer set, 97 start (SEQ ID NO:66) and L-11 start (SEQ ID NO:60). Fragment Stop was created and amplified from G-CSF Ser[17] sequence in pMON13037 using the primer set, 96 stop (SEQ ID NO:67 and L-11 stop (SEQ ID NO:61). The full-length new N terminus/C-terminus G-CSF Ser[17] gene was created and amplified from the annealed Fragments Start and Stop using 97 start and 96 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13185.

E. coli strain JM101 was transformed with pMON13185 for protein expression and protein isolation from inclusion bodies.

The plasmid, pMON13185, contains the DNA sequence of (SEQ ID NO:67) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Pne Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser (SEQ ID NO:169)
```

EXAMPLE 57

Construction of pMON13186

The new N-terminus/C-terminus gene in pMON13186 was created using Method I as described in Materials and Methods. Fragment Start was created and amplified from G-CSF Ser$^{17}$ sequence in pMON13037 using the primer set, 126 start (SEQ ID NO:68) and L-11 start (SEQ ID NO:60). Fragment Stop was created and amplified from G-CSF Ser$^{17}$ sequence in pMON13037 using the primer set, 125 stop (SEQ ID NO:69) and L-11 stop (SEQ ID NO:61). The full-length new N terminus/C-terminus G-CSF Ser$^{17}$ gene was created and amplified from the annealed Fragments Start and Stop using 126 start and 125 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13186.

*E. coli* strain JM101 was transformed with pMON13186 for protein expression and protein isolation from inclusion bodies.

The plasmid, pMON13186, contains the DNA sequence of (SEQ ID NO:98) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Ser Gly Gly Ser Gly Gly Ser Gln Ser Phe Leu Leu Lys Ser Leu
Glu Gln Val Arg Lys Ile Gln Gly Asp Gly Ala Ala Leu Gln Glu
Lys Leu Cys Ala Thr Tyr Lys Leu Cys His Pro Glu Glu Leu Val
Leu Leu Gly His Ser Leu Gly Ile Pro Trp Ala Pro Leu Ser Ser
Cys Pro Ser Gln Ala Leu Gln Leu Ala Gly Cys Leu Ser Gln Leu
His Ser Gly Leu Phe Leu Tyr Gln Gly Leu Leu Gln Ala Leu Glu
Gly Ile Ser Pro Glu Leu Gly Pro Thr Leu Asp Thr Leu Gln Leu
Asp Val Ala Asp Phe Ala Thr Thr Ile Trp Gln Gln Met Glu Glu
Leu Gly (SEQ ID NO:170)
```

EXAMPLE 58

Construction of pMON13187

The new N-terminus/C-terminus gene in pMON13187 was created using Method I as described in Materials and Methods. Fragment Start was created and amplified from G-CSF Ser$^{17}$ sequence in pMON13037 using the primer set, 126 start (SEQ ID NO:68) and L-11 start (SEQ ID NO:60). Fragment Stop was created and amplified from G-CSF Ser$^{17}$ sequence in pMON13037 using the primer set, 125 stop (SEQ ID NO:69) and L-11 stop (SEQ ID NO:61). The full-length new N terminus/C-terminus G-CSF Ser$^{17}$ gene was created and amplified from the annealed Fragments Start and Stop using 126 start and 125 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13187.

E. coli strain JM101 was transformed with pMON13187 for protein expression and protein isolation from inclusion bodies.

The plasmid, pMON13187, contains the DNA sequence of (SEQ ID NO:99) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Ser Gly Gly Ser Gly Gly Ser Gln Ser Phe Leu Leu Lys Ser Leu
Glu Gln Val Arg Lys Ile Gln Gly Asp Gly Ala Ala Leu Gln Glu
Lys Leu Cys Ala Thr Tyr Lys Leu Cys His Pro Glu Glu Leu Val
Leu Leu Gly His Ser Leu Gly Ile Pro Trp Ala Pro Leu Ser Ser
Cys Pro Ser Gln Ala Leu Gln Leu Ala Gly Cys Leu Ser Gln Leu
His Ser Gly Leu Phe Leu Tyr Gln Gly Leu Leu Gln Ala Leu Glu
Gly Ile Ser Pro Glu Leu Gly Pro Thr Leu Asp Thr Leu Gln Leu
Asp Val Ala Asp Phe Ala Thr Thr Ile Trp Gln Gln Met Glu Glu
Leu Gly   (SEQ ID NO:171)
```

EXAMPLE 59

Construction of pMON13188

The new N-terminus/C-terminus gene in pMON13188 was created using Method I as described in Materials and Methods. Fragment Start was created and amplified from G-CSF Ser¹⁷ sequence in pMON13037 using the primer set, 133 start (SEQ ID NO:70) and L-11 start (SEQ ID NO:60). Fragment Stop was created and amplified from G-CSF Ser¹⁷ sequence in pMON13037 using the primer set, 132 stop (SEQ ID NO:71) and L-11 stop (SEQ ID NO:61). The full-length new N terminus/C-terminus G-CSF Ser¹⁷ gene was created and amplified from the annealed Fragments Start and Stop using 133 start and 132 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13188.

E. coli strain JM101 was transformed with pMON13188 for protein expression and protein isolation from inclusion bodies.

The plasmid, pMON13188, contains the DNA sequence of (SEQ ID NO:100) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Ser Gly Gly Ser Gly Gly Ser
Gln Ser Phe Leu Leu Lys Ser Leu Glu Gln Val Arg Lys Ile Gln
Gly Asp Gly Ala Ala Leu Gln Glu Lys Leu Cys Ala Thr Tyr Lys
Leu Cys His Pro Glu Glu Leu Val Leu Leu Gly His Ser Leu Gly
Ile Pro Trp Ala Pro Leu Ser Ser Cys Pro Ser Gln Ala Leu Gln
Leu Ala Gly Cys Leu Ser Gln Leu His Ser Gly Leu Phe Leu Tyr
Gln Gly Leu Leu Gln Ala Leu Glu Gly Ile Ser Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro   (SEQ ID NO:172)
```

EXAMPLE 60

Construction of pMON13189

The new N-terminus/C-terminus gene in pMON13189 was created using Method I as described in Materials and Methods. Fragment Start was created and amplified from G-CSF Ser$^{17}$ sequence in pMON13037 using the primer set, 133 start (SEQ ID NO:70) and L-11 start (SEQ ID NO:60). Fragment Stop was created and amplified from G-CSF Ser$^{17}$ sequence in pMON13037 using the primer set, 132 stop (SEQ ID NO:71) and L-11 stop (SEQ ID NO:61). The full-length new N terminus/C-terminus G-CSF Ser$^{17}$ gene was created and amplified from the annealed Fragments Start and Stop using 133 start and 132 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13189.

*E. coli* strain JM101 was transformed with pMON13189 for protein expression and protein isolation from inclusion bodies.

The plasmid, pMON13189, contains the DNA sequence of (SEQ ID NO:101) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Lys Ala Gly Asp Trp
Gln Glu Phe Arg Glu Lys Leu Thr Phe Tyr Leu Val Thr Leu Glu
Gln Ala Gln Glu Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Ser Gly Gly Ser Gly Gly Ser
Gln Ser Phe Leu Leu Lys Ser Leu Glu Gln Val Arg Lys Ile Gln
Gly Asp Gly Ala Ala Leu Gln Glu Lys Leu Cys Ala Thr Tyr Lys
Leu Cys His Pro Glu Glu Leu Val Leu Leu Gly His Ser Leu Gly
Ile Pro Trp Ala Pro Leu Ser Ser Cys Pro Ser Gln Ala Leu Gln
Leu Ala Gly Cys Leu Ser Gln Leu His Ser Gly Leu Phe Leu Tyr
Gln Gly Leu Leu Gln Ala Leu Glu Gly Ile Ser Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro    (SEQ ID NO:173)
```

EXAMPLE 61

Construction of pMON13190

The new N-terminus/C-terminus gene in pMON13190 was created using Method I as described in Materials and Methods. Fragment Start was created and amplified from G-CSF Ser$^{17}$ sequence in pMON13037 using the primer set, 142 start (SEQ ID NO:72) and L-11 start (SEQ ID NO:60). Fragment Stop was created and amplified from G-CSF Ser$^{17}$ sequence in pMON13037 using the primer set, 141 stop (SEQ ID NO:73) and L-11 stop (SEQ ID NO:61). The full-length new N terminus/C-terminus G-CSF Ser$^{17}$ gene was created and amplified from the annealed Fragments Start and Stop using 142 start and 141 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13190.

E. coli strain JM101 was transformed with pMON13190 for protein expression and protein isolation from inclusion bodies.

The plasmid, pMON13190, contains the DNA sequence of (SEQ ID NO:102) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Ser Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser Pro Glu Leu Gly Pro Thr Leu Asp Thr Leu Gln Leu Asp
Val Ala Asp Phe Ala Thr Thr Ile Trp Gln Gln Met Glu Glu Leu
Gly Met Ala Pro Ala Leu Gln Pro Thr Gln Gly Ala Met Pro Ala
Phe Ala (SEQ ID NO:174)
```

EXAMPLE 62

Construction of pMON13191

The new N-terminus/C-terminus gene in pMON13191 was created using Method I as described in Materials and Methods. Fragment Start was created and amplified from G-CSF Ser[17] sequence in pMON13037 using the primer set, 142 start (SEQ ID NO:72) and L-11 start (SEQ ID NO:60). Fragment Stop was created and amplified from G-CSF Ser[17] sequence in pMON13037 using the primer set, 141 stop (SEQ ID NO:73) and L-11 stop (SEQ ID NO:61). The full-length new N terminus/C-terminus G-CSF Ser[17] gene was created and amplified from the annealed Fragments Start and Stop using 142 start and 141 stop.

The resulting DNA fragment which contains the new gene was digested with restriction endonucleases NcoI and HindIII and purified using a Magic DNA Clean-up System kit (Promega, Madison, Wis.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON13191.

E. coli strain JM101 was transformed with pMON13191 for protein expression and protein isolation from inclusion bodies.

The plasmid, pMON13191, contains the DNA sequence of (SEQ ID NO:103) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Ser
Gly Gly Ser Gly Gly Ser Gln Ser Phe Leu Leu Lys Ser Leu Glu
Gln Val Arg Lys Ile Gln Gly Asp Gly Ala Ala Leu Gln Glu Lys
Leu Cys Ala Thr Tyr Lys Leu Cys His Pro Glu Glu Leu Val Leu
Leu Gly His Ser Leu Gly Ile Pro Trp Ala Pro Leu Ser Ser Cys
Pro Ser Gln Ala Leu Gln Leu Ala Gly Cys Leu Ser Gln Leu His
Ser Gly Leu Phe Leu Tyr Gln Gly Leu Leu Gln Ala Leu Glu Gly
Ile Ser Pro Glu Leu Gly Pro Thr Leu Asp Thr Leu Gln Leu Asp
Val Ala Asp Phe Ala Thr Thr Ile Trp Gln Gln Met Glu Glu Leu
Gly Met Ala Pro Ala Leu Gln Pro Thr Gln Gly Ala Met Pro Ala
Phe Ala (SEQ ID NO:175)
```

EXAMPLE 63

Construction of pMON13192

The new N-terminus/C-terminus gene in pMON13192 was created using Method II as described in Materials and Methods. Fragment Start was created and amplified from G-CSF sequence in pMON13037 using the primer set, 39 start (SEQ ID NO:64) and P-bl start (SEQ ID NO:62). Fragment Stop was created and amplified from G-CSF Ser[17] sequence in pMON13037 using the primer set, 38 stop (SEQ ID NO:65) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser[17] gene and was digested with restriction endonucleases NcoI and HindIII. The digested DNA was resolved on a 1% TAE gel, stained with ethidium bromide and the full-length new N-terminus/C-terminus G-CSF Ser[17] gene was isolated using Geneclean (Bio101, Vista, Calif.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13192.

*E. coli* strain JM101 was transformed with pMON13192 for protein expression and protein isolation from inclusion bodies.

The plasmid, pMON13192, contains the DNA sequence of (SEQ ID NO:104) which encodes the following amino acid sequence:

13192.Pept

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Thr Pro Leu
Gly Pro Ala Ser Ser Leu Pro Gln Ser Phe Leu Leu Lys Ser Leu
Glu Gln Val Arg Lys Ile Gln Gly Asp Gly Ala Ala Leu Gln Glu
Lys Leu Cys Ala Thr (SEQ ID NO:176)
```

EXAMPLE 64

Construction of pMON13193

The new N-terminus/C-terminus gene in pMON13193 was created using Method II as described in Materials and Methods. Fragment Start was created and amplified from G-CSF Ser[17] sequence in pMON13037 using the primer set, 39 start (SEQ ID NO:64) and P-bl start (SEQ ID NO:62). Fragment Stop was created and amplified from G-CSF Ser[17] sequence in pMON13037 using the primer set, 38 stop (SEQ ID NO:65) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser[17] gene and was digested with restriction endonucleases NcoI and HindIII. The digested DNA was resolved on a 1% TAE gel, stained with ethidium bromide and the full-length new N-terminus/C-terminus G-CSF Ser[17] gene was isolated using Geneclean (Bio101, Vista, Calif.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13193.

E. coli strain JM101 was transformed with pMON13193 for protein expression and protein isolation from inclusion bodies.

The plasmid, pMON13193, contains the DNA sequence of (SEQ ID NO:105) encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Tyr Val Gln Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Thr Pro Leu
Gly Pro Ala Ser Ser Leu Pro Gln Ser Phe Leu Leu Lys Ser Leu
Glu Gln Val Arg Lys Ile Gln Gly Asp Gly Ala Ala Leu Gln Glu
Lys Leu Cys Ala Thr (SEQ ID NO:177)
```

EXAMPLE 65

Construction of pMON25190

The new N-terminus/C-terminus gene in pMON25190 was created using Method II as described in Materials and Methods. Fragment Start was created and amplified from G-CSF sequence in pMON13037 using the primer set, 97 start (SEQ ID NO:66) and P-bl start (SEQ ID NO:62). Fragment Stop was created and amplified from G-CSF Ser$^{17}$ sequence in pMON13037 using the primer set, 96 stop (SEQ ID NO:67) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser$^{17}$ gene was isolated using Geneclean (Bio101, Vista, Calif.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON25190.

*E. coli* strain JM101 was transformed with pMON25190 for protein expression and protein isolation from inclusion bodies.

The plasmid, pMON25190, contains the DNA sequence of (SEQ ID NO:106) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Ser Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser  (SEQ ID NO:178)
```

EXAMPLE 66

Construction of pMON25191

The new N-terminus/C-terminus gene in pMON25191 was created using Method II as described in Materials and Methods. Fragment Start was created and amplified from G-CSF Ser[17] sequence in pMON13037 using the primer set, 97 start (SEQ ID NO:66) and P-bl start (SEQ ID NO:62). Fragment Stop was created and amplified from G-CSF Ser[17] sequence in pMON13037 using the primer set, 96 stop (SEQ ID NO:98) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser[17] gene and was digested with restriction endonucleases NcoI and HindIII. The digested DNA was resolved on a 1% TAE gel, stained with ethidium bromide and the full-length new N-terminus/C-terminus G-CSF Ser[17] gene was isolated using Geneclean (Bio101, Vista, Calif.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON25191.

*E. coli* strain JM101 was transformed with pMON25191 for protein expression and protein isolation from inclusion bodies.

The plasmid, pMON25191, contains the DNA sequence of (SEQ ID NO:107) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Pro Glu Leu Gly
Pro Thr Leu Asp Thr Leu Gln Leu Asp Val Ala Asp Phe Ala Thr
Thr Ile Trp Gln Gln Met Glu Glu Leu Gly Met Ala Pro Ala Leu
Gln Pro Thr Gln Gly Ala Met Pro Ala Phe Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
```

-continued

Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser (SEQ ID NO:179)

EXAMPLE 67

Construction of pMON13194

The new N-terminus/C-terminus gene in pMON13194 was created using Method II as described in Materials and Methods. Fragment Start was created and amplified from G-CSF Ser$^{17}$ sequence in pMON13037 using the primer set, 126 start (SEQ ID NO:68) and P-bl start (SEQ ID NO:62). Fragment Stop was created and amplified from G-CSF Ser$^{17}$ sequence in pMON13037 using the primer set, 125 stop (SEQ ID NO:67) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser$^{17}$ gene was isolated using Geneclean (Bio101, Vista, Calif.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13194.

*E. coli* strain JM101 was transformed with pMON13194 for protein expression and protein isolation from inclusion bodies.

The plasmid, pMON13194, contains the DNA sequence of (SEQ ID NO:108) which encodes the following amino acid sequence:

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Lys Ala Gly Asp Trp
Gln Glu Phe Arg Glu Lys Leu Thr Phe Tyr Leu Val Thr Leu Glu
Gln Ala Gln Glu Gln Tyr Val Glu Gly Gly Gly Gly Ser Pro
Gly Gly Gly Ser Gly Gly Gly Ser Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Thr Pro Leu Gly Pro Ala Ser Ser Leu Pro Gln Ser Phe Leu Leu
Lys Ser Leu Glu Gln Val Arg Lys Ile Gln Gly Asp Gly Ala Ala
Leu Gln Glu Lys Leu Cys Ala Thr Tyr Lys Leu Cys His Pro Glu
Glu Leu Val Leu Leu Gly His Ser Leu Gly Ile Pro Trp Ala Pro
Leu Ser Ser Cys Pro Ser Gln Ala Leu Gln Leu Ala Gly Cys Leu
Ser Gln Leu His Ser Gly Leu Phe Leu Tyr Gln Gly Leu Leu Gln
Ala Leu Glu Gly Ile Ser Pro Glu Leu Gly Pro Thr Leu Asp Thr
Leu Gln Leu Asp Val Ala Asp Phe Ala Thr Thr Ile Trp Gln Gln
Met Glu Glu Leu Gly (SEQ ID NO:180)

EXAMPLE 68

Construction of pMON13195

The new N-terminus/C-terminus gene in pMON13195 was created using Method II as described in Materials and Methods. Fragment Start was created and amplified from G-CSF Ser$^{17}$ sequence in pMON13037 using the primer set, 126 start (SEQ ID NO:68) and P-bl start (SEQ ID NO:62). Fragment Stop was created and amplified from G-CSF Ser$^{17}$ sequence in pMON13037 using the primer set, 125 stop (SEQ ID NO:69) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser$^{17}$ gene was isolated using Geneclean (Bio101, Vista, Calif.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13195.

E. coli strain JM101 was transformed with pMON13195 for protein expression and protein isolation from inclusion bodies.

The plasmid, pMON13195, contains the DNA sequence of (SEQ ID NO:109) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Met Ala Pro Ala
Leu Gln Pro Thr Gln Gly Ala Met Pro Ala Phe Ala Ser Ala Phe
Gln Arg Arg Ala Gly Gly Val Leu Val Ala Ser His Leu Gln Ser
Phe Leu Glu Val Ser Tyr Arg Val Leu Arg His Leu Ala Gln Pro
Thr Pro Leu Gly Pro Ala Ser Ser Leu Pro Gln Ser Phe Leu Leu
Lys Ser Leu Glu Gln Val Arg Lys Ile Gln Gly Asp Gly Ala Ala
Leu Gln Glu Lys Leu Cys Ala Thr Tyr Lys Leu Cys His Pro Glu
Glu Leu Val Leu Leu Gly His Ser Leu Gly Ile Pro Trp Ala Pro
Leu Ser Ser Cys Pro Ser Gln Ala Leu Gln Leu Ala Gly Cys Leu
Ser Gln Leu His Ser Gly Leu Phe Leu Tyr Gln Gly Leu Leu Gln
Ala Leu Glu Gly Ile Ser Pro Glu Leu Gly Pro Thr Leu Asp Thr
Leu Gln Leu Asp Val Ala Asp Phe Ala Thr Thr Ile Trp Gln Gln
Met Glu Glu Leu Gly (SEQ ID NO:181)
```

EXAMPLE 69

Construction of pMON13196

The new N-terminus/C-terminus gene in pMON13196 was created using Method II as described in Materials and Methods. Fragment Start was created and amplified from G-CSF sequence in pMON13037 using the primer set, 133 start (SEQ ID NO:70) and P-bl start (SEQ ID NO:62). Fragment Stop was created and amplified from G-CSF Ser$^{17}$ sequence in pMON13037 using the primer set, 132 stop (SEQ ID NO:71) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser$^{17}$ gene was isolated using Geneclean (Bio101, Vista, Calif.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13196.

*E. coli* strain JM101 was transformed with pMON13196 for protein expression and protein isolation from inclusion bodies.

The plasmid, pMON13196, contains the DNA sequence of (SEQ ID NO:110) which encodes the following amino acid sequence:

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Thr Gln Gly Ala
Met Pro Ala Phe Ala Ser Ala Phe Gln Arg Arg Ala Gly Gly Val
Leu Val Ala Ser His Leu Gln Ser Phe Leu Glu Val Ser Tyr Arg
Val Leu Arg His Leu Ala Gln Pro Thr Pro Leu Gly Pro Ala Ser
Ser Leu Pro Gln Ser Phe Leu Leu Lys Ser Leu Glu Gln Val Arg
Lys Ile Gln Gly Asp Gly Ala Ala Leu Gln Glu Lys Leu Cys Ala
Thr Tyr Lys Leu Cys His Pro Glu Glu Leu Val Leu Leu Gly His
Ser Leu Gly Ile Pro Trp Ala Pro Leu Ser Ser Cys Pro Ser Gln
Ala Leu Gln Leu Ala Gly Cys Leu Ser Gln Leu His Ser Gly Leu
Phe Leu Tyr Gln Gly Leu Leu Gln Ala Leu Glu Gly Ile Ser Pro
Glu Leu Gly Pro Thr Leu Asp Thr Leu Gln Leu Asp Val Ala Asp
Phe Ala Thr Thr Ile Trp Gln Gln Met Glu Glu Leu Gly Met Ala
Pro Ala Leu Gln Pro (SEQ ID NO:182)

EXAMPLE 70

Construction of pMON13197

The new N-terminus/C-terminus gene in pMON13197 was created using Method II as described in Materials and Methods. Fragment Start was created and amplified from G-CSF Ser$^{17}$ sequence in pMON13037 using the primer set, 133 start (SEQ ID NO:70) and P-bl start (SEQ ID NO:62). Fragment Stop was created and amplified from G-CSF Ser$^{17}$ sequence in pMON13037 using the primer set, 132 stop (SEQ ID NO:71) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser$^{17}$ gene was isolated using Geneclean (Bio101, Vista, Calif.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13197.

*E. coli* strain JM101 was transformed with pMON13197 for protein expression and protein isolation from inclusion bodies.

The plasmid, pMON13197, contains the DNA sequence of (SEQ ID NO:lll) which encodes the following amino acid sequence:

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Tyr Lys Leu Cys
His Pro Glu Glu Leu Val Leu Leu Gly His Ser Leu Gly Ile Pro
Trp Ala Pro Leu Ser Ser Cys Pro Ser Gln Ala Leu Gln Leu Ala
Gly Cys Leu Ser Gln Leu His Ser Gly Leu Phe Leu Tyr Gln Gly
Leu Leu Gln Ala Leu Glu Gly Ile Ser Pro Glu Leu Gly Pro Thr
Leu Asp Thr Leu Gln Leu Asp Val Ala Asp Phe Ala Thr Thr Ile
Trp Gln Gln Met Glu Glu Leu Gly Met Ala Pro Ala Leu Gln Pro
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Thr Pro Leu

-continued

Gly Pro Ala Ser Ser Leu Pro Gln Ser Phe Leu Leu Lys Ser Leu
Glu Gln Val Arg Lys Ile Gln Gly Asp Gly Ala Ala Leu Gln Glu
Lys Leu Cys Ala Thr (SEQ ID NO:183)

EXAMPLE 71

Construction of pMON13198

The new N-terminus/C-terminus gene in pMON13198 was created using Method II as described in Materials and Methods. Fragment Start was created and amplified from G-CSF sequence in pMON13037 using the primer set, 142 start (SEQ ID NO:72) and P-bl start (SEQ ID NO:62). Fragment Stop was created and amplified from G-CSF Ser$^{17}$ sequence in pMON13037 using the primer set, 141 stop (SEQ ID NO:73) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser$^{17}$ gene was isolated using Geneclean (Bio101, Vista, Calif.). The intermediate plasmid, pMON13180, was digested with restriction endonucleases HindIII and AflIII, resulting in a 4023 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13198.

E. coli strain JM101 was transformed with pMON13198 for protein expression and protein isolation from inclusion bodies.

The plasmid, pMON13198, contains the DNA sequence of (SEQ ID NO:112) which encodes the following amino acid sequence:

Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Gly Gly Ser Gly Gly Gly Ser Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser Pro Glu Leu Gly Pro Thr Leu Asp Thr Leu
Gln Leu Asp Val Ala Asp Phe Ala Thr Thr Ile Trp Gln Gln Met
Glu Glu Leu Gly Met Ala Pro Ala Leu Gln Pro Thr Gln Gly Ala
Met Pro Ala Phe Ala (SEQ ID NO:184)

EXAMPLE 72

Construction of pMON13199

The new N-terminus/C-terminus gene in pMON13199 was created using Method II as described in Materials and Methods. Fragment Start was created and amplified from G-CSF Ser$^{17}$ sequence in pMON13037 using the primer set, 142 start (SEQ ID NO:72) and P-bl start (SEQ ID NO:62). Fragment Stop was created and amplified from G-CSF Ser$^{17}$ sequence in pMON13037 using the primer set, 141 stop (SEQ ID NO:73) and P-bl stop (SEQ ID NO:63). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934.

The intermediate plasmid described above contained the full length new N-terminus/C-terminus G-CSF Ser$^{17}$ gene and was digested with restriction endonucleases NcoI and HindIII. The digested DNA was resolved on a 1% TAE gel, stained with ethidium bromide and the full-length new N-terminus/C-terminus G-CSF Ser[17] gene was isolated using Geneclean (Bio101, Vista, Calif.). The intermediate plasmid, pMON13181, was digested with restriction endonucleases HindIII and AflIII, resulting in a 4068 base pair vector fragment, and purified using a Magic DNA Clean-up System kit (Promega, Madison, Wis.). The purified restriction fragments were combined and ligated using T4 DNA ligase (Boehringer Mannheim, Indianapolis, Ind.). A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insertion of the new gene. The resulting plasmid was designated pMON13199.

*E. coli* strain JM101 was transformed with pMON13199 for protein expression and protein isolation from inclusion bodies.

The plasmid, pMON13199, contains the DNA sequence of (SEQ ID NO:113) which encodes the following amino acid sequence:

```
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Asn Ala Ser Gly Ile
Glu Ala Ile Leu Arg Asn Leu Gln Pro Cys Leu Pro Ser Ala Thr
Ala Ala Pro Ser Arg His Pro Ile Ile Ile Lys Ala Gly Asp Trp
Gln Glu Phe Arg Glu Lys Leu Thr Phe Tyr Leu Val Thr Leu Glu
Gln Ala Gln Glu Gln Gln Tyr Val Glu Gly Gly Gly Gly Ser Pro
Gly Glu Pro Ser Gly Pro Ile Ser Thr Ile Asn Pro Ser Pro Pro
Ser Lys Glu Ser His Lys Ser Pro Asn Met Ala Ser Ala Phe Gln
Arg Arg Ala Gly Gly Val Leu Val Ala Ser His Leu Gln Ser Phe
Leu Glu Val Ser Tyr Arg Val Leu Arg His Leu Ala Gln Pro Thr
Pro Leu Gly Pro Ala Ser Ser Leu Pro Gln Ser Phe Leu Leu Lys
Ser Leu Glu Gln Val Arg Lys Ile Gln Gly Asp Gly Ala Ala Leu
Gln Glu Lys Leu Cys Ala Thr Tyr Lys Leu Cys His Pro Glu Glu
Leu Val Leu Leu Gly His Ser Leu Gly Ile Pro Trp Ala Pro Leu
Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala
Leu Glu Gly Ile Ser Pro Glu Leu Gly Pro Thr Leu Asp Thr Leu
Gln Leu Asp Val Ala Asp Phe Ala Thr Thr Ile Trp Gln Gln Met
Glu Glu Leu Gly Met Ala Pro Ala Leu Gln Pro Thr Gln Gly Ala
Met Pro Ala Phe Ala (SEQ ID NO:185)
```

EXAMPLE 73

Construction of Tandemly-Duplicated Plasmid Template, Syntan1

To create the tandemly-duplicated hIL-3 receptor agonist pMON13416 template, Syntan1, three DNAs were joined by means of ligation using T4 DNA ligase (Boehringer Mannheim). The three DNAs are: 1) pMON13046, containing hIL-3 receptor agonist pMON13416, digested with BstEII and SnaBI; 2) the annealed complimentary pair of synthetic oligonucleotides, L1syn.for (SEQ ID NO:48) and L1syn.rev (SEQ ID NO:49), which contain sequence encoding the linker that connects the C-terminal and N-terminal ends of the original protein and a small amount of surrounding pMON13416 sequence and which when properly assembled result in BstEII and ClaI ends; and 3) a portion of hIL-3 receptor agonist pMON13416 digested from pMON13046 with ClaT (DNA had been grown in the dam-cells, DM1 (Life Technologies)) and SnaBI. The digested DNAs were resolved on a 0.9% TAE gel, stained with ethidium bromide and isolated using Geneclean (Bio101).

A portion of the ligation reaction was used to transform *E. coli* strain DH5α cells (Life Technologies, Gaithersburg, Md.). Miniprep DNA was isolated from the transformants, and the transformants were screened using a PCR based assay. Plasmid DNA from selected transformants was sequenced to obtain the correct template. The resulting plasmid was designated syntan1 and contains the DNA sequence of (SEQ ID NO:84).

EXAMPLE 74

Construction of Tandemly-Duplicated Template, Syntan3

To create the tandemly-duplicated hIL-3 receptor agonist pMON13416 template, syntan3, three DNAs were joined by means of ligation using T4 DNA ligase (Boehringer Mannheim). The three DNAs are: 1) pMON13046, containing hIL-3 receptor agonist pMON13416, digested with BstEII and SnaBI; 2) the annealed complimentary pair of synthetic oligonucleotides, L3syn.for (SEQ ID NO:50) and L3syn.rev (SEQ ID NO:51), which contain sequence encoding the linker that connects the C-terminal and N-terminal ends of the original protein and a small amount of surrounding pMON13416 sequence and which when properly assembled result in BstEII and SnaBI ends; and 3) a portion of hIL-3 receptor agonist pMON13416 digested from pMON13046 with ClaI (DNA had been grown in the dam-cells, DM1 (Life Technologies)) and SnaBI. The digested DNAs were resolved on a 0.9% TAE gel, stained with ethidium bromide and isolated using Geneclean (Bio101).

A portion of the ligation reaction was used to transform *E. coli* strain DH5α cells (Life Technologies, Gaithersburg, Md.). Miniprep DNA was isolated from the transformants, and the transformants were screened using a PCR based assay. Plasmid DNA from selected transformants was sequenced to obtain the correct template. The resulting plasmid was designated syntan3 and contains the DNA sequence of (SEQ ID NO:85).

EXAMPLE 75

Construction of pMON31104

The new N-terminus/C-terminus gene in pMON31104 was created using Method III as described in Materials and Methods. The full length new N-terminus/C-terminus gene of hIL-3 receptor agonist pMON13416 was created and amplified from the intermediate plasmid, Syntan1, using the primer set 35 start (SEQ ID NO:52) and 34 rev (SEQ ID NO:53).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector, pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31104.

*E. coli* strain JM101 was transformed with pMON31104 for protein expression and protein isolation from inclusion bodies.

The plasmid, pMON31104, contains the DNA sequence of (SEQ ID NO:86) which encodes the following amino acid sequence:

```
Leu Asp Pro Asn Asn Leu Asn Asp Glu Asp Val Ser Ile Leu Met
Asp Arg Asn Leu Arg Leu Pro Asn Leu Glu Ser Phe Val Arg Ala
Val Lys Asn Leu Glu Asn Ala Ser Gly Ile Glu Ala Ile Leu Arg
Asn Leu Gln Pro Cys Leu Pro Ser Ala Thr Ala Ala Pro Ser Arg
His Pro Ile Ile Ile Lys Ala Gly Asp Trp Gln Glu Phe Arg Glu
Lys Leu Thr Phe Tyr Leu Val Thr Leu Glu Gln Ala Gln Glu Gln
Gln Gly Gly Gly Ser Asn Cys Ser Ile Met Ile Asp Glu Ile Ile
His His Leu Lys Arg Pro Pro Ala Pro Leu Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Glu Leu Gly Met
Ala Pro Ala Leu Gln Pro (SEQ ID NO:186)
```

EXAMPLE 76

Construction of pMON31105

The new N-terminus/C-terminus gene in pMON31105 was created using Method III as described in Materials and Methods. The full length new N-terminus/C-terminus gene of hIL-3 receptor agonist pMON13416 was created and amplified from the intermediate plasmid, Syntan1, using the primer set 70 start (SEQ ID NO:54) and 69 rev (SEQ ID NO:55).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31105.

E. coli strain JM101 was transformed with pMON31105 for protein expression and protein isolation from inclusion bodies.

The plasmid, pMON31105, contains the DNA sequence of (SEQ ID NO:87) which encodes the protein with the following amino acid sequence:

```
Asn Ala Ser Gly Ile Glu Ala Ile Leu Arg Asn Leu Gln Pro Cys
Leu Pro Ser Ala Thr Ala Ala Pro Ser Arg His Pro Ile Ile Ile
Lys Ala Gly Asp Trp Gln Glu Phe Arg Glu Lys Leu Thr Phe Tyr
Leu Val Thr Leu Glu Gln Ala Gln Glu Gln Gly Gly Gly Ser
Asn Cys Ser Ile Met Ile Asp Glu Ile Ile His His Leu Lys Arg
Pro Pro Ala Pro Leu Leu Asp Pro Asn Asn Leu Asn Asp Glu Asp
Val Ser Ile Leu Met Asp Arg Asn Leu Arg Leu Pro Asn Leu Glu
Ser Phe Val Arg Ala Val Lys Asn Leu Glu Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Glu Leu Gly Met
Ala Pro Ala Leu Gln Pro (SEQ ID NO:187)
```

EXAMPLE 77

Construction of pMON31106

The new N-terminus/C-terminus gene in pMON31106 was created using Method III as described in Materials and Methods. The full length new N-terminus/C-terminus gene of hIL-3 receptor agonist pMON13416 was created and amplified from the intermediate plasmid, Syntan1, using the primer set 91 start (SEQ ID NO:56) and 90 rev (SEQ ID NO:57).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31106.

E. coli strain JM101 was transformed with pMON31106 for protein expression and protein isolation from inclusion bodies.

The plasmid, pMON31106, contains the DNA sequence of (SEQ ID NO:80) which encodes the protein with the following amino acid sequence:

```
Ala Pro Ser Arg His Pro Ile Ile Ile Lys Ala Gly Asp Trp Gln
Glu Phe Arg Glu Lys Leu Thr Phe Tyr Leu Val Thr Leu Glu Gln
Ala Gln Glu Gln Gln Gly Gly Gly Ser Asn Cys Ser Ile Met Ile
Asp Glu Ile Ile His His Leu Lys Arg Pro Pro Ala Pro Leu Leu
Asp Pro Asn Asn Leu Asn Asp Glu Asp Val Ser Ile Leu Met Asp
Arg Asn Leu Arg Leu Pro Asn Leu Glu Ser Phe Val Arg Ala Val
Lys Asn Leu Glu Asn Ala Ser Gly Ile Glu Ala Ile Leu Arg Asn
Leu Gln Pro Cys Leu Pro Ser Ala Thr Ala Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Glu Leu Gly Met
Ala Pro Ala Leu Gln Pro   (SEQ ID NO:188)
```

EXAMPLE 78

Construction of pMON31107

The new N-terminus/C-terminus gene in pMON31107 was created using Method III as described in Materials and Methods. The full length new N-terminus/C-terminus gene of hIL-3 receptor agonist pMON13416 was created and amplified from the intermediate plasmid, Syntan1, using the primer set 101 start (SEQ ID NO:58) and 100 rev (SEQ ID NO:59).

The resulting DNA fragment which contains the new gene was digested with restriction endonucleases NcoI and SnaBI. The digested The DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31107.

E. coli strain JM101 was transformed with pMON31107 for protein expression and protein isolation from inclusion bodies.

The plasmid, pMON31107, contains the DNA sequence of (SEQ ID NO:89) which encodes the following amino acid sequence:

```
Ala Gly Asp Trp Gln Glu Phe Arg Glu Lys Leu Thr Phe Tyr Leu
Val Thr Leu Glu Gln Ala Gln Glu Gln Gln Gly Gly Gly Ser Asn
Cys Ser Ile Met Ile Asp Glu Ile Ile His His Leu Lys Arg Pro
Pro Ala Pro Leu Leu Asp Pro Asn Asn Leu Asn Asp Glu Asp Val
Ser Ile Leu Met Asp Arg Asn Leu Arg Leu Pro Asn Leu Glu Ser
Phe Val Arg Ala Val Lys Asn Leu Glu Asn Ala Ser Gly Ile Glu
Ala Ile Leu Arg Asn Leu Gln Pro Cys Leu Pro Ser Ala Thr Ala
Ala Pro Ser Arg His Pro Ile Ile Ile Lys Tyr Val Glu Gly Gly
Gly Gly Ser Pro Gly Glu Pro Ser Gly Pro Ile Ser Thr Ile Asn
Pro Ser Pro Pro Ser Lys Glu Ser His Lys Ser Pro Asn Met Ala
Thr Gln Gly Ala Met Pro Ala Phe Ala Ser Ala Phe Gln Arg Arg
Ala Gly Gly Val Leu Val Ala Ser His Leu Gln Ser Phe Leu Glu
Val Ser Tyr Arg Val Leu Arg His Leu Ala Gln Pro Ser Gly Gly
Ser Gly Gly Ser Gln Ser Phe Leu Leu Lys Ser Leu Glu Gln Val
Arg Lys Ile Gln Gly Asp Gly Ala Ala Leu Gln Glu Lys Leu Cys
Ala Thr Tyr Lys Leu Cys His Pro Glu Glu Leu Val Leu Leu Gly
His Ser Leu Gly Ile Pro Trp Ala Pro Leu Ser Ser Cys Pro Ser
Gln Ala Leu Gln Leu Ala Gly Cys Leu Ser Gln Leu His Ser Gly
Leu Phe Leu Tyr Gln Gly Leu Leu Gln Ala Leu Glu Gly Ile Ser
Pro Glu Leu Gly Pro Thr Leu Asp Thr Leu Gln Leu Asp Val Ala
Asp Phe Ala Thr Thr Ile Trp Gln Gln Met Glu Glu Leu Gly Met
Ala Pro Ala Leu Gln Pro (SEQ ID NO:189)
```

EXAMPLE 79

Construction of pMON31108

The new N-terminus/C-terminus gene in pMON31108 was created using Method III as described in Materials and Methods. The full length new N-terminus/C-terminus gene of hIL-3 receptor agonist pMON13416 was created and amplified from the intermediate plasmid, Syntan3, using the primer set 35 start (SEQ ID NO:52) and 34 rev (SEQ ID NO:53).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31108.

*E. coli* strain JM101 was transformed with pMON31108 for protein expression and protein isolation from inclusion bodies.

The plasmid, pMON31108, contains the DNA sequence of (SEQ ID NO:90) which encodes the following amino acid sequence:

```
Leu Asp Pro Asn Asn Leu Asn Asp Glu Asp Val Ser Ile Leu Met
Asp Arg Asn Leu Arg Leu Pro Asn Leu Glu Ser Phe Val Arg Ala
Val Lys Asn Leu Glu Asn Ala Ser Gly Ile Glu Ala Ile Leu Arg
Asn Leu Gln Pro Cys Leu Pro Ser Ala Thr Ala Ala Pro Ser Arg
His Pro Ile Ile Ile Lys Ala Gly Asp Trp Gln Glu Phe Arg Glu
Lys Leu Thr Phe Tyr Leu Val Thr Leu Glu Gln Ala Gln Glu Gln
Gln Gly Gly Gly Ser Gly Gly Gly Ser Gly Gly Ser Asn Cys
Ser Ile Met Ile Asp Glu Ile Ile His His Leu Lys Arg Pro Pro
Ala Pro Leu Tyr Val Glu Gly Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:190)
```

EXAMPLE 80

Construction of pMON31109

The new N-terminus/C-terminus gene in pMON31109 was created using Method III as described in Materials and Methods. The full length new N-terminus/C-terminus gene of hIL-3 receptor agonist pMON13416 was created and amplified from the intermediate plasmid, Syntan3, using the primer set 70 start (SEQ ID NO:54) and 69 rev (SEQ ID NO:55).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31109.

E. coli strain JM101 was transformed with pMON31109 for protein expression and protein isolation from inclusion bodies.

The plasmid, pMON31109, contains the DNA sequence of (SEQ ID NO:91) which encodes the following amino acid sequence:

```
Asn Ala Ser Gly Ile Glu Ala Ile Leu Arg Asn Leu Gln Pro Cys
Leu Pro Ser Ala Thr Ala Ala Pro Ser Arg His Pro Ile Ile Ile
Lys Ala Gly Asp Trp Gln Glu Phe Arg Glu Lys Leu Thr Phe Tyr
Leu Val Thr Leu Glu Gln Ala Gln Glu Gln Gln Gly Gly Gly Ser
Gly Gly Gly Ser Gly Gly Gly Ser Asn Cys Ser Ile Met Ile Asp
Glu Ile Ile His His Leu Lys Arg Pro Pro Ala Pro Leu Leu Asp
Pro Asn Asn Leu Asn Asp Glu Asp Val Ser Ile Leu Met Asp Arg
Asn Leu Arg Leu Pro Asn Leu Glu Ser Phe Val Arg Ala Val Lys
Asn Leu Glu Tyr Val Glu Gly Gly Gly Gly Ser Pro Glu Pro
Ser Gly Pro Ile Ser Phr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:191)
```

EXAMPLE 81

Construction of pMON31110

The new N-terminus/C-terminus gene in pMON31110 was created using Method III as described in Materials and Methods. The full length new N-terminus/C-terminus gene of hIL-3 receptor agonist pMON13416 was created and amplified from the intermediate plasmid, Syntan3, using the primer set 91 start (SEQ ID NO:56) and 90 rev (SEQ ID NO:57).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform E. coli strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31110.

E. coli strain JM101 was transformed with pMON31110 for protein expression and protein isolation from inclusion bodies.

The plasmid, pMON31110, contains the DNA sequence of (SEQ ID NO:92) which encodes the following amino acid sequence:

```
Ala Pro Ser Arg His Pro Ile Ile Ile Lys Ala Gly Asp Trp Gln
Glu Phe Arg Glu Lys Leu Thr Phe Tyr Leu Val Thr Leu Glu Gln
Ala Gln Glu Gln Gln Gly Gly Gly Ser Gly Gly Gly Ser Gly Gly
Gly Ser Asn Cys Ser Ile Met Ile Asp Glu Ile Ile His His Leu
Lys Arg Pro Pro Ala Pro Leu Leu Asp Pro Asn Asn Leu Asn Asp
Glu Asp Val Ser Ile Leu Met Asp Arg Asn Leu Arg Leu Pro Asn
Leu Glu Ser Phe Val Arg Ala Val Lys Asn Leu Glu Asn Ala Ser
Gly Ile Glu Ala Ile Leu Arg Asn Leu Gln Pro Cys Leu Pro Ser
Ala Thr Ala Tyr Val Glu Gly Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:192)
```

EXAMPLE 82

Construction of pMON31111

The new N-terminus/C-terminus gene in pMON31111 was created using Method III as described in Materials and Methods. The full length new N-terminus/C-terminus gene of hIL-3 receptor agonist pMON13416 was created and amplified from the intermediate plasmid, Syntan3, using the primer set 101 start (SEQ ID NO:58) and 100 rev (SEQ ID NO:59).

The resulting DNA fragment which contains the new gene was digested with restriction endonucleases NcoI and SnaBI. The digested DNA fragment was resolved on a 1% TAE gel, stained with ethidium bromide and isolated using Geneclean (Bio101, Vista, Calif.). The purified digested DNA fragment was ligated into the expression vector pMON13189, using T4 DNA ligase (Boehringer Mannheim, Indianapolis, Ind.). The pMON13189 DNA had been previously digested with NcoI and SnaBI to remove the hIL3 receptor agonist pMON13416 coding sequence and the 4254 base pair vector fragment was isolated using Geneclean (Bio101, Vista, Calif.) after resolution on a 0.8% TAE gel and staining with ethidium bromide. A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON31111.

*E. coli* strain JM101 was transformed with pMON31111 for protein expression and protein isolation from inclusion bodies.

The plasmid, pMON31111, contains the DNA sequence of (SEQ ID NO:93) which encodes the following amino acid sequence:

```
Ala Gly Asp Trp Gln Glu Phe Arg Glu Lys Leu Thr Phe Tyr Leu
Val Thr Leu Glu Gln Ala Gln Glu Gln Gln Gly Gly Gly Ser Gly
Gly Gly Ser Gly Gly Gly Ser Asn Cys Ser Ile Met Ile Asp Glu
Ile Ile His His Leu Lys Arg Pro Pro Ala Pro Leu Leu Asp Pro
Asn Asn Leu Asn Asp Glu Asp Val Ser Ile Leu Met Asp Arg Asn
Leu Arg Leu Pro Asn Leu Glu Ser Phe Val Arg Ala Val Lys Asn
Leu Glu Asn Ala Ser Gly Ile Glu Ala Ile Leu Arg Asn Leu Gln
Pro Cys Leu Pro Ser Ala Thr Ala Ala Pro Ser Arg His Pro Ile
Ile Ile Lys Tyr Val Glu Gly Gly Gly Gly Ser Pro Gly Glu Pro
Ser Gly Pro Ile Ser Thr Ile Asn Pro Ser Pro Pro Ser Lys Glu
Ser His Lys Ser Pro Asn Met Ala Thr Gln Gly Ala Met Pro Ala
Phe Ala Ser Ala Phe Gln Arg Arg Ala Gly Gly Val Leu Val Ala
Ser His Leu Gln Ser Phe Leu Glu Val Ser Tyr Arg Val Leu Arg
His Leu Ala Gln Pro Ser Gly Gly Ser Gly Gly Ser Gln Ser Phe
Leu Leu Lys Ser Leu Glu Gln Val Arg Lys Ile Gln Gly Asp Gly
Ala Ala Leu Gln Glu Lys Leu Cys Ala Thr Tyr Lys Leu Cys His
Pro Glu Glu Leu Val Leu Leu Gly His Ser Leu Gly Ile Pro Trp
Ala Pro Leu Ser Ser Cys Pro Ser Gln Ala Leu Gln Leu Ala Gly
Cys Leu Ser Gln Leu His Ser Gly Leu Phe Leu Tyr Gln Gly Leu
Leu Gln Ala Leu Glu Gly Ile Ser Pro Glu Leu Gly Pro Thr Leu
Asp Thr Leu Gln Leu Asp Val Ala Asp Phe Ala Thr Thr Ile Trp
Gln Gln Met Glu Glu Leu Gly Met Ala Pro Ala Leu Gln Pro
(SEQ ID NO:193)
```

EXAMPLE 83

Construction of pMON31112

Construction of pMON31112, a plasmid containing DNA sequence encoding a multi-functional hematopoietic receptor agonist which activates the hIL-3 receptor and G-CSF receptor. Plasmid, pMON13189 DNA was digested with restriction enzymes NcoI and XmaI resulting in an NcoI, XmaI vector fragment that was isolated and purified from a 0.8% agarose gel. The DNA from a second plasmid, pMON13222 (WO 94/12639, U.S. Ser. No. 08/411,796) was digested with NcoI and EcoRI resulting in a 281 base pair NcoI, EcoRI fragment. This fragment was isolated and purified from a 1.0% agarose gel. Two oligonucleotides SYNNOXA1.REQ (SEQ ID NO:240) and SYNNOXA2.REQ (SEQ ID NO:241) were annealed and ligated with the 281 base pair DNA fragment from pMON13222 to the DNA vector fragment from pMON13189. A portion of the ligation mixture was then transformed into *E. coli* K-12 strain JM101. Transformant bacteria were selected on ampicillin-containing plates. Plasmid DNA was isolated, analyzed by restriction analysis to show the presence of an EcoRV fragment, and sequenced to confirm the correct inserts.

The plasmid, pMON31112, contains the DNA sequence of (SEQ ID NO:114) which encodes the following amino acid sequence:

```
MetAlaAsnCysSerAsnMetIleAspGluIleIleThrHisLeuLysGlnProPro
LeuProLeuLeuAspPheAsnAsnLeuAsnGlyGluAspGlnAspIleLeuMetAsp
AsnAsnLeuArgArgProAsnLeuGluAlaPheAsnArgAlaValLysSerLeuGln
AsnAlaSerAlaIleGluSerIleLeuLysAsnLeuLeuProCysLeuProLeuAla
ThrAlaAlaProThrArgHisProIleHisIleLysAspGlyAspTrpAsnGluPhe
ArgArgLysLeuThrPheTyrLeuLysThrLeuGluAsnAlaGlnAlaGlnGlnTyr
ValGluGlyGlyGlyGlySerProGlyGluProSerGlyProIleSerThrIleAsn
ProSerProProSerLysGluSerHisLysSerProAsnMetAlaThrGlnGlyAla
MetProAlaPheAlaSerAlaPheGlnArgArgAlaGlyGlyValLeuValAlaSer
HisLeuGlnSerPheLeuGluValSerTyrArgValLeuArgHisLeuAlaGlnPro
SerGlyGlySerGlyGlySerGlnSerPheLeuLeuLysSerLeuGluGlnValArg
LysIleGlnGlyAspGlyAlaAlaLeuGlnGluLysLeuCysAlaThrTyrLysLeu
CysHisProGluGluLeuValLeuLeuGlyHisSerLeuGlyIleProTrpAlaPro
LeuSerSerCysProSerGlnAlaLeuGlnLeuAlaGlyCysLeuSerGlnLeuHis
SerGlyLeuPheLeuTyrGlnGlyLeuLeuGlnAlaLeuGluGlyIleSerProGlu
LeuGlyProThrLeuAspThrLeuGlnLeuAspValAlaAspPheAlaThrThrIle
TrpGlnGlnMetGluGluLeuGlyMetAlaProAlaLeuGlnPro
(SEQ ID NO:199)
```

Construction of pMON31113

Construction of pMON31113, a plasmid containing DNA sequence encoding a multi-functional hematopoietic receptor agonist which activates the hIL-3 receptor and G-CSF receptor. Plasmid, pMON13197 DNA was digested with restriction enzymes NcoI and XmaI resulting in an NcoI, XmaI vector fragment that was isolated and purified from a 0.8% agarose gel. The DNA from a second plasmid, pMON13239 (WO 94/12639, U.S. Ser. No. 08/411,796) was digested with NcoI and EcoRI resulting in a 281 base pair NcoI, EcoRI fragment. This fragment was isolated and purified from a 1.0% agarose gel. Two oligonucleotides SYNNOXA1.REQ (SEQ ID NO:240) and SYNNOXA2.REQ (SEQ ID NO:241) were annealed and ligated with the 281 base pair DNA fragment from pMON13239 to the DNA vector fragment from pMON13197. A portion of the ligation mixture was then transformed into *E. coli* K-12 strain JM101. Transformant bacteria were selected on ampicillin-containing plates. Plasmid DNA was isolated, analyzed by restriction analysis to show the presence of an EcoRV fragment, and sequenced to confirm the correct inserts.

The plasmid, pMON31113, contains the DNA sequence of (SEQ ID NO:115) which encodes the following amino acid sequence:

```
MetAlaAsnCysSerAsnMetIleAspGluIleIleThrHisLeuLysGlnProPro
LeuProLeuLeuAspPheAsnAsnLeuAsnGlyGluAspGlnAspIleLeuMetGlu
AsnAsnLeuArgArgProAsnLeuGluAlaPheAsnArgAlaValLysSerLeuGln
AsnAlaSerAlaIleGluSerIleLeuLysAsnLeuLeuProCysLeuProLeuAla
ThrAlaAlaProThrArgHisProIleIleIleArgAspGlyAspTrpAsnGluPhe
ArgArgLysLeuThrPheTyrLeuLysThrLeuGluAsnAlaGlnAlaGlnGlnTyr
ValGluGlyGlyGlyGlySerProGlyGluProSerGlyProIleSerThrIleAsn
ProSerProProSerLysGluSerHisLysSerProAsnMetAlaThrGlnGlyAla
MetProAlaPheAlaSerAlaPheGlnArgArgAlaGlyGlyValLeuValAlaSer
HisLeuGlnSerPheLeuGluValSerTyrArgValLeuArgHisLeuAlaGlnPro
ThrProLeuGlyProAlaSerSerLeuProGlnSerPheLeuLeuLysSerLeuGlu
GlnValArgLysIleGlnGlyAspGlyAlaAlaLeuGlnGluLysLeuCysAlaThr
TyrLysLeuCysHisProGluGluLeuValLeuLeuGlyHisSerLeuGlyIlePro
TrpAlaProLeuSerSerCysProSerGlnAlaLeuGlnLeuAlaGlyCysLeuSer
GlnLeuHisSerGlyLeuPheLeuTyrGlnGlyLeuLeuGlnAlaLeuGluGlyIle
SerProGluLeuGlyProThrLeuAspThrLeuGlnLeuAspValAlaAspPheAla
ThrThrIleTrpGlnGlnMetGluGluLeuGlyMetAlaProAlaLeuGlnPro
(SEQ ID NO:200)
```

EXAMPLE 85

Construction of pMON31114

Construction of pMON31114, a plasmid containing DNA sequence encoding a multi-functional hematopoietic receptor agonist which activates the hIL-3 receptor and G-CSF receptor. Plasmid, pMON13189 DNA was digested with restriction enzymes NcoI and XmaI resulting in an NcoI, XmaI vector fragment that was isolated and purified from a 0.8% agarose gel. The DNA from a second plasmid, pMON13239 (WO 94/12639, U.S. Ser. No. 08/411,796), was digested with NcoI and EcoRI resulting in a 281 base pair NcoI, EcoRI fragment. This fragment was isolated and purified from a 1.0% agarose gel. Two oligonucleotides SYNNOXA1.REQ (SEQ ID NO:240) and SYNNOXA2.REQ (SEQ ID NO:241) were annealed and ligated with the 281 base pair DNA fragment from pMON13239 to the DNA vector fragment from pMON13189. A portion of the ligation mixture was then transformed into *E. coli* K-12 strain JM101. Transformant bacteria were selected on ampicillin-containing plates. Plasmid DNA was isolated, analyzed by restriction analysis to show the presence of an EcoRV fragment, and sequenced to confirm the correct inserts.

The plasmid, pMON31114, contains the DNA sequence of (SEQ ID NO:116) which encodes the following amino acid sequence:

```
MetAlaAsnCysSerAsnMetIleAspGluIleIleThrHisLeuLysGlnProPro
LeuProLeuLeuAspPheAsnAsnLeuAsnGlyGluAspGlnAspIleLeuMetGlu
AsnAsnLeuArgArgProAsnLeuGluAlaPheAsnArgAlaValLysSerLeuGln
AsnAlaSerAlaIleGluSerIleLeuLysAsnLeuLeuProCysLeuProLeuAla
ThrAlaAlaProThrArgHisProIleIleIleArgAspGlyAspTrpAsnGluPhe
ArgArgLysLeuThrPheTyrLeuLysThrLeuGluAsnAlaGlnAlaGlnGlnTyr
ValGluGlyGlyGlyGlySerProGlyGluProSerGlyProIleSerThrIleAsn
ProSerProProSerLysGluSerHisLysSerProAsnMetAlaThrGlnGlyAla
MetProAlaPheAlaSerAlaPheGlnArgArgAlaGlyGlyValLeuValAlaSer
HisLeuGlnSerPheLeuGluValSerTyrArgValLeuArgHisLeuAlaGlnPro
SerGlyGlySerGlyGlySerGlnSerPheLeuLeuLysSerLeuGluGlnValArg
LysIleGlnGlyAspGlyAlaAlaLeuGlnGluLysLeuCysAlaThrTyrLysLeu
CysHisProGluGluLeuValLeuLeuGlyHisSerLeuGlyIleProTrpAlaPro
LeuSerSerCysProSerGlnAlaLeuGlnLeuAlaGlyCysLeuSerGlnLeuHis
SerGlyLeuPheLeuTyrGlnGlyLeuLeuGlnAlaLeuGluGlyIleSerProGlu
LeuGlyProThrLeuAspThrLeuGlnLeuAspValAlaAspPheAlaThrThrIle
TrpGlnGlnMetGluGluLeuGlyMetAlaProAlaLeuGlnPro
(SEQ ID NO:201)
```

EXAMPLE 86

Construction of pMON31115

Construction of pMON31115, a plasmid containing DNA sequence encoding a multi-functional hematopoietic receptor agonist which activates the hIL-3 receptor and G-CSF receptor. Plasmid, pMON13197 DNA was digested with restriction enzymes NcoI and XmaI resulting in an NcoI, XmaI vector fragment that was isolated and purified from a 0.8% agarose gel. The DNA from a second plasmid, pMON13222, was digested with NcoI and EcoRI resulting in a 281 base pair NcoI, EcoRI fragment. This fragment was isolated and purified from a 1.0% agarose gel. Two oligonucleotides SYNNOXA1.REQ (SEQ ID NO:240) and SYNNOXA2.REQ (SEQ ID NO:241) were annealed and ligated with the 281 base pair DNA fragment from pMON13222 to the DNA vector fragment from pMON13197. A portion of the ligation mixture was then transformed into *E. coli* K-12 strain JM101. Transformant bacteria were selected on ampicillin-containing plates. Plasmid DNA was isolated, analyzed by restriction analysis to show the presence of an EcoRV fragment, and sequenced to confirm the correct inserts.

The plasmid, pMON31115, contains the DNA sequence of (SEQ ID NO:117) which encodes the following amino acid sequence:

```
MetAlaAsnCysSerAsnMetIleAspGluIleIleThrHisLeuLysGlnProPro
LeuProLeuLeuAspPheAsnAsnLeuAsnGlyGluAspGlnAspIleLeuMetAsp
AsnAsnLeuArgArgProAsnLeuGluAlaPheAsnArgAlaValLysSerLeuGln
AsnAlaSerAlaIleGluSerIleLeuLysAsnLeuLeuProCysLeuProLeuAla
ThrAlaAlaProThrArgHisProIleHisIleLysAspGlyAspTrpAsnGluPhe
ArgArgLysLeuThrPheTyrLeuLysThrLeuGluAsnAlaGlnAlaGlnGlnTyr
ValGluGlyGlyGlyGlySerProGlyGluProSerGlyProIleSerThrIleAsn
ProSerProProSerLysGluSerHisLysSerProAsnMetAlaThrGlnGlyAla
MetProAlaPheAlaSerAlaPheGlnArgArgAlaGlyGlyValLeuValAlaSer
HisLeuGlnSerPheLeuGluValSerTyrArgValLeuArgHisLeuAlaGlnPro
ThrProLeuGlyProAlaSerSerLeuProGlnSerPheLeuLeuLysSerLeuGlu
GlnValargLysIleGlnGlyAspGlyAlaAlaLeuGlnGluLysLeuCysAlaThr
TyrLysLeuCysHisProGluGluLeuValLeuLeuGlyHisSerLeuGlyIlePro
TrpAlaProLeuSerSerCysProSerGlnAlaLeuGlnLeuAlaGlyCysLeuSer
GlnLeuHisSerGlyLeuPheLeuTyrGlnGlyLeuLeuGlnAlaLeuGluGlyIle
SerProGluLeuGlyProThrLeuAspThrLeuGlnLeuAspValAlaAspPheAla
ThrThrIleTrpGlnGlnMetGluGluLeuGlyMetAlaProAlaLeuGlnPro
(SEQ ID NO:202)
```

EXAMPLE 87

Determination of the in vitro activity of multi-functional hematopoietic receptor agonist proteins The protein concentration of the multi-functional hematopoietic receptor agonist protein can be determined using a sandwich ELISA based on an affinity purified polyclonal antibody. Alternatively the protein concentration can be determined by amino acid composition analysis. The bioactivity of the multi-functional hematopoietic receptor agonist can be determined in a number of in vitro assays. For example a multi-functional hematopoietic receptor agonist which binds the hIL-3 receptor and G-CSF receptor can be assayed in cell proliferation assays using cell lines expressing the hIL-3 and/or G-CSF receptors. One such assay is the AML-193 cell proliferation assay. AML-193 cells respond to IL-3 and G-CSF which allows for the combined bioactivity of the IL-3/G-CSF multi-functional hematopoietic receptor agonist to be determined. Another such assay is the TF1 cell proliferation assay.

In addition other factor dependent cell lines, such as M-NFS-60 (ATCC. CRL 1838) or 32D which are murine IL-3 dependent cell line, may be used. The activity of IL-3 is species specific whereas G-CSF is not, therefore the bioactivity of the G-CSF component of the IL-3/G-CSF multi-functional hematopoietic receptor agonist can be determined independently. Cell lines, such as BHK or murine Baf/3, which do not express the receptor for a given ligand can be transfected with a plasmid containing a gene encoding the desired receptor. An example of such a cell line is BaF3 transfected with the hG-CSF receptor (BaF3/hG-CSF). The activity of the multi-functional hematopoietic receptor agonist in these cell lines can be compared with hIL-3 or G-CSF alone or together. The bioactivity of examples of multi-functional hematopoietic receptor agonists of the present invention assayed in the BaF3/hG-CSF cell proliferation and TF1 cell proliferation assays is shown in Table 5 and Table 6. The bioactivity of the multi-functional hematopoietic receptor agonist is expressed as relative activity compared with a standard protein pMON13056 (WO 95/21254). The bioactivity of examples of multi-functional hematopoietic receptor agonists of the present invention assayed in the BaF3/c-mpl cell proliferation and TF1 cell proliferation assays is shown in Table 7 and Table 8.

TABLE 5

CELL PROLIFERATIVE ACTIVITY
OF DUAL IL-3/G-CSF RECEPTOR AGONISTS

| pMON | BaF3/hG-CSF receptor cell proliferation assay relative activity* | TF1 cell proliferation assay relative activity* |
|---|---|---|
| 13182 | 0.015 | 1.1 |
| 13183 | 0.02 | nd |
| 13184 | 0.01 | 0.3 |
| 13185 | 0.023 | 0.36 |
| 13186 | 0.36 | 0.45 |
| 13187 | 0.07 | 0.26 |
| 13188 | 0.64 | 1.3 |
| 13189 | 0.58 | 1.37 |
| 13190 | 0.045 | 1.2 |
| 13191 | 0.14 | 2.7 |
| 13192 | 0.09 | 2.2 |
| 13193 | 0.06 | 3.0 |
| 25190 | nd | nd |
| 25191 | 0.43 | 1.2 |
| 13194 | nd | nd |
| 13195 | 1.3 | 4.3 |
| 13196 | 0.66 | 0.5 |
| 13197 | 0.6 | 0.77 |
| 13198 | 0.6 | 0.5 |
| 13199 | nd | nd |
| 15982 | 0.7 | 1.9 |
| 15981 | 0.068 | 1.2 |
| 15965 | 0.7 | 0.82 |

TABLE 5-continued

CELL PROLIFERATIVE ACTIVITY
OF DUAL IL-3/G-CSF RECEPTOR AGONISTS

| pMON | BaF3/hG-CSF receptor cell proliferation assay relative activity* | TF1 cell proliferation assay relative activity* |
|---|---|---|
| 15966 | 0.36 | 1.48 |
| 15967 | 0.62 | 1.37 | nd = not determined
*The bioactivity of the multi-functional hematopoietic receptor agonist is expressed as relative activity compared with a standard protein pMON13056. n = 3 or greater

TABLE 6

CELL PROLIFERATIVE ACTIVITY
OF DUAL IL-3/G-CSF RECEPTOR AGONISTS

| pMON | BaF3/hG-CSF receptor cell proliferation assay relative activity | TF1 cell proliferation assay relative activity |
|---|---|---|
| 31104 | + | + |
| 31105 | + | + |
| 31106 | + | + |
| 31107 | nd | nd |
| 31108 | + | + |
| 31109 | + | + |
| 31110 | nd | nd |
| 31111 | nd | nd |
| 31112 | + | + |
| 31113 | + | + |
| 31114 | + | + |
| 31115 | + | + |
| 31116 | nd | nd |
| 31117 | nd | nd | nd = not determined
† The bioactivity (n = 1 or 2) of the multi-functional hematopoietic receptor agonist is expressed as relative activity compared with a standard protein pMON13056.
"+" indicates that the molecule was comparable to pMON13056.

TABLE 7

CELL PROLIFERATION ACTIVITY

| pMON | Baf3/c-mpl receptor cell proliferation assay activity* | TF1 cell proliferation assay activity |
|---|---|---|
| 28505 | − | + |
| 28506 | − | + |
| 28507 | − | + |
| 28508 | − | + |
| 28509 | − | + |
| 28510 | − | + |
| 28511 | + | + |
| 28512 | + | + |
| 28513 | + | + |
| 28514 | + | + |
| 28519 | − | + |
| 28520 | − | + |
| 28521 | − | + |
| 28522 | − | + |
| 28523 | − | + |
| 28524 | − | + |
| 28525 | + | + |
| 28526 | + | + |
| 28533 | − | + |
| 28534 | − | + |

TABLE 7-continued

CELL PROLIFERATION ACTIVITY

| pMON | Baf3/c-mpl receptor cell proliferation assay activity* | TF1 cell proliferation assay activity |
|---|---|---|
| 28535 | − | + |
| 28536 | − | + |
| 28537 | − | + |
| 28538 | − | + |
| 28539 | + | + |
| 28540 | + | + |
| 28541 | + | + |
| 28542 | + | + |
| 28543 | + | + |
| 28544 | + | + |
| 28545 | + | + |

*Activity measured in the Baf3 cell line transfected with the c-mpl receptor, relative to c-mpl ligand (1–153).
† Activity measured relative to pMON13056.

In a similar manner other factor dependent cell lines known to those skilled in the art can be used to measure the bioactivity of the desired multi-functional hematopoietic receptor agonist. The methylcellulose assay can be used to determine the effect of the multi-functional hematopoietic receptor agonists on the expansion of the hematopoietic progenitor cells and the pattern of the different types of hematopoietic colonies in vitro. The methylcellulose assay can provide an estimate of precursor frequency since one measures the frequency of progenitors per 100,000 input cells. Long term, stromal dependent cultures have been used to delineate primitive hematopoietic progenitors and stem cells. This assay can be used to determine whether the multi-functional hematopoietic receptor agonist stimulates the expansion of very primitive progenitors and/or stem cells. In addition, limiting dilution cultures can be performed which will indicate the frequency of primitive progenitors stimulated by the multi-functional hematopoietic receptor agonist.

TABLE 8

| pMON # | IL-3 agonist activity (AML cell proliferation assay) | c-mpl receptor agonist activity (Baf/3-c-mpl cell proliferation assay |
|---|---|---|
| 28505 | + | − |
| 28506 | + | − |
| 28507 | + | − |
| 28508 | + | − |
| 28509 | + | − |
| 28510 | + | − |
| 28511 | + | + |
| 28512 | + | + |
| 28513 | + | + |
| 28514 | + | + |
| 28515 | + | + |
| 28519 | + | − |
| 28520 | + | − |
| 28521 | + | − |
| 28522 | + | − |
| 28523 | + | − |
| 28524 | + | − |
| 28525 | + | + |
| 28526 | + | + |
| 28527 | + | + |
| 28528 | + | + |
| 28529 | + | + |
| 28535 | + | − |
| 28539 | + | + |

TABLE 8-continued

| pMON # | IL-3 agonist activity (AML cell proliferation assay) | c-mpl receptor agonist activity (Baf/3-c-mpl cell proliferation assay |
|---|---|---|
| 28540 | + | + |
| 28541 | + | + |
| 28542 | + | + |
| 28545 | + | + |

EXAMPLE 88

G-CSF variants which contain single or multiple amino acid substitutions were made using PCR mutagenesis techniques as described in WO 94/12639 and WO 94/12638. These and other variants (i.e. amino acid substitutions, insertions or deletions and N-terminal or C-terminal extensions) could also be made, by one skilled in the art, using a variety of other methods including synthetic gene assembly or site-directed mutagenesis (see Taylor et al., Nucl. Acids Res., 13: 7864–8785 [1985]; Kunkel et al., Proc. Natl. Acad. Sci. USA, 82: 488–492 [1985]; Sambrook et al., Molecular Cloning: A Laboratory Manual, 2nd ed., Cold Spring Harbor Laboratory Press, Cold Spring Harbor, N.Y., [1989], (WO 94/12639) and (WO 94/12638)). These substitutions can be made one at a time or in combination with other amino acid substitutions, and/or deletions, and/or insertions and/or extensions. After sequence verification of the changes, the plasmid DNA can be transfected into an appropriate mammalian cell, insect cell or bacterial strain such as E. coli for production. Known variants of G-CSF, which are active, include substitutions at positions 1 (Thr to Ser, Arg or Gly), 2 (Pro to Leu), 3 (Leu to Arg or Ser) and 17 (Cys to Ser) and deletions of amino acids 1–11 (Kuga et al. Biochemicla and Biophysical Research Comm. 159:103–111 (1989)). These G-CSF amino acid substitution variants can be used as the template to create the G-CSF receptor agonists in which a new N-terminus and new C-terminus are created. Examples of G-CSF amino acid substitution variants are shown in Table 9.

EXAMPLE 89

Bioactivity determination of G-CSF amino acid substitution variants

The G-CSF amino acid substitution variants can be assayed for cell proliferation activity using the Baf/3 cell line transfected with the human G-CSF receptor. The bioactivity of examples of G-CSF amino acid substitution variants is shown in Table 9 relative to native human G-CSF. A "+" indicates a comparable activity to native and a "−" indicates significantly reduced or no measurable activity.

TABLE 9

CELL PROLIFERATION ACTIVITY OF G-CSF VARIANTS IN BAF3 CELL LINE TRANSFECTED WITH THE HUMAN G-CSF RECEPTOR

| aa position | native aa | mutant aa | activity* |
|---|---|---|---|
| 13 | Phe | Ser | + |
| 13 | Phe | His | + |
| 13 | Phe | Thr | + |
| 13 | Phe | Pro | + |
| 16 | Lys | Pro | + |
| 16 | Lys | Ser | + |
| 16 | Lys | Thr | + |
| 16 | Lys | His | + |

TABLE 9-continued

CELL PROLIFERATION ACTIVITY OF G-CSF VARIANTS IN BAF3 CELL LINE TRANSFECTED WITH THE HUMAN G-CSF RECEPTOR

| aa position | native aa | mutant aa | activity* |
|---|---|---|---|
| 18 | Leu | Pro | + |
| 18 | Leu | Thr | + |
| 18 | Leu | His | + |
| 18 | Leu | Cys | + |
| 18 | Leu | Ile | + |
| 19 | Glu | Ala | − |
| 19 | Glu | Thr | − |
| 19 | Glu | Arg | − |
| 19 | Glu | Pro | − |
| 19 | Glu | Leu | − |
| 19 | Glu | Ser | − |
| 22 | Arg | Tyr | + |
| 22 | Arg | Ser | + |
| 22 | Arg | Ala | + |
| 22 | Arg | Thr | + |
| 24 | Ile | Pro | + |
| 24 | Ile | Leu | + |
| 24 | Ile | Tyr | + |
| 27 | Asp | Gly | + |
| 30 | Ala | Ile | + |
| 30 | Ala | Leu | + |
| 34 | Lys | Ser | + |
| 43 | His | Gly | + |
| 43 | His | Thr | + |
| 43 | His | Val | + |
| 43 | His | Lys | + |
| 43 | His | Trp | + |
| 43 | His | Ala | + |
| 43 | His | Arg | + |
| 43 | His | Cys | + |
| 43 | His | Leu | + |
| 44 | Pro | Arg | + |
| 44 | Pro | Asp | + |
| 44 | Pro | Val | + |
| 44 | Pro | Ala | + |
| 44 | Pro | His | + |
| 44 | Pro | Gln | + |
| 44 | Pro | Trp | + |
| 44 | Pro | Gly | + |
| 44 | Pro | Thr | + |
| 46 | Glu | Ala | + |
| 46 | Glu | Arg | + |
| 47 | Leu | Thr | + |
| 49 | Leu | Phe | + |
| 49 | Leu | Arg | + |
| 49 | Leu | Ser | + |
| 50 | Leu | His | + |
| 54 | Leu | His | + |
| 67 | Gln | Lys | + |
| 67 | Gln | Leu | + |
| 67 | Gln | Cys | + |
| 70 | Gln | Pro | + |
| 70 | Gln | Leu | + |
| 70 | Gln | Arg | + |
| 70 | Gln | Ser | + |
| 104 | Asp | Gly | + |
| 104 | Asp | Val | + |
| 108 | Leu | Ala | + |
| 108 | Leu | Val | + |
| 108 | Leu | Arg | + |
| 108 | Leu | Gly | + |
| 108 | Leu | Trp | + |
| 108 | Leu | Gln | + |
| 115 | Thr | His | + |
| 115 | Thr | Leu | + |
| 115 | Thr | Ala | + |
| 144 | Phe | His | + |
| 144 | Phe | Arg | + |
| 144 | Phe | Pro | + |
| 144 | Phe | Leu | + |
| 144 | Phe | Glu | + |
| 146 | Arg | Gln | + |
| 147 | Arg | Gln | + |
| 156 | His | Asp | − |
| 156 | His | Ser | + |
| 156 | His | Gly | + |
| 159 | Ser | Arg | + |
| 159 | Ser | Thr | + |
| 159 | Ser | Tyr | + |
| 159 | Ser | Val | + |
| 159 | Ser | Gly | + |
| 162 | Glu | Gly | − |
| 162 | Glu | Trp | + |
| 162 | Glu | Leu | + |
| 163 | Val | Arg | + |
| 163 | Val | Ala | + |
| 163 | Val | Gly | + |
| 165 | Tyr | Cys | nd |
| 169 | Ser | Leu | + |
| 169 | Ser | Cys | + |
| 169 | Ser | Arg | + |
| 170 | His | Arg | + |
| 170 | His | Ser | + |

*activity relative to native hG-CSF
nd = not determined

EXAMPLE 90

Cysteine Substitution Variants

The multi-functional receptor agonists may comprise sequence rearranged c-mpl receptor agonist, which also have the substitution of the cysteine residues at position 7 and/or 151 with an another amino acid, which can be prepared by the methods described in Examples 1–89 and by other methods known to those skilled in the art. One such c-mpl receptor agonist has the breakpoint at 115/116 and alanine at positions 7 and 151. This c-mpl receptor agonist has the following amino acid:

```
MetAlaGlyArgThrThrAlaHisLysAspProAsnAlaIlePheLeuSerPheGlnHis
LeuLeuArgGlyLysValArgPheLeuMetLeuValGlyGlySerThrLeuAlaValArg
GluPheGlyGlyAsnMetAlaSerProAlaProProAlaAlaAspLeuArgValLeuSer
LysLeuLeuArgAspSerHisValLeuHisSerArgLeuSerGlnCysProGluValHis
ProLeuProThrProValLeuLeuProAlaValAspPheSerLeuGlyGluTrpLysThr
GlnMetGluGluThrLysAlaGlnAspIleLeuGlyAlaValThrLeuLeuLeuGluGly
ValMetAlaAlaArgGlyGlnLeuGlyProThrCysLeuSerSerLeuLeuGlyGlnLeu
SerGlyGlnValArgLeuLeuLeuGlyAlaLeuGlnSerLeuLeuGlyThrGlnLeuPro
```

ProGln (SEQ ID NO:284), and is encoded by the following DNA sequence;

```
  1  ATGGCTGGCA GGACCACAGC TCACAAGGAT CCCAATGCCA TCTTCCTGAG
 51  CTTCCAACAC CTGCTCCGAG GAAAGGTGCG TTTCCTGATG CTTGTAGGAG
101  GGTCCACCCT CGCCGTCAGG GAATTCGGCG GCAACATGGC GTCTCCGGCG
151  CCGCCTGCTG CTGACCTCCG AGTCCTCAGT AAACTGCTTC GTGACTCCCA
201  TGTCCTTCAC AGCAGACTGA GCCAGTGCCC AGAGGTTCAC CCTTTGCCTA
251  CACCTGTCCT GCTGCCTGCT GTGGACTTTA GCTTGGGAGA ATGGAAAACC
301  CAGATGGAGG AGACCAAGGC ACAGGACATT CTGGGAGCAG TGACCCTTCT
351  GCTGGAGGGA GTGATGGCAG CACGGGGACA ACTGGGACCC ACTTGCCTCT
401  CATCCCTCCT GGGGCAGCTT TCTGGACAGG TCCGTCTCCT CCTTGGGGCC
451  CTGCAGAGCC TCCTTGGAAC CCAGCTTCCT CCACAG
     (SEQ ID NO:287).
```

Another c-mpl receptor agonist has the breakpoint at 81/82 and alanine at positions 7 and 151. This c-mpl receptor agonist has the following amino acid;

```
MetAlaGlyProThrCysLeuSerSerLeuLeuGlyGlnLeuSerGlyGlnValArgLeu
LeuLeuGlyAlaLeuGlnSerLeuLeuGlyThrGlnLeuProProGlnGlyArgThrThr
AlaHisLysAspProAsnAlaIlePheLeuSerPheGlnHisLeuLeuArgGlyLysVal
ArgPheLeuMetLeuValGlyGlySerThrLeuAlaValArgGluPheGlyGlyAsnMet
AlaSerProAlaProProAlaAlaAspLeuArgValLeuSerLysLeuLeuArgAspSer
HisValLeuHisSerArgLeuSerGlnCysProGluValHisProLeuProThrProVal
LeuLeuProAlaValAspPheSerLeuGlyGluTrpLysThrGlnMetGluGluThrLys
AlaGlnAspIleLeuGlyAlaValThrLeuLeuLeuGluGlyValMetAlaAlaArgGly
```

GlnLeu, (SEQ ID NO:285), and is encoded by the following DNA sequence;

```
  1  ATGGCTGGAC CCACTTGCCT CTCATCCCTC CTGGGGCAGC TTTCTGGACA
 51  GGTCCGTCTC CTCCTTGGGG CCCTGCAGAG CCTCCTTGGA ACCCAGCTTC
101  CTCCACAGGG CAGGACCACA GCTCACAAGG ATCCCAATGC CATCTTCCTG
151  AGCTTCCAAC ACCTGCTCCG AGGAAAGGTG CGTTTCCTGA TGCTTGTAGG
201  AGGGTCCACC CTCGCCGTCA GGGAATTCGG CGGCAACATG GCGTCTCCGG
251  CGCCGCCTGC TGCTGACCTC CGAGTCCTCA GTAAACTGCT TCGTGACTCC
301  CATGTCCTTC ACAGCAGACT GAGCCAGTGC CCAGAGGTTC ACCCTTTGCC
351  TACACCTGTC CTGCTGCCTG CTGTGGACTT TAGCTTGGGA GAATGGAAAA
401  CCCAGATGGA GGAGACCAAG GCACAGGACA TTCTGGGAGC AGTGACCCTT
451  CTGCTGGAGG GAGTGATGGC AGCACGGGGA CAACTG
     (SEQ ID NO:286)
```

EXAMPLES 91–103

The plasmids in Table 10 contain genes encoding multi-functional hematopoietic receptor agonists comprising a sequence rearranged G-CSF receptor agonists that were made by the method of Horlich et al (*Protein Eng.* 5:427–431, 1992). As described in Materials and Methods, the tandem repeat of the G-CSF Ser$^{17}$ gene was maintained on a pACYC177 based plasmid (Chang and Cohen, *J. Bacteriol.* 1341141–1156, 1978), containing the sequence; GAG ATG GCT, encoding; Asp Met Ala, following immediately downstream of amino acid 174 of the first copy of the G-CSF Ser$^{17}$ gene and immediately preceeding amino acid 1 of the second copy of the G-CSF Ser$^{17}$ gene. The resulting sequence rearranged G-CSF receptor agonists have the linker; Asp Met Ala, between the original C-terminus and original N-terminus of G-CSF Ser$^{17}$. The sequence rearranged G-CSF receptor agonists encoded by the plasmids of Table 10 were identified using a G-CSF receptor binding screen (Wantanabe et al. *Analyt. Biochem* 195:38–44, 1991). The multi-functional receptor agonists shown in Table 10 had G-CSF receptor binding comparable to or better than native recombinant hG-CSF.

TABLE 10

| plasmid designation | breakpoint | gene sequence | protein sequence |
|---|---|---|---|
| pMON16017 | 2–3 | SEQ ID NO:294 | SEQ ID NO:306 |
| pMON16018 | 10–11 | SEQ ID NO:288 | SEQ ID NO:300 |
| pMON16019 | 12–13 | SEQ ID NO:291 | SEQ ID NO:303 |
| pMON16021 | 48–49 | SEQ ID NO:295 | SEQ ID NO:307 |
| pMON16022 | 59–60 | SEQ ID NO:296 | SEQ ID NO:308 |
| pMON16023 | 66–67 | SEQ ID NO:297 | SEQ ID NO:309 |
| pMON16024 | 68–69 | SEQ ID NO:298 | SEQ ID NO:310 |
| pMON16025 | 122–123 | SEQ ID NO:289 | SEQ ID NO:301 |
| pMON16028 | 158–159 | SEQ ID NO:292 | SEQ ID NO:304 |
| pMON16025 | 70–71 | SEQ ID NO:299 | SEQ ID NO:311 |
| pMON16027 | 124–125 | SEQ ID NO:290 | SEQ ID NO:302 |
| pMON16020 | 18–19 | SEQ ID NO:293 | SEQ ID NO:305 |
| pMON16029 | 169–170 | SEQ ID NO:313 | SEQ ID NO:312 |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

More details concerning the molecular biology techniques, protein purification and bioassays can be found in WO 94/12639, WO 94/12638, WO 95/20976, WO 95/21197, WO 95/20977, WO 95/21254, are hereby incorporated by reference in their entirety.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

What is claimed is:

1. A hematopoietic protein comprising; an amino acid sequence of the formula:

R1-L1-R2, R2-L1-R1, R1-R2, or R2-R1 wherein R1 is a biologically active human c-mpl ligand comprising a modified amino acid sequence selected from the group consisting of:

(a) an amino acid sequence of SEQ ID NO:256 wherein;

Xaa at position 112 is deleted or Leu, Ala, Val, Ile, Pro, Phe, Trp, or Met;

Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn; and wherein the N-terminus is joined to the C-terminus directly or through a linker (L2) capable of joining the N-terminus to the C-terminus wherein new C-termini and N-termini are created between the amino acid reside pairs of SEQ ID NO:256 selected from the group consisting of:

26–27, 27–28, 28–29, 29–30, 30–31, 32–33, 33–34, 34–35, 36–37, 37–38, 38–39, 40–41, 41–42, 42–43, 43–44, 44–45, 46–47, 47–48, 48–49, 50–51, 51–52, 52–53, 53–54, 54–55, 55–56, 56–57, 57–58, 58–59, 59–60, 78–79, 79–80, 80–81, 81–82, 82–83, 83–84, 84–85, 85–86, 86–87, 87–88, 88–89, 108–109, 109–110, 110–111, 111–112, 112–113, 113–114, 114–115, 115–116, 116–117, 117–118, 118–119, 119–120, 120–121, 121–122, 122–123, 123–124, 124–125, 125–126, 126–127 or 127–128; and (b) an amino acid sequence of SEQ ID NO:283 wherein;

Xaa at position 7 is Ser or Ala;

Xaa at position 112 is deleted or Leu, Ala, Val, Ile, Pro, Phe, Trp, or Met;

Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn;

Xaa at position 151 is Ser or Ala;

wherein the N-terminus is joined to the C-terminus directly or through a linker (L2) capable of joining the N-terminus to the C-terminus wherein new C-termini and N-termini are created between the amino acid reside pairs of SEQ ID NO:283 selected from the group consisting of:

26–27, 27–28, 28–29, 29–30, 30–31, 32–33, 33–34, 34–35, 36–37, 37–38, 38–39, 40–41, 41–42, 42–43,

43–44, 44–45, 46–47, 47–48, 48–49, 50–51, 51–52, 52–53, 53–54, 54–55, 55–56, 56–57, 57–58, 58–59, 59–60, 78–79, 79–80, 80–81, 81–82, 82–83, 83–84, 84–85, 85–86, 86–87, 87–88, 88–89, 108–109, 109–110, 110–111, 111–112, 112–113, 113–114, 114–115, 115–116, 116–117, 117–118, 118–119, 119–120, 120–121, 121–122, 122–123, 123–124, 124–125, 125–126, 126–127 or 127–128;

R2 is selected from the group consisting of: a biologically active human IL-3 variant comprising a modified amino acid sequence of (SEQ ID NO:2)

wherein Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Gly, Trp, Lys, Phe, Leu, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn,. Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser., Pro, Tyr, or Leu;

wherein from 1 to 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said modified human IL-3 amino acid sequence;

a colony stimulating factor, a cytokine, a lymphokine, an interleukin, and a hematopoietic growth factor;

L1 is a linker capable of linking R1 to R2; and said hematopoietic protein is optionally immediately preceded by (methionine-1), (alanine-1) or (methionine-2, alanine-1).

2. The hematopoietic protein as recited in claim 1 wherein said protein is selected from the group consisting of;

SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, and SEQ ID NO:239.

3. A nucleic acid molecule encoding said hematopoietic protein of claim 2.

4. The nucleic acid molecule according to claim 3 selected from group consisting of:

SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, and SEQ ID NO:154.

5. The hematopoietic protein as recited in claim 1 wherein said c-mpl receptor agonist is selected from the group consisting of:

```
MetAlaGlyArgThrThrAlaHisLysAspProAsnAlaIlePheLeuSerPheGlnHis
LeuLeuArgGlyLysValArgPheLeuMetLeuValGlyGlySerThrLeuAlaValArg
GluPheGlyGlyAsnMetAlaSerProAlaProProAlaAlaAspLeuArgValLeuSer
LysLeuLeuArgAspSerHisValLeuHisSerArgLeuSerGlnCysProGluValHis
ProLeuProThrProValLeuLeuProAlaValAspPheSerLeuGlyGluTrpLysThr
GlnMetGluGluThrLysAlaGlnAspIleLeuGlyAlaValThrLeuLeuLeuGluGly
ValMetAlaAlaArgGlyGlnLeuGlyProThrCysLeuSerSerLeuLeuGlyGlnLeu
SerGlyGlnValArgLeuLeuLeuGlyAlaLeuGlnSerLeuLeuGlyThrGlnLeuPro
ProGln (SEQ ID NO:284); and
```

-continued
```
MetAlaGlyProThrCysLeuSerSerLeuLeuGlyGlnLeuSerGlyGlnValArgLeu
LeuLeuGlyAlaLeuGlnSerLeuLeuGlyThrGlnLeuProProGlnGlyArgThrThr
AlaHisLysAspProAsnAlaIlePheLeuSerPheGlnHisLeuLeuArgGlyLysVal
ArgPheLeuMetLeuValGlyGlySerThrLeuAlaValArgGluPheGlyGlyAsnMet
AlaSerProAlaProProAlaAlaAspLeuArgValLeuSerLysLeuLeuArgAspSer
HisValLeuHisSerArgLeuSerGlnCysProGluValHisProLeuProThrProVal
LeuLeuProAlaValAspPheSerLeuGlyGluTrpLysThrGlnMetGluGluThrLys
AlaGlnAspIleLeuGlyAlaValThrLeuLeuLeuGluGlyValMetAlaAlaArgGly
GlnLeu (SEQ ID NO:285)
```

6. A nucleic acid molecule encoding said hematopoietic protein of claim 5.

7. A nucleic acid molecule encoding said hematopoietic protein of claim 1.

8. A method for selective ex vivo expansion of hematopoietic stem cells, comprising the steps of;
   (a) separating hematopoietic stem cells from other cells;
   (b) culturing the separated hematopoietic stem cells from step (a) with a selected culture medium comprising; an amount of the hematopoietic protein of claim 1, effective to expand said hematopoietic stem cells; and
   (c) harvesting the cultured hematopoietic cells of step (b).

9. A method for treatment of a patient having a hematopoietic disorder, comprising the steps of;
   (a) removing hematopoietic cells from said patient;
   (b) separating hematopoietic stem cells from other cells removed from said patient;
   (c) culturing said separated hematopoietic stem cells from step (b) with a selected culture medium comprising; an amount of the hematopoietic protein of claim 1 effective to expand and/or differentiate the hematopoietic stem cells;
   (d) harvesting the cultured hematopoietic cells from step (c); and
   (e) introducing the cultured hematopoietic cells from step (d) into said patient to increase the number of hematopoietic cells.

10. A method of expanding the transducing hematopoietic cells for use in gene therapy, comprising the steps of;
    (a) removing hematopoietic cells from a patient;
    (b) separating hematopoietic stem cells from other cells removed from the patient in step (a);
    (c) culturing said separated hematopoietic stem cells from step (b) with a selected culture medium comprising; an amount of the hematopoietic protein of claim 1 effective to expand the hematopoietic stem cells;
    (d) transducing the cultured hematopoietic cells from step (c) by introducing DNA into said cultured hematopoietic cells; and
    (e) harvesting said transduced hematopoietic cells.

11. A pharmaceutical composition comprising; the hematopoietic protein according to claim 1; at least one colony stimulating factor, cytokine, lymphokine, interleukin, or hematopoietic growth factor selected from the group consisting of: GM-CSF, G-CSF, c-mpl ligand (TPO), MGDF, M-CSF, erythropoietin (EPO), IL-1, IL-4, IL-2, IL-3, IL-5, IL-6, IL-7, IL-8, IL-9, IL-10, IL-11, IL-12, IL-13, IL-15, IL-16, LIF, flt3 ligand, and stem cell factor (SCF); and a pharmaceutically acceptable carrier.

12. A method of stimulating the production of hematopoietic cells in a patient comprising the step of; administering to said patient an amount of the composition as recited in claim 11, effective to stimulate the production of hematopoietic cells.

13. A method for selective ex vivo expansion of hematopoietic cells, comprising the steps of;
    (a) culturing hematopoietic cells with a culture medium comprising; an amount of the composition of claim 11, effective to expand said hematopoietic cells; and
    (b) harvesting the cultured hematopoietic cells of step (a).

14. A method for selective ex vivo expansion of hematopoietic stem cells, comprising the steps of;
    (a) separating hematopoietic stem cells from other cells;
    (b) culturing the separated hematopoietic stem cells from step (a) with a selected culture medium comprising; an amount of the composition of claim 11, effective to expand said hematopoietic stem cells; and
    (c) harvesting the cultured hematopoietic cells of step (b).

15. A method for treatment of a patient having a hematopoietic disorder, comprising the steps of;
    (a) removing hematopoietic cells from said patient;
    (b) separating hematopoietic stem cells from other cells removed from said patient;
    (c) culturing said separated hematopoietic stem cells from step (b) with a selected culture medium comprising; an amount of the composition of claim 11, effective to expand and/or differentiate the hematopoietic stem cells;
    (d) harvesting the cultured hematopoietic cells from step (c); and
    (e) introducing the cultured hematopoietic cells from step (d) into said patient to increase the number of hematopoietic cells.

16. A method of expanding and transducing hematopoietic cells for use in gene therapy, comprising the steps of;
    (a) removing hematopoietic cells from a patient;
    (b) separating hematopoietic stem cells from other cells removed from the patient in step (a);
    (c) culturing said separated hematopoietic stem cells from step (b) with a selected culture medium comprising; an amount of the hematopoietic protein of claim 11 effective to expand the hematopoietic stem cells;
    (d) transducing the cultured hematopoietic cells from step (c) by introducing DNA into said cultured hematopoietic cells; and
    (e) harvesting said transduced hematopoietic cells.

17. A hematopoietic protein comprising; an amino acid sequence of the formula:

R1-L1-R2, R2-L1-R1, R1-R2, or R2-R1 wherein R1 is a biologically active human c-mpl ligand comprising a modified amino acid sequence of SEQ ID NO:256
wherein;
   Xaa at position 112 is deleted or Leu, Ala, Val, Ile, Pro, Phe, Trp, or Met;
   Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn; and wherein the N-terminus is joined to the C-terminus directly or through a linker (L2) capable of joining the N-terminus to the C-terminus wherein new C-termini and N-termini are created between the amino acid reside pairs of SEQ ID NO:256 selected from the group consisting of:

26–27, 27–28, 28–29, 29–30, 30–31, 32–33, 33–34, 34–35, 36–37, 37–38, 38–39, 40–41, 41–42, 42–43, 43–44, 44–45, 46–47, 47–48, 48–49, 50–51, 51–52, 52–53, 53–54, 54–55, 55–56, 56–57, 57–58, 58–59, 59–60, 78–79, 79–80, 80–81, 81–82, 82–83, 83–84, 84–85, 85–86, 86–87, 87–88, 88–89, 108–109, 109–110, 110–111, 111–112, 112–113, 113–114, 114–115, 115–116, 116–117, 117–118, 118–119, 119–120, 120–121, 121–122, 122–123, 123–124, 124–125, 125–126, 126–127 or 127–128;

R2 is selected from the group consisting of: a biologically active human IL-3 variant comprising a modified amino acid sequence of SEQ ID NO:2 wherein Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Gly, Trp, Lys, Phe, Leu, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or. Gly;

Xaa at position 58 is Leu, Ser, Asp, Arg, Gln, Val, or Cys;

Xaa at position 59 is Glu Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position Ill is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser,.Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 1 to 14 amino acids are optionally deleted from the N-terminus and/or from 1 to 15 amino acids are optionally deleted from the C-terminus of said modified human IL-3 amino acid sequence; and wherein from 1 to 44 of the amino acids designated by Xaa are different from the corresponding amino acids of native (1–133) human interleukin-3;

a colony stimulating factor, a cytokine, a lymphokine, an interleukin, and a hematopoietic growth factor;

L1 is a linker capable of linking R1 to R2; and said hematopoietic protein is optionally immediately preceded by (methionine-1), (alanine-1) or (methionine-2, alanine-1).

18. A nucleic acid molecule encoding said hematopoietic protein of claim 17.

19. The hematopoietic protein of claim 1 or 17 wherein said colony stimulating factor, cytokine, interleukin, or hematopoietic growth factor, is selected from the group consisting of GM-CSF, G-CSF, G-CSF Ser17, c-mpl ligand (TPO), MGDF, M-CSF, erythropoietin (EPO), IL-1, IL-4, IL-2, IL-3, IL-5, IL 6, IL-7, IL-8, IL-9, IL-10, IL-11, IL-12, IL-13, IL-15, LIF, flt3 ligand, human growth hormone, and stem cell factor (SCF).

20. The hematopoietic protein as recited in claim 19 wherein said linker (L2) is selected from the group consisting of SEQ ID NO: 12, SEQ ID NO: 242, SEQ ID NO: 243, SEQ ID NO: 244, SEQ ID NO: 245, SEQ ID NO: 246, SEQ ID NO: 247 and SEQ ID NO: 248.

21. A method for treatment of a patient having a hematopoietic disorder, comprising the steps of;
    (a) removing hematopoietic cells from said patient;
    (b) separating hematopoietic stem cells from other cells removed from said patient;
    (c) culturing said separated hematopoietic stem cells from step (b) with a selected culture medium comprising; an amount of the hematopoietic protein of claim 20 effective to expand and/or differentiate the hematopoietic stem cells;
    (d) harvesting the cultured hematopoietic cells from step (c); and
    (e) introducing the cultured hematopoietic cells from step (d) into said patient to increase the number of hematopoietic cells.

22. A nucleic acid molecule encoding said hematopoietic protein of claim 20.

23. A method of producing a hematopoietic protein comprising: growing under suitable nutrient conditions, a host cell transformed or transfected with a replicable vector comprising a nucleic acid molecule of claim 22 under conditions which result in the expression of said hematopoietic protein and recovering said hematopoietic protein.

24. A pharmaceutical composition comprising; the hematopoietic protein according to claim 20 and a pharmaceutically acceptable carrier.

25. A method of stimulating the production of hematopoietic cells in a patient comprising the step of; administering to said patient an amount of the hematopoietic protein as recited in claim 20, effective to stimulate the production of hematopoietic cells.

26. A method for selective ex vivo expansion of hematopoietic stem cells, comprising the steps of;
    (a) separating hematopoietic stem cells from other cells;

(b) culturing the separated hematopoietic stem cells from step (a) with a selected culture medium comprising; an amount of the hematopoietic protein of claim 20, effective to expand said hematopoietic stem cells; and (c) harvesting the cultured hematopoietic cells of step (b).

27. A method of expanding and transducing hematopoietic cells for use in gene therapy, comprising the steps of;

(a) removing hematopoietic cells from a patient;

(b) separating hematopoietic stem cells from other cells removed from the patient in step (a);

(c) culturing said separated hematopoietic stem cells from step (b) with a selected culture medium comprising; an amount of the hematopoietic protein of claim 20 effective to expand the hematopoietic stem cells;

(d) transducing the cultured hematopoietic cells from step (c) by introducing DNA into said cultured hematopoietic cells; and (e) harvesting said transduced hematopoietic cells.

28. A nucleic acid molecule encoding said hematopoietic protein of claim 19.

29. A method of producing a hematopoietic protein comprising: growing under suitable nutrient conditions, a host cell transformed or transfected with a replicable vector comprising a nucleic acid molecule of claim 28 under conditions which result in the expression of said hematopoietic protein and recovering said hematopoietic protein.

30. A pharmaceutical composition comprising; the hematopoietic protein according to claim 19 and a pharmaceutically acceptable carrier.

31. A method of stimulating the production of hematopoietic cells in a patient comprising the step of; administering to said patient an amount of the hematopoietic protein as recited in claim 19, effective to stimulate the production of hematopoietic cells.

32. A method for selective ex vivo expansion of hematopoietic cells, comprising the steps of;

(a) culturing hematopoietic cells with a culture medium comprising; an amount of the hematopoietic protein of claim 19, effective to expand said hematopoietic cells; and (b) harvesting the cultured hematopoietic cells of step (a).

33. A method for selective ex vivo expansion of hematopoietic stem cells, comprising the steps of;

(a) separating hematopoietic stem cells from other cells;

(b) culturing the separated hematopoietic stem cells from step (a) with a selected culture medium comprising; an amount of the hematopoietic protein of claim 19, effective to expand said hematopoietic stem cells; and (c) harvesting the cultured hematopoietic cells of step (b).

34. A method for treatment of a patient having a hematopoietic disorder, comprising the steps of;

(a) removing hematopoietic cells from said patient;

(b) separating hematopoietic stem cells from other cells removed from said patient;

(c) culturing said separated hematopoietic stem cells from step (b) with a selected culture medium comprising; an amount of the hematopoietic protein of claim 19 effective to expand and/or differentiate the hematopoietic stem cells;

(d) harvesting the cultured hematopoietic cells from step (c); and (e) introducing the cultured hematopoietic cells from step (d) into said patient to increase the number of hematopoietic cells.

35. A method of expanding and transducing hematopoietic cells for use in gene therapy, comprising the steps of;

(a) removing hematopoietic cells from a patient;

(b) separating hematopoietic stem cells from other cells removed from the patient in step (a);

(c) culturing said separated hematopoietic stem cells from step (b) with a selected culture medium comprising; an amount of the hematopoietic protein of claim 19 effective to expand the hematopoietic stem cells;

(d) transducing the cultured hematopoietic cells from step (c) by introducing DNA into said cultured hematopoietic cells; and (e) harvesting said transduced hematopoietic cells.

36. A hematopoietic protein comprising; an amino acid sequence of the formula:

R1-L1-R2, R2-L1-R1, R1-R2, or R2-R1 wherein R1 is a biologically active human c-mpl ligand comprising a modified amino acid sequence of SEQ ID NO:256 wherein;

Xaa at position 112 is deleted or Leu, Ala, Val, Ile, Pro, Phe, Trp, or Met;

Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn; and wherein the N-terminus is joined to the C-terminus directly or through a linker (L2) capable of joining the N-terminus to the C-terminus wherein new C-termini and N-termini are created between the amino acid reside pairs of SEQ ID NO:256 selected from the group consisting of:

26–27, 27–28, 28–29, 29–30, 30–31, 32–33, 33–34, 34–35, 36–37, 37–38, 38–39, 40–41, 41–42, 42–43, 43–44, 44–45, 46–47, 47–48, 48–49, 50–51, 51–52, 52–53, 53–54, 54–55, 55–56, 56–57, 57–58, 58–59, 59–60, 78–79, 79–80, 80–81, 81–82, 82–83, 83–84, 84–85, 85–86, 86–87, 87–88, 88–89, 108–109, 109–110, 110–111, 111–112, 112–113, 113–114, 114–115, 115–116, 116–117, 117–118, 118–119, 119–120, 120–121, 121–122, 122–123, 123–124, 124–125, 125–126, 126–127 or 127–128;

R2 is a biologically active human IL-3 variant comprising a modified amino acid sequence of SEQ ID NO:2 wherein Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Gly, Trp, Lys, Phe, Leu, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 1 to 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said modified human IL-3 amino acid sequence;
L1 is a linker capable of linking R1 to R2; and
said hematopoietic protein is optionally immediately preceded by (methionine-1), (alanine-1) or (methionine-2, alanine-1).

37. The hematopoietic protein as recited in claim 36 wherein in said modified human IL-3 sequence the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 101 wherein Xaa is Asp;

position 105 wherein Xaa is Asn, or Pro;

position 108 wherein Xaa is Arg, Ala, or Ser;

position 116 wherein Xaa is Lys;

position 121 wherein Xaa is Ala, or Ile;

position 122 wherein Xaa is Gln, or Ile;

position 123 wherein Xaa is Ala, Met or Glu.

38. A nucleic acid molecule encoding said hematopoietic protein of claim 37.

39. The hematopoietic protein as recited in claim 36 wherein said modified human IL-3 sequence is selected from the group consisting of SEQ ID NO: 225, SEQ ID NO: 226, SEQ ID NO: 227, and SEQ ID NO: 228.

40. A nucleic acid molecule encoding said hematopoietic protein of claim 39.

41. The hematopoietic protein as recited in claim 36 wherein said modified human IL-3 sequence differs from native human IL-3 by substitution of Asp for Glu at position 50.

42. A nucleic acid molecule encoding said hematopoietic protein of claim 41.

43. A nucleic acid molecule encoding said hematopoietic protein of claim 36.

44. A hematopoietic protein comprising an amino acid sequence of the formula:

R1-L1-R2, R2-L1-R1, R1-R2, or R2-R1 wherein R1 is a biologically active human c-mpl ligand comprising a modified amino acid sequence of SEQ ID NO:256 wherein;

Xaa at position 112 is deleted or Leu, Ala, Val, Ile, Pro, Phe, Trp, or Met;

Xaa at position 113 is deleted or Pro, Phe, Ala, Val, Leu, Ile, Trp, or Met;

Xaa at position 114 is deleted or Pro, Phe, Ala, Val, Leu, Ile, Trp, or Met;

Xaa at position 115 is deleted or Gln, Gly, Ser, Thr, Tyr, or Asn; and wherein the N-terminus is joined to the C-terminus directly or through a linker (L2) capable of joining the N-terminus to the C-terminus wherein new C-termini and N-termini are created between the amino acid reside pairs of SEQ ID NO:256 selected from the group consisting of:

26–27, 27–28, 28–29, 29–30, 30–31, 32–33, 33–34, 34–35, 36–37, 37–38, 38–39, 40–41, 41–42, 42–43, 43–44, 44–45, 46–47, 47–48, 48–49, 50–51, 51–52, 52–53, 53–54, 54–55, 55–56, 56–57, 57–58, 58–59, 59–60, 78–79, 79–80, 80–81, 81–82, 82–83, 83–84, 84–85, 85–86, 86–87, 87–88, 88–89, 108–109, 109–110, 110–111, 111–112, 112–113, 113–114, 114–115, 115–116, 116–117, 117–118, 118–119, 119–120, 120–121, 121–122, 122–123, 123–124, 124–125, 125–126, 126–127 or 127–128;

wherein R2 is G-CSF or G-CSF Ser17;

L1 is a linker capable of linking R1 to R2; and said hematopoietic protein is optionally immediately preceded by (methionine-1), (alanine-1) or (methionine-2, alanine-1).

45. A nucleic acid molecule encoding said hematopoietic protein of claim 44.

46. The hematopoietic protein as recited in claim 1, 17, 36, 37, 39, 41, or 44 wherein said linker (L2) is selected from the group consisting of SEQ ID NO: 12, SEQ ID NO: 242, SEQ ID NO: 243, SEQ ID NO: 244, SEQ ID NO: 245, SEQ ID NO: 246, SEQ ID NO: 247 and SEQ ID NO: 248.

47. A nucleic acid molecule encoding said hematopoietic protein of claim 46.

48. A method of producing a hematopoietic protein comprising: growing under suitable nutrient conditions, a host cell transformed or transfected with a replicable vector comprising a nucleic acid molecule of claim 47 under conditions which result in the expression of said hematopoietic protein and recovering said hematopoietic protein.

49. A pharmaceutical composition comprising; the hematopoietic protein according to claim 46 and a pharmaceutically acceptable carrier.

50. A method of stimulating the production of hematopoietic cells in a patient comprising the step of; administering to said patient an amount of the hematopoietic protein as recited in claim 46, effective to stimulate the production of hematopoietic cells.

51. A method for selective ex vivo expansion of hematopoietic cells, comprising the steps of;

(a) culturing hematopoietic cells with a culture medium comprising; an amount of the hematopoietic protein of claim 46, effective to expand said hematopoietic cells; and (b) harvesting the cultured hematopoietic cells of step (a).

52. A method for selective ex vivo expansion of hematopoietic stem cells, comprising the steps of;

(a) separating hematopoietic stem cells from other cells;

(b) culturing the separated hematopoietic stem cells from step (a) with a selected culture, medium comprising; an amount of the hematopoietic protein of claim 46, effective to expand said hematopoietic stem cells; and (c) harvesting the cultured hematopoietic cells of step (b).

53. A method for treatment of a patient having a hematopoietic disorder, comprising the steps of;

(a) removing hematopoietic cells from said patient;

(b) separating hematopoietic stem cells from other cells removed from said patient;

(c) culturing said separated hematopoietic stem cells from step (b) with a selected culture medium comprising; an amount of the hematopoietic protein of claim 46 effective to expand and/or differentiate the hematopoietic stem cells;

(d) harvesting the cultured hematopoietic cells from step (c); and (e) introducing the cultured hematopoietic cells from step (d) into said patient to increase the number of hematopoietic cells.

54. A method of expanding and transducing hematopoietic cells for use in gene therapy, comprising the steps of;

(a) removing hematopoietic cells from a patient;

(b) separating hematopoietic stem cells from other cells removed from the patient in step (a);

(c) culturing said separated hematopoietic stem cells from step (b) with a selected culture medium comprising; an amount of the hematopoietic protein of claim 46 effective to expand the hematopoietic stem cells;

(d) transducing the cultured hematopoietic cells from step (c) by introducing DNA into said cultured hematopoietic cells; and (e) harvesting said transduced hematopoietic cells.

55. A method of producing a hematopoietic protein comprising: growing under suitable nutrient conditions, a host cell transformed or transfected with a replicable vector comprising a nucleic acid molecule of claim 7, 18, 43, 38, 40, 42, 45, 3, 4, or 6 under conditions which result in the expression of said hematopoietic protein and recovering said hematopoietic protein.

56. A pharmaceutical composition comprising; the hematopoietic protein according to claim 1, 17, 36, 37, 39, 41, 44, 2, or 5 and a pharmaceutically acceptable carrier.

57. A method of stimulating the production of hematopoietic cells in a patient comprising the step of; administering to said patient an amount of the hematopoietic protein as recited in claim 1, 17, 36, 37, 39, 41, 44, 2, or 5, effective to stimulate the production of hematopoietic cells.

58. A method for selective ex vivo expansion of hematopoietic cells, comprising the steps of;

(a) culturing hematopoietic cells with a culture medium comprising; an amount of the hematopoietic protein of claim 1, 17, 36, 37, 39, 41, 44, 2, or 5, effective to expand said hematopoietic cells; and (b) harvesting the cultured hematopoietic cells of step (a).

* * * * *